US012030904B2

(12) United States Patent
Lazerwith et al.

(10) Patent No.: US 12,030,904 B2
(45) Date of Patent: *Jul. 9, 2024

(54) PHOSPHOLIPID COMPOUNDS AND USES THEREOF

(71) Applicant: Gilead Sciences, Inc., Foster City, CA (US)

(72) Inventors: Scott E. Lazerwith, San Francisco, CA (US); Jonathan William Medley, San Bruno, CA (US); Philip A. Morganelli, Oakland, CA (US); Devan Naduthambi, San Bruno, CA (US); Thomas P. Stratton, San Francisco, CA (US); Peiyuan Wang, San Mateo, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/301,179

(22) Filed: Apr. 14, 2023

(65) Prior Publication Data

US 2023/0250117 A1    Aug. 10, 2023

Related U.S. Application Data

(63) Continuation of application No. 17/409,261, filed on Aug. 23, 2021, now Pat. No. 11,773,122.

(60) Provisional application No. 63/151,509, filed on Feb. 19, 2021, provisional application No. 63/092,386, filed on Oct. 15, 2020, provisional application No. 63/069,449, filed on Aug. 24, 2020.

(51) Int. Cl.
*C07F 9/6561* (2006.01)
*A61P 31/12* (2006.01)

(52) U.S. Cl.
CPC ............ *C07F 9/6561* (2013.01); *A61P 31/12* (2018.01)

(58) Field of Classification Search
CPC .................................................. C07F 9/6561
See application file for complete search history.

(56) References Cited

U.S. PATENT DOCUMENTS

| | | | |
|---|---|---|---|
| 4,921,951 | A | 5/1990 | Shuto et al. |
| 11,530,195 | B1 | 12/2022 | Liang et al. |
| 11,541,071 | B1 | 1/2023 | Liang et al. |
| 11,702,406 | B1 | 7/2023 | Wu |
| 11,773,122 | B2 | 10/2023 | Lazerwith et al. |
| 2022/0081455 | A1 | 3/2022 | Lazerwith et al. |
| 2022/0143052 | A1 | 5/2022 | Lazerwith et al. |
| 2022/0396550 | A1 | 12/2022 | Ghosh et al. |
| 2022/0411401 | A1 | 12/2022 | Ghosh et al. |
| 2023/0074535 | A1 | 3/2023 | Bohmann et al. |
| 2023/0085986 | A1 | 3/2023 | Zhang et al. |
| 2023/0108588 | A1 | 4/2023 | Nieman et al. |
| 2023/0113114 | A1 | 4/2023 | Brown et al. |
| 2023/0159451 | A1 | 5/2023 | Yang et al. |
| 2023/0212199 | A1* | 7/2023 | Chun ..................... A61K 45/06 514/141 |
| 2023/0248753 | A1 | 8/2023 | Lazerwith et al. |

FOREIGN PATENT DOCUMENTS

| | | |
|---|---|---|
| CN | 111393243 B | 12/2022 |
| CN | 112010916 B | 12/2022 |
| CN | 115466225 A | 12/2022 |
| CN | 115490681 A | 12/2022 |
| CN | 115504964 A | 12/2022 |
| CN | 115518058 A | 12/2022 |
| CN | 115521208 A | 12/2022 |
| CN | 115521316 A | 12/2022 |
| CN | 115521337 A | 12/2022 |
| CN | 113292565 B | 1/2023 |
| CN | 115554303 A | 1/2023 |
| CN | 115572298 A | 1/2023 |
| CN | 115583954 A | 1/2023 |
| CN | 115594734 A | 1/2023 |
| CN | 115636817 A | 1/2023 |
| CN | 115650959 A | 1/2023 |
| CN | 115651022 A | 1/2023 |
| CN | 111233929 B | 2/2023 |
| CN | 115703796 A | 2/2023 |
| CN | 115710297 A | 2/2023 |
| CN | 115716833 A | 2/2023 |
| CN | 115785080 A | 3/2023 |
| CN | 115806570 A | 3/2023 |
| CN | 115819423 A | 3/2023 |
| CN | 115850338 A | 3/2023 |
| CN | 112645982 B | 4/2023 |
| CN | 115887471 A | 4/2023 |
| CN | 115894443 A | 4/2023 |
| CN | 115894498 A | 4/2023 |
| CN | 115894504 A | 4/2023 |
| CN | 115894587 A | 4/2023 |
| CN | 115947759 A | 4/2023 |

(Continued)

OTHER PUBLICATIONS

International Search Report and Written Opinion dated Nov. 16, 2021 on International Application No. PCT/US2021/047145.
Lo, K. et al. (2021) "Broad-spectrum in vitro antiviral activity of ODBG-P-RVn: an orally-available, lipid-modified monophosphate prodrug of remdesivir parent nucleoside (GS-441524)" bioRxiv; doi: https://doi.org/10.1101/2021.08.06.455494.
Lo, K. et al. (2021) "Broad-spectrum in vitro antiviral activity of ODBG-P-RVn: an orally-available, lipid-modified monophosphate prodrug of remdesivir parent nucleoside (GS-441524)" Microbiology Spectrum; DOI: https://doi.org/10.1128/Spectrum.01537-21.
Office Action dated Jul. 21, 2022 for Taiwan Appl. No. 110131250.
Schooley, R. et al. (2020) "Rethinking Remdesivir: Synthesis of Lipid Prodrugs that Substantially Enhance Anti-Coronavirus Activity" bioRxiv preprint, doi: https://doi.org/10.1101/2020.08.26.269159.

(Continued)

*Primary Examiner* — Laura L Stockton

(57) ABSTRACT

Compounds and methods of using said compounds, singly or in combination with additional agents, and pharmaceutical compositions of said compounds for the treatment of viral infections are disclosed.

18 Claims, No Drawings

(56) References Cited

FOREIGN PATENT DOCUMENTS

| | | |
|---|---|---|
| EP | 4159211 A1 | 4/2023 |
| IN | 202121023147 A | 11/2022 |
| IN | 202211013566 A | 11/2022 |
| IN | 202121025051 A | 12/2022 |
| JP | 2023-26155 A | 2/2023 |
| KR | 10-2023-0018351 A | 2/2023 |
| KR | 10-2023-0049329 A | 4/2023 |
| RU | 2791737 C1 | 3/2023 |
| WO | WO-9000555 A1 | 1/1990 |
| WO | WO-9639831 A1 | 12/1996 |
| WO | WO-0139724 A2 | 6/2001 |
| WO | WO-0190121 A2 | 11/2001 |
| WO | WO-0191737 A2 | 12/2001 |
| WO | WO-2006066074 A2 | 6/2006 |
| WO | WO-2006130217 A2 | 12/2006 |
| WO | WO-2010/002877 A2 | 1/2010 |
| WO | WO-10002877 A2 | 1/2010 |
| WO | WO-10039548 A2 | 4/2010 |
| WO | WO-2010039548 A2 | 4/2010 |
| WO | WO-2011100131 A2 | 8/2011 |
| WO | WO-2011150288 A1 | 12/2011 |
| WO | WO-2013096679 A1 | 6/2013 |
| WO | WO-2014100505 A1 | 6/2014 |
| WO | WO-2014/143643 A1 | 9/2014 |
| WO | WO-14143643 A1 | 9/2014 |
| WO | WO-2014209979 A1 | 12/2014 |
| WO | WO-2015054465 A1 | 4/2015 |
| WO | WO-2015200205 A1 | 12/2015 |
| WO | WO-2015200219 A1 | 12/2015 |
| WO | WO-2017165489 A1 | 9/2017 |
| WO | WO-2018169946 A1 | 9/2018 |
| WO | WO-2019027905 A1 | 2/2019 |
| WO | WO-2019053696 A1 | 3/2019 |
| WO | WO-2019133712 A1 | 7/2019 |
| WO | WO-2019169323 A1 | 9/2019 |
| WO | WO-2021167882 A1 | 8/2021 |
| WO | WO-2022020793 A1 | 1/2022 |
| WO | WO-2022046631 A1 | 3/2022 |
| WO | WO-2022081973 A1 | 4/2022 |
| WO | WO-2022/262820 A1 | 12/2022 |
| WO | WO-2022/268111 A1 | 12/2022 |
| WO | WO-2022/268145 A1 | 12/2022 |
| WO | WO-2022/270478 A1 | 12/2022 |
| WO | WO-2022265964 A1 | 12/2022 |
| WO | WO-2023/002409 A1 | 1/2023 |
| WO | WO-2023/003610 A1 | 1/2023 |
| WO | WO-2023/004291 A1 | 1/2023 |
| WO | WO-2023/272571 A1 | 1/2023 |
| WO | WO-2023/277341 A1 | 1/2023 |
| WO | WO-2023/279031 A1 | 1/2023 |
| WO | WO-2023/281063 A1 | 1/2023 |
| WO | WO-2023/283256 A1 | 1/2023 |
| WO | WO-2023/283831 A1 | 1/2023 |
| WO | WO-2023/285654 A2 | 1/2023 |
| WO | WO-2023/008530 A1 | 2/2023 |
| WO | WO-2023/009187 A1 | 2/2023 |
| WO | WO-2023/011443 A1 | 2/2023 |
| WO | WO-2023/011994 A1 | 2/2023 |
| WO | WO-2023/012329 A1 | 2/2023 |
| WO | WO-2023/014758 A1 | 2/2023 |
| WO | WO-2023/019614 A1 | 2/2023 |
| WO | WO-2023/021092 A1 | 2/2023 |
| WO | WO-2023/021132 A1 | 2/2023 |
| WO | WO-2023/022216 A1 | 2/2023 |
| WO | WO-2023/022231 A1 | 2/2023 |
| WO | WO-2023/023469 A1 | 2/2023 |
| WO | WO-2023/023631 A1 | 2/2023 |
| WO | WO-2023/023651 A1 | 2/2023 |
| WO | WO-2023/025319 A1 | 3/2023 |
| WO | WO-2023/027198 A1 | 3/2023 |
| WO | WO-2023/028286 A1 | 3/2023 |
| WO | WO-2023/029477 A1 | 3/2023 |
| WO | WO-2023/030347 A1 | 3/2023 |
| WO | WO-2023/030459 A1 | 3/2023 |
| WO | WO-2023/033098 A1 | 3/2023 |
| WO | WO-2023/034854 A1 | 3/2023 |
| WO | WO-2023/036140 A1 | 3/2023 |
| WO | WO-2023/036945 A1 | 3/2023 |
| WO | WO-2023/039330 A2 | 3/2023 |
| WO | WO-2023/040733 A1 | 3/2023 |
| WO | WO-2023/042879 A1 | 3/2023 |
| WO | WO-2023/043816 A1 | 3/2023 |
| WO | WO-2023/043830 A1 | 3/2023 |
| WO | WO-2023/044171 A1 | 3/2023 |
| WO | WO-2023/044462 A1 | 3/2023 |
| WO | WO-2023/046900 A1 | 3/2023 |
| WO | WO-2023/048151 A1 | 3/2023 |
| WO | WO-2023/049643 A1 | 3/2023 |
| WO | WO-2023/051657 A1 | 4/2023 |
| WO | WO-2023/052638 A1 | 4/2023 |
| WO | WO-2023/052772 A1 | 4/2023 |
| WO | WO-2023/054292 A1 | 4/2023 |
| WO | WO-2023/054732 A2 | 4/2023 |
| WO | WO-2023/054759 A1 | 4/2023 |
| WO | WO-2023/055702 A1 | 4/2023 |
| WO | WO-2023/056936 A1 | 4/2023 |
| WO | WO-2023/059792 A1 | 4/2023 |
| WO | WO-2023/063884 A2 | 4/2023 |
| WO | WO-2023/064493 A1 | 4/2023 |

OTHER PUBLICATIONS

Schooley, R. et al. (2021) "Rethinking Remdesivir: Synthesis, Antiviral Activity, and Pharmacokinetics of Oral Lipid Prodrugs" Antimicrobial Agents and Chemotherapy, 65(10): 1-13.

Warren, T. et al. (2022) "Therapeutic efficacy of the small molecule GS-5734 against Ebola virus in rhesus monkeys" Nature, 531: 19 pages.

Gershkovich, P. and Hoffman, A. (2005) "Uptake of lipophilic drugs by plasma derived isolated chylomicrons: Linear correlation with intestinal lymphatic bioavailability", Eur J Pharm Sci, 26(5):394-404.

Hostetler, K. (2009) "Alkoxyalkyl prodrugs of acyclic nucleoside phosphonates enhance oral antiviral activity and reduce toxicity: Current state of the art", Antiviral Res, 82(2): A84-A98.

Lanier, E. et al. (2010) "Development of Hexadecyloxypropyl Tenofovir (CMX157) for Treatment of Infection Caused by Wild-Type and Nucleoside/Nucleotide-Resistant HIV", Antimicrob Agents Chemother, 54(7):2901-2909.

Lee, J. et al. (2018) "Lipophilic activated ester prodrug approach for drug delivery to the intestinal lymphatic system", J Control Release, 286:10-19.

Painter, G. et al. (2007) "Evaluation of Hexadecyloxypropyl-9-R-[2-(Phosphonomethoxy)Propyl]-Adenine, CMX157, as a Potential Treatment for Human Immunodeficiency Virus Type 1 and Hepatitis B Virus Infections", Antimicrob Agents Chemother, 51(10):3505-3509.

Ruiz, J. et al. (2011) "Synthesis, metabolic stability and antiviral evaluation of various alkoxyalkyl esters of cidofovir and 9-(S)-[3-hydroxy-2-(phosphonomethoxy)propyl]adenine", Bioorg Med Chem, 19(9):2950-2958.

Valiaeva, N. et al. (2011) "Synthesis and antiviral evaluation of 9-(S)-[3-alkoxy-2-(phosphonomethoxy)propyl]nucleoside alkoxyalkyl esters: Inhibitors of hepatitis C virus and HIV-1 replication", Bioorg Med Chem, 19(15):4616-4625.

Wang, Y. et al. (2020) "Remdesivir in adults with severe COVID-19: a randomised, double-blind, placebo-controlled, multicentre trial", The Lancet, 395(10236):1569-1578.

Malin, J. et al. (2020) "Remdesivir against COVID-19 and Other Viral Diseases", Clin Microbiol Rev, 34(1):e00162-20, Epublished Oct. 14, 2020.

HHS ASPR (2022) "What Are the Possible Treatment Options for Covid-19?", Retrieved from the Internet on Nov. 3, 2022, https://aspr.hhs.gov/COVID-19/Treatments/Pages/Possible-Treatment-Options-for-COVID19.aspx#oral-antivirals.

Non-Final Office Action dated Feb. 9, 2023 for U.S. Appl. No. 17/409,261.

(56) References Cited

OTHER PUBLICATIONS

Intl. Preliminary Report on Patentability dated Mar. 9, 2023 for Intl. Appl. No. PCT/US2021/047145.
Final Office Action dated May 8, 2023 for U.S. Appl. No. 17/409,261.
Notice of Allowance dated Jun. 1, 2023 for U.S. Appl. No. 17/409,261.
Examination Report dated Jul. 24, 2023 for Australian Appl. No. 2021330835.
Notice of Opposition (Laboratorios Legrand S.A.) dated Jul. 26, 2023 for Colombian Appl. No. NC2023/0001953.
Office Action dated Aug. 14, 2023 for European Appl. No. 21772895.5.
Office Action dated Feb. 26, 20246 for Japan Application No. 2023-513115.

* cited by examiner

PHOSPHOLIPID COMPOUNDS AND USES THEREOF

CROSS REFERENCE

This is a Continuation of Application of U.S. patent application Ser. No. 17/409,261, filed on Aug. 23, 2021, which claims the benefit under 35 U.S.C. § 119(e) of U.S. Provisional Application Nos. 63/069,449 filed on Aug. 24, 2020; 63/092,386 filed on Oct. 15, 2020; and 63/151,509 filed on Feb. 19, 2021. The entire contents of these applications are incorporated herein by reference in their entirety.

BACKGROUND

There is a need for compounds and methods for treating viral infections, for example Paramyxoviridae, Pneumoviridae, Picornaviridae, Flaviviridae, Filoviridae, Arenaviridae, Orthomyxovirus, and Coronaviridae infections. The present disclosure addresses these and other needs.

SUMMARY

In one aspect, the disclosure provides a compound of Formula I:

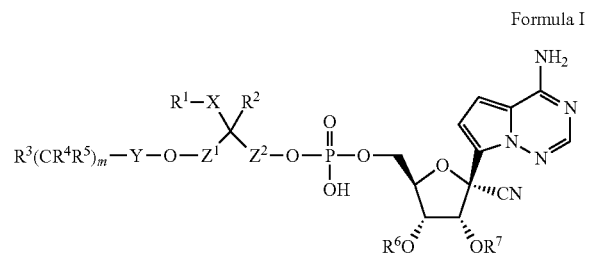

Formula I or a pharmaceutically acceptable salt thereof, wherein:
$Z^1$ is —$CH_2$— or —$CH_2$—$CH_2$—;
$Z^2$ is —$CH_2$— or —$CH_2$—$CH_2$—;
X is bond, —O—, —$(CR^{12A}R^{12B})_q$—, —$O(CR^{12A}R^{12B})_q$, or —$OCR^{12A}R^{12B}$—$(CR^{13}$=$CR^4)$—;
wherein
each $R^{12A}$ is independently H, $C_1$-$C_6$ alkyl, or phenyl;
each $R^{12B}$ is independently H or $C_1$-$C_6$ alkyl; or
$R^{12A}$ and $R^{12B}$ on same carbon are joined together to form a $C_3$-$C_6$ cycloalkylene;
$R^{13}$ is H, $C_1$-$C_6$ alkyl, or phenyl;
$R^{14}$ is H, $C_1$-$C_6$ alkyl, or phenyl;
q is 1 or 2;
$R^1$ is H, $C_1$-$C_{20}$ alkyl, $C_3$-$C_{10}$ cycloalkyl, 4 to 6 membered heterocyclyl containing one, two or three heteroatoms selected from N, O, and S, $C_6$-$C_{10}$ aryl, or 5-10 membered heteroaryl containing one, two or three heteroatoms selected from N, S, and O; wherein when $R^1$ is not H, the $R^1$ group is optionally substituted with one or two $R^{1A}$ groups;
wherein each $R^{1A}$ is independently a $C_1$-$C_3$ alkyl, phenyl, halo, $C_1$-$C_3$ alkoxy, cyano, or $C_1$-$C_3$haloalkyl; or wherein two $R^{1A}$ on same or adjacent carbons are joined together to from a 3 to 6 membered cycloalkyl or 4 to 6 membered heterocyclyl ring containing one, two or three heteroatoms selected from N, S, and O;
$R^2$ is H or $C_1$-$C_3$ alkyl;
Y is absent, phenylene, or $C_3$-$C_6$ cycloalkylene;
$R^3$ is H, $C_1$-$C_3$ alkyl, halo, $C_1$-$C_3$ haloalkyl, or $C_3$-$C_6$ cycloalkyl;
each $R^4$ is independently H, $C_1$-$C_3$ alkyl, halo, $C_1$-$C_3$ haloalkyl, or $C_3$-$C_6$ cycloalkyl; or $R^1$ group together with the $R^4$ group of one adjacent carbon atom forms a double bond;
each $R^5$ is independently H, $C_1$-$C_3$ alkyl, halo, $C_1$-$C_3$ haloalkyl, or $C_3$-$C_6$ cycloalkyl;
$R^6$ is H or —$C(O)C_1$-$C_6$ alkyl;
$R^7$ is H or —$C(O)C_1$-$C_6$ alkyl; and
m is an integer from 10 to 21.

In another aspect, the disclosure provides a pharmaceutical formulation comprising a pharmaceutically effective amount of a compound of Formula I, or a pharmaceutically acceptable salt thereof, and a pharmaceutically acceptable carrier or excipient.

In another aspect, the disclosure provides a method of treating or preventing a viral infection in a human in need thereof, wherein the method comprises administering to the human a compound of Formula I, or a pharmaceutically acceptable salt thereof.

In another aspect, the disclosure provides a method for manufacturing a medicament for treating or preventing a viral infection in a human in need thereof, characterized in that a compound of Formula I, or a pharmaceutically acceptable salt thereof, is used.

In another aspect the disclosure provides use of a compound of Formula I, or a pharmaceutically acceptable salt thereof, for the manufacture of a medicament for the treatment or prevention of a viral infection in a human in need thereof.

DETAILED DESCRIPTION OF THE INVENTION

I. General

The invention relates generally to methods and compounds for treating or preventing viral infections, for example paramyxoviridae, pneumoviridae, picornaviridae, flaviviridae, filoviridae, arenaviridae, orthomyxovirus, and coronaviridae.

II. Definitions

Unless stated otherwise, the following terms and phrases as used herein are intended to have the following meanings:

As used herein, "a compound of the disclosure" or "a compound of Formula I" means a compound of Formula I, or a pharmaceutically acceptable salt, thereof. Similarly, the phrase "a compound of Formula (number)" means a compound of that formula and pharmaceutically acceptable salts thereof.

"Alkyl" refers to an unbranched or branched saturated hydrocarbon chain. For example, an alkyl group can have 1 to 20 carbon atoms (i.e, $C_1$-$C_{20}$ alkyl), 1 to 8 carbon atoms (i.e., $C_1$-$C_8$ alkyl), 1 to 6 carbon atoms (i.e., $C_1$-$C_6$ alkyl), or 1 to 3 carbon atoms (i.e., $C_1$-$C_3$ alkyl). Examples of suitable alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)$ $CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)$ $CH(CH_3)_2$), 3-methyl-1-butyl (—$CH_2CH_2CH(CH_3)_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), and 3,3-dimethyl-2-butyl (—CH(CH$_3$)C(CH$_3$)$_3$).

"Alkoxy" means a group having the formula —O-alkyl, in which an alkyl group, as defined above, is attached to the parent molecule via an oxygen atom. The alkyl portion of an alkoxy group can have 1 to 20 carbon atoms (i.e., $C_1$-$C_{20}$ alkoxy), 1 to 12 carbon atoms (i.e., $C_1$-$C_{12}$ alkoxy), 1 to 8 carbon atoms (i.e., $C_1$-$C_8$ alkoxy), 1 to 6 carbon atoms (i.e., $C_1$-$C_6$ alkoxy) or 1 to 3 carbon atoms (i.e., $C_1$-$C_3$ alkoxy). Examples of suitable alkoxy groups include, but are not limited to, methoxy (—O—CH$_3$ or —OMe), ethoxy (—OCH$_2$CH$_3$ or —OEt), t-butoxy (—O—C(CH$_3$)$_3$ or —OtBu) and the like.

"Haloalkyl" is an alkyl group, as defined above, in which one or more hydrogen atoms of the alkyl group is replaced with a halogen atom. The alkyl portion of a haloalkyl group can have 1 to 20 carbon atoms (i.e., $C_1$-$C_{20}$ haloalkyl), 1 to 12 carbon atoms (i.e., $C_1$-$C_{12}$ haloalkyl), 1 to 8 carbon atoms (i.e., $C_1$-$C_8$ haloalkyl), 1 to 6 carbon atoms (i.e., $C_1$-$C_6$ alkyl) or 1 to 3 carbon atoms (i.e., $C_1$-$C_3$ alkyl). Examples of suitable haloalkyl groups include, but are not limited to, —CF$_3$, —CHF$_2$, —CFH$_2$, —CH$_2$CF$_3$, and the like.

"Aryl" means an aromatic hydrocarbon radical derived by the removal of one hydrogen atom from a single carbon atom of a parent aromatic ring system. For example, an aryl group can have 6 to 20 carbon atoms, 6 to 14 carbon atoms, or 6 to 10 carbon atoms. Typical aryl groups include, but are not limited to, radicals derived from benzene (e.g., phenyl), substituted benzene, naphthalene, anthracene, biphenyl, and the like.

"Cycloalkyl" refers to a saturated or partially saturated cyclic alkyl group having a single ring or multiple rings including fused, bridged, and spiro ring systems. As used herein, cycloalkyl has from 3 to 20 ring carbon atoms (i.e., $C_{3-20}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). Examples of cycloalkyl groups include cyclopropyl, cyclobutyl, cyclopentyl, cyclohexyl, cycloheptyl, and cyclooctyl.

The term "halo" as used herein, refers to —F, —Cl, —Br or —I. In one embodiment, a halo group is —F or —Cl. In another embodiment, a halo group is —F.

"Heterocycle" or "heterocyclyl" refer to a saturated or unsaturated cyclic alkyl group, with one or more ring heteroatoms independently selected from nitrogen, oxygen and sulfur. A heterocyclyl may be a single ring or multiple rings wherein the multiple rings may be fused, bridged, or spiro. As used herein, heterocyclyl has 3 to 20 ring atoms (i.e., 3 to 20 membered heterocyclyl), 3 to 12 ring atoms (i.e., 3 to 12 membered heterocyclyl), 3 to 10 ring atoms (i.e., 3 to 10 membered heterocyclyl), 3 to 8 ring atoms (i.e., 3 to 8 membered heterocyclyl), 4 to 12 ring carbon atoms (i.e., 4 to 12 membered heterocyclyl), 4 to 8 ring atoms (i.e., 4 to 8 membered heterocyclyl), or 4 to 6 ring atoms (i.e., 4 to 6 membered heterocyclyl). Examples of heterocyclyl groups include pyrrolidinyl, piperidinyl, piperazinyl, oxetanyl, dioxolanyl, azetidinyl, and morpholinyl. The terms heterocycle or heterocyclyl do not encompass or overlap with heteroaryls as defined below.

"Heteroaryl" refers to an aromatic group having a single ring, multiple rings, or multiple fused rings, with one or more ring heteroatoms independently selected from nitrogen, oxygen, and sulfur. As used herein, heteroaryl includes 1 to 20 ring atoms (i.e., $C_{1-20}$ heteroaryl), 3 to 12 ring atoms (i.e., $C_{3-12}$ heteroaryl), or 3 to 8 ring atoms (i.e., $C_{3-8}$ heteroaryl); and 1 to 5 ring heteroatoms, 1 to 4 ring heteroatoms, 1 to 3 ring heteroatoms, 1 to 2 ring heteroatoms, or 1 ring heteroatom independently selected from nitrogen, oxygen, and sulfur. Examples of heteroaryl groups include pyrimidinyl, purinyl, pyridyl, pyridazinyl, benzothiazolyl, and pyrazolyl. Heteroaryl does not encompass or overlap with aryl as defined above.

The term "optionally substituted" in reference to a particular moiety of the compound of Formula I (e.g., an optionally substituted aryl group) refers to a moiety wherein all substituents are hydrogen or wherein one or more of the hydrogens of the moiety may be replaced by the listed substituents.

Unless otherwise specified, the carbon atoms of the compounds of Formula I are intended to have a valence of four. If in some chemical structure representations, carbon atoms do not have a sufficient number of variables attached to produce a valence of four, the remaining carbon substituents needed to provide a valence of four should be assumed to be hydrogen.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, refers to the act of treating, as "treating" is defined immediately above.

The term "therapeutically effective amount", as used herein, is the amount of compound of Formula I present in a composition described herein that is needed to provide a desired level of drug in the secretions and tissues of the airways and lungs, or alternatively, in the bloodstream of a subject to be treated to give an anticipated physiological response or desired biological effect when such a composition is administered by the chosen route of administration. The precise amount will depend upon numerous factors, for example the particular compound of Formula I, the specific activity of the composition, the delivery device employed, the physical characteristics of the composition, its intended use, as well as patient considerations such as severity of the disease state, patient cooperation, etc., and can readily be determined by one skilled in the art based upon the information provided herein.

The term "adjacent carbons" as used herein refers to consecutive carbons atoms that are directly attached to each other. For example, in

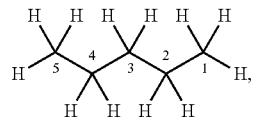

$C_1$ and $C_2$ are adjacent carbons, $C_2$ and $C_3$ are adjacent carbons, $C_3$ and $C_4$ are adjacent carbons, and $C_4$ and $C_5$ are adjacent carbons. Similarly, in

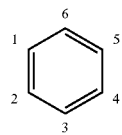

$C_1$ and $C_2$ are adjacent carbons, $C_2$ and $C_3$ are adjacent carbons, $C_3$ and $C_4$ are adjacent carbons, and $C_4$ and $C_5$ are adjacent carbons, $C_5$ and $C_6$ are adjacent carbons and $C_6$ and $C_1$ are adjacent carbons.

Certain commonly used alternative chemical names may or may not be used. For example, a divalent group such as a divalent "alkyl" group, a divalent "aryl" group, a divalent "cycloalkyl" group etc., may also be referred to as an "alkylene" group or an "alkylenyl" group, or alkylyl group; an "arylene" group or an "arylenyl" group, or arylyl group; a "cycloalkylene" group or an "cycloalkylenyl" group, or cycloalkylyl group respectively.

III. Compounds

Provided herein are compounds of Formula I:

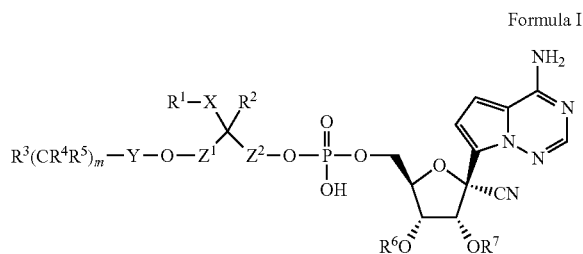

Formula I or a pharmaceutically acceptable salt thereof, wherein:
$Z^1$ is —$CH_2$— or —$CH_2$—$CH_2$—;
$Z^2$ is —$CH_2$— or —$CH_2$—$CH_2$—;
X is bond, —O—, —$(CR^{12A}R^{12B})_q$—, —$O(CR^{12A}R^{12B})_q$, or —$OCR^{12A}R^{12B}$—$(CR^{13}$=$CR^{14})$—; wherein
 each $R^{12A}$ is independently H, $C_1$-$C_6$ alkyl, or phenyl;
 each $R^{12B}$ is independently H or $C_1$-$C_6$ alkyl; or
 $R^{12A}$ and $R^{12B}$ on same carbon are joined together to form a $C_3$-$C_6$ cycloalkylene;
$R^{13}$ is H, $C_1$-$C_6$ alkyl, or phenyl;
$R^{14}$ is H, $C_1$-$C_6$ alkyl, or phenyl;
q is 1 or 2;
$R^1$ is H, $C_1$-$C_{20}$ alkyl, $C_3$-$C_{10}$ cycloalkyl, 4 to 6 membered heterocyclyl containing one, two or three heteroatoms selected from N, O, and S, $C_6$-$C_{10}$ aryl, or 5-10 membered heteroaryl containing one, two or three heteroatoms selected from N, S, and O; wherein when $R^1$ is not H, the $R^1$ group is optionally substituted with one or two $R^{1A}$ groups;
 wherein each $R^{1A}$ is independently a $C_1$-$C_3$ alkyl, phenyl, halo, $C_1$-$C_3$ alkoxy, cyano, or $C_1$-$C_3$ haloalkyl; or wherein two $R^{1A}$ on same or adjacent carbons are joined together to from a 3 to 6 membered cycloalkyl or 4 to 6 membered heterocyclyl ring containing one, two or three heteroatoms selected from N, S, and O;
$R^2$ is H or $C_1$-$C_3$ alkyl;
Y is absent, phenylene, or $C_3$-$C_6$ cycloalkylene;
$R^3$ is H, $C_1$-$C_3$ alkyl, halo, $C_1$-$C_3$ haloalkyl, or $C_3$-$C_6$ cycloalkyl;
each $R^4$ is independently H, $C_1$-$C_3$ alkyl, halo, $C_1$-$C_3$ haloalkyl, or $C_3$-$C_6$ cycloalkyl; or $R^1$ group together with the $R^4$ group of one adjacent carbon atom forms a double bond;
each $R^5$ is independently H, $C_1$-$C_3$ alkyl, halo, $C_1$-$C_3$ haloalkyl, or $C_3$-$C_6$ cycloalkyl;
$R^6$ is H or —$C(O)C_1$-$C_6$ alkyl;
$R^7$ is H or —$C(O)C_1$-$C_6$ alkyl; and
m is an integer from 10 to 21.

In some embodiments of the compounds of Formula I, $Z^1$ is —$CH_2$— and $Z^2$ is —$CH_2$—. In some embodiments, at least one of $Z^1$ and $Z^2$ is —$CH_2$—$CH_2$—. In some embodiments, both $Z^1$ and $Z^2$ are —$CH_2$—$CH_2$—. In some embodiments, $Z^1$ is —$CH_2$—$CH_2$— and $Z^2$ is —$CH_2$—. In some embodiments, $Z^1$ is —$CH_2$— and $Z^2$ is —$CH_2$—$CH_2$—.

In some embodiments, the compound of Formula I has a Formula II:

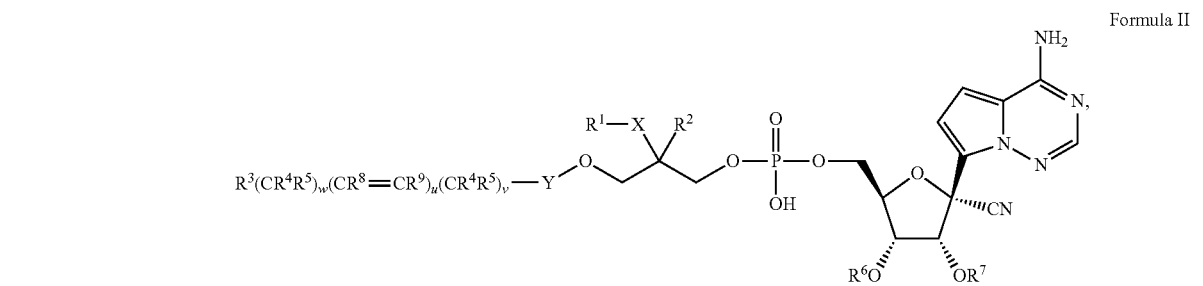

Formula II wherein
$R^8$ is H, $C_1$-$C_3$ alkyl, halo, $C_1$-$C_3$ haloalkyl, or $C_3$-$C_6$ cycloalkyl;
$R^9$ is H, $C_1$-$C_3$ alkyl, halo, $C_1$-$C_3$ haloalkyl, or $C_3$-$C_6$ cycloalkyl;
w and v is independently an integer from 10 to 21;
u is 0 or 1; and
w+u+v is an integer from 10 to 21.

In some embodiments of the compound of Formula II, u is 0. In some embodiments, u is 1. In some embodiments, u is 1, $R^8$ is H, $C_1$-$C_3$ alkyl, halo, $C_1$-$C_3$ haloalkyl, or $C_3$-$C_6$ cycloalkyl, and $R^9$ is H, $C_1$-$C_3$ alkyl, halo, $C_1$-$C_3$ haloalkyl, or $C_3$-$C_6$ cycloalkyl. In some embodiments, u is 1, $R^8$ is H, $C_1$-$C_3$ alkyl, halo, or $C_1$-$C_3$ haloalkyl, and $R^9$ is H, $C_1$-$C_3$ alkyl, halo, or $C_1$-$C_3$ haloalkyl. In some embodiments, u is 1, $R^8$ is H, $C_1$-$C_3$ alkyl or halo, and $R^9$ is H, $C_1$-$C_3$ alkyl or halo. In some embodiments, u is 1, $R^8$ is H or $C_1$-$C_3$ alkyl, and $R^9$ is H or $C_1$-$C_3$ alkyl. In some embodiments, u is 1, $R^8$ is H or methyl, and $R^9$ is H or methyl. In some embodiments, u is 1, $R^8$ is H, and $R^9$ is H.

In some embodiments, the compound of Formula I or II has a Formula III:

Formula III wherein n is an integer from 8 to 19.

In some embodiments of the compounds of Formula I, II, and III, X is —O—, —(CR$^{12A}$R$^{12B}$)$_q$—, —O(CR$^{12A}$R$^{12B}$)$_q$—, or —OCR$^{12A}$R$^{12B}$—(CR$^{13}$═CR$^{14}$)—, wherein q is 1 or 2. In some embodiments X is a bond, —O—, —(CR$^{12A}$R$^{12B}$)—, —O(CR$^{12A}$R$^{12B}$)—, or —OCR$^{12A}$R$^{12B}$—(CR$^{13}$═CR$^{14}$)—. In some embodiments, X is a bond, —O—, —(CR$^{12A}$R$^{12B}$)$_2$—, —O(CR$^{12A}$R$^{12B}$)$_2$—, or —OCR$^{12A}$R$^{12B}$—(CR$^{13}$═CR$^{14}$)—. In some embodiments, X is —O—, —O(CR$^{12A}$R$^{12B}$)$_q$—, or —OCR$^{12A}$R$^{12B}$—(CR$^{13}$═CR$^{14}$)—, wherein q is 1 or 2. In some embodiments, X is —O—, —O(CR$^{12A}$R$^{12B}$)—, or —OCR$^{12A}$R$^{12B}$—(CR$^{13}$═CR$^{14}$)—. In some embodiments, X is —O—, —O(CR$^{12A}$R$^{12B}$)$_2$—, or —OCR$^{12A}$R$^{12B}$—(CR$^{13}$═CR$^{14}$)—. In some embodiments X is a bond, —O—, —(CR$^{12A}$R$^{12B}$)$_q$—, —O(CR$^{12A}$R$^{12B}$)$_q$—, wherein q is 1 or 2. In some embodiments X is a bond, —O—, —(CR$^{12A}$R$^{12B}$)$_2$—, —O(CR$^{12A}$R$^{12B}$)$_2$—. In some embodiments X is a bond, —O—, —(CR$^{12A}$R$^{12B}$)—, —O(CR$^{12A}$R$^{12B}$)—. In some embodiments, X is O. In some embodiments X is —(CR$^{12A}$R$^{12B}$)$_q$—, where q is 1 or 2. In some embodiments X is —(CR$^{12A}$R$^{12B}$)—. In some embodiments X is —(CR$^{12A}$R$^{12B}$)$_2$—. In some embodiments, X is —O(CR$^{12A}$R$^{12B}$)$_q$—, where q is 1 or 2. In some embodiments, X is —O(CR$^{12A}$R$^{12B}$)—. In some embodiments, X is —O(CR$^{12A}$R$^{12B}$)$_2$—.

In some embodiments of the compounds of Formula I, II, and III, each $R^{12A}$ is independently H, $C_1$-$C_6$ alkyl, or phenyl; each $R^{12B}$ is independently H or $C_1$-$C_6$ alkyl; $R^{13}$ is H, $C_1$-$C_6$ alkyl, or phenyl; and $R^{14}$ is H, $C_1$-$C_6$ alkyl, or phenyl. In some embodiments, each $R^{12A}$ is independently H or $C_1$-$C_6$ alkyl; each $R^{12B}$ is independently H or $C_1$-$C_6$ alkyl; $R^{13}$ is H or $C_1$-$C_6$ alkyl; and $R^{14}$ is H or $C_1$-$C_6$ alkyl. In some embodiments, each $R^{12A}$ is independently H or $C_1$-$C_3$ alkyl, each $R^{12B}$ is independently H or $C_1$-$C_3$ alkyl, $R^{13}$ is H or $C_1$-$C_3$ alkyl, and $R^{14}$ is H or $C_1$-$C_3$ alkyl. In some embodiments, each $R^{12A}$ is H, each $R^{12B}$ is H, $R^{13}$ is H and $R^{14}$ is H.

In some embodiments of the compound of Formula I, II, and III, X is a bond, —O—, —(CR$^{12A}$R$^{12B}$)$_q$—, —O(CR$^{12A}$R$^{12B}$)$_q$—; where q is 1 or 2; each $R^{12A}$ is independently H, $C_1$-$C_6$ alkyl, or phenyl; and each $R^{12B}$ is independently H or $C_1$-$C_6$ alkyl. In some embodiments of the compound of Formula I, X is a bond, —O—, —(CR$^{12A}$R$^{12B}$)$_q$—, —O(CR$^{12A}$R$^{12B}$)$_q$—; where q is 1 or 2; each $R^{12A}$ is independently H or $C_1$-$C_6$ alkyl; and each $R^{12B}$ is independently H or $C_1$-$C_3$ alkyl. In some embodiments of the compound of Formula I, X is a bond, —O—, —(CR$^{12A}$R$^{12B}$)$_q$—, —O(CR$^{12A}$R$^{12B}$)$_q$—; where q is 1 or 2; each $R^{12A}$ is independently H or $C_1$-$C_3$ alkyl; and each $R^{12B}$ is independently H or $C_1$-$C_3$ alkyl. In some embodiments of the compound of Formula I, X is a bond, —O—, —(CR$^{12A}$R$^{12B}$)$_q$—, —O(CR$^{12A}$R$^{12B}$)$_q$—; where q is 1 or 2; each $R^{12A}$ is H; and each $R^{12B}$ is H. In some embodiments of the compound of Formula I, X is a bond, —O—, —CH$_2$—, —CH$_2$CH$_2$—, —OCH$_2$—, or —O(CH$_2$)$_2$—. In some embodiments of the compound of Formula I, X is a bond, —O—, —OCH$_2$—, or —CH$_2$CH$_2$—.

In some embodiments of the compound of Formula I, II, and III, X is —O—, —(CR$^{12A}$R$^{12B}$)$_q$—, —O(CR$^{12A}$R$^{12B}$)$_q$—; where q is 1 or 2; each $R^{12A}$ is independently H, $C_1$-$C_6$ alkyl, or phenyl; and each $R^{12B}$ is independently H or $C_1$-$C_6$ alkyl. In some embodiments of the compound of Formula I, X is —O—, —(CR$^{12A}$R$^{12B}$)$_q$—, —O(CR$^{12A}$R$^{12B}$)$_q$—; where q is 1 or 2; each $R^{12A}$ is independently H or $C_1$-$C_6$ alkyl; and each $R^{12B}$ is independently H or $C_1$-$C_6$ alkyl. In some embodiments of the compound of Formula I, X is —O—, —(CR$^{12A}$R$^{12B}$)$_q$—, —O(CR$^{12A}$R$^{12B}$)$_q$—; where q is 1 or 2; each $R^{12A}$ is independently H or $C_1$-$C_3$ alkyl; and each $R^{12B}$ is independently H or $C_1$-$C_3$ alkyl. In some embodiments of the compound of Formula I, X is —O—, —(CR$^{12A}$R$^{12B}$)$_q$—, —O(CR$^{12A}$R$^{12B}$)$_q$—; where q is 1 or 2; each $R^{12A}$ is H; and each $R^{12B}$ is H.

In some embodiments of the compound of Formula I, II, and III, X is —O—, —(CR$^{12A}$R$^{12B}$)—, —O(CR$^{12A}$R$^{12B}$)—; where $R^{12A}$ is H, $C_1$-$C_6$ alkyl, or phenyl; and $R^{12B}$ is H or $C_1$-$C_6$ alkyl. In some embodiments of the compound of Formula I, X is —O—, —(CR$^{12A}$R$^{12B}$)—, —O(CR$^{12A}$R$^{12B}$)—, where $R^{12A}$ is H or $C_1$-$C_6$ alkyl, and $R^{12B}$ H or $C_1$-$C_6$ alkyl. In some embodiments of the compound of Formula I, X is —O—, —(CR$^{12A}$R$^{12B}$)—, —O(CR$^{12A}$R$^{12B}$)—, where $R^{12A}$ is H or $C_1$-$C_3$ alkyl, and $R^{12B}$ is H or $C_1$-$C_3$ alkyl. In some embodiments of the compound of Formula I, X is —O—, —(CR$^{12A}$R$^{12B}$)—, —O(CR$^{12A}$R$^{12B}$)—; where $R^{12A}$ is H, and $R^{12B}$ is H.

In some embodiments of the compound of Formula I, II, and III, X is —O—, —(CR$^{12A}$R$^{12B}$)$_2$—, —O(CR$^{12A}$R$^{12B}$)$_2$—; where each $R^{12A}$ is independently H, $C_1$-$C_6$ alkyl, or phenyl; and each $R^{12B}$ is independently H or $C_1$-$C_6$ alkyl. In some embodiments of the compound of Formula I, X is —O—, —(CR$^{12A}$R$^{12B}$)$_2$—, —O(CR$^{12A}$R$^{12B}$)$_2$—, where each $R^{12A}$ is independently H or $C_1$-$C_6$ alkyl, and each $R^{12B}$ is independently H or $C_1$-$C_6$ alkyl. In some embodiments of the compound of Formula I, X is —O—, —(CR$^{12A}$R$^{12B}$)$_2$—, —O(CR$^{12A}$R$^{12B}$)$_2$—, where each $R^{12A}$ is independently H or $C_1$-$C_3$ alkyl, and each $R^{12B}$ is independently H or $C_1$-$C_3$ alkyl. In some embodiments of the compound of Formula I, X is —O—, —(CR$^{12A}$R$^{12B}$)$_2$—, —O(CR$^{12A}$R$^{12B}$)$_2$—; where each $R^{12A}$ is H and each $R^{12B}$ is H.

In some embodiments of the compounds of Formula I, II, and III, X is —O—, —OCH$_2$—, —OCH$_2$—CH$_2$—, —CH$_2$—, —CH$_2$—CH$_2$— or —OCH$_2$—(CH═CH)—. In some embodiments, X is —O—, —OCH$_2$—, —CH$_2$— or —OCH$_2$—(CH═CH)—. In some embodiments, X is —O—. In some embodiments, X is —CH$_2$— or —CH$_2$—CH$_2$—. In some embodiments, X is —CH$_2$—CH$_2$—. In some embodiments, X is —CH$_2$—.

In some embodiments of the compounds of Formula I, II, and III, X is —O—, —OCH$_2$—, —OCH$_2$—CH$_2$— or —OCH$_2$—(CH═CH)—. In some embodiments, X is —O—, —OCH$_2$—, or —OCH$_2$—(CH═CH)—. In some embodiments, X is —O—. In some embodiments, X is —OCH$_2$—. In some embodiments, X is —OCH$_2$—CH$_2$—. In some embodiments, X is —OCH$_2$—(CH═CH)—.

In some embodiments, of the compounds of Formula I, II, and III, X is a bond. In some embodiments of the compound of Formula I, II, or III, Y is phenylene or $C_3$-$C_6$ cycloalkylene. In some embodiments, Y is

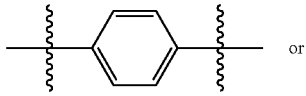 or

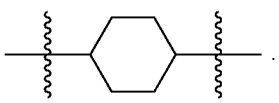.

In some embodiments, Y is phenylene. In some embodiments, Y is

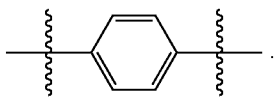.

In some embodiments, Y is $C_3$-$C_6$ cycloalkylene. In some embodiments, Y is cyclohexylene. In some embodiments, Y is

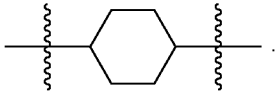.

In some embodiments, Y is absent. In some embodiments, Y is absent or phenylene. In some embodiments, Y is absent or $C_3$-$C_6$ cycloalkylene.

In some embodiments, the compound of Formula I, II, or III has a Formula IV:

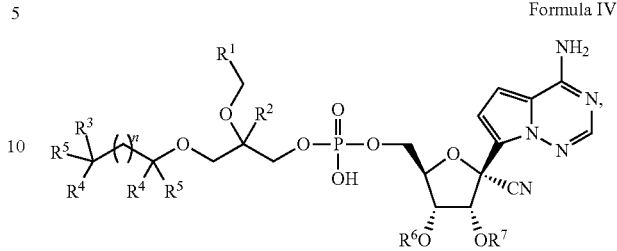

Formula IV wherein n is an integer from 8 to 19.

In some embodiments of the compounds of Formula I, II, III, or IV, $R^2$ is H. In some embodiments, $R^2$ is $C_1$-$C_3$ alkyl. In some embodiments, $R^2$ is methyl or ethyl. In some embodiments, $R^2$ is methyl. In some embodiments, $R^2$ is ethyl. In some embodiments, $R^2$ is H, methyl or ethyl. In some embodiments, $R^2$ is H or methyl. In some embodiments, $R^2$ is H or ethyl.

In some embodiments of the compounds of Formula III or IV, n is an integer from 11-18.

In some embodiments, n is an integer from 13-18. In some embodiments, n is an integer from 14-18. In some embodiments n is 15, 16, 17, or 18. In some embodiments n is 15. In some embodiments n is 16. In some embodiments n is 17. In some embodiments n is 18.

In some embodiments of the compounds of Formula I, II, III, or IV, each $R^5$ is independently H, $C_1$-$C_3$ alkyl, halo, $C_1$-$C_3$ haloalkyl, or $C_3$-$C_6$ cycloalkyl. In some embodiments, each $R^5$ is independently H, $C_1$-$C_3$ alkyl, halo, or $C_1$-$C_3$ haloalkyl. In some embodiments, each $R^5$ is independently H, $C_1$-$C_3$ alkyl, or halo. In some embodiments, each $R^5$ is independently H, or $C_1$-$C_3$ alkyl. In some embodiments, each $R^5$ is independently H, methyl or ethyl. In some embodiments, each $R^5$ is independently H or methyl. In some embodiments, each $R^5$ is independently H or ethyl. In some embodiments, each $R^5$ is H. In some embodiments, each $R^5$ is methyl. In some embodiments, each $R^5$ is ethyl.

In some embodiments of the compounds of Formula I, II, III, and IV, each $R^4$ is independently H, $C_1$-$C_3$ alkyl, halo, $C_1$-$C_3$ haloalkyl, or $C_3$-$C_6$ cycloalkyl. In some embodiments, each $R^4$ is independently H, $C_1$-$C_3$ alkyl, halo, or $C_1$-$C_3$ haloalkyl. In some embodiments, each $R^4$ is independently H, $C_1$-$C_3$ alkyl, or halo. In some embodiments, each $R^4$ is independent H, or $C_1$-$C_3$ alkyl. In some embodiments each $R^4$ is independently H, methyl or ethyl. In some embodiments, each $R^4$ is H. In some embodiments, each $R^4$ is methyl. In some embodiments, each $R^4$ is ethyl.

In some embodiments, the compound of Formula I, II, III, or IV has a Formula V:

Formula V

In some embodiments, the compound of Formula I, II, III, IV or V has a Formula V has a Formula Va:

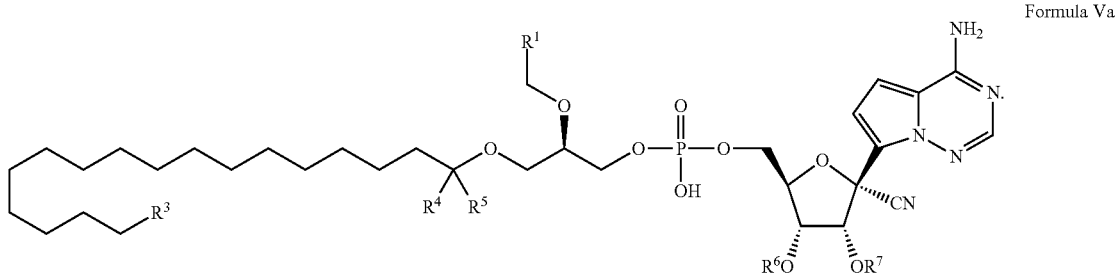

Formula Va

In some embodiments, the compound of Formula I, II, III, IV or V has a Formula Vb:

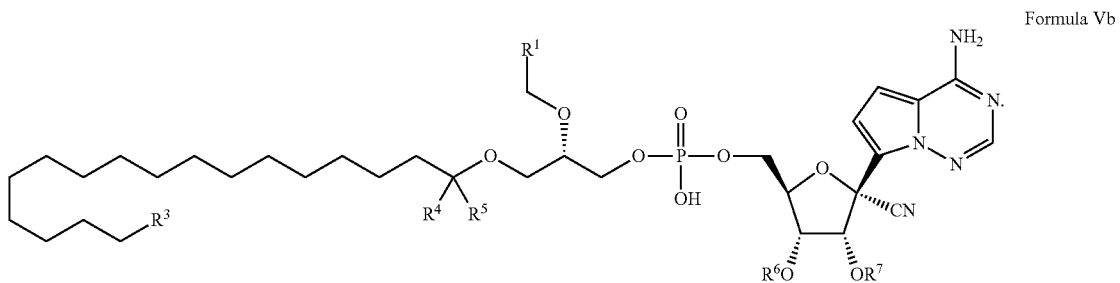

Formula Vb

In some embodiments of the compounds of Formula I, II, III, IV, V, Va, or Vb, $R^3$ is H, $C_1$-$C_3$ alkyl, $C_1$-$C_3$ haloalkyl, or $C_3$-$C_6$ cycloalkyl. In some embodiments, $R^3$ is H, $C_1$-$C_3$ alkyl or $C_3$-$C_6$ cycloalkyl. In some embodiments, $R^3$ is H, methyl, ethyl, propyl or cyclopropyl. In some embodiments, $R^3$ is H, methyl, ethyl, isopropyl or cyclopropyl. In some embodiments, $R^3$ is H. In some embodiments, $R^3$ is methyl. In some embodiments, $R^3$ is ethyl. In some embodiments, $R^3$ is cyclopropyl.

In some embodiments of the compounds of Formula V, Va or Vb, $R^4$ is H, $C_1$-$C_3$ alkyl, halo, $C_1$-$C_3$ haloalkyl, or $C_3$-$C_6$ cycloalkyl. In some embodiments, $R^4$ is H, $C_1$-$C_3$ alkyl, halo, or $C_1$-$C_3$ haloalkyl. In some embodiments, $R^4$ is H, $C_1$-$C_3$ alkyl, or halo. In some embodiments, $R^4$ is H, or $C_1$-$C_3$ alkyl. In some embodiments, $R^4$ is H, methyl or ethyl.

In some embodiments, $R^4$ is H. In some embodiments, $R^4$ is methyl. In some embodiments, $R^4$ is ethyl.

In some embodiments of the compounds of Formula V, Va, or Vb, $R^5$ is independently H, $C_1$-$C_3$ alkyl, halo, $C_1$-$C_3$ haloalkyl, or $C_3$-$C_6$ cycloalkyl. In some embodiments, $R^5$ is H, $C_1$-$C_3$ alkyl, halo, or $C_1$-$C_3$ haloalkyl. In some embodiments, $R^5$ is H, $C_1$-$C_3$ alkyl, or halo. In some embodiments, $R^5$ is H or $C_1$-$C_3$ alkyl. In some embodiments, $R^5$ is H, methyl or ethyl. In some embodiments, $R^5$ is independently H or methyl. In some embodiments, $R^5$ is independently H or ethyl. In some embodiments, $R^5$ is H. In some embodiments, $R^5$ is methyl. In some embodiments, $R^5$ is ethyl.

In some embodiments, the compound of Formula I, II, III, IV, V, Va or Vb is a compound of Formula VI:

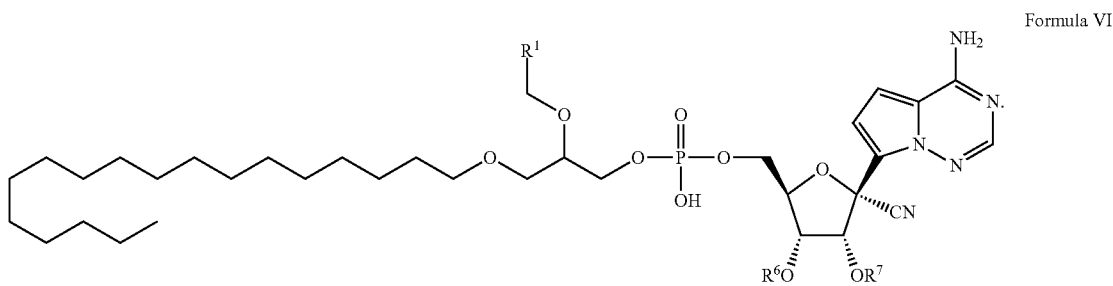

Formula VI

In some embodiments, the compound of Formula I, II, III, IV, V, Va or VI is a compound of Formula VIa:

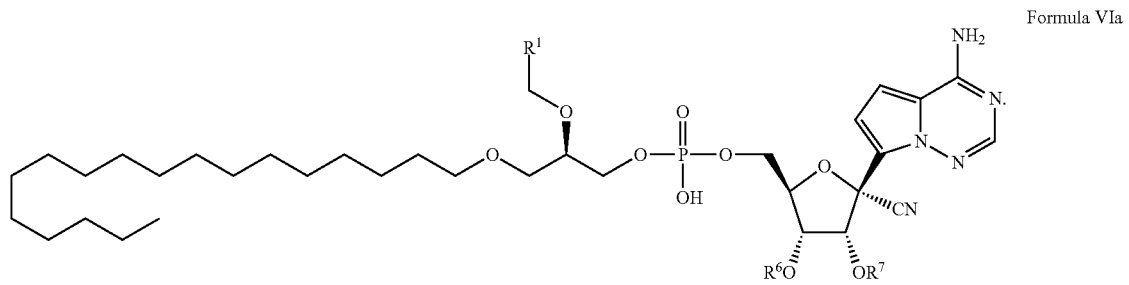

Formula VIa

In some embodiments, the compound of Formula I, II, III, IV, V, Vb or VI is a compound of Formula VIb:

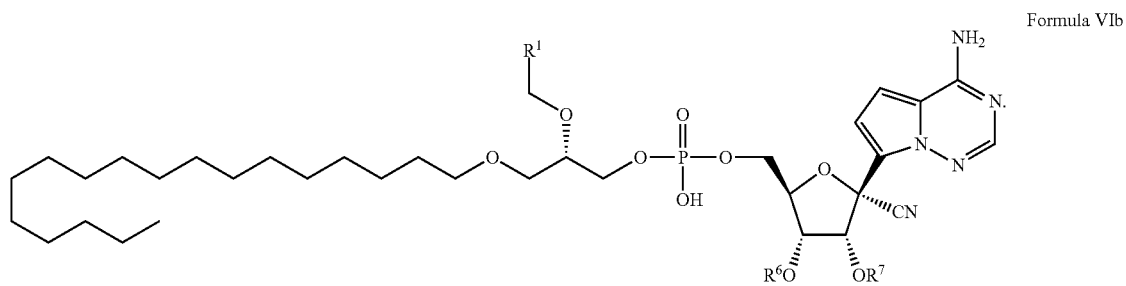

Formula VIb

In some embodiments of the compounds of Formula I, II, III, IV, V, Va, Vb, VI, VIa, and VIb, $R^1$ is $C_1$-$C_{20}$ alkyl, $C_3$-$C_{10}$ cycloalkyl, 4 to 6 membered heterocyclyl containing one, two or three heteroatoms selected from N, O, and S, $C_6$-$C_{10}$ aryl, or 5-10 membered heteroaryl containing one, two or three heteroatoms selected from N, S, and O; wherein the $R^1$ group is optionally substituted with one or two $R^{1A}$ groups. In some embodiments, $R^1$ is H, $C_1$-$C_6$ alkyl, $C_3$-$C_{10}$ cycloalkyl, 4 to 6 membered heterocyclyl containing one, two or three heteroatoms selected from N, O, and S, $C_6$-$C_{10}$ aryl, or 5-10 membered heteroaryl containing one, two or three heteroatoms selected from N, S, and O; wherein when $R^1$ is not H, the $R^1$ group is optionally substituted with one or two $R^{1A}$ groups. In some embodiments, $R^1$ is $C_1$-$C_{20}$ alkyl, $C_3$-$C_{10}$ cycloalkyl, or 5-6 membered heterocyclyl containing one, two or three heteroatoms selected from N, S, and O; wherein the $R^1$ group is optionally substituted with one or two RA groups. In some embodiments, $R^1$ is $C_1$-$C_6$ alkyl, $C_3$-$C_{10}$ cycloalkyl, or 5-6 membered heterocyclyl containing one, two or three heteroatoms selected from N, S, and O; wherein the $R^1$ group is optionally substituted with one or two $R^{1A}$ groups. In some embodiments, $R^1$ is $C_1$-$C_{20}$ alkyl, $C_3$-$C_{10}$ cycloalkyl, $C_6$-$C_{10}$ aryl, or 5-10 membered heteroaryl containing one, two or three heteroatoms selected from N, S, and O; wherein the $R^1$ group is optionally substituted with one or two RA groups. In some embodiments, $R^1$ is $C_1$-$C_6$ alkyl, $C_3$-$C_{10}$ cycloalkyl, $C_6$-$C_{10}$ aryl, or 5-10 membered heteroaryl containing one, two or three heteroatoms selected from N, S, and O; wherein the $R^1$ group is optionally substituted with one or two $R^{1A}$ groups. In some embodiments, $R^1$ is $C_1$-$C_{20}$ alkyl, $C_3$-$C_{10}$ cycloalkyl, or $C_6$-$C_{10}$ aryl; wherein the $R^1$ group is optionally substituted with one or two $R^{1A}$ groups. In some embodiments, $R^1$ is $C_1$-$C_6$ alkyl, $C_3$-$C_{10}$ cycloalkyl, or $C_6$-$C_{10}$ aryl; wherein the $R^1$ group is optionally substituted with one or two $R^{1A}$ groups. In some embodiments, $R^1$ is $C_1$-$C_{20}$ alkyl or $C_6$-$C_{10}$ aryl; wherein the $R^1$ group is optionally substituted with one or two $R^{1A}$ groups. In some embodiments, $R^1$ is $C_1$-$C_6$ alkyl or $C_6$-$C_{10}$ aryl; wherein the $R^1$ group is optionally substituted with one or two $R^{1A}$ groups. In some embodiments, $R^1$ is $C_1$-$C_{20}$ alkyl optionally substituted with one or two $R^{1A}$ groups. In some embodiments, $R^1$ is $C_1$-$C_6$ alkyl optionally substituted with one or two $R^{1A}$ groups.

In some embodiments of the compounds of Formula I, II, III, IV, V, Va, Vb, VI, VIa, and VIb, $R^1$ is $C_6$-$C_{10}$ aryl optionally substituted with one or two $R^{1A}$ groups. In some embodiments, $R^1$ is phenyl, napthyl, thiophenyl, cyclohexyl, methyl, ethyl, or propyl.

In some embodiments of the compounds of Formula I, II, III, IV, V, Va, Vb, VI, VIa, and VIb, $R^1$ is unsubstituted. In some embodiments, $R^1$ is substituted with one $R^{1A}$ group. In some embodiments, $R^1$ is substituted with two $R^{1A}$ groups. In some embodiments, each $R^{1A}$ is independently $C_1$-$C_3$ alkyl, phenyl, halo, $C_1$-$C_3$ alkoxy, cyano, or $C_1$-$C_3$haloalkyl. In some embodiments, $R^{1A}$ is independently methyl, phenyl, chloro, fluoro, methoxy, cyano, or $CF_3$. In some embodiments, two $R^{1A}$ on same or adjacent carbons are joined together to from a 3 to 6 membered cycloalkyl or 4 to 6 membered heterocyclyl ring containing one, two or three heteroatoms selected from N, S, and O. In some embodiments, two $R^{1A}$ on same or adjacent carbons are joined together to from a 3 to 6 membered cycloalkyl. In some embodiments, two $R^{1A}$ on same or adjacent carbons are joined together to from a 5 membered cycloalkyl. In some embodiments, two $R^{1A}$ on same or adjacent carbons are joined together to from a 4 to 6 membered heterocyclyl ring containing one, two or three heteroatoms selected from N, S, and O.

In some embodiments of the compounds of Formula I, II, III, IV, V, Va, Vb, VI, VIa, and VIb, $R^1$ is substituted with one $R^{1A}$ group. In some embodiments, $R^1$ is substituted with two $R^{1A}$ groups. In some embodiments, each $R^{1A}$ is independently $C_1$-$C_3$ alkyl, phenyl, halo, $C_1$-$C_3$ alkoxy, cyano, or $C_1$-$C_3$ haloalkyl. In some embodiments, each $R^{1A}$ is independently methyl, phenyl, chloro, fluoro, methoxy, cyano, $CHF_2$, or $CF_3$. In some embodiments, each $R^{1A}$ is independently methyl, phenyl, chloro, fluoro, methoxy, cyano, or $CF_3$. In some embodiments, each $R^{1A}$ is independently methyl, phenyl, chloro, fluoro, methoxy, ethoxy, cyano, $CHF_2$, or $CF_3$. In some embodiments, each $R^{1A}$ is independently methyl, phenyl, chloro, fluoro, methoxy, ethoxy, cyano, or $CF_3$. In some embodiments, each $R^{1A}$ is independently chloro, fluoro, or cyano. In some embodiments, at least one $R^{1A}$ is cyano. In some embodiments, at least one $R^{1A}$ is cyano, and the other $R^{1A}$, if present, is a cyano or halo.

In some embodiments of the compounds of Formula I, II, III, IV, V, Va, Vb, VI, VIa, and VIb, $R^1$ is $C_3$-$C_{10}$ cycloalkyl, 4 to 6 membered heterocyclyl containing one, two or three heteroatoms selected from N, O, and S, $C_6$-$C_{10}$ aryl, or 5-10 membered heteroaryl containing one, two or three heteroatoms selected from N, S, and O; wherein the $R^1$ group is substituted with one or two $R^{1A}$ groups. In some embodiments, at least one $R^{1A}$ is cyano. In some embodiments, at least one $R^{1A}$ is cyano, and the other $R^{1A}$, if present, is selected from the group consisting of $C_1$-$C_3$ alkyl, phenyl, halo, $C_1$-$C_3$ alkoxy, cyano, or $C_1$-$C_3$ haloalkyl. In some embodiments, at least one $R^{1A}$ is cyano, and the other $R^{1A}$, if present, is cyano or halo.

In some embodiments of the compounds of Formula I, II, III, IV, V, Va, Vb, VI, VIa, and VIb, $R^1$ is $C_6$-$C_{10}$ aryl or 5-10 membered heteroaryl containing one, two or three heteroatoms selected from N, S, and O; wherein the $R^1$ group is substituted with one or two $R^{1A}$ groups. In some embodiments, at least one $R^{1A}$ is cyano. In some embodiments, at least one $R^{1A}$ is cyano, and the other $R^{1A}$, if present, is selected from the group consisting of $C_1$-$C_3$ alkyl, phenyl, halo, $C_1$-$C_3$ alkoxy, cyano, or $C_1$-$C_3$ haloalkyl. In some embodiments, at least one $R^{1A}$ is cyano, and the other $R^{1A}$, if present, is cyano or halo.

In some embodiments of the compounds of Formula I, II, III, IV, V, Va, Vb, VI, VIa, and VIb, $R^1$ is phenyl; wherein the $R^1$ group is substituted with one or two $R^{1A}$ groups. In some embodiments, at least one $R^{1A}$ is cyano. In some embodiments, at least one $R^{1A}$ is cyano, and the other $R^{1A}$, if present, is selected from the group consisting of $C_1$-$C_3$ alkyl, phenyl, halo, $C_1$-$C_3$ alkoxy, cyano, or $C_1$-$C_3$ haloalkyl. In some embodiments, at least one $R^{1A}$ is cyano, and the other $R^{1A}$, if present, is cyano or halo.

In some embodiments of the compounds of Formula I, II, III, IV, V, Va, Vb, VI, VIa, and VIb, $R^1$ is

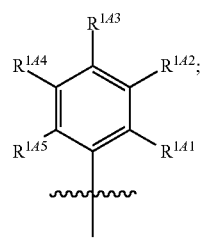

each $R^{1A1}$, $R^{1A2}$, $R^{1A3}$, $R^{1A4}$, and $R^{1A5}$ is independently H, $C_1$-$C_3$ alkyl, phenyl, halo, $C_1$-$C_3$ alkoxy, cyano or $C_1$-$C_3$ haloalkyl; wherein at least one of $R^{1A2}$, $R^{1A3}$, and $R^{1A4}$ is CN and at least three of $R^{1A1}$, $R^{1A2}$, $R^{1A3}$, $R^{1A4}$, and $R^{1A5}$ are H. In some embodiments, each $R^{1A1}$, $R^{1A2}$, $R^{1A3}$, $R^{1A4}$, and $R^{1A5}$ is independently H, halo or cyano; wherein at least one of $R^{1A2}$, $R^{1A3}$, and $R^{1A4}$ is CN; and at least three of $R^{1A1}$, $R^{1A2}$, $R^{1A3}$, $R^{1A4}$, and $R^{1A5}$ are H.

In some embodiments of the compound of Formula I, II, III, IV, V, Va, Vb, VI, VIa, and VIb, $R^1$ is selected from the group consisting of H,

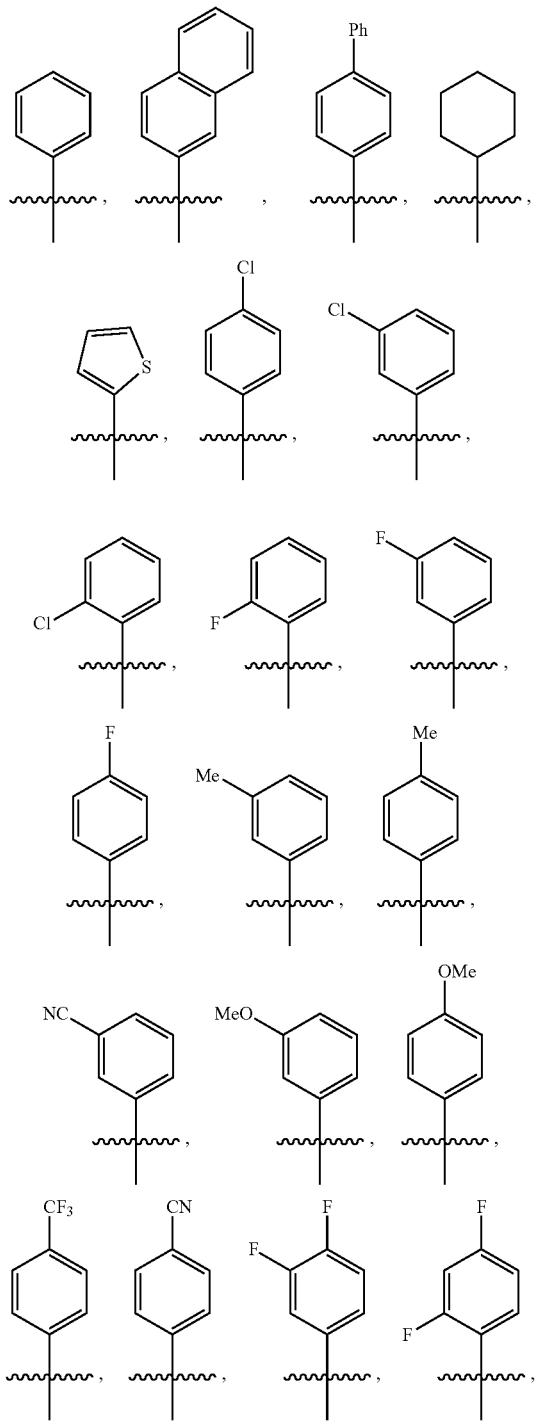

-continued
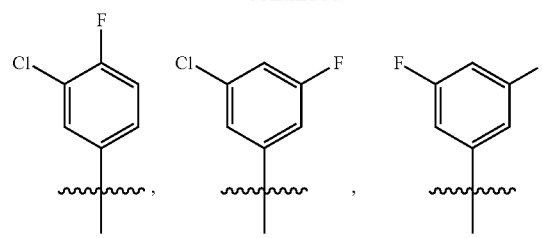
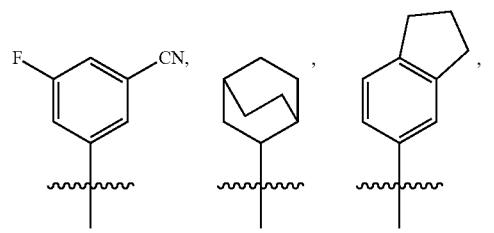
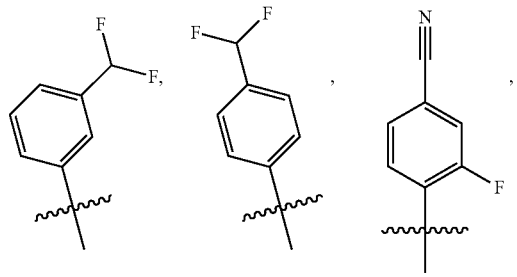
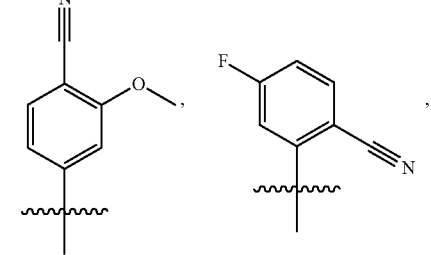
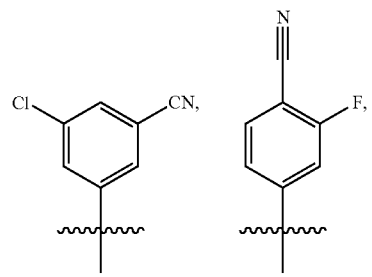
-continued
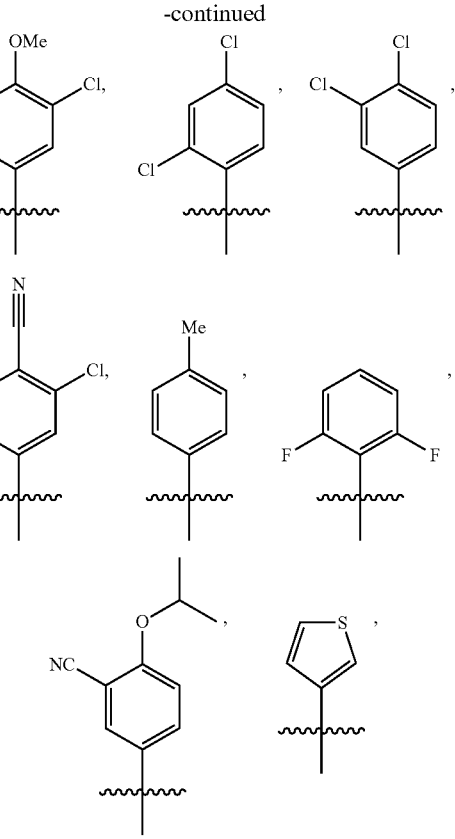
—CH$_3$, —CH(CH$_3$)$_2$, —C(CH$_3$)$_3$, —CH$_2$CH(CH$_3$)$_2$, —C(CH$_3$)$_2$CH$_2$CH$_3$, and —C$_{16}$H$_{33}$.
In some embodiments of the compound of Formula I, II, III, IV, V, Va, Vb, VI, VIa, and VIb, R$^1$ is selected from the group consisting of H,
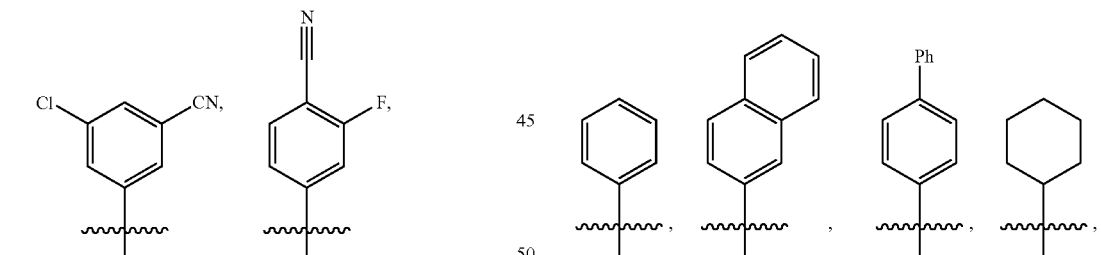
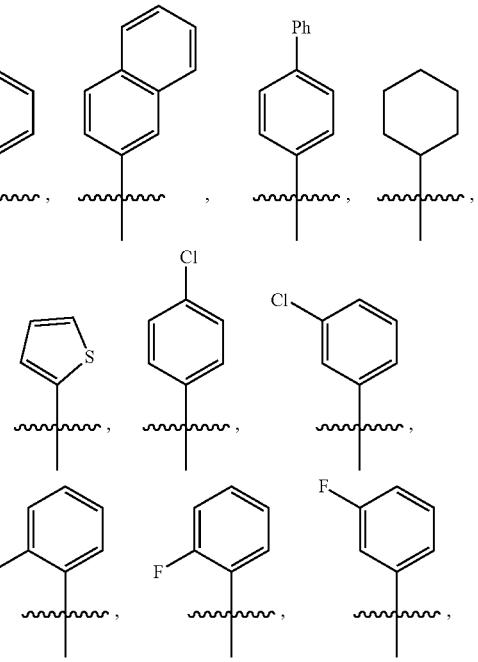

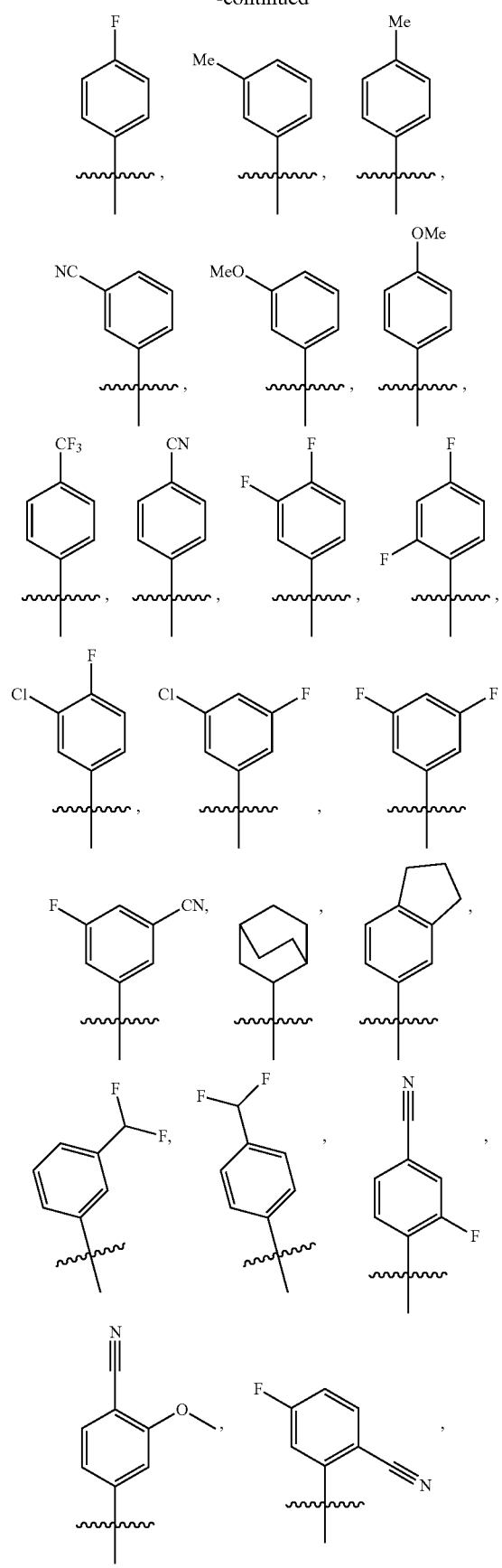
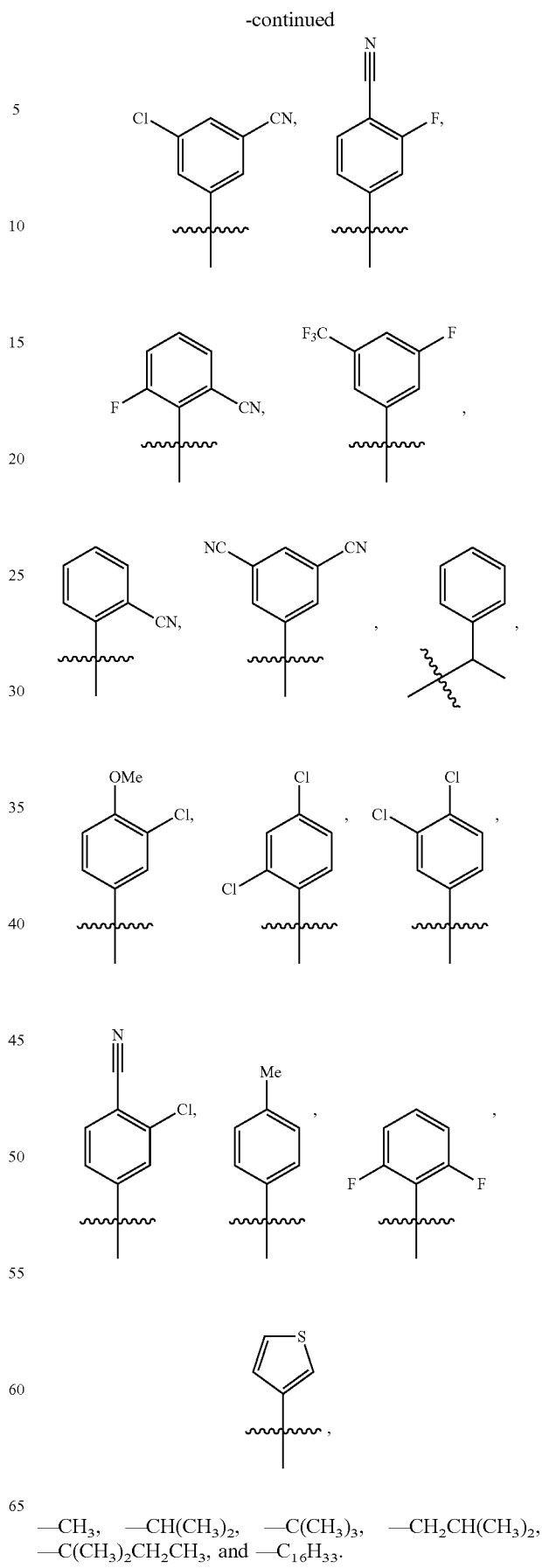
—CH$_3$, —CH(CH$_3$)$_2$, —C(CH$_3$)$_3$, —CH$_2$CH(CH$_3$)$_2$, —C(CH$_3$)$_2$CH$_2$CH$_3$, and —C$_{16}$H$_{33}$.

In some embodiments of the compound of Formula I, II, III, IV, V, Va, Vb, VI, VIa, and VIb, $R^1$ is selected from the group consisting of:

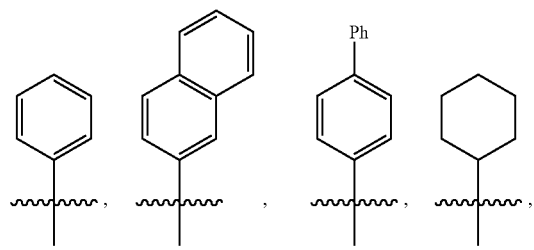

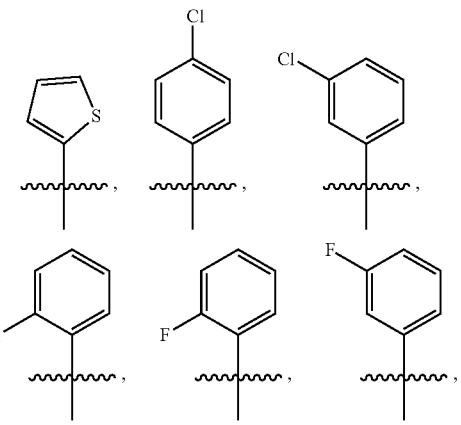

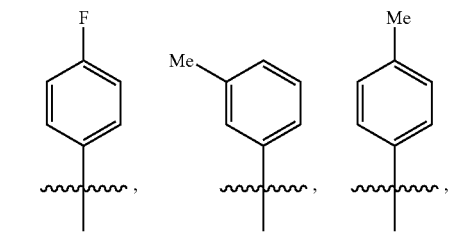

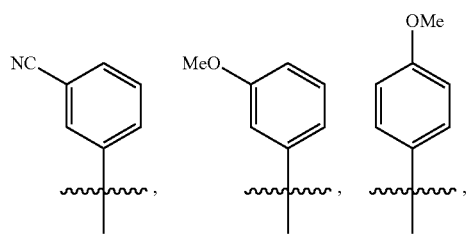

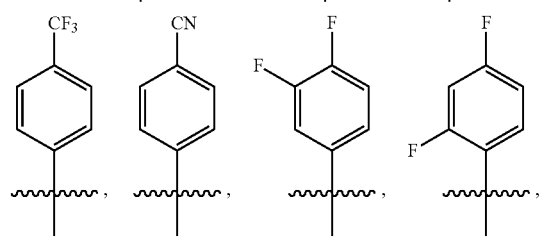

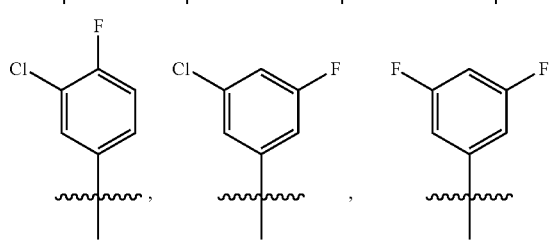

-continued

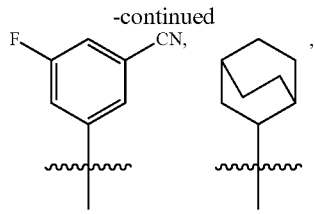

—$CH_3$, —$C(CH_3)_3$, and —$C(CH_3)_2CH_2CH_3$.

In some embodiments of the compound of Formula I, II, III, IV, V, Va, Vb, VI, VIa, and VIb, $R^1$ is selected from the group consisting of:

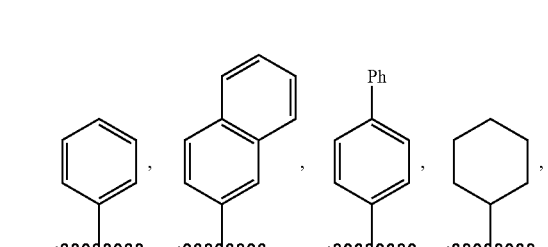

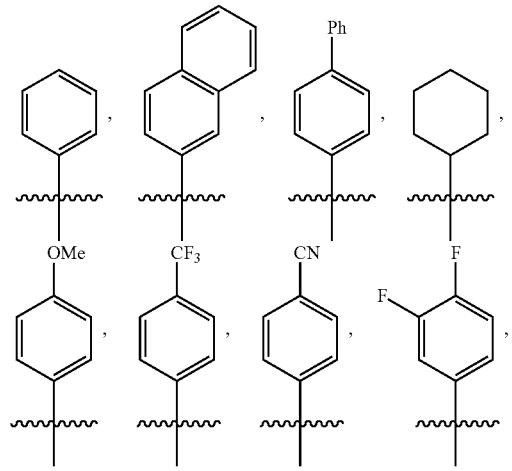

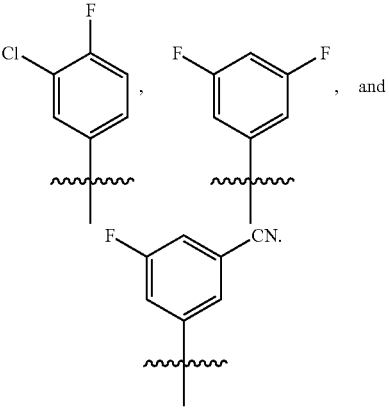

In some embodiments of the compound of Formula I, II, III, IV, V, Va, Vb, VI, VIa, and VIb, $R^1$ is selected from the group consisting of:

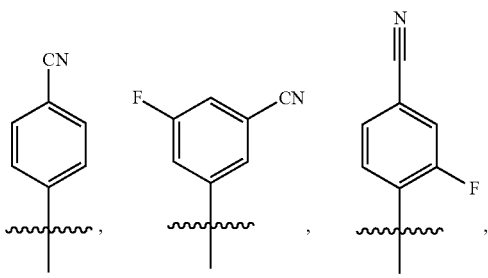

-continued
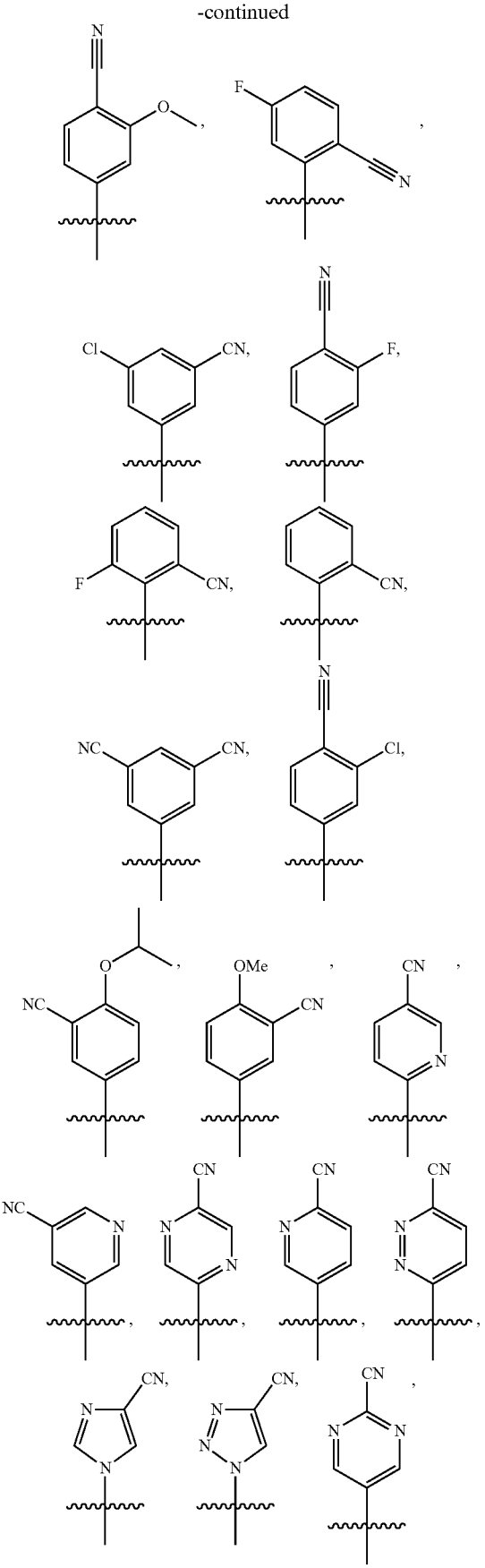
-continued
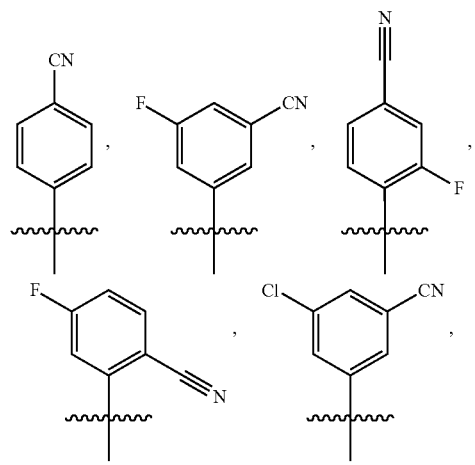
In some embodiments of the compound of Formula I, II, III, IV, V, Va, Vb, VI, VIa, and VIb, $R^1$ is selected from the group consisting of:

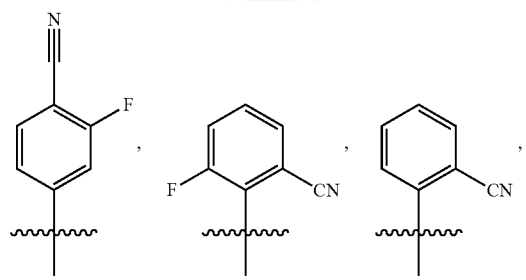
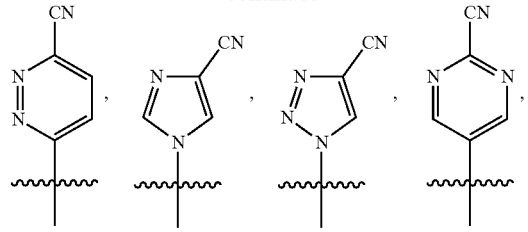
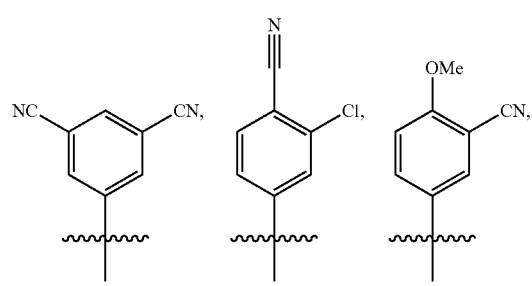
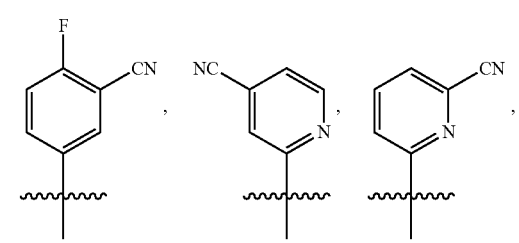
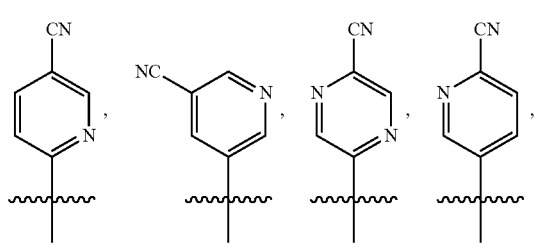
In some embodiments, the compound of Formula I, II, III, IV, V, Va or Vb is a compound of Formula VII:
Formula VII
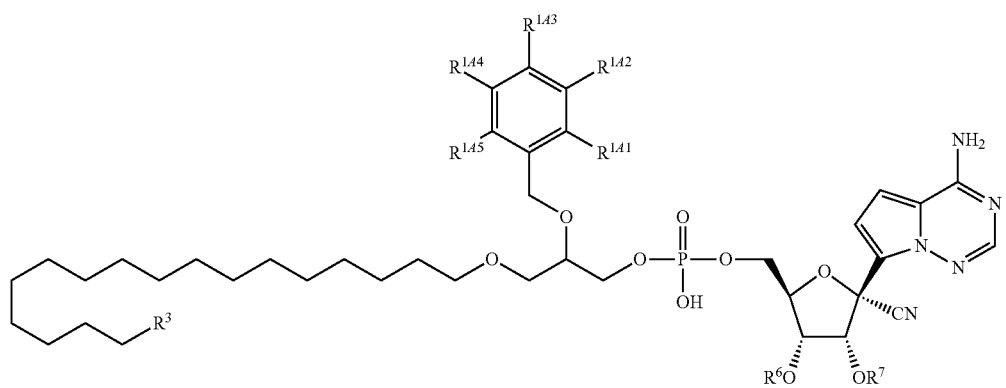

wherein each $R^{141}$, $R^{142}$, $R^{143}$, $R^{144}$, and $R^{145}$ is independently H, $C_1$-$C_3$ alkyl, phenyl, halo, $C_1$-$C_3$ alkoxy, cyano or $C_1$-$C_3$haloalkyl; wherein at least one of $R^{141}$, $R^{143}$, and $R^{144}$ is CN and at least three of $R^{141}$, $R^{142}$, $R^{143}$, $R^{144}$, and $R^{145}$ are H.

In some embodiments, the compound of Formula I, II, III, IV, V, Va or VII is a compound of Formula VIIa:

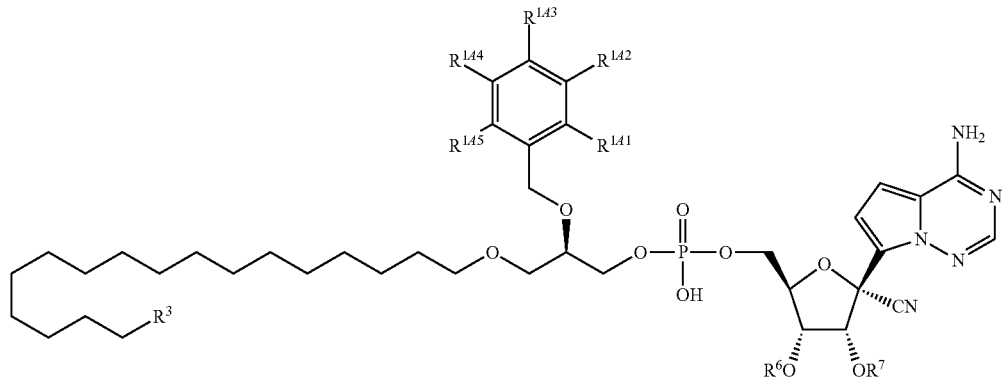

Formula VIIa wherein each $R^{141}$, $R^{142}$, $R^{143}$, $R^{144}$, and $R^{145}$ is independently H, $C_1$-$C_3$ alkyl, phenyl, halo, $C_1$-$C_3$ alkoxy, cyano or $C_1$-$C_3$haloalkyl; wherein at least one of $R^{142}$, $R^{143}$, and $R^{144}$ is CN and at least three of $R^{141}$, $R^{142}$, $R^{143}$, $R^{144}$, and $R^{145}$ are H.

In some embodiments, the compound of Formula I, II, III, IV, V, Vb or VII is a compound of Formula VIIb:

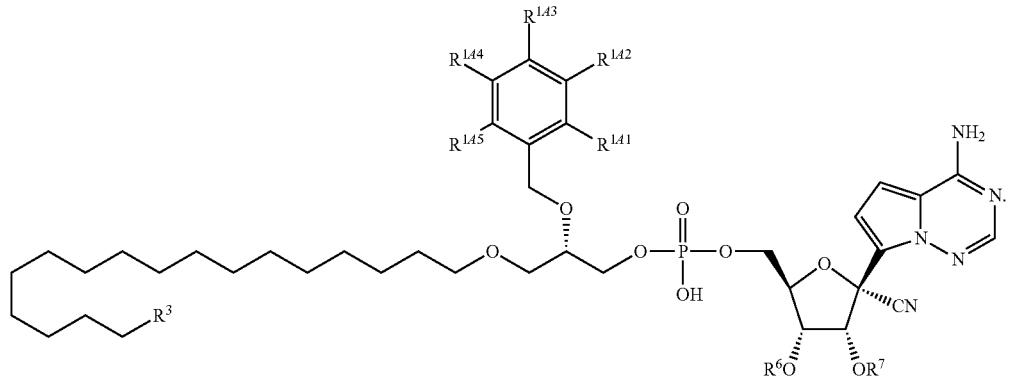

Formula VIIb wherein each $R^{141}$, $R^{142}$, $R^{143}$, $R^{144}$, and $R^{145}$ is independently H, $C_1$-$C_3$ alkyl, phenyl, halo, $C_1$-$C_3$ alkoxy, cyano or $C_1$-$C_3$haloalkyl; wherein at least one of $R^{142}$, $R^{143}$, and $R^{144}$ is CN and at least three of $R^{141}$, $R^{142}$, $R^{143}$, $R^{144}$, and $R^{145}$ are H.

In some embodiments of the compounds of Formula VII, VIIa, or VIIb, each $R^{141}$, $R^{142}$, $R^{143}$, $R^{144}$, and $R^{145}$ is independently H, halo or cyano; wherein at least one of $R^{142}$, $R^{143}$, and $R^{144}$ is CN and at least three of $R^{141}$, $R^{142}$, $R^{143}$, $R^{144}$, and $R^{145}$ are H.

In some embodiments of the compounds of Formula VII, VIIa, or VIIb, $R^3$ is H, $C_1$-$C_3$ alkyl, $C_1$-$C_3$ haloalkyl, or $C_3$-$C_6$ cycloalkyl. In some embodiments, $R^3$ is H, $C_1$-$C_3$ alkyl or $C_3$-$C_6$ cycloalkyl. In some embodiments, $R^3$ is H, methyl, ethyl, propyl or cyclopropyl. In some embodiments, $R^3$ is H, methyl, ethyl, isopropyl or cyclopropyl. In some embodiments, $R^3$ is H. In some embodiments, $R^3$ is methyl. In some embodiments, $R^3$ is ethyl. In some embodiments, $R^3$ is cyclopropyl.

In some embodiments of the compounds of Formula I, II, III, IV, V, Va, Vb, VI, VIa, VIb, VII, VIIa, or VIIb, $R^6$ and $R^7$ are both H. In some embodiments, each $R^6$ and $R^7$ is independently —C(O)$C_1$-$C_6$ alkyl. In some embodiments, each $R^6$ and $R^7$ is independently H or —C(O)$C_1$-$C_3$ alkyl. In some embodiments, each $R^6$ and $R^7$ is independently H or —C(O)CH(CH)$_2$. In some embodiments, $R^6$ is H and $R^7$ is —C(O)$C_1$-$C_6$ alkyl. In some embodiments, $R^6$ is H and $R^7$ is —C(O)$C_1$-$C_3$ alkyl. In some embodiments, $R^6$ is H and $R^7$ is —C(O)CH(CH)$_2$. In some embodiments, $R^7$ is H and $R^6$ is —C(O)$C_1$-$C_6$ alkyl. In some embodiments, $R^7$ is H and $R^6$ is —C(O)$C_1$-$C_3$ alkyl. In some embodiments, $R^7$ is H and $R^6$ is —C(O)CH(CH)$_2$.

In some embodiments, the compound of Formula I, II, III, IV, V, Va, Vb, VIa, or VIb is selected from the group consisting of:
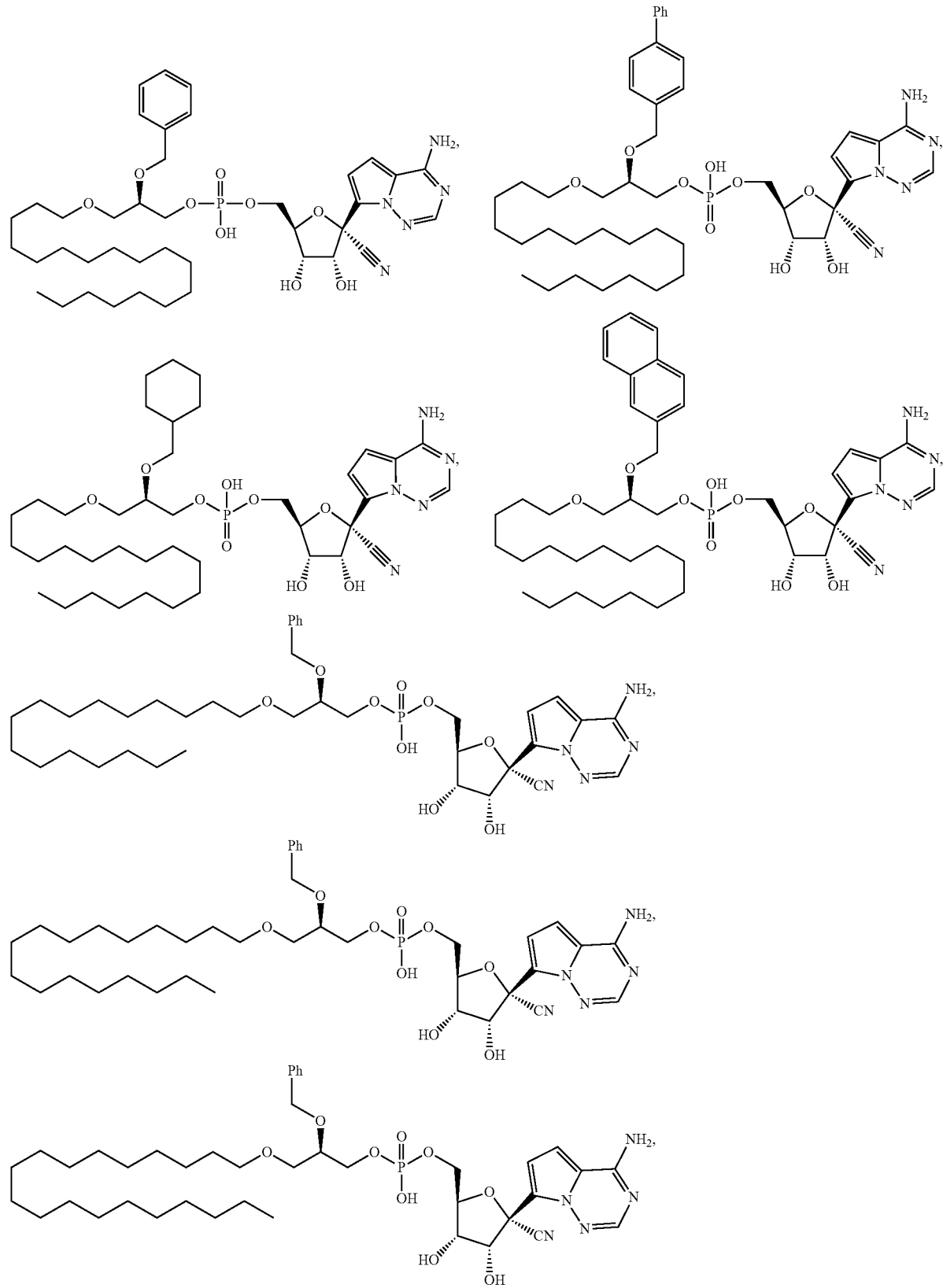

-continued
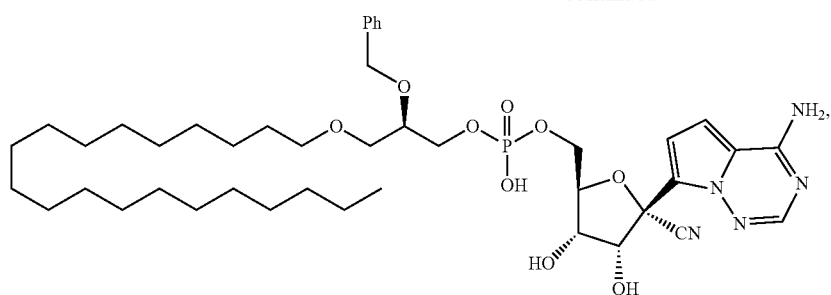
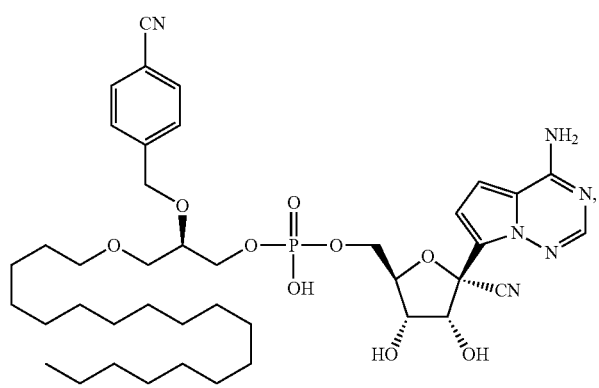
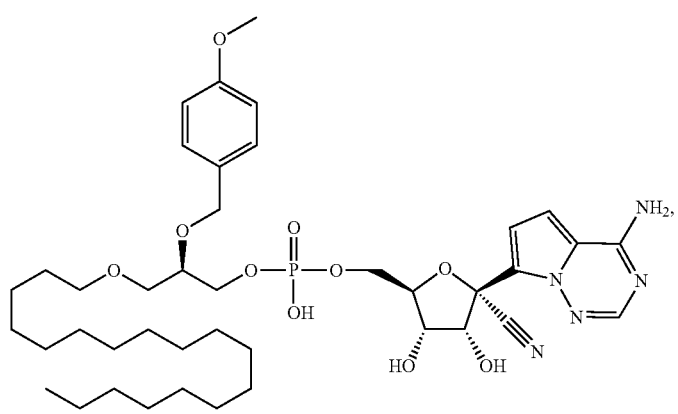
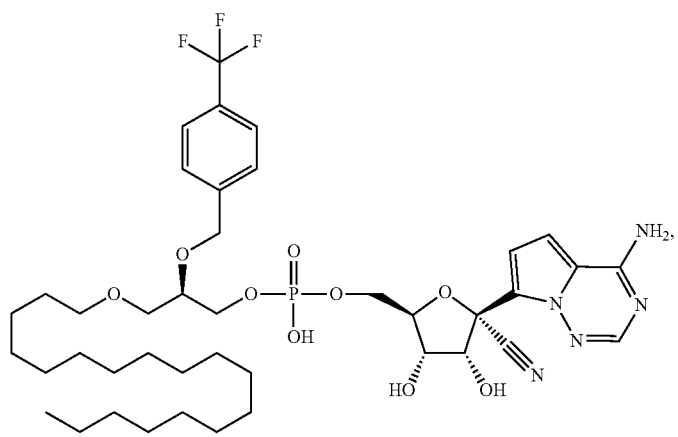

33
34
-continued
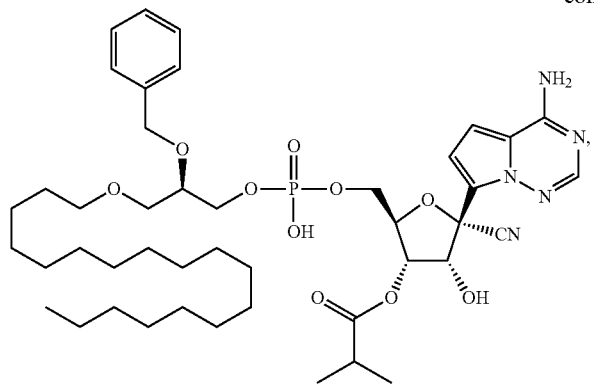
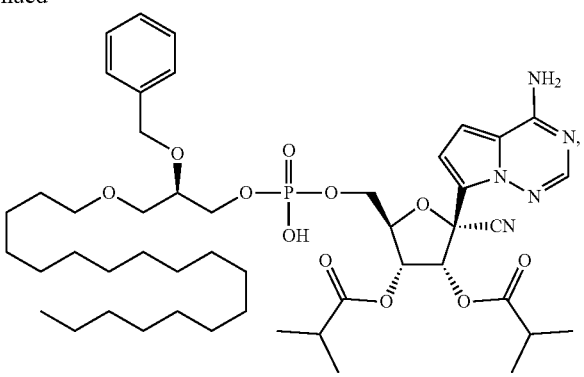
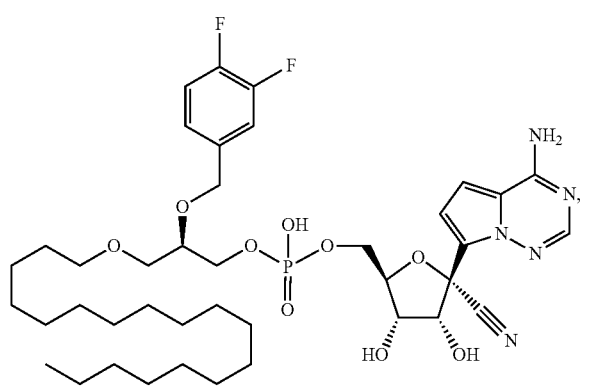
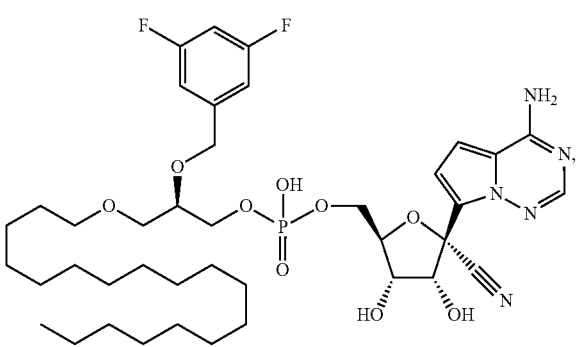
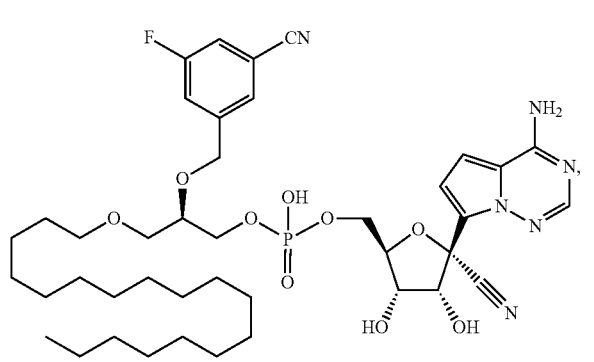
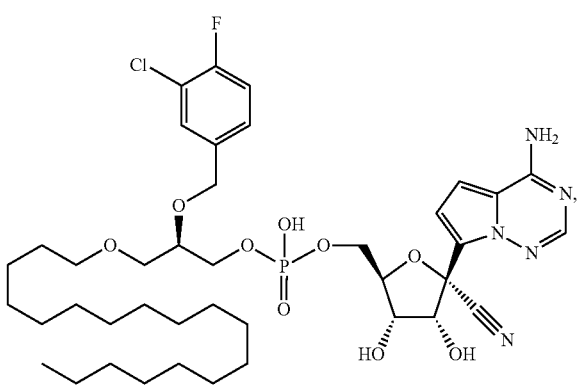
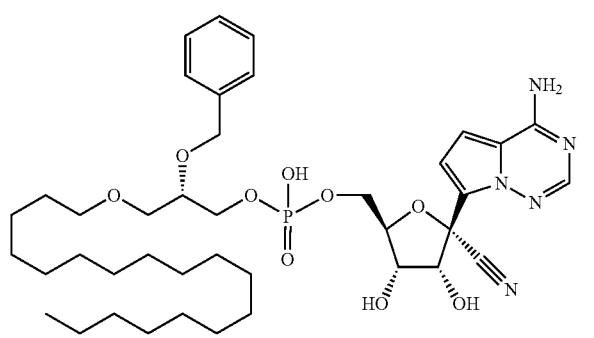
and a pharmaceutically acceptable salt thereof.

In some embodiments, the compound of Formula I, II, III, IV, V, Va, Vb, VIa, or VIb is selected from the group consisting of:
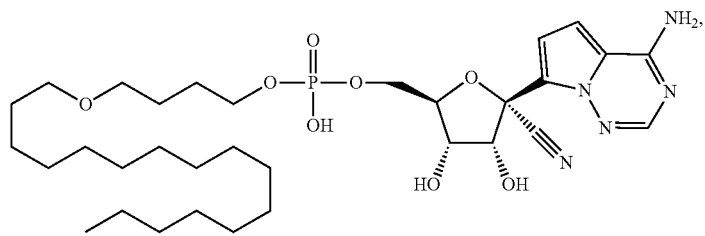
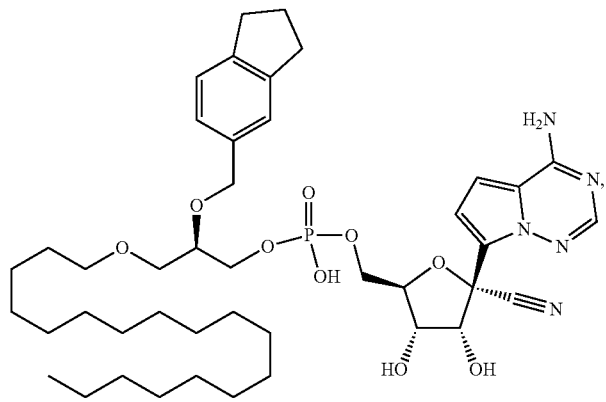
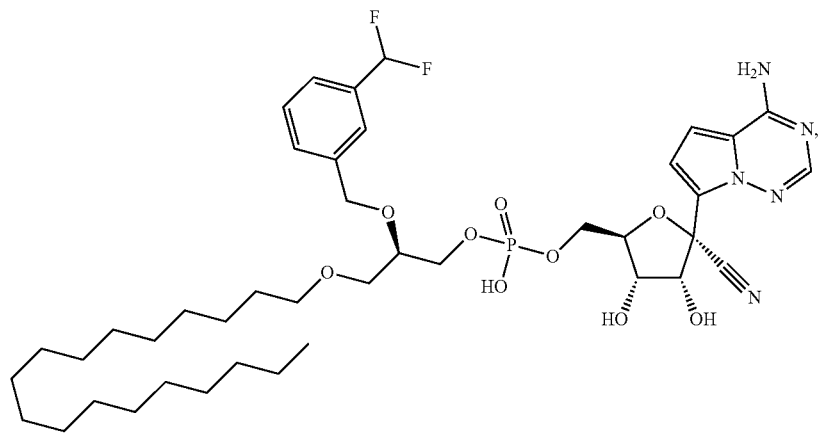
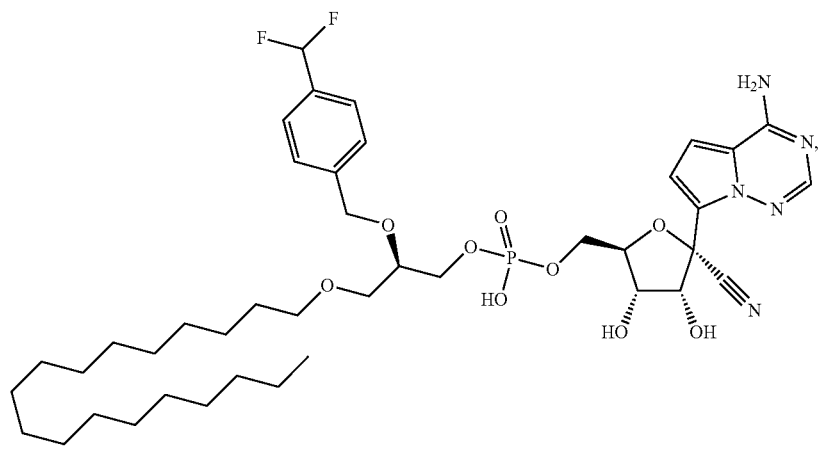

-continued
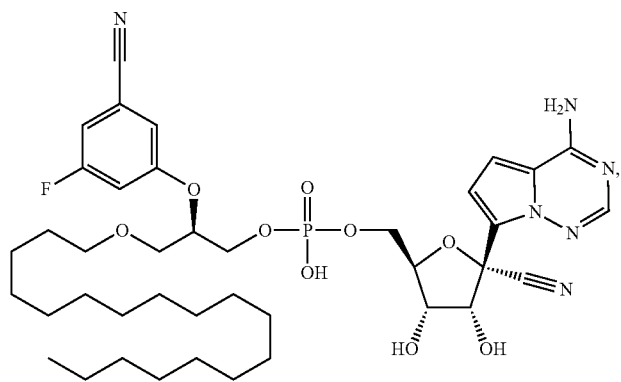
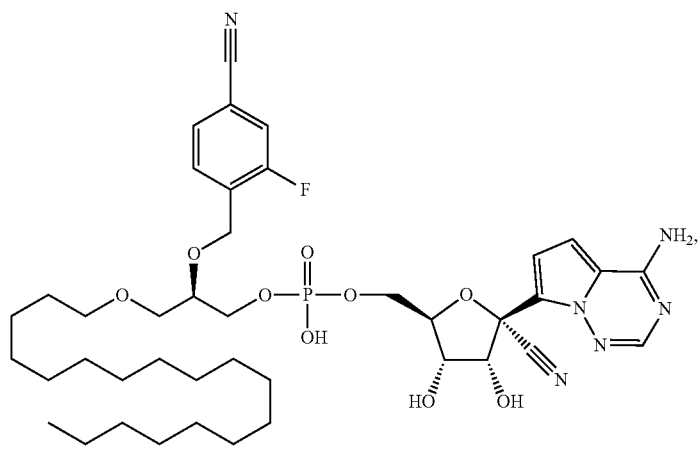
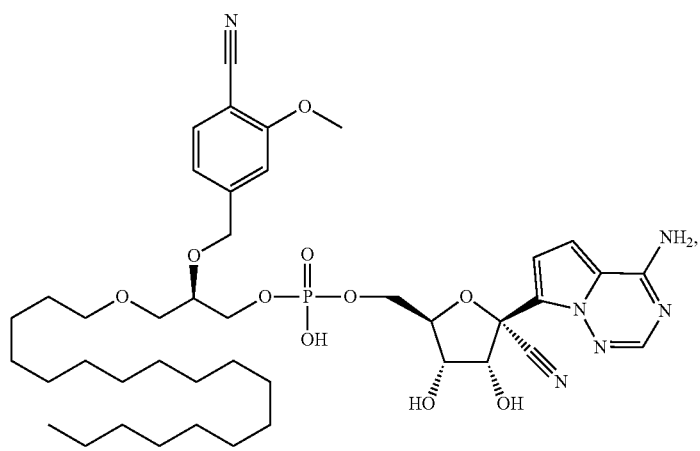
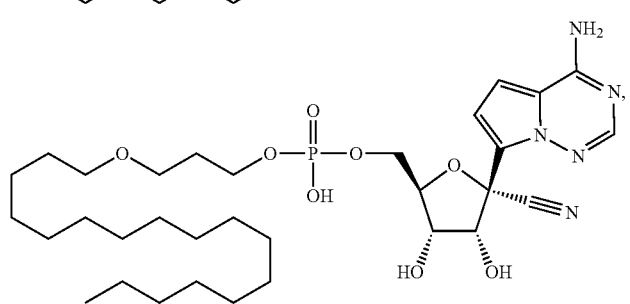

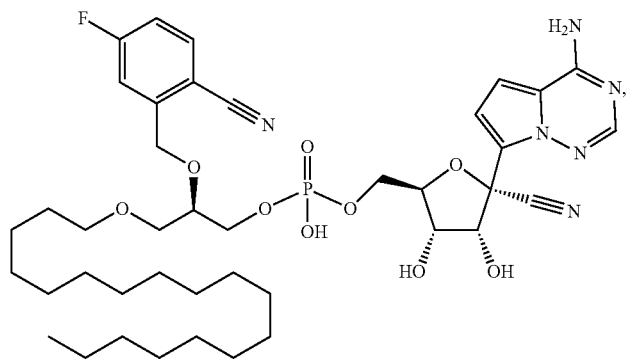
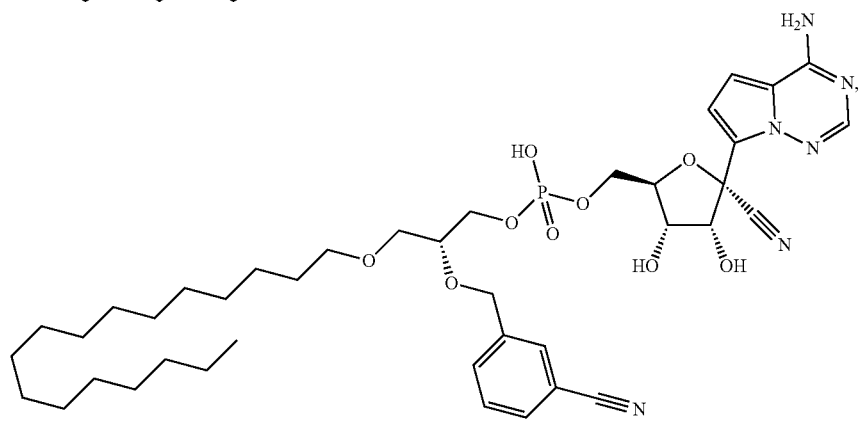
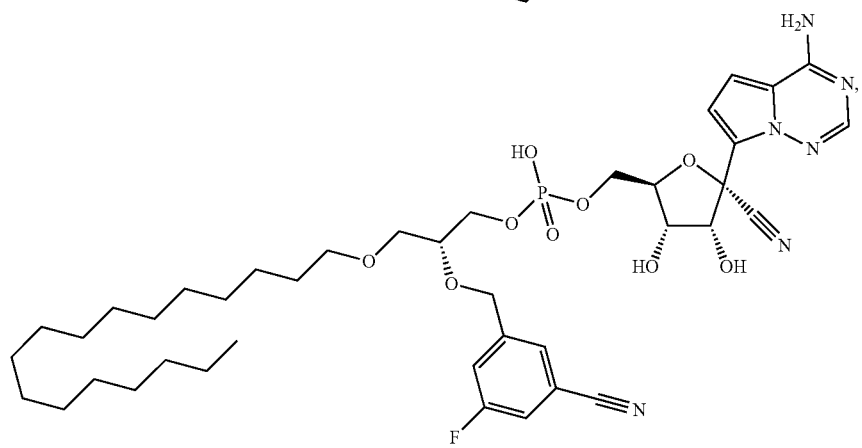
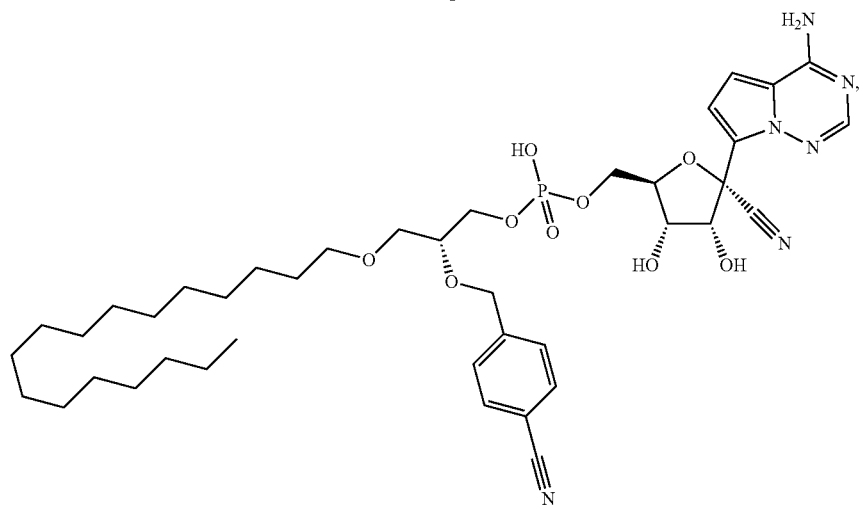

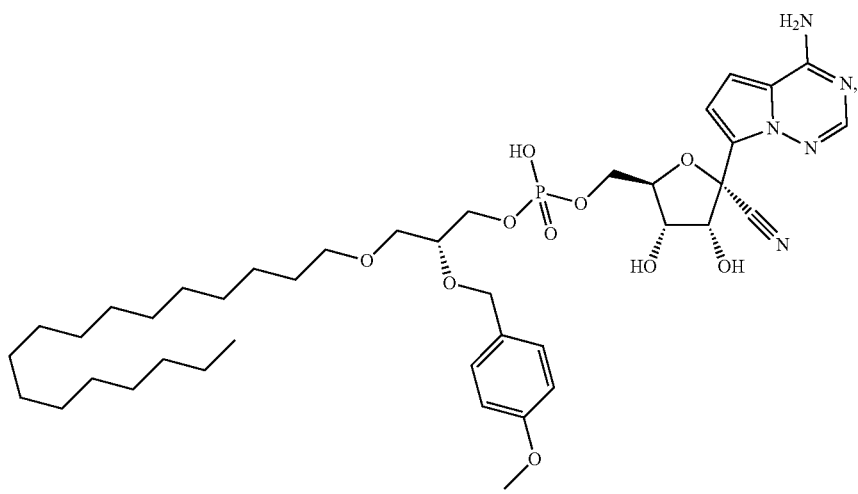
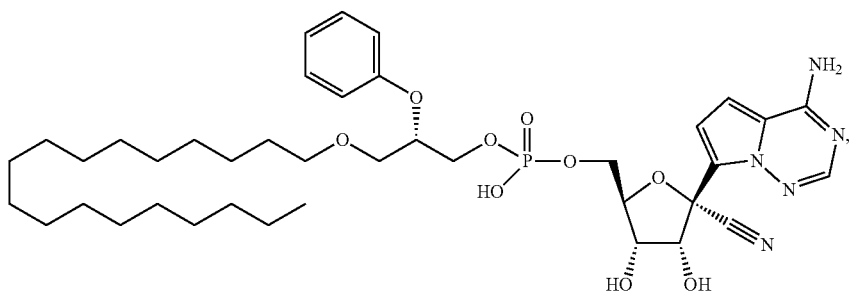
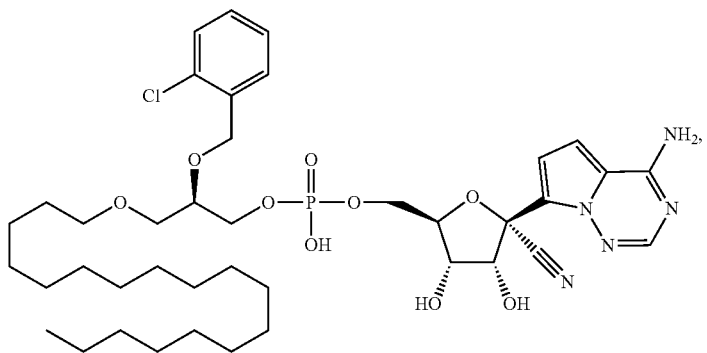
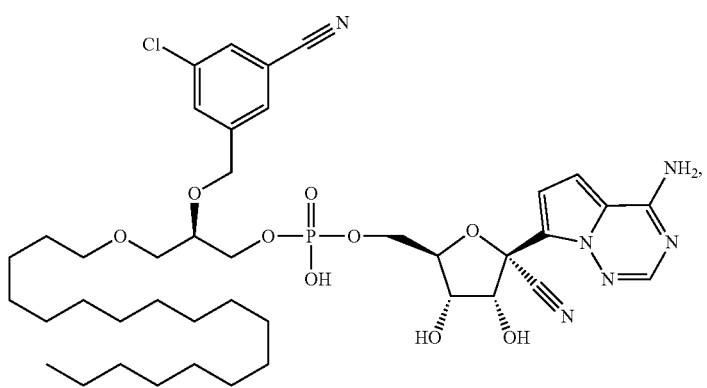

-continued
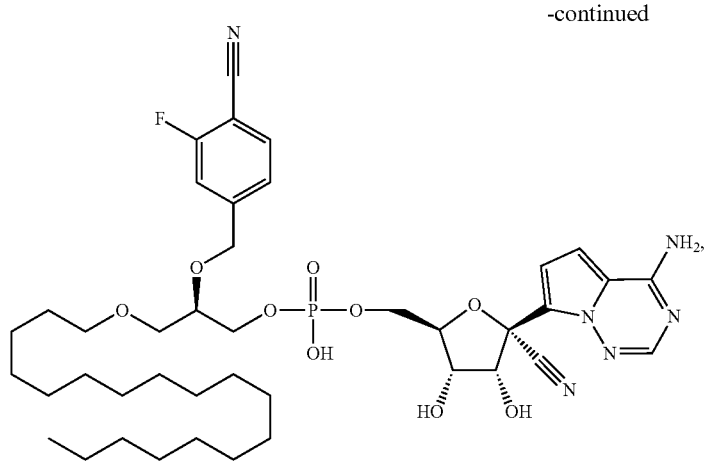
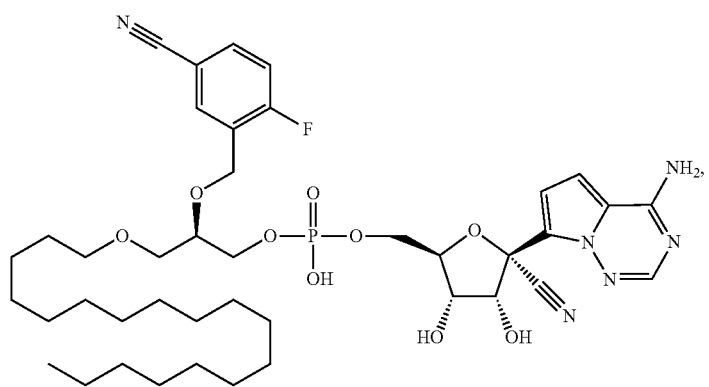
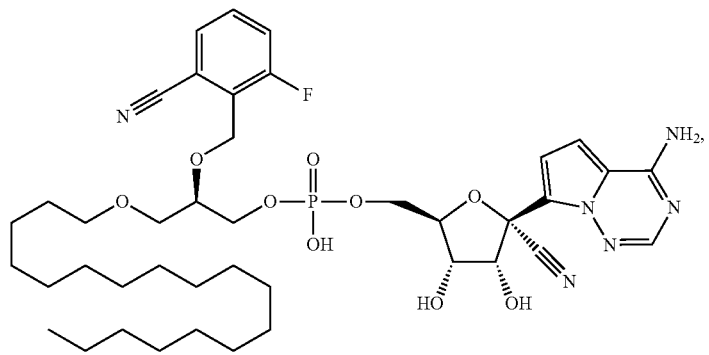
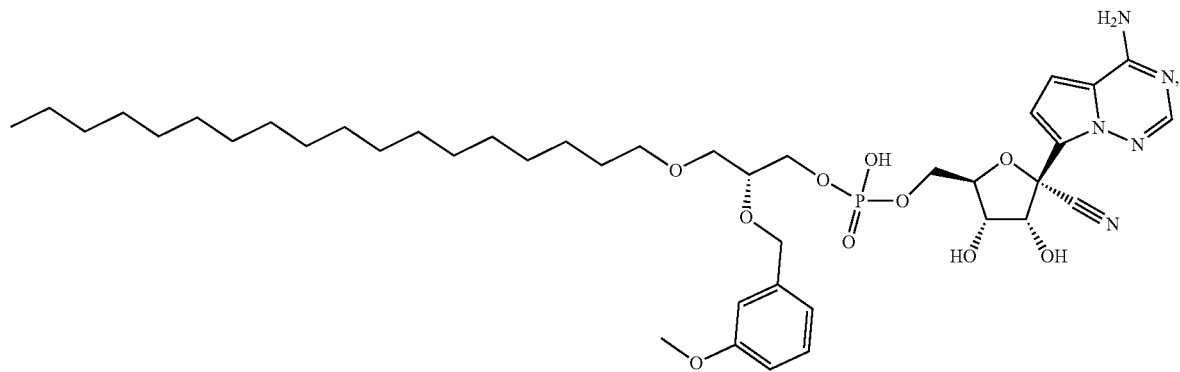

-continued
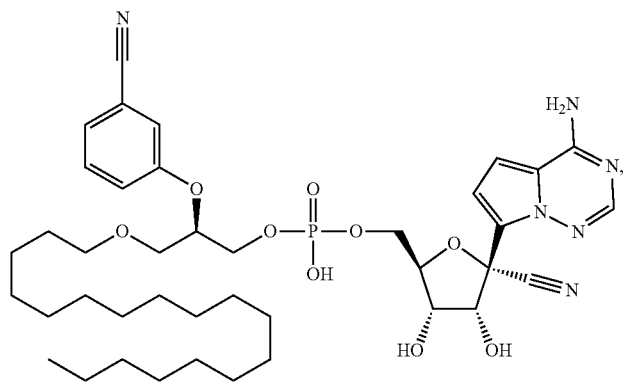
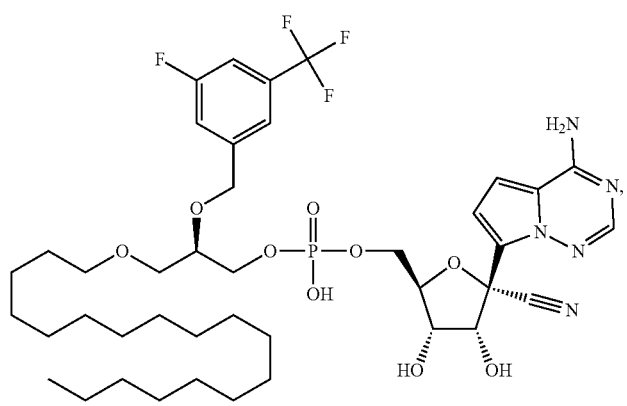
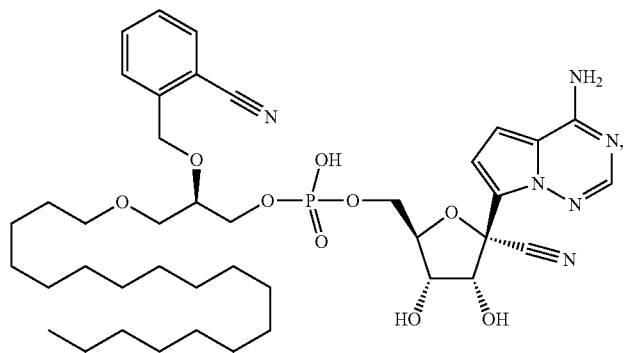
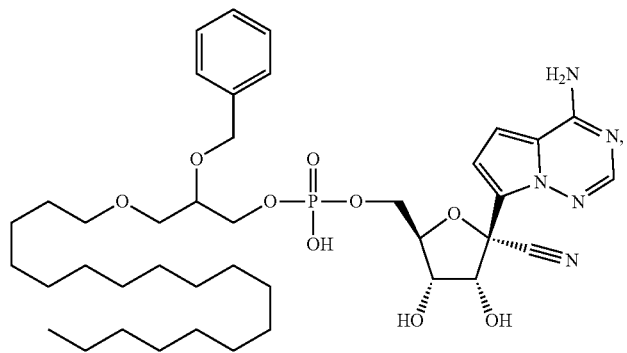

-continued
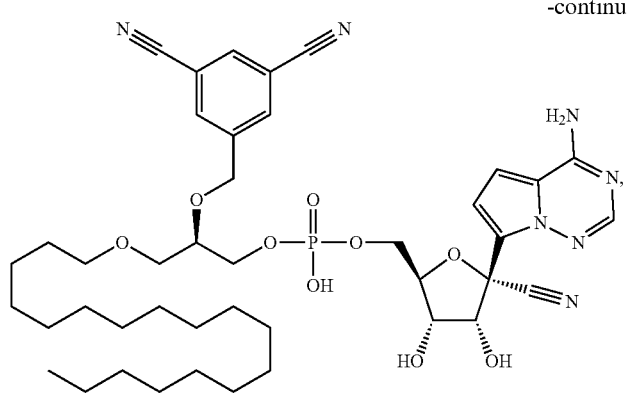
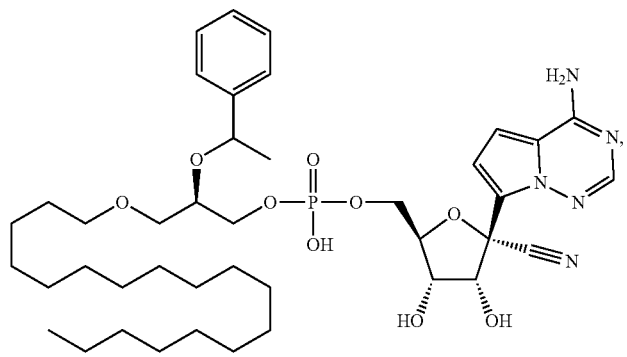
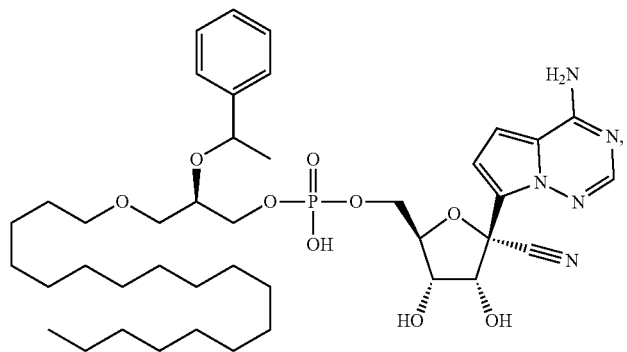
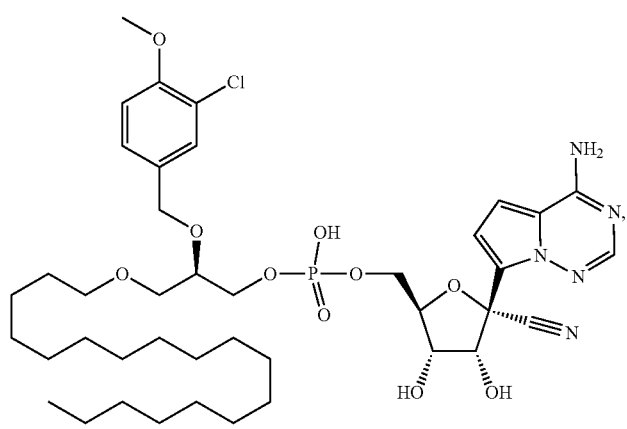

-continued
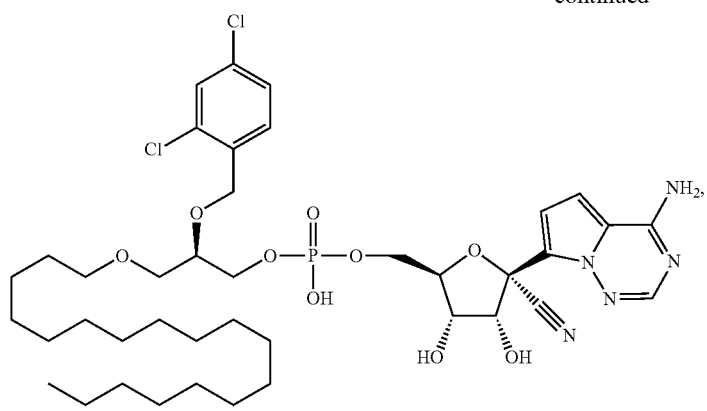
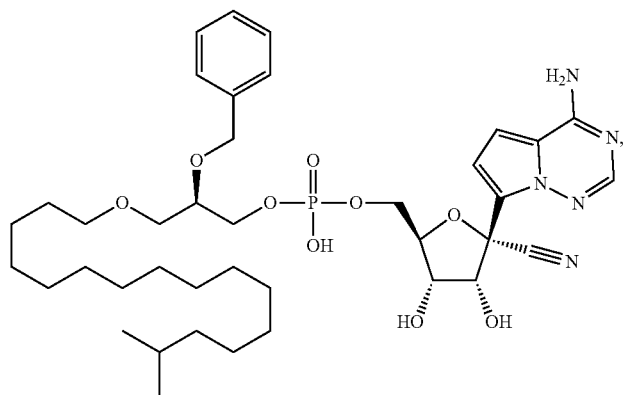
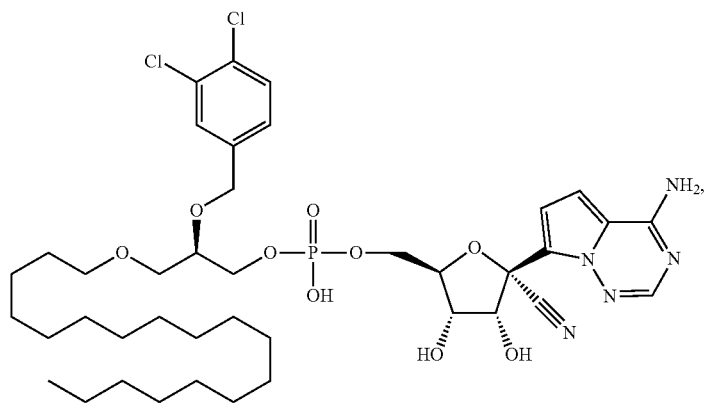
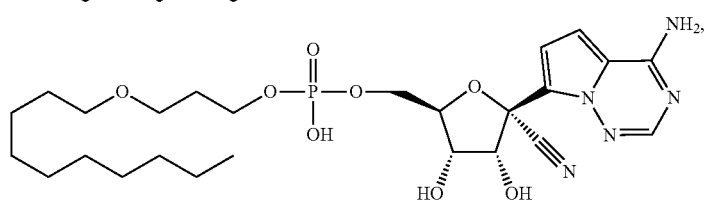
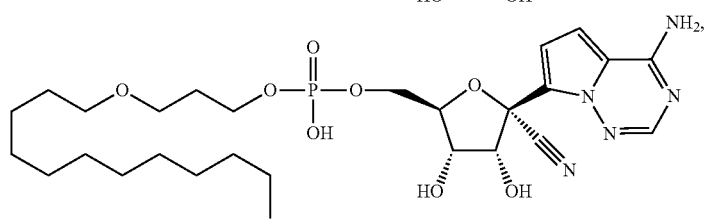

-continued
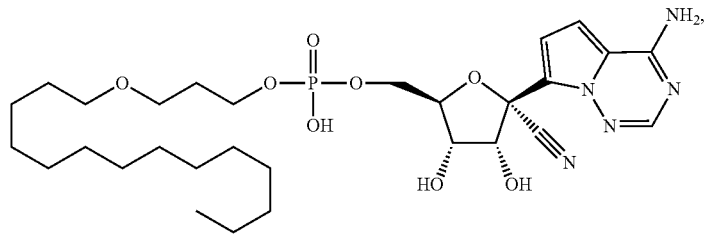
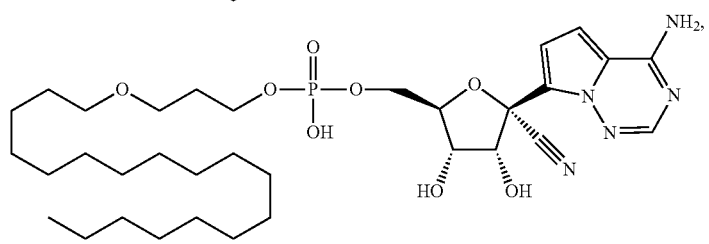
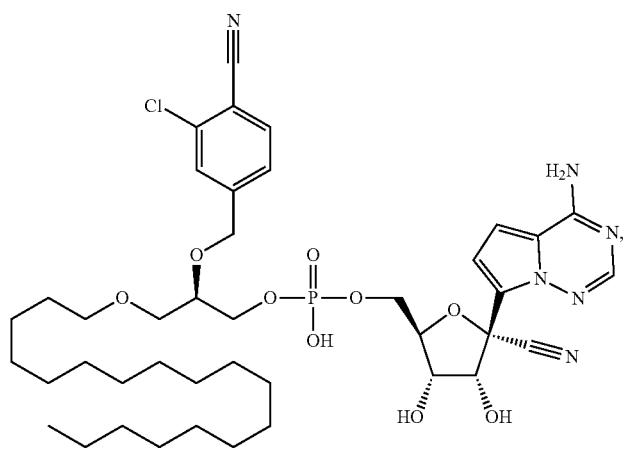
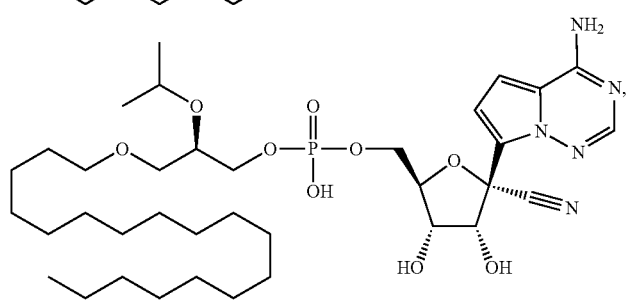
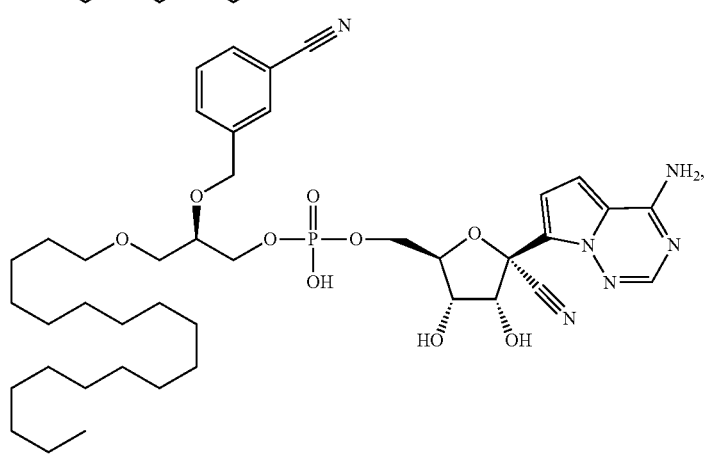

-continued
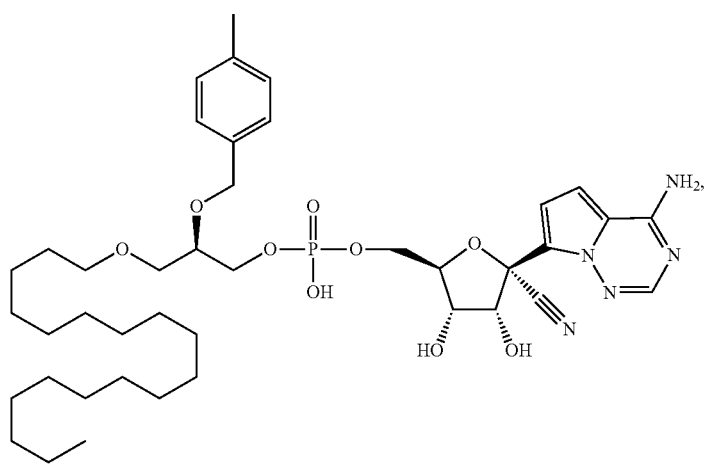
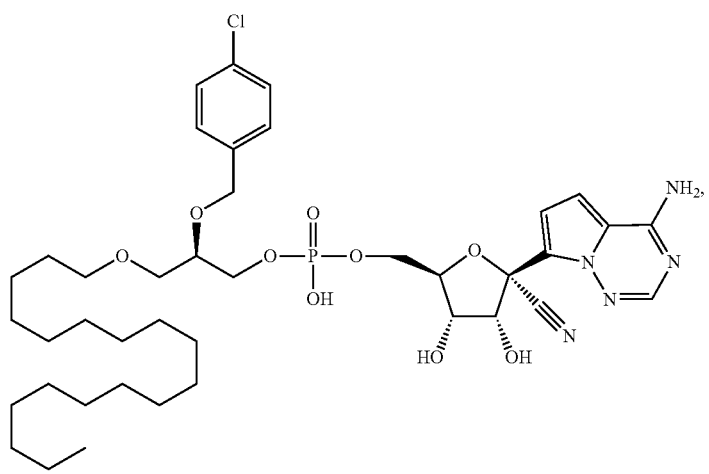
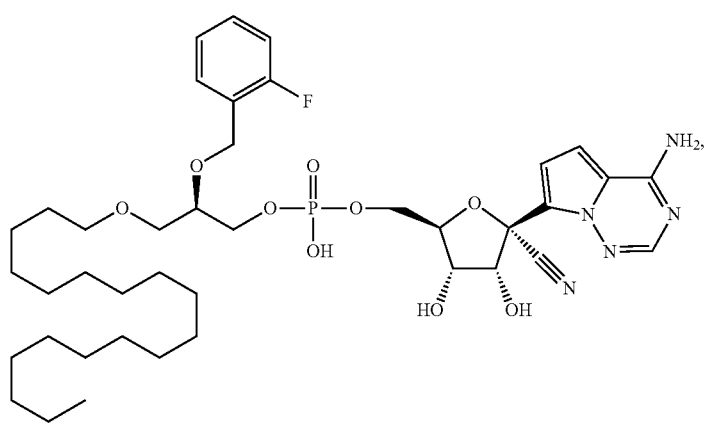

-continued
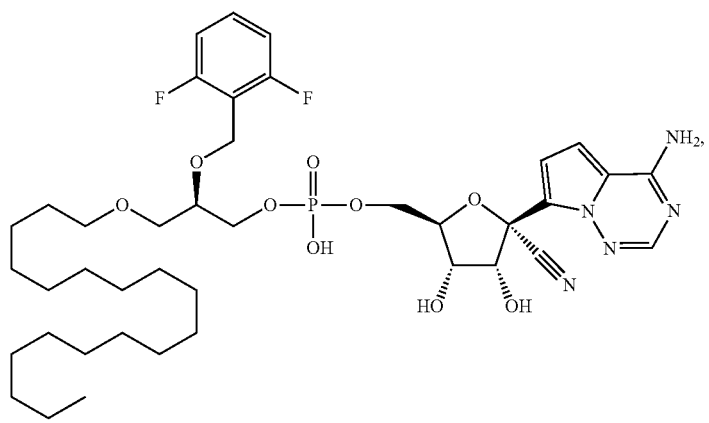
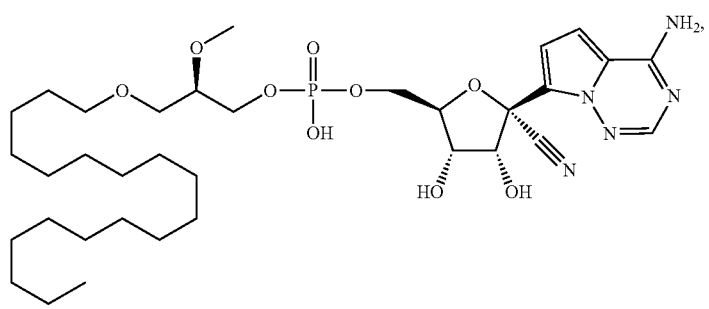
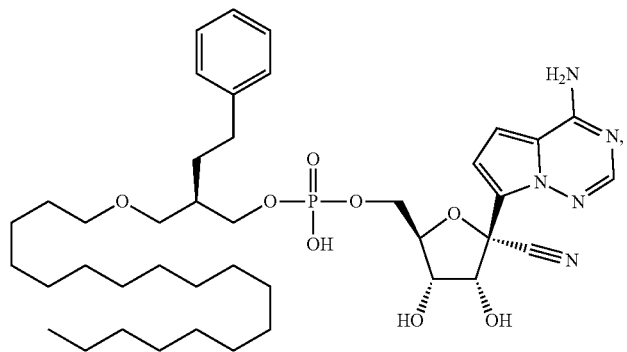
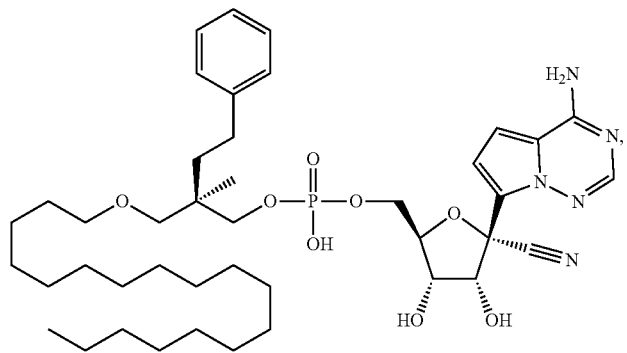

-continued
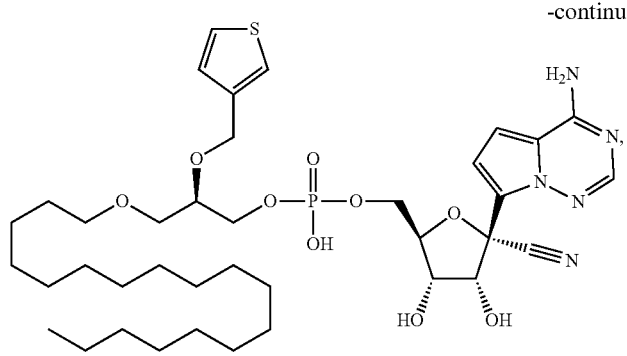
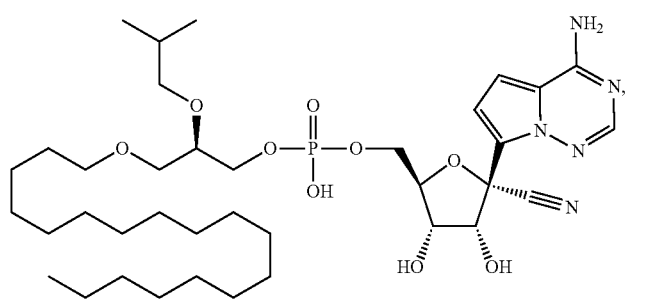
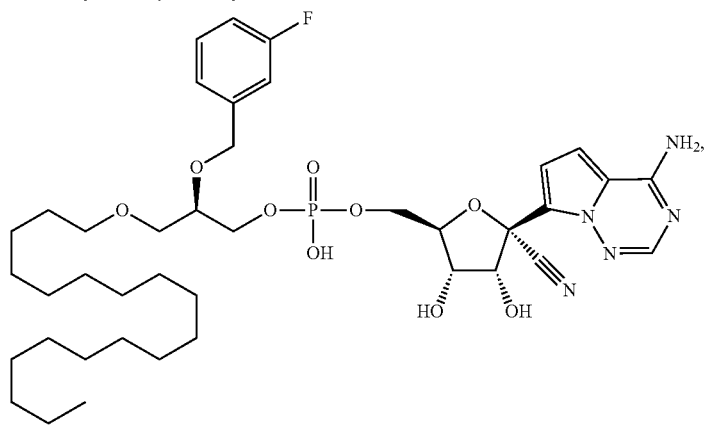
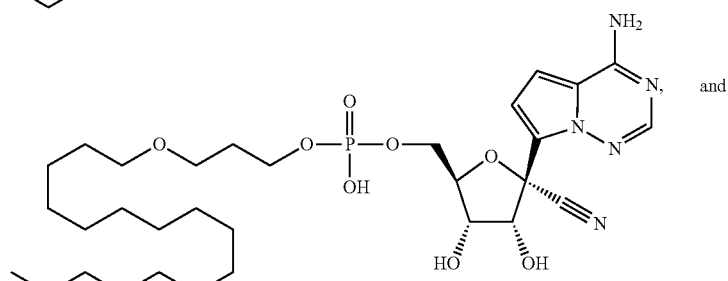
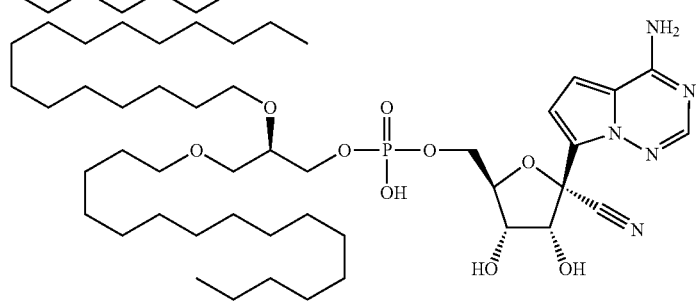
or a pharmaceutically acceptable salt thereof.

In some embodiments, the compound of Formula I, II, III, IV, V, Va, Vb, VIa, or VIb is selected from the group consisting of:
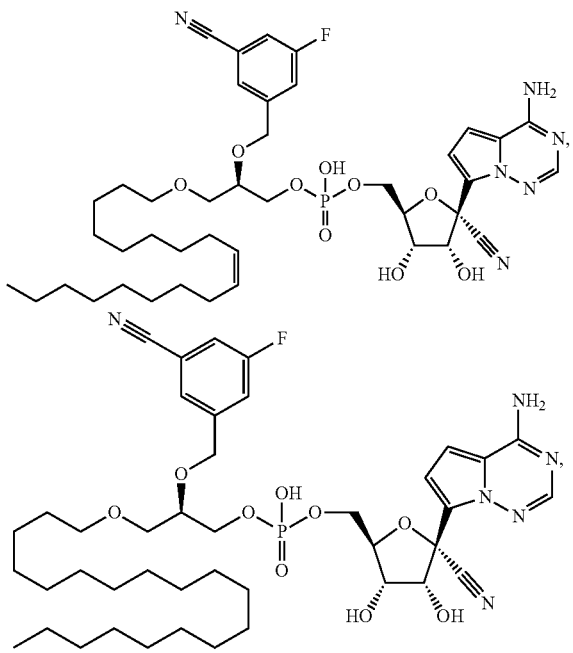
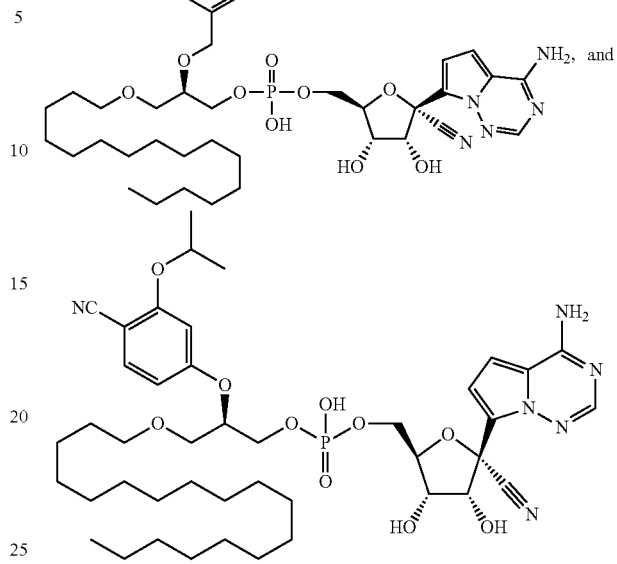
or a pharmaceutically acceptable salt thereof.
In some embodiments, the compound of Formula I, II, III, IV, V, Va, Vb, VI, VIa, VIb, VII, VIIa, or VIIb is selected from the group consisting of:
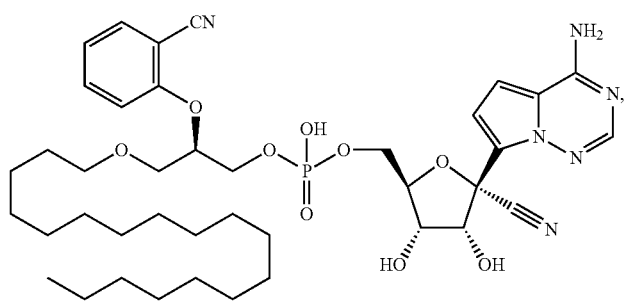
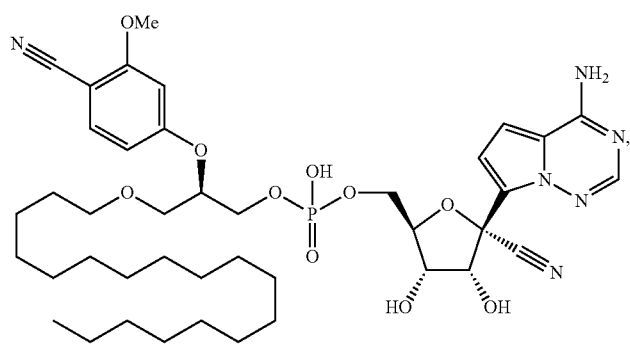

-continued
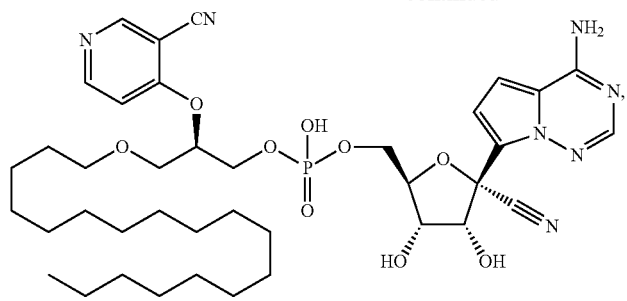
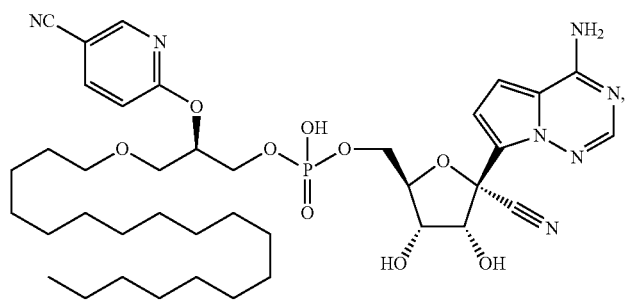
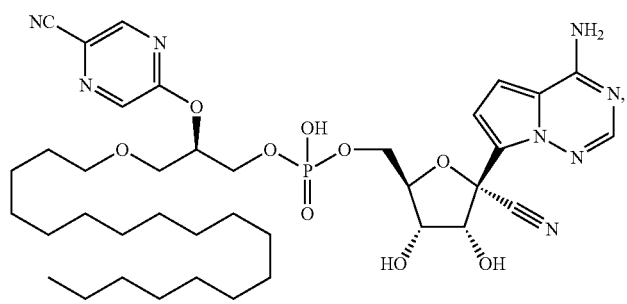
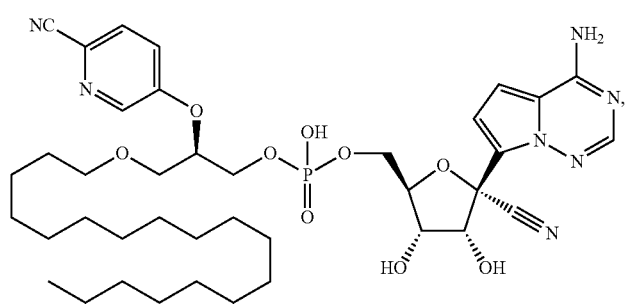
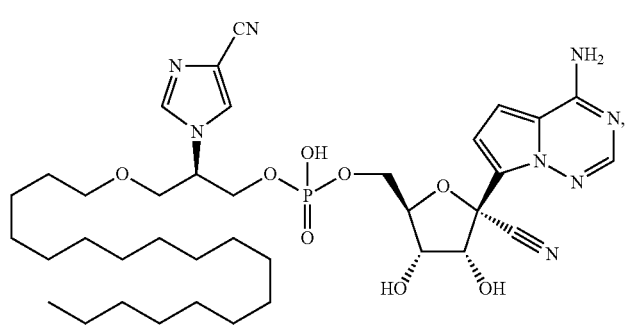

-continued
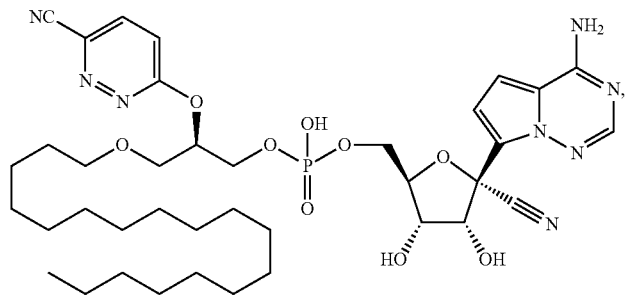
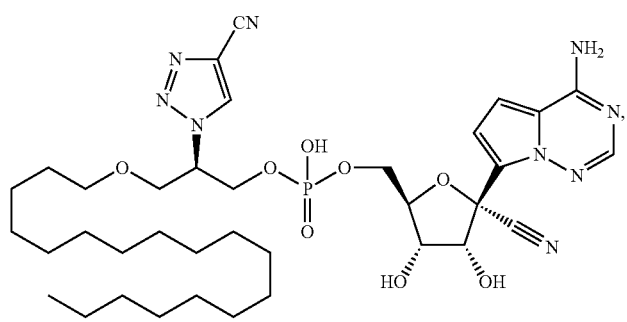
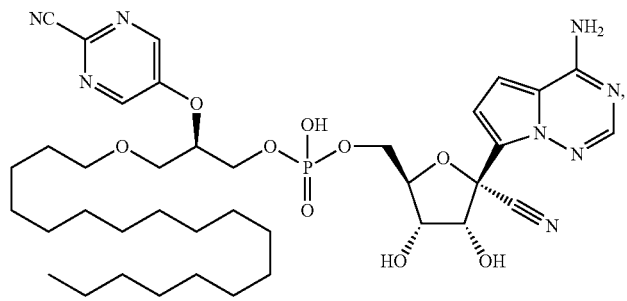
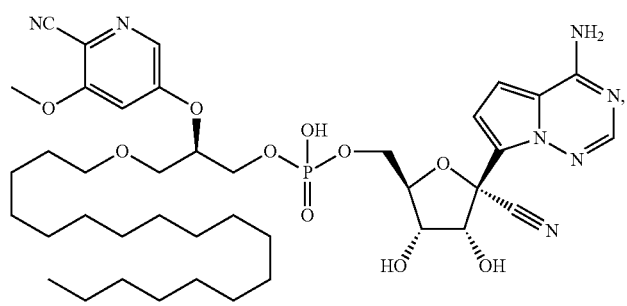
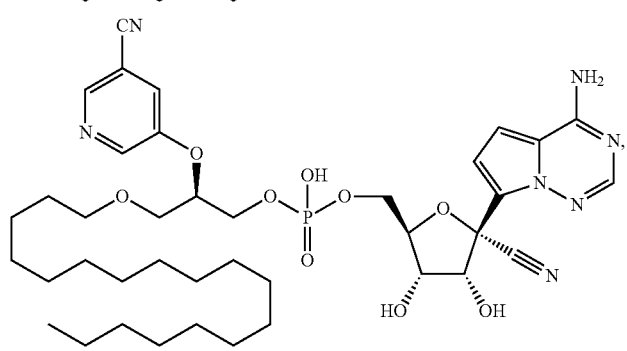

-continued
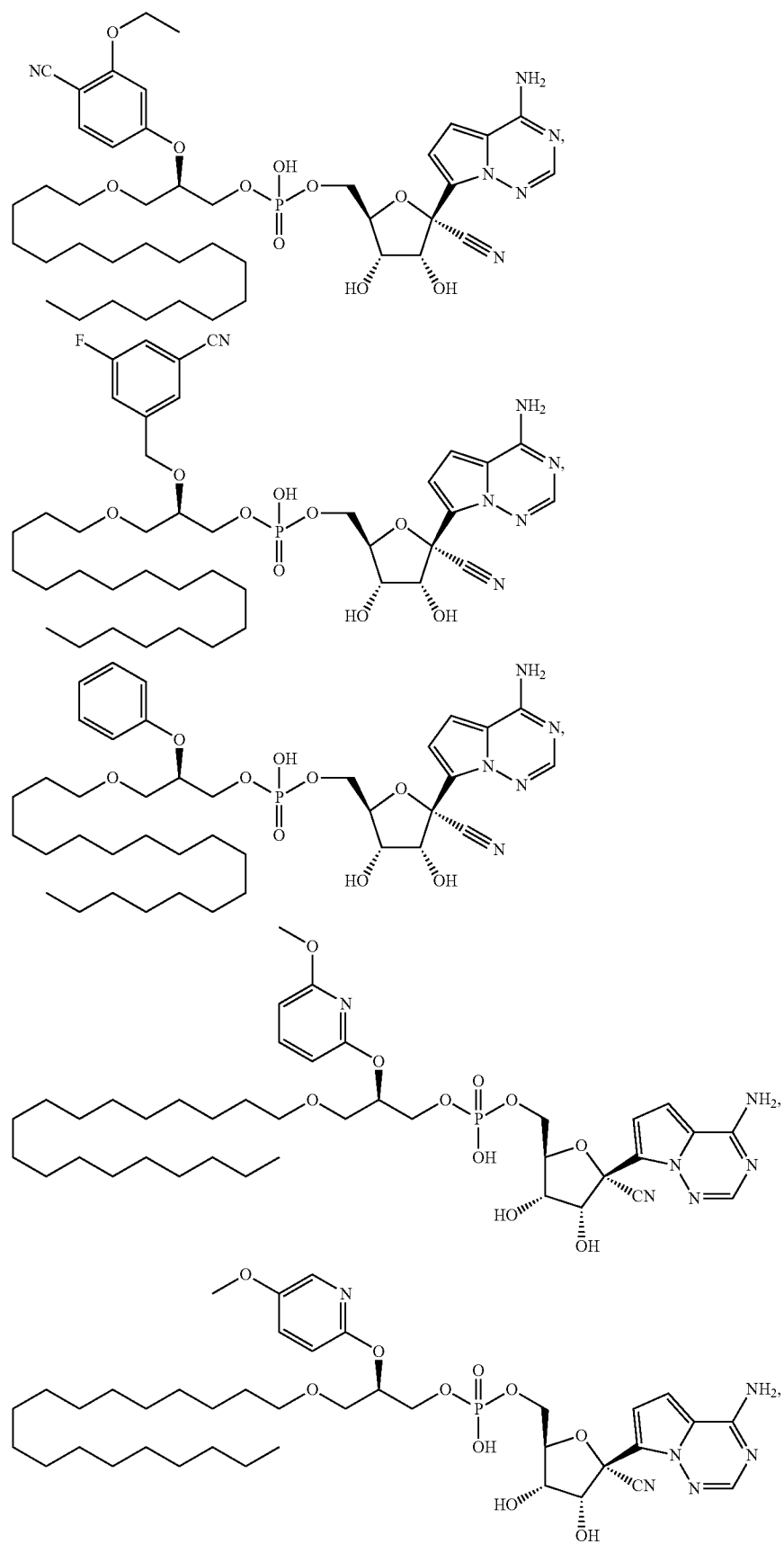

-continued
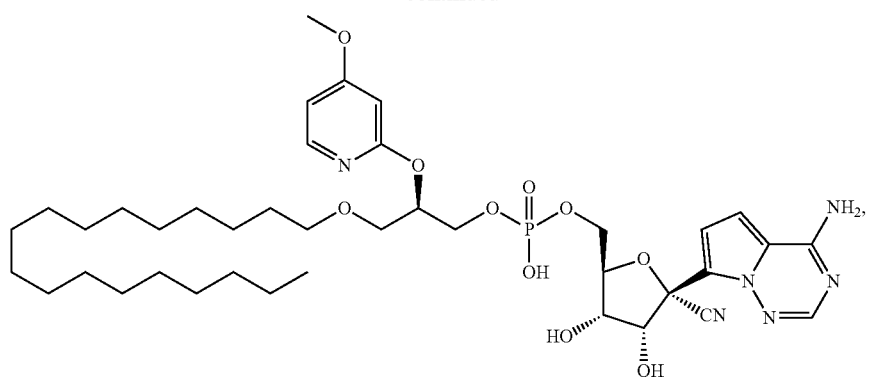
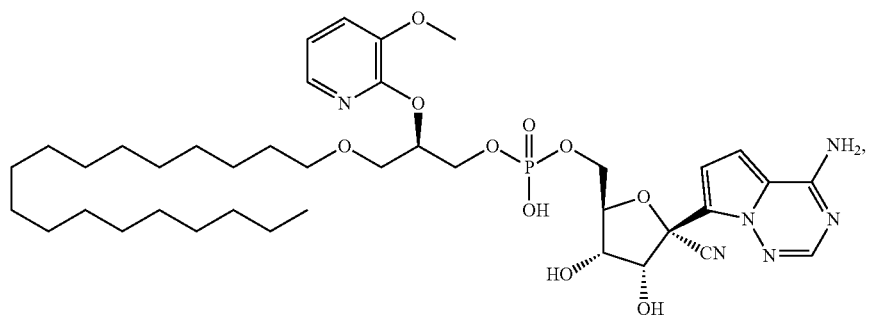
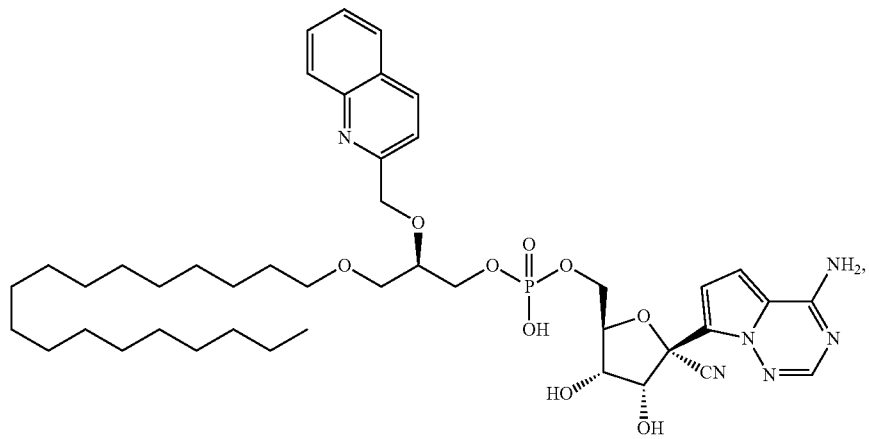
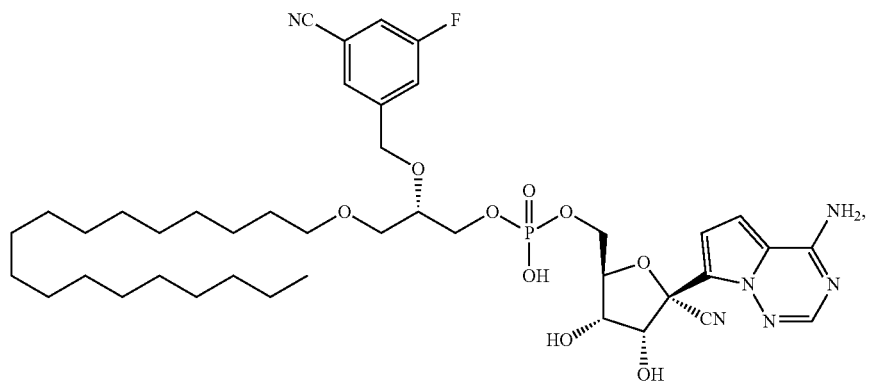

-continued
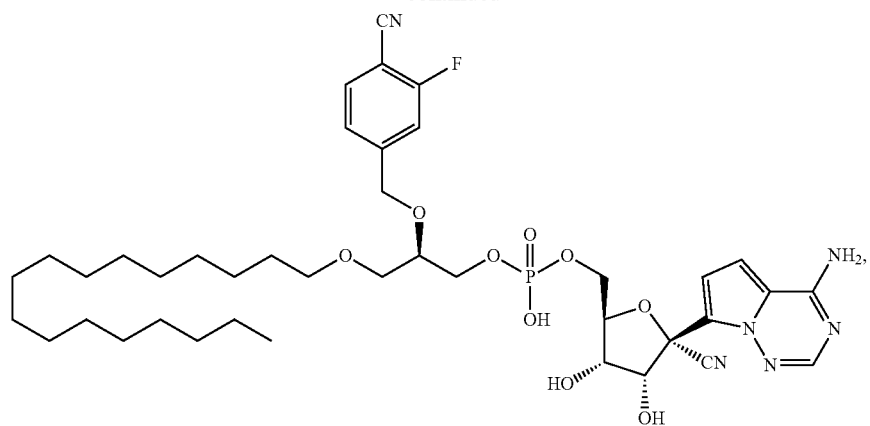
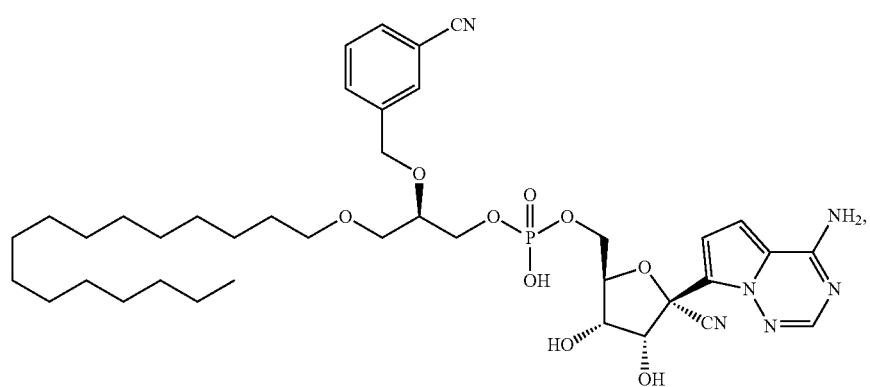
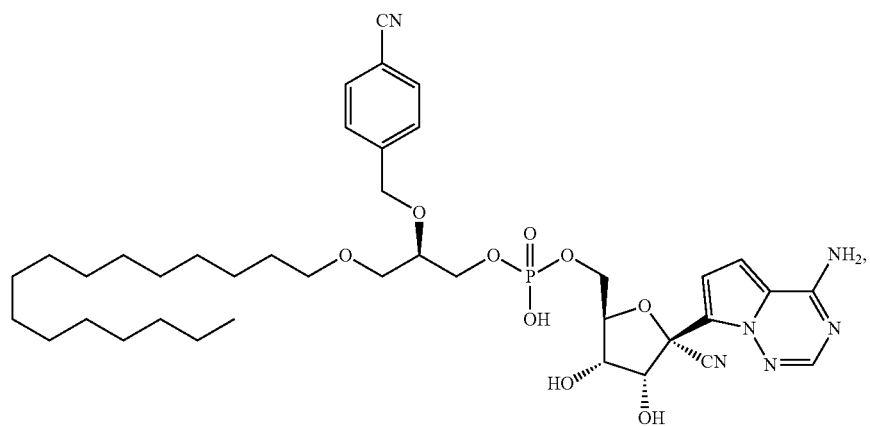
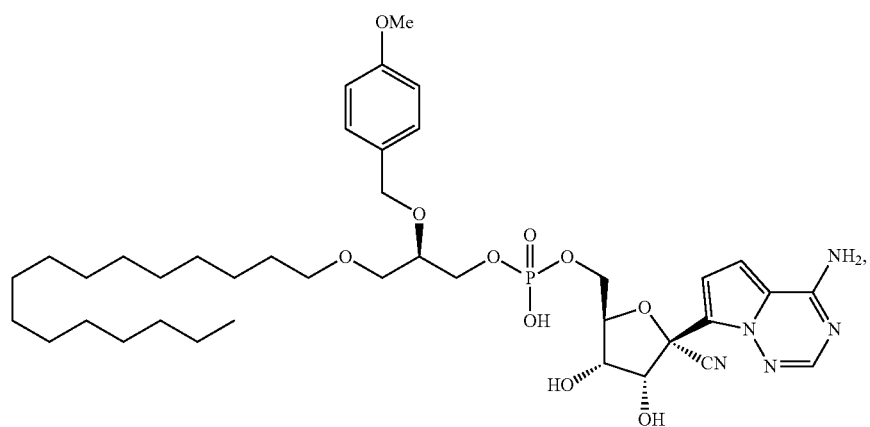

-continued
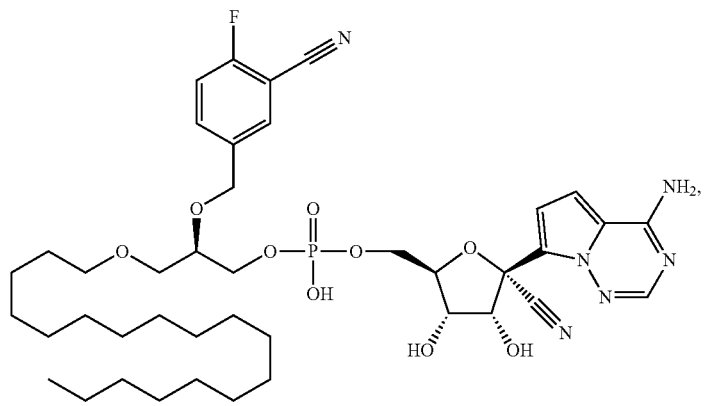
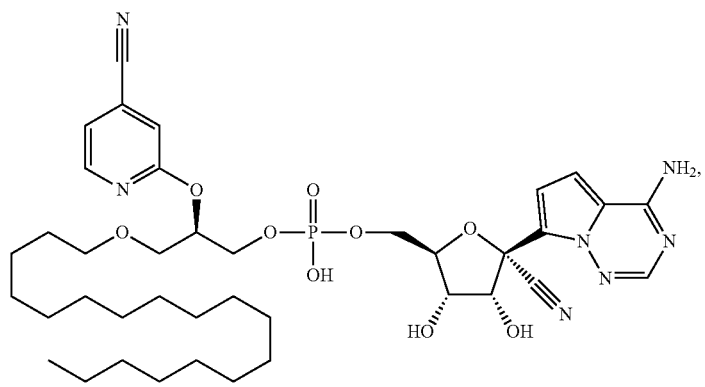
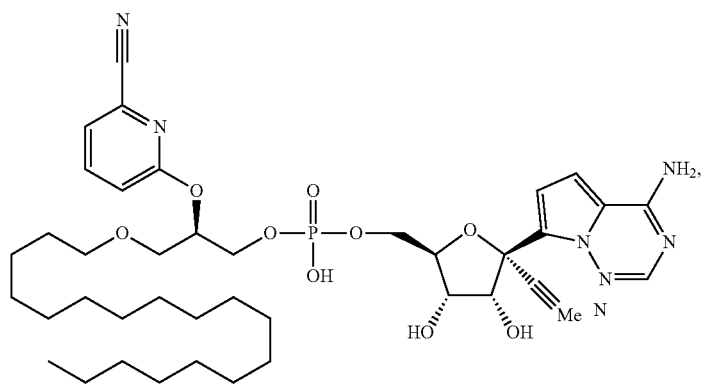
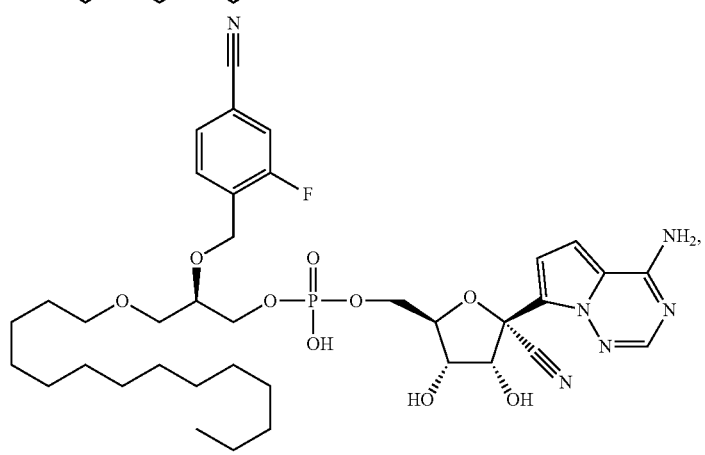

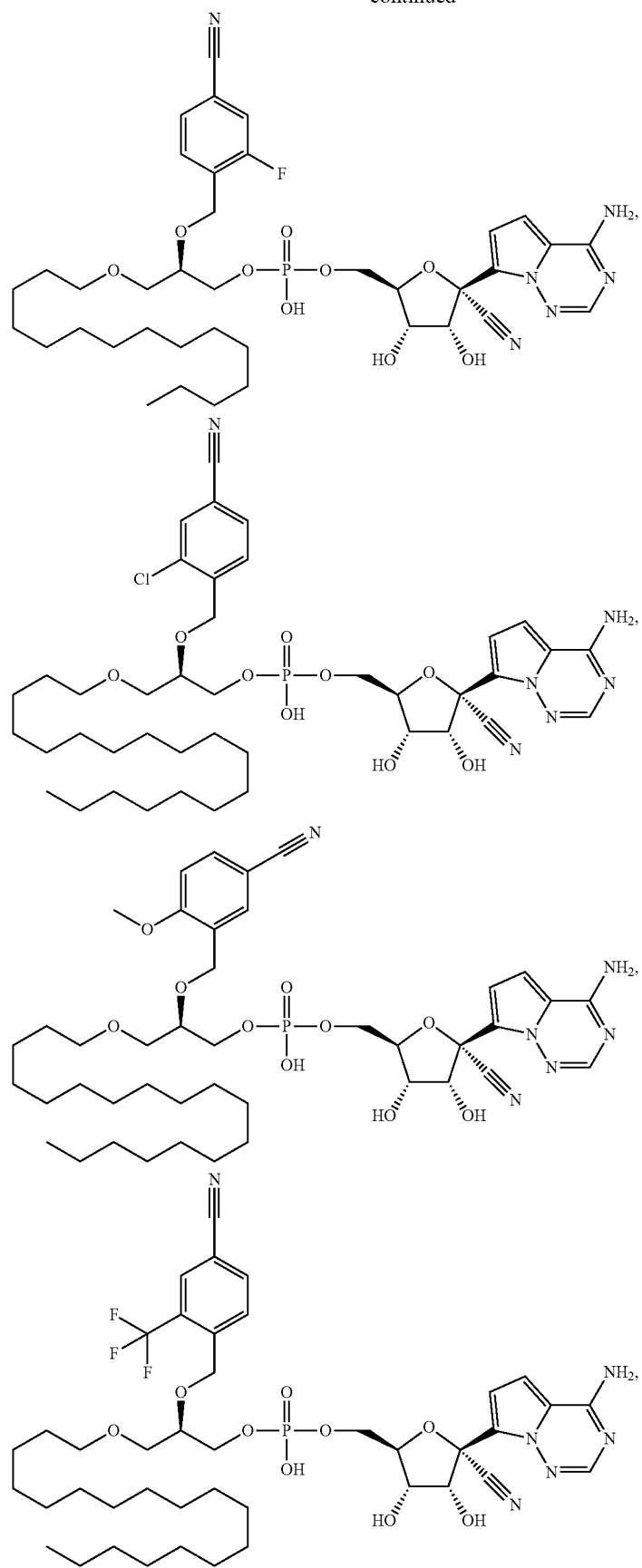

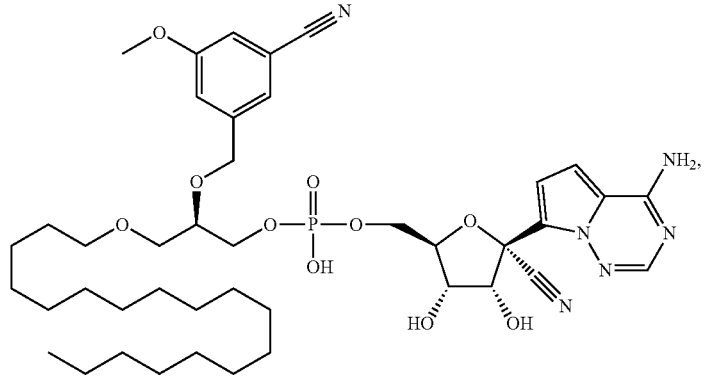
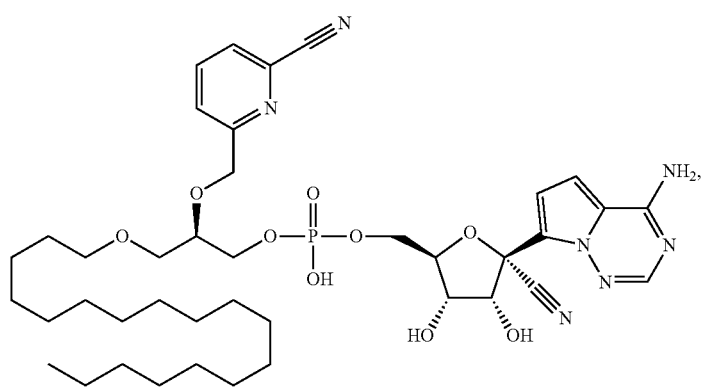
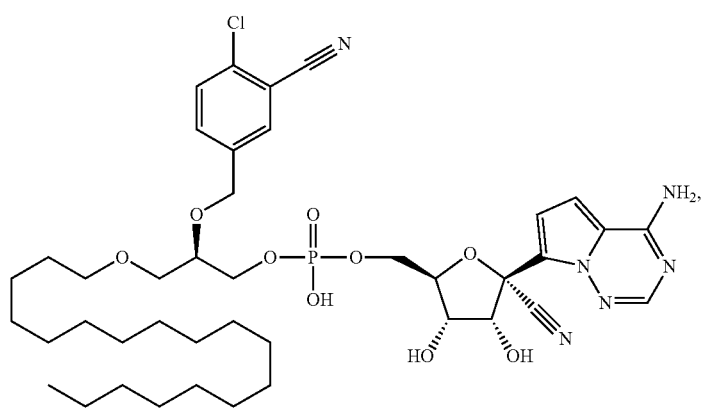
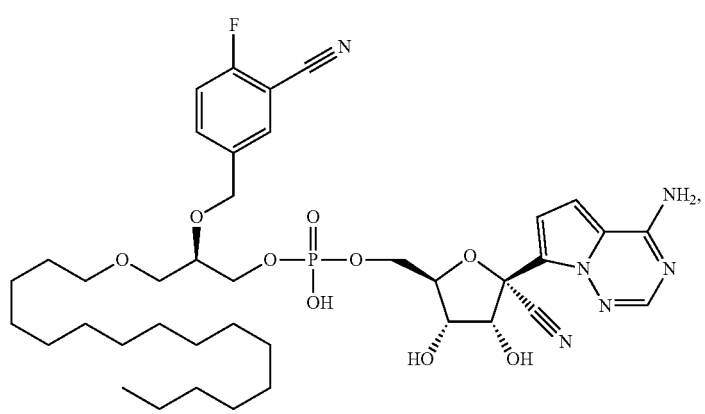

-continued
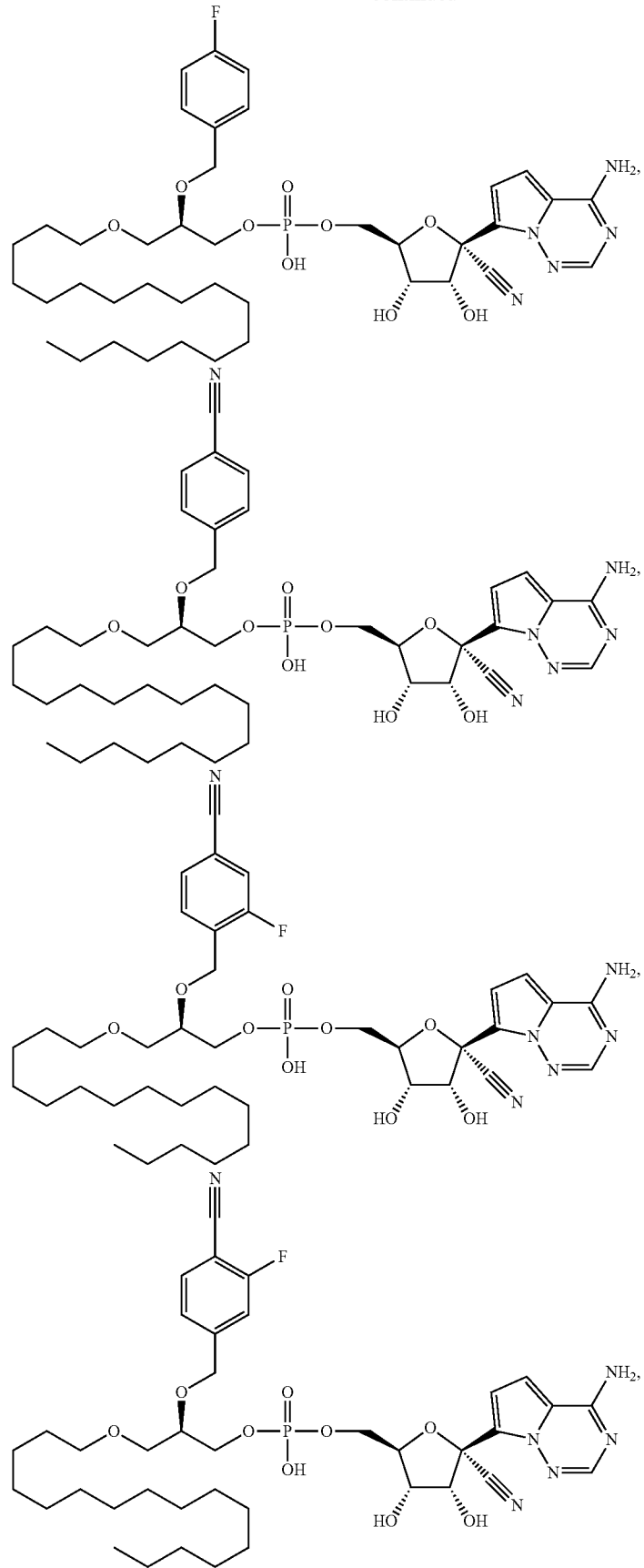

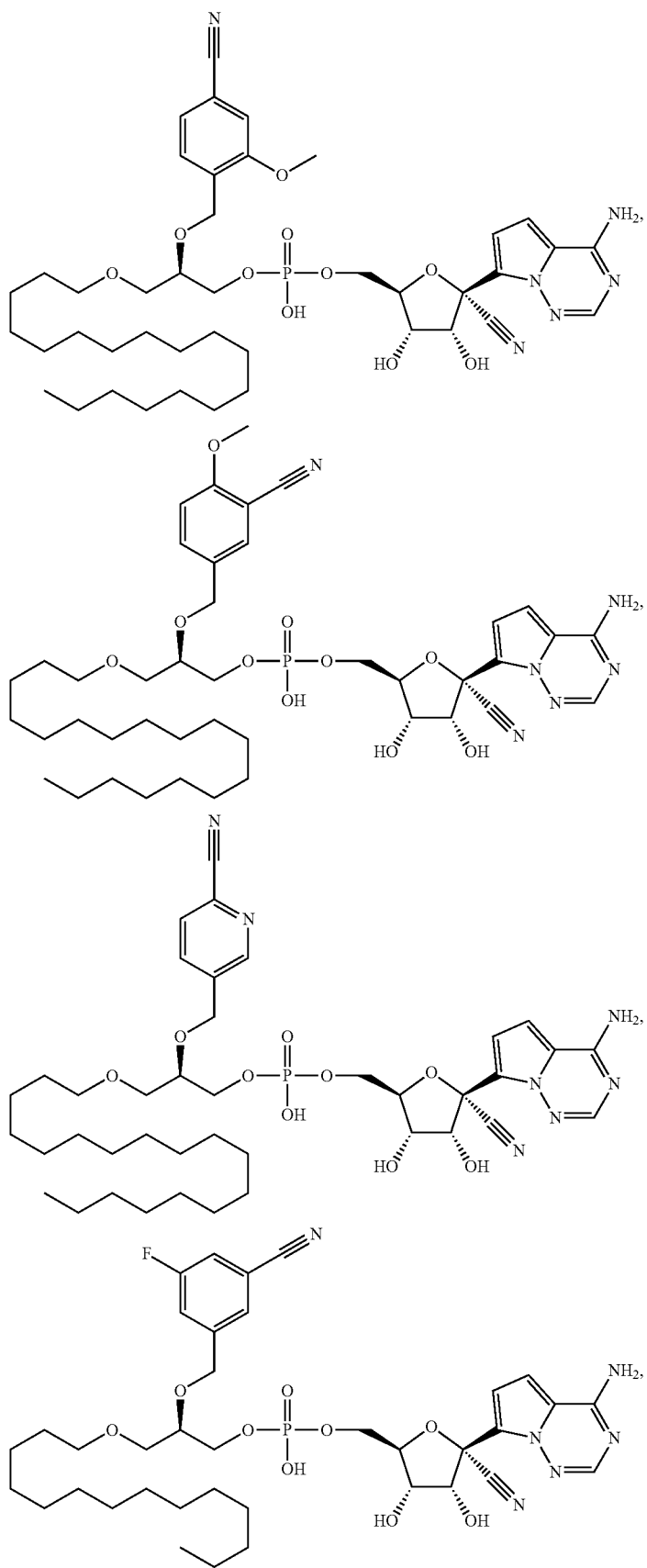

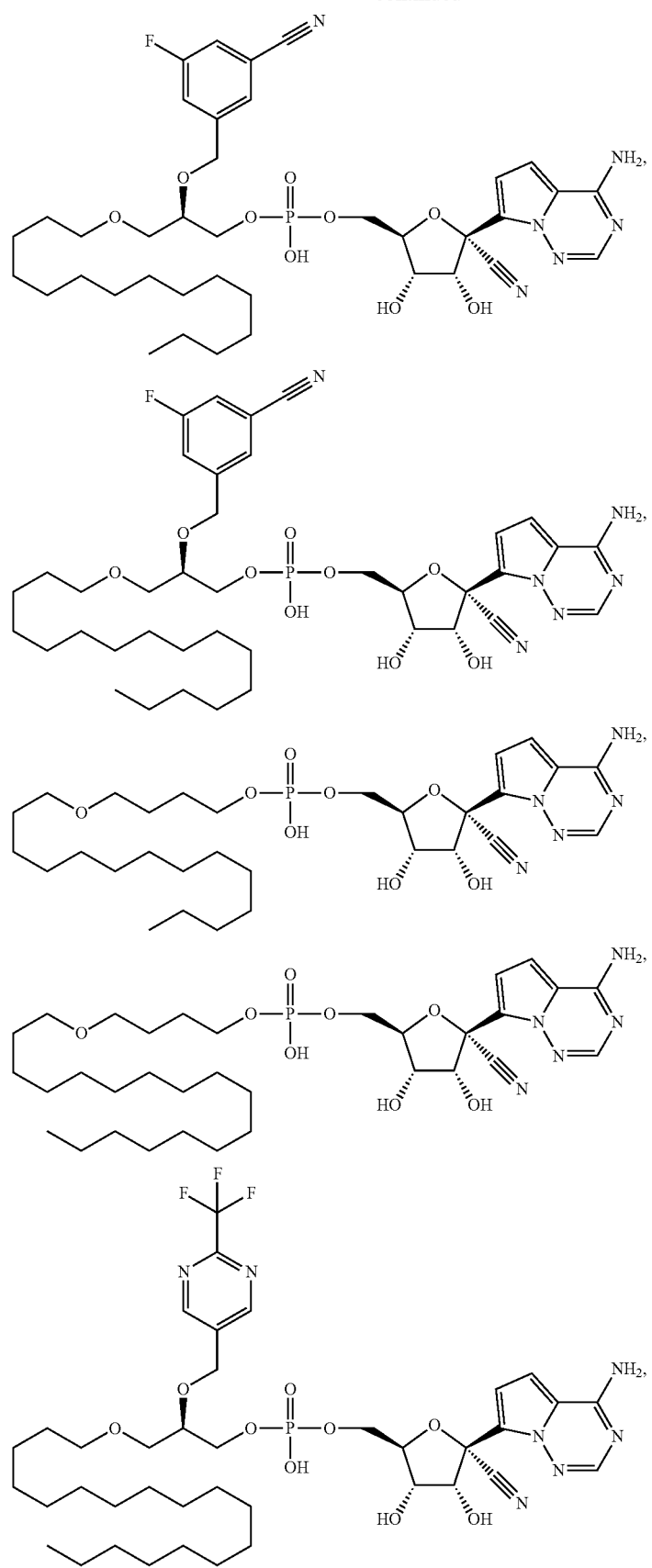

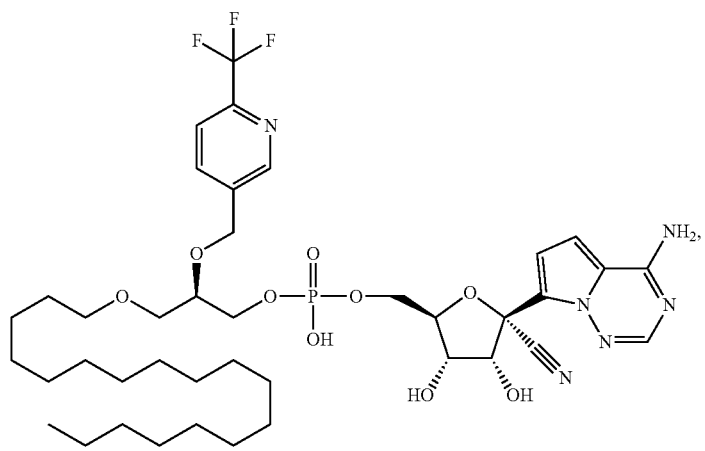
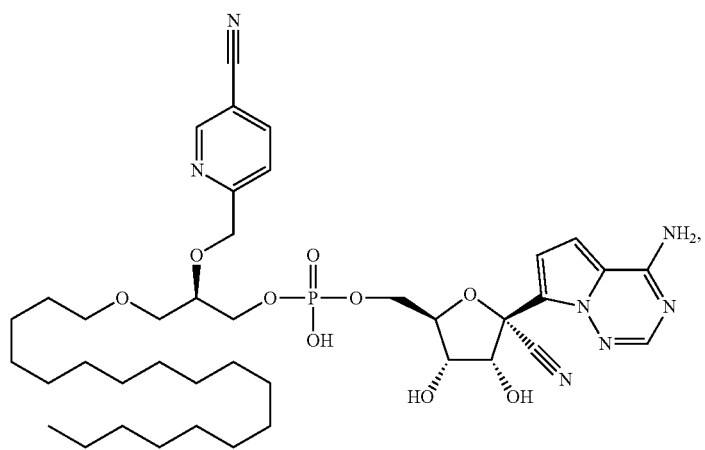
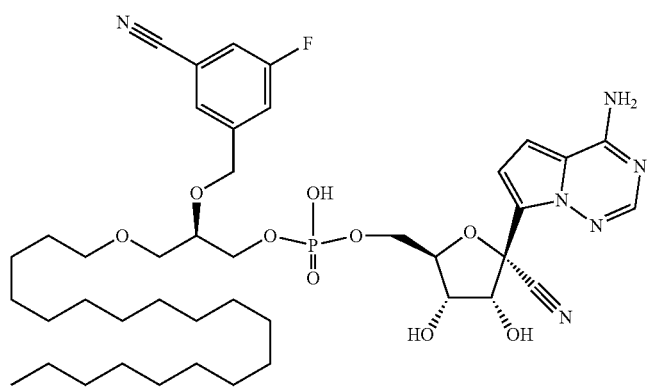
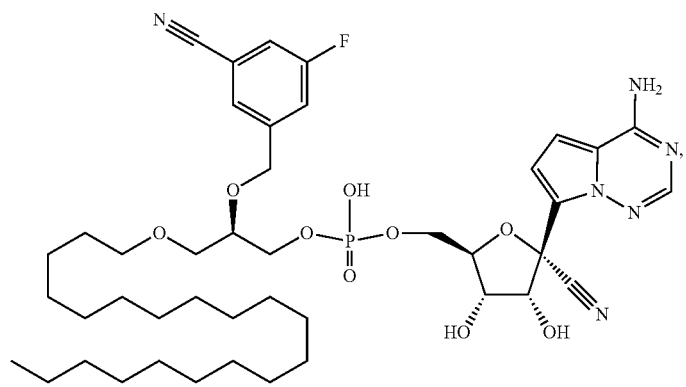

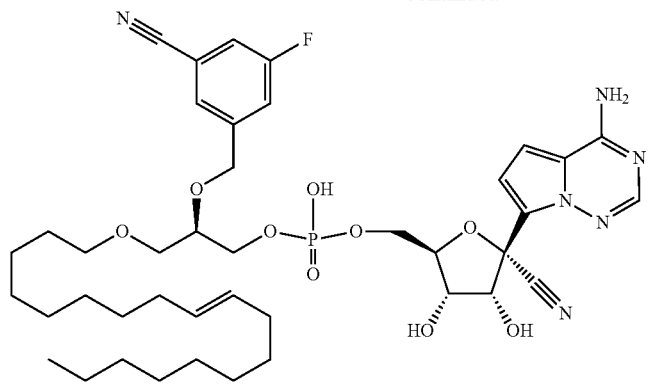
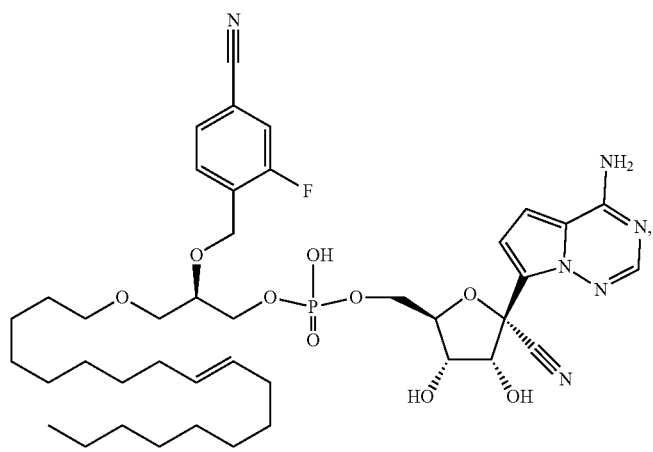
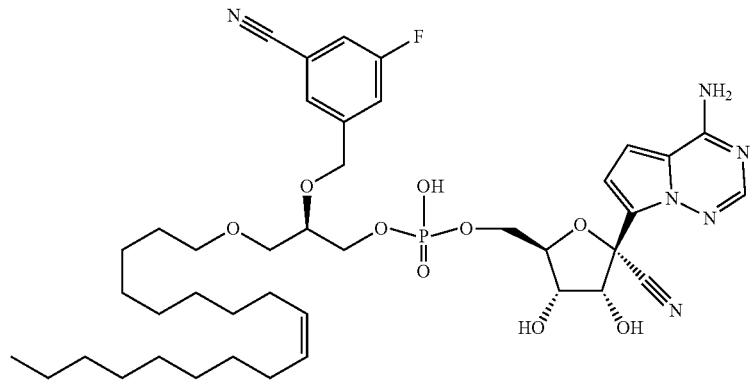
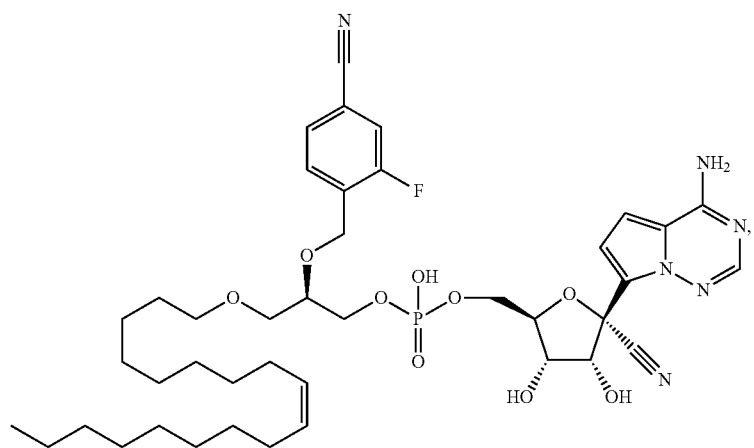

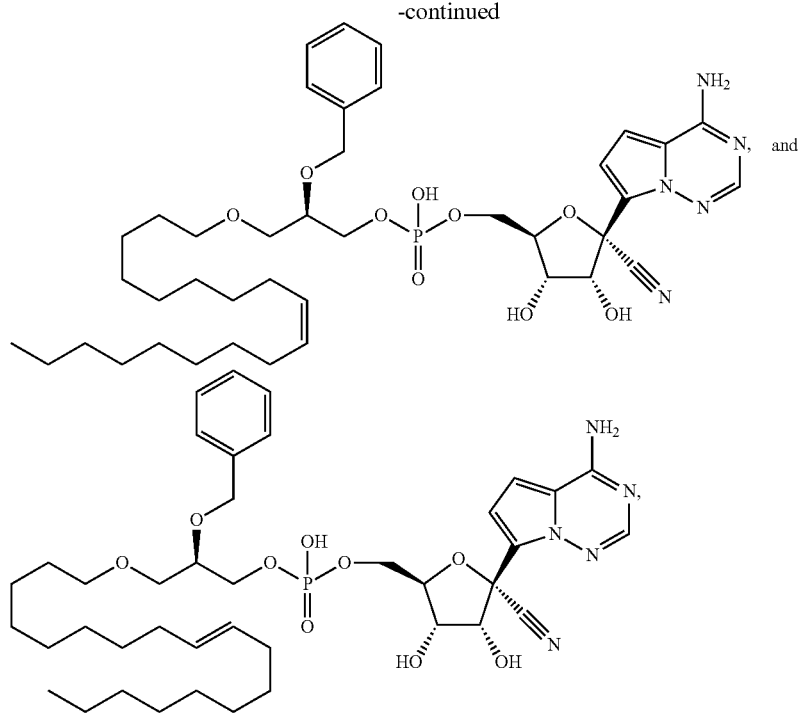

or a pharmaceutically acceptable salt thereof.

In some embodiments, the compound of Formula I, II, III, IV, V, Va, Vb, VIa, VIb, VII, VIIa, or VIIb is selected from the group consisting of the compounds described below in Examples 9, 16, 23, 26, 30, 31, 34-36, 39, 50, 51, 53, 54, 65-86, 93-96, 98-109, 111-119, and 124-130.

In some embodiments, the compound of Formula I, II, III, IV, V, Va, Vb, VIa, VIb, VII, VIIa, or VIb is selected from the group consisting of the compounds described below in Examples 9, 16, 23, 26, 30, 31, 34-36, 39, 50, 51, 53, 65-71, 73, 75-82, 84, 86, 93-96, 98-103, 107-109, 111-113, 116-119, and 124-130, or a pharmaceutically acceptable salt thereof.

Any reference to the compounds of the invention described herein also includes a reference to a pharmaceutically acceptable salt thereof. Examples of pharmaceutically acceptable salts of the compounds of the invention include salts derived from an appropriate base, such as an alkali metal or an alkaline earth (for example, Na$^+$, Li$^+$, K$^+$, Ca$^{+2}$ and Mg$^{+2}$), ammonium and NR$_4^+$ (wherein R is defined herein). Pharmaceutically acceptable salts of a nitrogen atom or an amino group include (a) acid addition salts formed with inorganic acids, for example, hydrochloric acid, hydrobromic acid, sulfuric acid, sulfamic acids, phosphoric acid, nitric acid and the like; (b) salts formed with organic acids such as, for example, acetic acid, oxalic acid, tartaric acid, succinic acid, maleic acid, fumaric acid, gluconic acid, citric acid, malic acid, ascorbic acid, benzoic acid, isethionic acid, lactobionic acid, tannic acid, palmitic acid, alginic acid, polyglutamic acid, naphthalenesulfonic acid, methanesulfonic acid, p-toluenesulfonic acid, benzenesulfonic acid, naphthalenedisulfonic acid, polygalacturonic acid, malonic acid, sulfosalicylic acid, glycolic acid, 2-hydroxy-3-naphthoate, pamoate, salicylic acid, stearic acid, phthalic acid, mandelic acid, lactic acid, ethanesulfonic acid, lysine, arginine, glutamic acid, glycine, serine, threonine, alanine, isoleucine, leucine and the like; and (c) salts formed from elemental anions for example, chlorine, bromine, and iodine. Pharmaceutically acceptable salts of a compound of a hydroxy group include the anion of said compound in combination with a suitable cation such as Na$^+$ and NR$_4^+$.

The compounds disclosed herein (e.g. compounds of Formula I, II, III, IV, V, Va, Vb, VI, VIa, and VIb) and its pharmaceutically acceptable salts may exist as different polymorphs or pseudopolymorphs. As used herein, crystalline polymorphism means the ability of a crystalline compound to exist in different crystal structures. The crystalline polymorphism may result from differences in crystal packing (packing polymorphism) or differences in packing between different conformers of the same molecule (conformational polymorphism). As used herein, crystalline pseudopolymorphism means the ability of a hydrate or solvate of a compound to exist in different crystal structures. The pseudopolymorphs of the instant invention may exist due to differences in crystal packing (packing pseudopolymorphism) or due to differences in packing between different conformers of the same molecule (conformational pseudopolymorphism). The instant invention comprises all polymorphs and pseudopolymorphs of the compounds of Formula I, Ia, Ib, II, IIa, IIb, III, IIIa, IIIb, or IIIc, and their pharmaceutically acceptable salts.

The compounds disclosed herein (e.g. compounds of Formula I, II, III, IV, V, Va, Vb, VI, VIa, and VIb) and its pharmaceutically acceptable salts may also exist as an amorphous solid. As used herein, an amorphous solid is a solid in which there is no long-range order of the positions of the atoms in the solid. This definition applies as well when the crystal size is two nanometers or less. Additives, including solvents, may be used to create the amorphous forms of the instant invention. The instant invention comprises all amorphous forms of the compounds of Formula I, II, III, IV, V, Va, Vb, VI, VIa, and VIb, and their pharmaceutically acceptable salts.

For therapeutic use, salts of active ingredients of the compounds of the invention will be pharmaceutically acceptable, i.e. they will be salts derived from a pharmaceutically acceptable acid or base. However, salts of acids or bases which are not pharmaceutically acceptable may also find use, for example, in the preparation or purification of a pharmaceutically acceptable compound. All salts, whether or not derived from a pharmaceutically acceptable acid or base, are within the scope of the present invention.

It is also to be understood that the compositions herein comprise compounds of the invention in their un-ionized, as well as zwitterionic form, and combinations with stoichiometric amounts of water as in hydrates.

It is to be noted that all enantiomers, diastereomers, and racemic mixtures, tautomers, polymorphs, pseudopolymorphs of compounds within the scope of Formula I, II, III, IV, V, Va, Vb, VI, VIa, or VIb and pharmaceutically acceptable salts thereof are embraced by the present invention. All mixtures of such enantiomers and diastereomers are within the scope of the present invention.

The compounds of the invention, exemplified by Formula I, II, III, IV, V, Va, Vb, VI, VIa, or VIb may have chiral centers, e.g. chiral carbon or phosphorus atoms. The compounds of the invention thus include racemic mixtures of all stereoisomers, including enantiomers, diastereomers, and atropisomers. In addition, the compounds of the invention include enriched or resolved optical isomers at any or all asymmetric, chiral atoms. In other words, the chiral centers apparent from the depictions are provided as the chiral isomers or racemic mixtures. Both racemic and diastereomeric mixtures, as well as the individual optical isomers isolated or synthesized, substantially free of their enantiomeric or diastereomeric partners, are all within the scope of the invention. The racemic mixtures are separated into their individual, substantially optically pure isomers through appropriate techniques such as, for example, the separation of diastereomeric salts formed with optically active adjuncts, e.g., acids or bases followed by conversion back to the optically active substances. In most instances, the desired optical isomer is synthesized by means of stereospecific reactions, beginning with the appropriate stereoisomer of the desired starting material.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., Stereochemistry of Organic Compounds (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l, D and L, or (+) and (−) are employed to designate the sign of rotation of plane-polarized light by the compound, with S, (−), or l meaning that the compound is levorotatory while a compound prefixed with R, (+), or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The compounds of the invention may also exist as tautomeric isomers in certain cases. Although only one delocalized resonance structure may be depicted, all such forms are contemplated within the scope of the invention. For example, ene-amine tautomers can exist for purine, pyrimidine, imidazole, guanidine, amidine, and tetrazole systems and all their possible tautomeric forms are within the scope of the invention.

Any formula or structure given herein, including Formula I, II, III, IV, V, Va, Vb, VI, VIa, and VIb compounds, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl and $^{125}$I. Various isotopically labeled compounds of the present disclosure, for example those into which radioactive isotopes such as $^3$H, $^{13}$C and $^{14}$C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also includes compounds of Formula I in which from 1 to x hydrogens attached to a carbon atom is/are replaced by deuterium, in which x is the number of hydrogens in the molecule. Such compounds exhibit increased resistance to metabolism and are thus useful for increasing the half-life of any compound of Formula I when administered to a mammal, particularly a human. See, for example, Foster, "Deuterium Isotope Effects in Studies of Drug Metabolism", Trends Pharmacol. Sci. 5(12):524-527 (1984). In view of the present disclosure, such compounds are synthesized by means known in the art, for example by employing starting materials in which one or more hydrogens have been replaced by deuterium.

Deuterium labeled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compound of Formula I.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

Whenever a compound described herein is substituted with more than one of the same designated group, e.g., "R" or "R'", then it will be understood that the groups may be the same or different, i.e., each group is independently selected.

Wavy lines, ⁓, indicate the site of covalent bond attachments to the adjoining substructures, groups, moieties, or atoms.

IV. Pharmaceutical Formulations

The compounds disclosed herein (e.g. compounds of Formula I, II, III, IV, V, Va, Vb, VIa and VIb) may be formulated with conventional carriers and excipients. For example, tablets will contain excipients, glidants, fillers, binders and the like. Aqueous formulations are prepared in sterile form, and when intended for delivery by other than oral administration generally will be isotonic. All formulations may optionally contain excipients such as those set forth in the "Handbook of Pharmaceutical Excipients" (1986). Excipients include ascorbic acid and other antioxidants, chelating agents such as EDTA, carbohydrates such as dextran, hydroxyalkylcellulose, hydroxyalkylmethylcellulose, stearic acid and the like. The pH of the formulations ranges from about 3 to about 11, but is ordinarily about 7 to 10. In some embodiments, the pH of the formulations ranges from about 2 to about 5, but is ordinarily about 3 to 4.

While it is possible for the compounds of the disclosure ("the active ingredients") to be administered alone it may be preferable to present them as pharmaceutical formulations. The formulations, both for veterinary and for human use, of the invention comprise at least one active ingredient, as above defined, together with one or more acceptable carriers therefor and optionally other therapeutic ingredients, particularly those additional therapeutic ingredients as discussed herein. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any appropriate method known in the art of pharmacy. Techniques and formulations generally are found in Remington's Pharmaceutical Sciences (Mack Publishing Co., Easton, PA). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

In some embodiments, the compounds disclosed have pharmacokinetic properties (for e.g. good oral bioavailability) suitable for oral administration of the compounds. In some embodiments, the formulations of the present invention are suitable for oral administration and are presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

In some embodiments, the tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

For infections of the eye or other external tissues e.g. mouth and skin, the formulations are applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate. Further emulgents and emulsion stabilizers suitable for use in the formulation of the invention include Tween® 80.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present invention comprise a compound according to the invention together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcellulose, sodium alginate, polyvinylpyrrolidone, gum tragacanth and gum acacia, and dispersing or wetting agents such as a naturally-occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin. Further non-limiting examples of suspending agents include Cyclodextrin. In some embodiments, the suspending agent is Sulfobutyl ether beta-cyclodextrin (SEB-beta-CD), for example Captisol®.

Oil suspensions may be formulated by suspending the active ingredient in a vegetable oil, such as *arachis* oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or *arachis* oil, a mineral oil, such as liquid paraffin, or a mixture of these. Suitable emulsifying agents include naturally-occurring gums, such as gum acacia and gum tragacanth, naturally-occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables. Among the acceptable vehicles and solvents that may be employed are water, Ringer's solution isotonic sodium chloride solution, and hypertonic sodium chloride solution.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hr can occur.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10%, and particularly about 1.5% w/w.

Formulations suitable for topical administration in the mouth include lozenges comprising the active ingredient in a flavored basis, usually sucrose and acacia or tragacanth;

pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

In some embodiments, the compounds disclosed herein are administered by inhalation. In some embodiments, formulations suitable for intrapulmonary or nasal administration have a particle size for example in the range of 0.1 to 500 microns, such as 0.5, 1, 30, 35 etc., which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents. In some embodiments, the compounds used herein are formulated and dosed as dry powder. In some embodiments, the compounds used herein are formulated and dosed as a nebulized formulation. In some embodiments, the compounds used herein are formulated for delivery by a face mask. In some embodiments, the compounds used herein are formulated for delivery by a face tent.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention are used to provide controlled release pharmaceutical formulations containing as active ingredient one or more compounds of the invention ("controlled release formulations") in which the release of the active ingredient are controlled and regulated to allow less frequency dosing or to improve the pharmacokinetic or toxicity profile of a given active ingredient.

V. Kits

Also provided herein are kits that includes a compound disclosed herein (e.g. compounds of Formula I, II, III, IV, V, Va, Vb, VI, VIa, or VIb), a pharmaceutically acceptable salt, stereoisomer, mixture of stereoisomers or tautomer thereof. In some embodiments the kits described herein may comprise a label and/or instructions for use of the compound in the treatment of a disease or condition in a subject (e.g., human) in need thereof. In some embodiments, the disease or condition is viral infection.

In some embodiments, the kit may also comprise one or more additional therapeutic agents and/or instructions for use of additional therapeutic agents in combination with the compound of Formula I in the treatment of the disease or condition in a subject (e.g., human) in need thereof.

In some embodiments, the kits provided herein comprises individual dose units of a compound as described herein, or a pharmaceutically acceptable salt, racemate, enantiomer, diastereomer, tautomer, polymorph, pseudopolymorph, amorphous form, hydrate or solvate thereof. Examples of individual dosage units may include pills, tablets, capsules, prefilled syringes or syringe cartridges, IV bags, inhalers, nebulizers etc., each comprising a therapeutically effective amount of the compound in question, or a pharmaceutically acceptable salt, racemate, enantiomer, diastereomer, tautomer, polymorph, pseudopolymorph, amorphous form, hydrate or solvate thereof. In some embodiments, the kit may contain a single dosage unit and in others multiple dosage units are present, such as the number of dosage units required for a specified regimen or period.

Also provided are articles of manufacture that include a compound of Formula I, or a pharmaceutically acceptable salt, stereoisomer, mixture of stereoisomers or tautomer thereof; and a container. In some embodiments, the container of the article of manufacture is a vial, jar, ampoule, preloaded syringe, blister package, tin, can, bottle, box, an intravenous bag, an inhaler, or a nebulizer.

VI. Administration

One or more compounds of the invention are administered by any route appropriate to the condition to be treated. Suitable routes include oral, rectal, inhalation, pulmonary, topical (including buccal and sublingual), vaginal and parenteral (including subcutaneous, intramuscular, intravenous, intradermal, intrathecal and epidural), and the like. In some embodiments, the compounds disclosed herein are administered by inhalation or intravenously. It will be appreciated that the preferred route may vary with for example the condition of the recipient.

In the methods of the present invention for the treatment of a viral infection, the compounds of the present invention can be administered at any time to a human who may come into contact with the virus or is already suffering from the viral infection. In some embodiments, the compounds of the present invention can be administered prophylactically to humans coming into contact with humans suffering from the viral infection or at risk of coming into contact with humans suffering from the viral infection, e.g. healthcare providers. In some embodiments, administration of the compounds of the present invention can be to humans testing positive for the viral infection but not yet showing symptoms of the viral infection. In some embodiments, administration of the compounds of the present invention can be to humans upon commencement of symptoms of the viral infection.

In some embodiments, the methods disclosed herein comprise event driven administration of the compound of Formula I, or a pharmaceutically acceptable salt thereof, to the subject.

As used herein, the terms "event driven" or "event driven administration" refer to administration of the compound of Formula I, or a pharmaceutically acceptable salt thereof, (1) prior to an event (e.g., 2 hours, 1 day, 2 days, 5 day, or 7 or more days prior to the event) that would expose the individual to the virus (or that would otherwise increase the individual's risk of acquiring the viral infection); and/or (2) during an event (or more than one recurring event) that would expose the individual to the virus (or that would otherwise increase the individual's risk of acquiring the viral infection); and/or (3) after an event (or after the final event in a series of recurring events) that would expose the individual to the virus (or that would otherwise increase the individual's risk of acquiring the viral infection). In some embodiments, the event driven administration is performed pre-exposure of the subject to the virus. In some embodiments, the event driven administration is performed post-exposure of the subject to the virus. In some embodiments, the event driven administration is performed pre-exposure of the subject to the virus and post-exposure of the subject to the virus.

In certain embodiments, the methods disclosed herein involve administration prior to and/or after an event that would expose the individual to the virus or that would otherwise increase the individual's risk of acquiring the viral infection, e.g., as pre-exposure prophylaxis (PrEP) and/or as post-exposure prophylaxis (PEP). In some embodiments, the methods disclosed herein comprise pre-exposure prophylaxis (PrEP). In some embodiments, methods disclosed herein comprise post-exposure prophylaxis (PEP).

In some embodiments, the compound of Formula I, or a pharmaceutically acceptable salt thereof, is administered before exposure of the subject to the virus.

In some embodiments, the compound of Formula I, or a pharmaceutically acceptable salt thereof, is administered before and after exposure of the subject to the virus.

In some embodiments, the compound of Formula I, or a pharmaceutically acceptable salt thereof, is administered after exposure of the subject to the virus.

An example of event driven dosing regimen includes administration of the compound of Formula I, or a pharmaceutically acceptable salt thereof, within 24 to 2 hours prior to the virus, followed by administration of the compound of Formula I, or a pharmaceutically acceptable salt, every 24 hours during the period of exposure, followed by a further administration of the compound of Formula I, or a pharmaceutically acceptable salt thereof, after the last exposure, and one last administration of the compound of Formula I, or a pharmaceutically acceptable salt thereof, 24 hours later.

A further example of an event driven dosing regimen includes administration of the compound of Formula I, or a pharmaceutically acceptable salt thereof, within 24 hours before the viral exposure, then daily administration during the period of exposure, followed by a last administration approximately 24 hours later after the last exposure (which may be an increased dose, such as a double dose).

Effective dose of active ingredient depends at least on the nature of the condition being treated, toxicity, whether the compound is being used prophylactically or against an active viral infection, the method of delivery, and the pharmaceutical formulation, and will be determined by the clinician using conventional dose escalation studies. It can be expected to be from about 0.0001 to about 100 mg/kg body weight per day; typically, from about 0.01 to about 10 mg/kg body weight per day; more typically, from about 0.01 to about 5 mg/kg body weight per day; most typically, from about 0.05 to about 0.5 mg/kg body weight per day. For example, the daily candidate dose for an adult human of approximately 70 kg body weight will range from 1 mg to 1000 mg, preferably between 5 mg and 500 mg, and may take the form of single or multiple doses.

Any suitable period of time for administration of the compounds of the present invention is contemplated. For example, administration can be for from 1 day to 100 days, including 2, 3, 4, 5, 6, 7, 8, 9, 10, 15, 20, 25, 30, 40, 50, 60, 70, 80, or 90 days. The administration can also be for from 1 week to 15 weeks, including 2, 3, 4, 5, 6, 7, 8, 9, 10, 11, 12, 13, or 14 weeks. Longer periods of administration are also contemplated.

In some embodiments, the compounds disclosed herein are administered once daily. In some embodiments, the compounds disclosed herein are administered once every alternate day. In some embodiments, the compounds disclosed herein are administered once a week. In some embodiments, the compounds disclosed herein are administered twice a week.

In some embodiments, one or more compounds disclosed herein are administered once daily. The once daily dose may be administered for as long as required, for example for up to 5 days, up to 7 days, up to 10 days, up to 15 days, up to 20 days, up to 25 days, up to a month or longer. In some embodiments, the once daily dose is administered for up to 20 days, up to 15 days, up to 14 days, up to 13 days, up to 12 days, up to 10 days, up to 8 days, up to 6 days, up to 4 days, up to 3 days, up to 2 days or for one day.

In some embodiments, the one or more compounds disclosed herein are dosed once daily, for about 6 to 12 days, for example for about 8-10 days. In some embodiments, the one or more compounds are administered once daily for about 9 days. In some embodiments, the one or more compounds are administered once daily for about 10 days. In some embodiments about 50-150 mg of one or more compounds disclosed herein is administered once daily for about 5 to 12 days, for e.g. for about 10 days. In some embodiments about 100 mg of one or more compounds disclosed herein is administered once daily for about 5 to 12 days, for e.g. for about 10 days.

VI. Methods of Use

The present disclosure also provides a method of treating or preventing a viral infection in a subject (e.g. human) in need thereof, the method comprising administering to the subject a compound described herein.

In some embodiments, the present disclosure provides a method of treating a viral infection in a subject (e.g. human) in need thereof, the method comprising administering to a subject in need thereof a compound described herein.

In some embodiments, the present disclosure provides for methods of treating or preventing a viral infection in a subject (e.g. human) in need thereof, the method comprising administering to the subject a compound disclosed herein and at least one additional active therapeutic or prophylactic agent.

In some embodiments, the present disclosure provides for methods of treating a viral infection in a subject (e.g. human) in need thereof, the method comprising administering to the subject a compound disclosed herein, and at least one additional active therapeutic agent.

In some embodiments, the present disclosure provides for methods of inhibiting a viral polymerase in a cell, the methods comprising contacting the cell infected a virus with a compound disclosed herein, whereby the viral polymerase is inhibited.

In some embodiments, the present disclosure provides for methods of inhibiting a viral polymerase in a cell, the methods comprising contacting the cell infected a virus with a compound disclosed herein, and at least one additional active therapeutic agent, whereby the viral polymerase is inhibited.

Also provided here are the uses of the compounds disclosed herein for use in treating or preventing a viral infection in a subject in need thereof. For example, provided herein are uses of the compounds disclosed herein for use in treating a viral infection in a subject in need thereof.

In some embodiments, the viral infection is a paramyxoviridae virus infection. As such, in some embodiments, the present disclosure provides methods for treating a paramyxoviridae infection in a subject (e.g. a human) in need thereof, the method comprising administering to the subject a compound disclosed herein. Paramyxoviridae viruses include, but are not limited to Nipah virus, Hendra virus, measles, mumps, and parainfluenza virus. In some embodiments, the Paramyxoviridae virus is a Sosuga virus.

In some embodiments, the viral infection is a pneumoviridae virus infection. As such, in some embodiments, the present disclosure provides a method of treating a pneumoviridae virus infection in a human in need thereof, the method comprising administering to the human a compound provided herein. Pneumoviridae viruses include, but are not limited to, respiratory snycytial virus and human metapneumovirus. In some embodiments, the pneumoviridae virus infection is a respiratory syncytial virus infection. In some embodiments, the pneumoviridae virus infection is human metapneumovirus infection.

In some embodiments, the present disclosure provides a compound disclosed herein, for use in the treatment of a pneumoviridae virus infection in a human in need thereof. In some embodiments, the pneumoviridae virus infection is a respiratory syncytial virus infection. In some embodiments, the pneumoviridae virus infection is human metapneumovirus infection.

In some embodiments, the present disclosure provides methods for treating a RSV infection in a human in need thereof, the method comprising administering to the human a compound provided herein. In some embodiments, the human is suffering from a chronic respiratory syncytial viral infection. In some embodiments, the human is acutely infected with RSV.

In some embodiments, a method of inhibiting RSV replication is provided, wherein the method comprises administering to a human in need thereof, a compound disclosed herein, wherein the administration is by inhalation.

In some embodiments, the present disclosure provides a method for reducing the viral load associated with RSV infection, wherein the method comprises administering to a human infected with RSV a compound disclosed herein.

In some embodiments, the viral infection is a picornaviridae virus infection. As such, in some embodiments, the present disclosure provides a method of treating a picornaviridae virus infection in a human in need thereof, the method comprising administering to the human a compound of the present disclosure. Picornaviridae viruses are enteroviruses causing a heterogeneous group of infections including herpangina, aseptic meningitis, a common-cold-like syndrome (human rhinovirus infection), a non-paralytic poliomyelitis-like syndrome, epidemic pleurodynia (an acute, febrile, infectious disease generally occurring in epidemics), hand-foot-mouth syndrome, pediatric and adult pancreatitis and serious myocarditis. In some embodiments, the Picornaviridae virus infection is human rhinovirus infection. In some embodiments, the Picornaviridae virus infection is enterovirus infection. In some embodiments, the Picornaviridae virus infection is selected from the group consisting of Coxsackie A virus infection, Coxsackie A virus infection, enterovirus D68 infection, enterovirus B69 infection, enterovirus D70 infection, enterovirus A71 infection, and poliovirus infection.

In some embodiments, the present disclosure provides a compound, for use in the treatment of a picornaviridae virus infection in a human in need thereof. In some embodiments, the picornaviridae virus infection is human rhinovirus infection.

In some embodiments, the viral infection is a flaviviridae virus infection. As such, in some embodiments, the present disclosure provides a method of treating a flaviviridae virus infection in a human in need thereof, the method comprising administering to the human a compound described herein. Representative flaviviridae viruses include, but are not limited to, dengue, Yellow fever, West Nile, Zika, Japanese encephalitis virus, and Hepatitis C (HCV). In some embodiments, the flaviviridae virus infection is a dengue virus infection. In some embodiments, the flaviviridae virus infection is a yellow fever virus infection. In some embodiments, the flaviviridae virus infection is a West Nile virus infection. In some embodiments, the flaviviridae virus infection is a zika virus infection. In some embodiments, the flaviviridae virus infection is a Japanese ensephalitis virus infection. In some embodiments, the flaviviridae virus infection is a hepatitis C virus infection.

In some embodiments, the present disclosure provides use of a compound disclosed herein for treatment of a flaviviridae virus infection in a human in need thereof. In some embodiments, the flaviviridae virus infection is a dengue virus infection. In some embodiments, the flaviviridae virus infection is a yellow fever virus infection. In some embodiments, the flaviviridae virus infection is a West Nile virus infection. In some embodiments, the flaviviridae virus infection is a zika virus infection. In some embodiments, the flaviviridae virus infection is a hepatitis C virus infection.

In some embodiments, the viral infection is a filoviridae virus infection. As such, in some embodiments, provided herein is a method of treating a filoviridae virus infection in a human in need thereof, the method comprising administering to the human a compound disclosed herein. Representative filoviridae viruses include, but are not limited to, ebola (variants Zaire, Bundibugio, Sudan, Tai forest, or Reston) and marburg. In some embodiments, the filoviridae virus infection is an ebola virus infection. In some embodiments, the filoviridae virus infection is a marburg virus infection.

In some embodiments, the present disclosure provides a compound for use in the treatment of a filoviridae virus infection in a human in need thereof. In some embodiments, the filoviridae virus infection is an ebola virus infection. In some embodiments, the filoviridae virus infection is a marburg virus infection.

In some embodiments, the viral infection is a coronavirus infection. As such, in some embodiments, provided herein is a method of treating a coronavirus infection in a human in need thereof, wherein the method comprises administering to the human a compound provided herein. In some embodiments, the coronavirus infection is a Severe Acute Respiratory Syndrome (SARS) infection, Middle Eastern Respiratory Syndrome (MERS) infection, SARS-CoV-2 infection, other human coronavirus (229E, NL63, OC43, HKU1, or WIV1) infections, zoonotic coronavirus (PEDV or HKU CoV isolates such as HKU3, HKU5, or HKU9) infections. In some embodiments, the viral infection is a Severe Acute Respiratory Syndrome (SARS) infection. In some embodiments, the viral infection is a Middle Eastern Respiratory Syndrome (MERS) infection. In some embodiments, the viral infection is SARS-CoV-2 infection. In some embodiments, the viral infection is a zoonotic coronavirus infection, In some embodiments, the viral infection is caused by a virus having at least 70% sequence homology to a viral polymerase selected from the group consisting of SARS CoV polymerase, MERS CoV polymerase and SARS-CoV-2. In some embodiments, the viral infection is caused by a virus having at least 80% sequence homology to a viral polymerase selected from the group consisting of SARS CoV polymerase, MERS CoV polymerase and SARS-CoV-2. In some embodiments, the viral infection is caused by a virus having at least 90% sequence homology to a viral polymerase selected from the group consisting of SARS CoV polymerase, MERS CoV polymerase and SARS-CoV-2. In some embodiments, the viral infection is caused by a virus having at least 95% sequence homology to a viral polymerase selected from the group consisting of SARS CoV polymerase, MERS CoV polymerase and SARS-CoV-2.

In some embodiments, the present disclosure provides a compound for use in the treatment of a coronavirus virus infection in a human in need thereof. In some embodiments, the coronavirus infection is a Severe Acute Respiratory Syndrome (SARS) infection, Middle Eastern Respiratory Syndrome (MERS) infection, SARS-CoV-2 infection, other human coronavirus (229E, NL63, OC43, HKU1, or WIV1) infections, zoonotic coronavirus (PEDV or HKU CoV isolates such as HKU3, HKU5, or HKU9) infections. In some embodiments, the viral infection is a Severe Acute Respiratory Syndrome (SARS) infection. In some embodiments, the viral infection is a Middle Eastern Respiratory Syndrome (MERS) infection. In some embodiments, the viral infection is SARS-CoV-2 infection (COVID19).

In some embodiments, the viral infection is an arenaviridae virus infection. As such, in some embodiments, the disclosure provides a method of treating an arenaviridae virus infection in a human in need thereof, the method comprising administering to the human a compound disclosed herein. In some embodiments, the arenaviridae virus infection is a Lassa infection or a Junin infection.

In some embodiments, the present disclosure provides a compound for use in the treatment of a arenaviridae virus infection in a human in need thereof. In some embodiments, the arenaviridae virus infection is a Lassa infection or a Junin infection.

In some embodiments, the viral infection is an orthomyxovirus infection, for example, an influenza virus infection. In some embodiments, the viral infection is an influenza virus A, influenza virus B, or influenza virus C infection.

In some embodiments, the viral infection is a nairovirus infection. As such, in some embodiments, the disclosure provides a method of treating a nairovirus infection in a human in need thereof, the method comprising administering to the human a compound disclosed herein. In some embodiments, the nairovirus infection is a Crimean-Congo hemorrhagic fever virus infection. In some embodiments, the nairovirus infection is a Hazara virus infection.

As described more fully herein, the compounds described herein can be administered with one or more additional therapeutic agent(s) to an individual (e.g. a human) infected with a viral infection. The additional therapeutic agent(s) can be administered to the infected individual at the same time as the compound of the present disclosure or before or after administration of the compound of the present disclosure.

VIII. Combination Therapy

The compounds described herein can also be used in combination with one or more additional therapeutic or prophylactic agents. As such, also provided herein are methods for treatment of viral infections in a subject in need thereof, wherein the methods comprise administering to the subject a compound disclosed herein and a therapeutically effective amount of one or more additional therapeutic or prophylactic agents. In some embodiments, the methods comprise administering to the subject a compound disclosed herein and a therapeutically effective amount of one or more additional therapeutic agents.

In some embodiments, the additional therapeutic agent is an antiviral agent. Any suitable antiviral agent can be used in the methods described herein. In some embodiments, the antiviral agent is selected from the group consisting of 5-substituted 2'-deoxyuridine analogues, nucleoside analogues, pyrophosphate analogues, nucleoside reverse transcriptase inhibitors, non-nucleoside reverse transcriptase inhibitors, protease inhibitors, integrase inhibitors, entry inhibitors, acyclic guanosine analogues, acyclic nucleoside phosphonate analogues, HCV NS5A/NS5B inhibitors, influenza virus inhibitors, interferons, immunostimulators, oligonucleotides, antimitotic inhibitors, and combinations thereof.

In some embodiments, the additional therapeutic agent is a 5-substituted 2'-deoxyuridine analogue. For example, in some embodiments, the additional therapeutic agent is selected from the group consisting of idoxuridine, trifluridine, brivudine [BVDU], and combinations thereof.

In some embodiments, the additional therapeutic agent is a nucleoside analogue. For example, in some embodiments, the additional therapeutic agent is selected from the group consisting of vidarabine, entecavir (ETV), telbivudine, lamivudine, adefovir dipivoxil, tenofovir disoproxil fumarate (TDF) and combinations thereof. In some embodiments, the additional therapeutic agent is favipiravir, ribavirin, galidesivir, β-D-N4-hydroxycytidine or a combination thereof.

In some embodiments, the additional therapeutic agent is a pyrophosphate analogue. For example, in some embodiments, the additional therapeutic agent is foscarnet or phosphonoacetic acid. In some embodiments, the additional therapeutic agent is foscarnet.

In some embodiments, the additional therapeutic agent is nucleoside reverse transcriptase inhibitor. In some embodiments, the antiviral agent is zidovudine, didanosine, zalcitabine, stavudine, lamivudine, abacavir, emtricitabine, and combinations thereof.

In some embodiments, the additional therapeutic agent is a non-nucleoside reverse transcriptase inhibitor. In some embodiments, the antiviral agent is selected from the group consisting of nevirapine, delavirdine, efavirenz, etravirine, rilpivirine, and combinations thereof.

In some embodiments, the additional therapeutic agent is a protease inhibitor. In some embodiments, the protease inhibitor is a HIV protease inhibitor. For example, in some embodiments, the antiviral agent is selected from the group consisting of saquinavir, ritonavir, indinavir, nelfinavir, amprenavir, lopinavir, atazanavir, fosamprenavir, darunavir, tipranavir, cobicistat, and combinations thereof. In some embodiments, the antiviral agent is selected from the group consisting of saquinavir, ritonavir, indinavir, nelfinavir, amprenavir, lopinavir, atazanavir, fosamprenavir, darunavir, tipranavir, and combinations thereof. In some embodiments, the protease inhibitor is a HCV NS3/4A protease inhibitor. For example, in some embodiments, the additional therapeutic agent is selected from the group consisting of voxilaprevir, asunaprevir, boceprevir, paritaprevir, simeprevir, telaprevir, vaniprevir, grazoprevir, ribavirin, danoprevir, faldaprevir, vedroprevir, sovaprevir, deldeprevir, narlaprevir and combinations thereof. In some embodiments, the additional therapeutic agent is selected from the group consisting of voxilaprevir, asunaprevir, boceprevir, paritaprevir, simeprevir, telaprevir, vaniprevir, grazoprevir, and combinations thereof.

In some embodiments, the additional therapeutic agent is an integrase inhibitor. For example, in some embodiments, the additional therapeutic agent is selected from the group consisting of raltegravir, dolutegravir, elvitegravir, abacavir, lamivudine, and combinations thereof. In some embodiments, the additional therapeutic agent is selected from the group consisting of bictegravir, raltegravir, dolutegravir, cabotegravir, elvitegravir, and combinations thereof. In some embodiments, the additional therapeutic agent is selected from the group consisting of bictegravir, dolutegravir, and cabotegravir, and combinations thereof. In some embodiments, the additional therapeutic agent is bictegravir.

In some embodiments, the additional therapeutic agent is an entry inhibitor. For example, in some embodiments, the additional therapeutic agent is selected from the group consisting of docosanol, enfuvirtide, maraviroc, ibalizumab, fostemsavir, leronlimab, ibalizumab, fostemsavir, leronlimab, palivizumab, respiratory syncytial virus immune globulin, intravenous [RSV-IGIV], varicella-zoster immunoglobulin [VariZIG], varicella-zoster immune globulin [VZIG]), and combinations thereof.

In some embodiments, the additional therapeutic agent is an acyclic guanosine analogue. For example, in some embodiments, the additional therapeutic agent is selected from the group consisting of acyclovir, ganciclovir, valacyclovir (also known as valaciclovir), valganciclovir, penciclovir, famciclovir, and combinations thereof.

In some embodiments, the additional therapeutic agent is an acyclic nucleoside phosphonate analogues. For example, in some embodiments, the additional therapeutic agent is selected from a group consisting of cidofovir, adefovir, adefovir dipivoxil, tenofovir, TDF, emtricitabine, efavirenz, rilpivirine, elvitegravir, and combinations thereof. In some embodiments, the additional therapeutic agent is selected from the group consisting of cidofovir, adefovir, adefovir dipivoxil, tenofovir, TDF, and combinations thereof. In some embodiments, the additional therapeutic agent is selected from the group consisting of cidofovir, adefovir dipivoxil, TDF, and combinations thereof.

In some embodiments, the additional therapeutic agent is a HCV NS5A/NS5B inhibitor. In some embodiments, the additional therapeutic agent is a NS3/4A protease inhibitor. In some embodiments, the additional therapeutic agent is a NS5A protein inhibitor. In some embodiments, the additional therapeutic agent is a NS5B polymerase inhibitor of the nucleoside/nucleotide type. In some embodiments, the additional therapeutic agent is a NS5B polymerase inhibitor of the nonnucleoside type. In some embodiments, the additional therapeutic agent is selected from the group consisting of daclatasvir, ledipasvir, velpatasvir, ombitasvir, elbasvir, sofosbuvir, dasabuvir, ribavirin, asunaprevir, simeprevir, paritaprevir, ritonavir, elbasvir, grazoprevir, and combinations thereof hi some embodiments, the additional therapeutic agent is selected from the group consisting of daclatasvir, ledipasvir, velpatasvir, ombitasvir, elbasvir, sofosbuvir, dasabuvir, and combinations thereof.

In some embodiments, the additional therapeutic agent is an influenza virus inhibitor. In some embodiments, the additional therapeutic agents is a matrix 2 inhibitor. For example, in some embodiments, the additional therapeutic agent is selected from the group consisting of amantadine, rimantadine, and combinations thereof. In some embodiments, the additional therapeutic agent is a neuraminidase inhibitor. For example, in some embodiments, the additional therapeutic agent is selected from the group consisting of zanamivir, oseltamivir, peramivir, laninamivir octanoate, and combinations thereof. In some embodiments, the additional therapeutic agent is a polymerase inhibitor. For example, in some embodiments, the additional therapeutic agent is selected from the group consisting of ribavirin, favipiravir, and combinations thereof. In some embodiments, the additional therapeutic agent is selected from the group consisting of amantadine, rimantadine, arbidol (umifenovir), baloxavir marboxil, oseltamivir, peramivir, ingavirin, laninamivir octanoate, zanamivir, favipiravir, ribavirin, and combinations thereof. In some embodiments, the additional therapeutic agent is selected from the group consisting of amantadine, rimantadine, zanamivir, oseltamivir, peramivir, laninamivir octanoate, ribavirin, favipiravir, and combinations thereof.

In some embodiments, the additional therapeutic agent is an interferon. In some embodiments, the additional therapeutic agent is selected from the group consisting of interferon alfacon 1, interferon alfa 1b, interferon alfa 2a, interferon alfa 2b, pegylated interferon alfacon 1, pegylated interferon alfa 1b, pegylated interferon alfa 2a (PegIFNα-2a), and PegIFNα-2b. e embodiments, the additional therapeutic agent is selected from the group consisting of interferon alfacon 1, interferon alfa 1b, interferon alfa 2a, interferon alfa 2b, pegylated interferon alfa 2a (PegIFNα-2a), and PegIFNα-2b. In some embodiments, the additional therapeutic agent is selected from the group consisting of interferon alfacon 1, pegylated interferon alfa 2a (PegIFNα-2a), PegIFNα-2b, and ribavirin. In some embodiments, the additional therapeutic agent is pegylated interferon alfa-2a, pegylated interferon alfa-2b, or a combination thereof.

In some embodiments, the additional therapeutic agent is an immunostimulatory agent. In some embodiments, the additional therapeutic agent is an oligonucleotide. In some embodiments, the additional therapeutic agent is an antimitotic inhibitor. For example, in some embodiments, the additional therapeutic agent is selected from the group consisting of fomivirsen, podofilox, imiquimod, sinecatechins, and combinations thereof.

In some embodiments, the additional therapeutic agent is selected from the group consisting of besifovir, nitazoxanide, REGN2222, doravirine, sofosbuvir, velpatasvir, daclatasvir, asunaprevir, beclabuvir, FV100, and letermovir, and combinations thereof.

In some embodiments, the additional therapeutic agent is an agent for treatment of RSV. For example, in some embodiments, the antiviral agent is ribavirin, ALS-8112 or presatovir. For example, in some embodiments, the antiviral agent is ALS-8112 or presatovir.

In some embodiments, the additional therapeutic agent is an agent for treatment of picornavirus. In some embodiments, the additional therapeutic agent is selected from the group consisting of hydantoin, guanidine hydrochloride, L-buthionine sulfoximine, Py-11, and combinations thereof. In some embodiments, the additional therapeutic agent is a picornavirus polymerase inhibitor. In some embodiments, the additional therapeutic agent is rupintrivir.

In some embodiments, the additional therapeutic agent is an agent for treatment of malaria. In some embodiments, the additional therapeutic agent is chloroquine.

In some embodiments, the additional therapeutic agent is selected from the group consisting of hydroxychloroquine, chloroquine, artemether, lumefantrine, atovaquone, proguanil, tafenoquine, pyronaridine, artesunate, artenimol, piperaquine, artesunate, amodiaquine, pyronaridine, artesunate, halofantrine, quinine sulfate, mefloquine, solithromycin, pyrimethamine, MMV-390048, ferroquine, artefenomel mesylate, ganaplacide, DSM-265, cipargamin, artemisone, and combinations thereof.

In some embodiments, the additional therapeutic agent is an agent for treatment of coronavirus. In some embodiments, the additional therapeutic agent is selected from a group consisting of IFX-1, FM-201, CYNK-001, DPP4-Fc, ranpirnase, nafamostat, LB-2, AM-1, anti-viroporins, and combinations thereof.

In some embodiments, the additional therapeutic agent is an agent for treatment of ebola virus. For example, in some embodiments, the additional therapeutic agent is selected from the group consisting of ribavirin, palivizumab, motavizumab, RSV-IGIV (RespiGam®), MEDI-557, A-60444, MDT-637, BMS-433771, amiodarone, dronedarone, verapamil, Ebola Convalescent Plasma (ECP), TKM-100201, BCX4430 ((2S,3S,4R,5R)-2-(4-amino-5H-pyrrolo[3,2-d]pyrimidin-7-yl)-5-(hydroxymethyl)pyrrolidine-3,4-diol), favipiravir (also known as T-705 or Avigan), T-705 monophosphate, T-705 diphosphate, T-705 triphosphate, FGI-106 (1-N,7-N-bis[3-(dimethylamino)propyl]-3,9-dimethylquinolino[8,7-h]quinolone-1,7-diamine), JK-05, TKM-Ebola, ZMapp, rNAPc2, VRC-EBOADC076-00-VP, OS-2966, MVA-BN filo, brincidofovir, Vaxart adenovirus vector 5-based ebola vaccine, Ad26-ZEBOV, FiloVax vaccine, GOVX-E301, GOVX-E302, ebola virus entry inhibitors (NPC1 inhibitors), rVSV-EBOV, and combinations thereof. In some embodiments, the additional therapeutic agent is ZMapp, mAB114, REGEN-EB3, and combinations thereof.

In some embodiments, the additional therapeutic agent is an agent for treatment of HCV. In some embodiments, the additional therapeutic agent is a HCV polymerase inhibitor. For example, in some embodiments, the additional therapeutic agent is selected from the group consisting of sofosbuvir, GS-6620, PSI-938, ribavirin, tegobuvir, radalbuvir, MK-0608, and combinations thereof. In some embodiments, the additional therapeutic agent is a HCV protease inhibitor. For example, in some embodiments, the additional therapeutic agent is selected from the group consisting of such as GS-9256, vedroprevir, voxilaprevir, and combinations thereof.

In some embodiments, the additional therapeutic agent is a NS5A inhibitor. For example, in some embodiments, the additional therapeutic agent is selected from the group consisting of ledipasvir, velpatasvir, and combinations thereof.

In some embodiments, the additional therapeutic agent is an anti HBV agent. For example, in some embodiments, the additional therapeutic agent is tenofovir disoproxil fumarate and emtricitabine, or a combination thereof. Examples of additional anti HBV agents include but are not limited to alpha-hydroxytropolones, amdoxovir, antroquinonol, beta-hydroxycytosine nucleosides, ARB-199, CCC-0975, ccc-R08, elvucitabine, ezetimibe, cyclosporin A, gentiopicrin (gentiopicroside), HH-003, hepalatide, JNJ-56136379, nitazoxanide, birinapant, NJK14047, NOV-205 (molixan, BAM-205), oligotide, mivotilate, feron, GST-HG-131, levamisole, Ka Shu Ning, alloferon, WS-007, Y-101 (Ti Fen Tai), rSIFN-co, PEG-IIFNm, KW-3, BP-Inter-014, oleanolic acid, HepB-nRNA, cTP-5 (rTP-5), HSK-II-2, HEISCO-106-1, HEISCO-106, Hepbarna, IBPB-0061A, Hepuyinfen, DasKloster 0014-01, ISA-204, Jiangantai (Ganxikang), MIV-210, OB-AI-004, PF-06, picroside, DasKloster-0039, hepulantai, IMB-2613, TCM-800B, reduced glutathione, RO-6864018, RG-7834, QL-007sofosbuvir, ledipasvir, UB-551, and ZH-2N, and the compounds disclosed in US20150210682, (Roche), US 2016/0122344 (Roche), WO2015173164, WO2016023877, US2015252057A (Roche), WO16128335A1 (Roche), WO16120186A1 (Roche), US2016237090A (Roche), WO16107833A1 (Roche), WO16107832A1 (Roche), US2016176899A (Roche), WO16102438A1 (Roche), WO16012470A1 (Roche), US2016220586A (Roche), and US2015031687A (Roche). In some embodiments, the additional therapeutic agent is a HBV polymerase inhibitor. Examples of HBV DNA polymerase inhibitors include, but are not limited to, adefovir (HEPSERA®), emtricitabine (EMTRIVA®), tenofovir disoproxil fimarate (VIREAD®), tenofovir alafenamide, tenofovir, tenofovir disoproxil, tenofovir alafenamide fiumarate, tenofovir alafenamide hemifimarate, tenofovir dipivoxil, tenofovir dipivoxil fimarate, tenofovir octadecyloxyethyl ester, CMX-157, tenofovir exalidex, besifovir, entecavir (BARACLUDE®), entecavir maleate, telbivudine (TYZEKA®), filocilovir, pradefovir, clevudine, ribavirin, lamivudine (EPIVIR-HBV®), phosphazide, famciclovir, fusolin, metacavir, SNC-019754, FMCA, AGX-1009, AR-II-04-26, HIP-1302, tenofovir disoproxil aspartate, tenofovir disoproxil orotate, and HS-10234. In some embodiments, the additional therapeutic agent is a HBV capsid inhibitor.

In some embodiments, the additional therapeutic agent is an agent for treatment of HIV. In some embodiments, the additional therapeutic agent is selected from the group consisting of HIV protease inhibitors, HIV integrase inhibitors, entry inhibitors, HIV nucleoside reverse transcriptase inhibitors, HIV nonnucleoside reverse transcriptase inhibitors, acyclic nucleoside phosphonate analogues, and combinations thereof.

In some embodiments, the additional therapeutic agent is selected from the group consisting of HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, immunomodulators, immunotherapeutic agents, antibody-drug conjugates, gene modifiers, gene editors (such as CRISPR/Cas9, zinc finger nucleases, homing nucleases, synthetic nucleases, TALENs), and cell therapies (such as chimeric antigen receptor T-cell, CAR-T, and engineered T cell receptors, TCR-T, autologous T cell therapies).

In some embodiments, the additional therapeutic agent is selected from the group consisting of combination drugs for HIV, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, and bispecific antibodies, and "antibody-like" therapeutic proteins, and combinations thereof.

In some embodiments, the additional therapeutic agent is a HIV combination drug. Examples of the HIV combination drugs include, but are not limited to ATRIPLA® (efavirenz, tenofovir disoproxil fumarate, and emtricitabine); BIKTARVY® (bictegravir, emtricitabine, and tenofovir alafenamide); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); SYMTUZA® (darunavir, tenofovir alafenamide hemifumarate, emtricitabine, and cobicistat); SYMFI™ (efavirenz, lamivudine, and tenofovir disoproxil fumarate); CIMDU™ (lamivudine and tenofovir disoproxil fumarate); tenofovir and lamivudine; tenofovir alafenamide and emtricitabine; tenofovir alafenamide hemifumarate and emtricitabine; tenofovir alafenamide hemifumarate, emtricitabine, and rilpivirine; tenofovir alafenamide hemifumarate, emtricitabine, cobicistat, and elvitegravir; COMBIVIR® (zidovudine and lamivudine; AZT+3TC); EPZICOM® (LIVEXA®; abacavir sulfate and lamivudine; ABC+3TC); KALETRA® (ALUVIA®; lopinavir and ritonavir); TRIUMEQ® (dolutegravir, abacavir, and lamivudine); TRIZIVIR® (abacavir sulfate, zidovudine, and lamivudine; ABC+AZT+3TC); atazanavir and cobicistat; atazanavir sulfate and cobicistat; atazanavir sulfate and ritonavir; darunavir and cobicistat; dolutegravir and rilpivirine; dolutegravir and rilpivirine hydrochloride; dolutegravir, abacavir sulfate, and lamivudine; lamivudine, nevirapine, and zidovudine; raltegravir and lamivudine; doravirine, lamivudine, and tenofovir disoproxil fumarate; doravirine, lamivudine, and tenofovir disoproxil; dapivirine+levonorgestrel, dolutegravir+lamivudine, dolutegravir+emtricitabine+tenofovir alafenamide, elsulfavirine+emtricitabine+tenofovir disoproxil, lamivudine+abacavir+zidovudine, lamivudine+abacavir, lamivudine+tenofovir disoproxil fumarate, lamivudine+zidovudine+nevirapine, lopinavir+ritonavir, lopinavir+ritonavir+abacavir+lamivudine, lopinavir+ritonavir+zidovudine+lamivudine, tenofovir+lamivudine, and tenofovir disoproxil fumarate+emtricitabine+rilpivirine hydrochloride, lopinavir, ritonavir, zidovudine and lamivudine.

In some embodiments, the additional therapeutic agent is a HIV protease inhibitor. For example, in some embodiments the additional therapeutic agent is selected from the group consisting of saquinavir, ritonavir, indinavir, nelfinavir, amprenavir, lopinavir, atazanavir, fosamprenavir, darunavir, tipranavir, cobicistat, ASC-09, AEBL-2, MK-8718, GS-9500, GS-1156, and combinations thereof. For example, in some embodiments the additional therapeutic agent is selected from the group consisting of saquinavir, ritonavir, indinavir, nelfinavir, amprenavir, lopinavir, atazanavir, fosamprenavir, darunavir, tipranavir, cobicistat. In some embodiments, the additional therapeutic agent is selected from the group consisting of amprenavir, atazanavir, brecanavir, darunavir, fosamprenavir, fosamprenavir calcium, indinavir, indinavir sulfate, lopinavir, nelfinavir, nelfinavir mesylate, ritonavir, saquinavir, saquinavir mesylate, tipranavir, DG-17, TMB-657 (PPL-100), T-169, BL-008, MK-8122, TMB-607, TMC-310911, and combinations thereof.

In some embodiments, the additional therapeutic agent is a HIV integrase inhibitor. For example, in some embodiments, the additional therapeutic agent is selected from the group consisting of raltegravir, elvitegravir, dolutegravir, abacavir, lamivudine, bictegravir and combinations thereof. In some embodiments, the additional therapeutic agent is bictegravir. In some embodiments, the additional therapeutic agent is selected from a group consisting of bictegravir, elvitegravir, curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, raltegravir, dolutegravir, JTK-351, bictegravir, AVX-15567, BMS-986197, cabotegravir (long-acting injectable), diketo quinolin-4-1 derivatives, integrase-LEDGF inhibitor, ledgins, M-522, M-532, NSC-310217, NSC-371056, NSC-48240, NSC-642710, NSC-699171, NSC-699172, NSC-699173, NSC-699174, stilbenedisulfonic acid, T-169, VM-3500, cabotegravir, and combinations thereof.

In some embodiments, the additional therapeutic agent is a HIV entry inhibitor. For example, in some embodiments, the additional therapeutic agent is selected from the group consisting of enfuvirtide, maraviroc, and combinations thereof. Further examples of HIV entry inhibitors include, but are not limited to, cenicriviroc, CCR5 inhibitors, gp41 inhibitors, CD4 attachment inhibitors, DS-003 (BMS-599793), gp120 inhibitors, and CXCR4 inhibitors. Examples of CCR5 inhibitors include aplaviroc, vicriviroc, maraviroc, cenicriviroc, leronlimab (PRO-140), adaptavir (RAP-101), nifeviroc (TD-0232), anti-GP120/CD4 or CCR5 bispecific antibodies, B-07, MB-66, polypeptide C25P, TD-0680, and vMIP (Haimipu). Examples of CXCR4 inhibitors include plerixafor, ALT-1188, N15 peptide, and vMIP (Haimipu).

In some embodiments, the additional therapeutic agent is a HIV nucleoside reverse transcriptase inhibitors. In some embodiments, the additional therapeutic agent is a HIV nonnucleoside reverse transcriptase inhibitors. In some embodiments, the additional therapeutic agent is an acyclic nucleoside phosphonate analogue. In some embodiments, the additional therapeutic agent is a HIV capsid inhibitor.

In some embodiments, the additional therapeutic agent is a HIV nucleoside or nucleotide inhibitor of reverse transcriptase. For example, the additional therapeutic agent is selected from the group consisting of adefovir, adefovir dipivoxil, azvudine, emtricitabine, tenofovir, tenofovir alafenamide, tenofovir alafenamide fumarate, tenofovir alafenamide hemifumarate, tenofovir disoproxil, tenofovir disoproxil fumarate, tenofovir disoproxil hemifumarate, VIDEX® and VIDEX EC® (didanosine, ddI), abacavir, abacavir sulfate, alovudine, apricitabine, censavudine, didanosine, elvucitabine, festinavir, fosalvudine tidoxil, CMX-157, dapivirine, doravirine, etravirine, OCR-5753, tenofovir disoproxil orotate, fozivudine tidoxil, islatravir, lamivudine, phosphazid, stavudine, zalcitabine, zidovudine, rovafovir etalafenamide (GS-9131), GS-9148, MK-8504, MK-8591, MK-858, VM-2500, KP-1461, and combinations thereof.

In some embodiments, the additional therapeutic agent is a HIV non-nucleoside or non-nucleotide inhibitor of reverse transcriptase. For example, the additional agent is selected from the group consisting of dapivirine, delavirdine, delavirdine mesylate, doravirine, efavirenz, etravirine, lentinan, MK-8583, nevirapine, rilpivirine, TMC-278LA, ACC-007, AIC-292, KM-023, PC-1005, elsulfavirine rilp (VM-1500), combinations thereof.

In some embodiments, the additional therapeutic agents are selected from ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); adefovir; adefovir dipivoxil; cobicistat; emtricitabine; tenofovir; tenofovir disoproxil; tenofovir disoproxil fumarate; tenofovir alafenamide; tenofovir alafenamide hemifumarate; TRIUMEQ® (dolutegravir, abacavir, and lamivudine); dolutegravir, abacavir sulfate, and lamivudine; raltegravir; raltegravir and lamivudine; maraviroc; enfuvirtide; ALUVIA® (KALETRA®; lopinavir and ritonavir); COMBIVIR® (zidovudine and lamivudine; AZT+3TC); EPZICOM® (LIVEXA®; abacavir sulfate and lamivudine; ABC+3TC); TRIZIVIR® (abacavir sulfate, zidovudine, and lamivudine; ABC+AZT+3TC); rilpivirine; rilpivirine hydrochloride; atazanavir sulfate and cobicistat; atazanavir and cobicistat; darunavir and cobicistat; atazanavir; atazanavir sulfate; dolutegravir; elvitegravir; ritonavir; atazanavir sulfate and ritonavir; darunavir; lamivudine; prolastin; fosamprenavir; fosamprenavir calcium efavirenz; etravirine; nelfinavir; nelfinavir mesylate; interferon; didanosine; stavudine; indinavir; indinavir sulfate; tenofovir and lamivudine; zidovudine; nevirapine; saquinavir; saquinavir mesylate; aldesleukin; zalcitabine; tipranavir; amprenavir; delavirdine; delavirdine mesylate; Radha-108 (receptol); lamivudine and tenofovir disoproxil fumarate; efavirenz, lamivudine, and tenofovir disoproxil fumarate; phosphazid; lamivudine, nevirapine, and zidovudine; abacavir; and abacavir sulfate.

In some embodiments, the additional therapeutic agent is selected from the group consisting of colistin, valrubicin, icatibant, bepotastine, epirubicin, epoprosetnol, vapreotide, aprepitant, caspofungin, perphenazine, atazanavir, efavirenz, ritonavir, acyclovir, ganciclovir, penciclovir, prulifloxacin, bictegravir, nelfinavir, tegobuvi, nelfinavir, praziquantel, pitavastatin, perampanel, eszopiclone, and zopiclone.

In some embodiments, the additional therapeutic agent is an inhibitor of Bruton tyrosine kinase (BTK, AGMXI, AT, ATK, BPK, IGHD3, IMD1, PSCTK1, XLA; NCBI Gene ID: 695). For example, in some embodiments, the additional therapeutic agent is selected from the group consisting of(S)-6-amino-9-(1-(but-2-ynoyl)pyrrolidin-3-yl)-7-(4-phenoxyphenyl)-7H-purin-8(9H)-one, acalabrutinib (ACP-196), BGB-3111, CB988, HM71224, ibrutinib (Imbruvica), M-2951 (evobrutinib), M7583, tirabrutinib (ONO-4059), PRN-1008, spebrutinib (CC-292), TAK-020, vecabrutinib, ARQ-531, SHR-1459, DTRMWXHS-12, TAS-5315, AZD6738, calquence, danvatirsen, and combinations thereof. In some embodiments, the additional therapeutic agent is selected from a group consisting of tirabrutinib, ibrutinib, acalabrutinib, and combinations thereof. In some embodiments, the additional therapeutic agent is selected from a group consisting of tirabrutinib, ibrutinib, and combinations thereof. In some embodiments, the additional therapeutic agent is tyrphostin A9 (A9).

In some embodiments, the additional therapeutic agent is a KRAS inhibitor. For example, in some embodiments, the additional therapeutic agent is selected from the group consisting of AMG-510, COTI-219, MRTX-1257, ARS-3248, ARS-853, WDB-178, BI-3406, BI-1701963, ARS-1620 (G12C), SML-8-73-1 (G12C), Compound 3144 (G12D), Kobe0065/2602 (Ras GTP), RT11, MRTX-849 (G12C) and K-Ras(G12D)-selective inhibitory peptides, including KRpep-2 (Ac-RRCPLYISYDPVCRR-NH2), KRpep-2d (Ac-RRRRCPLYISYDPVCRRRR-NH2), and combinations thereof.

In some embodiments, the additional therapeutic agent is a proteasome inhibitor. For example, in some embodiments, the additional therapeutic agent is selected from a group consisting of ixazomib, carfilzomib, marizomib, bortezomib, and combinations thereof in some embodiments, the additional therapeutic agent is carfilzomib.

In some embodiments, the additional therapeutic agent is a vaccine. For example, in some embodiments, the additional therapeutic agent is a DNA vaccine, RNA vaccine, live-attenuated vaccine, therapeutic vaccine, prophylactic vaccine, protein based vaccine, or a combination thereof. In some embodiments, the additional therapeutic agent is mRNA-1273. In some embodiments, the additional therapeutic agent is INO-4800 or INO-4700. In some embodiments, the additional therapeutic agent is live-attenuated RSV vaccine MEDI-559, human monoclonal antibody REGN2222 against RSV, palivizumab, respiratory syncytial virus immune globulin, intravenous [RSV-IGIV], and combinations thereof. In some embodiments, the additional therapeutic agent is a HBV vaccine, for example pediarix, engerix-B, and recombivax HB. In some embodiments, the additional therapeutic agent is a VZV vaccine, for example zostavax and varivax. In some embodiments, the additional therapeutic agent is a HPV vaccine, for example cervarix, gardasil 9, and gardasil. In some embodiments, the additional therapeutic agent is an influenza virus vaccine. For example, a (i) monovalent vaccine for influenza A (e.g. influenza A [H5N1] virus monovalent vaccine and influenza A [H1N1] 2009 virus monovalent vaccines), (ii) trivalent vaccine for influenza A and B viruses (e.g. Afluria, Agriflu, Fluad, Fluarix, Flublok, Flucelvax, FluLaval, Fluvirin, and Fluzone), and (iii) quadrivalent vaccine for influenza A and B viruses (FluMist, Fluarix, Fluzone, and FluLaval). In some embodiments, the additional therapeutic agent is a human adenovirus vaccine (e.g.

Adenovirus Type 4 and Type 7 Vaccine, Live, Oral). In some embodiments, the additional therapeutic agent is a rotavirus vaccine (e.g. Rotarix for rotavirus serotype G1, G3, G4, or G9 and RotaTeq for rotavirus serotype G1, G2, G3, or G4). In some embodiments, the additional therapeutic agent is a hepatitis A virus vaccine (e.g. Havrix and Vagta). In some embodiments, the additional therapeutic agent is poliovirus vaccines (e.g. Kinrix, Quadracel, and Ipol). In some embodiments, the additional therapeutic agent is a yellow fever virus vaccine (e.g. YF-Vax). In some embodiments, the additional therapeutic agent is a Japanese encephalitis virus vaccines (e.g. Ixiaro and JE-Vax). In some embodiments, the additional therapeutic agent is a measles vaccine (e.g. M-M-R II and ProQuad). In some embodiments, the additional therapeutic agent is a mumps vaccine (e.g. M-M-R II and ProQuad). In some embodiments, the additional therapeutic agent is a rubella vaccine (e.g. M-M-R II and ProQuad). In some embodiments, the additional therapeutic agent is a varicella vaccine (e.g. ProQuad). In some embodiments, the additional therapeutic agent is a rabies vaccine (e.g. Imovax and RabAvert). In some embodiments, the additional therapeutic agent is a variola virus (smallpox) vaccine (ACAM2000). In some embodiments, the additional therapeutic agent is a and hepatitis E virus (HEV) vaccine (e.g. HEV239). In some embodiments, the additional therapeutic agent is a 2019-nCov vaccine.

In some embodiments, the additional therapeutic agent is an antibody, for example a monoclonal antibody. For example, the additional therapeutic agent is an antibody against 2019-nCov selected from the group consisting of the Regeneron antibodies, the Wuxi Antibodies, the Vir Biotechnology Antibodies, antibodies that target the SARS-CoV-2 spike protein, antibodies that can neutralize SARS-CoV-2 (SARS-CoV-2 neutralizing antibodies), and combinations thereof. In some embodiments, the additional therapeutic agent is anti-SARS CoV antibody CR-3022. In some embodiments, the additional therapeutic agent is aPD-1 antibody. In some embodiments, the additional therapeutic agent is REGN-COV2. In some embodiments, the additional therapeutic agent is LY-CoV555.

In some embodiments, the additional therapeutic agent is recombinant cytokine gene-derived protein injection.

In some embodiments, the additional therapeutic agent is a polymerase inhibitor. In some embodiments, the additional therapeutic agent is a DNA polymerase inhibitor. For example, in some embodiments, the additional therapeutic agent is cidofovir. In some embodiments, the additional therapeutic agent is a RNA polymerase inhibitor. For example, in some embodiments, the additional therapeutic agent is selected from the group consisting of ribavirin, favipiravir, lamivudine, pimodivir and combination thereof.

In some embodiments, the additional therapeutic agent is selected from the group consisting of lopinavir, ritonavir, interferon-alpha-2b, ritonavir, arbidol, hydroxychloroquine, darunavir and cobicistat, abidol hydrochloride, oseltamivir, litonavir, emtricitabine, tenofovir alafenamide fumarate, baloxavir marboxil, ruxolitinib, and combinations thereof.

In some embodiments, the additional therapeutic agent is selected from the group consisting of 6'-fluorinated aristeromycin analogues, acyclovir fleximer analogues, disulfiram, thiopurine analogues, ASC09F, GC376, GC813, phenylisoserine derivatives, neuroiminidase inhibitor analogues, pyrithiobac derivatives, bananins and 5-hydroxychromone derivatives, SSYA10-001, griffithsin, HR2P-M1, HR2P-M2, P21S10, Dihydrotanshinone E-64-C and E-64-D, OC43-HR2P, MERS-5HB, 229E-HR1P, 229E-HR2P, resveratrol, 1-thia-4-azaspiro[4.5]decan-3-one derivatives, gemcitabine hydrochloride, loperamide, recombinant interferons, cyclosporine A, alisporivir, imatinib mesylate, dasatinib, selumetinib, trametinib, rapamycin, saracatinib, chlorpromazine, triflupromazine, fluphenazine, thiethylperazine, promethazine, cyclophilin inhibitors, K11777, camostat, k22, teicoplanin derivatives, benzo-heterocyclic amine derivatives N30, mycophenolic acid, silvestrol, and combinations thereof.

In some embodiments, the additional therapeutic agent is an antibody. In some embodiments, the additional therapeutic agent is an antibody that binds to a coronavirus, for example an antibody that binds to SARS or MERS. In some embodiments, the additional therapeutic agent is a of 2019-nCoV virus antibody.

In some embodiments, the additional therapeutic agent in a steroid, for example corticosteroid. In some embodiments, the additional therapeutic agent is dexamethasone.

Compositions of the invention are also used in combination with other active ingredients. For the treatment of 2019-nCoV virus infections, preferably, the other active therapeutic agent is active against coronavirus infections, for example 2019-nCoV virus infections. The compounds and compositions of the present invention are also intended for use with general care provided patients with 2019-nCoV viral infections, including parenteral fluids (including dextrose saline and Ringer's lactate) and nutrition, antibiotic (including metronidazole and cephalosporin antibiotics, such as ceftriaxone and cefuroxime) and/or antifungal prophylaxis, fever and pain medication, antiemetic (such as metoclopramide) and/or antidiarrheal agents, vitamin and mineral supplements (including Vitamin K and zinc sulfate), anti-inflammatory agents (such as ibuprofen or steroids), corticosteroids such as methylprednisolone, immonumodulatory medications (e.g. interferon), other small molecule or biologics antiviral agents targeting 2019-nCoV (such as but not limited to lopinavir/ritonavir, EIDD-1931, favipiravir, ribavirine, neutralizing antibodies, etc.), vaccines, pain medications, and medications for other common diseases in the patient population, such anti-malarial agents (including artemether and artesunate-lumefantrine combination therapy), typhoid (including quinolone antibiotics, such as ciprofloxacin, macrolide antibiotics, such as azithromycin, cephalosporin antibiotics, such as ceftriaxone, or aminopenicillins, such as ampicillin), or shigellosis. In some embodiments, the additional therapeutic agent is dihydroartemisinin/piperaquine.

In some embodiments, the additional therapeutic agent is an immunomodulator. Examples of immune-based therapies include toll-like receptors modulators such as tlr, tlr2, tlr3, tlr4, tlr5, tlr6, tlr7, tlr8, tlr9, tlr10, tlr11, tlr12, and tlr13; programmed cell death protein 1 (Pd-1) modulators; programmed death-ligand 1 (Pd-L1) modulators; IL-15 modulators; DermaVir; interleukin-7; plaquenil (hydroxychloroquine); proleukin (aldesleukin, IL-2); interferon alfa; interferon alfa-2b; interferon alfa-n3; pegylated interferon alfa; interferon gamma; hydroxyurea; mycophenolate mofetil (MPA) and its ester derivative mycophenolate mofetil (MMF); ribavirin; polymer polyethyleneimine (PEI); gepon; IL-12; WF-10; VGV-1; MOR-22; BMS-936559; CYT-107, interleukin-15/Fc fusion protein, AM-0015, ALT-803, NIZ-985, NKTR-255, NKTR-262, NKTR-214, normferon, peginterferon alfa-2a, peginterferon alfa-2b, recombinant interleukin-15, Xmab-24306, RPI-MN, STING modulators, RIG-I modulators, NOD2 modulators, SB-9200, and IR-103. In some embodiments, the additional therapeutic agent is fingolimod, leflunomide, or a combination thereof. In some embodiments, the additional therapeutic agent is thalidomide.

In some embodiments, the additional therapeutic agent is an IL-6 inhibitor, for example tocilizumab, sarilumab, or a combination thereof.

In some embodiments, the additional therapeutic agent is an anti-TNF inhibitor. For example, the additional therapeutic agent is adalimumab, etanercept, golimumab, infliximab, or a combination thereof.

In some embodiments, the additional therapeutic agent is a JAK inhibitor, for example the additional therapeutic agent is baricitinib, filgotinib, olumiant, or a combination thereof.

In some embodiments, the additional therapeutic agent is an inflammation inhibitor, for example pirfenidone.

In some embodiments, the additional therapeutic agent is an antibiotic for secondary bacterial pneumonia. For example, the additional therapeutic agent is macrolide antibiotics (e.g. azithromycin, clarithromycin, and *Mycoplasma pneumoniae*), fluoroquinolones (e.g. ciprofloxacin and levofloxacin), tetracyclines (e.g. doxycycline and tetracycline), or a combination thereof.

In some embodiments, the compounds disclosed herein are used in combination with pneumonia standard of care (see e.g. Pediatric Community Pneumonia Guidelines, CID 2011:53 (1 October)). Treatment for pneumonia generally involves curing the infection and preventing complications. Specific treatment will depend on several factors, including the type and severity of pneumonia, age and overall health of the individuals. The options include: (i) antibiotics, (ii) cough medicine, and (iii) fever reducers/pain relievers (for e.g. aspirin, ibuprofen (Advil, Motrin IB, others) and acetaminophen (Tylenol, others)). In some embodiments, the additional therapeutic agent is bromhexine anti-cough.

In some embodiments, the compounds disclosed herein are used in combination with immunoglobulin from cured COVID-19 patients. In some embodiments, the compounds disclosed herein are used in combination with plasma transfusion. In some embodiments, the compounds disclosed herein are used in combination with stem cells.

In some embodiments, the additional therapeutic agent is an TLR agonist. Examples of TLR agonists include, but are not limited to, vesatolimod (GS-9620), GS-986, IR-103, lefitolimod, tilsotolimod, rintatolimod, DSP-0509, AL-034, G-100, cobitolimod, AST-008, motolimod, GSK-1795091, GSK-2245035, VTX-1463, GS-9688, LHC-165, BDB-001, RG-7854, telratolimod.RO-7020531.

In some embodiments, the additional therapeutic agent is selected from the group consisting of bortezomid, flurazepam, ponatinib, sorafenib, paramethasone, clocortolone, flucloxacillin, sertindole, clevidipine, atorvastatin, cinolazepam, clofazimine, fosaprepitant, and combinations thereof.

In some embodiments, the additional therapeutic agent is carrimycin, suramin, triazavirin, dipyridamole, bevacizumab, meplazumab, GD31 (*rhizobium*), NLRP inflammasome inhibitor, or α-ketoamine. In some embodiments, the additional therapeutic agent is recombinant human angiotensin-converting enzyme 2 (rhACE2). In some embodiments, the additional therapeutic agent is viral macrophage inflammatory protein (vMIP).

In some embodiments, the additional therapeutic agent is an anti-viroporin therapeutic. For example, the additional therapeutic agent is BIT-314 or BIT-225. In some embodiments, the additional therapeutic agent is coronavirus E protein inhibitor. For example, the additional therapeutic agent is BIT-009. Further examples of additional therapeutic agents include those described in WO-2004112687, WO-2006135978, WO-2018145148, and WO-2009018609.

It is also possible to combine any compound of the disclosure with one or more additional active therapeutic agents in a unitary dosage form for simultaneous or sequential administration to a patient. The combination therapy may be administered as a simultaneous or sequential regimen. When administered sequentially, the combination may be administered in two or more administrations.

Co-administration of a compound of the disclosure with one or more other active therapeutic agents generally refers to simultaneous or sequential administration of a compound of the disclosure and one or more other active therapeutic agents, such that therapeutically effective amounts of the compound of the disclosure and one or more other active therapeutic agents are both present in the body of the patient.

Co-administration includes administration of unit dosages of the compounds of the invention before or after administration of unit dosages of one or more other active therapeutic agents, for example, administration of the compounds of the invention within seconds, minutes, or hours of the administration of one or more other active therapeutic agents. For example, a unit dose of a compound of the disclosure can be administered first, followed within seconds or minutes by administration of a unit dose of one or more other active therapeutic agents. Alternatively, a unit dose of one or more other therapeutic agents can be administered first, followed by administration of a unit dose of a compound of the disclosure within seconds or minutes. In some cases, it may be desirable to administer a unit dose of a compound of the disclosure first, followed, after a period of hours (e.g., 1-12 hours), by administration of a unit dose of one or more other active therapeutic agents. In other cases, it may be desirable to administer a unit dose of one or more other active therapeutic agents first, followed, after a period of hours (e.g., 1-12 hours), by administration of a unit dose of a compound of the disclosure.

The combination therapy may provide "synergy" and "synergistic", i.e. the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g. in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together. A synergistic anti-viral effect denotes an antiviral effect which is greater than the predicted purely additive effects of the individual compounds of the combination.

1. Combination Therapy for the Treatment of Pneumoviridae

The compounds provided herein are also used in combination with other active therapeutic agents. For the treatment of Pneumoviridae virus infections, preferably, the other active therapeutic agent is active against Pneumoviridae virus infections, particularly respiratory syncytial virus infections and/or metapneumovirus infections. Non-limiting examples of these other active therapeutic agents active against RSV are ribavirin, palivizumab, motavizumab, RSV-IGIV (RespiGam®), MEDI-557, A-60444 (also known as RSV604), MDT-637, BMS-433771, ALN-RSV0, ALX-0171 and mixtures thereof. Other non-limiting examples of other active therapeutic agents active against respiratory syncytial virus infections include respiratory syncytial virus protein F inhibitors, such as AK-0529; RV-521, ALX-0171, JNJ-53718678, BTA-585, and presatovir; RNA polymerase inhibitors, such as lumicitabine and ALS-8112; anti-RSV G protein antibodies, such as anti-G-protein mAb; viral replication inhibitors, such as nitazoxanide.

In some embodiments, the other active therapeutic agent may be a vaccine for the treatment or prevention of RSV, including but not limited to MVA-BN RSV, RSV-F, MEDI-8897, JNJ-64400141, DPX-RSV, SynGEM, GSK-3389245A, GSK-300389-1A, RSV-MEDI deltaM2-2 vaccine, VRC-RSVRGP084-00VP, Ad35-RSV-FA2, Ad26-RSV-FA2, and RSV fusion glycoprotein subunit vaccine.

Non-limiting examples of other active therapeutic agents active against metapneumovirus infections include sialidase modulators such as DAS-181; RNA polymerase inhibitors, such as ALS-8112; and antibodies for the treatment of Metapneumovirus infections, such as EV-046113.

In some embodiments, the other active therapeutic agent may be a vaccine for the treatment or prevention of metapneumovirus infections, including but not limited to mRNA-1653 and rHMPV-Pa vaccine.

2. Combination Therapy for the Treatment of Picornaviridae

The compounds provided herein are also used in combination with other active therapeutic agents. For the treatment of Picornaviridae virus infections, preferably, the other active therapeutic agent is active against Picornaviridae virus infections, particularly Enterovirus infections. Non-limiting examples of these other active therapeutic agents are capsid binding inhibitors such as pleconaril, BTA-798 (vapendavir) and other compounds disclosed by Wu, et al. (U.S. Pat. No. 7,078,403) and Watson (U.S. Pat. No. 7,166,604); fusion sialidase protein such as DAS-181; a capsid protein VP1 inhibitor such as VVX-003 and AZN-001; a viral protease inhibitor such as CW-33; a phosphatidylinositol 4 kinase beta inhibitor such as GSK-480 and GSK-533; anti-EV71 antibody.

In some embodiments, the other active therapeutic agent may be a vaccine for the treatment or prevention of Picornaviridae virus infections, including but not limited to EV71 vaccines, TAK-021, and EV-D68 adenovector-based vaccine.

3. Combination Therapy for Respiratory Infections

Many of the infections of the Pneumoviridae and Picornaviridae viruses are respiratory infections. Therefore, additional active therapeutics used to treat respiratory symptoms and sequelae of infection may be used in combination with the compounds provided herein. The additional agents are preferably administered orally or by direct inhalation. For example, other preferred additional therapeutic agents in combination with the compounds provided herein for the treatment of viral respiratory infections include, but are not limited to, bronchodilators and corticosteroids.

Glucocorticoids

Glucocorticoids, which were first introduced as an asthma therapy in 1950 (Carryer, Journal of Allergy, 21, 282-287, 1950), remain the most potent and consistently effective therapy for this disease, although their mechanism of action is not yet fully understood (Morris, J. Allergy Clin. Immunol., 75 (1 Pt) 1-13, 1985). Unfortunately, oral glucocorticoid therapies are associated with profound undesirable side effects such as truncal obesity, hypertension, glaucoma, glucose intolerance, acceleration of cataract formation, bone mineral loss, and psychological effects, all of which limit their use as long-term therapeutic agents (Goodman and Gilman, 10th edition, 2001). A solution to systemic side effects is to deliver steroid drugs directly to the site of inflammation. Inhaled corticosteroids (ICS) have been developed to mitigate the severe adverse effects of oral steroids. Non-limiting examples of corticosteroids that may be used in combinations with the compounds provided herein are dexamethasone, dexamethasone sodium phosphate, fluorometholone, fluorometholone acetate, loteprednol, loteprednol etabonate, hydrocortisone, prednisolone, fludrocortisones, triamcinolone, triamcinolone acetonide, betamethasone, beclomethasone diproprionate, methylprednisolone, fluocinolone, fluocinolone acetonide, flunisolide, fluocortin-21-butylate, flumethasone, flumetasone pivalate, budesonide, halobetasol propionate, mometasone furoate, fluticasone, AZD-7594, ciclesonide; or a pharmaceutically acceptable salts thereof.

Anti-Inflammatory Agents

Other anti-inflammatory agents working through anti-inflammatory cascade mechanisms are also useful as additional therapeutic agents in combination with the compounds provided herein for the treatment of viral respiratory infections. Applying "anti-inflammatory signal transduction modulators" (referred to in this text as AISTM), like phosphodiesterase inhibitors (e.g. PDE-4, PDE-5, or PDE-7 specific), transcription factor inhibitors (e.g. blocking NFκB through IKK inhibition), or kinase inhibitors (e.g. blocking P38 MAP, JNK, PI3K, EGFR or Syk) is a logical approach to switching off inflammation as these small molecules target a limited number of common intracellular pathways—those signal transduction pathways that are critical points for the anti-inflammatory therapeutic intervention (see review by P. J. Barnes, 2006). These non-limiting additional therapeutic agents include: 5-(2,4-Difluoro-phenoxy)-1-isobutyl-1H-indazole-6-carboxylic acid (2-dimethylamino-ethyl)-amide (P38 Map kinase inhibitor ARRY-797); 3-Cyclopropylmethoxy-N-(3,5-dichloro-pyridin-4-yl)-4-difluorormethoxy-benzamide (PDE-4 inhibitor Roflumilast); 4-[2-(3-cyclopentyloxy-4-methoxyphenyl)-2-phenyl-ethyl]-pyridine (PDE-4 inhibitor CDP-840); N-(3,5-dichloro-4-pyridinyl)-4-(difluoromethoxy)-8-[(methylsulfonyl)amino]-1-dibenzofurancarboxamide (PDE-4 inhibitor Oglemilast); N-(3,5-Dichloro-pyridin-4-yl)-2-[1-(4-fluorobenzyl)-5-hydroxy-1H-indol-3-yl]-2-oxo-acetamide (PDE-4 inhibitor AWD 12-281); 8-Methoxy-2-trifluoromethyl-quinoline-5-carboxylic acid (3,5-dichloro-1-oxy-pyridin-4-yl)-amide (PDE-4 inhibitor Sch 351591); 4-[5-(4-Fluorophenyl)-2-(4-methanesulfinyl-phenyl)-1H-imidazol-4-yl]-pyridine (P38 inhibitor SB-203850); 4-[4-(4-Fluoro-phenyl)-1-(3-phenyl-propyl)-5-pyridin-4-yl-1H-imidazol-2-yl]-but-3-yn-1-ol (P38 inhibitor RWJ-67657); 4-Cyano-4-(3-cyclopentyloxy-4-methoxy-phenyl)-cyclohexanecarboxylic acid 2-diethylamino-ethyl ester (2-diethyl-ethyl ester prodrug of Cilomilast, PDE-4 inhibitor); (3-Chloro-4-fluorophenyl)-[7-methoxy-6-(3-morpholin-4-yl-propoxy)-quinazolin-4-yl]-amine (Gefitinib, EGFR inhibitor); and 4-(4-Methyl-piperazin-1-ylmethyl)-N-[4-methyl-3-(4-pyridin-3-yl-pyrimidin-2-ylamino)-phenyl]-benzamide (Imatinib, EGFR inhibitor).

δ2-Adrenoreceptor Agonist Bronchodilators

Combinations comprising inhaled P2-adrenoreceptor agonist bronchodilators such as formoterol, albuterol or salmeterol with the compounds provided herein are also suitable, but non-limiting, combinations useful for the treatment of respiratory viral infections.

Combinations of inhaled P2-adrenoreceptor agonist bronchodilators such as formoterol or salmeterol with ICS's are also used to treat both the bronchoconstriction and the inflammation (Symbicort® and Advair®, respectively). The combinations comprising these ICS and P2-adrenoreceptor agonist combinations along with the compounds provided herein are also suitable, but non-limiting, combinations useful for the treatment of respiratory viral infections.

Other examples of Beta 2 adrenoceptor agonists are bedoradrine, vilanterol, indacaterol, olodaterol, tulobuterol, formoterol, abediterol, salbutamol, arformoterol, levalbuterol, fenoterol, and TD-5471.

Anticholinergics

For the treatment or prophylaxis of pulmonary bronchoconstriction, anticholinergics are of potential use and, therefore, useful as an additional therapeutic agent in combination with the compounds provided herein for the treatment of viral respiratory infections. These anticholinergics include, but are not limited to, antagonists of the muscarinic receptor (particularly of the M3 subtype) which have shown therapeutic efficacy in man for the control of cholinergic tone in COPD (Witek, 1999); 1-{4-Hydroxy-1-[3,3,3-tris-(4-fluoro-phenyl)-propionyl]-pyrrolidine-2-carbonyl}-pyrrolidine-2-carboxylic acid (1-methyl-piperidin-4-ylmethyl)- amide; 3-[3-(2-Diethylamino-acetoxy)-2-phenyl-propionyloxy]-8-isopropyl-8-methyl-8-azonia-bicyclo [3.2.1]octane (Ipratropium-N,N-diethylglycinate); 1-Cyclohexyl-3,4-dihydro-1H-isoquinoline-2-carboxylic acid 1-aza-bicyclo[2.2.2]oct-3-yl ester (Solifenacin); 2-Hydroxymethyl-4-methanesulfinyl-2-phenyl-butyric acid 1-aza-bicyclo[2.2.2]oct-3-yl ester (Revatropate); 2-{1-[2-(2,3-Dihydro-benzofuran-5-yl)-ethyl]-pyrrolidin-3-yl}-2,2-diphenyl-acetamide (Darifenacin); 4-Azepan-1-yl-2,2-diphenyl-butyramide (Buzepide); 7-[3-(2-Diethylamino-acetoxy)-2-phenyl-propionyloxy]-9-ethyl-9-methyl-3-oxa-9-azonia-tricyclo[3.3.1.02,4]nonane (Oxitropium-N,N-diethylglycinate); 7-[2-(2-Diethylamino-acetoxy)-2,2-dithiophen-2-yl-acetoxy]-9,9-dimethyl-3-oxa-9-azonia-tricyclo[3.3.1.02,4]nonane (Tiotropium-N,N-diethylglycinate); Dimethylamino-acetic acid 2-(3-diisopropylamino-1-phenyl-propyl)-4-methyl-phenyl ester (Tolterodine-N,N-dimethylglycinate); 3-[4,4-Bis-(4-fluoro-phenyl)-2-oxo-imidazolidin-1-yl]-1-methyl-1-(2-oxo-2-pyridin-2-yl-ethyl)-pyrrolidinium; 1-[1-(3-Fluoro-benzyl)-piperidin-4-yl]-4,4-bis-(4-fluoro-phenyl)-imidazolidin-2-one; 1-Cyclooctyl-3-(3-methoxy-1-aza-bicyclo[2.2.2]oct-3-yl)-1-phenyl-prop-2-yn-1-ol; 3-[2-(2-Diethylamino-acetoxy)-2,2-di-thiophen-2-yl-acetoxy]-1-(3-phenoxy-propyl)-1-azonia-bicyclo[2.2.2]octane (Aclidinium-N,N-diethylglycinate); or (2-Diethylamino-acetoxy)-di-thiophen-2-yl-acetic acid 1-methyl-1-(2-phenoxy-ethyl)-piperidin-4-yl ester; revefenacin, glycopyrronium bromide, umeclidinium bromide, tiotropium bromide, aclidinium bromide, bencycloquidium bromide.

Mucolytic Agents

The compounds provided herein may also be combined with mucolytic agents to treat both the infection and symptoms of respiratory infections. A non-limiting example of a mucolytic agent is ambroxol. Similarly, the compounds may be combined with expectorants to treat both the infection and symptoms of respiratory infections. A non-limiting example of an expectorant is guaifenesin.

Nebulized hypertonic saline is used to improve immediate and long-term clearance of small airways in patients with lung diseases (Kuzik, *J. Pediatrics* 2007, 266). Thus, the compounds provided herein may also be combined with nebulized hypertonic saline particularly when the virus infection is complicated with bronchiolitis. The combination of the compound provided herein with hypertonic saline may also comprise any of the additional agents discussed above. In some embodiments, about 3% hypertonic saline is used.

4. Combination Therapy for the Treatment of Flaviviridae Virus Infections

The compounds and compositions provided herein are also used in combination with other active therapeutic agents. For the treatment of Flaviviridae virus infections, preferably, the other active therapeutic agent is active against Flaviviridae virus infections.

For treatment of the dengue virus infection, non-limiting examples of the other active therapeutic agents are host cell factor modulators, such as GBV-006; fenretinide ABX-220, BRM-211; alpha-glucosidase 1 inhibitors, such as celgosivir; platelet activating factor receptor (PAFR) antagonists, such as modipafant; cadherin-5/Factor Ia modulators, such as FX-06; NS4B inhibitors, such as JNJ-8359; viral RNA splicing modulators, such as ABX-202; a NS5 polymerase inhibitor; a NS3 protease inhibitor; and a TLR modulator.

In some embodiments, the other active therapeutic agent may be a vaccine for the treatment or prevention of dengue, including but not limited to TetraVax-DV, Dengvaxia®, DPIV-001, TAK-003, live attenuated dengue vaccine, tetravalent dengue fever vaccine, tetravalent DNA vaccine, rDEN2delta30-7169; and DENV-1 PIV.

5. Combination Therapy for the Treatment of Filoviridae Virus Infections

The compounds provided herein are also used in combination with other active therapeutic agents. For the treatment of Filoviridae virus infections, preferably, the other active therapeutic agent is active against Filoviridae virus infections, particularly Marburg virus, Ebola virus and Cueva virus infections. Non-limiting examples of these other active therapeutic agents are: ribavirin, palivizumab, motavizumab, RSV-IGIV (RespiGam®), MEDI-557, A-60444, MDT-637, BMS-433771, amiodarone, dronedarone, verapamil, Ebola Convalescent Plasma (ECP), TKM-100201, BCX4430 ((2S,3S,4R,5R)-2-(4-amino-5H-pyrrolo[3,2-d]pyrimidin-7-yl)-5-(hydroxymethyl)pyrrolidine-3,4-diol), TKM-Ebola, T-705 monophosphate, T-705 diphosphate, T-705 triphosphate, FGI-106 (1-N,7-N-bis[3-(dimethylamino)propyl]-3,9-dimethylquinolino[8,7-h]quinolone-1,7-diamine), rNAPc2, OS-2966, brincidofovir, remdesivir; RNA polymerase inhibitors, such as galidesivir, favipiravir (also known as T-705 or Avigan), JK-05; host cell factor modulators, such as GMV-006; cadherin-5/factor Ia modulators, such as FX-06; and antibodies for the treatment of Ebola, such as REGN-3470-3471-3479 and ZMapp.

Other non-limiting active therapeutic agents active against Ebola include an alpha-glucosidase 1 inhibitor, a cathepsin B inhibitor, a CD29 antagonist, a dendritic ICAM-3 grabbing nonintegrin 1 inhibitor, an estrogen receptor antagonist, a factor VII antagonist HLA class II antigen modulator, a host cell factor modulator, a Interferon alpha ligand, a neutral alpha glucosidase AB inhibitor, a niemann-Pick C1 protein inhibitor, a nucleoprotein inhibitor, a polymerase cofactor VP35 inhibitor, a Serine protease inhibitor, a tissue factor inhibitor, a TLR-3 agonist, a viral envelope glycoprotein inhibitor, and an Ebola virus entry inhibitors (NPC1 inhibitors).

In some embodiments, the other active therapeutic agent may be a vaccine for the treatment or prevention of Ebola, including but not limited to VRC-EBOADC076-00-VP, adenovirus-based Ebola vaccine, rVSV-EBOV, rVSVN4CT1-EBOVGP, MVA-BN Filo+Ad26-ZEBOV regimen, INO-4212, VRC-EBODNA023-00-VP, VRC-EBOADC069-00-VP, GamEvac-combi vaccine, SRC VB Vector, HPIV3/EboGP vaccine, MVA-EBOZ, Ebola recombinant glycoprotein vaccine, Vaxart adenovirus vector 5-based Ebola vaccine, FiloVax vaccine, GOVX-E301, and GOVX-E302.

The compounds provided herein may also be used in combination with phosphoramidate morpholino oligomers (PMOs), which are synthetic antisense oligonucleotide analogs designed to interfere with translational processes by forming base-pair duplexes with specific RNA sequences. Examples of PMOs include but are not limited to AVI-7287, AVI-7288, AVI-7537, AVI-7539, AVI-6002, and AVI-6003.

The compounds provided herein are also intended for use with general care provided to patients with Filoviridae viral infections, including parenteral fluids (including dextrose saline and Ringer's lactate) and nutrition, antibiotic (including metronidazole and cephalosporin antibiotics, such as ceftriaxone and cefuroxime) and/or antifungal prophylaxis, fever and pain medication, antiemetic (such as metoclopramide) and/or antidiarrheal agents, vitamin and mineral supplements (including Vitamin K and zinc sulfate), anti-inflammatory agents (such as ibuprofen), pain medications, and medications for other common diseases in the patient population, such anti-malarial agents (including artemether and artesunate-lumefantrine combination therapy), typhoid (including quinolone antibiotics, such as ciprofloxacin, macrolide antibiotics, such as azithromycin, cephalosporin antibiotics, such as ceftriaxone, or aminopenicillins, such as ampicillin), or shigellosis.

IX. Compound Preparation

In some embodiments, the present disclosure provides processes and intermediates useful for preparing the compounds provided herein or pharmaceutically acceptable salts thereof.

Compounds described herein can be purified by any of the means known in the art, including chromatographic means, such as high performance liquid chromatography (HPLC), preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography.

During any of the processes for preparation of the compounds provided herein, it may be necessary and/or desirable to protect sensitive or reactive groups on any of the molecules concerned. This may be achieved by means of conventional protecting groups as described in standard works, such as T. W. Greene and P. G. M. Wuts, "Protective Groups in Organic Synthesis," 4$^{th}$ ed., Wiley, New York 2006. The protecting groups may be removed at a convenient subsequent stage using methods known from the art.

Exemplary chemical entities useful in methods of the embodiments will now be described by reference to illustrative synthetic schemes for their general preparation herein and the specific examples that follow. Skilled artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the particular pendant groups.

The methods of the present disclosure generally provide a specific enantiomer or diastereomer as the desired product, although the stereochemistry of the enantiomer or diastereomer was not determined in all cases. When the stereochemistry of the specific stereocenter in the enantiomer or diastereomer is not determined, the compound is drawn without showing any stereochemistry at that specific stereocenter even though the compound can be substantially enantiomerically or disatereomerically pure.

Representative syntheses of compounds of the present disclosure are described in the schemes below, and the particular examples that follow.

X. Examples

Intermediate 1-2: (R)-2-(benzyloxy)-3-(octadecyloxy)propyl bis(4-nitrophenyl) phosphate

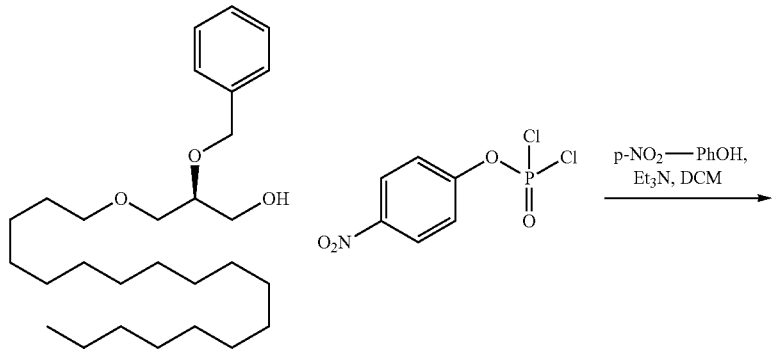

1-1

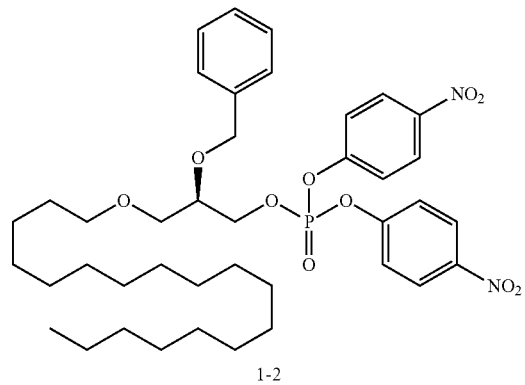

1-2

4-nitrophenyl phosphorodichloridate (1.41 g, 5.52 mmol) was dissolved in DCM (36 mL). The resulting solution was cooled in an ice bath and a separate solution of 1-O-octadecyl-2-O-benzyl-sn-glycerol (intermediate 1-1, 2 g, 4.6 mmol) in DCM (10 mL) was added. Triethylamine (1.12 g, 11 mmol) was then added in a drop-wise manner. The ice bath was then removed. After 1 h 45 min additional triethylamine (0.239 g, 2.35 mmol) was added, followed by 4-nitrophenol. The reaction progress was monitored by LC/MS and TLC. The reaction was diluted with $Et_2O$ and the resulting solids were removed by filtration. The filtrate was concentrated, and intermediate 1-2 was isolated by silica gel column chromatography (25 g load cartridge, 120 g Combiflash HP Gold Column, eluent ramp from 100% hexanes to 30% EtOAc/hexanes).

$^1$H NMR (400 MHz, Chloroform-d) δ 8.21-8.08 (m, 4H), 7.38-7.21 (m, 9H), 4.66-4.55 (m, 2H), 4.52 (ddd, J=10.5, 7.1, 3.2 Hz, 1H), 4.38 (ddd, J=10.8, 8.5, 5.5 Hz, 1H), 3.83-3.76 (m, 1H), 3.57-3.46 (m, 2H), 3.39 (t, J=6.6 Hz, 2H), 1.57-1.46 (m, 2H), 1.33-1.17 (m, 30H), 0.90-0.80 (m, 3H).

$^{31}$P NMR (162 MHz, Chloroform-d) δ −19.447.

Intermediate 1-4: ((3aR,4R,6R,6aR)-6-(4-aminopyrrolo[2,1-f][1,2,4]triazin-7-yl)-6-cyano-2,2-dimethyl-tetrahydrofuro[3,4-d][1,3]dioxol-4-yl)methyl ((R)-2-(benzyloxy)-3-(octadecyloxy)propyl) (4-nitrophenyl) phosphate Intermediate 1-2 (0.503 g, 0.664 mmol) and intermediate 1-3 (J. Med. Chem., 2017, 60(5), p. 1648; 0.2 g, 0.604 mmol) were dissolved in THF. $MgCl_2$ (0.287 g, 3.02 mmol) was added in one portion at room temperature. The reaction was placed in a 50° C. bath and stirred for 10 min. To the resulting mixture DIPEA was added in a drop-wise manner. Reaction progress was monitored by LC/MS. The reaction was cooled to room temperature and concentrated. The resulting residue was taken up in DCM using sonication, and intermediate 1-4 was isolated by silica gel column chromatography (12 g load cartridge, 40 g Combiflash HP Gold Column, eluent ramp from 100% hexanes to 100% EtOAc).

$^1$H NMR (400 MHz, Chloroform-d) δ 7.93-7.86 (m, 1H), 7.84-7.77 (m, 2H), 7.30-7.18 (m, 5H), 7.18-7.08 (m, 2H), 6.89 (t, J=4.8 Hz, 1H), 6.53 (dd, J=6.7, 4.6 Hz, 1H), 6.01 (brs, 2H), 5.40 (dd, J=13.8, 6.9 Hz, 1H), 4.87 (ddd, J=10.9, 6.9, 4.3 Hz, 1H), 4.64-4.48 (m, 3H), 4.43 (ddd, J=10.8, 6.8, 4.0 Hz, 1H), 4.39-2.27 (m, 2H), 4.25-4.14 (m, 1H), 3.78-3.68 (m, 1H), 3.53-3.40 (m, 2H), 3.36 (td, J=6.7, 2.2 Hz, 2H), 1.70 (s, 3H), 1.55-1.42 (m, 2H), 1.33 (d, J=3.8 Hz, 3H), 1.30-1.14 (m, 30H), 0.83 (t, J=6.7 Hz, 3H).

$^{31}$P NMR (162 MHz, Chloroform-d) δ −7.275 (s), −7.608 (s).

MS m/z 949.10 [M+1]

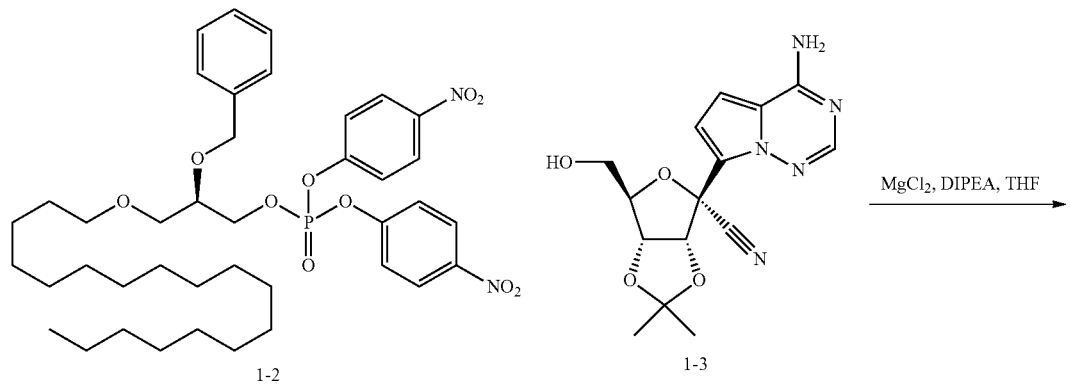

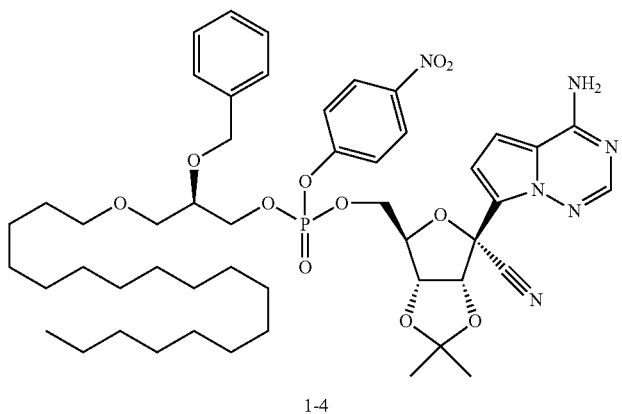

Intermediate 1-5: ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl ((R)-2-(benzyloxy)-3-(octadecyloxy)propyl) hydrogen phosphate

Intermediate 1-6: Triethylammonium (R)-2-(benzyloxy)-3-(octadecyloxy)propyl (2-chlorophenyl) phosphate

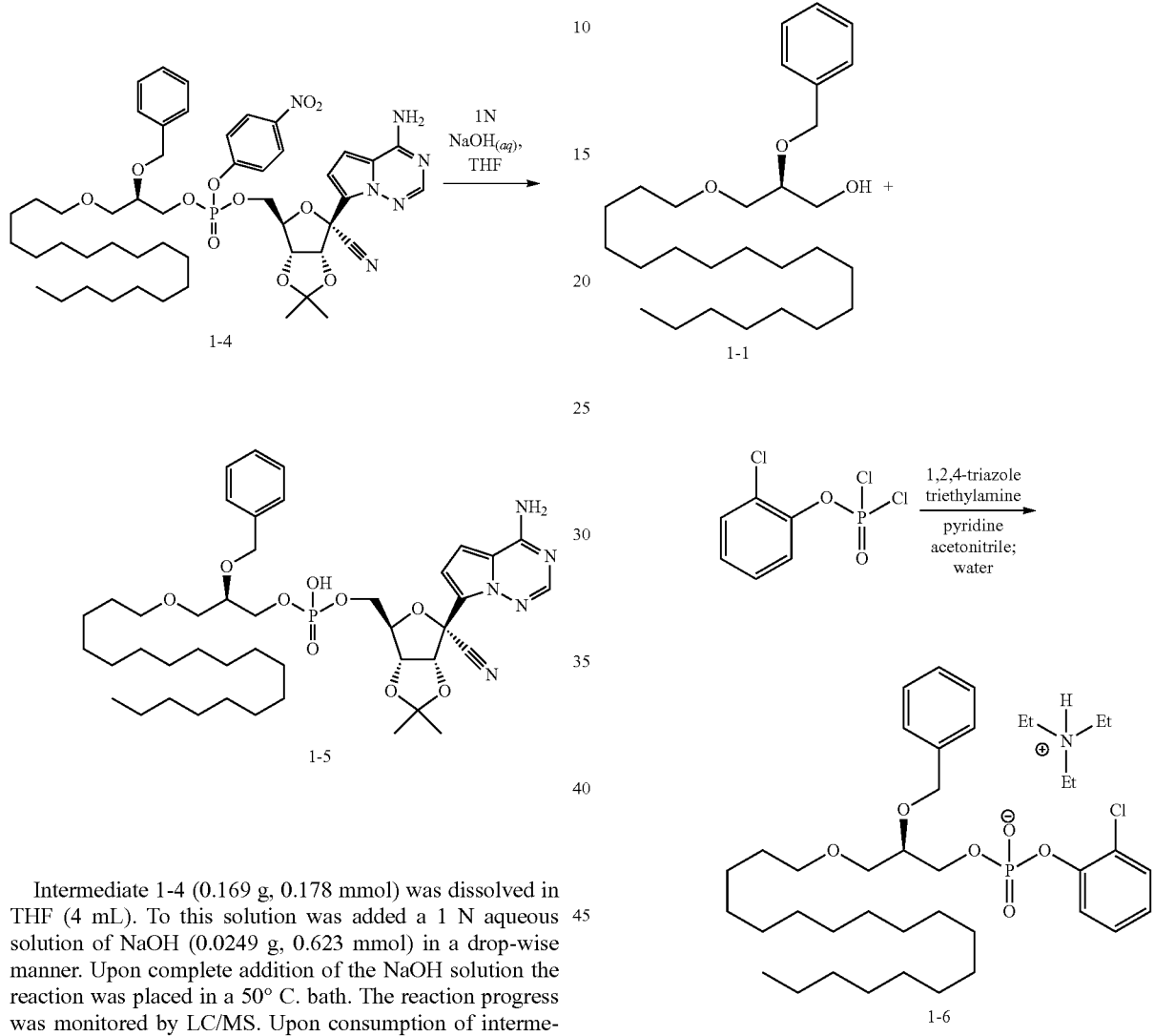

Intermediate 1-4 (0.169 g, 0.178 mmol) was dissolved in THF (4 mL). To this solution was added a 1 N aqueous solution of NaOH (0.0249 g, 0.623 mmol) in a drop-wise manner. Upon complete addition of the NaOH solution the reaction was placed in a 50° C. bath. The reaction progress was monitored by LC/MS. Upon consumption of intermediate 1-4 the reaction was cooled in an ice bath. A 2 N aqueous solution of HCl was added until the reaction pH~4 was achieved. The reaction was concentrated, and the resulting residue was taken up in DCM with sonication. Intermediate 1-5 was isolated by silica gel column chromatography (12 g load cartridge, 24 g Combiflash HP Gold Column, eluent ramp from 100% DCM to 20% MeOH/DCM).

$^1$H NMR (400 MHz, MeOH-$d_3$) δ 7.86 (s, 1H), 7.35-7.15 (m, 5H), 6.93-6.85 (m, 2H), 5.32 (d, J=6.6 Hz, 1H), 5.00 (dd, J=6.6, 3.1 Hz, 1H), 4.64-4.51 (m, 3H), 4.03 (t, J=5.4 Hz, 2H), 3.94-3.83 (m, 2H), 3.73-3.64 (m, 1H), 3.53-3.40 (m, 2H), 3.37 (td, J=6.5, 1.6 Hz, 2H), 1.69 (s, 3H), 1.51 (pent, J=6.7 Hz, 2H), 1.39 (s, 3H), 1.36-1.21 (m, 30H), 0.92-0.86 (m, 3H).

$^{31}$P NMR (162 MHz, MeOH-$d_3$) δ 2.852--0.151 (brs).

MS m/z=828.69 [M+1], 1656.24 [2M+1]

1,2,4-Triazole (1.33 g, 19.3 mmol) and triethylamine (2.69 mL, 19.3 mmol) were added sequentially to a stirred solution of 2-chlorophenyl phosphorodichloridate (1.45 mL, 8.97 mmol) in acetonitrile (30 mL) at 0° C., and the resulting mixture was warmed to room temperature. After 40 min, a solution of intermediate 1-1 (3.90 g, 8.97 mmol) in pyridine (40 mL) was added slowly via cannula. After 5 h, triethylamine (5.0 mL) and water (1.5 mL) were added sequentially. After 25 min, saturated aqueous sodium bicarbonate solution was added. After 10 min, saturated aqueous sodium bicarbonate solution was added, and the aqueous layer was extracted with dichloromethane (4 times). The combined organic layers were dried over anhydrous sodium sulfate, filtered, and concentrated under reduced pressure to give intermediate 1-6.

LCMS: 623.3 [M–$C_6H_{16}N$]$^-$.

Intermediate 1-7: ((3aR,4R,6R,6aR)-6-(4-Aminopyrrolo[2,1-f][1,2,4]triazin-7-yl)-6-cyano-2,2-dimethyltetrahydrofuro[3,4-d][1,3]dioxol-4-yl)methyl ((R)-2-(benzyloxy)-3-(octadecyloxy)propyl) (2-chlorophenyl) phosphate

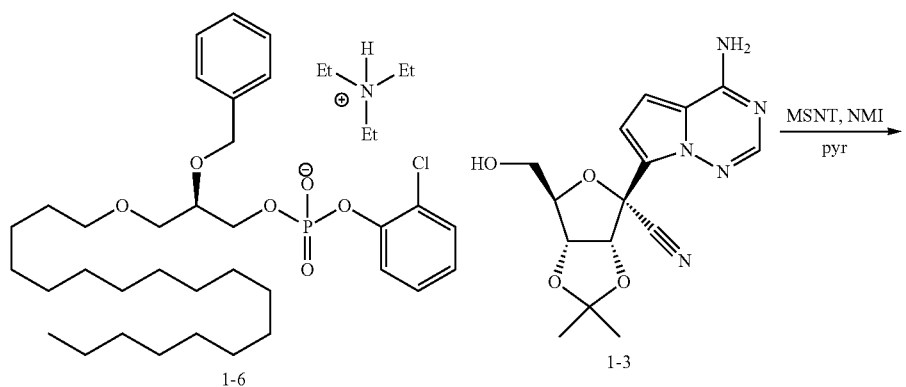

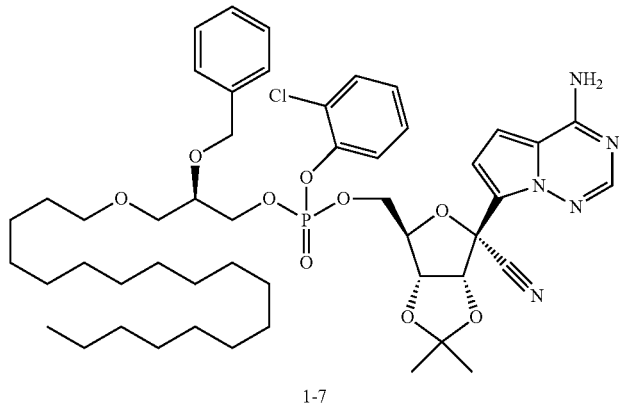

1-(Mesitylsulfonyl)-3-nitro-1H-1,2,4-triazole (4.02 g, 13.6 mmol), intermediate 1-3 (3.00 g, 9.05 mmol), and 1-methylimidazole (1.08 mL, 13.6 mmol) were added sequentially to a stirred solution of intermediate 1-6 (5.92 g, 8.15 mmol) in pyridine at room temperature. After 4 h, the resulting mixture was cooled to 0° C. and saturated aqueous sodium bicarbonate solution and brine were added sequentially. The aqueous layer was extracted with dichloromethane (2×400 mL), and the combined organic layers were dried over anhydrous sodium sulfate, were filtered, and were concentrated under reduced pressure. The residue was purified by flash column chromatography on silica gel (0 to 100% ethyl acetate in hexanes) to give intermediate 1-7.

LCMS: 938.5.

Alternate Synthesis of Intermediate 1-5-((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl ((R)-2-(benzyloxy)-3-(octadecyloxy)propyl) hydrogen phosphate Example 1: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-(benzyloxy)-3-(octadecyloxy)propyl) hydrogen phosphate (1)

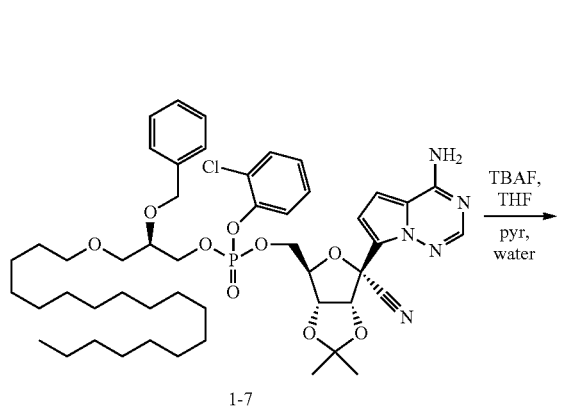

1-7

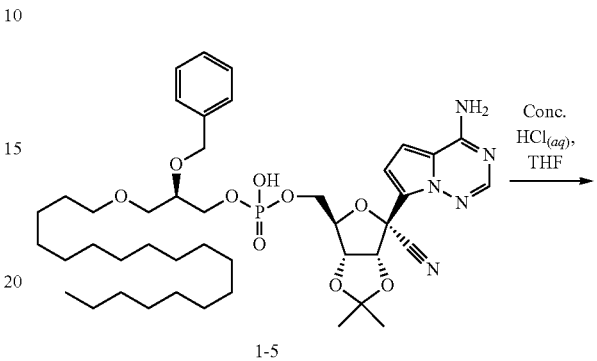

1-5

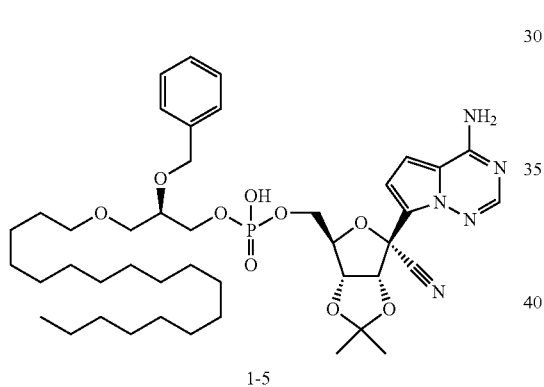

1-5

Tetrabutylammonium fluoride solution (1.0 M in tetrahydrofuran, 12.8 mL, 13 mmol) was added via syringe to a stirred mixture of intermediate 1-7 (4.00 g, 4.26 mmol), pyridine (5.0 mL), water (5.0 mL), and tetrahydrofuran (35 mL) at room temperature. After 2 h, the resulting mixture was cooled to 0° C. Saturated aqueous sodium bicarbonate solution (15 mL) and water (10 mL) were added sequentially, and the resulting mixture was concentrated under reduced pressure. Dichloromethane and water were added sequentially, and aqueous hydrogen chloride solution (2.0 M) was added until the pH of the aqueous layer was 3. The aqueous layer was extracted with dichloromethane (4 times). The combined organic layers were washed with a mixture of brine and saturated aqueous sodium bicarbonate solution (pH=8, 2 times), dried over anhydrous sodium sulfate, filtered, and concentrated under reduced pressure. The residue was purified by flash column chromatography on silica gel (0 to 20% methanol in dichloromethane) to give intermediate 1-5. LCMS: 828.5.

Intermediate 1-5 (0.15 g, 0.181 mmol) was dissolved in THF (4 mL). The resulting solution was cooled in an ice bath. Concentrated aqueous HCl (1.25 mL, 14.9 mmol) was added in a drop-wise fashion. The cold bath was removed the reaction was stirred vigorously. The reaction progress was monitored by LC/MS. After consumption of intermediate 1-5 the reaction was concentrated. The residue was taken up in a MeOH, DCM mixture and concentrated. The resulting residue was taken up in DCM and compound 1 was isolated by silica gel column chromatography (12 g load cartridge, 24 g Combiflash HP Gold Column, eluent ramp from 100% DCM to 20% MeOH/DCM).

$^1$H NMR (400 MHz, ACN-$d_3$) δ 7.85 (s, 1H), 7.35-7.17 (m, 5H), 6.96 (d, J=4.6 Hz, 1H), 6.90 (d, J=4.6 Hz, 1H), 4.81 (d, J=5.3 Hz, 1H), 4.66-4.54 (m, 2H), 4.37-4.31 (m, 1H), 4.22 (t, J=5.5 Hz, 1H), 4.18-4.01 (m, 2H), 3.97-3.82 (m, 2H), 3.72-3.65 (m, 1H), (qd, J=10.5, 4.9 Hz, 2H), 3.41-3.34 (m, 2H), 1.50 (pent, J=7.0 Hz, 2H), 1.37-1.20 (m, 30H), 0.92-0.86 (m, 3H).

MS m/z=786.92 [M−1], 1572.67 [2(M−1)]

Intermediate 2-1: (R)-(2-([1,1'-biphenyl]-4-yl-methoxy)-3-(octadecyloxy)propoxy) (tert-butyl)dimethylsilane

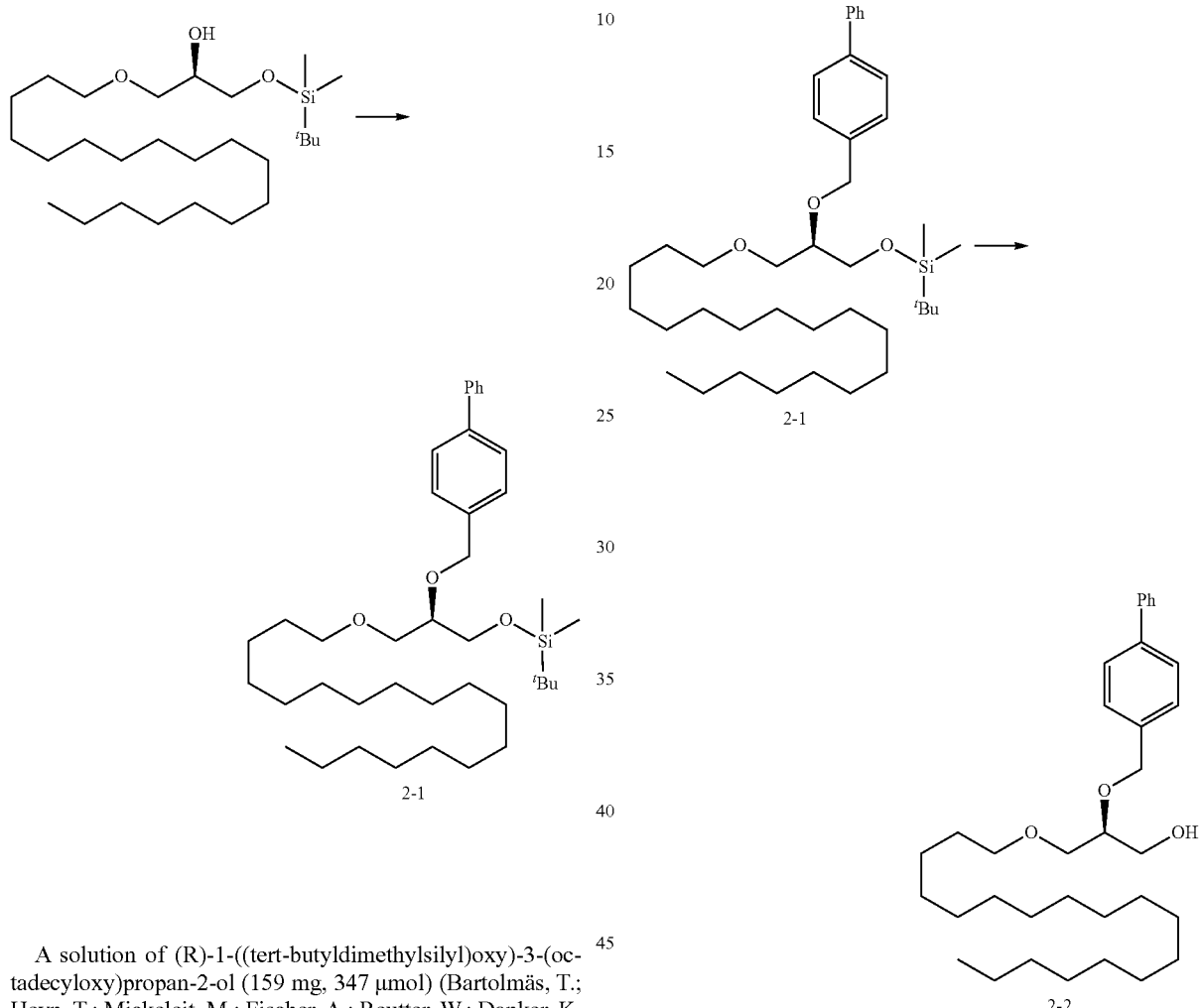

A solution of (R)-1-((tert-butyldimethylsilyl)oxy)-3-(octadecyloxy)propan-2-ol (159 mg, 347 μmol) (Bartolmäs, T.; Heyn, T.; Mickeleit, M.; Fischer, A.; Reutter, W.; Danker, K. *J. Med. Chem.* 2005, 48, 6750) in tetrahydrofuran (2.0 mL) was added via cannula to a vigorously stirred mixture of sodium hydride (60% wt dispersion in mineral oil, 46.6 mg, 1.22 mmol) in tetrahydrofuran (3.0 mL) at 0° C. After 30 min, 4-(bromomethyl)-1,1'-biphenyl (300 mg, 1.22 mmol) was added, and the resulting mixture was warmed to room temperature. After 21 h, saturated aqueous ammonium chloride solution (3.0 mL) and ethyl acetate (60 mL) were added sequentially. The organic layer was washed with a mixture of water and brine (2:1 v:v, 30 mL), was dried over anhydrous magnesium sulfate, was filtered, and was concentrated under reduced pressure. The residue was purified by flash column chromatography on silica gel (0 to 5% ethyl acetate in hexanes) to give intermediate 2-1.

$^1$H NMR (400 MHz, Acetonitrile-d$_3$) δ 7.73-7.60 (m, 4H), 7.53-7.42 (m, 4H), 7.42-7.35 (m, 1H), 4.71 (s, 2H), 3.80-3.65 (m, 2H), 3.64-3.47 (m, 3H), 3.47-3.39 (m, 2H), 1.62-1.46 (m, 2H), 1.42-1.17 (m, 30H), 0.97-0.83 (m, 12H), 0.09 (s, 6H).

Intermediate 2-2: (S)-2-([1,1'-biphenyl]-4-yl-methoxy)-3-(octadecyloxy)propan-1-ol Tetrabutylammonium fluoride solution (1.0 M in tetrahydrofuran, 756 μL, 760 μmol) was added via syringe to a stirred solution of intermediate 2-1 (200 mg, 320 μmol) in tetrahydrofuran (3.0 mL) at room temperature. After 85 min, saturated aqueous ammonium chloride solution (1.0 mL) and diethyl ether (30 mL) were added sequentially. The organic layer was washed with water (20 mL), was dried over anhydrous magnesium sulfate, was filtered, and was concentrated under reduced pressure. The residue was purified by flash column chromatography on silica gel (0 to 30% ethyl acetate in hexanes) to give intermediate 2-2.

LCMS: 533.4 [M+Na]$^+$.

Intermediate 2-3: (R)-2-([1,1'-biphenyl]-4-yl-methoxy)-3-(octadecyloxy)propyl bis(4-nitrophenyl) phosphate

Intermediate 2-4: (R)-2-([1,1'-biphenyl]-4-yl-methoxy)-3-(octadecyloxy)propyl (((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl) (4-nitrophenyl) phosphate

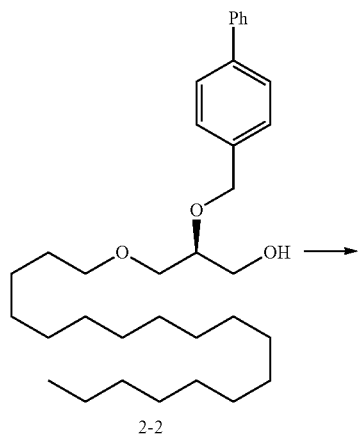

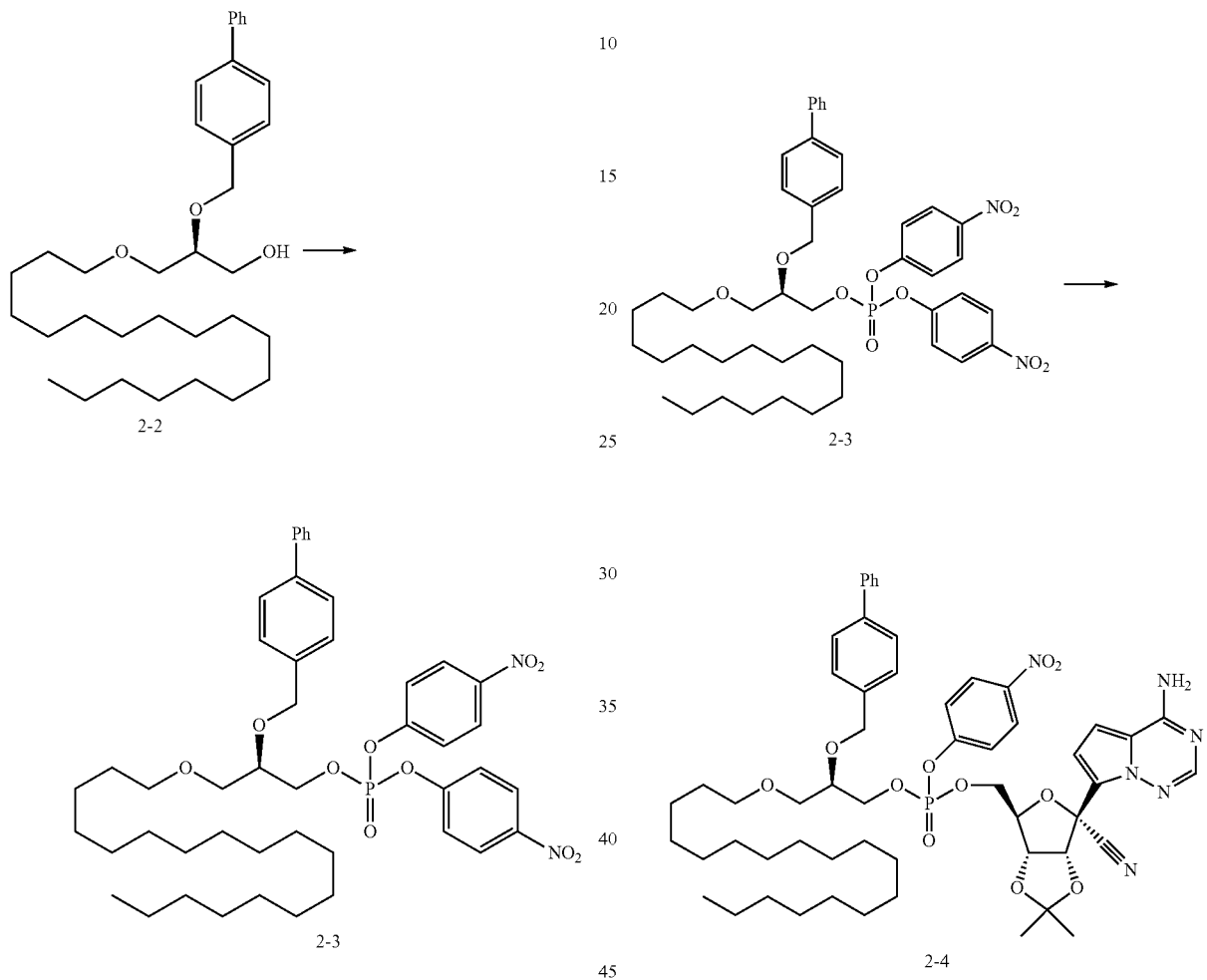

Triethylamine (10.8 μL, 77.8 μmol) was added via syringe to a stirred mixture of intermediate 2-2 (33.1 mg, 64.8 μmol), 4-nitrophenyl phosphorodichloridate (19.9 mg, 77.8 μmol), and dichloromethane (3.0 mL) at 0° C. After 60 min, the resulting mixture was warmed to room temperature. After 30 min, 4-nitrophenyl phosphorodichloridate (20.0 mg, 78.1 μmol) and triethylamine (20.0 μL, 143 μmol) were added sequentially. After 60 min, 4-nitrophenyl phosphorodichloridate (60.0 mg, 234 μmol) and triethylamine (50.0 μL, 359 μmol) were added sequentially. After 70 min, 4-nitrophenol (150 mg, 1.08 mmol) and triethylamine (200 μL, 1.43 mmol) were added sequentially. After 50 min, diethyl ether (60 mL) and aqueous citric acid solution (10% wt, 10 mL) were added sequentially. The organic layer was washed with water (50 mL), dried over anhydrous magnesium sulfate, filtered, and concentrated under reduced pressure. The residue was purified by flash column chromatography on silica gel (0 to 30% ethyl acetate in hexanes) to give intermediate 2-3.

LCMS: 855.4 $[M+Na]^+$.

A vigorously stirred mixture of intermediate 2-3 (190 mg, 228 μmol), intermediate 1-3 (75.6 mg, 228 μmol), magnesium chloride (217 mg, 2.28 mmol), and tetrahydrofuran (2.5 mL) was heated to 50° C. After 5 min, N,N-diisopropylethylamine (397 μL, 2.28 mmol) was added over 1 min via syringe. After 60 min, the resulting mixture was cooled to room temperature, and a mixture of citric acid (726 mg), aqueous sodium hydroxide solution (2.0 M, 4 mL), and water (10 mL) was added. Ethyl acetate (60 mL) was added, and the organic layer was washed with a mixture of water and brine (2:1 v:v, 30 mL), dried over anhydrous magnesium sulfate, filtered, and concentrated under reduced pressure. The residue was purified by flash column chromatography on silica gel (0 to 4.5% methanol in dichloromethane) to give intermediate 2-4.

LCMS: 1025.5.

Example 2: (R)-2-([1,1'-biphenyl]-4-ylmethoxy)-3-(octadecyloxy)propyl (((2R,3S,4R,5R)-5-(4-aminopyrrolo[2,1-f][1,2,4]triazin-7-yl)-5-cyano-3,4-dihydroxytetrahydrofuran-2-yl)methyl) hydrogen phosphate

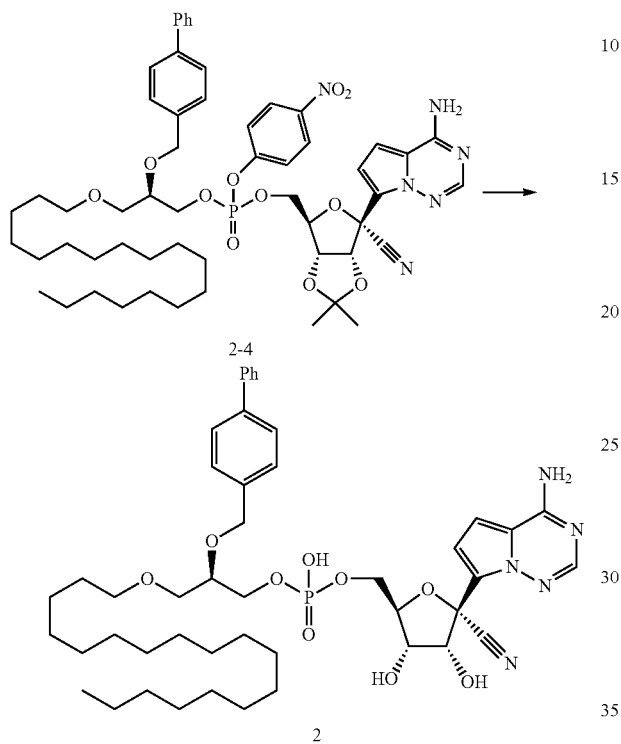

Aqueous sodium hydroxide solution (2.0 M, 276 µL, 552 µmol) was added via syringe to a vigorously stirred solution of intermediate 2-4 (162 mg, 158 µmol) in tetrahydrofuran (1.8 mL) at room temperature, and the resulting mixture was heated to 50° C. After 60 min, aqueous sodium hydroxide solution (2.0 M, 150 µL, 300 µmol) was added via syringe. After 150 min, the resulting mixture was cooled to room temperature. Aqueous hydrogen chloride solution (2.0 M, 400 µL) and a mixture of citric acid (706 mg), aqueous sodium hydroxide solution (2.0 M, 3.67 mL), aqueous hydrogen chloride solution (2.0 M, 1.83 mL), water (5 mL), and brine (10 mL) were added sequentially. The aqueous layer was extracted with dichloromethane (3×30 mL), and the combined organic layers were dried over anhydrous magnesium sulfate, were filtered, and were concentrated under reduced pressure. The residue was dissolved in tetrahydrofuran (2.0 mL) and was stirred vigorously at room temperature. Concentrated hydrogen chloride (625 µL, 7.5 mmol) was added via syringe. After 165 min, a mixture of citric acid (706 mg), aqueous sodium hydroxide solution (2.0 M, 1.83 mL), water (15 mL), aqueous sodium hydroxide solution (6.0 M, 250 µL), and brine (10 mL) was added. The aqueous layer was extracted sequentially with a mixture of dichloromethane and ethyl acetate (2:5 v:v, 70 mL), ethyl acetate (2×50 mL), and tetrahydrofuran (2×50 mL). The combined organic layers were dried over anhydrous magnesium sulfate, were filtered, and were concentrated under reduced pressure. The residue was purified by reverse phase preparative HPLC (2-propanol/water) to give compound 2.

$^1$H NMR (400 MHz, DMSO-d$_6$-methanol-d$_4$) δ 7.92 (s, 1H), 7.63 (d, J=7.5 Hz, 2H), 7.59 (d, J=8.1 Hz, 2H), 7.48-7.28 (m, 5H), 6.91 (d, J=4.5 Hz, 1H), 6.85 (d, J=4.8 Hz, 1H), 4.68-4.52 (m, 3H), 4.39-3.25 (m, 11H), 1.54-0.99 (m, 32H), 0.85 (t, J=6.6 Hz, 3H). LCMS: 864.0.

Intermediate 3-1: (S)-2-(cyclohexylmethoxy)-3-(octadecyloxy)propan-1-ol

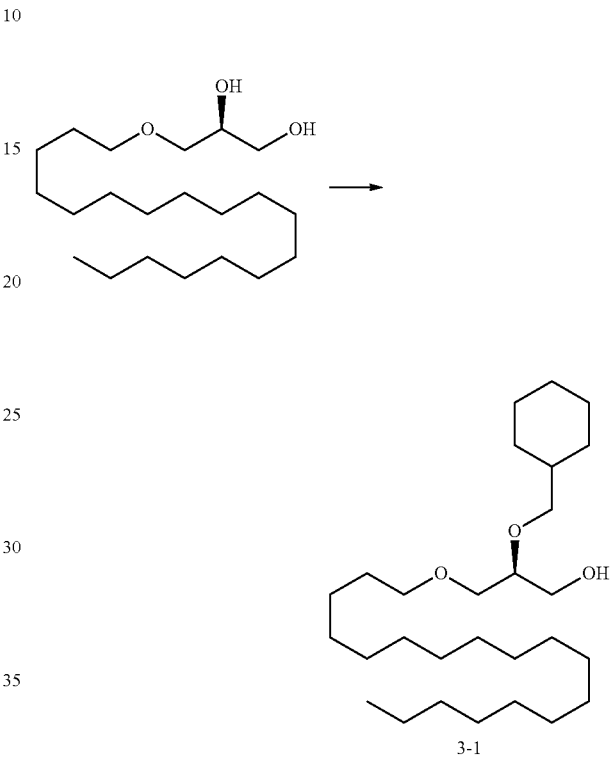

A vigorously stirred mixture of (S)-3-(octadecyloxy)propane-1,2-diol (250 mg, 726 µmol), cyclohexanecarbaldehyde (92.3 µL, 762 µmol), 4-methylbenzenesulfonic acid monohydrate (13.8 mg, 72.6 µmol), anhydrous magnesium sulfate (162 mg, 1.34 mmol), and dichloromethane (3.0 mL) was heated to 60° C. After 80 min, the resulting mixture was cooled to room temperature, and potassium carbonate (101 mg, 726 µmol) was added. After 10 min, the resulting mixture was filtered through celite, and the filter cake was extracted with dichloromethane (8 mL). The combined filtrates were stirred and were cooled to −40° C. Diisobutylaluminum hydride solution (1.0 M in toluene, 5.80 mL, 5.8 mmol) was added via syringe, and the resulting mixture was warmed to −10° C. over 145 min. The resulting mixture was warmed to room temperature. After 22 h, methanol (2.0 mL) was added slowly via syringe. Water (50 mL) and aqueous hydrogen chloride solution (2.0 M, 20 mL) were added sequentially, and the aqueous layer was extracted with dichloromethane (2×60 mL). The combined organic layers were dried over anhydrous magnesium sulfate, filtered, and concentrated under reduced pressure. The residue was purified by flash column chromatography on silica gel (0 to 10% ethyl acetate in hexanes) to give intermediate 3-1.

Example 3: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-(cyclohexylmethoxy)-3-(octadecyloxy)propyl) hydrogen phosphate

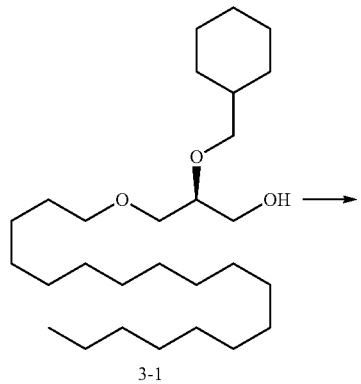

3-1

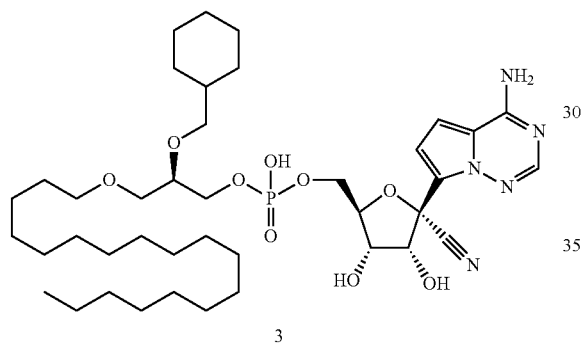

3

Compound 3 was synthesized in a manner similar to compound 2 using (S)-2-(cyclohexylmethoxy)-3-(octadecyloxy)propan-1-ol instead of (S)-2-([1,1'-biphenyl]-4-ylmethoxy)-3-(octadecyloxy)propan-1-ol.

$^1$H NMR (400 MHz, DMSO-$d_6$-methanol-$d_4$) δ 7.94 (s, 1H), 6.93 (d, J=4.5 Hz, 1H), 6.84 (d, J=4.5 Hz, 1H), 4.65 (d, J=4.9 Hz, 1H), 4.31-3.06 (m, 13H), 1.72-1.00 (m, 43H), 0.86 (t, J=6.7 Hz, 3H). $^{31}$P NMR (162 MHz, DMSO-$d_6$) δ −1.13 (s, 1P). LCMS: 794.1.

Intermediate 4-1: (S)-2-(cyclohexylmethoxy)-3-(octadecyloxy)propan-1-ol

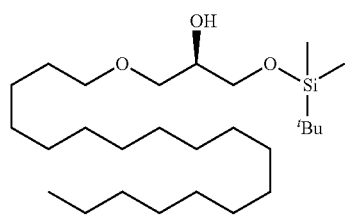

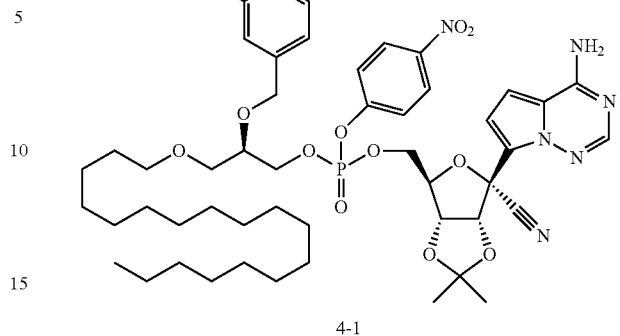

4-1

Intermediate 4-1 was synthesized in a manner similar to Intermediate 2-4 using 2-(bromomethyl)naphthalene instead of 4-(bromomethyl)-1,1'-biphenyl.

Example 4: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-(naphthalen-2-ylmethoxy)-3-(octadecyloxy)propyl) hydrogen phosphate (4)

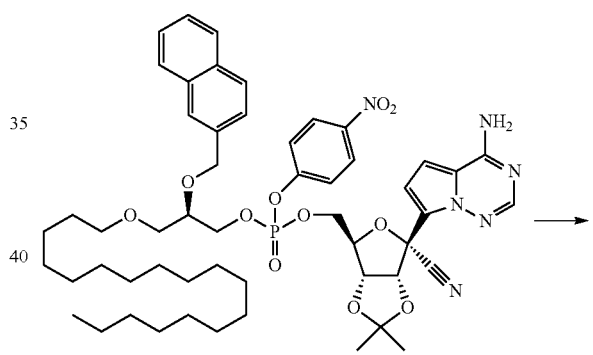

4-1

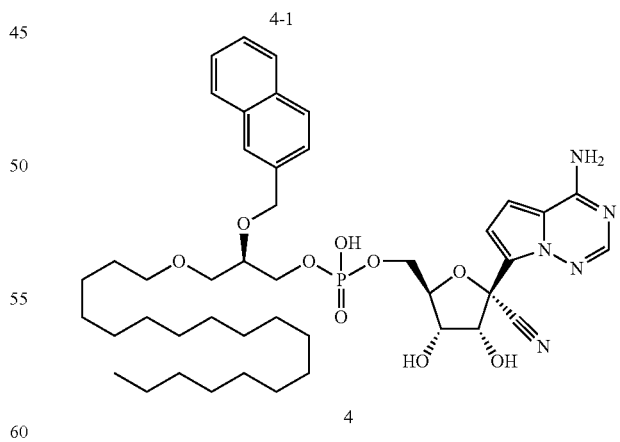

4

Aqueous sodium hydroxide solution (2.0 M, 800 μL, 1.6 mmol) was added via syringe to a vigorously stirred solution of intermediate 4-1 (250 mg, 250 μmol) in tetrahydrofuran (1.8 mL) at room temperature, and the resulting mixture was heated to 56° C. After 186 min, the resulting mixture was cooled to room temperature. Aqueous hydrogen chloride solution (2.0 M, 800 μL) and a mixture of citric acid (706 mg), aqueous sodium hydroxide solution (2.0 M, 1.83 mL), water (5 mL), and brine (10 mL) were added sequentially. The aqueous layer was extracted with 2-methyltetrahydrofuran (2×30 mL), and the combined organic layers were dried over anhydrous magnesium sulfate, were filtered, and were concentrated under reduced pressure. The residue was dissolved in tetrahydrofuran (1.2 mL) and was stirred vigorously at room temperature. Concentrated hydrogen chloride (250 μL, 3.0 mmol) was added via syringe. After 165 min, triethylamine (600 μL) was added via syringe, and the resulting mixture was purified by reverse phase preparative HPLC (2-propanol/water) to give compound 4 as a triethylammonium salt. $^1$H NMR (400 MHz, Methanol-$d_4$) δ 7.86 (s, 1H), 7.84-7.75 (m, 4H), 7.52-7.40 (m, 3H), 7.00 (d, J=4.6 Hz, 1H), 6.88 (d, J=4.6 Hz, 1H), 4.86-4.71 (m, 3H), 4.35 (t, J=4.5 Hz, 1H), 4.25 (t, J=5.4 Hz, 1H), 4.23-4.11 (m, 1H), 4.07 (dt, J=11.4, 4.6 Hz, 1H), 3.92 (hept, J=5.4 Hz, 2H), 3.83-3.75 (m, 1H), 3.52 (qd, J=10.7, 5.1 Hz, 2H), 3.40 (t, J=6.5 Hz, 2H), 3.22 (q, J=7.3 Hz, 6H), 1.60-1.18 (m, 41H), 0.97-0.86 (m, 3H). LCMS: 838.1.

Intermediate 5-1:
(R)-3-(hexadecyloxy)-2-hydroxypropyl 4-methylbenzenesulfonate

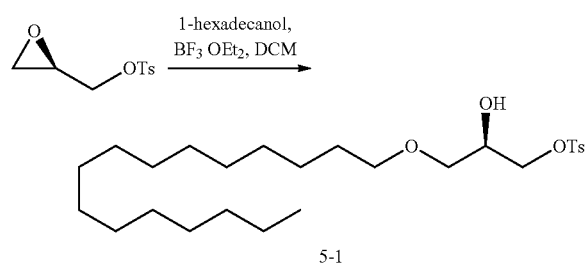

(R)-oxiran-2-ylmethyl 4-methylbenzenesulfonate (507 mg, 2.22 mmol) and 1-hexadecanol (547 mg, 2.26 mmol) were dissolved in DCM (10 mL) and treated with several drops trifluoroborane etherate. The resulting solution was stirred for 18 hours at which point solvent was removed under reduced pressure and the resultant residue precipitated from hexanes to afford intermediate 5-1.

$^1$H NMR (400 MHz, Chloroform-d) δ. 7.83 (d, J=8.0 Hz, 2H), 7.38 (d, J=8.0 Hz, 2H), 4.21-3.90 (m, 2H), 3.55-3.26 (m, 3H), 2.48 (s, 3H), 1.53 (s, 3H), 1.28 (s, 28H), 0.90 (t, J=6.6 Hz, 3H).

MS m/z 471.0

Intermediate 5-2: (R)-2-(benzyloxy)-3-(hexadecyloxy)propyl 4-methylbenzene sulfonate

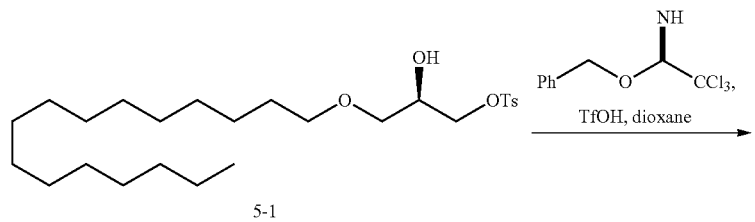

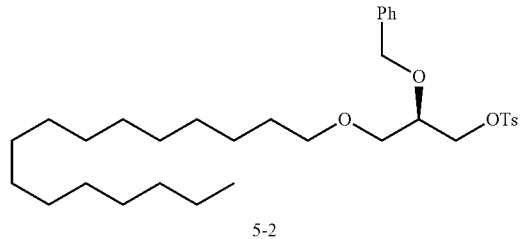

Intermediate 5-1 (216 mg, 0.459 mmol) was dissolved in dioxane (4 mL) and treated with benzyl 2,2,2-trichloroethanimidate (0.175 mL, 0.942 mmol) followed by several drops of trifluoromethane sulfonic acid. The reaction mixture was stirred for 90 minutes at which point additional benzyl 2,2,2-trichloroethanimidate (0.1 mL, 0.538 mol) and several drops of trifluoromethane sulfonic acid were added. The reaction mixture was stirred for 18 hours at which point additional benzyl 2,2,2-trichloroethanimidate (0.2 mL, 1.08 mmol) and several drops of trifluoromethane sulfonic acid were added. The reaction mixture was stirred for 90 minutes at which point the reaction mixture was diluted with dichloromethane, washed sequentially with saturated aqueous sodium bicarbonate and water, dried over sodium sulfate, filtered, and evaporated under reduced pressure. Intermediate 5-2 was isolated from the resultant residue by silica gel column chromatography (0-20% EtOAc:hexanes eluent ramp).

$^1$H NMR (400 MHz, Chloroform-d) δ. 7.81 (d, J=8.3 Hz, 2H), 7.45-7.24 (m, 7H), 4.22 (dd, J=10.4, 4.1 Hz, 1H), 4.11 (dd, J=10.4, 5.8 Hz, 1H), 3.78 (qd, J=5.5, 4.1 Hz, 1H), 3.48 (dd, J=5.3, 4.1 Hz, 2H), 3.38 (t, J=6.7 Hz, 2H), 2.46 (s, 3H), 1.51 (t, J=6.7 Hz, 2H), 1.29 (s, 28H), 0.91 (t, J=6.7 Hz, 3H).

Intermediate 5-3: (S)-2-(benzyloxy)-3-(hexadecyloxy)propan-1-ol

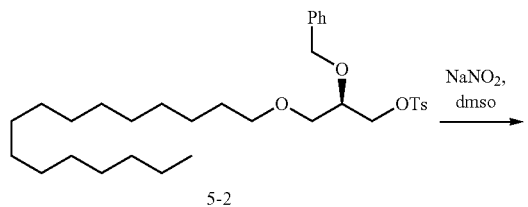

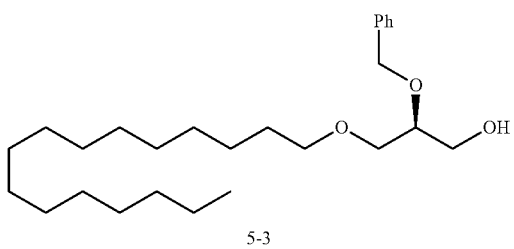

Intermediate 5-2 (257 mg, 0.458 mmol) was dissolved in DMSO (10 mL) and treated with sodium nitrite (976 mg, 14.1 mmol) then heated to 40° C. for 18 hours at which point the reaction mixture was diluted with water, extracted to dichloromethane, dried over sodium sulfate, filtered, and evaporated under reduced pressure. Intermediate 5-3 was isolated from the resultant residue by silica gel column chromatography (0-25% EtOAc:hexanes eluent ramp).

$^1$H NMR (400 MHz, Chloroform-d) δ. 7.47-7.22 (m, 5H), 4.74 (d, J=11.8 Hz, 1H), 4.65 (d, J=11.8 Hz, 1H), 3.78 (q, J=6.2 Hz, 1H), 3.69 (dq, J=6.4, 4.8 Hz, 2H), 3.62 (dd, J=10.0, 4.7 Hz, 1H), 3.56 (dd, J=10.0, 5.2 Hz, 1H), 3.46 (td, J=6.7, 1.6 Hz, 2H), 2.22 (d, J=20.1 Hz, 1H), 1.59 (p, J=6.7 Hz, 2H), 1.28 (s, 28H), 0.94-0.87 (m, 3H).

MS m/z=406.9

Intermediate 5-4: (R)-2-(benzyloxy)-3-(hexadecyloxy)propyl bis(4-nitrophenyl) phosphate

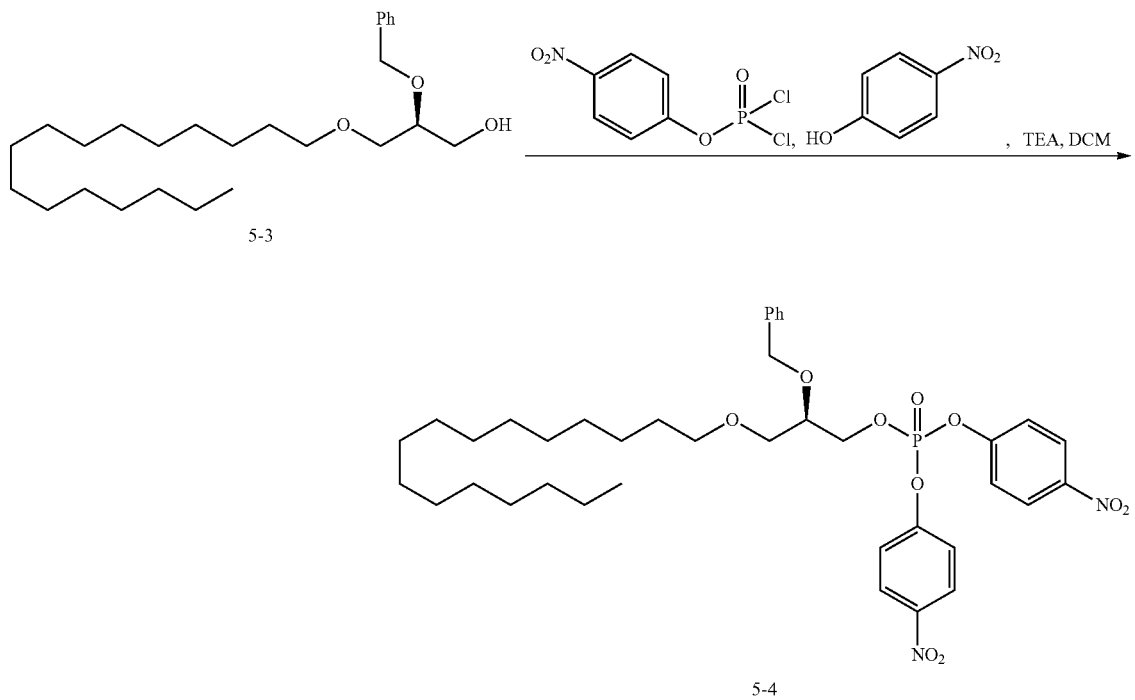

Intermediate 5-3 (21.0 mg, 0.0516 mmol) was dissolved in DCM (2 mL) and treated with triethylamine (0.0300 mL, 0.215 mmol) and 4-nitrophenyl dichlorophosphate (46.0 mg, 0.180 mmol). The reaction mixture was stirred for 30 minutes at which point additional triethylamine (0.0500 mL, 0.359 mmol) and 4-nitrophenyl dichlorophosphate (100 mg, 0.391 mmol) were added and stirring continued for 1 hour. Triethylamine (0.100 mL, 0.717 mmol) and 4-nitrophenol (160 mg, 1.15 mmol) were subsequently added and stirring continued for 20 minutes at which point the reaction mixture was diluted with diethyl ether and filtered to remove solids and the filtrate evaporated under reduced pressure. Intermediate 5-4 was isolated from the resultant residue by silica gel column chromatography (0-20% EtOAc:hexanes eluent ramp).

$^1$H NMR (400 MHz, Chloroform-d) δ. 8.26-8.10 (m, 4H), 7.45-7.21 (m, 9H), 4.68 (d, J=11.5 Hz, 1H), 4.64-4.53 (m, 2H), 4.45 (ddd, J=10.8, 8.4, 5.5 Hz, 1H), 3.86 (ddt, J=5.0, 3.3, 1.7 Hz, 1H), 3.60 (dd, J=10.1, 4.9 Hz, 1H), 3.54 (dd, J=10.1, 6.5 Hz, 1H), 3.44 (t, J=6.7 Hz, 2H), 1.56 (t, J=7.0 Hz, 2H), 1.27 (d, J=2.9 Hz, 28H), 0.90 (t, J=6.8 Hz, 3H).

$^{31}$P NMR (162 MHz, Chloroform-d) δ. 13.36 (t, J=7.9 Hz).

Intermediate 5-5: ((3aR,4R,6R,6aR)-6-(4-aminopyr-rolo[2,1-f][1,2,4]triazin-7-yl)-6-cyano-2,2-dimethyl-tetrahydrofuro[3,4-d][1,3]dioxol-4-yl)methyl ((R)-2-(benzyloxy)-3-(hexadecyloxy)propyl) (4-nitrophenyl) phosphate

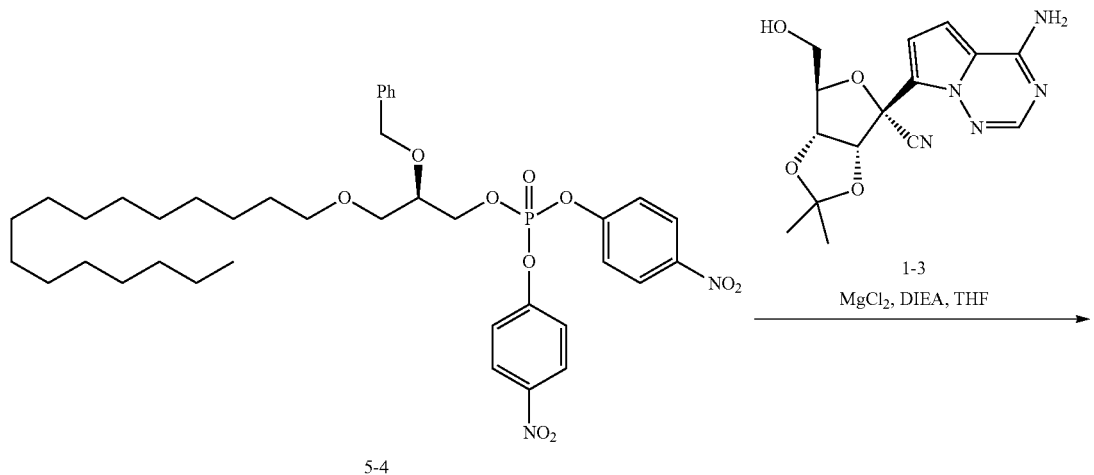

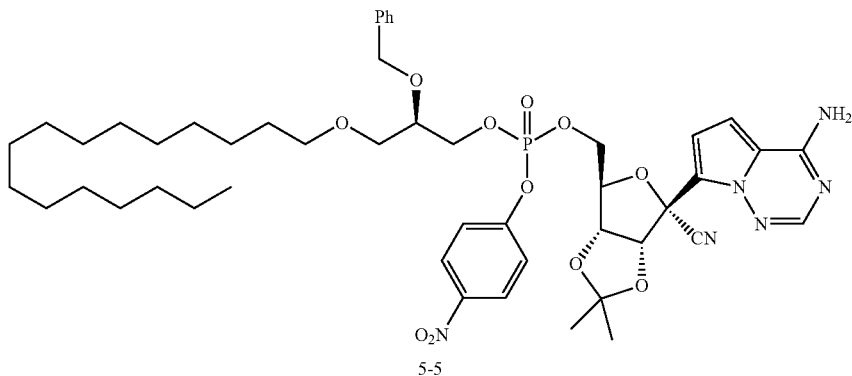

Intermediate 5-4 (39.0 mg, 0.0545 mmol) and intermediate 1-3 (19.5 mg, 0.0589 mmol) were dissolved in THF (2 mL) and treated with magnesium chloride (28.0 mg, 0.294 mmol). The resultant solution was stirred at 50° C. for 15 minutes at which point N,N-diisopropylethylamine (0.0500 mL, 0.287 mmol) was added and stirring continued at 50° C. for an additional 2 hours. Solvent was removed under reduced pressure and intermediate 5-5 isolated from the resulting residue by silica gel column chromatography (0-5% MeOH:DCM eluent ramp).

$^1$H NMR (400 MHz, Chloroform-d) δ. 8.00-7.81 (m, 3H), 7.37-7.26 (m, 5H), 7.19 (dd, J=15.2, 9.0 Hz, 2H), 6.99 (dd, J=7.6, 4.6 Hz, 1H), 6.60 (t, J=4.9 Hz, 1H), 5.77 (s, 2H), 5.46 (dd, J=15.5, 6.9 Hz, 1H), 4.94 (ddd, J=11.3, 6.9, 4.3 Hz, 1H), 4.72-4.30 (m, 6H), 4.31-4.19 (m, 1H), 3.86-3.72 (m, 1H), 3.61-3.45 (m, 2H), 3.42 (t, J=6.7 Hz, 2H), 1.77 (s, 3H), 1.55 (t, J=6.9 Hz, 2H), 1.40 (d, J=3.8 Hz, 3H), 1.27 (s, 28H), 0.90 (t, J=6.7 Hz, 3H).

$^{31}$P NMR (162 MHz, Chloroform-d) δ 0.7.24 (q, J=7.2 Hz), −7.60 (q, J=7.4 Hz).

MS m/z 921.6

Example 5: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-(benzyloxy)-3-(hexadecyloxy)propyl) hydrogen phosphate (5)

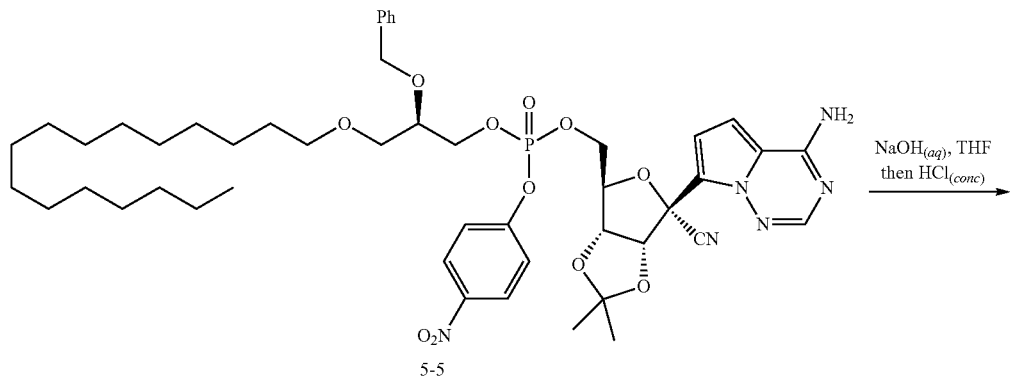

5-5

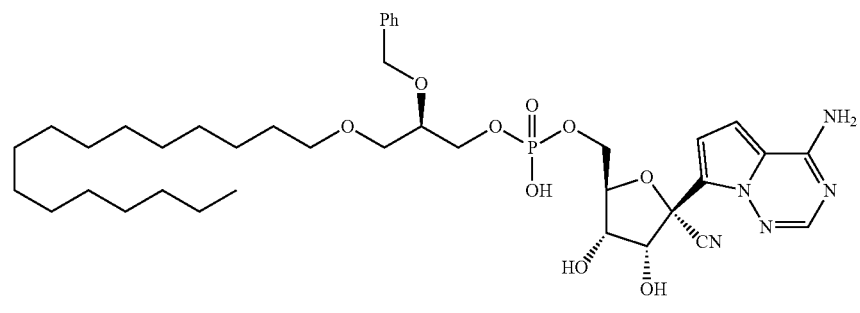

5

Intermediate 5-5 (13.0 mg, 0.0141 mmol) was dissolved in THF (1 mL THF), treated with a 2 M aqueous solution of NaOH (0.075 mL, 0.15 mmol), and heated to 50° C. The reaction solution was stirred for 2 hours at which point the reaction flask was placed in an ice bath and acidified with concentrated aqueous HCl. The reaction solution was warmed to room temperature and stirred 18 hours at which point triethylamine was titrated in until a yellow tint persisted at which point solvent was removed under reduced pressure. The resulting residue was taken up in 4:1 MeOH: dioxane and compound 5 was isolated as a triethylammonium salt by preparative HPLC (60-100% water:i-PrOH eluent ramp).

$^1$H NMR (400 MHz, Chloroform-d) δ. 7.91 (s, 1H), 7.35-7.19 (m, 5H), 6.90 (d, J=4.5 Hz, 1H), 6.85 (d, J=4.6 Hz, 1H), 4.65-4.51 (m, 3H), 3.95 (dd, J=6.4, 4.9 Hz, 1H), 3.75 (s, 2H), 3.64 (dd, J=5.8, 4.1 Hz, 1H), 3.49-3.26 (m, 6H), 3.17-3.04 (m, 7H), 1.45 (t, J=6.8 Hz, 2H), 1.31-1.14 (m, 34H), 0.89-0.81 (m, 3H).

MS m/z 760.2

Example 6: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-(benzyloxy)-3-(heptadecyloxy)propyl) hydrogen phosphate

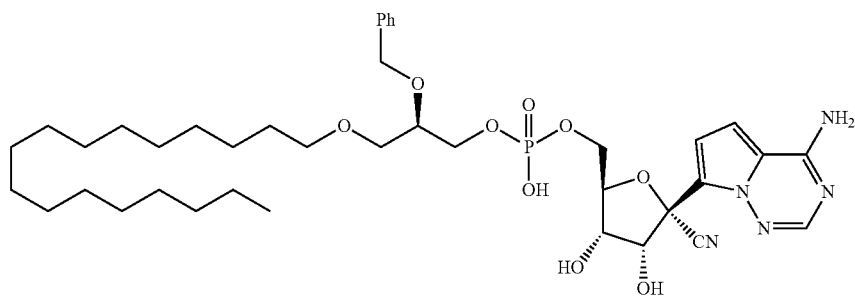

6

Compound 6 was synthesized as a triethyl ammonium salt in a manner similar to compound 5 using 1-heptadecanol in place of 1-hexadecanol.

¹H NMR (400 MHz, DMSO-d₆) δ 7.91 (s, 1H), 7.35-7.18 (m, 5H), 6.90 (d, J=4.6 Hz, 1H), 6.84 (d, J=4.4 Hz, 1H), 4.57 (d, J=7.5 Hz, 1H), 4.18-3.12 (m, 13H), 3.09 (q, J=7.3 Hz, 6H), 1.45 (p, J=6.9 Hz, 2H), 1.32-1.13 (m, 37H), 0.85 (t, J=6.6 Hz, 3H).

MS m/z 774.0.

Example 7: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-(benzyloxy)-3-(nonadecyloxy)propyl) hydrogen phosphate (7)

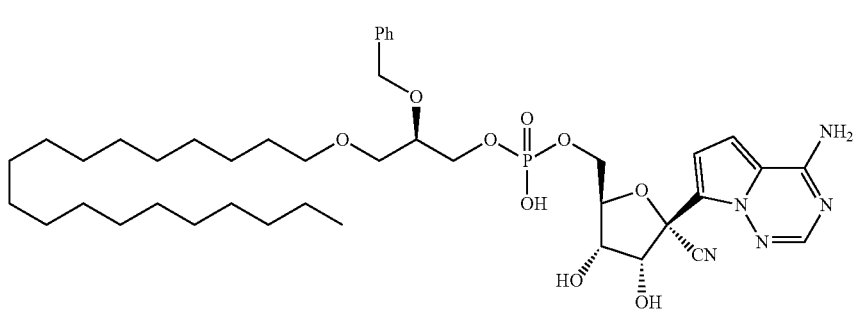

7

Compound 7 was synthesized as a triethylammonium salt in a manner similar to compound 5 using 1-nonadecanol in place of 1-hexadecanol.

¹H NMR (400 MHz, Chloroform-d) δ. 7.91 (s, 1H), 7.36-7.20 (m, 5H), 6.90 (d, J=4.5 Hz, 1H), 6.84 (d, J=4.5 Hz, 1H), 4.64-4.50 (m, 3H), 3.94 (dd, J=6.5, 4.9 Hz, 1H), 3.83 (q, J=5.9 Hz, 1H), 3.72 (t, J=5.7 Hz, 2H), 3.67-3.59 (m, 1H), 3.49-3.28 (m, 811), 3.16-3.02 (m, 5H), 1.44 (q, J=6.7 Hz, 2H), 1.23 (d, J=5.8 Hz, 32H), 1.17 (t, J=7.3 Hz, 9H), 0.89-0.81 (m, 3H).

MS m/z=802.2

Example 8: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-(benzyloxy)-3-(icosyloxy)propyl) hydrogen phosphate

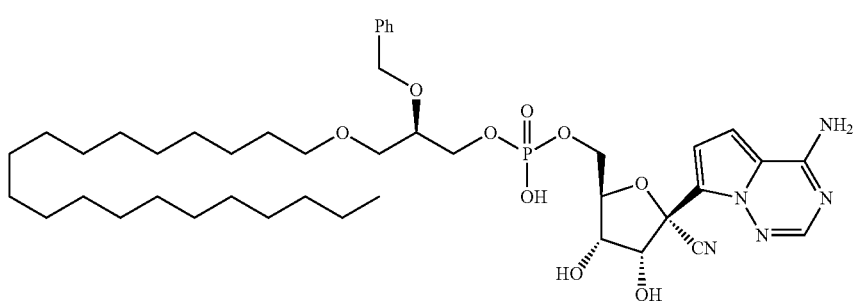

8

Compound 8 was synthesized as a triethylammonium salt in a manner similar to compound 5 using 1-icosanol in place of 1-hexadecanol.

$^{1}$H NMR (400 MHz, Chloroform-d) δ. 7.91 (s, 1H), 7.35-7.18 (m, 5H), 6.90 (d, J=4.5 Hz, 1H), 6.85 (d, J=4.5 Hz, 1H), 4.64-4.51 (m, 3H), 4.15 (t, J=5.2 Hz, 1H), 3.94 (dd, J=6.5, 4.9 Hz, 1H), 3.85 (d, J=5.7 Hz, 1H), 3.74 (d, J=6.1 Hz, 2H), 3.66-3.27 (m, 7H), 3.13 (td, J=3.2, 1.6 Hz, 2H), 3.08 (t, J=7.3 Hz, 3H), 1.31-1.14 (m, 45H), 0.89-0.81 (m, 3H).

MS m/z 816.2

Intermediate 9-1: (S)-3-(Octadecyloxy)propane-1,2-diol [1-O-Octadecyl-sn-glycerol]

1H), 3.60-3.37 (m, 4H), 1.58 (q, J=7.1 Hz, 2H), 1.45 (s, 3H), 1.39 (s, 3H), 1.27 (s, 30H), 0.90 (t, J=6.7 Hz, 3H).

To a solution of above crude intermediate (5 g, 13 mmol) in methanol (80 mL), 2 M HCl solution (13 mL, 26 mmol) was added and the solution was heated to reflux for 4 h. After cooling to room temperature, the mixture was poured into water, the organic layers were extracted with ether, dried over $Na_2SO_4$ and the solvents were removed under vacuum to give small volume, the product was precipitated from hexanes, yielding intermediate 9-1.

$^{1}$H NMR (400 MHz, Chloroform-d) δ 3.93-3.84 (m, 1H), 3.79-3.64 (m, 2H), 3.61-3.42 (m, 4H), 1.59 (q, J=6.9 Hz, 2H), 1.28 (s, 30H), 0.96-0.84 (m, 3H).

Intermediate 9-2: 1-O-Octadecyl-3-O-tert-butyldimethylsilyl-sn-glycerol

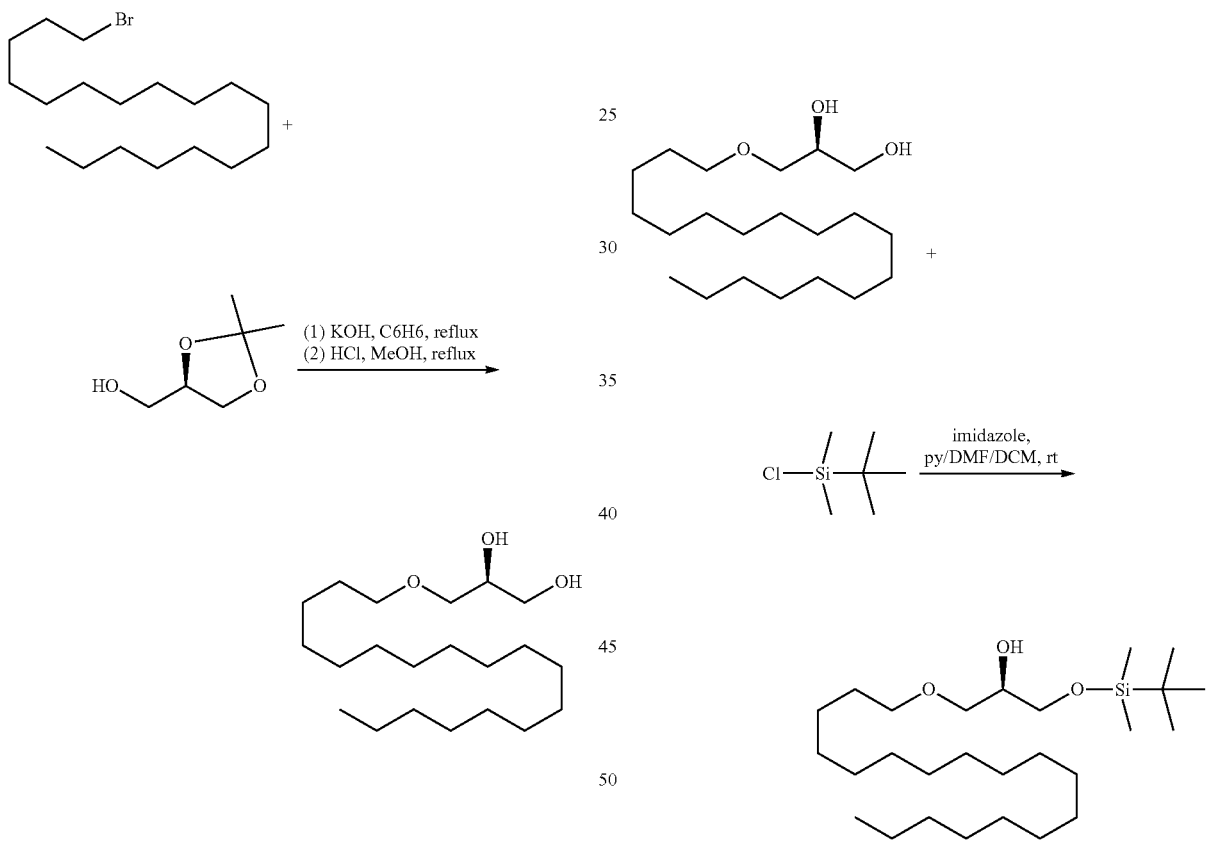

A mixture of (R)-(−)-2,2-dimethyl-1,3-dioxolane-4-methanol (6.68 g, 50.6 mmol), powdered potassium hydroxide (10 g, 178 mmol) and 1-bromooctadecane (16.9 g, 50.6 mmol) in benzene (100 mL) were stirred under reflux for 15 hours, while removing the water formed by azeotropic distillation. The reaction mixture was then cooled to room temperature, filtered, then the volume of the solvent was reduced to half. Water (100 mL) was added and the mixture was then extracted with diethyl ether (3×100 mL), the combined organic phase was combined, dried over $Na_2SO_4$, filtered and the solvent was then removed under reduced pressure to give intermediate.

$^{1}$H NMR (400 MHz, Chloroform-d) δ 4.29 (p, J=6.0 Hz, 1H), 4.08 (dd, J=8.3, 6.4 Hz, 1H), 3.75 (dd, J=8.2, 6.4 Hz, To a solution of (S)-3-(Octadecyloxy) propane-1,2-diol (3 g, 8.71 mmol) and imidazole (120 mg, 0.75 mmol) in a mixture of pyridine (45 mL), $CH_2Cl_2$ (5 mL) and DMF (5 mL) was added tert-butylchlorodimethylsilane (1.44 g, 9.58 mmol) at 0° C. After being stirred at room temperature for 5 h, the reaction mixture was diluted with water (10 mL), then extracted with $CH_2Cl_2$, and dried over $Na_2SO_4$. The solvent was evaporated, and the residue was purified by flash chromatography (0-30% EtOAc in hexanes), giving the product.

$^{1}$H NMR (400 MHz, Chloroform-d) δ 3.93-3.77 (m, 1H), 3.73-3.60 (m, 2H), 3.53-3.38 (m, 4H), 1.72-1.48 (m, 2H), 1.27 (s, 30H), 1.01-0.83 (m, 12H), 0.11 (d, J=11.7 Hz, 6H).

Intermediate 9-3: (R)-4-(((1-((tert-butyldimethylsilyl)oxy)-3-(octadecyloxy)propan-2-yl)oxy)methyl)benzonitrile Intermediate 9-4: (S)-4-(((1-hydroxy-3-(octadecyloxy)propan-2-yl)oxy)methyl)benzonitrile

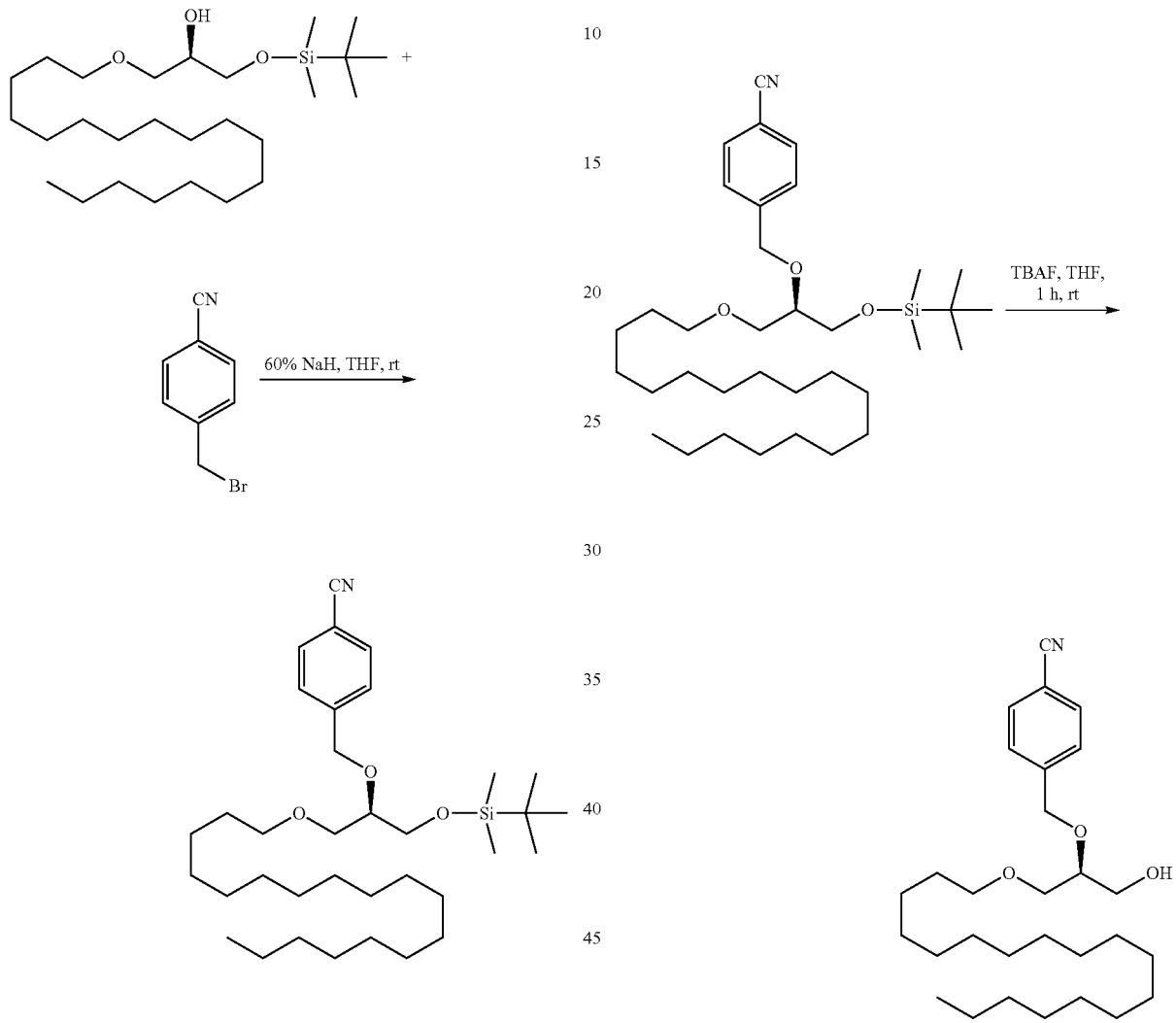

NaH (60% oil dispersion, 143 mg, 3.74 mmol) was suspended in THF (8 ml) and cooled to 0 C. A solution of 1-O-Octadecyl-3-O-tert-butyldimethylsilyl-sn-glycerol (350 mg, 0.763 mmol) in THF (3 ml) was added over 30 seconds. After 30 min at 0° C. a solution of 4-(bromomethyl)benzonitrile (493 mg, 2.52 mmol) in THF (3 ml) was added. The mixture was stirred for 16 h at room temperature. The reaction was quenched with water (15 ml). The mixture was extracted with EtOAC. The combined organic phase was dried over sodium sulfate and the solvent was removed under reduced pressure. The residue was purified by flash chromatography (0-30% EtOAc in hexanes), giving the product.

$^1$H NMR (400 MHz, Chloroform-d) δ 7.77-7.58 (m, 2H), 7.58-7.42 (m, 2H), 4.79 (s, 1H), 4.50 (m, 2H), 3.86-3.34 (m, 6H), 1.58 (m, 2H), 1.27 (m, 30H), 0.91 (m, 12H), 0.07 (s, 6H).

To a solution of silyl protected compound 9-3 (480 mg, 0.836 mmol) in THF (3.6 mL) at 0° C., 1 M TBAF in THF (1 mL, 1 mmol) was added and stirred for 1 h. It was diluted with water (3 mL) and extracted with EtOAc (2×10 mL). The combined organic layers were washed with water (2×5 mL), brine dried (Na$_2$SO$_4$), evaporated and the residue was purified by column chromatography (silica gel, 0-60% ethyl acetate in hexanes) to give the product.

$^1$H NMR (400 MHz, DMSO-d6) δ 7.81 (d, J=1.8 Hz, 1H), 7.79 (d, J=1.9 Hz, 1H), 7.54 (q, J=8.1 Hz, 2H), 4.81-4.62 (m, 3H), 3.60-3.39 (m, 6H), 1.46 (q, J=6.7 Hz, 2H), 1.23 (m, 30H), 0.95-0.72 (m, 3H).

Intermediate 9-5: tert-butyl (7-((3aR,4R,6R,6aR)-6-((((2-chlorophenoxy)((R)-2-((4-cyanobenzyl)oxy)-3-(octadecyloxy)propoxy)phosphoryl)oxy)methyl)-4-cyano-2,2-dimethyltetrahydrofuro[3,4-d][1,3]dioxol-4-yl)pyrrolo[2,1-f][1,2,4]triazin-4-yl)carbamate

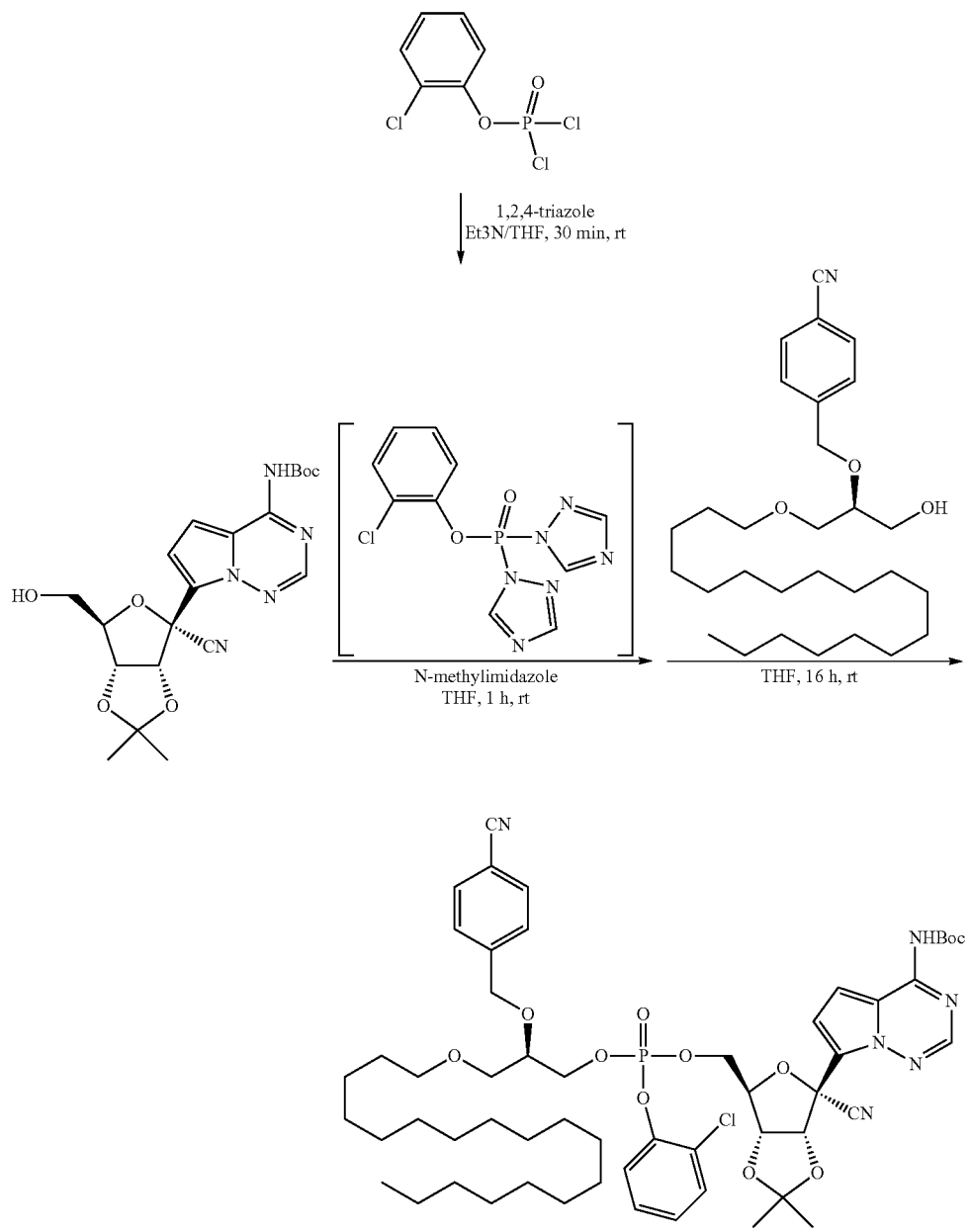

To a solution of 1,2,4-trizole (43 mg, 0.62 mmol) and triethylamine (87 uL, 0.62 mmol) in anhydrous THF (0.4 mL) was added a solution of 2-chlorophenyl dichlorophosphate (76 mg, 0.31 mmol) in THF (0.4 mL). The mixture was stirred for 30 min. and then filtered. To the filtrate were added sequentially, additional THF (1.2 mL), the nucleoside (100 mg, 0.232 mmol), and 1-methylimidazole (26 mg, 0.31 mmol). After 1 h, (S)-4-(((1-hydroxy-3-(octadecyloxy)propan-2-yl)oxy)methyl)benzonitrile (107 mg, 0.232 mmol) was added to the mixture and stirred overnight at room temperature. The solvent was evaporated and the residue was purified by flash chromatography on silica gel (0-15% MeOH in $CH_2Cl_2$) to afford a compound (136 mg, 55%).

$^1$H NMR (400 MHz, Chloroform-d) δ 8.35-8.10 (m, 1H), 7.65 (d, 2H), 7.58 (m, 1H), 7.49 (d, J=8.0 Hz, 2H), 7.46-7.31 (m, 2H), 7.23-7.00 (m, 3H), 5.53-5.23 (m, 1H), 5.06-4.10 (m, 6H), 3.91-3.26 (m, 5H), 1.77 (m, 2H), 1.59 (s, 6H), 1.47 (s, 9H), 1.27 (s, 30H), 0.89 (t, J=6.7 Hz, 3H).

$^{31}$P NMR (162 MHz, Chloroform-d) δ −6.94 (m).

Example 9: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((4-cyanobenzyl)oxy)-3-(octadecyloxy)propyl) hydrogen phosphate (9)

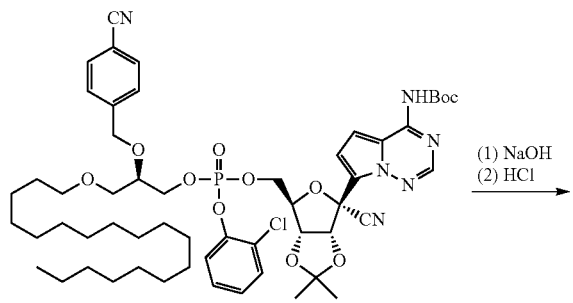

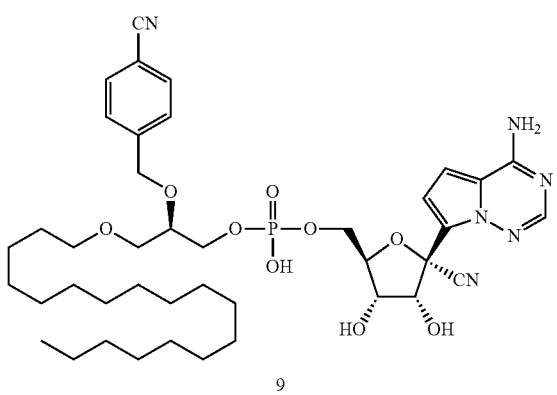

The above intermediate (130 mg, 0.122 mmol) was dissolved in THF (2.5 mL) and 0.5 N NaOH (0.9 mL, 3.6 eq) was added. The mixture was stirred at 50° C. for 4 h. The reaction progress was monitored by TLC. After consumption of intermediate, the mixture was neutralized with 1 N HCl at 0 C. The mixture was diluted with a pH 3 buffer solution and brine, and extracted twice with a mixture of DCM and MeOH. The combined organic layers were combined, dried over anhydrous $Na_2SO_4$, filtered and evaporated to give a residue.

The residue was dissolved in THF (0.6 mL). The resulting solution was cooled in an ice bath. Concentrated aqueous HCl (0.12 mL) was added. The cold bath was removed the reaction was stirred vigorously for 3 h. The mixture was neutralized with $Na_2CO_3$, diluted with MeOH, and filtered. The filtrate was evaporated to give a residue which was purified by prep-HPLC (Gemini column, 50-100% isopropanol in $H_2O$) to give compound 9.

$^1$H NMR (400 MHz, Methanol-$d_4$) δ 8.07-8.21 (d, 1H), 7.63 (dd, J=8.2, 1.7 Hz, 2H), 7.53 (dd, J=10.5, 8.2 Hz, 2H), 7.31 (dd, J=7.4, 4.8 Hz, 1H), 7.21 (dd, J=14.6, 4.8 Hz, 1H), 4.85-4.65 (m, 3H), 4.44-4.31 (m, 1H), 4.29-4.18 (m, 2H), 4.18-3.86 (m, 4H), 3.85-3.37 (m, 5H), 1.62 (s, 4H), 1.59-1.48 (m, 2H), 1.42-1.20 (m, 30H), 0.92 (t, J=6.8 Hz, 3H).

$^{31}$P NMR (162 MHz, Methanol-$d_4$) δ 0.16.

Example 10: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((4-methoxybenzyl)oxy)-3-(octadecyloxy)propyl) hydrogen phosphate (10)

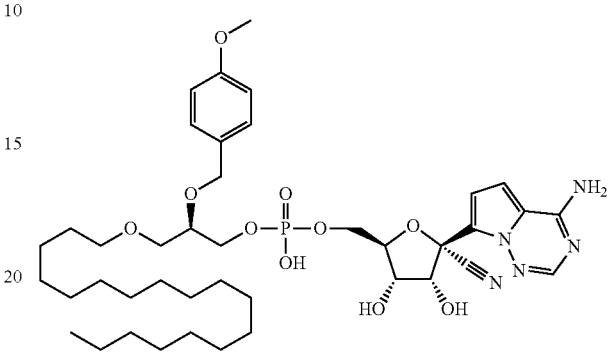

Compound 10 was synthesized in a manner similar to compound 9 using 4-methoxybenzyl bromide instead of 4-cyanobenzyl bromide.

$^1$H NMR (400 MHz, DMSO-$d_6$) δ 7.93 (m, 2H, 1 proton $D_2O$ exchangeable), 7.26-7.18 (m, 2H), 6.90 (d, J=4.5 Hz, 1H), 6.85 (m, 3H), 6.34 (d, J=6.1 Hz, 1H, $D_2O$ exchangeable), 4.64 (t, J=5.3 Hz, 1H), 4.55-4.41 (m, 2H), 4.30-4.05 (m, 2H), 4.06-3.78 (m, 5H), 3.72 (s, 3H), 3.70-3.59 (m, 1H), 1.43 (t, J=6.9 Hz, 2H), 1.22 (d, J=7.9 Hz, 30H), 0.93-0.78 (m, 3H).

$^{31}$P NMR (162 MHz, DMSO-$d_6$) δ −1.09.

Example 11: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-3-(octadecyloxy)-2-((4-(trifluoromethyl)benzyl)oxy)propyl) hydrogen phosphate (11)

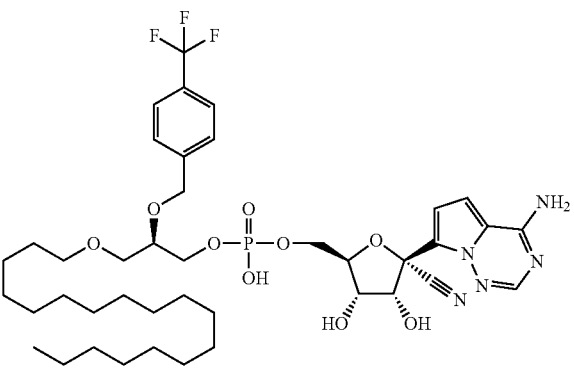

Compound 11 was synthesized in a manner similar to compound 9 using 4-trifluoromethylbenzyl bromide instead of 4-cyanobenzyl bromide.

$^1$H NMR (400 MHz, DMSO-$d_6$) δ 7.92 (m, 3H, 2 proton $D_2O$ exchangeable), 7.66 (d, J=8.1 Hz, 2H), 7.54 (d, J=8.0 Hz, 2H), 6.90 (d, J=4.5 Hz, 1H), 6.84 (d, J=4.5 Hz, 1H), 6.35

(d, J=6.0 Hz, 1H, D₂O exchangeable), 4.75-4.59 (m, 3H), 4.17 (m, 2H), 3.94 (m, 4H), 3.70 (m, 1H), 3.44 (m, 4H), 1.42 (m, 2H), 1.21 (m, 30H), 0.93-0.79 (m, 3H).
³¹P NMR (162 MHz, DMSO-d₆) δ −1.10 (m).

Intermediate 12-1: (R)-2-(benzyloxy)-3-(octadecyloxy)propyl (2-chlorophenyl) phosphate triethylammonium

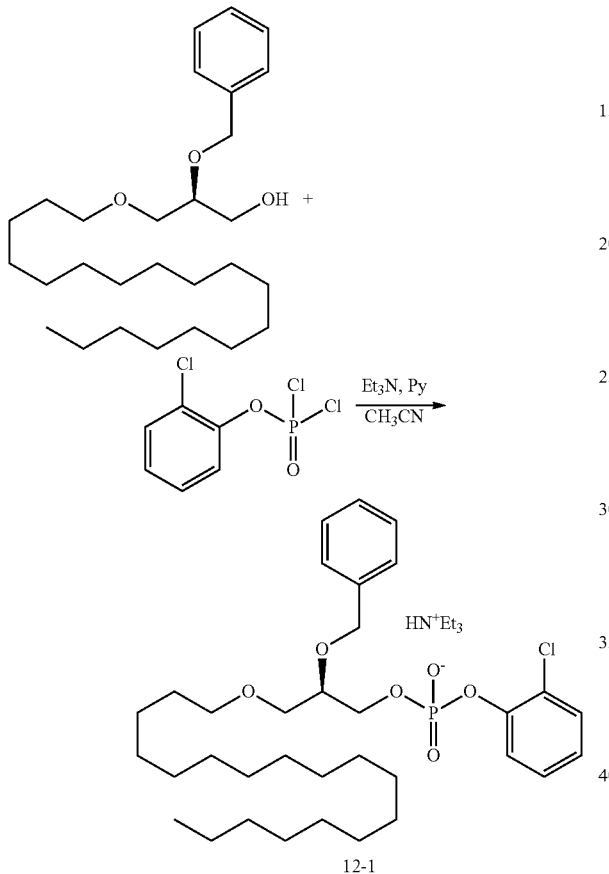

2-chlorophenyl phosphorodichloridate (2.2 g, 8.97 mmol) was dissolved in acetonitrile (30 mL) and cooled to 0° C. To this solution was added 1,2,4-triazole (1.33 g, 19.3 mmol), followed by TEA (2.69 mL, 19.3 mmol) slowly. The cold bath was removed and stirred at room temperature for 45 min. To stirred mixture was added a solution of (S)-2-(benzyloxy)-3-(octadecyloxy) propan-1-ol (3.9 g, 8.97 mmol) in pyridine (40 mL) slowly and stirred for 4 h at room temperature. To the mixture was added TEA (2.69 mL) followed by water (1.5 mL), stirred for 25 min and then added sat. NaHCO₃ (20 mL) stirred for additional 10 min. Diluted with more sat. NaHCO₃ and then extracted with DCM (2×100 mL). Combined organic layers were washed with 1:1:1 mixture of water, brine and sat. NaHCO₃ (180 mL). The combined organic layers were dried over Na₂SO₄, concentrated, co-evaporated with Toluene (50 ml×2), and dried under high vacuum. The crude product was dissolved in 5% MeOH/DCM, loaded on 220 g gold column, eluted with 0-40% MeOH, product elute at 20% MeOH/DCM, as two broad peaks (peaks streak long), pure fractions (checked by TLC/LCMS) combined and concentrated to afford intermediate 12-1.

MS m/z 625.4 [M+1]
¹H NMR (400 MHz, DMSO-d₆) δ 9.90 (s, 1H), 7.62 (dd, J=8.4, 1.4 Hz, 1H), 7.39-7.22 (m, 6H), 7.15 (td, J=8.3, 7.8, 1.7 Hz, 1H), 6.94 (td, J=7.7, 1.5 Hz, 1H), 4.56 (d, J=2.4 Hz, 2H), 4.17-4.05 (m, 1H), 3.89-3.74 (m, 2H), 3.69-3.59 (m, 1H), 3.47-3.26 (m, 6H), 3.04 (qd, J=7.2, 4.5 Hz, 5H), 1.43 (q, J=6.6 Hz, 2H), 1.23 (d, J=2.6 Hz, 32H), 1.16 (t, J=7.3 Hz, 9H), 0.90-0.81 (m, 3H).
³¹P NMR (162 MHz, DMSO-d₆) δ −5.82.

Intermediate 12-2: ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl ((R)-2-(benzyloxy)-3-(octadecyloxy)propyl) (2-chlorophenyl) phosphate

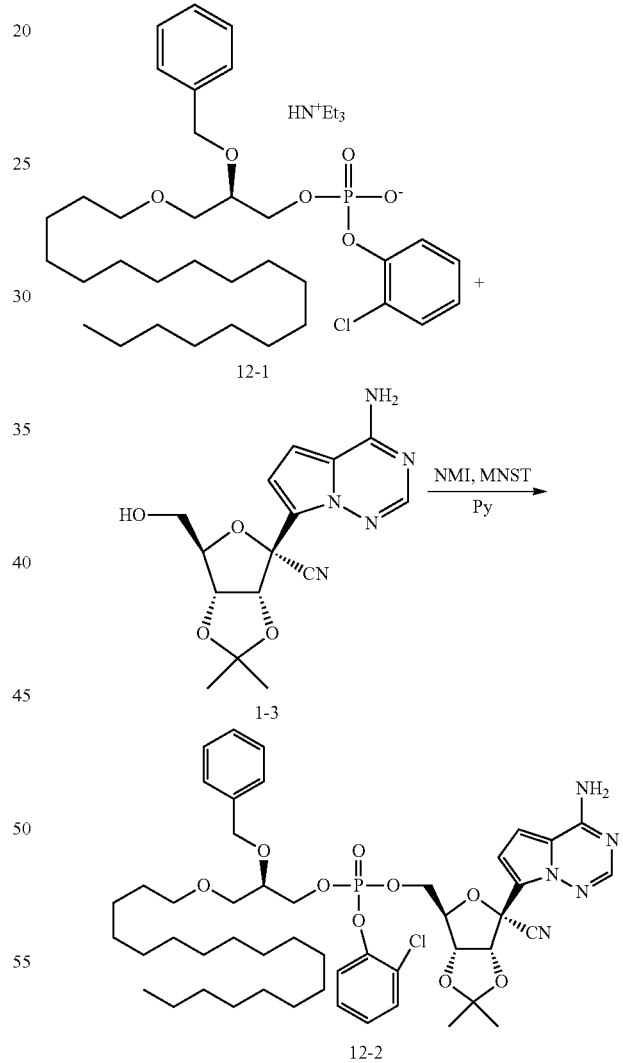

Intermediate 12-1 (3.0 g, 9.05 mmol) was dissolved in pyridine (80 mL). To this solution was added 1-(Mesitylene-2-sulfonyl)-3-nitro-1,2,4-triazole (4.02 g, 13.6 mmol), followed by intermediate 1-3 (3.0 g, 9.05 mmol). To this solution was added NMI (1.12 mL, 13.6 mmol) and the reaction was stirred at room temperature for 4 h. The reaction was cooled in an ice bath and quenched by slow addition of a saturated aqueous NaHCO₃ solution. The aqueous layer was diluted with a 1:1:1: mixture of water, a saturated aqueous NaHCO₃ solution and brine. The aqueous layer was extracted with DCM (2×400 mL) and the combined organics were dried over Na₂SO₄, which was removed by filtration. The filtrate was concentrated and intermediate 12-2 was isolated by silica gel column chromatography (220 g, Combi flash HP Gold Column, eluent ramp from 0-100% EtOAc/hexanes).

MS m/z=938.3 [M+1]

Intermediate 12-3: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-(benzyloxy)-3-(octadecyloxy)propyl) (2-chlorophenyl) phosphate

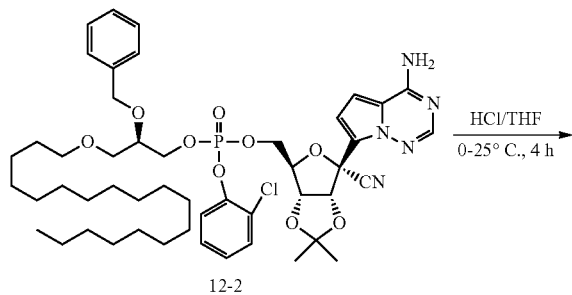

12-2

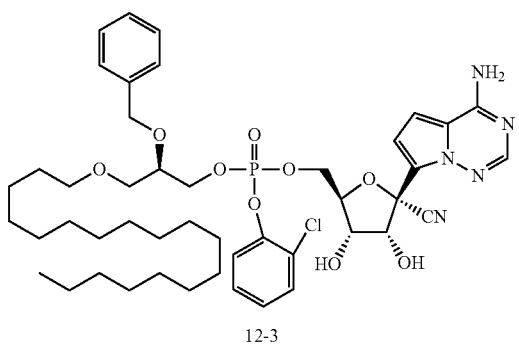

12-3

Intermediate 12-2 (0.5 g, 0.533 mmol) was dissolved in THF (20 mL). To this solution was added concentrated HCl (3.32 mL, 50.6 mmol) drop wise at 0° C. The reaction was warmed and stirred at room temperature over 4 h. Upon completion the reaction was concentrated, and the residue was co-evaporated with THF (2×30 mL) and DCM (2×30 mL). The resulting residue was taken up in DCM and intermediate 12-3 was isolated by silica gel column chromatography (40 g Combi flash HP Gold Column, eluent ramp from 0-40% MeOH/DCM).

MS m/z=898.4 [M+1]

Intermediate 12-4: (2R,3S,4R,5R)-5-(4-aminopyrrolo[2,1-f][1,2,4]triazin-7-yl)-2-(((((R)-2-(benzyloxy)-3-(octadecyloxy)propoxy)(2-chlorophenoxy)phosphoryl)oxy)methyl)-5-cyano-4-hydroxytetrahydrofuran-3-yl isobutyrate Intermediate 13-4: (2R,3R,4R,5R)-2-(4-aminopyrrolo[2,1-f][1,2,4]triazin-7-yl)-5-(((((R)-2-(benzyloxy)-3-(octadecyloxy)propoxy)(2-chlorophenoxy)phosphoryl)oxy)methyl)-2-cyanotetrahydrofuran-3,4-diyl bis(2-methylpropanoate)

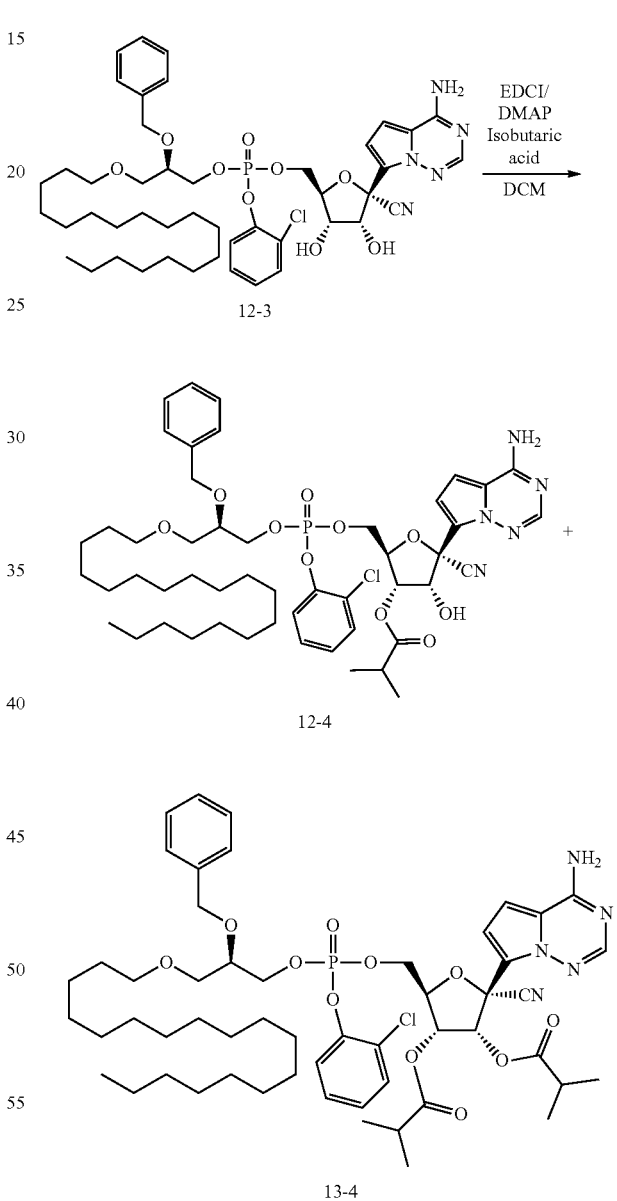

To a mixture of intermediate 12-3 (0.5 g, 0.557 mmol), 2-methylpropanoic acid (98.1 mg, 1.11 mmol), and EDCl (0.427 mg, 2.23 mmol) in DCM (10 mL) was added DMAP (0.272 mg, 2.23 mmol) in one portion. The resulting mixture was stirred at room temperature for 1.2 h. The reaction was diluted with DCM and washed with water, followed by saturated ammonium chloride solution, dried over sodium sulfate, and concentrated and dried under high vacuum. The obtained crude residue contains intermediate 12-4 and intermediate 13-4 conformed by LCMS and used for next step.

Intermediate 12-4: MS m/z=968.5 [M+1]

Intermediate 13-4: MS m/z=1038.7 [M+1]

Example 12: (2R,3S,4R,5R)-5-(4-aminopyrrolo[2,1-f][1,2,4]triazin-7-yl)-2-(((((R)-2-(benzyloxy)-3-(octadecyloxy)propoxy)(hydroxy)phosphoryl)oxy)methyl)-5-cyano-4-hydroxytetrahydrofuran-3-yl isobutyrate (12)

Example 13: (2R,3R,4R,5R)-2-(4-aminopyrrolo[2,1-f][1,2,4]triazin-7-yl)-5-(((((R)-2-(benzyloxy)-3-(octadecyloxy)propoxy)(hydroxy)phosphoryl)oxy)methyl)-2-cyanotetrahydrofuran-3,4-diyl bis(2-methylpropanoate) (13)

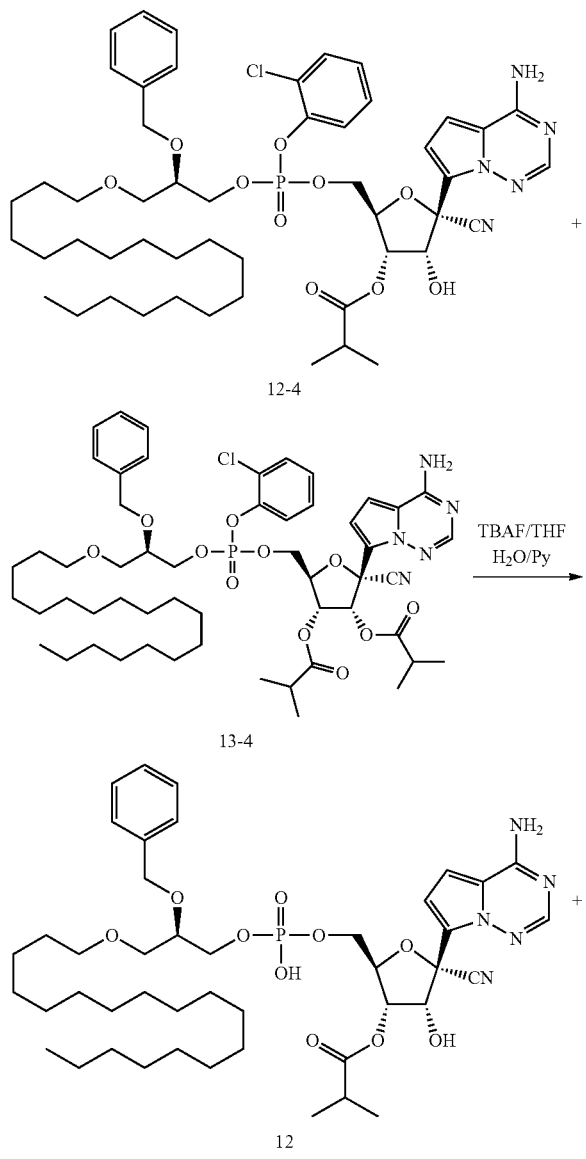

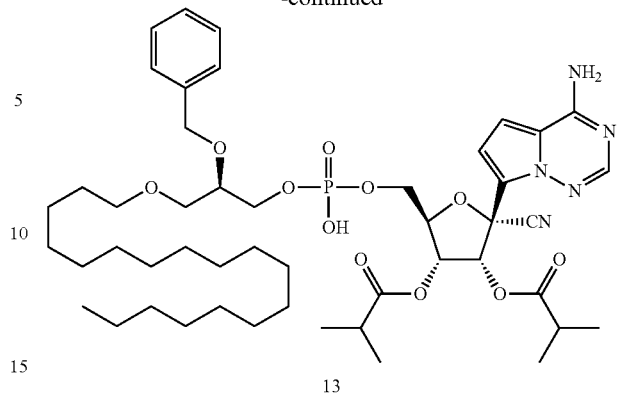

The crude mixture of intermediate 12-4 and intermediate 13-4 (0.5 g, 0.451 mmol) was dissolved in THF (10.2 mL) and added pyridine (1.25 mL) followed by water (1.25 mL). To the resulting clear homogenous solution was added a 1 M solution of TBAF in THF (1.8 mL, 0.43 mmol). The reaction was stirred at room temperature over 3 h. Upon completion of the reaction conformed by LCMS, the reaction was cooled in an ice bath and quenched with saturated aqueous NaHCO$_3$ solution (5 mL). The reaction concentrated to remove most of volatiles and partitioned between DCM and water. To the stirred solution was added 2 N HCl dropwise to adjust pH~3 and extracted with DCM (2×100 mL). The combined organic phase was washed with brine (pH of which was adjusted to 8 with saturated aqueous NaHCO$_3$ solution) once and dried over Na$_2$SO$_4$, which was removed by filtration. The filtrate was concentrated, and the crude product dissolved in mixture of MeOH/Dioxane/water (~6:1:0.1 mL), sonicated to complete dissolution, filtered and purified by preparative HPLC (Gemini, 10 uM, NX-C18, 110 Å 250×30 mm column, 60-100% 16 min, acetonitrile/water, and 100% acetonitrile 16 min gradient) to afford compound 12 and 13.

Compound 12

MS m/z=858.5 [M+1]

$^1$H NMR (400 MHz, Chloroform-d) δ 8.05 (s, 1H), 7.28 (s, 5H), 6.94 (d, J=4.6 Hz, 1H), 6.64 (d, J=4.7 Hz, 1H), 6.27 (d, J=5.9 Hz, 1H), 5.61 (s, 2H), 5.53 (dd, J=5.9, 4.2 Hz, 1H), 4.65 (q, J=4.1 Hz, 1H), 4.41 (qd, J=12.3, 4.1 Hz, 2H), 4.28-4.03 (m, 1H), 4.02-3.84 (m, 1H), 3.87-3.59 (m, 2H), 3.58-3.22 (m, 1H), 2.80-2.48 (m, 3H), 1.48 (d, J=32.7 Hz, 2H), 1.39-1.04 (m, 38H), 0.93 (dt, J=23.4, 7.1 Hz, 3H).

Compound 13

MS m/z 928.5 [M+1]

$^1$H NMR (400 MHz, Chloroform-d) δ 7.87 (s, 1H), 7.34-7.17 (m, 5H), 6.92 (s, 2H), 6.90 (d, J=4.8 Hz, 1H), 6.68 (d, J=4.7 Hz, 1H), 6.23 (d, J=6.0 Hz, 1H), 5.46 (dd, J=6.0, 4.2 Hz, 1H), 5.08 (t, J=2.8 Hz, 1H), 4.72-4.49 (m, 2H), 4.30 (qd, J=10.9, 4.5 Hz, 1H), 4.19 (ddd, J=11.9, 7.8, 4.2 Hz, 1H), 4.06 (dq, J=12.9, 6.7 Hz, 1H), 3.75 (td, J=8.7, 8.1, 3.2 Hz, 2H), 3.65 (dt, J=11.6, 3.0 Hz, 1H), 3.57-3.41 (m, 1H), 3.40-3.25 (m, 1H), 3.24-3.13 (m, 1H), 2.74-2.58 (m, 2H), 1.53-1.35 (m, 3H), 1.32-1.21 (m, 36H), 1.21-1.15 (m, 7H), 0.90 (t, J=6.7 Hz, 3H).

Intermediate 14-0: (2R)-1-[tert-butyl(dimethyl)silyl]oxy-3-octadecoxy-propan-2-ol

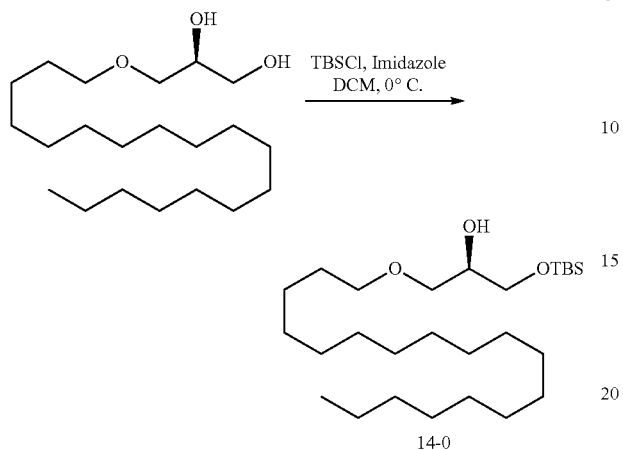

14-0

A solution of t-butyldimethylsilyl chloride (350 mg, 2.32 mmol) in dichloromethane (2 mL) was added to a solution of (2S)-3-octadecoxypropane-1,2-diol (500 mg, 1.45 mmol) and imidazole (198 mg, 2.90 mmol) in dichloromethane (5 mL) at 0° C. over a period of 1 min. After 2 h the ice bath was removed. After 3 h, the reaction was washed with water (5 mL). The aqueous phase was extracted with dichloromethane (10 mL). The combined organic phases were dried over sodium sulfate and the solvent was removed under reduced pressure. The residue was subjected to flash chromatography (0-30% ethyl acetate/hexanes). The fractions containing product were combined and the solvent was removed under reduced pressure, providing intermediate 14-0.

$^1$H NMR (400 MHz, Chloroform-d) δ 3.83 (p, J=5.4 Hz, 1H), 3.74-3.62 (m, 2H), 3.50-3.42 (m, 4H), 1.58 (q, J=7.0 Hz, 2H), 1.27 (m, 30H), 0.91 (m, 12H), 0.09 (s, 6H).

Intermediate 14-1: tert-butyl-[(2R)-2-[(3,4-difluorophenyl)methoxy]-3-octadecoxy-propoxy]-dimethyl-silane

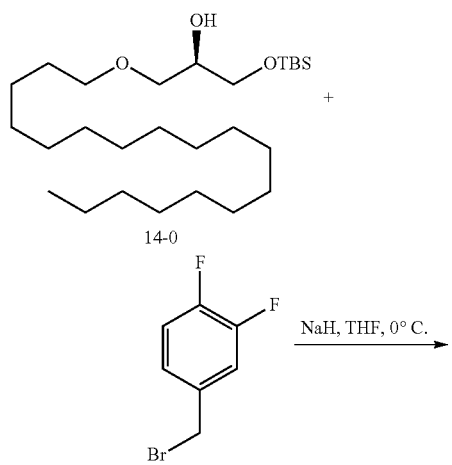

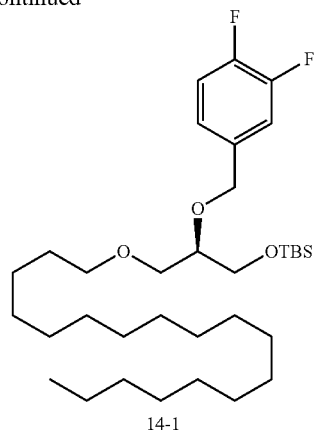

14-1

Sodium hydride 60% dispersion in mineral oil (53.4 mg, 1.39 mmol) was suspended in tetrahydrofuran (5 mL) and cooled to 0° C. A solution of the 14-0 (320 mg, 0.697 mmol) in tetrahydrofuran (2 mL) was added over 30 seconds. After 30 minutes a solution of 4-(bromomethyl)-1,2-difluorobenzene (178 uL, 1.39 mmol) in tetrahydrofuran (2 mL) was added. The ice bath was removed. After 16 h the reaction was judged to be complete by TLC (15% ethyl acetate/hexanes). The reaction was quenched with water (10 mL) at 0° C. The mixture was extracted with ethyl acetate (3×10 mL). The combined organic phases were dried over sodium sulfate and the solvent was removed under reduced pressure. The residue was subjected to flash chromatography (0-20% ethyl acetate/hexanes, using ELSD detection). The fractions containing product were combined and the solvent was removed under reduced pressure, providing intermediate 14-1.

$^1$H NMR (400 MHz, Chloroform-d) δ 7.25 (dd, J=7.4, 4.8 Hz, 1H), 7.18-7.03 (m, 2H), 4.67 (s, 2H), 3.71 (d, J=6.0 Hz, 2H), 3.63 (p, J=5.3 Hz, 1H), 3.56 (dd, J=10.3, 4.2 Hz, 1H), 3.50 (dd, J=10.3, 5.8 Hz, 1H), 3.45 (t, J=6.8 Hz, 2H), 1.58 (q, J=7.2 Hz, 2H), 1.27 (s, 30H), 0.91 (d, J=5.7 Hz, 12H), 0.08 (s, 6H).

$^{19}$F NMR (376 MHz, Chloroform-d) δ -138.62--138.83 (m), -140.54--140.77 (m).

Intermediate 14-2: (2S)-2-[(3,4-difluorophenyl)methoxy]-3-octadecoxy-propan-1-ol

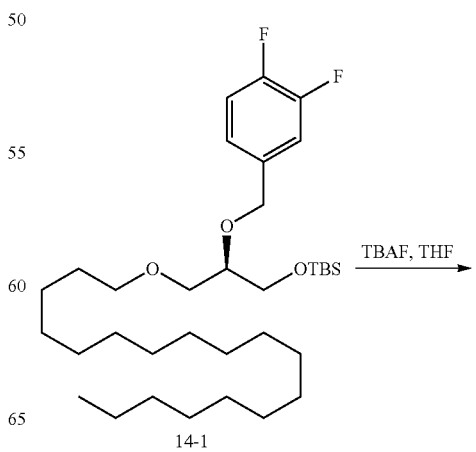

14-1

-continued

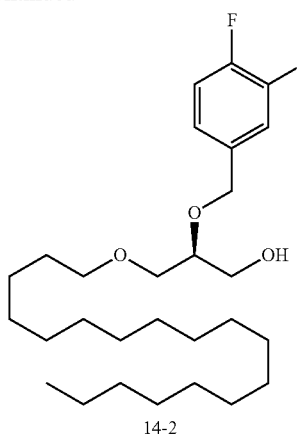

14-2

A solution of tetrabutylammonium fluoride in tetrahydrofuran (0.995 mL, 0.995 mmol) was added to a solution of intermediate 14-1 (194 mg, 0.332 mmol) in tetrahydrofuran (5 mL). After 45 minutes the reaction was diluted with ethyl acetate (20 mL). The organic phase was washed with water (3×5 mL) and brine (5 ml). The organic phase was dried over sodium sulfate and the solvent was removed under reduced pressure. The residue was subjected to flash chromatography (0-20% ethyl acetate/hexanes, using ELSD). The fractions containing product were combined and the solvent was removed under reduced pressure, providing intermediate 14-2.

Intermediate 14-3: [(2R)-2-[(3,4-difluorophenyl)methoxy]-3-octadecoxy-propyl] bis(4-nitrophenyl) phosphate

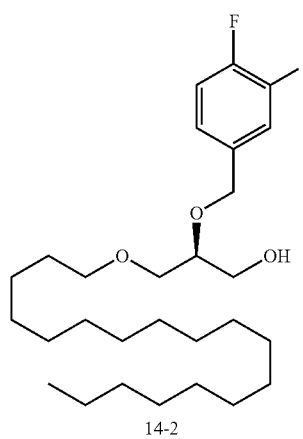

14-2

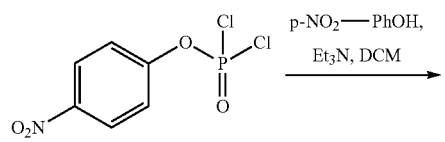

-continued

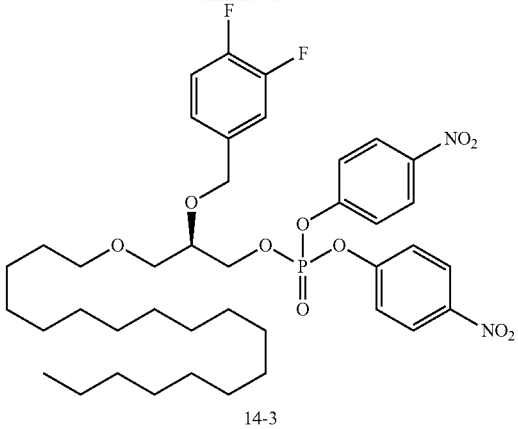

14-3

A solution of intermediate 14-2 (143 mg, 0.304 mmol) in dichloromethane (2 mL) was added to a solution of 4-nitrophenyl phosphorodichloridate (93.5 mg, 0.365 mmol) in dichloromethane (5 mL) at 0° C. Triethylamine (106 uL, 0.761 mmol) was added. After 5 minutes the bath was removed. After 2 hours 4-nitrophenol (59.3 mg, 0.426 mmol) was added. After 1 hour the reaction was diluted with ethyl acetate (20 mL) and washed with water (2×5 mL) and brine (5 mL). The residue was subjected to flash chromatography (0-50% ethyl acetate/hexanes). The fractions containing product were combined and the solvent was removed under reduced pressure, providing intermediate 14-3.

$^1$H NMR (400 MHz, Chloroform-d) δ 8.30-8.19 (m, 4H), 8.13 (d, J=9.1 Hz, 0.41H), 7.46-7.35 (m, 4H), 7.23-7.14 (m, 1H), 7.10 (dt, J=10.1, 8.1 Hz, 1H), 7.04-6.95 (m, 1H), 4.63-4.51 (m, 3H), 4.42 (m, 1H), 3.83 (m, 1H), 3.55 (m, 2H), 3.43 (t, J=6.6 Hz, 2H), 1.55 (q, J=6.8 Hz, 2H), 1.26 (m, 30H), 0.89 (t, J=6.7 Hz, 3H).

$^{19}$F NMR (376 MHz, Chloroform-d) δ −137.88 (ddd, J=21.0, 11.1, 8.0 Hz), −139.15--139.37 (m).

$^{31}$P NMR (162 MHz, Chloroform-d) δ −13.10 (t, J=8.0 Hz).

Intermediate 14-4: [(3aR,4R,6R,6aR)-4-(4-aminopyrrolo[2,1-f][1,2,4]triazin-7-yl)-4-cyano-2,2-dimethyl-6,6a-dihydro-3aH-furo[3,4-d][1,3]dioxol-6-yl]methyl [(2R)-2-[(3,4-difluorophenyl)methoxy]-3-octadecoxy-propyl] (4-nitrophenyl) phosphate

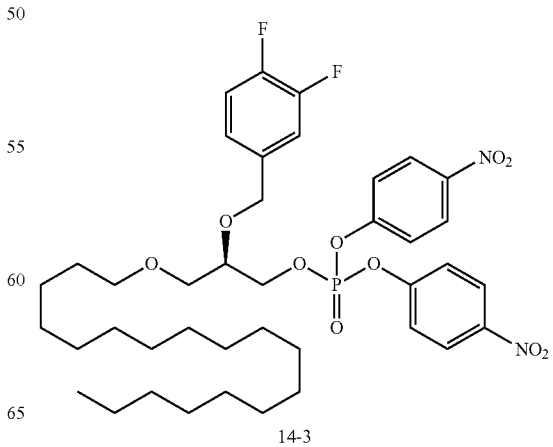

14-3

-continued

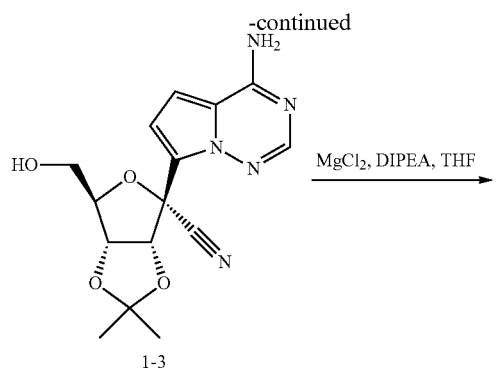

1-3

MgCl₂, DIPEA, THF

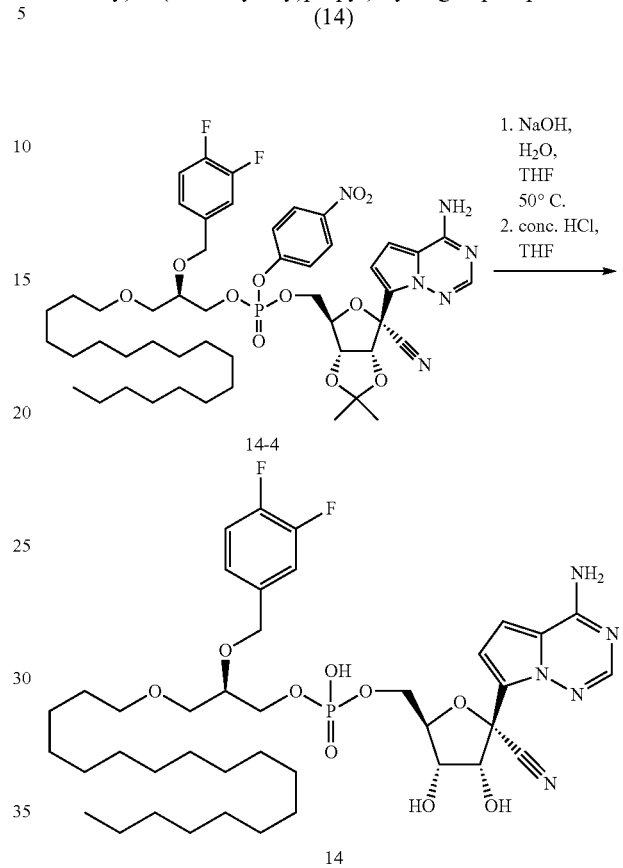

14-4

Magnesium chloride (31.3 mg, 0.329 mmol) was added to a solution of intermediate 14-3 (52.2 mg, 0.0658 mmol) and intermediate 1-3 (20.7 mg, 0.0625 mmol) in tetrahydrofuran (5 mL). The mixture was stirred at 50° C. for 15 minutes. The mixture was cooled briefly and N,N-diisopropylethylamine (0.057 mL, 0.329 mmol) was added. After 2 hours the reaction was quenched with water (5 mL) and brine (5 mL). The mixture was extracted with 2-methyltetrahydrofuran (3×10 mL). The combined organic phases were dried over sodium sulfate and the solvent was removed under reduced pressure. The residue was subjected to flash chromatography (0-10% methanol/dichloromethane). The fractions containing product were combined and the solvent was removed under reduced pressure, providing intermediate 14-4.

¹H NMR (400 MHz, Chloroform-d) δ 8.01 (d, J=9.1 Hz, 1H), 7.91-7.85 (m, 2H), 7.31-7.18 (m, 3H), 7.17-7.00 (m, 3H), 6.98 (dd, J=6.9, 4.6 Hz, 1H), 6.59 (t, J=4.6 Hz, 1H), 5.85 (m, 2H), 5.48 (dd, J=9.2, 6.9 Hz, 1H), 4.95 (m, 1H), 4.65-4.55 (m, 3H), 4.52 (m, 1H), 4.48-4.42 (m, 1H), 4.42-4.31 (m, 1H), 4.25 (m, 1H), 3.83-3.71 (m, 1H), 3.50 (m, 2H), 3.42 (td, J=6.7, 3.6 Hz, 2H), 1.76 (s, 3H), 1.54 (q, J=6.8 Hz, 2H), 1.40 (d, J=3.9 Hz, 3H), 1.37-1.20 (m, 30H), 0.95-0.86 (m, 3H).

MS m/z [M+1]=985.35

¹⁹F NMR (377 MHz, Chloroform-d) δ −137.94−−138.19 (m), −139.46−−139.82 (m).

³¹P NMR (162 MHz, Chloroform-d) δ −7.15 (p, J=7.4 Hz), −7.51 (p, J=7.4 Hz).

Example 14: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((3,4-difluorobenzyl)oxy)-3-(octadecyloxy)propyl) hydrogen phosphate (14)

A solution of sodium hydroxide (1 N, 0.14 mL, 0.14 mmol) was added to a solution of intermediate 14-4 (34.4 mg, 0.0349 mmol) in tetrahydrofuran (5 mL) and heated at 50° C. After 2 hours starting material remained. After 5 hours the reaction mixture was cooled and diluted with 2-methyltetrahydrofuran (10 mL) and hydrochloric acid (1 N, 0.3 mL, 0.3 mmol). The aqueous phase was extracted with 2-methyltetrahydrofuran (2×10 mL). The combined organic phases were washed with brine (10 mL) and dried over sodium sulfate. The residue was subjected to flash chromatography (0-20% methanol/dichloromethane). The fractions containing product were combined and the solvent was removed under reduced pressure, providing [(3aR,4R,6R,6aR)-4-(4-aminopyrrolo[2,1-f][1,2,4]triazin-7-yl)-4-cyano-2,2-dimethyl-6,6a-dihydro-3aH-furo[3,4-d][1,3]dioxol-6-yl]methyl [(2R)-2-[(3,4-difluorophenyl)methoxy]-3-octadecoxy-propyl] hydrogen phosphate.

MS m/z [M+1]=864.28

Concentrated hydrochloric acid (12 N, 0.30 mL, 3.69 mmol) was added to a solution of [(3aR,4R,6R,6aR)-4-(4-aminopyrrolo[2,1-f][1,2,4]triazin-7-yl)-4-cyano-2,2-dimethyl-6,6a-dihydro-3aH-furo[3,4-d][1,3]dioxol-6-yl]methyl [(2R)-2-[(3,4-difluorophenyl)methoxy]-3-octadecoxy-propyl] hydrogen phosphate (24.5 mg, 0.0295 mmol). After 2 hours triethylamine (0.51 mL, 3.69 mmol) was added. The minimum amount of methanol was added to the mixture to dissolve any solids. The solution was subjected to preparative HPLC (50-100% isopropanol/water over 20 minutes).

The fractions containing product were combined and the isopropanol was removed under reduced pressure. The residue was taken up in 1,4-dioxane (5 mL) and subjected to lyophilization. Repurification was required. The product was subjected to preparative HPLC (50-100% isopropanol/water over 20 minutes). The fractions containing product were combined and the isopropanol was removed under reduced pressure. The residue was taken up in 1,4-dioxane (5 mL) and subjected to lyophilization, providing compound 14.

$^1$H NMR (400 MHz, DMSO-d6) δ 12.13-12.04 (m, 0.15H), 8.12-7.67 (m, 3H), 7.42-7.24 (m, 2H), 7.18-7.10 (m, 1H), 6.94-6.74 (m, 2H), 6.27-6.20 (m, 1H), 5.92-5.83 (m, 1H), 4.67-4.48 (m, 3H), 4.24-4.10 (m, 1H), 4.03-3.89 (m, 1H), 3.89-3.77 (m, 1H), 3.72 (q, J=4.9 Hz, 1H), 3.68-3.57 (m, 3H), 3.57-3.40 (m, 2H), 3.40-3.27* (m, 2H/7H), 1.45 (p, J=6.7 Hz, 2H), 1.22 (d, J=7.6 Hz, 30H), 0.90-0.81 (m, 3H). *Peak overlaps with water.

$^{19}$F NMR (376 MHz, DMSO-d6) δ −139.77 (dddd, J=33.5, 25.3, 11.7, 8.2 Hz), −141.80 (dddt, J=37.3, 23.1, 11.8, 4.8 Hz).

$^{31}$P NMR (162 MHz, DMSO-d6) δ 0.26--0.34 (m).

MS m/z [M+1]=824.18

Example 15: [(2R,3S,4R,5R)-5-(4-aminopyrrolo[2,1-f][1,2,4]triazin-7-yl)-5-cyano-3,4-dihydroxy-tetrahydrofuran-2-yl]methyl [(2R)-2-[(3,5-difluorophenyl)methoxy]-3-octadecoxy-propyl] hydrogen phosphate (15)

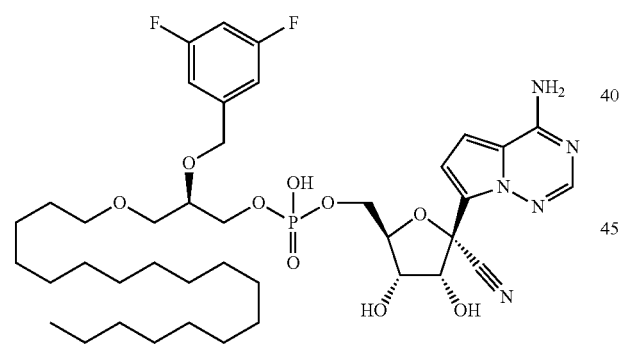

15

Compound 15 was synthesized in a manner similar to compound 14 using 5-(bromomethyl)-1,3-difluoro-benzene instead of 4-(bromomethyl)-1,2-difluoro-benzene.

$^1$H NMR (400 MHz, Methanol-d4) δ 7.87 (s, 1H), 6.98 (d, J=4.6 Hz, 1H), 6.96-6.91 (m, 2H), 6.89 (d, J=4.6 Hz, 1H), 6.75 (tt, J=9.2, 2.5 Hz, 1H), 4.84 (d, J=5.4 Hz, 1H), 4.72-4.55 (m, 2H), 4.44-4.36 (m, 1H), 4.27 (t, J=5.5 Hz, 1H), 4.25-4.14 (m, 1H), 4.14-4.04 (m, 1H), 3.97-3.84 (m, 2H), 3.77-3.66 (m, 2H), 3.59-3.43 (m, 2H), 3.43-3.37 (m, 2H), 1.59-1.48 (m, 2H), 1.40-1.21 (m, 30H), 0.91 (t, J=6.6 Hz, 3H).

$^{19}$F NMR (377 MHz, Methanol-d4) δ −112.53 (t, J=8.3 Hz).

$^{31}$P NMR (162 MHz, Methanol-d4) δ −0.65.

MS m/z [M+1]=824.17

Example 16: [(2R,3S,4R,5R)-5-(4-aminopyrrolo[2,1-f][1,2,4]triazin-7-yl)-5-cyano-3,4-dihydroxy-tetrahydrofuran-2-yl]methyl [(2R)-2-[(3-cyano-5-fluorophenyl)methoxy]-3-octadecoxy-propyl] hydrogen phosphate (16)

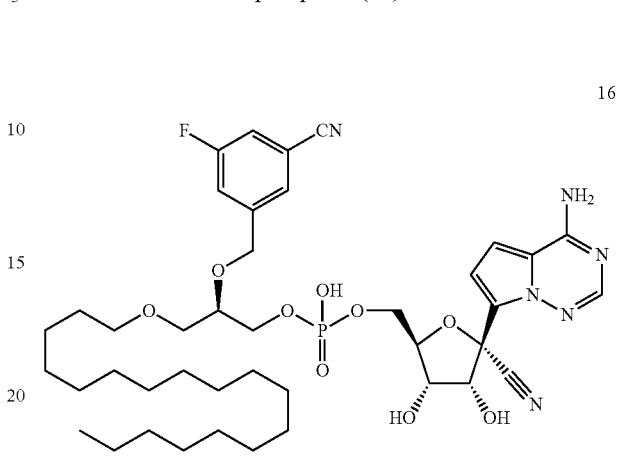

16

Compound 16 was synthesized in a manner similar to compound 14 using 5-(bromomethyl)-1-cyano-3-fluorobenzene instead of 4-(bromomethyl)-1,2-difluoro-benzene.

$^1$H NMR (400 MHz, Methanol-d4) δ 7.87 (s, 1H), 7.52 (s, 1H), 7.44 (dd, J=9.6, 2.5 Hz, 1H), 7.36 (d, J=8.3, 2.5 Hz, 1H), 6.98 (d, J=4.6 Hz, 1H), 6.88 (d, J=4.6 Hz, 1H), 4.85 (d, J=5.5 Hz, 1H), 4.78-4.60 (m, 2H), 4.42-4.33 (m, 1H), 4.27 (t, J=5.5 Hz, 1H), 4.22-4.13 (m, 1H), 4.13-4.03 (m, 1H), 4.00-3.83 (m, 2H), 3.79-3.63 (m, 1.7H), 3.62-3.44 (m, 2H), 3.44-3.35 (m, 2H), 1.61-1.48 (m, 2H), 1.40-1.20 (m, 30H), 0.91 (t, J=6.6 Hz, 3H).

$^{19}$F NMR (377 MHz, Methanol-d4) δ −112.78 (t, J=8.8 Hz).

$^{31}$P NMR (162 MHz, Methanol-d4) δ −0.47.

MS m/z [M+1]=831.21.

Example 17: [(2R,3S,4R,5R)-5-(4-aminopyrrolo[2,1-f][1,2,4]triazin-7-yl)-5-cyano-3,4-dihydroxy-tetrahydrofuran-2-yl]methyl [(2R)-2-[(3-cyano-5-fluorophenyl)methoxy]-3-octadecoxy-propyl] hydrogen phosphate (17)

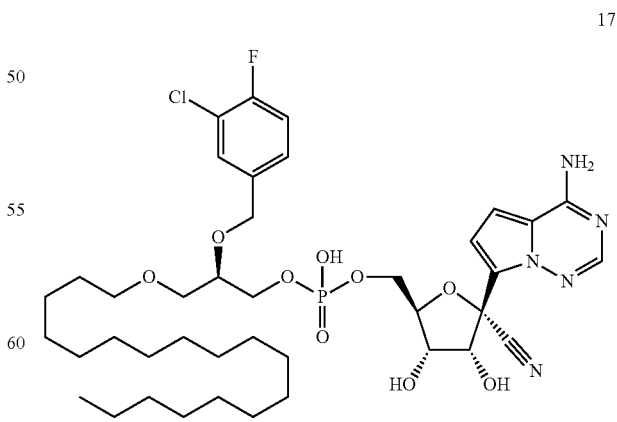

17

Compound 17 was synthesized in a manner similar to compound 14 using 4-(bromomethyl)-2-chloro-1-fluorobenzene instead of 4-(bromomethyl)-1,2-difluoro-benzene.

¹H NMR (400 MHz, Methanol-d4) δ 7.87 (s, 1H), 7.44 (dd, J=7.2, 2.1 Hz, 1H), 7.30-7.22 (m, 1H), 7.12 (t, J=8.8 Hz, 1H), 6.99 (d, J=4.6 Hz, 1H), 6.89 (d, J=4.6 Hz, 1H), 4.85 (d, J=5.4 Hz, 1H), 4.68-4.50 (m, 2H), 4.41-4.34 (m, 1H), 4.27 (t, J=5.4 Hz, 1H), 4.24-4.13 (m, 1H), 4.13-4.03 (m, 1H), 3.97-3.83 (m, 2H), 3.77-3.62 (m, 2H), 3.59-3.42 (m, 2H), 3.39 (td, J=6.5, 2.4 Hz, 2H), 1.59-1.47 (m, 2H), 1.39-1.20 (m, 30H), 0.91 (t, J=6.7 Hz, 3H).

¹⁹F NMR (377 MHz, Methanol-d4) δ −120.49 (td, J=8.4, 4.9 Hz).

³¹P NMR (162 MHz, Methanol-d4) δ −0.26.

MS m/z [M+1]=840.18

Intermediate 18-1: (S)-1-((tert-butyldimethylsilyl)oxy)-3-(octadecyloxy)propan-2-ol

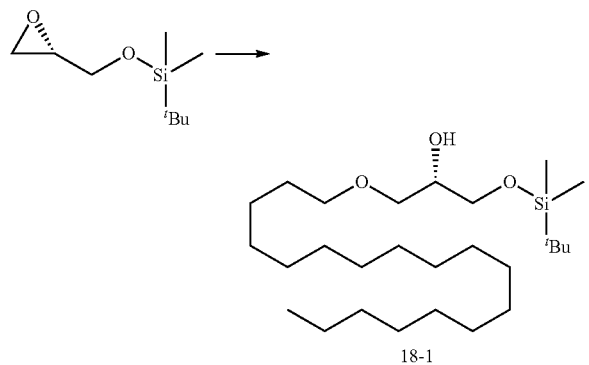

A solution of octadecan-1-ol (10.1 g, 37.4 mmol) in tetrahydrofuran (30 mL) was added by cannula to a vigorously stirred mixture of sodium hydride (1.50 g, 39.1 mmol) at 0° C. The reaction mixture was equipped with a reflux condenser and heated to 80° C. After 2 h, tert-butyl-dimethyl-[[(2S)-oxiran-2-yl]methoxy]silane (4.70 g, 25.0 mmol) was added by syringe. After 17 h, the reaction mixture was cooled to room temperature. Saturated aqueous ammonium chloride (50 mL), water (100 mL), and diethyl ether (200 mL) were added sequentially. The organic layer was extracted, was washed with water, was dried over anhydrous magnesium sulfate, was filtered, and was concentrated under reduced pressure. The residue was purified by flash column chromatography on silica gel (0 to 10% ethyl acetate in hexanes) to yield intermediate 18-1.

Intermediate 18-2: [(2S)-2-benzyloxy-3-octadecoxy-propoxy]-tert-butyl-dimethyl-silane

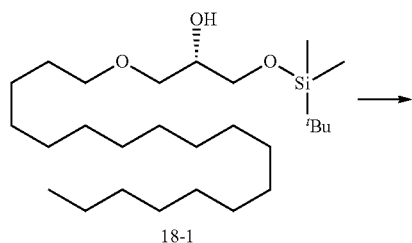

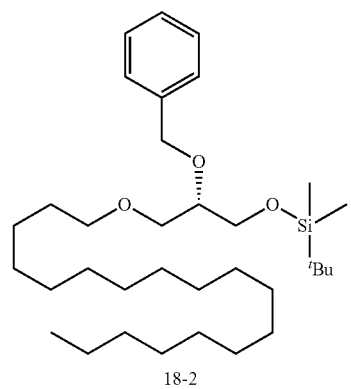

A solution of intermediate 18-1 (300 mg, 650 μmol) in tetrahydrofuran (3.0 mL) was added by syringe to a vigorously stirred mixture of sodium hydride (50 mg, 1.3 mmol) in tetrahydrofuran (6.0 mL) at 0° C. After 45 min, a solution of bromomethylbenzene (280 mg, 1.6 mmol) in tetrahydrofuran (3.0 mL) was added by syringe. The reaction mixture was warmed to room temperature. After 16 h, the reaction was cooled to 0° C. Water (30 mL), ethyl acetate (50 mL), and brine (20 mL) were added sequentially. The aqueous layer was extracted with ethyl acetate (2×40 mL). The combined organic layers were rinsed with brine (30 mL), were dried over anhydrous sodium sulfate, were filtered, and were concentrated under reduced pressure. The residue was purified by flash column chromatography on silica gel (0 to 20% ethyl acetate in hexanes) to yield intermediate 18-2.

Intermediate 18-3: (2R)-2-benzyloxy-3-octadecoxy-propan-1-ol

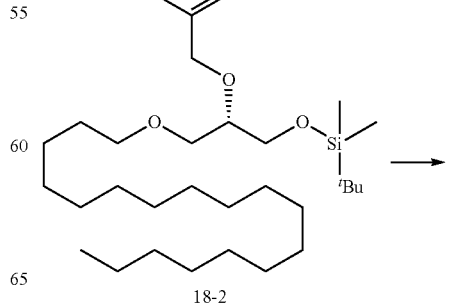

-continued

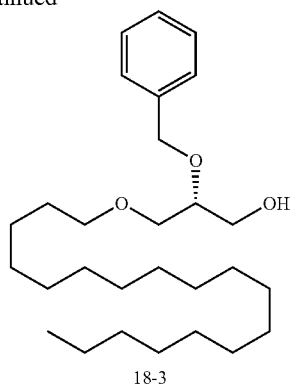

18-3

Tetrabutylammonium fluoride solution (1.0 M in tetrahydrofuran, 623 μL, 623 μmol) was added by syringe to a stirred solution of intermediate 18-2 (114 mg, 208 μmol) in tetrahydrofuran (3.0 mL). After 45 min, ethyl acetate (10 mL) and water (10 mL) were added sequentially. The organic layer was washed with water (10 mL) and brine (5 mL). The organic layer was dried over anhydrous sodium sulfate, filtered, and concentrated under reduced pressure. The residue was purified by flash chromatography on silica gel (0 to 20% ethyl acetate in hexanes) to yield intermediate 18-3.

Intermediate 18-4: [(2S)-2-benzyloxy-3-octadecoxy-propyl] bis(4-nitrophenyl) phosphate

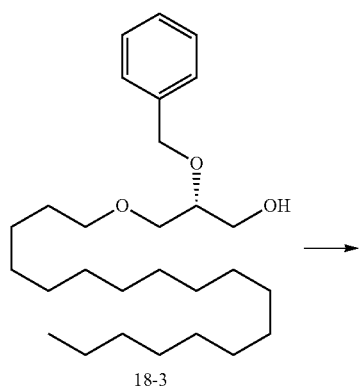

18-3

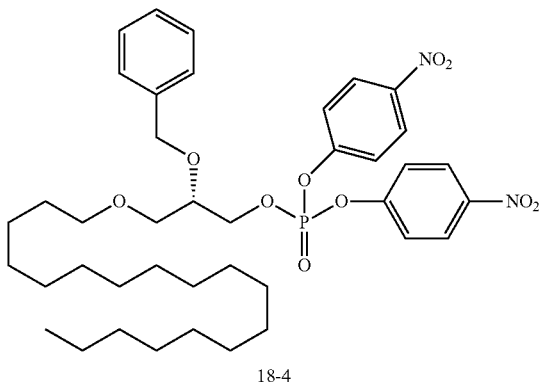

18-4

Intermediate 18-4 was prepared in a manner similar to intermediate 2-3, using intermediate 18-3 instead of intermediate 2-2.

Intermediate 18-5: [(3aR,4R,6R,6aR)-4-(4-aminopyrrolo[2,1-f][1,2,4]triazin-7-yl)-4-cyano-2,2-dimethyl-6,6a-dihydro-3aH-furo[3,4-d][1,3]dioxol-6-yl] methyl [(2S)-2-benzyloxy-3-octadecoxy-propyl] (4-nitrophenyl) phosphate

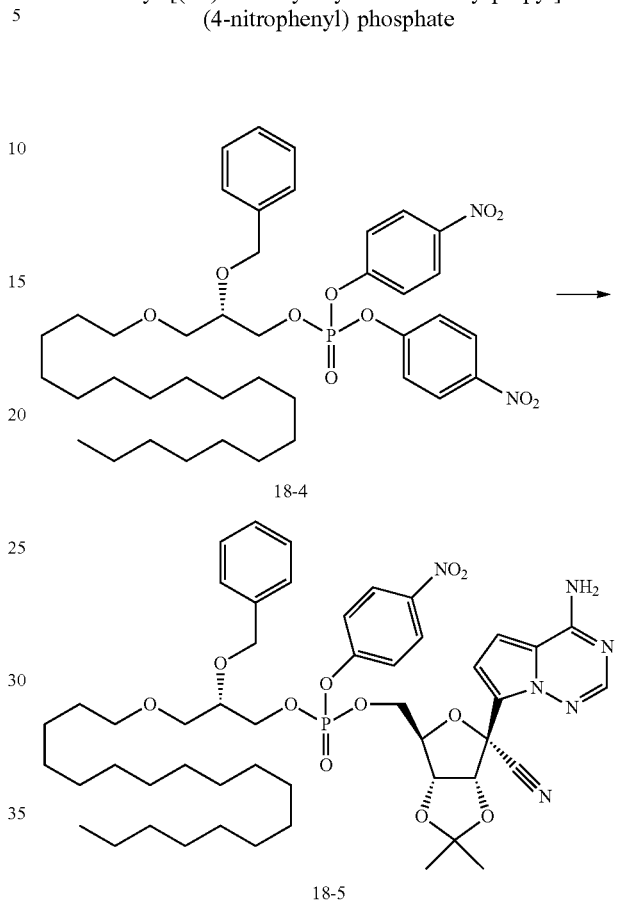

Intermediate 18-5 was prepared in a manner similar to intermediate 2-4, using intermediate 18-4 instead of intermediate 2-3.

Example 18: ((2R,3S,4R,5R)-5-(4-aminopyrrolo[2,1-f][1,2,4]triazin-7-yl)-5-cyano-3,4-dihydroxytetrahydrofuran-2-yl)methyl ((S)-2-(benzyloxy)-3-(octadecyloxy)propyl) hydrogen phosphate (18)

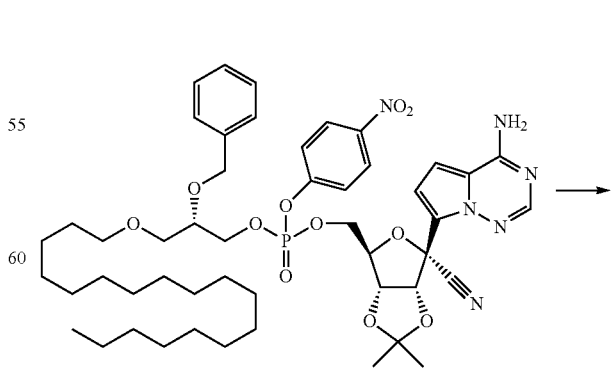

18-5

-continued

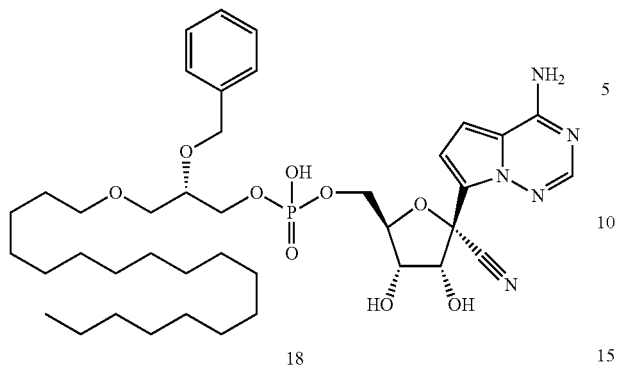

18

Aqueous sodium hydroxide solution (2.0 M, 62 µL, 130 µmol) was added to a vigorously stirred solution of intermediate 18-5 (12 mg, 13 µmol) in tetrahydrofuran (2.0 mL) at 50° C. After 90 min, the resulting mixture was cooled to room temperature. Several drops of concentrated hydrochloric acid were added until the resulting mixture had pH<1. After 16 h, triethylamine was added until mixture had pH>7, as indicated by yellow tint persisting. The mixture was purified by reverse phase preparative HPLC (2-propanol/water) to give compound 18 as a complex with triethylamine.

$^1$H NMR (400 MHz, Methanol-$d_4$) δ 7.87 (s, 1H), 7.34 (d, J=7.5 Hz, 2H), 7.28 (t, J=7.4 Hz, 2H), 7.23 (d, J=7.2 Hz, 1H), 7.01 (d, J=4.6 Hz, 1H), 6.89 (d, J=4.6 Hz, 1H), 4.83 (d, J=5.2 Hz, 2H), 4.66 (d, J=11.8 Hz, 1H), 4.62-4.52 (m, 2H), 4.34 (s, 1H), 4.26 (t, J=5.3 Hz, 1H), 4.17-3.98 (m, 2H), 3.87 (t, J=5.6 Hz, 2H), 3.71 (d, J=6.2 Hz, 1H), 3.47-3.42 (m, 1H), 3.39 (d, J=2.1 Hz, 1H), 1.51 (d, J=6.8 Hz, 2H), 1.29 (d, J=7.3 Hz, 30H), 0.92 (t, J=6.7 Hz, 3H).

LCMS: 788.305.

Intermediate 19-0: (3aR,4R,6R,6aR)-4-(4-aminopyrrolo[2,1-f][1,2,4]triazin-7-yl)-2,2-dimethyl-6-(((((2S,3aR,6S,7aR)-3a-methyl-6-(prop-1-en-2-yl)-2-sulfidohexahydrobenzo[d][1,3,2]oxathiaphosphol-2-yl)oxy)methyl)tetrahydrofuro[3,4-d][1,3]dioxole-4-carbonitrile

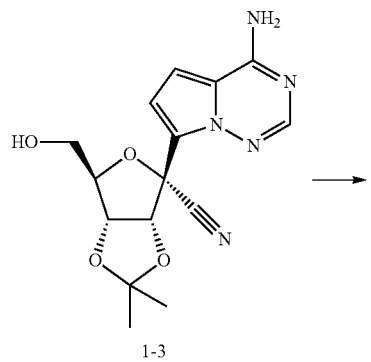

1-3

-continued

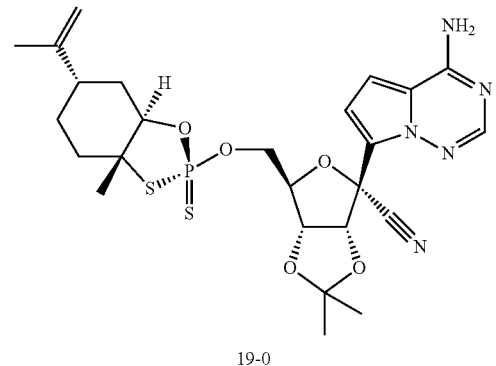

19-0

1,8-Diazabicyclo[5.4.0]undec-7-ene (609 µL, 4.07 mmol) was added over 2 min via syringe to a vigorously stirred mixture of intermediate 1-3 (1.00 g, 3.02 mmol), (2R,3aR,6S,7aR)-3a-Methyl-2-((perfluorophenyl)thio)-6-(prop-1-en-2-yl)hexahydrobenzo[d][1,3,2]oxathiaphosphole 2-sulfide (1.75 g, 3.92 mmol), and acetonitrile (24.0 mL) at room temperature. After 10 min, saturated aqueous ammonium chloride solution (10 mL) and ethyl acetate (100 mL) were added sequentially. The organic layer was washed with water (70 mL), and the aqueous layer was extracted with ethyl acetate (40 mL). The combined organic layers were dried over anhydrous magnesium sulfate, were filtered, and were concentrated under reduced pressure. The residue was purified by flash column chromatography on silica gel (0 to 10% methanol in dichloromethane) to give intermediate 19-0. LCMS: 578.2.

Intermediate 19-1: (3aR,4R,6R,6aR)-4-(4-aminopyrrolo[2,1-f][1,2,4]triazin-7-yl)-2,2-dimethyl-6-(((((2S,3aR,6S,7aR)-3a-methyl-2-oxido-6-(prop-1-en-2-yl)hexahydrobenzo[d][1,3,2]oxathiaphosphol-2-yl)oxy)methyl)tetrahydrofuro[3,4-d][1,3]dioxole-4-carbonitrile

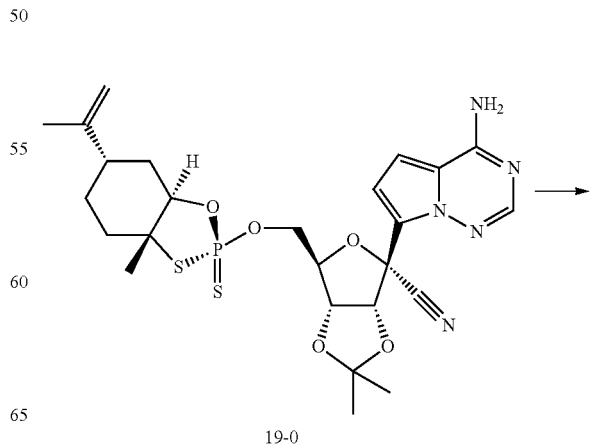

19-0

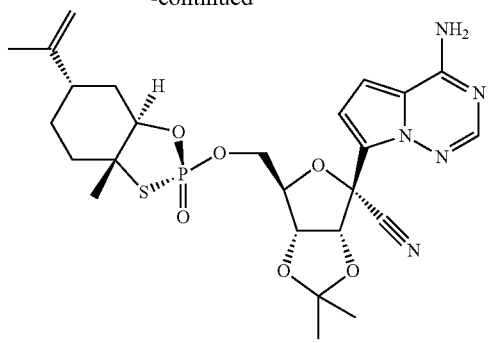

19-1

Selenium dioxide (316 mg, 2.84 mmol) was added to a vigorously stirred solution of intermediate 19-0 (1.57 g, 2.71 mmol) in acetonitrile (23.5 mL) and water (8.9 mL) at room temperature. After 60 min, ethyl acetate (250 mL) was added, and the resulting suspension was filtered through celite. The organic layer of the filtrate was washed with a mixture of water and brine (1:1 v:v, 120 mL), and the aqueous layer was extracted with ethyl acetate (75 mL). The combined organic layers were dried over anhydrous magnesium sulfate, were filtered, and were concentrated under reduced pressure. The residue was purified by flash column chromatography on silica gel (0 to 10% methanol in dichloromethane) to give intermediate 19-1. LCMS: 562.2.

Intermediate 19-2: (S)-2-((3-fluoro-5-(trifluoromethyl)benzyl)oxy)-3-(octadecyloxy)propan-1-ol

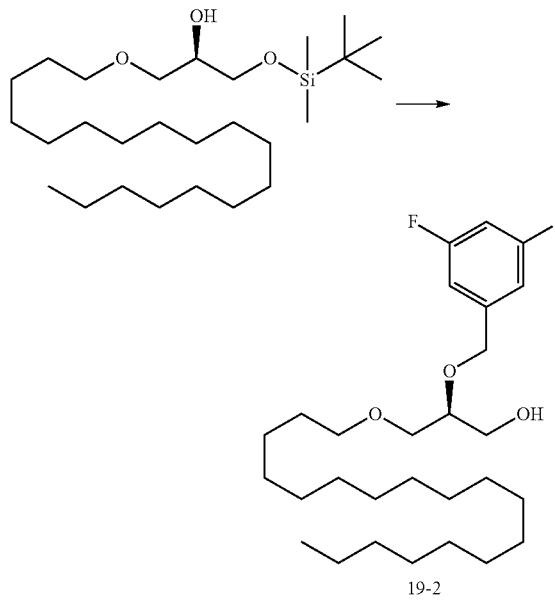

19-2

Potassium bis(trimethylsilyl)amide solution (1.0 M in tetrahydrofuran, 382 µL, 380 µmol) was added over 1 min via syringe to a stirred solution of (R)-1-(((tert-butyldimethylsilyl)oxy)-3-(octadecyloxy)propan-2-ol (159 mg, 347 µmol) in tetrahydrofuran (1.0 mL) at 0° C. After 10 min, 1-(bromomethyl)-3-fluoro-5-(trifluoromethyl)benzene (223 mg, 869 µmol) was added, and the resulting mixture was warmed to room temperature. After 50 min, concentrated hydrochloric acid (300 µL, 3.60 mmol) and methanol (0.3 mL) were added sequentially, and the resulting biphasic mixture was stirred vigorously. After 60 min, saturated aqueous sodium bicarbonate solution (15 mL), diethyl ether (40 mL), and ethyl acetate (20 mL) were added sequentially. The organic layer was washed with water (30 mL), was dried over anhydrous magnesium sulfate, was filtered, and was concentrated under reduced pressure. The residue was purified by flash column chromatography on silica gel (0 to 30% ethyl acetate in hexanes) to give intermediate 19-2. LCMS: 543.4 [M+Na]+.

Example 19: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((3-fluoro-5-(trifluoromethyl)benzyl)oxy)-3-(octadecyloxy)propyl) hydrogen phosphate (19)

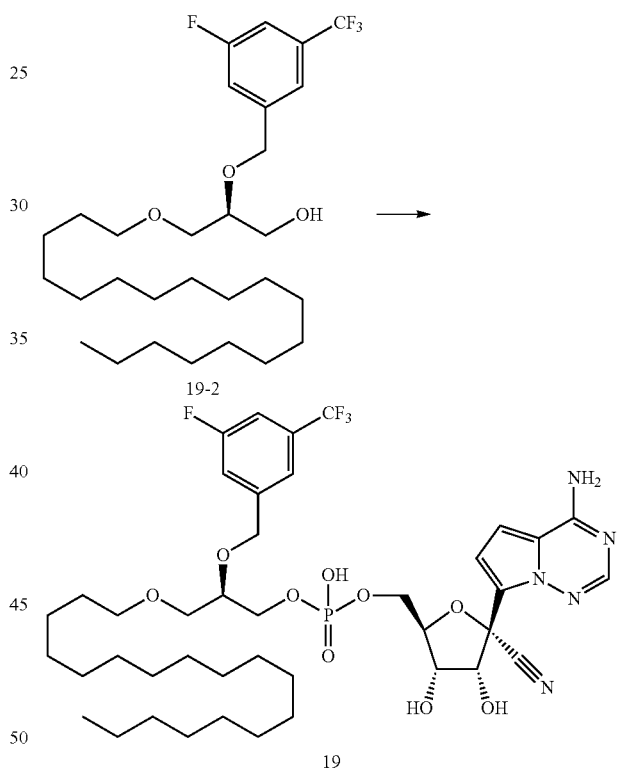

19

1,8-Diazabicyclo[5.4.0]undec-7-ene (10.7 µL, 71.2 µmol) was added over 1 min via syringe to a vigorously stirred mixture of intermediate 19-2 (18.5 g, 35.6 µmol), intermediate 19-1 (20.0 mg, 35.6 µmol), and tetrahydrofuran (0.7 mL) at room temperature. After 18 min, water (50 µL) and concentrated hydrochloric acid (300 µL, 3.60 mmol) were added sequentially. After 120 min, the resulting mixture was purified by reverse phase preparative HPLC (0.1% trifluoroacetic acid in methanol/water) to give compound 19. $^1$H NMR (400 MHz, Methanol-$d_4$) δ 8.06 (s, 1H), 7.49 (s, 1H), 7.43 (d, J=9.3 Hz, 1H), 7.33-7.25 (m, 2H), 7.20 (d, J=4.8 Hz, 1H), 4.97-4.68 (m, 3H), 4.40-4.31 (m, 1H), 4.25 (t, J=5.5 Hz, 1H), 4.23-4.15 (m, 1H), 4.14-4.05 (m, 1H), 4.04-3.90 (m, 2H), 3.86-3.79 (m, 1H), 3.63-3.31 (m, 4H), 1.63-1.49

(m, 2H), 1.40-1.20 (m, 30H), 0.92 (t, J=6.6 Hz, 3H). $^{31}$P NMR (162 MHz, Methanol-d$_4$) δ 0.19. LCMS: 872.4 [M−H]$^-$.

Example 20: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-3-(octadecyloxy)-2-(thiophen-3-ylmethoxy)propyl) hydrogen phosphate (20)

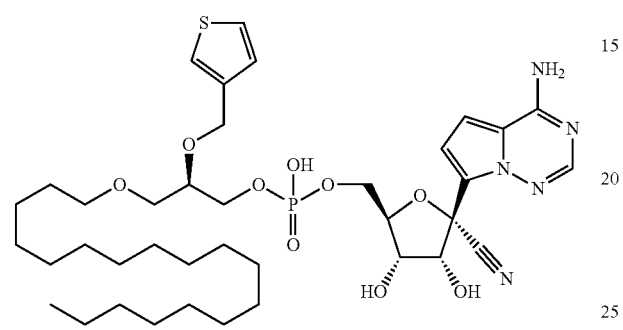

Compound 20 was synthesized in a manner similar to compound 4 using 3-(bromomethyl)thiophene instead of 2-(bromomethyl)naphthalene. $^1$H NMR (400 MHz, Methanol-d4) δ 7.91 (s, 1H), 7.34-7.27 (m, 2H), 7.07 (dd, J=4.9, 1.4 Hz, 1H), 7.04 (d, J=4.6 Hz, 1H), 6.96 (d, J=4.6 Hz, 1H), 4.83-4.79 (m, 1H), 4.69-4.57 (m, 2H), 4.39-4.31 (m, 1H), 4.26 (t, J=5.4 Hz, 1H), 4.14 (dt, J=11.5, 4.3 Hz, 1H), 4.09-4.02 (m, 1H), 3.94-3.79 (m, 2H), 3.74-3.65 (m, 1H), 3.56-3.36 (m, 4H), 3.23 (q, J=7.3 Hz, 6H), 1.61-1.42 (m, 2H), 1.38-1.19 (m, 39H), 0.94-0.86 (m, 3H). LCMS: 794.1.

Intermediate 21-1: (R)-triisopropyl((2-methyloxiran-2-yl)methoxy)silane

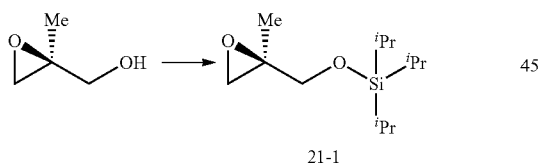

Chlorotriisopropylsilane (5.38 mL, 25.2 mmol) was added over 2 min via syringe to a stirred mixture of (S)-(2-methyloxiran-2-yl)methanol (1.81 mL, 22.6 mmol), triethylamine (5.49 mL, 39.4 mmol), 4-(dimethylamino)pyridine (208 mg, 1.70 mmol), and dichloromethane (30 mL) at 0° C. After 8 min, the resulting mixture was warmed to room temperature. After 20 h, the resulting mixture was poured into a biphasic mixture of diethyl ether (100 mL) at 0° C., aqueous citric acid solution (10% wt/v, 10 mL), and water (80 mL). The resulting mixture was agitated, and the layers were separated. The organic layer was washed with a mixture of water and saturated aqueous sodium bicarbonate solution (10:1 v:v, 90 mL), was dried over anhydrous magnesium sulfate, was filtered, and was concentrated under reduced pressure. The residue was purified by flash column chromatography on silica gel (0 to 4% ethyl acetate in hexanes) to give intermediate 21-1. LCMS: 245.2.

Intermediate 21-2: (R)-2-methyl-1-(octadecyloxy)-3-((triisopropylsilyl)oxy)propan-2-ol

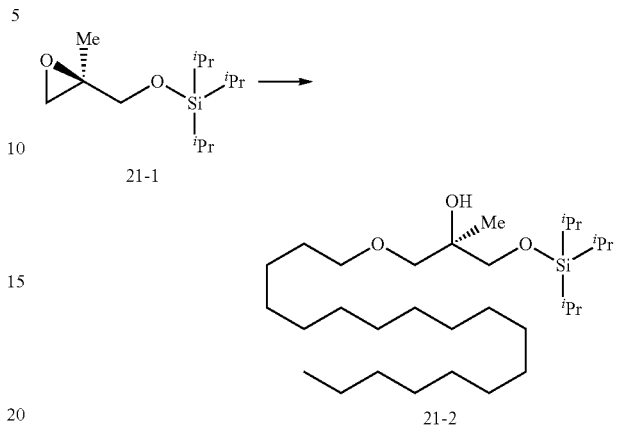

1-Octadecanol (2.13 g, 7.88 mmol) was added to a vigorously stirred mixture of sodium hydride (60% wt dispersion in mineral oil, 311 mg, 8.12 mmol) in 2-methyltetrahydrofuran (20 mL) at room temperature, and the resulting mixture was heated to 85° C. After 80 min, a solution of intermediate 21-1 (1.47 g, 6.01 mmol) in N,N-dimethylformamide (10 mL) was added via cannula, and the resulting mixture was heated to 90° C. After 17 h, the resulting mixture was cooled to room temperature, and saturated aqueous ammonium chloride solution (10 ml) and diethyl ether (500 mL) were added sequentially. The organic layer was washed with water (2×500 mL), was dried over anhydrous magnesium sulfate, was filtered, and was concentrated under reduced pressure. The residue was purified by flash column chromatography on silica gel (0 to 100% dichloromethane in hexanes to 0 to 2% ethyl acetate in dichloromethane) to give intermediate 21-2. LCMS: 515.5.

Example 21: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-(benzyloxy)-2-methyl-3-(octadecyloxy)propyl) hydrogen phosphate (21)

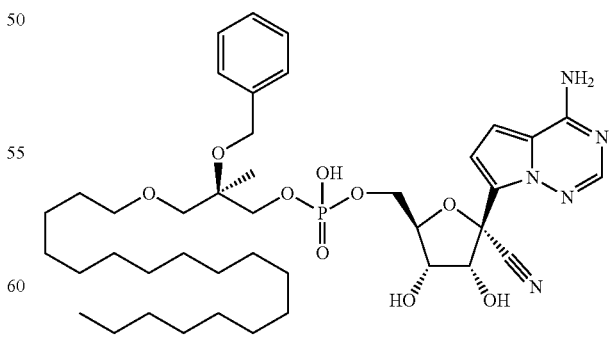

Compound 21 was synthesized in a manner similar to compound 4 using benzyl bromide instead of 2-(bromomethyl)naphthalene and using intermediate 21-2 instead of (R)-1-((tert-butyldimethylsilyl)oxy)-3-(octadecyloxy)propan-2-ol. $^1$H NMR (400 MHz, Methanol-d4) δ 7.93 (s, 1H), 7.32 (d, J=7.2 Hz, 2H), 7.29-7.23 (m, 2H), 7.23-7.16 (m, 1H), 7.07 (d, J=4.7 Hz, 1H), 7.03 (d, J=4.7 Hz, 1H), 4.80 (d, J=5.3 Hz, 1H), 4.56 (s, 2H), 4.34 (d, J=4.8 Hz, 1H), 4.26 (t, J=5.4 Hz, 1H), 4.16 (dt, J=11.6, 4.2 Hz, 1H), 4.07 (dt, J=10.3, 4.1 Hz, 1H), 3.93 (dd, J=10.3, 3.9 Hz, 1H), 3.85 (dd, J=10.3, 4.1 Hz, 1H), 3.56-3.37 (m, 3H), 3.23 (q, J=7.3 Hz, 6H), 1.62-1.49 (m, 2H), 1.45-1.08 (m, 42H), 0.92 (t, J=6.7 Hz, 3H). LCMS: 800.3 [M–H]$^-$.

Intermediate 22-1: (R)-(4-(benzyloxy)-3-((octadecyloxy)methyl)butyl)benzene

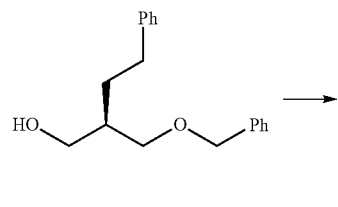

Sodium hydride (60% wt dispersion in mineral oil, 186 mg, 4.64 mmol) was added to a vigorously stirred solution of (R)-2-((benzyloxy)methyl)-4-phenylbutan-1-ol (419 mg, 1.55 mmol) (Muehlman, A.; Lindberg, J.; Classon, B.; Unge, T.; Hallberg, A.; Samuelsson, B. J. Med. Chem. 2001, 44, 3407) in N,N-dimethylformamide (2.5 mL) at room temperature. After 40 min, 1-bromooctadecane (1.32 mL, 3.87 mmol) and tetrahydrofuran (1.0 mL) were added sequentially. After 140 min, the resulting mixture was heated to 80° C. After 16.5 h, the resulting mixture was cooled to room temperature, and saturated aqueous ammonium chloride solution (5.0 mL) and diethyl ether (100 mL) were added sequentially. The organic layer was washed with water (2×100 mL), was dried over anhydrous magnesium sulfate, was filtered, and was concentrated under reduced pressure. The residue was purified by flash column chromatography on silica gel (0 to 20% ethyl acetate in hexanes) to give intermediate 22-1.

LCMS: 545.4 [M+Na]$^+$.

Intermediate 22-2: (S)-2-((octadecyloxy)methyl)-4-phenylbutan-1-ol

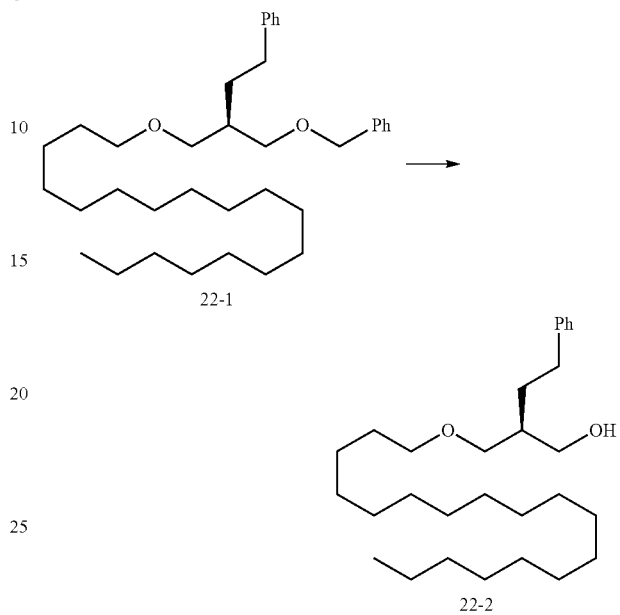

A vigorously stirred mixture of intermediate 22-1 (535 mg, 1.02 mmol), palladium (10% wt. on carbon, 109 mg, 102 μmol), tetrahydrofuran (3.0 mL), and ethanol (3.0 mL) was placed under an atmosphere of hydrogen gas (balloon) at room temperature. After 13 h, the resulting mixture was filtered through celite, and the filtrate was concentrated under reduced to give intermediate 22-2. LCMS: 455.4 [M+Na]$^+$.

Example 22: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((octadecyloxy)methyl)-4-phenylbutyl) hydrogen phosphate (22)

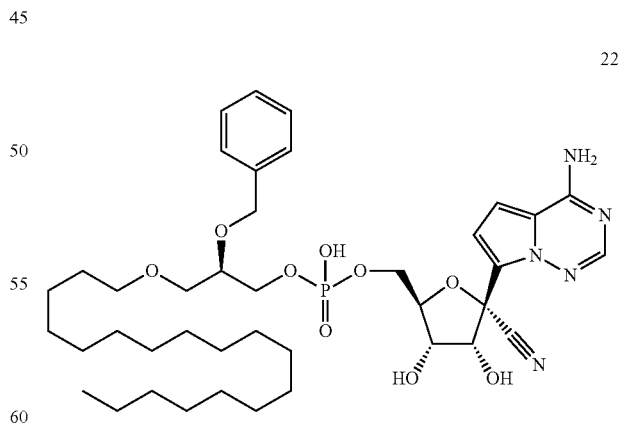

Compound 22 was synthesized in a manner similar to compound 2 using intermediate 22-2 instead of intermediate 2-2. $^1$H NMR (400 MHz, Methanol-d4) δ 7.95 (s, 1H), 7.27-7.06 (m, 7H), 4.82 (d, J=5.2 Hz, 1H), 4.37 (d, J=4.6 Hz, 1H), 4.28 (t, J=5.4 Hz, 1H), 4.16 (dt, J=11.5, 4.3 Hz, 1H), 4.11-3.74 (m, 3H), 3.53-3.28 (m, 4H), 3.23 (q, J=7.3 Hz, 6H), 2.73-2.53 (m, 2H), 1.83 (h, J=6.6 Hz, 1H), 1.66 (dd, J=14.3, 7.4 Hz, 2H), 1.59-1.41 (m, 2H), 1.41-1.09 (m, 39H), 0.92 (t, J=6.7 Hz, 3H). LCMS: 784.3 [M−H]⁻.

Intermediate 23-1: (S)-2-chloro-4-(((1-hydroxy-3-(octadecyloxy)propan-2-yl)oxy)methyl)benzonitrile

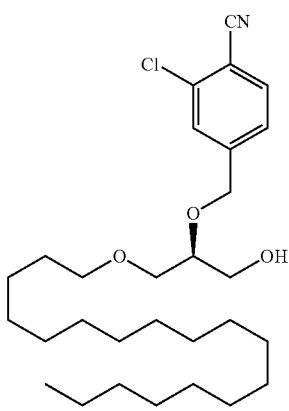

23-1

Intermediate 23-1 was synthesized in a manner similar to intermediate 2-2 using 4-(bromomethyl)-2-chlorobenzonitrile instead of 4-(bromomethyl)-1,1'-biphenyl. LCMS: 516.3 [M+Na]+.

Intermediate 23-2: ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl ((R)-2-((3-chloro-4-cyanobenzyl)oxy)-3-(octadecyloxy)propyl) (2-chlorophenyl) phosphate

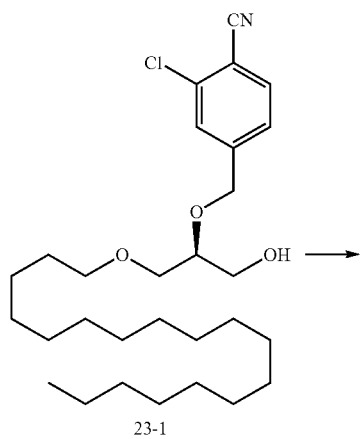

23-1

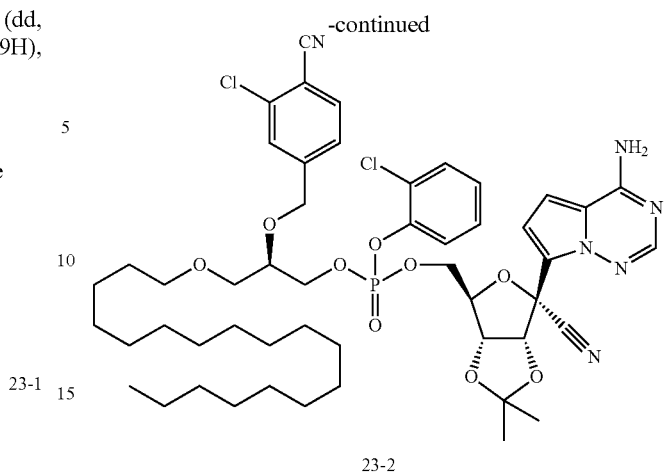

23-2

2-Chlorophenyl phosphorodichloridate (33.3 μL, 206 μmol) was added via syringe to a vigorously stirred mixture of 1,2,4-triazole (28.6 mg, 414 μmol), triethylamine (57.8 μL, 414 μmol), and tetrahydrofuran (0.4 mL) at room temperature. After 40 min, intermediate 1-3 (59.1 mg, 178 μmol), tetrahydrofuran (0.5 mL), and 1-methylimidazole (16.5 μL, 206 μmol) were added sequentially. After 60 min, a solution of intermediate 23-1 (76.7 mg, 155 μmol) in tetrahydrofuran (0.7 mL) was added via cannula. 1-Methylimidazole (20 μL, 250 μmol) were added. After 15 h, saturated aqueous sodium bicarbonate solution (10 mL), diethyl ether (40 mL), and ethyl acetate (20 mL) were added sequentially. The organic layer was washed with water (30 mL), was dried over anhydrous magnesium sulfate, was filtered, and was concentrated under reduced pressure. The residue was purified by flash column chromatography on silica gel (0 to 5% methanol in dichloromethane) to give intermediate 23-2. LCMS: 997.4.

Example 23: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((3-chloro-4-cyanobenzyl)oxy)-3-(octadecyloxy)propyl) hydrogen phosphate (23

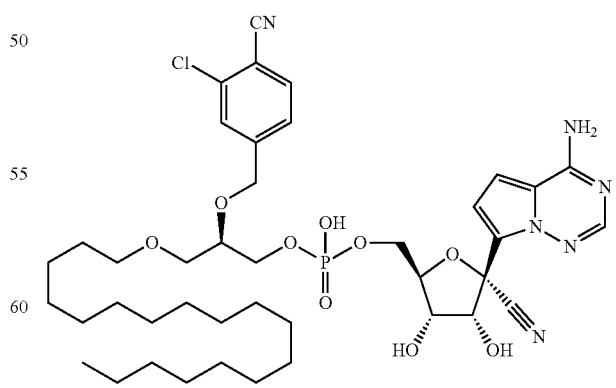

23

Tetrabutylammonium fluoride solution (1.0 M in tetrahydrofuran, 457 μL, 460 μmol) was added via syringe to a vigorously stirred mixture of intermediate 23-2 (152 mg, 152 μmol), pyridine (61.6 μL, 762 μmol), water (54.9 μL, 3.05 mmol), and tetrahydrofuran (0.1 mL) at room temperature. After 4 h, chlorotrimethylsilane (58.0 μL, 457 μmol) and concentrated hydrochloric acid (300 μL, 3.60 mmol) were added sequentially. After 150 min, the resulting mixture was purified by reverse phase preparative HPLC (0.1% trifluoroacetic acid in 2-propanol/water) to give compound 23. $^1$H NMR (400 MHz, Methanol-d4) δ 8.08 (s, 1H), 7.70 (d, J=8.0 Hz, 1H), 7.63 (d, J=1.4 Hz, 1H), 7.49-7.43 (m, 1H), 7.30 (d, J=4.8 Hz, 1H), 7.19 (d, J=4.8 Hz, 1H), 4.91-4.69 (m, 3H), 4.39-4.31 (m, 1H), 4.28-4.16 (m, 2H), 4.15-4.06 (m, 1H), 4.06-3.91 (m, 2H), 3.81 (p, J=5.2 Hz, 1H), 3.64-3.41 (m, 4H), 1.63-1.49 (m, 2H), 1.39-1.22 (m, 30H), 0.94-0.89 (m, 3H). LCMS: 845.6 [M−H]$^-$.

Intermediate 24-1: (S)-2-(benzyloxy)-3-((15-methylhexadecyl)oxy)propan-1-ol

Intermediate 24-1 was synthesized in a manner similar to intermediate 9-4 using benzyl bromide instead of 4-(bromomethyl)benzonitrile and using 1-bromo-15-methylhexadecane instead of 1-bromooctadecane. LCMS: 443.4 [M+Na]+.

Example 24: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-(benzyloxy)-3-((15-methylhexadecyl)oxy)propyl) hydrogen phosphate (24)

Compound 24 was synthesized in a manner similar to compound 19 using intermediate 24-1 instead of intermediate 19-2. $^1$H NMR (400 MHz, Methanol-d4) δ 8.01 (s, 1H), 7.36-7.32 (m, 2H), 7.32-7.26 (m, 2H), 7.26-7.19 (m, 2H), 7.17 (d, J=4.8 Hz, 1H), 4.78 (d, J=5.2 Hz, 1H), 4.66 (d, J=11.9 Hz, 1H), 4.61 (d, J=11.9 Hz, 1H), 4.39-4.31 (m, 1H), 4.26 (t, J=5.4 Hz, 1H), 4.17 (dq, J=12.8, 4.4 Hz, 1H), 4.13-4.02 (m, 1H), 4.01-3.86 (m, 2H), 3.75 (q, J=5.2 Hz, 1H), 3.61-3.38 (m, 4H), 1.69-1.47 (m, 3H), 1.40-1.08 (m, 24H), 0.98-0.81 (m, 6H). LCMS: 772.4 [M−H]$^-$.

Example 25: ((2R,3S,4R,5R)-5-(4-aminopyrrolo[2,1-f][1,2,4]triazin-7-yl)-5-cyano-3,4-dihydroxytetrahydrofuran-2-yl)methyl (4-(hexadecyloxy)butyl) hydrogen phosphate (25)

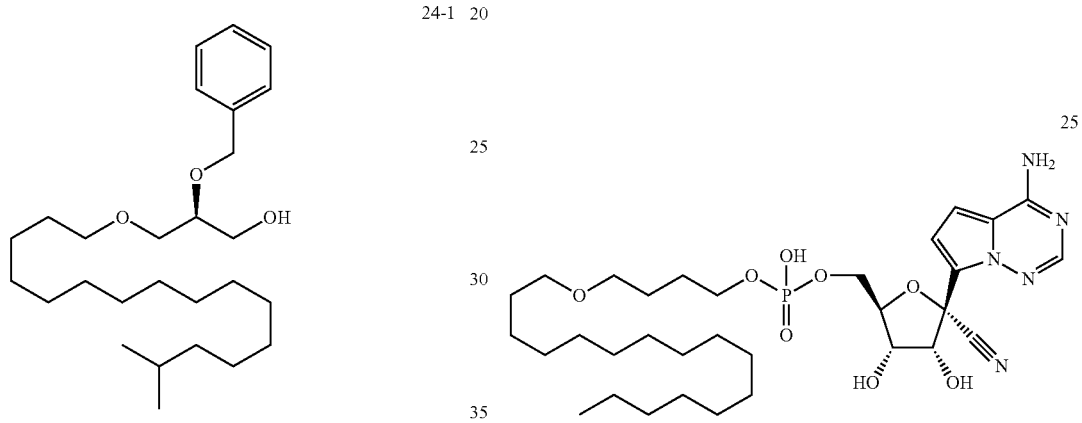

Compound 25 was synthesized in a manner similar to compound 55 using 1,4-butane diol instead of 1,3-propane diol and using 1-bromohexadecane instead of 1-bromoheptadecane.

$^1$H NMR (400 MHz, Methanol-d$_4$) δ 7.89 (s, 1H), 6.98 (d, J=4.6 Hz, 1H), 6.93 (d, J=4.6 Hz, 1H), 4.95-4.83 (m, 1H), 4.38 (t, J=4.4 Hz, 1H), 4.28 (t, J=5.4 Hz, 1H), 4.19-3.96 (m, 21H), 3.86-3.73 (m, 2H), 3.47-3.34 (m, 4H), 1.72-1.44 (m, 6H), 1.29 (s, 27H), 1.00-0.81 (m, 3H). LCMS: 668.2.

Intermediate 26-1: (R)-5-(((1-((tert-butyldimethylsilyl)oxy)-3-(octadecyloxy)propan-2-yl)oxy)methyl)isophthalonitrile

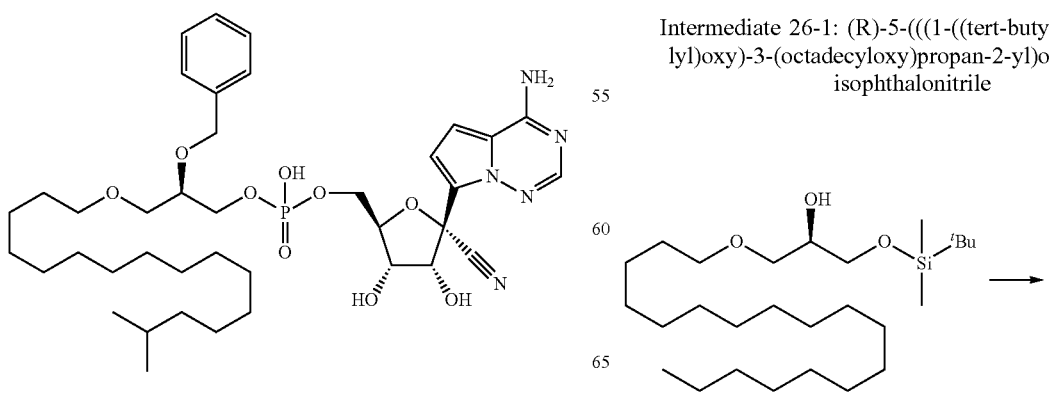

-continued

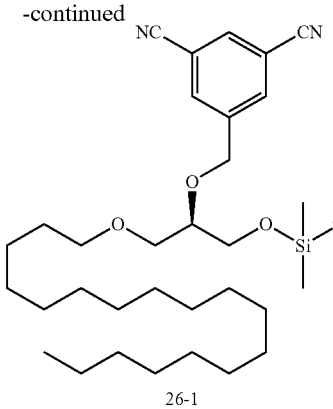

26-1

Potassium bis(trimethylsilyl)amide solution (1.0 M in tetrahydrofuran, 490 µL, 490 µmol) was added via syringe to a stirred solution of (R)-1-((tert-butyldimethylsilyl)oxy)-3-(octadecyloxy)propan-2-ol (150 mg, 327 µmol) in tetrahydrofuran (0.5 mL) at 0° C. After 5 min, a solution of 5-(iodomethyl)isophthalonitrile (437 mg, 1.63 mmol) in tetrahydrofuran (2.0 mL) was added via syringe, and the resulting mixture was warmed to room temperature. After 16 h, saturated aqueous ammonium chloride solution (10 mL), diethyl ether (40 mL), and ethyl acetate (20 mL) were added sequentially. The organic layer was washed with water (30 ml), was dried over anhydrous magnesium sulfate, was filtered, and was concentrated under reduced pressure. The residue was purified by flash column chromatography on silica gel (0 to 10% ethyl acetate in hexanes) to give the intermediate 26-1. LCMS: 621.5 [M+Na]$^+$.

Intermediate 26-2: (S)-5-(((1-hydroxy-3-(octadecyloxy)propan-2-yl)oxy)methyl)isophthalonitrile

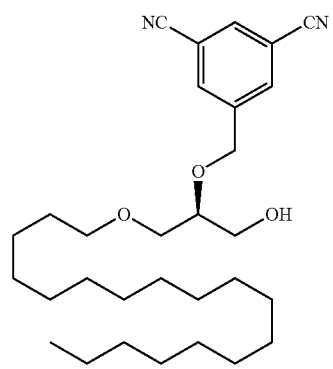

26-2

Intermediate 26-2 was synthesized in a manner similar to intermediate 2-2 using intermediate 26-1 instead of intermediate 2-1. LCMS: 507.4 [M+Na]$^+$.

Intermediate 26-3: ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl (2-chlorophenyl) ((R)-2-((3,5-dicyanobenzyl)oxy)-3-(octadecyloxy)propyl) phosphate

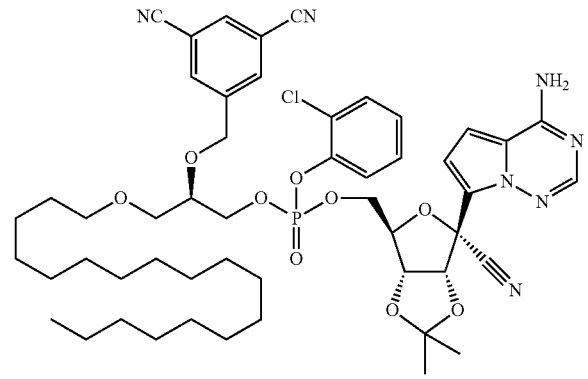

26-3

Intermediate 26-3 was synthesized in a manner similar to intermediate 23-2 using intermediate 26-2 instead of intermediate 23-1. LCMS: 988.4.

Example 26: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((3,5-dicyanobenzyl)oxy)-3-(octadecyloxy)propyl) hydrogen phosphate (26)

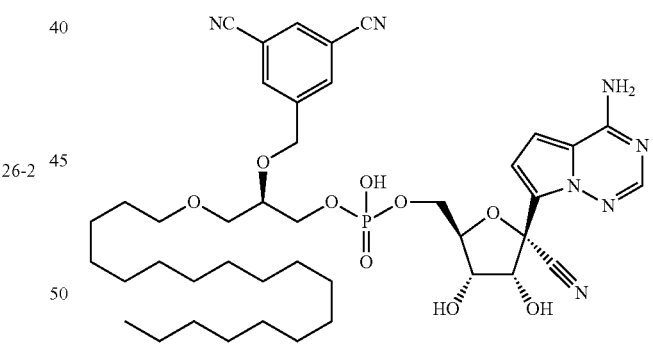

26

Tetrabutylammonium fluoride solution (1.0 M in tetrahydrofuran, 300 µL, 300 µmol) was added via syringe to a vigorously stirred mixture intermediate 26-3 (23.6 mg, 23.9 µmol), 4-(dimethylamino)pyridine (29.2 mg, 239 µmol), water (45.0 µL, 2.50 mmol), and tetrahydrofuran (0.1 mL) at room temperature. After 82 min, chlorotrimethylsilane (38.2 µL, 301 µmol) and concentrated hydrochloric acid (300 µL, 3.60 mmol) were added sequentially. After 140 min, the resulting mixture was purified by reverse phase preparative HPLC (0.1% trifluoroacetic acid in methanol/water) to give compound 26. $^1$H NMR (400 MHz, Methanol-d4) δ 8.07 (s, 1H), 8.01 (s, 3H), 7.31 (d, J=4.8 Hz, 1H), 7.20 (d, J=4.8 Hz, 1H), 4.93-4.70 (m, 3H), 4.38-4.28 (m, 1H), 4.25-4.16 (m, 2H), 4.16-4.05 (m, 1H), 4.06-3.90 (m, 2H), 3.82 (p, J=5.0

Hz, 1H), 3.63-3.41 (m, 4H), 1.65-1.51 (m, 2H), 1.38-1.22 (m, 30H), 0.95-0.86 (m, 3H). LCMS: 836.4 [M−H]⁻.

Intermediate 27-1: tert-butyldimethyl((2R)-3-(octadecyloxy)-2-(1-phenylethoxy)propoxy)silane

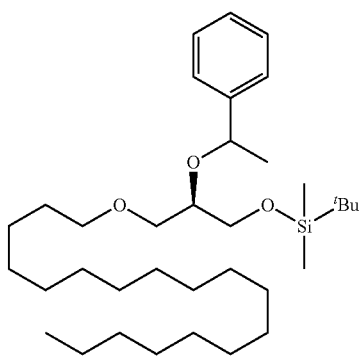

27-1

Intermediate 27-1 was synthesized as a 1:1 mixture of diastereomers in a manner similar to intermediate 5-2 using (R)-1-((tert-butyldimethylsilyl)oxy)-3-(octadecyloxy)propan-2-ol instead of intermediate 5-1 and using (R)-1-phenylethyl 2,2,2-trichloroacetimidate (WO 2011059021) instead of benzyl 2,2,2-trichloroacetimidate. LCMS: 585.6 [M+Na]⁺.

Intermediate 27-2: (2S)-3-(octadecyloxy)-2-(1-phenylethoxy)propan-1-ol (Faster Eluting Diastereomer on Silica Gel)

Intermediate 28-1: (2S)-3-(octadecyloxy)-2-(1-phenylethoxy)propan-1-ol (Slower Eluting Diastereomer on Silica Gel)

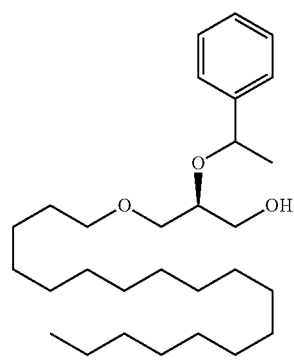

27-2

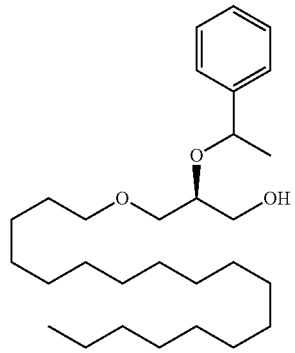

28-1

Intermediate 27-2 and intermediate 28-1 were synthesized in a manner similar to intermediate 2-2 using intermediate 27-1 instead of intermediate 2-1. The diastereomers were separated by flash column chromatography on silica gel (0 to 9% ethyl acetate in hexanes) to give intermediate 27-2 (faster eluting diastereomer) and intermediate 28-1 (slower eluting diastereomer). Intermediate 27-2: LCMS: 471.4 [M+Na]⁺. Intermediate 28-1: LCMS: 471.4 [M+Na]⁺.

Example 27: ((2R,3S,4R,5R)-5-(4-aminopyrrolo[2,1-f][1,2,4]triazin-7-yl)-5-cyano-3,4-dihydroxytetrahydrofuran-2-yl)methyl ((2R)-3-(octadecyloxy)-2-(1-phenylethoxy)propyl) hydrogen phosphate (27)

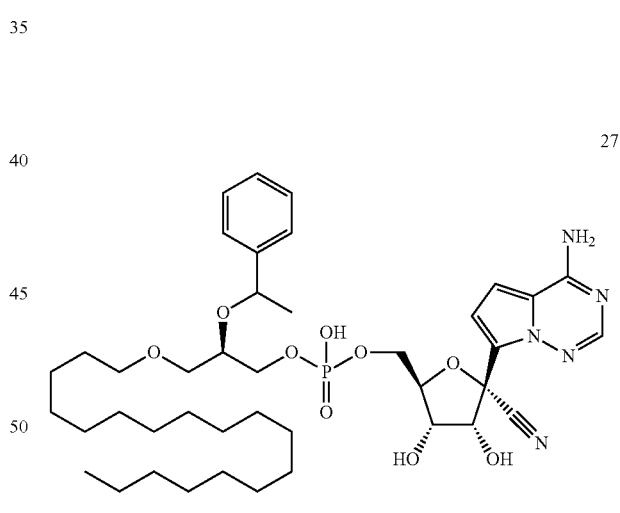

27

Compound 27 was synthesized in a manner similar to compound 26 using intermediate 27-2 instead of intermediate 26-2. ¹H NMR (400 MHz, Methanol-d4) δ 8.06 (s, 1H), 7.40-7.19 (m, 6H), 7.17 (d, J=4.8 Hz, 1H), 4.83-4.69 (m, 2H), 4.36-4.28 (m, 1H), 4.22 (t, J=5.4 Hz, 1H), 4.16-4.05 (m, 1H), 4.05-3.94 (m, 1H), 3.83-3.76 (m, 2H), 3.75-3.43 (m, 5H), 1.66-1.50 (m, 2H), 1.39 (d, J=6.4 Hz, 3H), 1.37-1.21 (m, 30H), 0.92 (t, J=6.7 Hz, 3H). LCMS: 800.3 [M−H]⁻.

Example 28: ((2R,3S,4R,5R)-5-(4-aminopyrrolo[2,1-f][1,2,4]triazin-7-yl)-5-cyano-3,4-dihydroxytetrahydrofuran-2-yl)methyl ((2R)-3-(octadecyloxy)-2-(1-phenylethoxy)propyl) hydrogen phosphate (28)

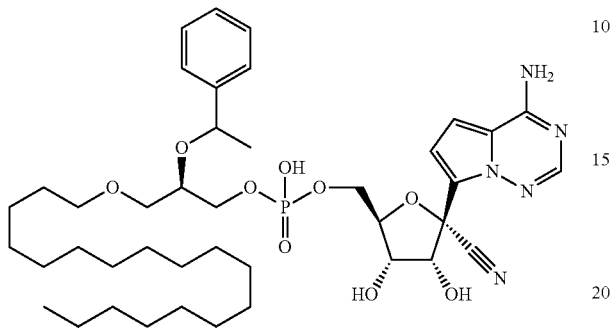

28

Compound 28 was synthesized in a manner similar to compound 26 using intermediate 28-1 instead of intermediate 26-2. $^1$H NMR (400 MHz, Methanol-d4) δ 8.07 (s, 1H), 7.40-7.34 (m, 2H), 7.34-7.28 (m, 3H), 7.25 (d, J=7.1 Hz, 1H), 7.21 (d, J=4.8 Hz, 1H), 4.81-4.70 (m, 2H), 4.41-4.33 (m, 1H), 4.30-4.16 (m, 2H), 4.16-4.06 (m, 1H), 4.05-3.85 (m, 2H), 3.62-3.53 (m, 1H), 3.42-3.22 (m, 4H), 1.51-1.40 (m, 2H), 1.38 (d, J=6.5 Hz, 3H), 1.35-1.21 (m, 30H), 0.91 (t, J=6.8 Hz, 3H). LCMS: 800.3 [M–H]$^-$.

Intermediate 29-1:
2,2-dimethyl-5-(phenoxymethyl)-1,3-dioxane

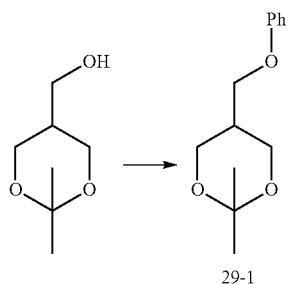

29-1

Methanesulfonyl chloride (1.53 mL, 19.8 mmol) was added over 3 min via syringe to a stirred mixture of (2,2-dimethyl-1,3-dioxan-5-yl)methanol (2.41 g, 16.5 mmol), triethylamine (3.21 mL, 23.1 mmol), and dichloromethane (35 mL) at 0° C., and the resulting mixture was warmed to room temperature. After 4 h, diethyl ether (200 mL) was added. The organic layer was washed sequentially with a mixture of aqueous phosphoric acid (85% wt/wt, 1.13 mL) in water (100 mL) and a mixture of water and saturated aqueous sodium bicarbonate solution (5:1 v:v, 60 mL), was dried over anhydrous magnesium sulfate, was filtered, and was concentrated under reduced pressure. The residue was dissolved in N,N-dimethylformamide (25 mL) at room temperature, and the resulting solution was stirred vigorously. Phenol (2.47 g, 26.2 mmol) and potassium carbonate (6.39 g, 45.9 mmol) were added sequentially, and the resulting mixture was heated to 95° C. After 18.5 h, the resulting mixture was cooled to room temperature, and saturated aqueous ammonium chloride solution (25 mL) and diethyl ether (500 mL) were added sequentially. The organic layer was washed with water (2×500 mL), was dried over anhydrous magnesium sulfate, was filtered, and was concentrated under reduced pressure. The residue was purified by flash column chromatography on silica gel (0 to 100% ethyl acetate in hexanes) to give intermediate 29-1. LCMS: 245.1 [M+Na]$^+$.

Intermediate 29-2:
2-(phenoxymethyl)propane-1,3-diol

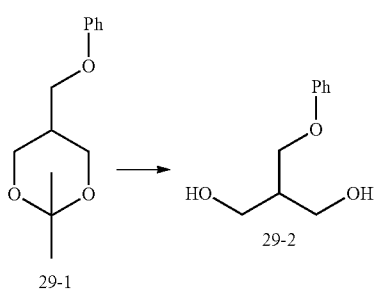

Concentrated hydrochloric acid (387 µL, 4.64 mmol) was added via syringe to a stirred solution of intermediate 29-1 (2.69 g, 12.1 mmol) in methanol (12 mL) and water (1.2 mL) at room temperature. After 4.5 h, sodium bicarbonate (1.02 g, 12.1 mmol) was added, and the resulting mixture was vigorously stirred. After 10 min, ethyl acetate (100 mL) and anhydrous magnesium sulfate were added, and the resulting suspension was filtered through celite. The filtrate was concentrated under reduced pressure, and the residue was purified by flash column chromatography on silica gel (0 to 100% ethyl acetate in hexanes) to give intermediate 29-2. LCMS: 183.0.

Intermediate 29-3:
3-(octadecyloxy)-2-(phenoxymethyl)propan-1-ol

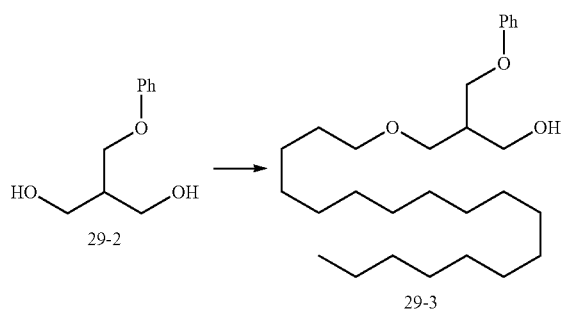 [SMILES: OCC(CO)COc1ccccc1 ; CCCCCCCCCCCCCCCCCCOCC(CO)COc1ccccc1]

Potassium bis(trimethylsilyl)amide solution (1.0 M in tetrahydrofuran, 2.63 mL, 2.6 mmol) was added over 1 min via syringe to a vigorously stirred solution of intermediate 29-2 (400 mg, 2.20 mmol) in N,N-dimethylformamide (6.0 mL) at 0° C., and the resulting mixture was warmed to room temperature. After 5 min, 1-bromooctadecane (732 mg, 2.20 mmol) and tetrahydrofuran (2.0 mL) were added sequentially, and the resulting mixture was heated to 80° C. After 18 h, the resulting mixture was cooled to room temperature over 40 min. Methanol (8.0 mL) and concentrated hydrochloric acid (723 µL, 8.78 mmol) were added sequentially. After 180 min, diethyl ether (125 mL) and ethyl acetate (20 mL) were added sequentially. The organic layer was washed with water (2×120 mL), was dried over anhydrous magnesium sulfate, was filtered, and was concentrated under reduced pressure. The residue was purified by flash column chromatography on silica gel (0 to 25% ethyl acetate in hexanes) to give intermediate 29-3. LCMS: 435.1.

Example 29: ((2R,3S,4R,5R)-5-(4-aminopyrrolo[2,1-f][1,2,4]triazin-7-yl)-5-cyano-3,4-dihydroxytetrahydrofuran-2-yl)methyl (3-(octadecyloxy)-2-(phenoxymethyl)propyl) hydrogen phosphate (29)

29

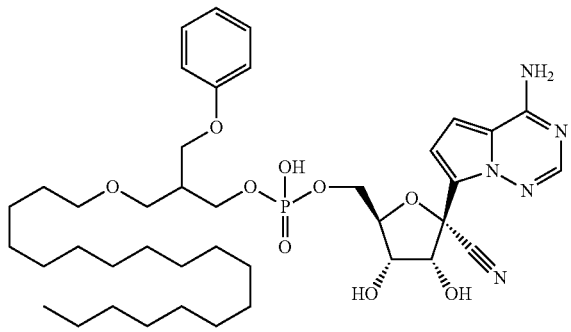

Compound 29 was synthesized as a 1:1 mixture of diastereomers in a manner similar to compound 26 using intermediate 29-3 instead of intermediate 26-2. $^1$H NMR (400 MHz, Methanol-d4) δ 8.00 (s, 0.5H), 7.99 (s, 0.5H), 7.24 (d, J=4.8 Hz, 1H), 7.22-7.14 (m, 3H), 6.89-6.80 (m, 3H), 4.73 (d, J=5.1 Hz, 1H), 4.35-4.26 (m, 1H), 4.22 (t, J=5.5 Hz, 1H), 4.19-4.09 (m, 1H), 4.10-3.91 (m, 5H), 3.57-3.48 (m, 2H), 3.39 (t, J=6.4 Hz, 2H), 2.37-2.22 (m, 1H), 1.57-1.45 (m, 2H), 1.36-1.17 (m, 30H), 0.88 (t, J=6.6 Hz, 3H). LCMS: 786.4 [M−H]$^−$.

Intermediate 30-1: (S)-1-((tert-butyldimethylsilyl)oxy)-3-(octadecyloxy)propan-2-yl 4-methylbenzenesulfonate

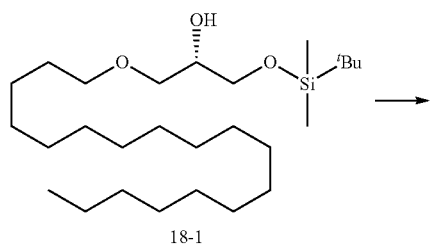

18-1

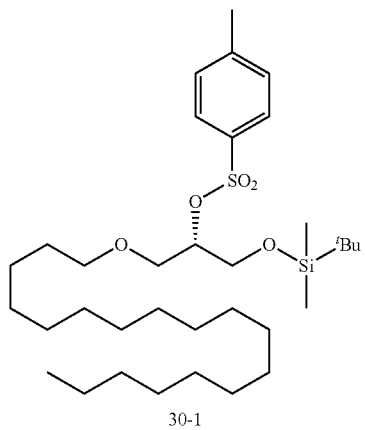

30-1

4-Toluenesulfonyl chloride (929 mg, 4.87 mmol) was added to a stirred mixture of intermediate 18-1 (1.40 g, 3.04 mmol), N,N-diisopropylethylamine (848 µL, 4.87 mmol), 4-(dimethylamino)pyridine (37.2 mg, 304 µmol), and dichloromethane (7.0 mL) at 0° C. After 2 min, the resulting mixture was warmed to room temperature. After 170 min, 4-(dimethylamino)pyridine (67.0 mg, 548 µmol) was added. After 30 min, the resulting mixture was heated to 65° C. After 17 h, the resulting mixture was cooled to room temperature, and diethyl ether (120 mL), ethyl acetate (20 mL), and aqueous hydrogen chloride solution (2.0 M, 5 mL) were added sequentially. The organic layer was washed sequentially with water (100 mL) and a mixture of water and saturated aqueous sodium bicarbonate solution (5:1 v:v, 100 mL), was dried over anhydrous magnesium sulfate, was filtered, and was concentrated under reduced pressure. The residue was purified by flash column chromatography on silica gel (0 to 50% dichloromethane in hexanes) to give intermediate 30-1. LCMS: 635.4 [M+Na]$^+$.

Intermediate 30-2: (S)-3-((1-hydroxy-3-(octadecyloxy)propan-2-yl)oxy)benzonitrile 30-1

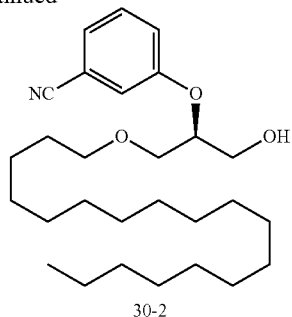

30-2

Potassium tert-pentoxide solution (1.7 M in toluene, 461 µL, 783 µmol) was added over 1 min via syringe to a vigorously stirred mixture of intermediate 30-1 (160 mg, 261 µmol), 3-hydroxybenzonitrile (103 mg, 861 µmol), and N,N-dimethylformamide (0.6 mL) at 0° C., and the resulting mixture was heated to 90° C. After 55 min, the resulting mixture was heated to 130° C. After 1 h, the resulting mixture was cooled to room temperature. After 14 h, diethyl ether (40 mL), saturated aqueous ammonium chloride solution (10 mL), and ethyl acetate (20 mL) were added sequentially. The organic layer was washed with water (2×40 mL), was dried over anhydrous magnesium sulfate, was filtered, and was concentrated under reduced pressure. The residue was dissolved in tetrahydrofuran (0.5 mL), and the resulting solution was stirred at room temperature. Tetrabutylammonium fluoride solution (1.0 M in tetrahydrofuran, 1.07 mL, 1.1 mmol) was added via syringe. After 60 min, saturated aqueous ammonium chloride solution (10 mL), diethyl ether (40 mL), and ethyl acetate (20 mL) were added sequentially. The organic layer was washed with water (40 mL), was dried over anhydrous magnesium sulfate, was filtered, and was concentrated under reduced pressure. The residue was purified by flash column chromatography on silica gel (0 to 30% ethyl acetate in hexanes) to give a mixture of intermediate 30-2. The mixture was purified by flash column chromatography on basic alumina (0 to 15% ethyl acetate in hexanes) to give intermediate 30-2. LCMS: 468.4 [M+Na]⁺.

Example 30: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-(3-cyanophenoxy)-3-(octadecyloxy)propyl) hydrogen phosphate (30)

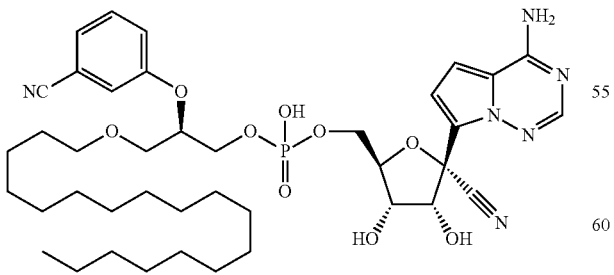

30

Compound 30 was synthesized in a manner similar to compound 19 using intermediate 30-2 instead of intermediate 19-2. ¹H NMR (400 MHz, Methanol-d4) δ 8.06 (s, 1H), 7.40 (dd, J=9.3, 7.5 Hz, 1H), 7.35-7.30 (m, 2H), 7.29 (d, J=4.7 Hz, 1H), 7.25 (dd, J=7.5, 1.4 Hz, 1H), 7.18 (d, J=4.8 Hz, 1H), 4.78 (d, J=5.2 Hz, 1H), 4.73-4.62 (m, 1H), 4.39-4.30 (m, 1H), 4.24 (t, J=5.4 Hz, 1H), 4.22-4.12 (m, 1H), 4.12-3.97 (m, 3H), 3.70 (dd, J=10.7, 3.8 Hz, 1H), 3.63 (dd, J=10.8, 6.1 Hz, 1H), 3.53-3.41 (m, 2H), 1.58-1.46 (m, 2H), 1.40-1.20 (m, 30H), 0.92 (t, J=6.8 Hz, 3H). LCMS: 797.4 [M−H]⁻.

Example 31: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-(3-cyano-5-fluorophenoxy)-3-(octadecyloxy)propyl) hydrogen phosphate (31)

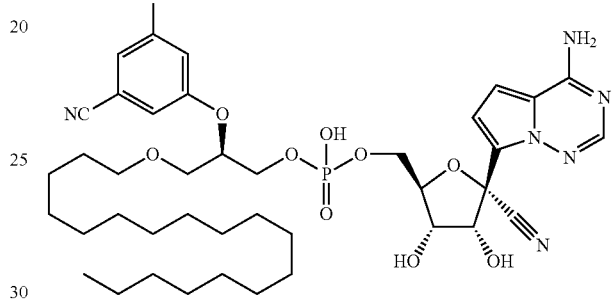

31

Compound 31 was synthesized in a manner similar to compound 30 using 3-fluoro-5-hydroxybenzonitrile instead of 3-hydroxybenzonitrile. ¹H NMR (400 MHz, Methanol-d4) δ 8.09 (s, 1H), 7.33 (d, J=4.7 Hz, 1H), 7.20 (d, J=4.3 Hz, 2H), 7.14 (dt, J=10.7, 2.4 Hz, 1H), 7.09-7.03 (m, 1H), 4.79-4.68 (m, 2H), 4.39-4.32 (m, 1H), 4.27-4.14 (m, 2H), 4.14-3.92 (m, 3H), 3.84-3.40 (m, 4H), 1.64-1.45 (m, 2H), 1.44-1.19 (m, 30H), 1.00-0.85 (m, 3H).
LCMS: 815.4 [M−H]⁻.

Example 32: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((3-(difluoromethyl)benzyl)oxy)-3-(octadecyloxy)propyl) hydrogen phosphate (32)

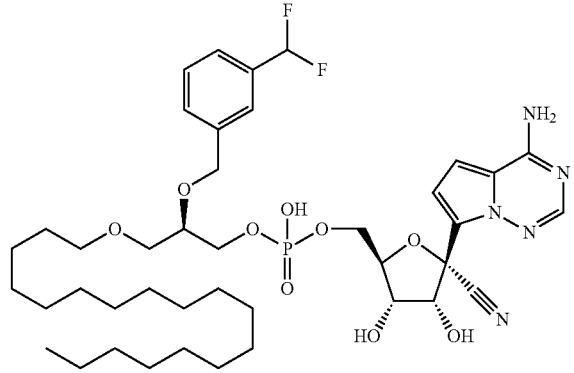

32

Compound 32 was synthesized in a manner similar to compound 19 using 1-(bromomethyl)-3-(difluoromethyl)benzene instead of 1-(bromomethyl)-3-fluoro-5-(trifluoromethyl)benzene. ¹H NMR (400 MHz, DMSO-d6) δ 7.94 (s, 1H), 7.53-7.41 (m, 4H), 7.18-6.74 (m, 3H), 4.73-4.54 (m, 3H), 4.18 (ddt, J=30.5, 6.1, 3.0 Hz, 2H), 4.08-3.85 (m, 4H), 3.77-3.66 (m, 1H), 1.44 (q, J=6.7 Hz, 2H), 1.22 (d, J=9.8 Hz, 28H), 0.93-0.79 (m, 3H). LCMS: 838.2.

Example 33: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((4-(difluoromethyl)benzyl)oxy)-3-(octadecyloxy)propyl) hydrogen phosphate (33)

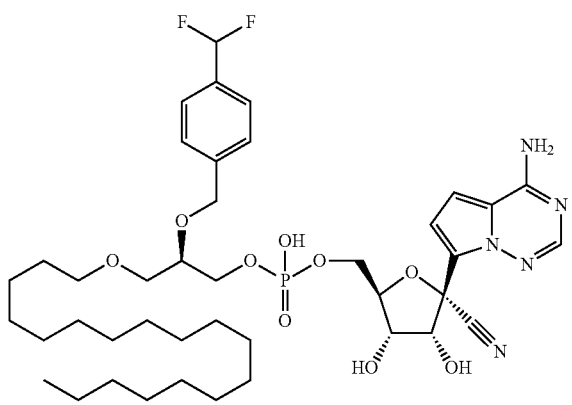

Compound 33 was synthesized in a manner similar to compound 19 using 1-(bromomethyl)-4-(difluoromethyl)benzene instead of 1-(bromomethyl)-3-fluoro-5-(trifluoromethyl)benzene. ¹H NMR (400 MHz, DMSO-d6) δ 7.95 (s, 1H), 7.51 (d, J=8.0 Hz, 2H), 7.45 (d, J=8.1 Hz, 2H), 7.17-6.81 (m, 3H), 4.71-4.57 (m, 3H), 3.78-3.64 (m, 1H), 3.44 (dd, J=5.2, 1.9 Hz, 2H), 3.34 (t, J=6.5 Hz, 2H), 3.13 (p, J=1.6 Hz, 1H), 1.44 (t, J=6.8 Hz, 2H), 1.22 (d, J=8.0 Hz, 32H), 0.96-0.78 (m, 3H). LCMS: 838.2.

Intermediate 34-1: (R)-1-((tert-butyldimethylsilyl)oxy)-3-(heptadecyloxy)propan-2-ol

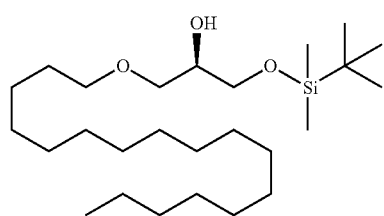

Intermediate 34-1 was synthesized in a manner similar to intermediate 9-2 using (S)-3-(heptadecyloxy) propane-1,2-diol instead of (S)-3-(octadecyloxy) propane-1,2-diol. ¹H NMR (400 MHz, Chloroform-d) δ 3.82 (q, J=5.3 Hz, 1H), 3.72-3.61 (m, 2H), 3.47 (td, J=6.7, 6.3, 1.4 Hz, 4H), 1.59 (t, J=7.1 Hz, 2H), 1.28 (s, 30H), 0.92 (s, 9H), 0.10 (s, 6H).

Example 34: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((3-cyanobenzyl)oxy)-3-(heptadecyloxy)propyl) hydrogen phosphate (34)

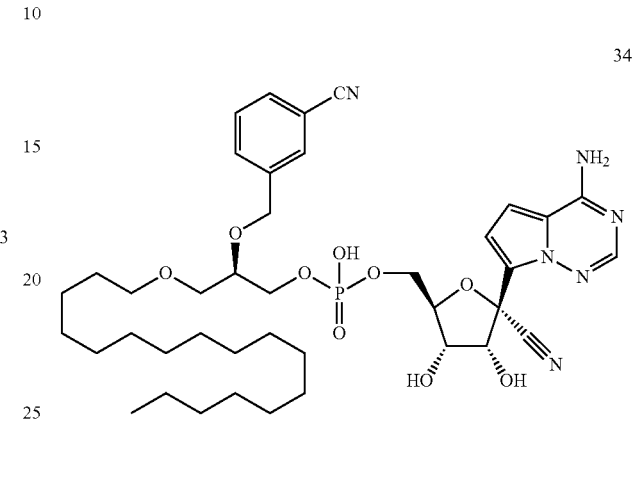

Compound 34 was synthesized in a manner similar to compound 19 using 3-(bromomethyl)benzonitrile instead of 1-(bromomethyl)-3-fluoro-5-(trifluoromethyl)benzene and intermediate 34-1 instead of (R)-1-((tert-butyldimethylsilyl)oxy)-3-(octadecyloxy)propan-2-ol.

¹H NMR (400 MHz, DMSO-d6, drop CD3OD) δ 7.96 (s, 1H), 7.75 (s, 1H), 7.71 (d, J=7.8 Hz, 1H), 7.65 (d, J=8.0 Hz, 1H), 7.52 (t, J=7.8 Hz, 1H), 6.97 (d, J=4.5 Hz, 1H), 6.86 (t, J=3.5 Hz, 1H), 4.66 (t, J=10.0 Hz, 4H), 4.23 (s, 2H), 3.76-3.55 (m, 4H), 3.44 (t, J=3.2 Hz, 2H), 3.36 (d, J=13.3 Hz, 5H), 3.08 (dd, J=25.4, 13.0 Hz, 3H), 2.80 (s, 4H), 1.45 (t, J=6.8 Hz, 3H), 1.22 (d, J=8.1 Hz, 33H), 0.85 (t, J=6.5 Hz, 3H). LCMS: 799.3.

Example 35: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((3-cyano-5-fluorobenzyl)oxy)-3-(heptadecyloxy)propyl) hydrogen phosphate (35)

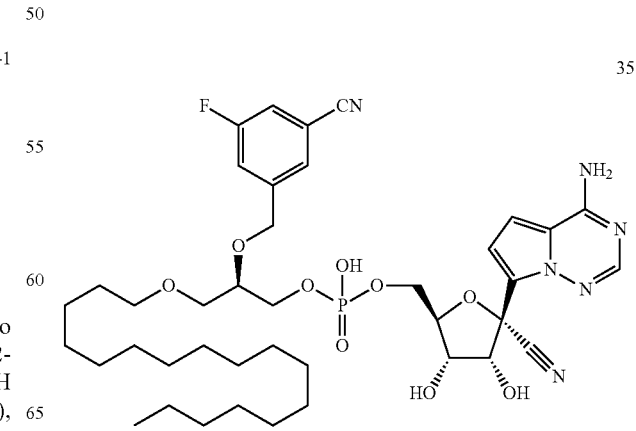

Compound 35 was synthesized in a manner similar to compound 19 using 3-(bromomethyl)-5-fluorobenzonitrile instead of 1-(bromomethyl)-3-fluoro-5-(trifluoromethyl)benzene and intermediate 34-1 instead of (R)-1-((tert-butyldimethylsilyl)oxy)-3-(octadecyloxy)propan-2-ol. $^1$H NMR (400 MHz, DMSO-d6, drop CD3OD) δ 7.92 (s, 1H), 7.71 (d, J=8.7 Hz, 1H), 7.63 (s, 1H), 7.53 (d, J=9.7 Hz, 1H), 6.91 (d, J=4.8 Hz, 1H), 6.84 (d, J=3.5 Hz, 1H), 4.72-4.56 (m, 2H), 3.71 (s, 1H), 3.47-3.38 (m, 2H), 3.33 (d, J=7.2 Hz, 2H), 3.13 (s, 2H), 1.45 (t, J=6.9 Hz, 2H), 1.22 (d, J=9.0 Hz, 29H), 0.85 (t, J=6.7 Hz, 3H). LCMS: 817.3.

Example 36: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((4-cyanobenzyl)oxy)-3-(heptadecyloxy)propyl) hydrogen phosphate (36)

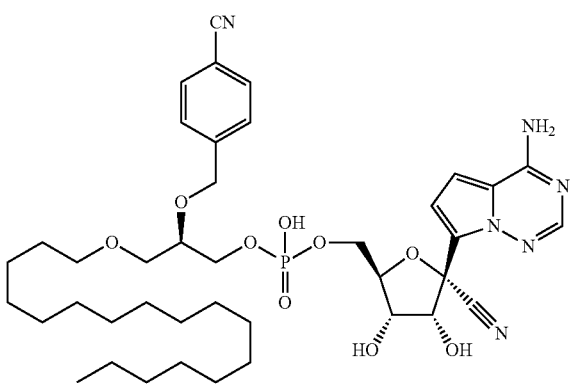

Compound 36 was synthesized in a manner similar to compound 19 using 4-(bromomethyl)benzonitrile instead of 1-(bromomethyl)-3-fluoro-5-(trifluoromethyl)benzene and intermediate 34-1 instead of (R)-1-((tert-butyldimethylsilyl)oxy)-3-(octadecyloxy)propan-2-ol.

$^1$H NMR (400 MHz, DMSO-d6) δ7.93 (d, J=2.6 Hz, 1H), 7.76 (d, J=8.1 Hz, 2H), 7.51 (d, J=7.7 Hz, 2H), 6.91 (d, J=3.4 Hz, 1H), 6.85 (d, J=3.7 Hz, 1H), 4.66 (dt, J=9.0, 3.5 Hz, 3H), 3.77-3.66 (m, 1H), 3.62 (d, J=12.3 Hz, 1H), 3.49-3.40 (m, 2H), 3.35 (q, J=9.5, 7.5 Hz, 3H), 3.10 (d, J=24.5 Hz, 1H), 2.81 (d, J=2.7 Hz, 1H), 1.43 (d, J=7.3 Hz, 2H), 1.22 (d, J=9.3 Hz, 26H), 0.85 (t, J=6.1 Hz, 3H). LCMS: 799.3.

Example 37: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-3-(heptadecyloxy)-2-((4-methoxybenzyl)oxy)propyl) hydrogen phosphate (37)

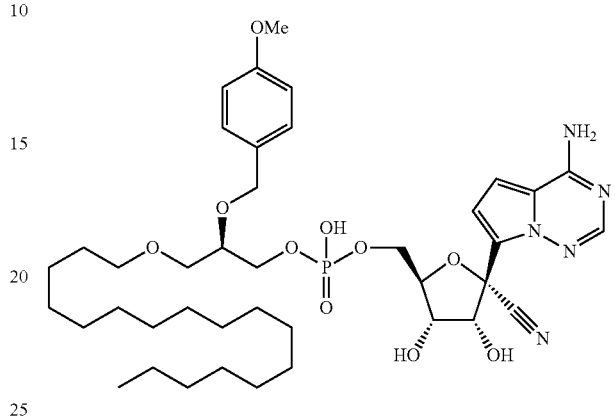

Compound 37 was synthesized in a manner similar to compound 19 using 1-(bromomethyl)-4-methoxybenzene instead of 1-(bromomethyl)-3-fluoro-5-(trifluoromethyl)benzene and intermediate 34-1 instead of (R)-1-((tert-butyldimethylsilyl)oxy)-3-(octadecyloxy)propan-2-ol. $^1$H NMR (400 MHz, DMSO-d6, drop CD3OD) δ 7.93 (d, J=2.8 Hz, 1H), 7.23 (d, J=8.2 Hz, 2H), 6.98-6.74 (m, 4H), 4.66 (d, J=4.6 Hz, 1H), 4.49 (d, J=4.8 Hz, 2H), 4.22 (s, 2H), 3.78-3.55 (m, 4H), 3.48-3.25 (m, 4H), 3.13 (s, 2H), 1.43 (s, 2H), 1.23 (d, J=5.5 Hz, 29H), 0.85 (d, J=7.5 Hz, 3H). LCMS: 804.2.

Intermediate 38-1: (R)-3-(octadecyloxy)-2-phenoxypropan-1-ol

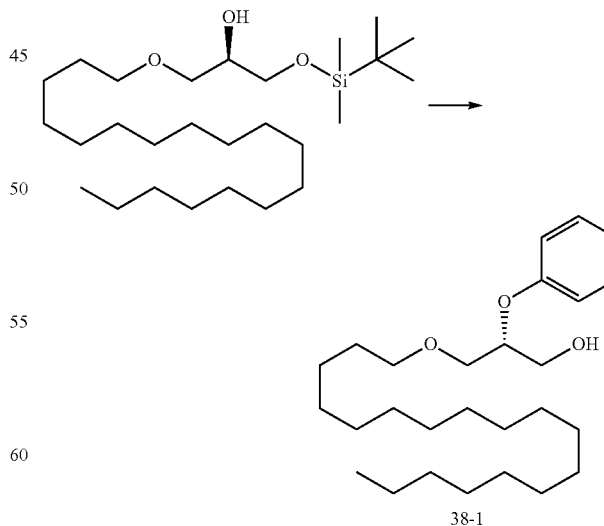

Triphenylphosphane (80.0 mg, 0.305 mmol) was added to a 0° C. chilled solution of (R)-1-((tert-butyldimethylsilyl)oxy)-3-(octadecyloxy)propan-2-ol (109 mg, 0.237 mmol), phenol (41.0 mg, 0.436 mmol), and diisopropyl azodicarboxylate (0.0750 mL, 0.359 mmol) in tetrahydrofuran (2 mL) THF. The reaction mixture was allowed to gradually warm to room temperature and stirred for 24 hours and which point solvent was removed under reduced pressure and crude product absorbed onto silica gel which was purified by flash column chromatography on silica gel (0 to 10% ethyl acetate in hexanes) to afford (S)-tert-butyldimethyl(3-(octadecyloxy)-2-phenoxypropoxy)silane. $^1$H NMR (400 MHz, Chloroform-d) δ 7.33-7.22 (m, 2H), 7.03-6.90 (m, 3H), 4.43 (q, J=5.1 Hz, 1H), 3.89-3.79 (m, 2H), 3.67 (qd, J=10.4, 4.9 Hz, 2H), 3.49 (td, J=6.5, 1.9 Hz, 2H), 1.63-1.53 (m, 2H), 1.27 (s, 30H), 0.90 (s, 9H), 0.08 (s, 3H), 0.06 (s, 3H).

A 1 M solution of tetra-n-butyl ammonium fluoride in tetrahydrofuran (0.500 mL, 0.500 mmol) was added to a solution of (S)-tert-butyldimethyl(3-(octadecyloxy)-2-phenoxypropoxy)silane (84.0 mg, 0.157 mmol) in tetrahydrofuran (2 mL). The reaction mixture was stirred for one hour at which point the reaction mixture was diluted with ethyl acetate and washed sequentially with 3*water followed by a saturated aqueous sodium chloride solution. The organic phase was then dried over sodium sulfate, filtered, and concentrated under reduced pressure. The residue was purified by flash column chromatography on silica gel (0 to 20% ethyl acetate in hexanes) to afford intermediate 38-1. $^1$H NMR (400 MHz, Chloroform-d) δ 7.38-7.29 (m, 2H), 7.04-6.86 (m, 3H), 4.19 (s, 1H), 4.05 (dd, J=5.5, 2.8 Hz, 2H), 3.62 (qd, J=9.7, 5.2 Hz, 2H), 3.51 (td, J=6.6, 1.8 Hz, 2H), 1.59 (d, J=12.7 Hz, 2H), 1.28 (s, 30H), 0.96-0.85 (m, 3H).

Example 38: ((2R,3S,4R,5R)-5-(4-aminopyrrolo[2,1-f][1,2,4]triazin-7-yl)-5-cyano-3,4-dihydroxytetrahydrofuran-2-yl)methyl ((S)-3-(octadecyloxy)-2-phenoxypropyl) hydrogen phosphate (38)

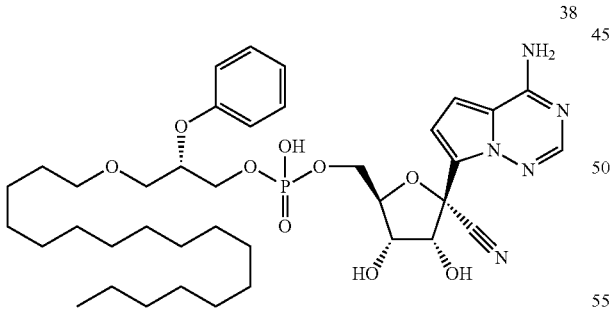

Compound 38 was synthesized in a manner similar to compound 2 using intermediate 38-1 instead of intermediate 2-2. $^1$H NMR (400 MHz, Methanol-d4) δ 7.93 (d, J=2.4 Hz, 1H), 7.20 (t, J=8.0 Hz, 2H), 7.07 (d, J=10.6 Hz, 2H), 6.85 (d, J=8.5 Hz, 3H), 4.52-3.98 (m, 7H), 3.82-3.38 (m, 6H), 3.15 (s, 1H), 1.51 (s, 2H), 1.27 (d, J=25.3 Hz, 44H), 0.91 (d, J=7.4 Hz, 3H). LCMS: 774.1.

Example 39: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((3-cyanobenzyl)oxy)-3-(octadecyloxy)propyl) hydrogen phosphate (39)

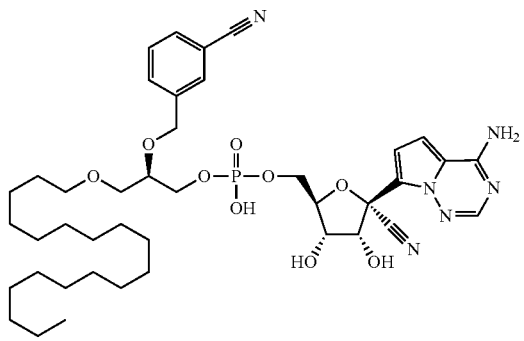

Compound 39 was synthesized as a 1:1 mixture of diastereomers in a manner similar to compound 16 replacing 3-(bromomethyl)-5-fluorobenzonitrile with 3-(bromomethyl)benzonitrile. $^1$H NMR (400 MHz, Methanol-d4) δ 7.89 (s, 1H), 7.70 (d, J=1.9 Hz, 1H), 7.62 (d, J=7.7 Hz, 1H), 7.57 (d, J=7.7 Hz, 1H), 7.45 (t, J=7.7 Hz, 1H), 7.00 (d, J=4.6 Hz, 1H), 6.93 (d, J=4.6 Hz, 1H), 4.83 (d, J=5.4 Hz, 1H), 4.76-4.62 (m, 2H), 4.40-4.33 (m, 1H), 4.25 (t, J=5.5 Hz, 1H), 4.23-4.14 (m, 1H), 4.14-4.05 (m, 1H), 4.00-3.85 (m, 2H), 3.79-3.70 (m, 1H), 3.57-3.44 (m, 2H), 3.44-3.37 (m, 2H), 3.18 (q, J=7.3 Hz, 2H), 1.59-1.49 (m, 2H), 1.39-1.20 (m, 30H), 0.91 (t, J=6.7 Hz, 3H).
$^{31}$P NMR (162 MHz, Methanol-d4) δ −0.41.
LCMS: 813.25 [M+H]$^+$ Example 40: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((4-methylbenzyl)oxy)-3-(octadecyloxy)propyl) hydrogen phosphate (40)

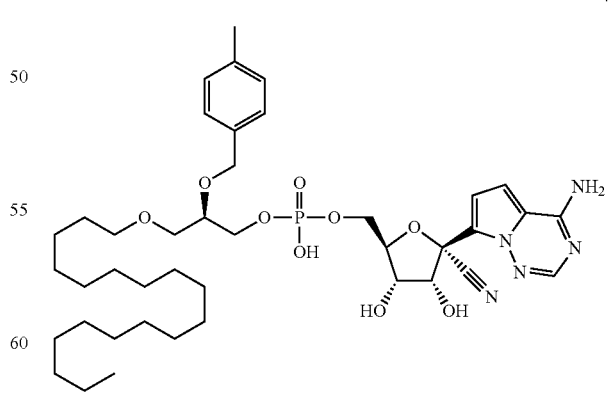

Compound 40 was synthesized as a 1:1 mixture of diastereomers in a manner similar to compound 16 replacing 3-(bromomethyl)-5-fluorobenzonitrile with 1-(bromomethyl)-4-methylbenzene. $^1$H NMR (400 MHz, Methanol-d4)

δ 7.87 (s, 1H), 7.19 (d, J=7.7 Hz, 2H), 7.07 (d, J=7.7 Hz, 2H), 6.98 (d, J=4.6 Hz, 1H), 6.89 (d, J=4.6 Hz, 1H), 4.83 (d, J=5.3 Hz, 1H), 4.62-4.52 (m, 2H), 4.42-4.35 (m, 1H), 4.27 (t, J=5.5 Hz, 1H), 4.24-4.13 (m, 1H), 4.13-4.04 (m, 1H), 3.98-3.85 (m, 2H), 3.76-3.66 (m, 1H), 3.58-3.42 (m, 2H), 3.38 (t, J=6.6 Hz, 2H), 2.29 (s, 3H), 1.57-1.45 (m, 2H), 1.42-1.17 (m, 30H), 0.91 (t, J=6.7 Hz, 3H).

$^{31}$P NMR (162 MHz, Methanol-d4) δ −0.57.

LCMS: 802.12 [M+H]$^+$

Example 41: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((4-chlorobenzyl)oxy)-3-(octadecyloxy)propyl) hydrogen phosphate (41)

41

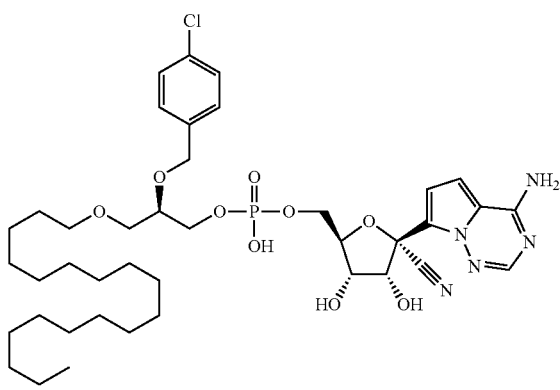

Compound 41 was synthesized as a 1:1 mixture of diastereomers in a manner similar to compound 16 replacing 3-(bromomethyl)-5-fluorobenzonitrile with 1-(bromomethyl)-4-chlorobenzene. $^1$H NMR (400 MHz, Methanol-d4) δ 7.87 (s, 1H), 7.30 (d, J=8.3 Hz, 2H), 7.25 (d, J=8.3 Hz, 2H), 6.98 (d, J=4.6 Hz, 1H), 6.89 (d, J=4.6 Hz, 1H), 4.84 (d, J=5.4 Hz, 1H), 4.67-4.53 (m, 2H), 4.42-4.34 (m, 1H), 4.27 (t, J=5.5 Hz, 1H), 4.23-4.13 (m, 1H), 4.13-4.03 (m, 1H), 3.99-3.83 (m, 2H), 3.78-3.64 (m, 1H), 3.57-3.42 (m, 2H), 3.38 (t, J=6.5, 1.9 Hz, 2H), 1.59-1.46 (m, 2H), 1.41-1.17 (m, 30H), 0.91 (t, J=6.7 Hz, 3H).

$^{31}$P NMR (162 MHz, Methanol-d4) δ −0.62.

LCMS: 822.16 [M+H]$^+$

Example 42: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((2-fluorobenzyl)oxy)-3-(octadecyloxy)propyl) hydrogen phosphate (42)

42

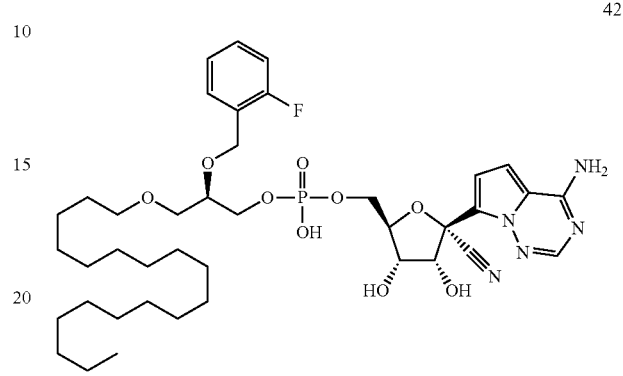

Compound 42 was synthesized as a 1:1 mixture of diastereomers in a manner similar to compound 16 replacing 3-(bromomethyl)-5-fluorobenzonitrile with 1-(bromomethyl)-2-fluorobenzene. $^1$H NMR (400 MHz, Methanol-d4) δ 7.87 (s, 1H), 7.52-7.45 (m, 1H), 7.30-7.22 (m, 1H), 7.11 (t, J=7.5 Hz, 1H), 7.07-7.01 (m, 1H), 6.99 (d, J=4.4 Hz, 1H), 6.89 (d, J=4.6 Hz, 1H), 4.84 (d, J=5.3 Hz, 1H), 4.76-4.67 (m, 2H), 4.41-4.33 (m, 1H), 4.27 (t, J=5.4 Hz, 1H), 4.19-4.11 (m, 1H), 4.11-4.04 (m, 1H), 3.98-3.86 (m, 2H), 3.79-3.62 (m, 2H), 3.60-3.51 (m, 1H), 3.51-3.43 (m, 1H), 3.39 (td, J=6.6, 2.5 Hz, 2H), 1.58-1.47 (m, 2H), 1.39-1.22 (m, 30H), 0.91 (t, J=6.7 Hz, 3H).

$^{31}$P NMR (162 MHz, Methanol-d4) δ −0.01.

$^{19}$F NMR (376 MHz, Methanol-d4) δ −121.40 (dt, J=12.1, 6.1 Hz).

LCMS: 806.19 [M+H]$^+$

Example 43: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((2,6-difluorobenzyl)oxy)-3-(octadecyloxy)propyl) hydrogen phosphate (43)

43

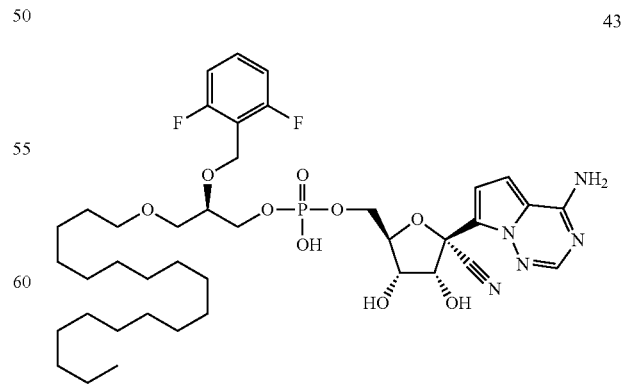

Compound 43 was synthesized as a 1:1 mixture of diastereomers in a manner similar to compound 16 replacing 3-(bromomethyl)-5-fluorobenzonitrile with 2-(bromomethyl)-1,3-difluorobenzene. ¹H NMR (400 MHz, Methanol-d4) δ 7.87 (s, 1H), 7.41-7.27 (m, 1H), 7.03-6.97 (m, 1H), 6.96-6.82 (m, 3H), 4.86-4.82 (m, 1H), 4.69 (s, 2H), 4.41-4.35 (m, 1H), 4.32-4.25 (m, 1H), 4.23-4.13 (m, 1H), 4.13-4.03 (m, 1H), 3.97-3.84 (m, 2H), 3.80-3.63 (m, 2H), 3.62-3.49 (m, 1H), 3.49-3.42 (m, 1H), 3.38 (t, J=6.6 Hz, 1H), 1.59-1.40 (m, 2H), 1.40-1.13 (m, 30H), 0.91 (t, J=6.6 Hz, 3H).

³¹P NMR (162 MHz, Methanol-d4) δ −0.93.

¹⁹F NMR (376 MHz, Methanol-d4) δ −117.21 (t, J=6.9 Hz).

LCMS: 824.19 [M+H]⁺

Example 44: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-methoxy-3-(octadecyloxy)propyl) hydrogen phosphate (44)

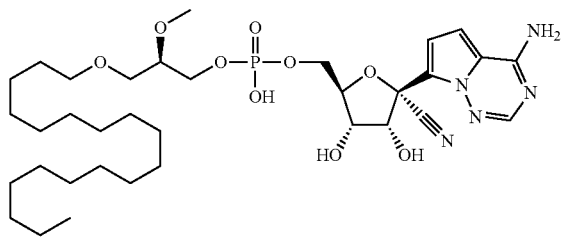 [SMILES: CCCCCCCCCCCCCCCCCCOC[C@H](COP(=O)(O)OC[C@H]1O[C@@](C#N)(c2ccc3c(N)ncnn23)[C@H](O)[C@@H]1O)OC]

Compound 44 was synthesized as a 1:1 mixture of diastereomers in a manner similar to compound 16 replacing 3-(bromomethyl)-5-fluorobenzonitrile with iodomethane. ¹H NMR (400 MHz, Methanol-d4) δ 7.90 (s, 1H), 7.00 (d, J=4.6 Hz, 1H), 6.92 (d, J=4.6 Hz, 1H), 4.88-4.79 (m, 1H), 4.42-4.35 (m, 1H), 4.28 (t, J=5.3 Hz, 1H), 4.24-4.11 (m, 1H), 4.11-4.02 (m, 1H), 3.92-3.76 (m, 2H), 3.77-3.63 (m, 1H), 3.63-3.45 (m, 2H), 3.44-3.37 (m, 5H), 1.61-1.48 (m, 2H), 1.41-1.22 (m, 30H), 0.91 (t, J=6.8 Hz, 3H).

³¹P NMR (162 MHz, Methanol-d4) δ −0.09.

LCMS: 712.16 [M+H]⁺

Example 45: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((3-fluorobenzyl)oxy)-3-(octadecyloxy)propyl) hydrogen phosphate (45)

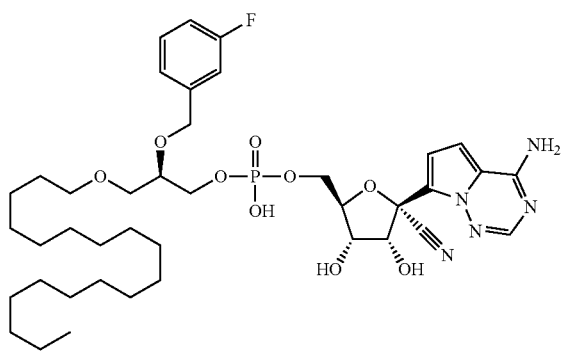 [SMILES: CCCCCCCCCCCCCCCCCCOC[C@H](COP(=O)(O)OC[C@H]1O[C@@](C#N)(c2ccc3c(N)ncnn23)[C@H](O)[C@@H]1O)OCc1cccc(F)c1]

Compound 45 was synthesized as a 1:1 mixture of diastereomers in a manner similar to compound 16 replacing 3-(bromomethyl)-5-fluorobenzonitrile with 1-(bromomethyl)-3-fluorobenzene. ¹H NMR (400 MHz, Methanol-d4) δ 7.87 (s, 1H), 7.28 (td, J=8.0, 5.7 Hz, 1H), 7.15-7.05 (m, 2H), 6.99 (d, J=4.6 Hz, 1H), 6.94 (td, J=8.5, 2.6 Hz, 1H), 6.89 (d, J=4.6 Hz, 1H), 4.84 (d, J=5.4 Hz, 1H), 4.72-4.54 (m, 2H), 4.45-4.33 (m, 1H), 4.27 (t, J=5.4 Hz, 1H), 4.21-4.12 (m, 1H), 4.12-4.04 (m, 1H), 3.98-3.84 (m, 2H), 3.77-3.64 (m, 1H), 3.55-3.44 (m, 2H), 3.44-3.36 (m, 2H), 1.59-1.47 (m, 2H), 1.40-1.18 (m, 30H), 0.91 (t, J=6.7 Hz, 3H).

³¹P NMR (162 MHz, Methanol-d4) δ 0.17.

¹⁹F NMR (377 MHz, Methanol-d4) δ −116.09 (td, J=9.3, 5.7 Hz).

LCMS: 806.20 [M+H]⁺

Intermediate 46-1: (R)-tert-butyldimethyl(2-((2-methylallyl)oxy)-3-(octadecyloxy)propoxy) silane Intermediate 46-1 was prepared in a manner similar to intermediate 2-1, using 3-bromo-2-methylpropene instead of 4-(bromomethyl)-1,1'-biphenyl. ¹H NMR (400 MHz, Chloroform-d) δ 5.02-4.98 (m, 1H), 4.89 (m, 1H), 4.06 (s, 2H), 3.69 (dd, J=5.1, 1.6 Hz, 1H), 3.58-3.51 (m, 2H), 3.50-3.40 (m, 4H), 1.77 (s, 3H), 1.56 (m, 2H), 1.28 (s, 30H), 0.91 (m, 12H), 0.09 (m, 6H).

Intermediate 46-2: (S)-2-((2-methylallyl)oxy)-3-(octadecyloxy)propan-1-ol

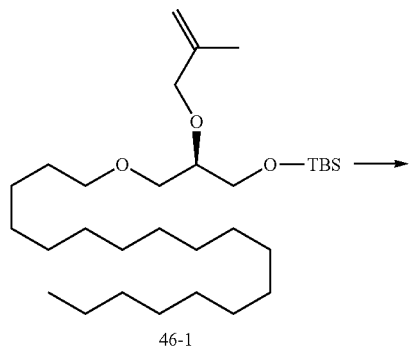

46-1

Tetrabutylammonium fluoride solution (1.0 M in tetrahydrofuran, 1.05 mL, 1.05 mmol) was added by syringe to a stirred solution of 46-1 (179 mg, 359 μmol) in tetrahydrofuran (10 mL) at room temperature. After 150 min, aqueous ammonium chloride solution (25 mL), diethyl ether (50 mL), and water (25 mL) were added sequentially. The organic layer was washed with water (50 mL), dried over anhydrous magnesium sulfate, filtered, and concentrated under reduced pressure. The residue was purified by flash chromatography on silica gel (0 to 25% ethyl acetate in hexanes) to yield intermediate 46-2. $^1$H NMR (400 MHz, Chloroform-d) δ 5.00 (m, 1H), 4.92-4.86 (m, 1H), 4.06 (s, 2H), 3.69 (dd, J=5.1, 1.6 Hz, 1H), 3.55 (m, 2H), 3.52-3.41 (m, 4H), 1.80-1.72 (s, 3H), 1.57 (m, 2H), 1.28 (s, 30H).

Intermediate 46-3: (S)-2-isobutoxy-3-(octadecyloxy)propan-1-ol

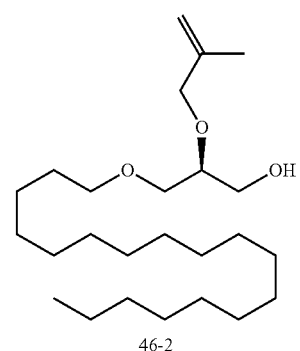

46-2

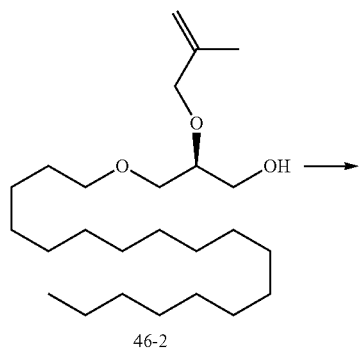

46-2

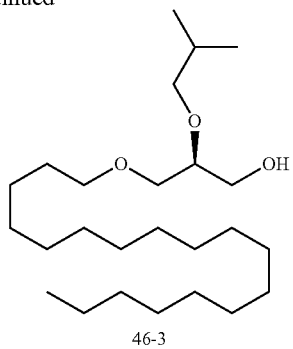

46-3

A vigorously stirred mixture of intermediate 46-2 (140 mg, 351 μmol), platinum (10% wt. on carbon, 193 mg, 98.0 μmol), tetrahydrofuran (1.5 mL), and ethanol (4.5 mL) was placed under an atmosphere of hydrogen gas (balloon) at room temperature. After 16 h, the reaction mixture was filtered through celite, and the filtrate was concentrated under reduced pressure to yield intermediate 46-3. $^1$H NMR (400 MHz, Chloroform-d) δ 3.80-3.72 (m, 1H), 3.65 (dd, J=11.4, 4.9 Hz, 1H), 3.59-3.38 (m, 4H), 3.31 (dd, J=9.1, 6.6 Hz, 1H), 1.88 (p, J=6.7 Hz, 1H), 1.63-1.52 (m, 2H), 1.28 (s, 30H), 0.99-0.83 (m, 6H).

Intermediate 46-4: (R)-2-isobutoxy-3-(octadecyloxy)propyl bis(4-nitrophenyl) phosphate

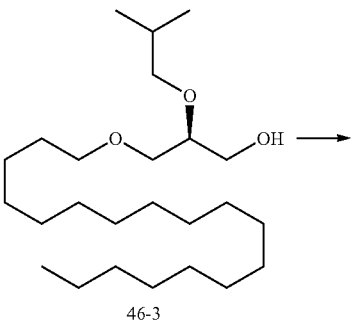

46-3

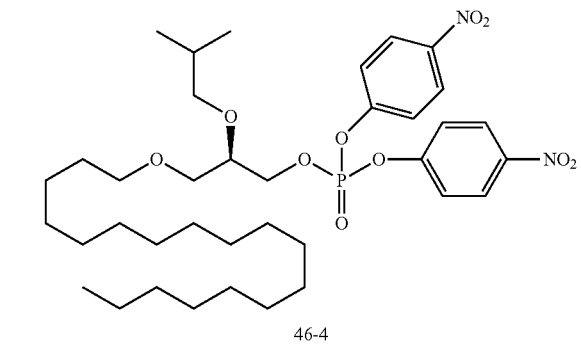

46-4

Intermediate 46-4 was prepared in a manner similar to intermediate 2-3, using 46-3 instead of intermediate 2-2. LCMS: 722.9.

Intermediate 46-5: ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl ((R)-2-isobutoxy-3-(octadecyloxy)propyl) (4-nitrophenyl) phosphate

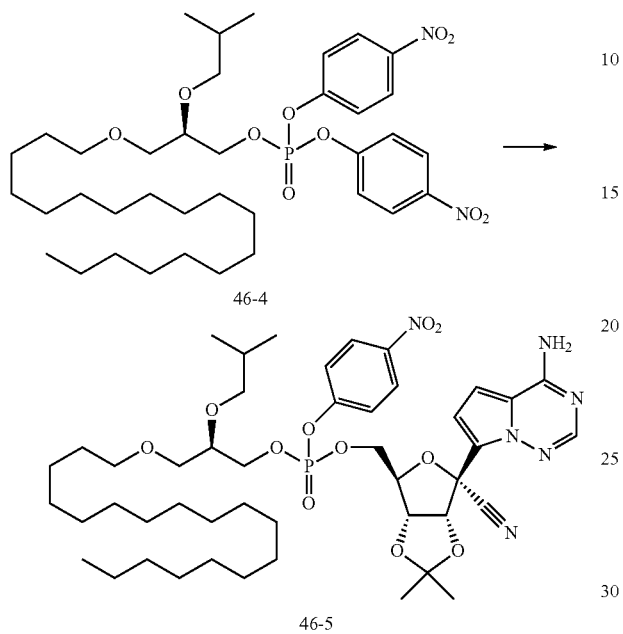

Intermediate 46-5 was prepared in a manner similar to intermediate 2-4, using 46-4 instead of intermediate 2-3. LCMS: 915.3.

Example 46: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-isobutoxy-3-(octadecyloxy)propyl) hydrogen phosphate (46)

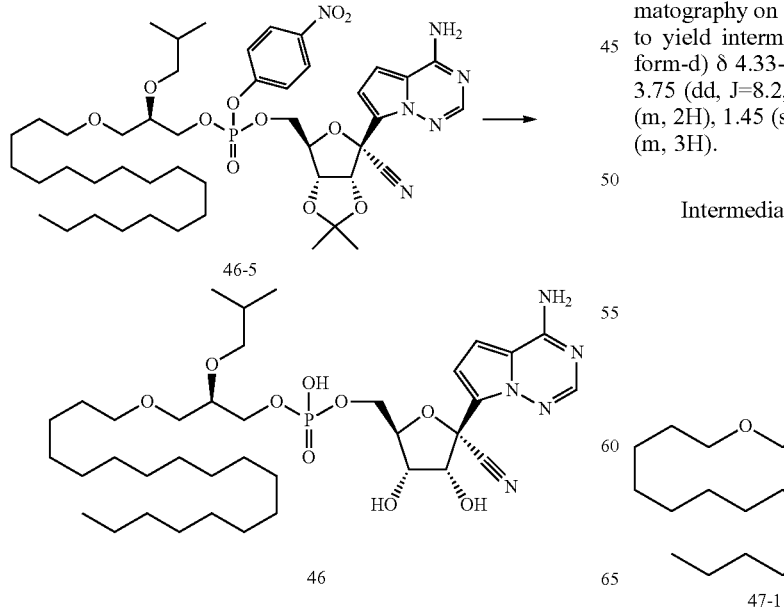

Compound 46 was prepared in a manner similar to compound 18, using 46-5 instead of intermediate 18-5. $^1$H NMR (400 MHz, Methanol-d4) δ 7.89 (s, 1H), 7.01 (d, J=4.6 Hz, 1H), 6.94 (d, J=4.6 Hz, 1H), 5.08 (m, 1H), 4.59 (s, 1H), 4.27 (t, J=5.3 Hz, 1H), 4.20-4.11 (m, 1H), 4.11-3.97 (m, 1H), 3.82 (t, J=5.5 Hz, 2H), 3.74-3.63 (m, 2H), 3.41 (m, 2H), 3.23 (m, 2H), 2.31 (m, 2H), 1.54 (m, 2H), 1.32 (m, 30H), 0.94-0.89 (m, 9H). LCMS: 754.1.

Intermediate 47-1: (R)-2,2-dimethyl-4-((octadecyloxy)methyl)-1,3-dioxolane

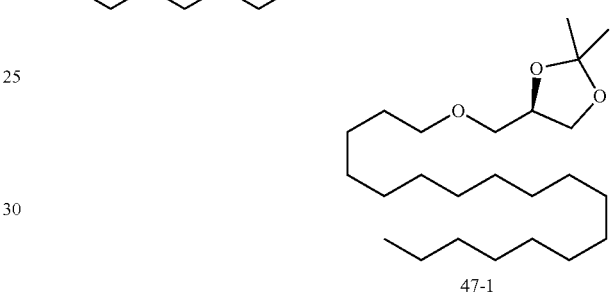

Acetone (458 μL, 6.18 mmol) was added by syringe to a rapidly stirring mixture of p-toluenesulfonic acid monohydrate (11.8 mg, 61.8 μmol) and (S)-3-(octadecyloxy)propane-1,2-diol (213 mg, 618 μmol) in dichloromethane (10 mL) at room temperature. After 90 min, the reaction mixture was heated to 50° C. After 30 min, the reaction was cooled to room temperature, and the solvent was removed under reduced pressure. The residue was purified by flash chromatography on silica gel (0 to 30% ethyl acetate in hexanes) to yield intermediate 47-1. $^1$H NMR (400 MHz, Chloroform-d) δ 4.33-4.23 (m, 1H), 4.08 (dd, J=8.3, 6.4 Hz, 1H), 3.75 (dd, J=8.2, 6.4 Hz, 1H), 3.59-3.38 (m, 4H), 1.63-1.50 (m, 2H), 1.45 (s, 3H), 1.39 (s, 3H), 1.28 (s, 30H), 0.94-0.86 (m, 3H).

Intermediate 47-2: (S)-2-isopropoxy-3-(octadecyloxy)propan-1-ol

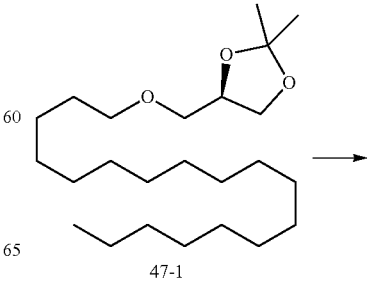

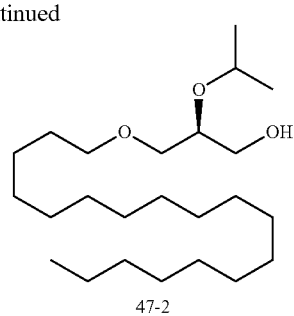

47-2

Dichloroborane methyl sulfide complex (52 µL, 380 µmol) was added by syringe to a rapidly stirred mixture of intermediate 47-1 (149 mg, 387 µmol) in tetrahydrofuran (750 µL) at −60° C. Reaction warmed to room temperature over 15 min. After 16 h, aqueous ammonium chloride solution (10 mL) and diethyl ether (10 mL) were added sequentially. The organic layer was washed with water (20 mL), was dried over anhydrous magnesium sulfate, was filtered, and was concentrated under reduced pressure. The residue was purified by flash chromatography on silica gel (0 to 30% ethyl acetate in hexanes) to yield intermediate 47-2. $^1$H NMR (400 MHz, Chloroform-d) δ 3.80 (p, J=6.1 Hz, 1H), 3.71 (dd, J=10.1, 3.4 Hz, 1H), 3.67-3.56 (m, 2H), 3.52 (dd, J=9.8, 4.8 Hz, 1H), 3.49-3.41 (m, 3H), 1.58 (m, 2H), 1.28 (d, J=1.9 Hz, 30H), 1.20 (dd, J=6.1, 0.9 Hz, 6H), 0.94-0.85 (m, 3H).

Intermediate 47-3: (R)-2-isopropoxy-3-(octadecyloxy)propyl bis(4-nitrophenyl) phosphate

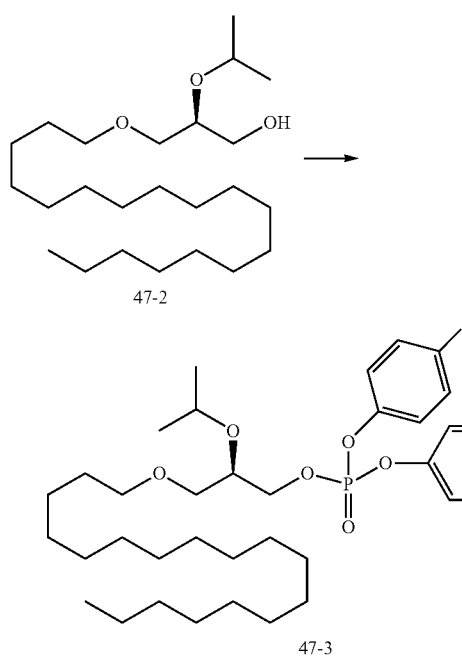

Intermediate 47-3 was prepared in a manner similar to 46-4, using 47-2 instead of 46-3.
LCMS: 731.2 [M+Na]$^+$.

Intermediate 47-4: ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl ((R)-2-isopropoxy-3-(octadecyloxy)propyl) (4-nitrophenyl) phosphate

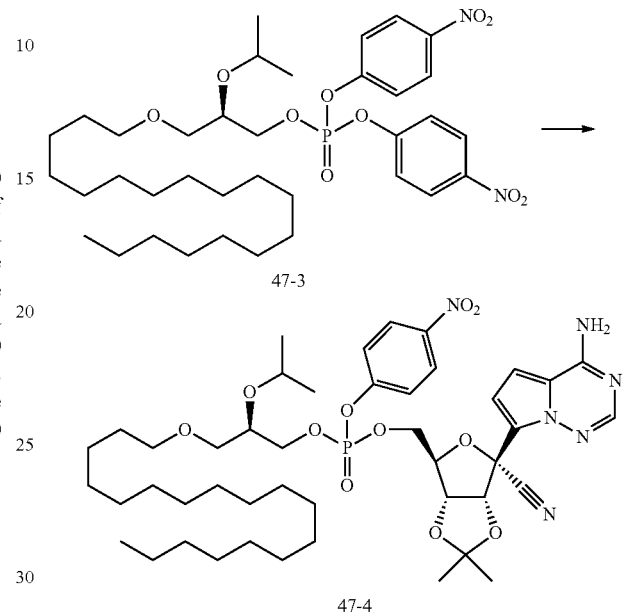

Intermediate 47-4 was prepared in a manner similar to 46-5, using 47-3 instead of 46-4.
LCMS: 923.4 [M+Na]$^+$.

Example 47: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-isopropoxy-3-(octadecyloxy)propyl) hydrogen phosphate (47)

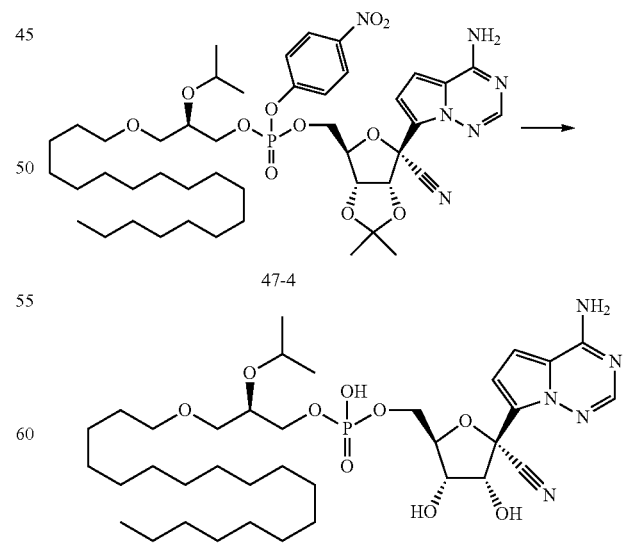

Potassium trimethylsilanolate (9.8 mg, 77 μmol) was added to a rapidly stirred mixture of 47-4 (23.0 mg, 25.5 μmol) in tetrahydrofuran (800 μL) at room temperature. After 45 min, potassium trimethylsilanolate (27 mg, 210 μmol) was added. After 45 min, concentrated hydrochloric acid (200 μL) was added. After 90 min, triethylamine was added until mixture had pH>7, as indicated by yellow tint persisting. The mixture was purified by reverse phase preparative HPLC (2-propanol/water) to give compound 47 as a salt with triethylamine. $^1$H NMR (400 MHz, Methanol-$d_4$) δ 7.98 (s, 1H), 7.11 (s, 2H), 4.82 (d, J=5.3 Hz, 1H), 4.36 (d, J=4.7 Hz, 1H), 4.27 (t, J=5.4 Hz, 1H), 4.22-4.13 (m, 1H), 4.12-4.03 (m, 1H), 3.86-3.74 (m, 3H), 3.74-3.63 (m, 1H), 3.59 (dd, J=11.2, 4.9 Hz, 1H), 3.54 (d, J=6.0 Hz, 1H), 3.47-3.39 (m, 2H), 1.56 (m, 2H), 1.30 (m, 30H), 1.12 (dd, J=6.1, 1.7 Hz, 6H), 0.96-0.88 (m, 3H).

LCMS: 738.4 [M−H]$^-$.

Intermediate 48-1: (R)-tert-butyl(2-((3,4-dichlorobenzyl)oxy)-3-(octadecyloxy)propoxy) dimethylsilane

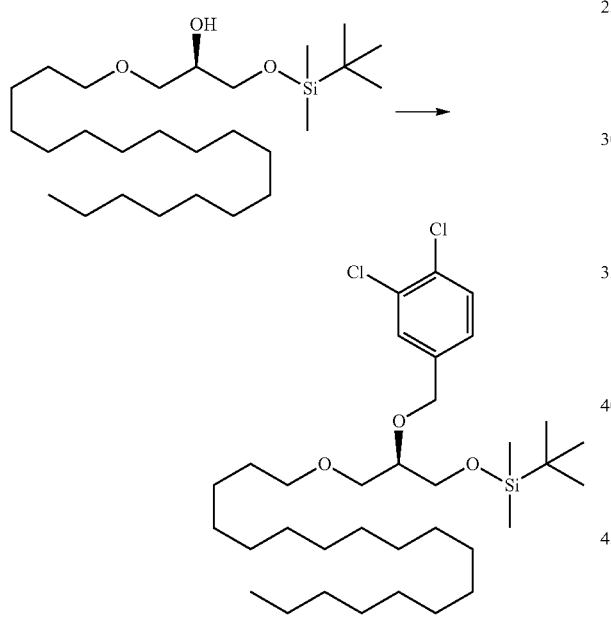

Sodium hydride (60% wt dispersion in mineral oil, 74 mg, 1.94 mmol) was added to a stirred solution of (R)-1-((tert-butyldimethylsilyl)oxy)-3-(octadecyloxy)propan-2-ol (335 mg, 730 μmol) in tetrahydrofuran (6 mL) at 0° C. After 30 min, 4-(bromomethyl)-1,2-dichlorobenzene (438 mg, 1.83 mmol) was added, and the resulting mixture was warmed to room temperature and stirred overnight. The suspension was then cooled to 0° C., quenched with water (5 mL), and extracted with ethyl acetate (3×20 mL). The combined organic fractions were then washed with brine (25 mL) and dried over magnesium sulfate. Following filtration and concentration, the crude residue was purified by flash column chromatography on silica gel (0 to 20% ethyl acetate in hexanes) to give intermediate 48-1. $^1$H NMR (400 MHz, Chloroform-d) δ 7.51 (d, J=1.9 Hz, 1H), 7.41 (d, J=8.2 Hz, 1H), 7.21 (dd, J=8.2, 2.0 Hz, 1H), 4.68 (s, 2H), 3.71 (d, J=5.9 Hz, 2H), 3.67-3.60 (m, 1H), 3.60-3.39 (m, 4H), 1.66-1.49 (m, 2H), 1.39-1.20 (m, 30H), 1.00-0.84 (m, 12H), 0.08 (s, 6H).

Intermediate 48-2: (S)-2-((3,4-dichlorobenzyl)oxy)-3-(octadecyloxy)propan-1-ol

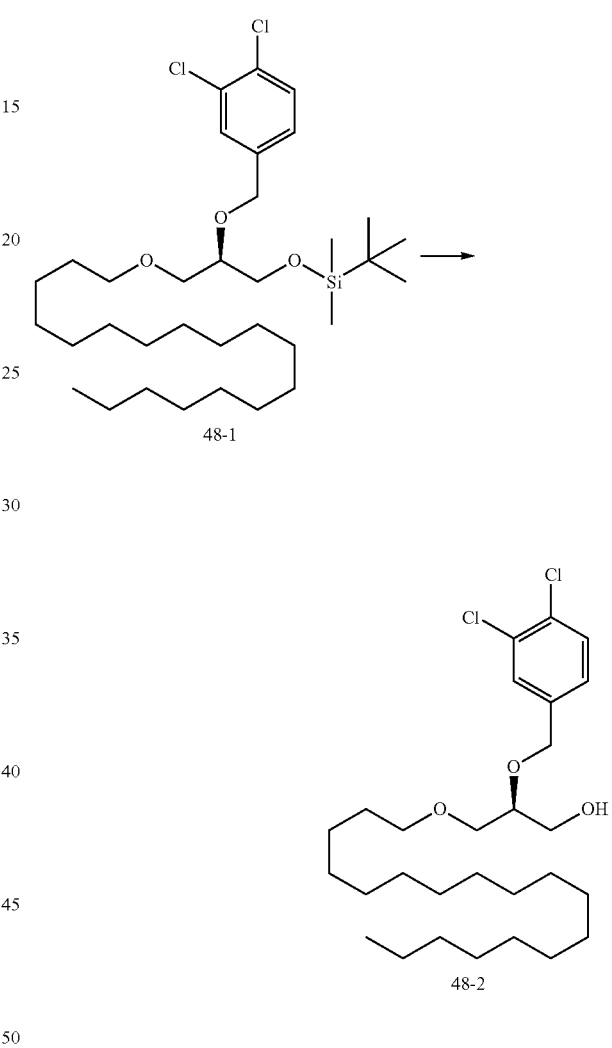

Tetrabutylammonium fluoride (1.0 M in tetrahydrofuran, 0.63 mL, 0.63 mmol) was added to a stirred solution of Intermediate 48-1 (323 mg, 523 μmol) in tetrahydrofuran (5 mL) at 0° C. After 1 hour, water was added (5 mL), and the mixture was extracted with ethyl acetate (3×20 mL). The combined organic fractions were then washed with brine (25 mL) and dried over magnesium sulfate. Following filtration and concentration, the crude residue was purified by flash column chromatography on silica gel (0 to 50% ethyl acetate in hexanes) to give intermediate 48-2. $^1$H NMR (400 MHz, Chloroform-d) δ 7.49 (d, J=1.9 Hz, 1H), 7.43 (d, J=8.2 Hz, 1H), 7.20 (dd, J=8.2, 2.0 Hz, 1H), 4.66 (q, J=12.3 Hz, 2H), 3.83-3.64 (m, 3H), 3.59 (qd, J=10.0, 5.0 Hz, 2H), 3.46 (td, J=6.7, 1.9 Hz, 2H), 2.11 (t, J=6.0 Hz, 1H), 1.65-1.55 (m, 2H), 1.28 (s, 30H), 0.90 (t, J=6.7 Hz, 3H).

213

Intermediate 48-3: ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl (2-chlorophenyl) ((R)-2-((3,4-dichlorobenzyl)oxy)-3-(octadecyloxy)propyl) phosphate

214

Intermediate 48-4: ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl ((R)-2-((3,4-dichlorobenzyl)oxy)-3-(octadecyloxy)propyl) hydrogen phosphate

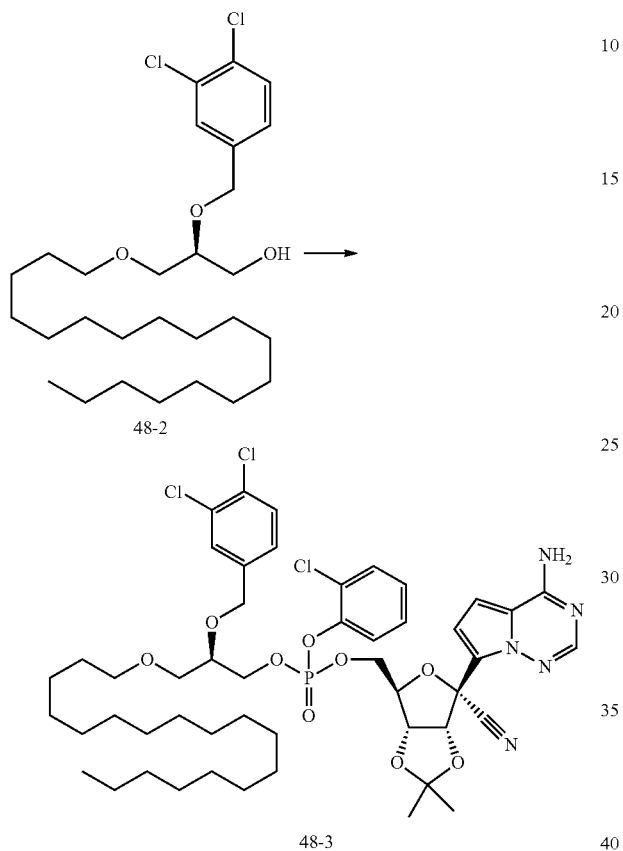

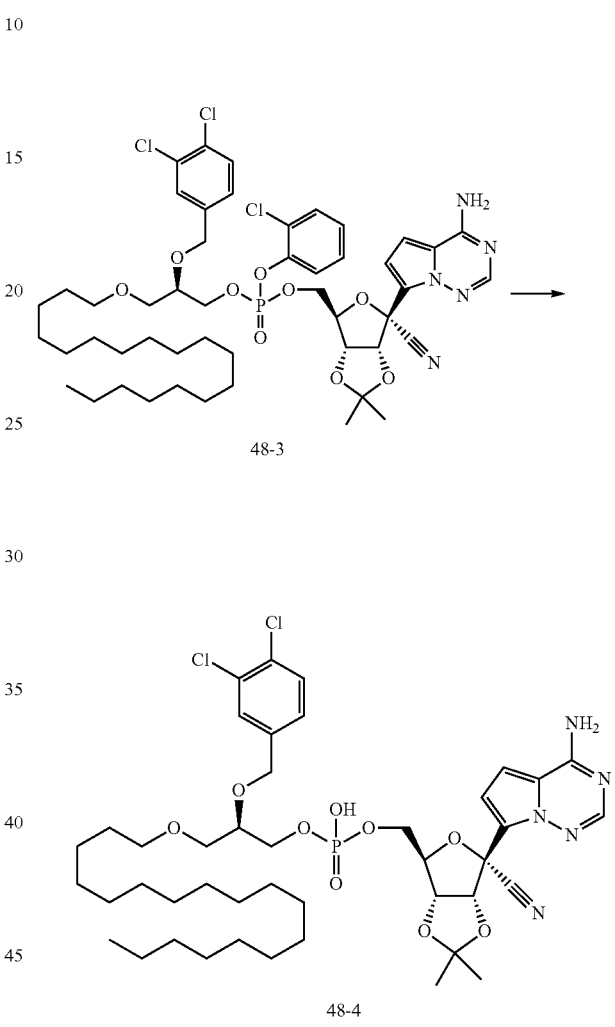

2-Chlorophenyl phosphorodichloridate (64.6 μL, 392 μmol) was added via syringe to a vigorously stirred mixture of 1,2,4-triazole (54.3 mg, 786 μmol), triethylamine (110 μL, 786 μmol), and tetrahydrofuran (0.6 mL) at room temperature. After 40 min, intermediate 1-3 (97.5 mg, 294 μmol), tetrahydrofuran (0.5 mL), and 1-methylimidazole (31.3 μL, 313 μmol) were added sequentially. After 60 min, a solution of intermediate 48-2 (148 mg, 294 μmol) in tetrahydrofuran (0.7 mL) was added via cannula. 1-Methylimidazole (20 μL, 392 μmol) were added. After 15 h, saturated aqueous sodium bicarbonate solution (10 mL), diethyl ether (40 mL), and ethyl acetate (20 mL) were added sequentially. The organic layer was washed with water (30 mL), was dried over anhydrous magnesium sulfate, was filtered, and was concentrated under reduced pressure. The residue was purified by flash column chromatography on silica gel (0 to 10% methanol in dichloromethane) to give intermediate 48-3. $^1$H NMR (400 MHz, Chloroform-d) δ 8.01 (d, J=1.6 Hz, 1H), 7.45-7.34 (m, 4H), 7.21-7.06 (m, 3H), 7.01 (t, J=4.6 Hz, 1H), 6.61 (dd, J=10.3, 4.7 Hz, 1H), 5.62 (s, 2H), 5.44 (dd, J=17.1, 6.8 Hz, 1H), 4.99 (ddd, J=9.2, 6.8, 4.0 Hz, 1H), 4.69-4.19 (m, 7H), 3.82-3.73 (m, 1H), 3.53-3.46 (m, 2H), 3.45-3.37 (m, 2H), 1.91-1.38 (m, 8H), 1.27 (d, J=2.7 Hz, 30H), 0.90 (t, J=6.7 Hz, 3H).

Sodium hydroxide (0.5 N, 715 μL, 357 μmol) was added to a solution of 48-3 (100 mg, 99.3 μmol) in tetrahydrofuran (4 mL), and the mixture was heated to 50° C. After 3 hours, concentrated hydrochloric acid was added (30 μL, 357 μmol). The residue was then concentrated and purified by flash column chromatography on silica gel (0 to 30% methanol in dichloromethane) to give intermediate 48-4. $^1$H NMR (400 MHz, Methanol-d$_4$) δ 7.88 (s, 1H), 7.50 (d, J=2.0 Hz, 1H), 7.41 (d, J=8.3 Hz, 1H), 7.24 (dd, J=8.2, 1.9 Hz, 1H), 6.93 (d, J=4.6 Hz, 1H), 6.88 (d, J=4.6 Hz, 1H), 5.40 (d, J=6.4 Hz, 1H), 5.03 (dd, J=6.5, 3.2 Hz, 1H), 4.65-4.50 (m, 3H), 4.06 (d, J=5.7 Hz, 2H), 3.95-3.84 (m, 2H), 3.78-3.66 (m, 1H), 3.56-3.34 (m, 4H), 1.72 (s, 3H), 1.60-1.47 (m, 2H), 1.42 (s, 3H), 1.38-1.12 (m, 30H), 1.02-0.84 (m, 3H).

Example 48: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((3,4-dichlorobenzyl)oxy)-3-(octadecyloxy)propyl) hydrogen phosphate (48)

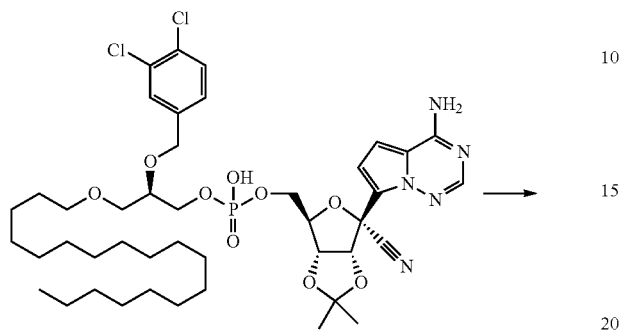

48-4

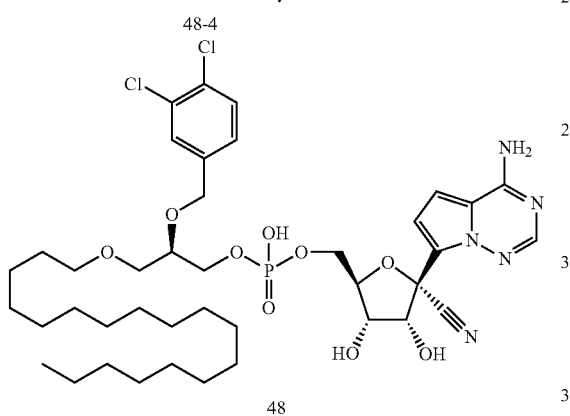

48

Concentrated hydrochloric acid (52.4 µL, 629 µmol) was added to a solution of 48-4 (47 mg, 52.4 µmol) in tetrahydrofuran (0.5 mL). After 3 hours, sodium carbonate (67 mg, 629 µmol), methanol (10 mL), and magnesium sulfate were added sequentially and stirred at room temperature for 10 minutes. Following filtration and concentration, the residue was purified by flash column chromatography on silica gel (0 to 50% methanol in dichloromethane) to give compound 48. $^1$H NMR (400 MHz, Methanol-d4) δ 7.87 (s, 1H), 7.50 (s, 1H), 7.44 (d, J=8.2 Hz, 1H), 7.24 (d, J=9.1 Hz, 1H), 6.96 (d, J=4.5 Hz, 1H), 6.89 (d, J=4.6 Hz, 1H), 4.95-4.75 (m, 1H), 4.60 (s, 2H), 4.39-4.33 (m, 1H), 4.20 (t, J=5.8 Hz, 2H), 4.14-4.08 (m, 1H), 4.05-3.86 (m, 2H), 3.76-3.68 (m, 1H), 3.52-3.25 (m, 4H), 1.57-1.50 (m, 2H), 1.39-1.25 (m, 30H), 0.92 (t, J=6.7 Hz, 3H).

Intermediate 49-1: (R)-tert-butyl(2-((3-chloro-4-methoxybenzyl)oxy)-3-(octadecyloxy) propoxy) dimethylsilane

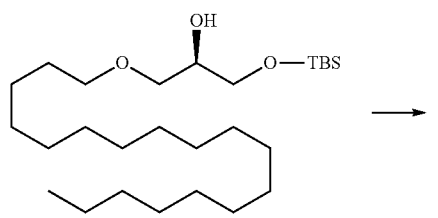

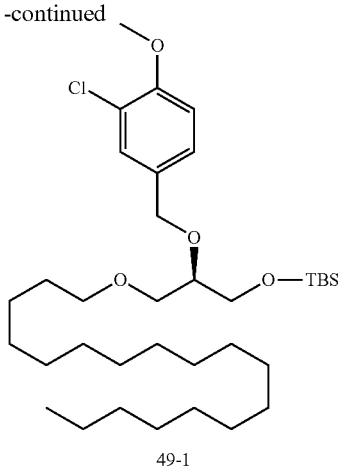

49-1

Intermediate 49-1 was prepared in a manner similar to intermediate 2-1, using 4-(bromomethyl)-2-chloro-1-methoxy-benzene instead of 4-(bromomethyl)-1,1-biphenyl. LCMS: 635.5 [M+Na]$^+$.

Intermediate 49-2: (S)-2-((3-chloro-4-methoxybenzyl)oxy)-3-(octadecyloxy)propan-1-ol

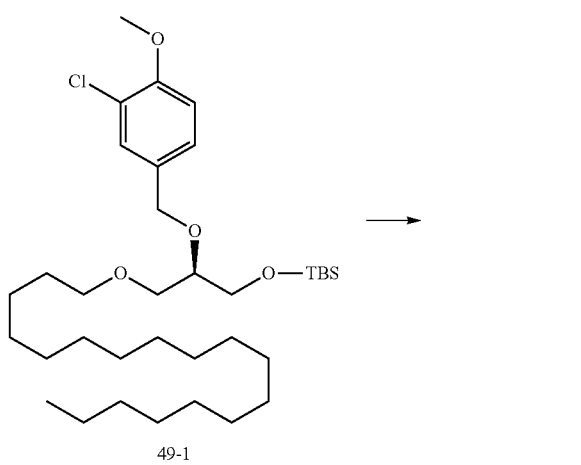

49-1

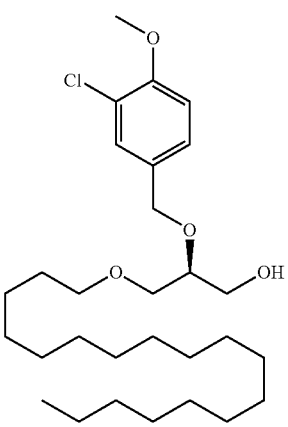

49-2

Intermediate 49-2 was prepared in a manner similar to intermediate 18-3, using 49-1 instead of intermediate 18-2. LCMS: 522.1 [M+Na]+.

Intermediate 49-3: ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl ((R)-2-((3-chloro-4-methoxybenzyl)oxy)-3-(octadecyloxy)propyl) (2-chlorophenyl) phosphate

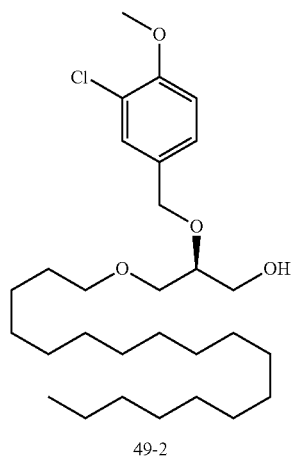

49-2

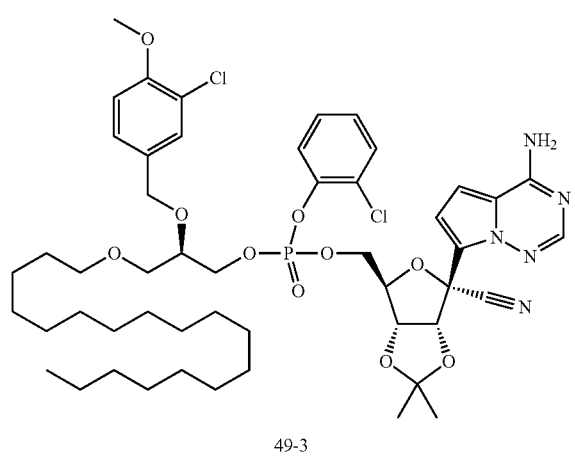

49-3

Intermediate 49-3 was prepared in a manner similar to 23-2, using 49-2 instead of 23-1.
LCMS: 1024.5 [M+Na]+.

Example 49: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((3-chloro-4-methoxybenzyl)oxy)-3-(octadecyloxy)propyl) hydrogen phosphate (49)

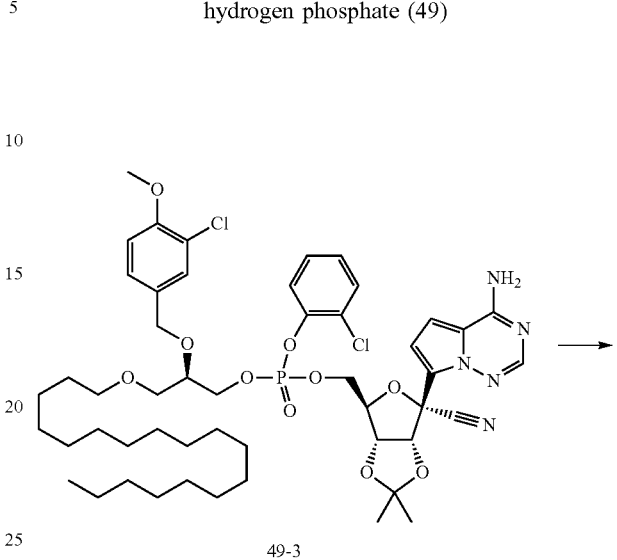

49-3

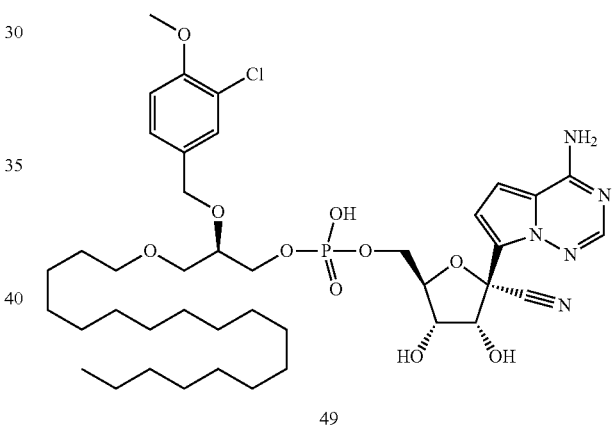

49

Tetrabutylammonium fluoride (1.0 M in tetrahydrofuran, 25 μL, 25 μmol) was added via syringe to a vigorously stirred mixture of intermediate 49-3, pyridine (3 μL, 40 μmol), water (3 L, 200 μmol), and tetrahydrofuran (100 μL). After 4 h, another 25 μL (25 μmol) of tetrabutylammonium fluoride was added via syringe. After 16 h, chlorotrimethylsilane (6 μL, 50 mol) and concentrated hydrochloric acid (200 μL, 2.40 mmol) were added sequentially. The resulting mixture was purified by reverse phase preparative HPLC (0.1% trifluoracetic acid in methanol/water) to yield compound 49. $^1$H NMR (400 MHz, Methanol-d4) δ 7.87 (s, 1H), 7.34 (d, J=2.2 Hz, 1H), 7.22 (d, J=7.3 Hz, 1H), 7.00 (d, J=4.5 Hz, 1H), 6.98 (s, 1H), 6.88 (d, J=4.6 Hz, 1H), 5.19 (s, 1H), 4.59 (d, J=4.7 Hz, 2H), 4.56 (s, 1H), 4.51 (s, 1H), 4.48 (s, 1H), 4.35 (s, 2H), 4.26 (t, J=5.4 Hz, 1H), 4.08 (s, 1H), 3.87 (s, 3H), 3.78-3.63 (m, 2H), 3.59 (s, 1H), 1.53 (s, 2H), 1.30 (d, J=10.7 Hz, 30H), 1.00-0.81 (m, 3H). LCMS: 850.5 [M−H]−.

Intermediate 50-1: (R)-2-(((1-((tert-butyldimethylsilyl)oxy)-3-(octadecyloxy)propan-2-yl)oxy)methyl) benzonitrile

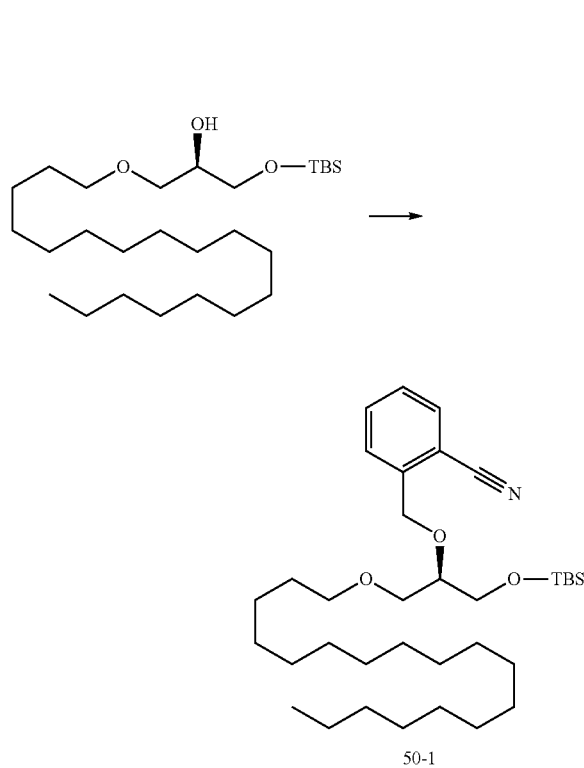

50-1

Intermediate 50-1 was prepared in a manner similar to intermediate 2-1, using 2-(bromomethyl)benzonitrile instead of 4-(bromomethyl)-1,1′-biphenyl. $^1$H NMR (400 MHz, Chloroform-d) δ 7.71 (d, J=7.8 Hz, 1H), 7.65 (dd, J=7.6, 1.2 Hz, 1H), 7.59 (td, J=7.7, 1.3 Hz, 1H), 7.38 (td, J=7.6, 1.2 Hz, 1H), 4.93 (s, 2H), 3.77 (d, J=5.4 Hz, 2H), 3.71 (tt, J=5.7, 4.4 Hz, 1H), 3.60 (qd, J=10.3, 4.9 Hz, 2H), 3.46 (td, J=6.6, 1.6 Hz, 2H), 1.58 (q, J=7.1 Hz, 2H), 1.27 (s, 30H), 0.91 (d, J=6.6 Hz, 12H), 0.09 (s, 6H).

Intermediate 50-2: (S)-2-(((1-hydroxy-3-(octadecyloxy)propan-2-yl)oxy)methyl) benzonitrile

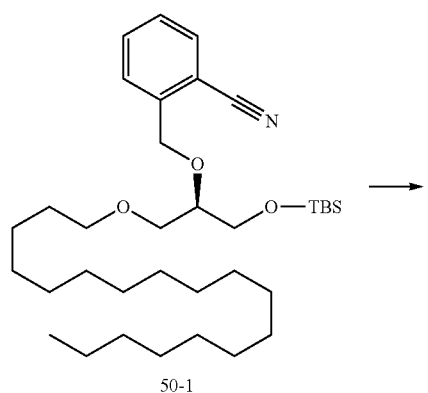

50-1

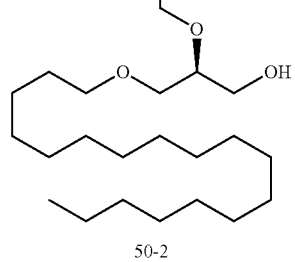

50-2

Intermediate 50-2 was prepared in a manner similar to intermediate 18-3, using 50-1 instead of intermediate 18-2. $^1$H NMR (400 MHz, Chloroform-d) δ 7.72-7.66 (m, 1H), 7.65-7.57 (m, 2H), 7.42 (ddd, J=7.7, 6.0, 2.8 Hz, 1H), 4.91 (d, J=12.2 Hz, 1H), 4.86 (d, J=12.2 Hz, 1H), 3.90-3.81 (m, 1H), 3.81-3.72 (m, 2H), 3.71-3.58 (m, 2H), 3.48 (td, J=6.6, 1.1 Hz, 2H), 1.67-1.49 (m, 2H), 1.28 (s, 30H), 0.90 (t, J=6.7 Hz, 3H).

Intermediate 50-3: ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl (2-chlorophenyl) ((R)-2-((2-cyanobenzyl)oxy)-3-(octadecyloxy)propyl) phosphate

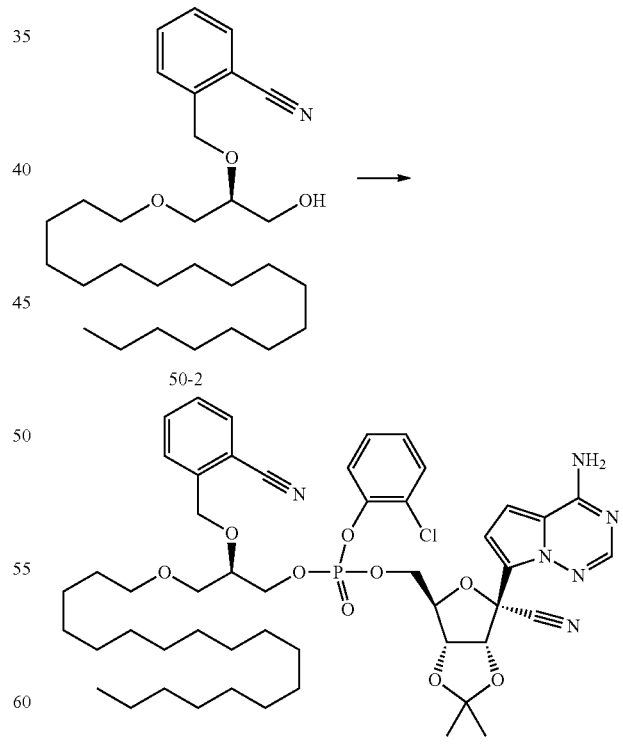

50-3

Intermediate 50-3 was prepared in a manner similar to 23-2, using 50-2 instead of 23-1.
LCMS: 963.3.

Example 50: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((2-cyanobenzyl)oxy)-3-(octadecyloxy)propyl) hydrogen phosphate (50)

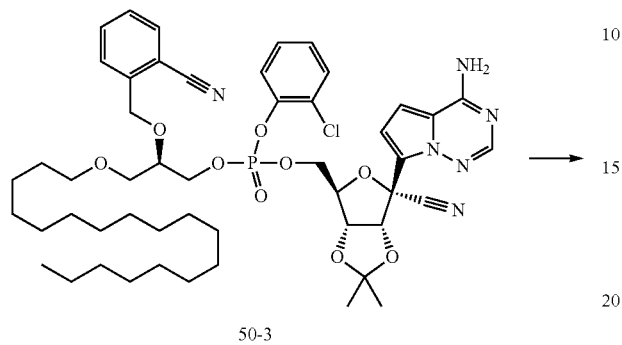

50-3

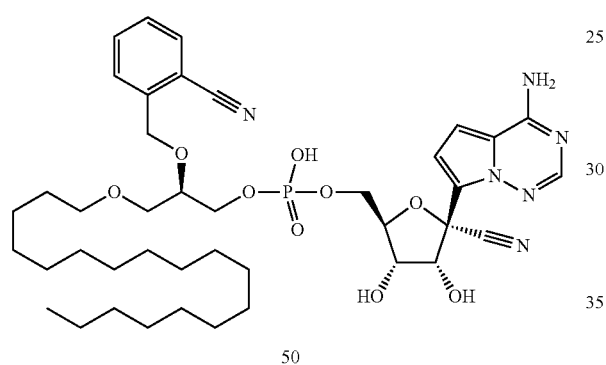

50

Compound 50 was prepared in a manner similar to 49, using intermediate 50-3 instead of 49-3. ¹H NMR (400 MHz, Methanol-d4) δ 8.06 (s, 1H), 7.69 (d, J=8.2 Hz, 2H), 7.63 (t, J=7.7 Hz, 1H), 7.48-7.38 (m, 1H), 7.37-7.26 (m, 1H), 7.20 (d, J=4.8 Hz, 1H), 4.78 (d, J=5.1 Hz, 2H), 4.64 (d, J=11.5 Hz, 1H), 4.35 (s, 2H), 4.26 (t, J=5.4 Hz, 1H), 4.23-4.14 (m, 1H), 4.14-4.06 (m, 1H), 3.98 (qt, J=11.1, 5.6 Hz, 2H), 3.83 (t, J=5.1 Hz, 1H), 3.58 (qd, J=10.6, 5.1 Hz, 2H), 3.45 (td, J=6.5, 2.4 Hz, 1H), 1.54 (t, J=7.0 Hz, 2H), 1.29 (d, J=7.9 Hz, 30H), 0.92 (t, J=6.5 Hz, 3H). LCMS: 813.2.

Intermediate 51-1: (R)-2-(((1-((tert-butyldimethylsilyl)oxy)-3-(octadecyloxy)propan-2-yl)oxy)methyl)-4-fluorobenzonitrile

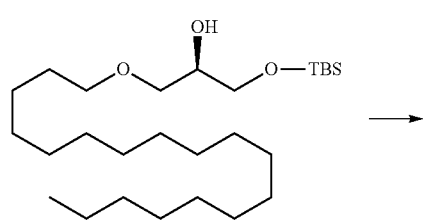

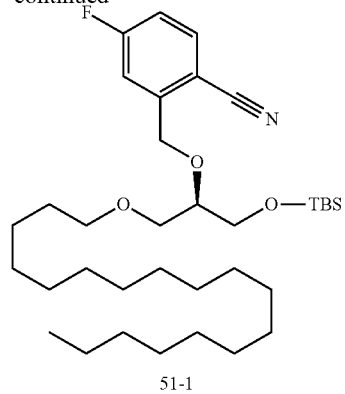

51-1

Intermediate 51-1 was prepared in a manner similar to intermediate 2-1, using 2-(bromomethyl)-4-fluoro-benzonitrile instead of 4-(bromomethyl)-1,1'-biphenyl. ¹H NMR (400 MHz, Chloroform-d) δ 7.64 (dd, J=8.6, 5.3 Hz, 1H), 7.52 (dd, J=9.5, 2.6 Hz, 1H), 7.06 (td, J=8.2, 2.6 Hz, 1H), 4.94 (s, 2H), 3.77 (d, J=4.9 Hz, 2H), 3.72 (tt, J=6.2, 4.5 Hz, 1H), 3.63-3.54 (m, 2H), 3.47 (tt, J=5.6, 1.9 Hz, 2H), 1.65-1.52 (m, 2H), 1.40-1.19 (m, 30H), 0.96-0.84 (m, 12H), 0.09 (s, 6H).

Intermediate 51-2: (S)-4-fluoro-2-(((1-hydroxy-3-(octadecyloxy)propan-2-yl)oxy)methyl) benzonitrile

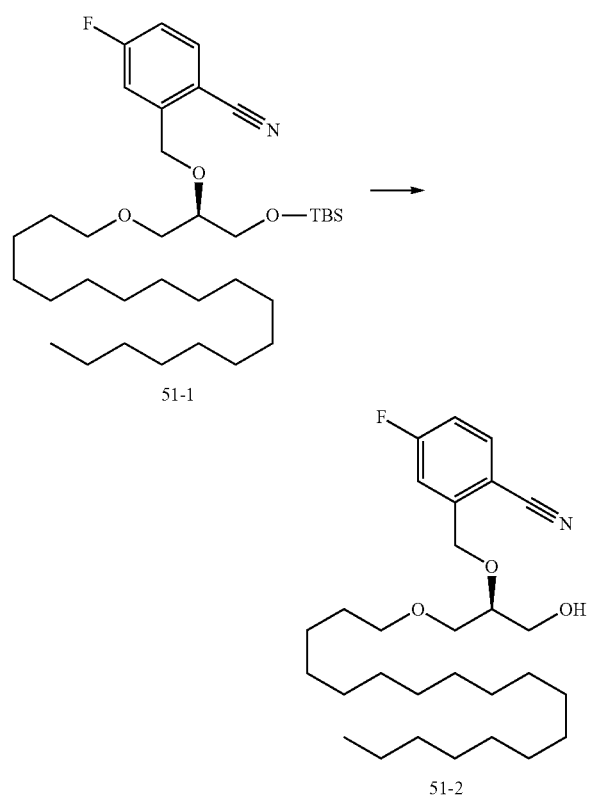

51-1

51-2

Intermediate 51-2 was prepared in a manner similar to intermediate 18-3, using 51-1 instead of intermediate 18-2. ¹H NMR (400 MHz, Chloroform-d) δ 7.69 (dd, J=8.6, 5.3

Hz, 1H), 7.39 (dd, J=9.2, 2.6 Hz, 1H), 7.11 (td, J=8.2, 2.6 Hz, 1H), 4.90 (d, J=3.4 Hz, 2H), 3.85 (d, J=9.0 Hz, 1H), 3.81-3.72 (m, 2H), 3.70-3.59 (m, 2H), 3.48 (td, J=6.6, 1.5 Hz, 2H), 2.22 (s, 1H), 1.58 (d, J=14.8 Hz, 2H), 1.28 (s, 30H), 0.94-0.86 (m, 3H).

Example 51: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((2-cyano-5-fluorobenzyl)oxy)-3-(octadecyloxy)propyl) hydrogen phosphate (51)

J=9.0 Hz, 1H), 7.19 (d, J=25.2 Hz, 1H), 7.00 (s, 1H), 6.90 (m, 1H), 4.36 (s, 2H), 4.28 (s, 2H), 4.14 (s, 1H), 3.89 (s, 2H), 3.78 (s, 1H), 3.71 (s, 4H), 3.61 (d, J=10.2 Hz, 2H), 1.56 (m, 2H), 1.30 (s, 30H), 0.91 (m, 3H). LCMS: 829.5 [M−H]⁻.

Example 52: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((2,3-dihydro-1H-inden-5-yl)methoxy)-3-(octadecyloxy)propyl) hydrogen phosphate (52)

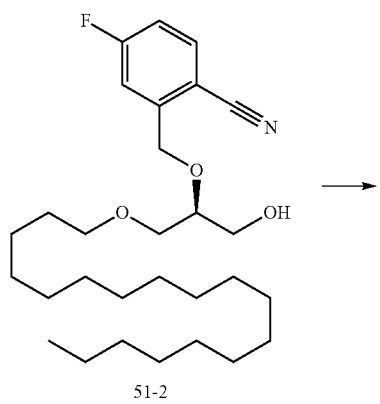

51-2

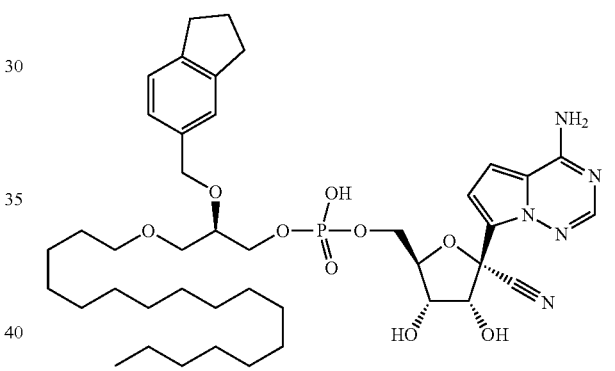

52

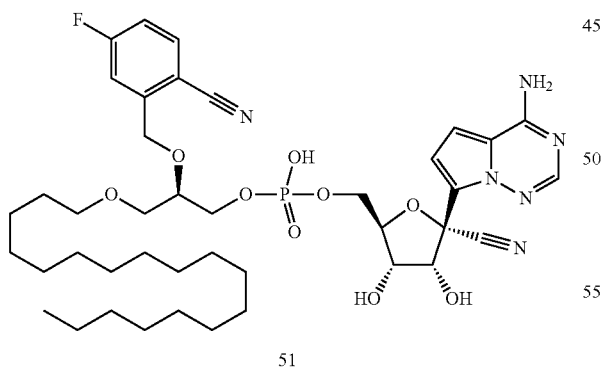

51

Compound 51 was prepared in a manner similar to compound 19, using 51-2 instead of 19-2. ¹H NMR (400 MHz, Methanol-d4) δ 7.87 (s, 1H), 7.73 (s, 1H), 7.48 (d, Compound 52 was prepared in a manner similar to compound 19, using 5-(bromomethyl)-2,3-dihydro-1H-indene instead of 1-(bromomethyl)-3-fluoro-5-(trifluoromethyl)benzene. ¹H NMR (400 MHz, Methanol-d4) δ 7.87 (s, 1H), 7.18 (s, 1H), 7.12-7.04 (m, 2H), 7.00 (d, J=4.6 Hz, 1H), 6.89 (d, J=4.6 Hz, 1H), 4.80 (d, J=5.3 Hz, 2H), 4.63-4.50 (m, 2H), 4.41-4.31 (m, 2H), 4.26 (t, J=5.3 Hz, 1H), 4.17-4.02 (m, 2H), 3.92-3.83 (m, 2H), 3.76-3.66 (m, 1H), 3.42-3.36 (m, 2H), 2.86 (t, J=7.4 Hz, 4H), 2.13-1.96 (m, 2H), 1.52 (t, J=6.8 Hz, 2H), 1.38-1.24 (m, 30H), 0.92 (t, J=6.7 Hz, 3H). LCMS: 828.2.

225

Intermediate 53-1: (R)-4-(((1-((tert-Butyldimethylsilyl)oxy)-3-(octadecyloxy)propan-2-yl)oxy)methyl)-3-fluorobenzonitrile

226

Intermediate 53-2: (S)-3-fluoro-4-(((1-hydroxy-3-(octadecyloxy)propan-2-yl)oxy)methyl) benzonitrile

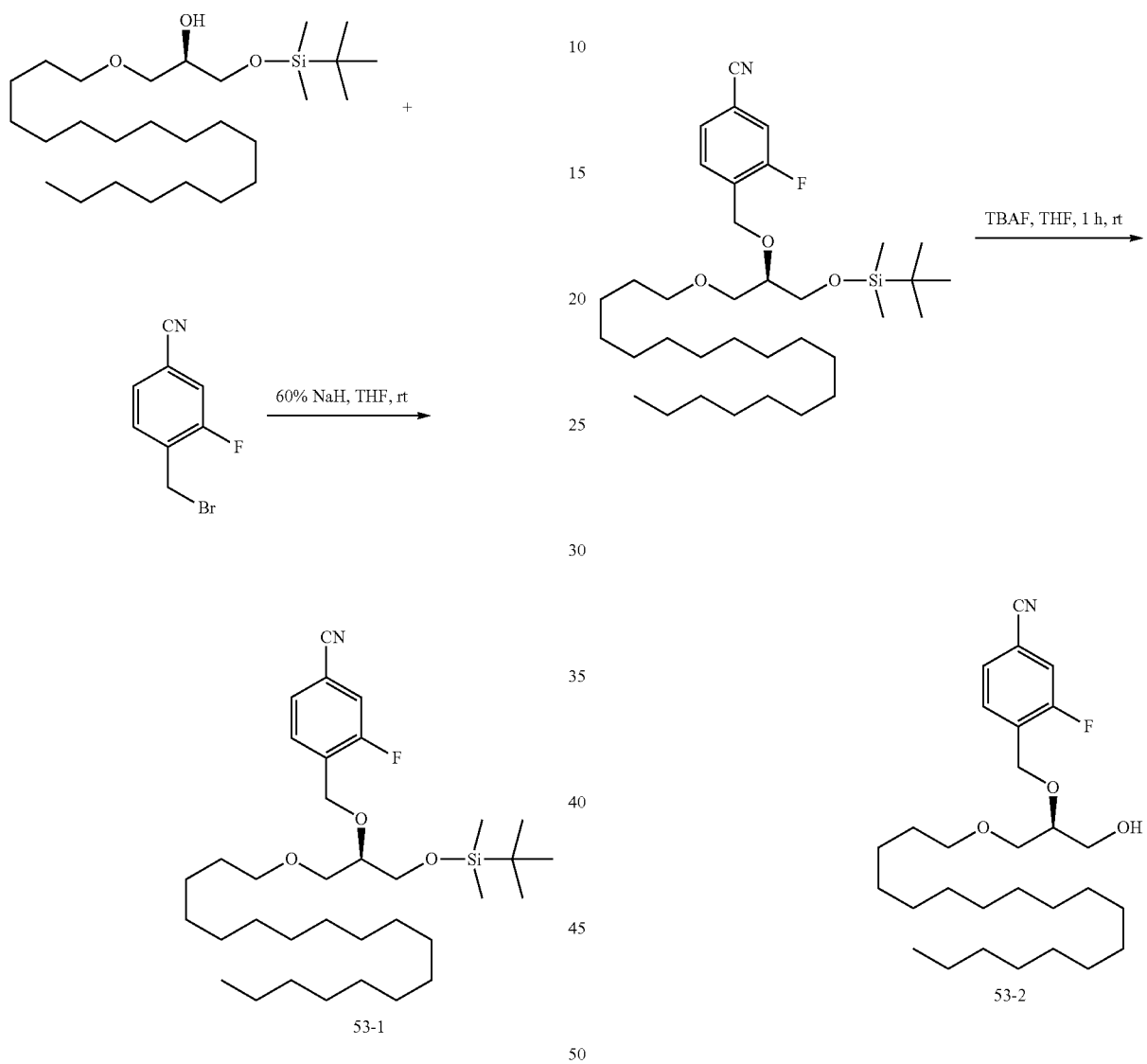

NaH (60% oil dispersion, 88 mg, 2.29 mmol, 3.5 eq) was suspended in THF (6 ml) and cooled to 0° C. A solution of 1-O-Octadecyl-3-O-tert-butyldimethylsilyl-sn-glycerol (300 mg, 0.654 mmol, 1 eq) in THF (2.5 ml) was added over 30 seconds. After 30 min at 0° C. a solution of alkyl bromide (560 mg, 2.62 mmol) in THF (2.5 ml) was added. The mixture was stirred for 16 h at room temperature. The reaction was quenched with water (15 mL). The mixture was extracted with EtOAc. The combined organic phase was dried over sodium sulfate and the solvent was removed under reduced pressure. The residue was purified by flash chromatography (0-30% EtOAc in hexanes), giving the product.

To a solution of silyl protected compound (342 mg, 0.578 mmol) in THF (3.3 mL) at 0° C., 1M TBAF in THF (1 mL, 1 mmol) was added and stirred for 1 h. It was diluted with water (3 mL) and extracted with EtOAc (2×10 mL). The combined organic layers were washed with water (2×5 mL), brine dried ($Na_2SO_4$), evaporated and purified the residue by column chromatography silica gel, 0-60% ethyl acetate in hexanes to give the product. $^1$H NMR (400 MHz, Chloroform-d) δ 7.66 (t, 1H), 7.47 (dd, 1H), 7.34 (dd, 1H), 4.92-4.73 (m, 2H), 3.90-3.66 (m, 3H), 3.61 (m, 2H), 3.45 (m, 2H), 2.21 (s, 1H), 1.57 (m, 2H), 1.26 (s, 26H), 0.94-0.81 (m, 3H).

Intermediate 53-3: ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl (2-chlorophenyl) ((R)-2-((4-cyano-2-fluorobenzyl)oxy)-3-(octadecyloxy)propyl) phosphate

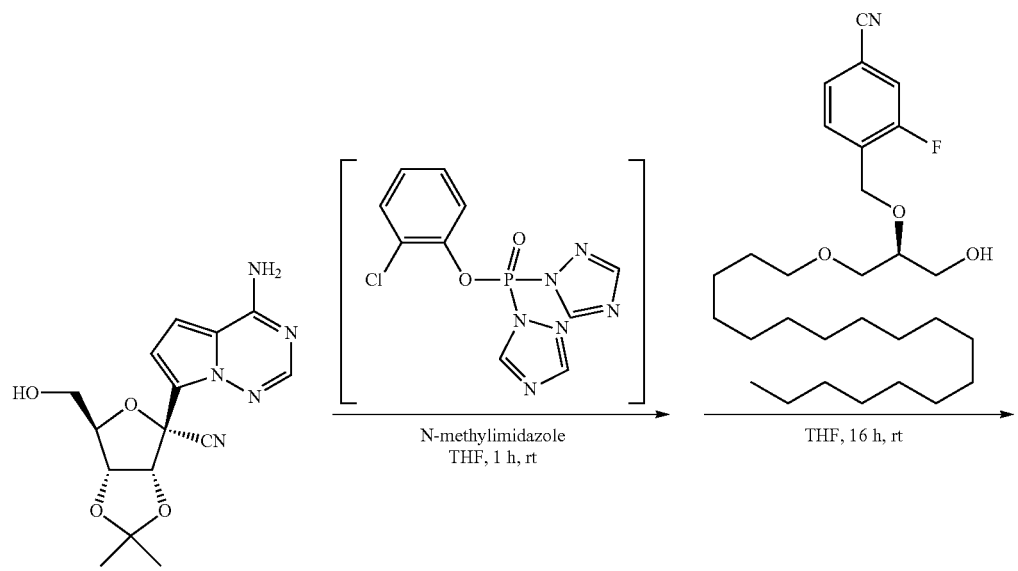

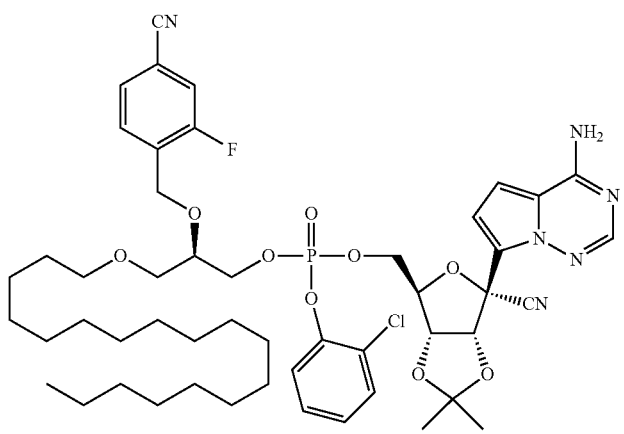

53-3

To a solution of 1,2,4-trizole (43 mg, 0.62 mmol) and triethylamine (87 uL, 0.62 mmol) in anhydrous THF (0.4 mL) was added a solution of 2-chlorophenyl dichlorophosphate (76 mg, 0.31 mmol) in THF (0.4 mL). The mixture was stirred for 30 min. and then filtered. To the filtrate were added sequentially, additional THF (1.2 mL), the nucleoside (77 mg, 0.232 mmol), and 1-methylimidazole (26 mg, 0.31 mmol). After 1 h, (S)-3-fluoro-4-(((1-hydroxy-3-(octadecyloxy)propan-2-yl)oxy)methyl)benzonitrile (107 mg, 0.232 mmol) was added to the mixture and stirred overnight at room temperature. The solvent was removed and the residue was purified by flash chromatography on silica gel (0-15% MeOH in CH$_2$Cl$_2$) to afford a compound.

Example 53: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((4-cyano-2-fluorobenzyl)oxy)-3-(octadecyloxy)propyl) hydrogen phosphate: (53)

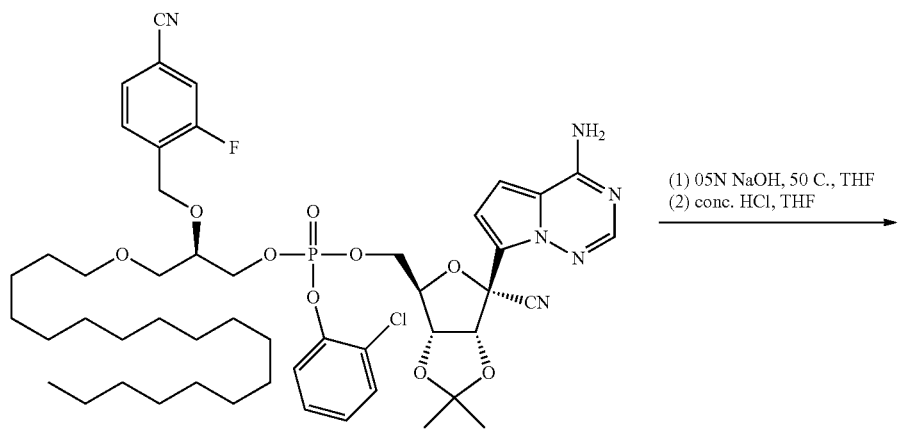

The above Intermediate 53-3 (250 mg, 0.255 mmol) was dissolved in THF (5 mL) and 0.5 N NaOH (1.9 mL) was added at 0° C. The mixture was stirred at 50° C. for 4 h. The reaction progress was monitored by TLC. After nearly compete consumption of intermediate, the mixture was neutralized with 4 N HCl at 0° C. The mixture was diluted with methanol and $Na_2SO_4$ was added. The mixture was filtered and the filtrated was evaporated to give a residue.

The residue was dissolved in THF (1.5 mL). The resulting solution was cooled in an ice bath. Concentrated aqueous HCl (0.3 mL) was added. The cold bath was removed the reaction was stirred vigorously for 3 h. The mixture was neutralized with $Na_2CO_3$, diluted with MeOH, and filtered. The filtrate was evaporated to give a residue which was purified by silica gel column chromatography (0-40% MeOH in DCM) to give the product. $^1$H NMR (400 MHz, Methanol-d4) δ 7.91 (s, 1H), 7.74 (t, J=7.5 Hz, 1H), 7.54-7.39 (m, 2H), 7.04 (d, J=4.7 Hz, 1H), 6.98 (d, J=4.6 Hz, 1H), 4.85-4.72 (m, 2H), 4.36 (m, 1H), 4.27 (m, 1H), 4.18 (m, 11H), 4.09 (m, 1H), 3.92 (m, 1H), 3.78 (t, 1H), 3.63-3.35 (m, 4H), 1.51 (m, 2H), 1.28 (d, 30H), 1.01-0.84 (m, 3H). $^{31}$P NMR (162 MHz, Methanol-d4) δ 0.28. MS: 831.22 (M+1).

Intermediate 54-1: (R)-4-(((1-((tert-butyldimethylsilyl)oxy)-3-(octadecyloxy)propan-2-yl)oxy)methyl)-2-methoxybenzonitrile

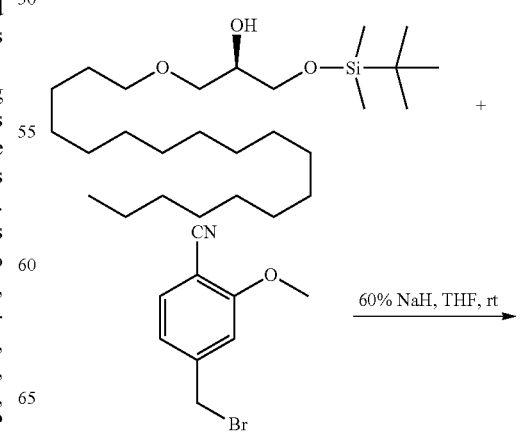

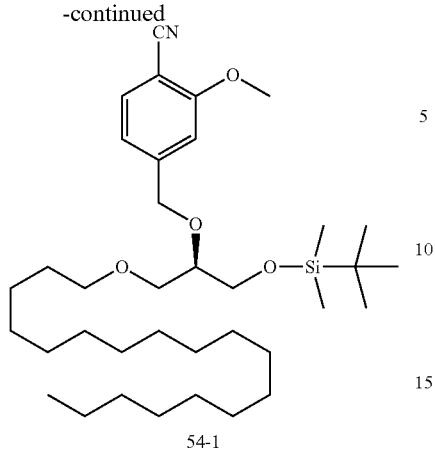

54-1

Intermediate 54-1 was synthesized in a manner similar to 53-1.

Intermediate 54-2: (S)-4-(((1-Hydroxy-3-(octadecyloxy)propan-2-yl)oxy)methyl)-2-methoxybenzonitrile

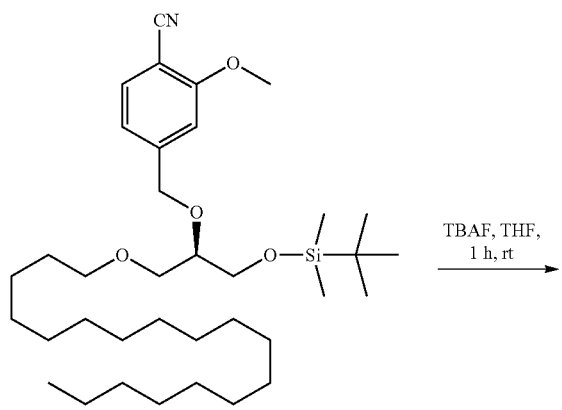

TBAF, THF, 1 h, rt

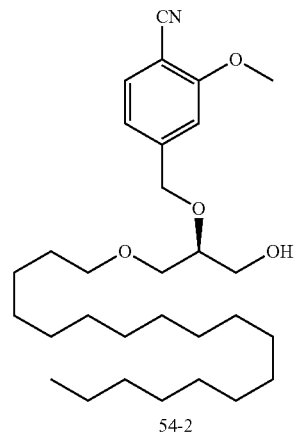

54-2

Intermediate 54-2 was synthesized in a manner similar to 53-2. $^1$H NMR (400 MHz, Chloroform-d) δ 7.50 (d, J=7.9 Hz, 1H), 7.04 (s, 1H), 6.98 (d, J=8.0 Hz, 1H), 4.82-4.63 (m, 2H), 3.94 (s, 3H), 3.83-3.53 (m, 4H), 3.45 (m, 2H), 2.25 (s, 1H), 1.56 (q, J=6.9 Hz, 2H), 1.26 (s, 30H), 0.88 (t, J=6.7 Hz, 3H).

Intermediate 54-3: ((3aR,4R,6R,6aR)-6-(4-Aminopyrrolo[2,1-f][1,2,4]triazin-7-yl)-6-cyano-2,2-dimethyltetrahydrofuro[3,4-d][1,3]dioxol-4-yl)methyl (2-chlorophenyl) ((R)-2-((4-cyano-2-fluorobenzyl)oxy)-3-(octadecyloxy)propyl) phosphate

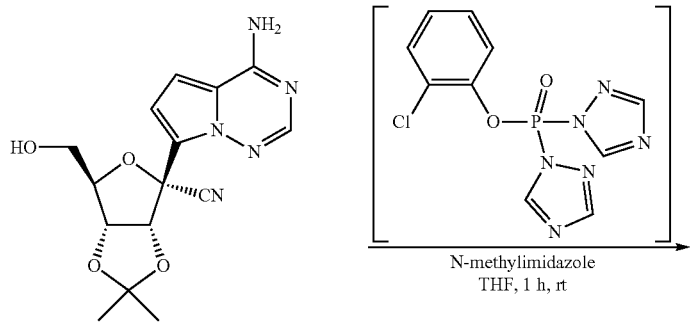

N-methylimidazole
THF, 1 h, rt

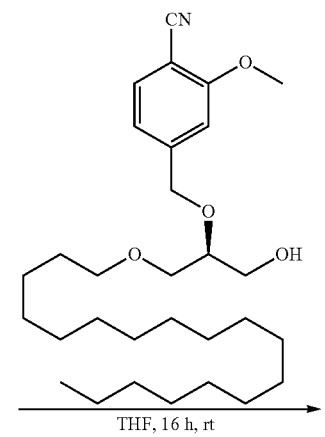

THF, 16 h, rt

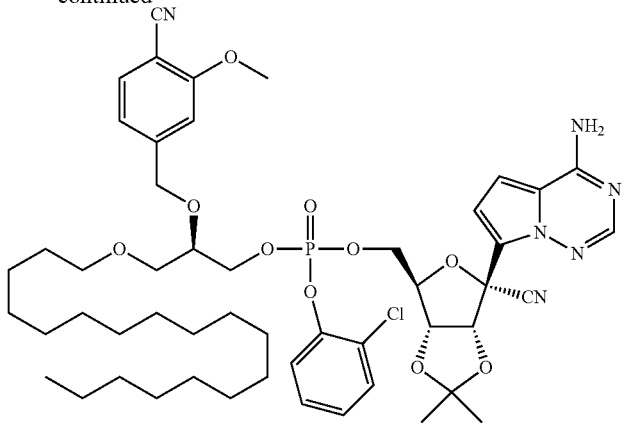

54-3

To a solution of 1,2,4-trizole (43 mg, 0.62 mmol) and triethylamine (87 uL, 0.62 mmol) in anhydrous THF (0.4 mL) was added a solution of 2-chlorophenyl dichlorophosphate (76 mg, 0.31 mmol) in THF (0.4 mL). The mixture was stirred for 30 min. and then filtered. To the filtrate were added sequentially, additional THF (1.2 mL), the nucleoside (77 mg, 0.232 mmol), and 1-methylimidazole (26 mg, 0.31 mmol). After 1 h, (S)-4-(((1-hydroxy-3-(octadecyloxy)propan-2-yl)oxy)methyl)-2-methoxybenzonitrile (115 mg, 0.235 mmol) was added to the mixture and stirred overnight at room temperature. The solvent was removed and the residue was purified by flash chromatography on silica gel (0-15% MeOH in $CH_2Cl_2$) to afford the compound.

Example 54: ((2R,3S,4R,5R)-5-(4-Aminopyrrolo[2,1-f][1,2,4]triazin-7-yl)-5-cyano-3,4-dihydroxytetrahydrofuran-2-yl)methyl ((R)-2-((4-cyano-3-methoxybenzyl)oxy)-3-(octadecyloxy)propyl) hydrogen phosphate (54)

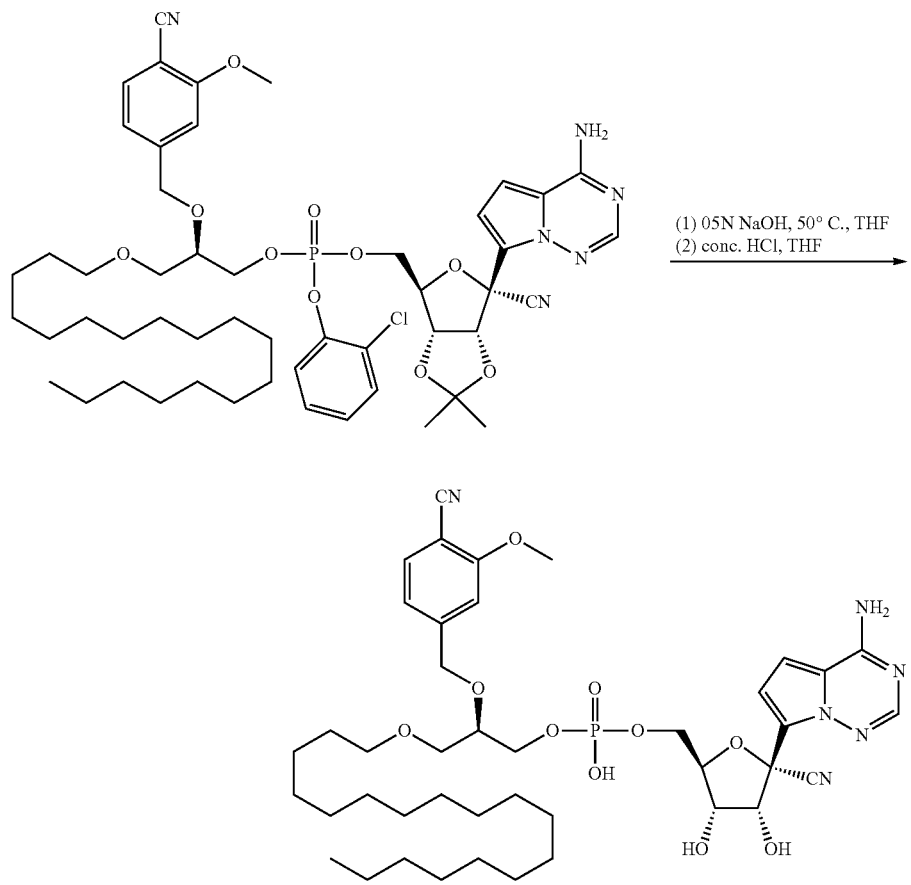

The above intermediate (222 mg, 0.223 mmol) was dissolved in THF (4.5 mL) and 0.5 N NaOH (1.6 mL) was added at 50° C. The mixture was stirred at 50° C. for 3 h. The reaction progress was monitored by TLC. After nearly compete consumption of intermediate, the mixture was neutralized with 4 N HCl at 0° C. The mixture was diluted with methanol and Na$_2$SO$_4$ was added. The mixture was filtered and the filtrated was evaporated to give a residue.

The residue was dissolved in THF (1.5 mL). The resulting solution was cooled in an ice bath. Concentrated aqueous HCl (0.3 mL) was added. The cold bath was removed the reaction was stirred vigorously for 3 h. The mixture was neutralized with Na$_2$CO$_3$, diluted with MeOH, and filtered. The filtrate was evaporated to give a residue which was purified by silica gel column chromatography (0-40% MeOH in DCM) to give the product. $^1$H NMR (400 MHz, DMSO-d6) δ 7.94 (s, 1H), 7.64 (d, J=7.9 Hz, 1H), 7.19 (s, 1H), 7.03 (d, J=7.9 Hz, 1H), 6.93 (d, J=4.6 Hz, 1H), 6.85 (d, 1H), 4.65 (d, 3H), 4.30-4.09 (m, 2H), 4.07-3.96 (m, 2H), 3.91 (d, 4H), 1.43 (d, 2H), 1.22 (d, 30H), 0.86 (t, 3H). $^{31}$P NMR (162 MHz, DMSO-d6) δ −1.11. MS: 843.28 (M+1).

Intermediate 55-1: Preparation of 3-(heptadecyloxy)propan-1-ol

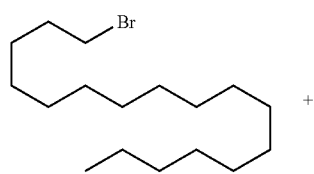

+

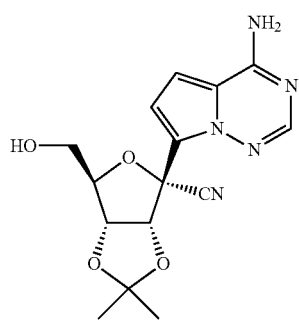

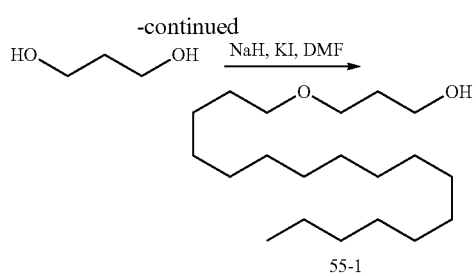

To a solution of 1,3-propanediol (1.03 g, 13.5 mmol) in dry DMF (6 mL) was added NaH (60% oil dispersion; 0.172 g, 4.5 mmol) in installments at 0° C. and the mixture was stirred at room temperature for 10 min. 1-bromoheptadecane (0.958 g, 3 mmol) and KI (498 mg, 3 mmol) were added and the mixture was heated at 95° C. for 4 h. After cooling, the mixture was poured into ice-water and extracted with DCM. The extracts were washed with brine, dried over Na$_2$SO$_4$ and evaporated. The resulting residue was purified by flash column chromatography (silica gel; AcOEt/hexane, 1:2) to provide a product as a solid. $^1$H NMR (400 MHz, Chloroform-d) δ 3.87-3.77 (m, 2H), 3.64 (t, J=5.7 Hz, 2H), 3.45 (t, J=6.6 Hz, 2H), 1.86 (m, 2H), 1.65-1.51 (m, 2H), 1.28 (s, 30H), 0.98-0.85 (m, 3H).

Intermediate 55-2: ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl (2-chlorophenyl) ((R)-2-((4-cyano-2-fluorobenzyl)oxy)-3-(octadecyloxy)propyl) phosphate

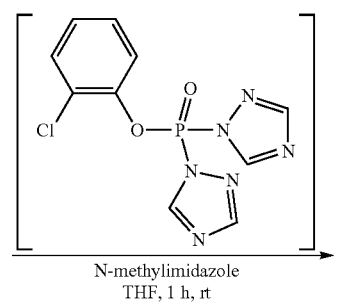

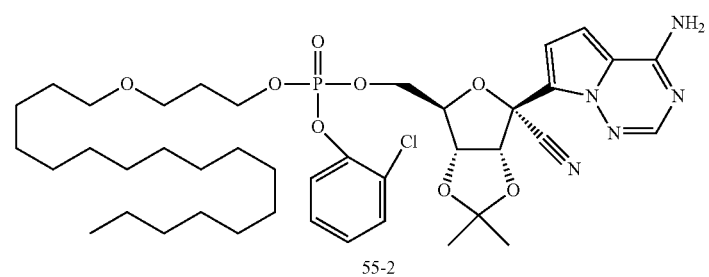

To a solution of 1,2,4-trizole (43 mg, 0.62 mmol) and triethylamine (87 uL, 0.62 mmol) in anhydrous THF (0.4 mL) was added a solution of 2-chlorophenyl dichlorophosphate (76 mg, 0.31 mmol) in THF (0.4 mL). The mixture was stirred for 30 min. and then filtered. To the filtrate were added sequentially, additional THF (1.2 mL), the nucleoside (77 mg, 0.232 mmol), and 1-methylimidazole (26 mg, 0.31 mmol). After 1 h, 3-(heptadecyloxy)propan-1-ol (74 mg, 0.235 mmol) was added to the mixture and stirred overnight at room temperature. The solvent was removed and the residue was purified by flash chromatography on silica gel (0-15% MeOH in $CH_2Cl_2$) to afford a compound.

Example 55: ((2R,3S,4R,5R)-5-(4-aminopyrrolo[2,1-f][1,2,4]triazin-7-yl)-5-cyano-3,4-dihydroxytetrahydrofuran-2-yl)methyl (3-(heptadecyloxy)propyl) hydrogen phosphate (55)

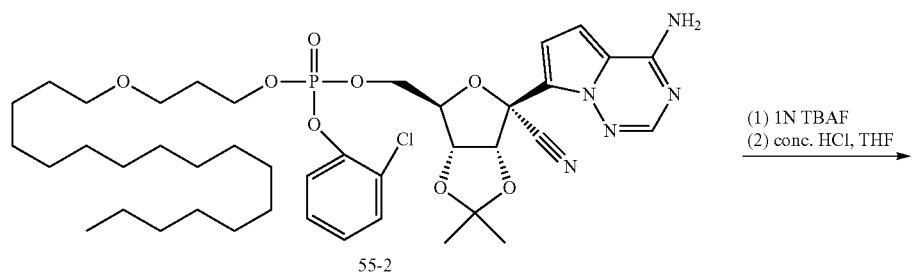

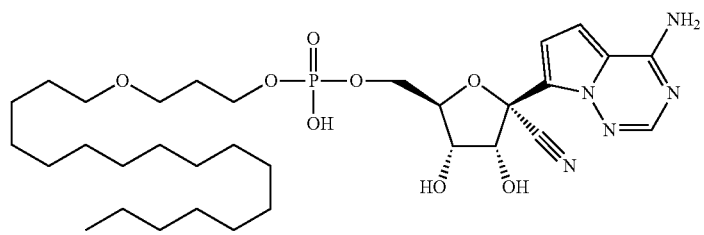

The above intermediate 55-2 (100 mg, 0.122 mmol) was dissolved in THF (1.2 mL) and 1N TBAF (1.5 mL), DMAP (149 mg, 1.22 mmol), and water (45 mg) was added. The reaction mixture was stirred at room temperature for 2 h. To the mixture, TMSCl (0.19 mL, 1.47 mmol), followed by conc. HCl (1.4 mL) were added. The mixture was stirred at room temperature for 2.5 h. Then, added 4-methylmorpholine (1.98 g) and diluted with MeOH. The mixture was filtered and purified by HPLC (60-100% ACN in water with 0.1% TFA) to give the product. $^1$H NMR (400 MHz, Methanol-d4) δ 8.10 (s, 1H), 7.37 (d, J=4.8 Hz, 1H), 7.20 (d, J=4.8 Hz, 1H), 4.77 (d, J=5.2 Hz, 1H), 4.44-4.34 (m, 1H), 4.31-4.19 (m, 2H), 4.14 (m, 1H), 4.00 (m, 2H), 3.51 (t, 2H), 3.42 (m, 2H), 1.88 (m, 2H), 1.55 (m, 2H), 1.40-1.22 (m, 30H), 0.98-0.85 (m, 3H). $^{31}$P NMR (162 MHz, Methanol-d4) δ −0.01. MS 668.24 (M+1).

Intermediate 56-1: 3-decoxypropan-1-ol

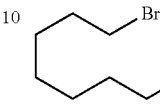

-continued

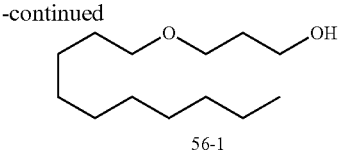

56-1 was synthesized in a manner similar to 55-1 using 1-bromodecane as alkylation agent. $^1$H NMR (400 MHz, DMSO-d6) δ 4.36 (t, J=5.1 Hz, 1H), 3.49-3.35 (m, 4H), 1.63 (p, J=6.4 Hz, 2H), 1.47 (t, J=6.7 Hz, 2H), 1.25 (s, 14H), 0.93-0.79 (m, 3H).

Intermediate 56-2: ((3aR,4R,6R,6aR)-6-(4-Aminopyrrolo[2,1-f][1,2,4]triazin-7-yl)-6-cyano-2,2-dimethyltetrahydrofuro[3,4-d][1,3]dioxol-4-yl)methyl (2-chlorophenyl) (3-(decyloxy)propyl) phosphate

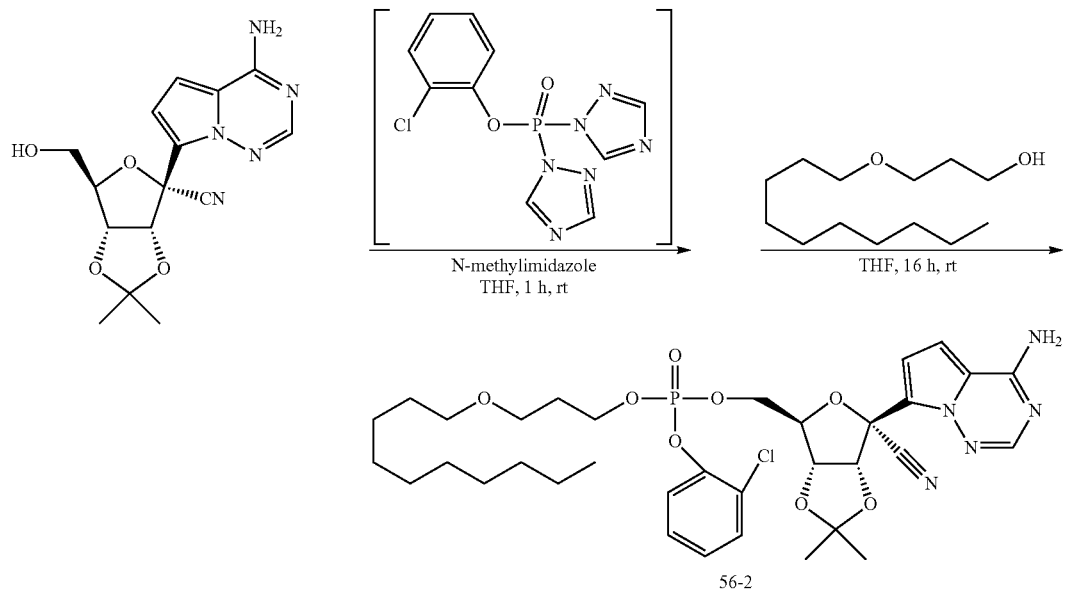

Intermediate 56-2 was synthesized in a manner similar to 55-2 using intermediate 3-decoxypropan-1-ol.

Example 56: ((2R,3S,4R,5R)-5-(4-Aminopyrrolo[2,1-f][1,2,4]triazin-7-yl)-5-cyano-3,4-dihydroxytetrahydrofuran-2-yl)methyl (3-(decyloxy)propyl) hydrogen phosphate (56)

DCM to give a product. MS: 610.20 (M+1). The above product was dissolved in THF (0.5 mL). The resulting solution was cooled in an ice bath. Concentrated aqueous HCl (0.1 mL) was added. The cold bath was removed the reaction was stirred vigorously for 3 h. The mixture was neutralized with Na$_2$CO$_3$, diluted with MeOH, and filtered. The solution was purified by prep-HPLC with Gilson prep HPLC (Gemini column, 40-100% CH$_3$CN in H$_2$O with

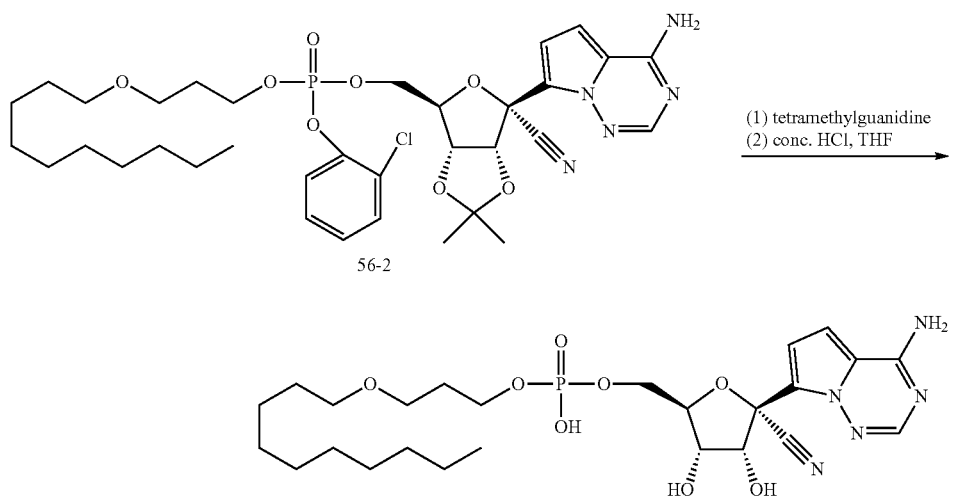

1,1,3,3-Tetramethylguanidine (61 mg, 0.53 mmol) and syn-2-pyridinealdoxime (0.11 g, 0.88 mmol) in THF (1 mL) were added to a solution of the 56-2 (63 mg, 0.088 mmol) in THF (1.8 mL) and stirred at room temperature overnight. The reaction was concentrated in vacuo, the residue was purified by flash chromatography with 0-50% MeOH in 0.1% TFA) go give the product. $^1$H NMR (400 MHz, Methanol-d4) δ 8.07 (s, 1H), 7.32 (d, J=4.8 Hz, 1H), 7.17 (d, J=4.8 Hz, 1H), 4.78 (m, 1H), 4.38 (m, 1H), 4.24 (m, 2H), 4.21-4.08 (m, 1H), 3.98 (m, 2H), 3.51 (m, 2H), 3.41 (m, 2H), 1.87 (m, 2H), 1.54 (t, 2H), 1.30 (d, 14H), 0.91 (t, 3H). $^{31}$P NMR (162 MHz, Methanol-d4) δ 0.18. MS: 570.16 (M+1).

Intermediate 57-1: Preparation 3-dodecoxypropan-1-ol

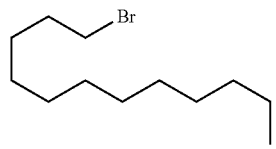

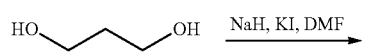

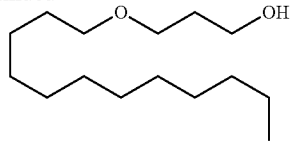

57-1

Intermediate 57-1 was synthesized in a manner similar to 55-1 using 1-bromodecane as alkylation agent. $^1$H NMR (400 MHz, DMSO-d6) δ 4.36 (t, J=5.1 Hz, 1H), 3.48-3.36 (m, 6H), 1.63 (m, 2H), 1.47 (m, 2H), 1.25 (s, 18H), 0.92-0.80 (m, 3H).

Intermediate 57-2: ((3aR,4R,6R,6aR)-6-(4-Aminopyrrolo[2,1-f][1,2,4]triazin-7-yl)-6-cyano-2,2-dimethyltetrahydrofuro[3,4-d][1,3]dioxol-4-yl)methyl (2-chlorophenyl) (3-(dodecyloxy)propyl) phosphate

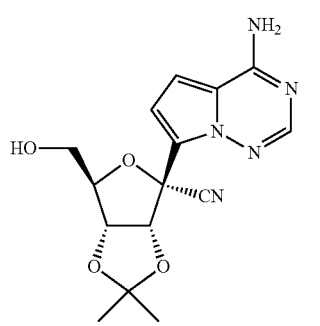 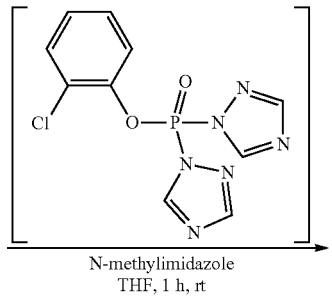 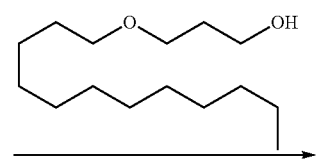

N-methylimidazole
THF, 1 h, rt

THF, 16 h, rt

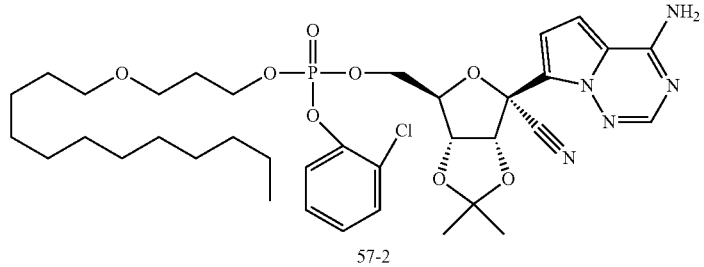

57-2

Intermediate 57-2 was synthesized in a manner similar to 55-2 using intermediate 3-dodecoxypropan-1-ol.

Example 57: ((2R,3S,4R,5R)-5-(4-Aminopyrrolo[2,1-f][1,2,4]triazin-7-yl)-5-cyano-3,4-dihydroxytetrahydrofuran-2-yl)methyl (3-(dodecyloxy)propyl) hydrogen phosphate (57)

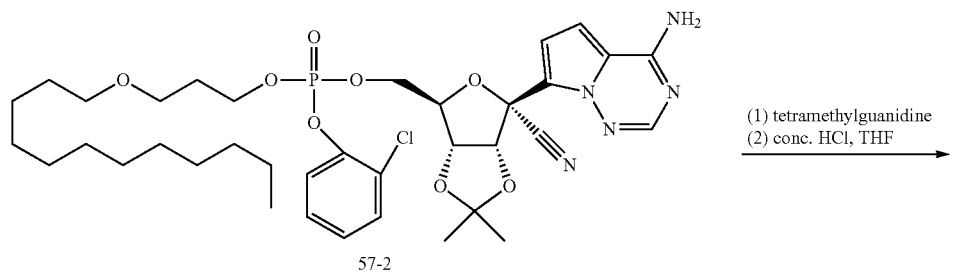

(1) tetramethylguanidine
(2) conc. HCl, THF 57-2

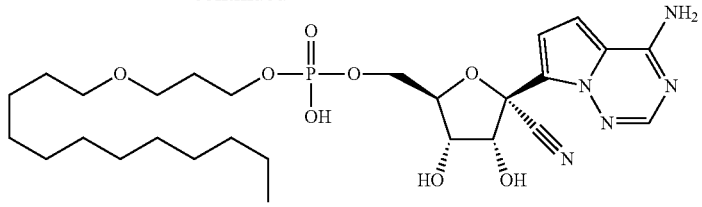

Compound 57 was synthesized in a manner similar to compound 56. ¹H NMR (400 MHz, Methanol-d4) δ 8.07 (s, 1H), 7.33 (d, J=4.8 Hz, 1H), 7.18 (d, J=4.8 Hz, 1H), 4.78 (d, J=5.2 Hz, 1H), 4.38 (dt, J=6.5, 3.4 Hz, 1H), 4.29-4.20 (m, 2H), 4.13 (m, 1H), 3.98 (m, 2H), 3.51 (m, 2H), 3.41 (m, 2H), 1.87 (m, 2H), 1.53 (m, 2H), 1.29 (s, 18H), 0.99-0.84 (m, 3H). ³¹P NMR (162 MHz, Methanol-d4) δ 0.22. MS: 596.18 (M+1).

Intermediate 58-1: Preparation 3-(tetradecyloxy)propan-1-ol

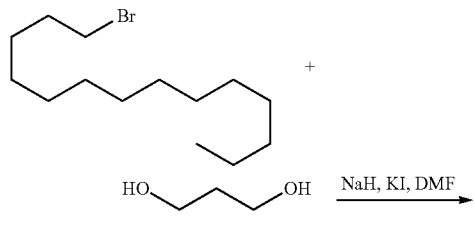

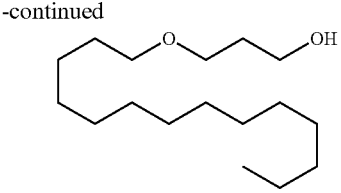

Intermediate 58-1 was synthesized in a manner similar to 55-1 using 1-bromotetradecane as alkylation agent. ¹H NMR (400 MHz, DMSO-d6) δ 4.36 (t, J=5.2 Hz, 1H), 3.49-3.35 (m, 5H), 1.63 (t, J=6.4 Hz, 2H), 1.47 (t, J=6.7 Hz, 2H), 1.25 (s, 22H), 0.94-0.79 (m, 3H).

Intermediate 58-2: ((3aR,4R,6R,6aR)-6-(4-Amino-pyrrolo[2,1-f][1,2,4]triazin-7-yl)-6-cyano-2,2-dimethyltetrahydrofuro[3,4-d][1,3]dioxol-4-yl)methyl (2-chlorophenyl) (3-(tetradecyloxy)propyl) phosphate

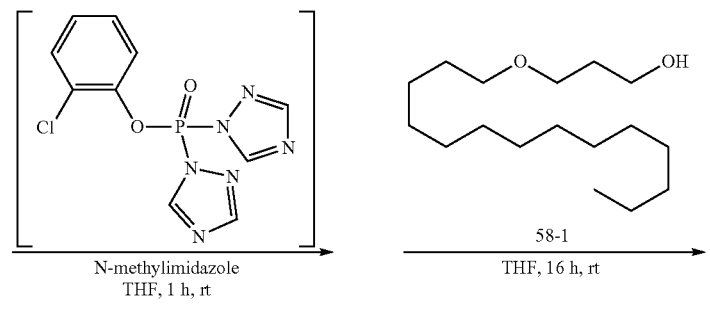

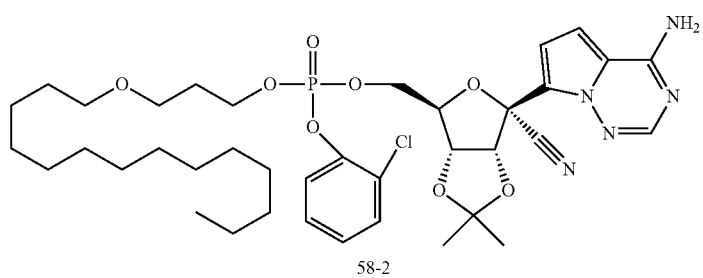

Intermediate 58-2 was synthesized in a manner similar to 55-2 using intermediate 3-(tetradecyloxy)propan-1-ol.

Example 58: ((2R,3S,4R,5R)-5-(4-Aminopyrrolo[2,1-f][1,2,4]triazin-7-yl)-5-cyano-3,4-dihydroxytetrahydrofuran-2-yl)methyl (3-(tetradecyloxy)propyl) hydrogen phosphate (58)

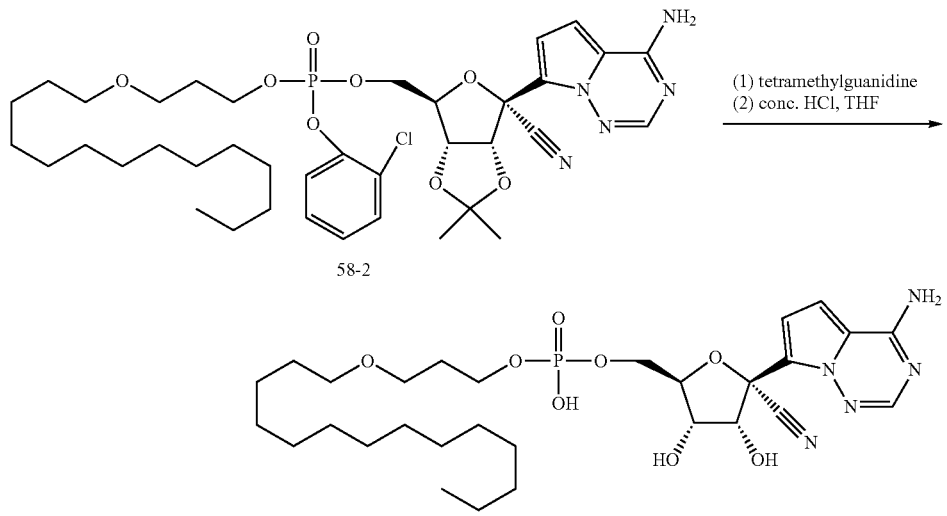

Compound 58 was synthesized in a manner similar to compound 56. $^{1}$H NMR (400 MHz, Methanol-d4) δ 8.09 (s, 1H), 7.35 (d, J=4.8 Hz, 1H), 7.19 (d, J=4.8 Hz, 1H), 4.77 (d, J=5.2 Hz, 1H), 4.43-4.32 (m, 1H), 4.24 (m, 2H), 4.13 (m, 1H), 3.99 (m, 2H), 3.51 m, 2H), 3.41 (m, 2H), 1.87 (m, 2H), 1.54 (m, 2H), 1.30 (s, 22H), 0.98-0.86 (m, 3H). $^{31}$P NMR (162 MHz, Methanol-d4) δ 0.09. MS: 626.19 (M+1).

Intermediate 59-1:
Preparation 3-octadecoxypropan-1-ol

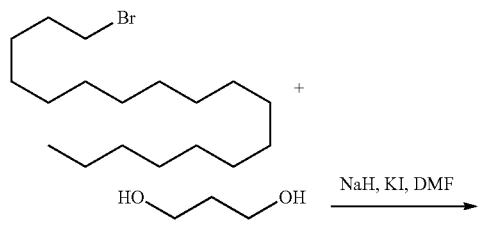

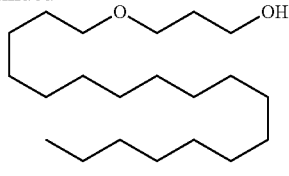

Intermediate 59-1 was synthesized in a manner similar to 55-1 using 1-bromooctadecane as alkylation agent. $^{1}$H NMR (400 MHz, DMSO-d6) δ 4.36 (t, J=5.1 Hz, 1H), 3.48-3.36 (m, 4H), 3.30 (s, 2H), 1.63 (m, 2H), 1.47 (m, 2H), 1.24 (s, 32H), 0.91-0.81 (m, 3H).

Intermediate 59-2: ((3aR,4R,6R,6aR)-6-(4-Aminopyrrolo[2,1-f][1,2,4]triazin-7-yl)-6-cyano-2,2-dimethyltetrahydrofuro[3,4-d][1,3]dioxol-4-yl)methyl (2-chlorophenyl) (3-(octadecyloxy)propyl) phosphate

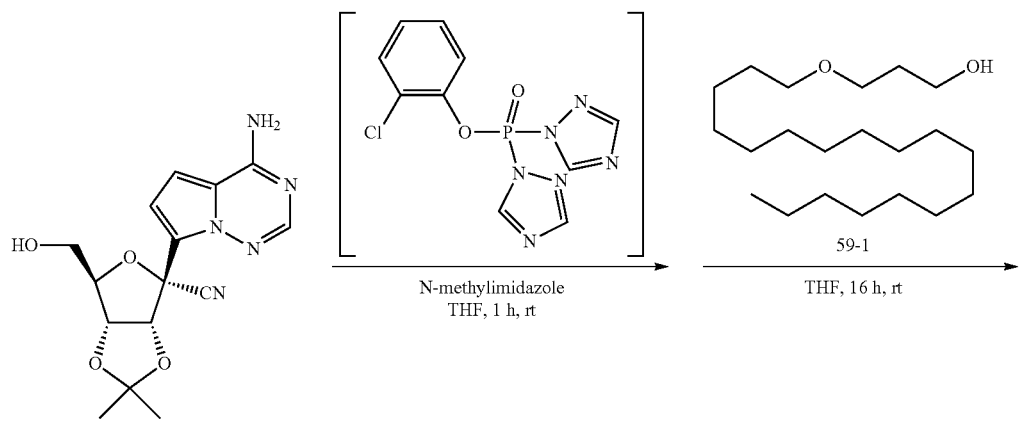

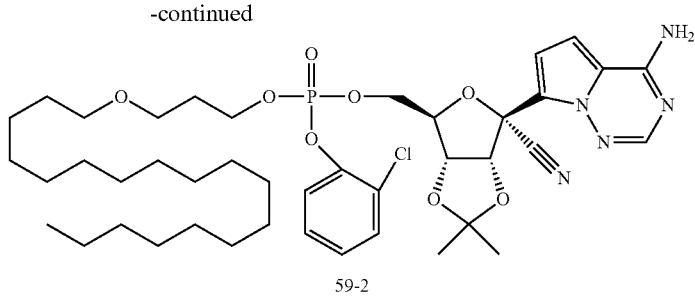

59-2

Intermediate 59-2 was synthesized in a manner similar to 55-2 using intermediate 3-octadecoxypropan-1-ol.

Example 59: ((2R,3S,4R,5R)-5-(4-Aminopyrrolo[2,1-f][1,2,4]triazin-7-yl)-5-cyano-3,4-dihydroxytetrahydrofuran-2-yl)methyl (3-(octadecyloxy)propyl) hydrogen phosphate (59)

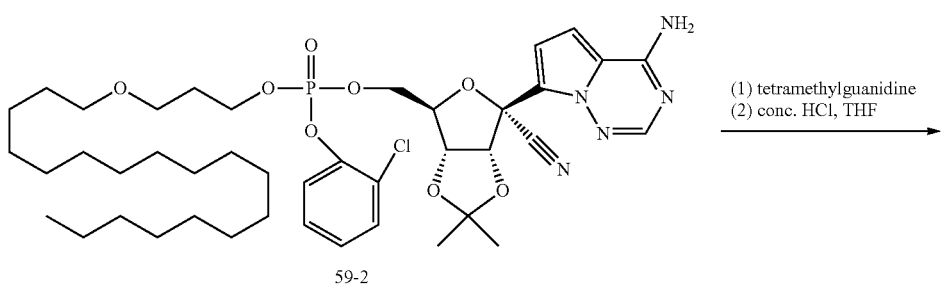

59-2

(1) tetramethylguanidine
(2) conc. HCl, THF

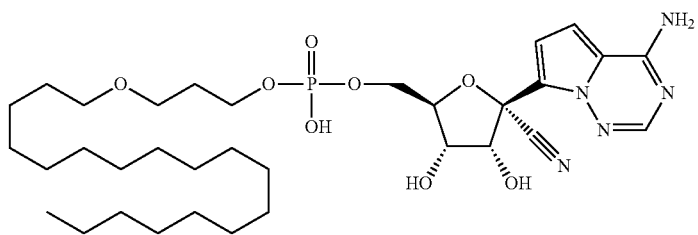

Compound 59 was synthesized in a manner similar to compound 56. $^1$H NMR (400 MHz, Methanol-d4) δ 8.16 (s, 1H), 7.48 (d, J=4.4 Hz, 1H), 7.19 (d, J=4.6 Hz, 1H), 4.74 (d, J=4.8 Hz, 1H), 4.46-4.01 (m, 7H), 3.52 (m, 2H), 3.42 (m, 2H), 1.91 (m, 2H), 1.55 (m, 2H), 1.30 (s, 32H), 0.91 (t, J=6.6 Hz, 3H). $^{31}$P NMR (162 MHz, Methanol-d4) δ −0.81. MS: 682.33 (M+1).

Intermediate 60-1: ((3aR,4R,6R,6aR)-6-(4-Aminopyrrolo[2,1-f][1,2,4]triazin-7-yl)-6-cyano-2,2-dimethyltetrahydrofuro[3,4-d][1,3]dioxol-4-yl)methyl (2-chlorophenyl) (3-(hexadecyloxy)propyl) phosphate

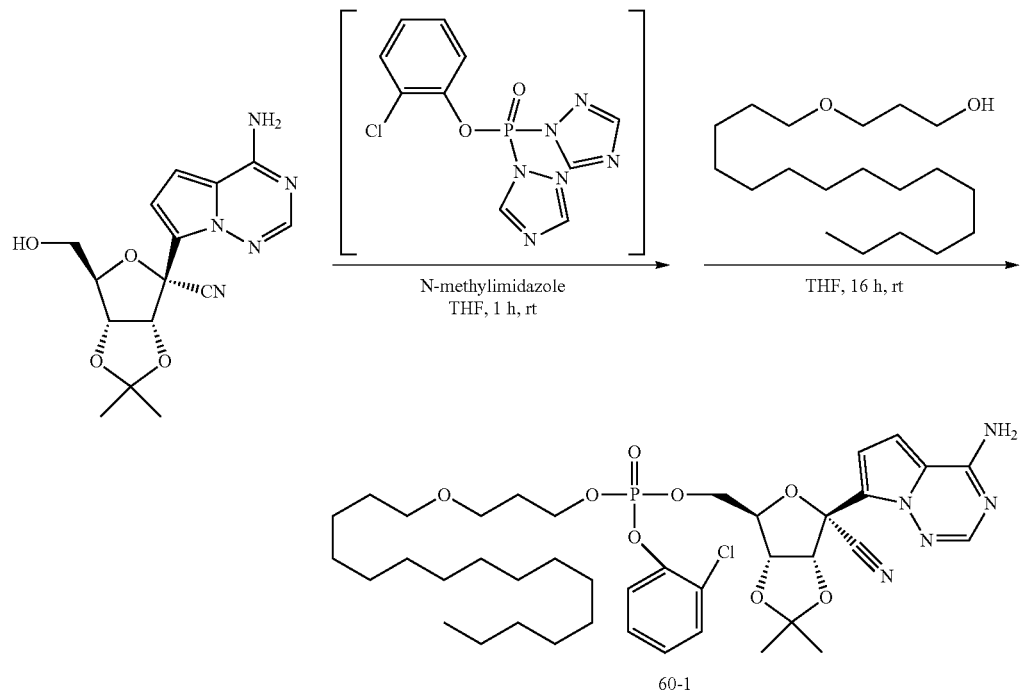

Intermediate 60-1 was synthesized in a manner similar to intermediate 55-2 using intermediate 3-(hexadecyloxy)propan-1-ol. MS: 804.36 (M+1).

Example 60: ((2R,3S,4R,5R)-5-(4-Aminopyrrolo[2,1-f][1,2,4]triazin-7-yl)-5-cyano-3,4-dihydroxytetrahydrofuran-2-yl)methyl (3-(hexadecyloxy)propyl) hydrogen phosphate (60)

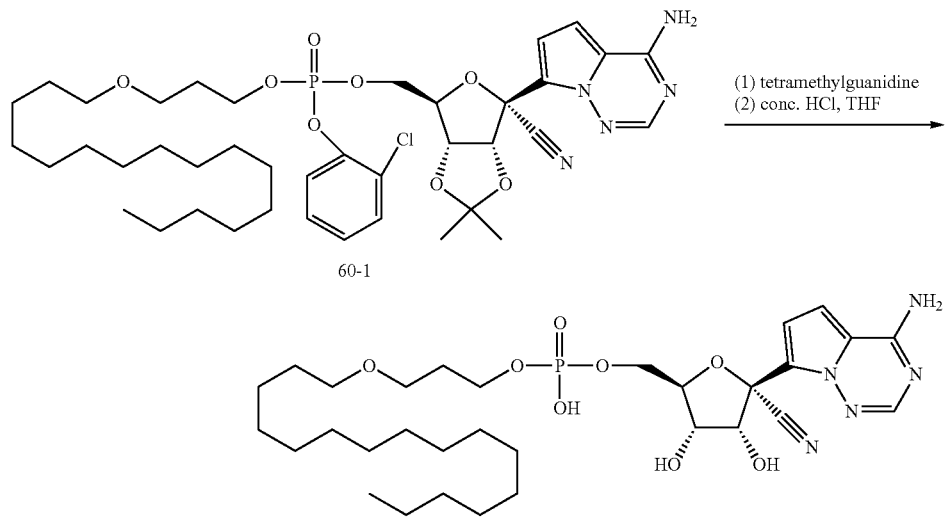

Compound 60 was synthesized in a manner similar to compound 56. $^1$H NMR (400 MHz, Methanol-d4) δ 8.10 (s, 1H), 7.38 (d, J=4.8 Hz, 1H), 7.20 (d, J=4.8 Hz, 1H), 4.77 (m, 1H), 4.38 (m, 1H), 4.30-4.18 (m, 2H), 4.14 (m, 1H), 4.00 (m, 2H), 3.51 (m, 2H), 3.42 (m, 2H), 1.87 (m, 2H), 1.54 (m, 2H), 1.30 (s, 28H), 0.92 (t, J=6.8 Hz, 3H). $^{31}$P NMR (162 MHz, Methanol-d4) δ −0.11 (t, J=6.1 Hz). MS: 654.24 (M+1).

Intermediate 61-1: ((3aR,4R,6R,6aR)-6-(4-Amino-pyrrolo[2,1-f][1,2,4]triazin-7-yl)-6-cyano-2,2-dimethyltetrahydrofuro[3,4-d][1,3]dioxol-4-yl)methyl ((R)-2,3-bis(hexadecyloxy)propyl) (2-chlorophenyl) phosphate

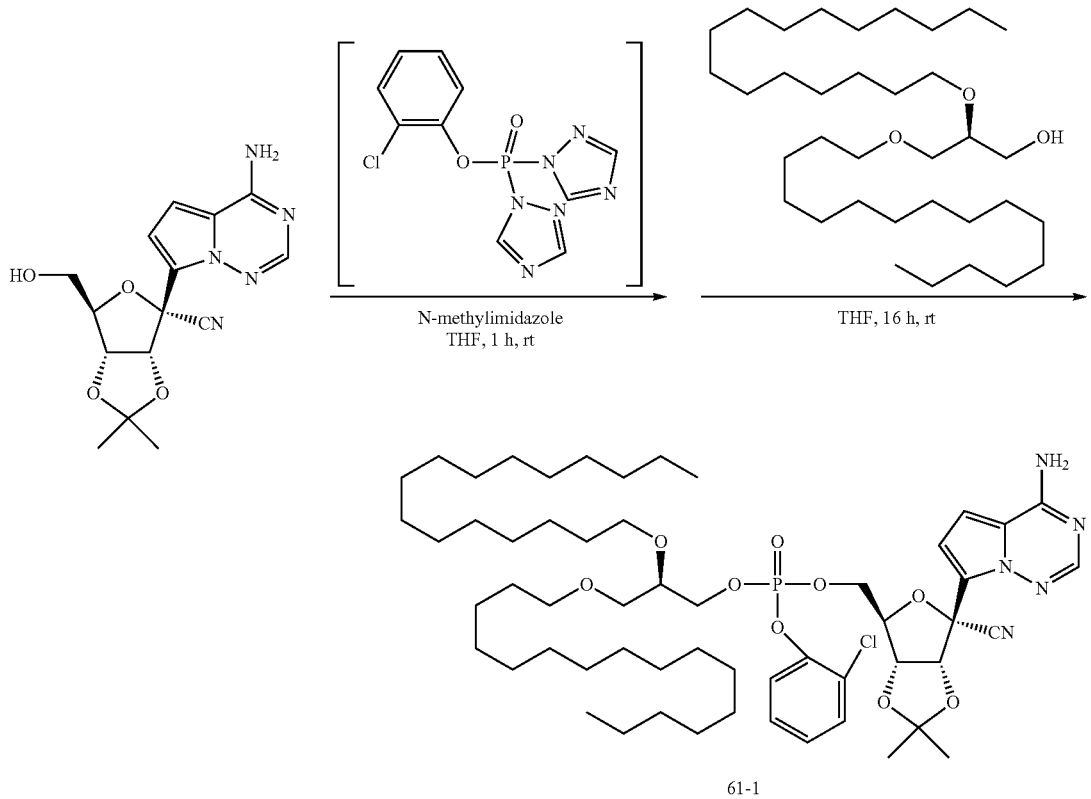

Intermediate 61-1 was synthesized in a manner similar to 55-2 using intermediate (S)-2,3-bis(hexadecyloxy)propan-1-ol.

Example 61: ((2R,3S,4R,5R)-5-(4-Aminopyrrolo[2,1-f][1,2,4]triazin-7-yl)-5-cyano-3,4-dihydroxytetrahydrofuran-2-yl)methyl ((R)-2,3-bis(hexadecyloxy)propyl) hydrogen phosphate (61)

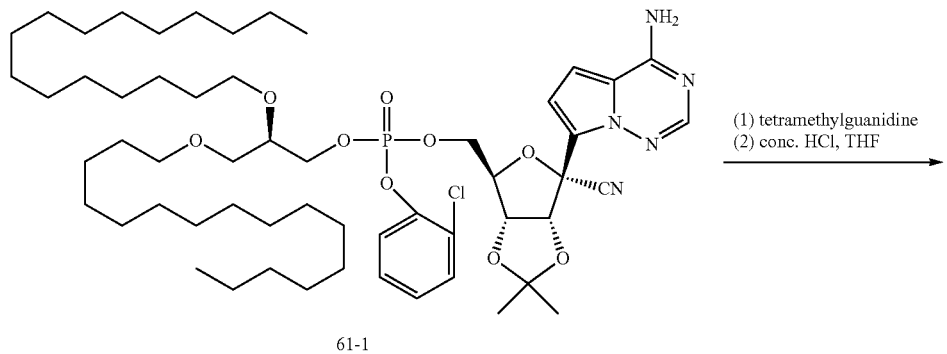

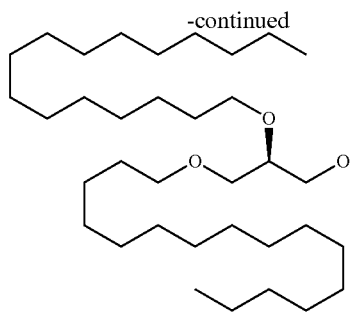

Compound 61 was synthesized in a manner similar to compound 56. ¹H NMR (400 MHz, DMSO-d6) δ 12.01 (s, 1H), 7.91 (s, 2H), 6.90 (d, J=4.5 Hz, 1H), 6.82 (d, J=4.5 Hz, 1H), 6.14 (d, J=5.7 Hz, 1H), 4.59 (m, 1H), 4.12 (m, 1H), 3.93 (m, 1H), 3.81 (m, 1H), 3.66-3.51 (m, 1H), 3.42 (m, 4H), 1.92 (s, 4H), 1.43 (m, 4H), 1.23 (m, 52H), 0.85 (t, J=6.6 Hz, 6H). 31P NMR (162 MHz, DMSO-d6) δ −0.36.

Example 62: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((2,4-dichlorobenzyl)oxy)-3-(octadecyloxy)propyl) hydrogen phosphate (62)

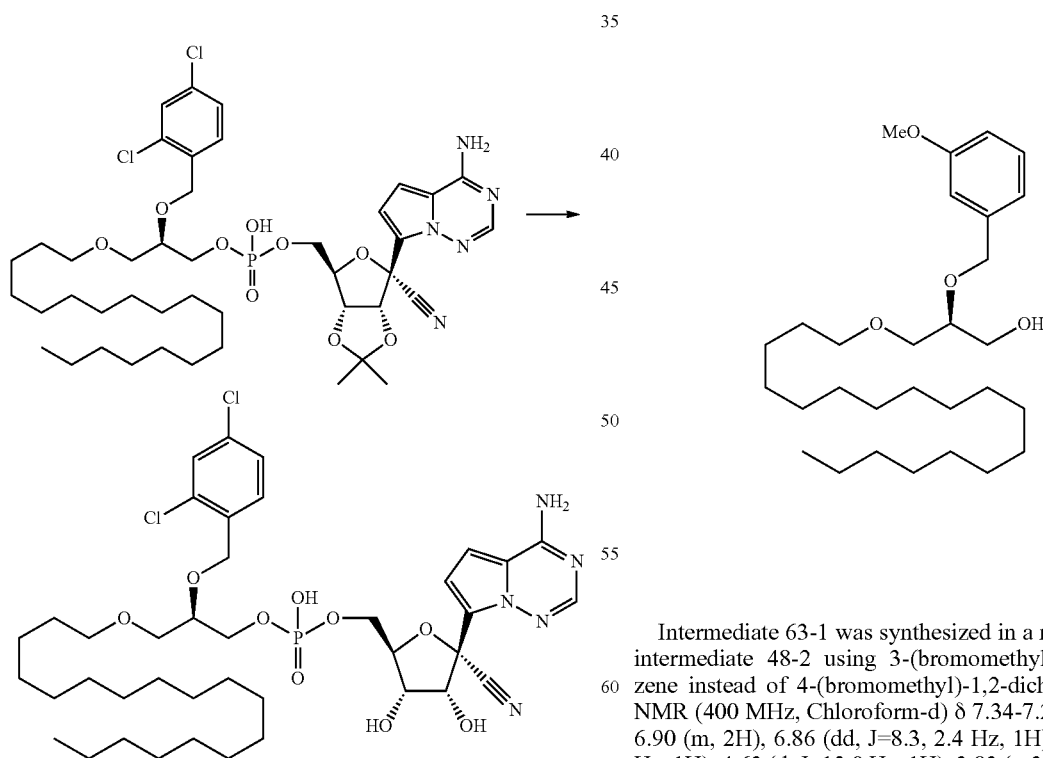

Compound 62 was synthesized in a manner similar to example 48 using 4-(bromomethyl)-1,3-dichlorobenzene instead of 4-(bromomethyl)-1,2-dichlorobenzene. ¹H NMR (400 MHz, Methanol-d4) δ 7.87 (s, 1H), 7.57 (d, J=8.3 Hz, 1H), 7.37 (d, J=2.1 Hz, 1H), 7.27 (dd, J=8.3, 2.1 Hz, 1H), 6.94 (dd, J=43.6, 4.6 Hz, 2H), 4.84 (d, J=5.4 Hz, 1H), 4.70 (s, 2H), 4.36 (t, J=4.1 Hz, 1H), 4.28 (t, J=5.3 Hz, 1H), 4.19-3.99 (m, 2H), 3.88 (hept, J=5.6 Hz, 2H), 3.75 (qd, J=5.4, 3.5 Hz, 1H), 3.58-3.45 (m, 2H), 3.43-3.37 (m, 2H), 1.52 (p, J=6.5 Hz, 2H), 1.31-1.21 (m, 30H), 0.92 (t, J=6.8 Hz, 3H). ³¹P NMR (162 MHz, Methanol-d4) δ 0.45.

Intermediate 63-1: (S)-2-((3-methoxybenzyl)oxy)-3-(octadecyloxy)propan-1-ol

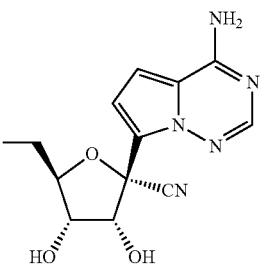

Intermediate 63-1 was synthesized in a manner similar to intermediate 48-2 using 3-(bromomethyl)-1-methoxybenzene instead of 4-(bromomethyl)-1,2-dichlorobenzene. ¹H NMR (400 MHz, Chloroform-d) δ 7.34-7.23 (m, 1H), 6.99-6.90 (m, 2H), 6.86 (dd, J=8.3, 2.4 Hz, 1H), 4.72 (d, J=11.9 Hz, 1H), 4.63 (d, J=12.0 Hz, 1H), 3.83 (s, 3H), 3.81-3.75 (m, 1H), 3.74-3.65 (m, 2H), 3.62 (dd, J=10.0, 4.4 Hz, 1H), 3.56 (dd, J=10.0, 5.1 Hz, 1H), 3.46 (td, J=6.7, 1.7 Hz, 2H), 1.65-1.50 (m, 2H), 1.43-1.19 (m, 30H), 0.90 (t, J=6.6 Hz, 3H).=\

Example 63: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((3-methoxybenzyl)oxy)-3-(octadecyloxy)propyl) hydrogen phosphate (63)

Example 64: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((2-chlorobenzyl)oxy)-3-(octadecyloxy)propyl) hydrogen phosphate (64)

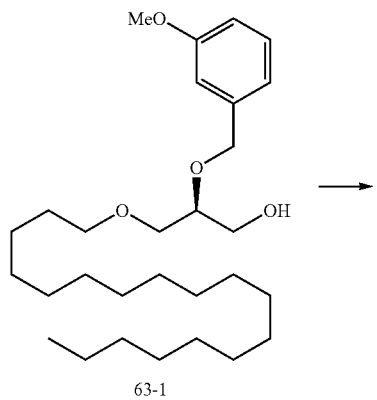

63-1

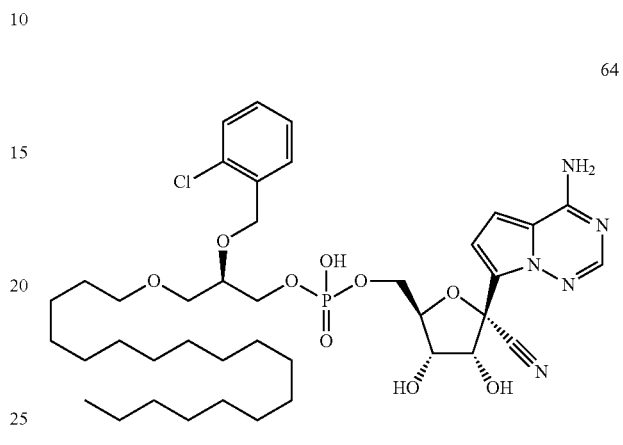

64

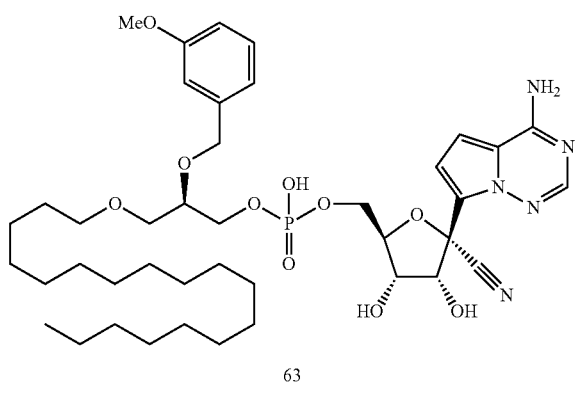

63

1,8-Diazabicyclo[5.4.0]undec-7-ene (10.6 μL, 71.2 μmol) was added over 1 min via syringe to a vigorously stirred mixture of intermediate 63-1 (33.1 mg, 71.2 μmol), intermediate 19-1 (20.0 mg, 35.6 μmol), and tetrahydrofuran (0.7 mL) at room temperature. After 15 min, water (50 μL) and concentrated hydrochloric acid (300 μL, 3.60 mmol) were added sequentially. After 120 min, the resulting mixture was purified by reverse phase preparative HPLC (0.1% trifluoroacetic acid in methanol/water) to give compound 63. $^1$H NMR (400 MHz, Methanol-d4) δ 7.87 (s, 1H), 7.19 (t, J=7.9 Hz, 1H), 7.00 (d, J=4.6 Hz, 1H), 6.95-6.91 (m, 1H), 6.91-6.84 (m, 2H), 6.81-6.75 (m, 1H), 4.81 (d, J=5.3 Hz, 1H), 4.69-4.51 (m, 2H), 4.38-4.32 (m, 1H), 4.26 (t, J=5.3 Hz, 1H), 4.19-4.00 (m, 2H), 3.92-3.85 (m, 1H), 3.78 (s, 3H), 3.74-3.30 (m, 4H), 1.58-1.48 (m, 2H), 1.40-1.20 (m, 30H), 0.92 (t, J=6.7 Hz, 3H). $^{31}$P NMR (162 MHz, Methanol-d4) δ 0.45. LCMS: 816.4 [M–H]$^-$.

Compound 64 was synthesized in a manner similar to compound 63 using 2-(bromomethyl)-1-chlorobenzene instead of 3-(bromomethyl)-1-methoxybenzene. $^1$H NMR (400 MHz, Methanol-d4) δ 8.00 (s, 1H), 7.57 (d, J=7.1 Hz, 1H), 7.33 (dd, J=7.5, 1.8 Hz, 1H), 7.25 (td, J=7.2, 1.8 Hz, 2H), 7.22-7.10 (m, 2H), 4.94-4.78 (m, 1H), 4.74 (s, 2H), 4.37-4.32 (m, 1H), 4.28 (t, J=5.4 Hz, 1H), 4.22-4.12 (m, 1H), 4.09 (dd, J=10.2, 5.5 Hz, 1H), 3.96 (p, J=5.5 Hz, 2H), 3.85-3.76 (m, 1H), 3.63-3.28 (m, 4H), 1.59-1.49 (m, 2H), 1.35-1.24 (m, 30H), 0.91 (t, 3H). $^{31}$P NMR (162 MHz, Methanol-d4) δ 0.25. LCMS: 820.4 [M–H]$^-$.

Example 65: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((2-cyano-6-fluorobenzyl)oxy)-3-(octadecyloxy)propyl) hydrogen phosphate (65)

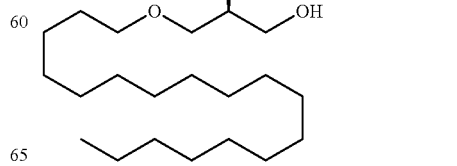

-continued

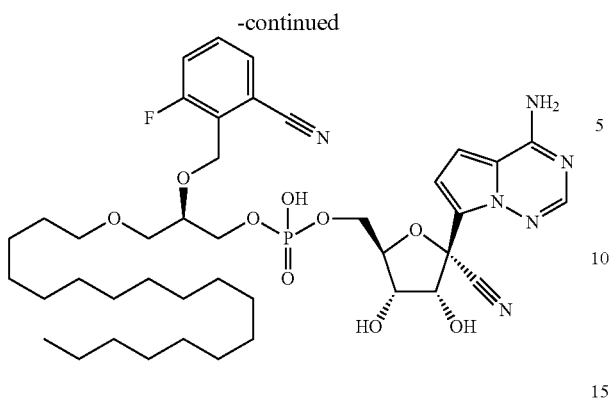

Compound 65 was synthesized in a manner similar to compound 63 using 2-(bromomethyl)-3-fluorobenzonitrile instead of 3-(bromomethyl)-1-methoxybenzene. $^1$H NMR (400 MHz, Methanol-d4) δ 7.87 (s, 1H), 7.56 (dd, J=7.7, 1.3 Hz, 1H), 7.50 (td, J=8.0, 5.2 Hz, 1H), 7.44-7.39 (m, 1H), 7.00 (d, J=4.6 Hz, 1H), 6.88 (d, J=4.6 Hz, 1H), 4.90-4.58 (m, 3H), 4.34 (t, J=4.4 Hz, 1H), 4.28 (t, J=5.4 Hz, 1H), 4.19-4.02 (m, 2H), 3.91 (t, J=5.5 Hz, 2H), 3.80 (p, J=5.3 Hz, 1H), 3.62-3.48 (m, 2H), 3.46-3.39 (m, 2H), 1.54-1.42 (m, 2H), 1.38-1.24 (m, 30H), 0.91 (t, 3H). $^{31}$P NMR (162 MHz, Methanol-d4) δ 0.34. LCMS: 829.4 [M–H]$^-$.

Example 66: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((5-cyano-2-fluorobenzyl)oxy)-3-(octadecyloxy)propyl) hydrogen phosphate (66)

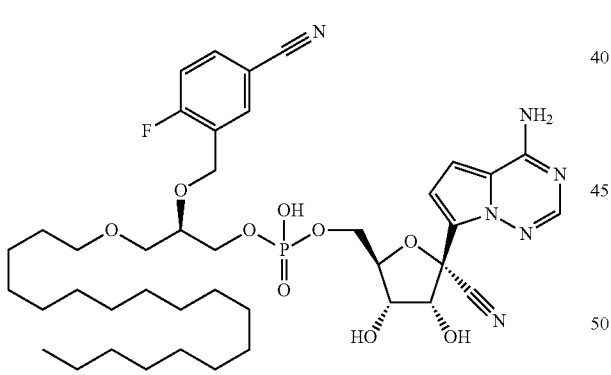

Compound 66 was synthesized in a manner similar to compound 63 using 3-(bromomethyl)-4-fluorobenzonitrile instead of 3-(bromomethyl)-1-methoxybenzene. $^1$H NMR (400 MHz, Methanol-d4) δ 8.07 (s, 1H), 7.97-7.88 (m, 1H), 7.68 (ddd, J=7.4, 4.8, 2.2 Hz, 1H), 7.32 (d, J=4.8 Hz, 1H), 7.26 (d, J=9.2 Hz, 1H), 7.23-7.20 (m, 1H), 4.96-4.74 (m, 3H), 4.38-4.32 (m, 1H), 4.30-4.22 (m, 1H), 4.22-4.17 (m, 1H), 4.11 (td, J=11.7, 11.1, 5.3 Hz, 1H), 3.98 (qt, J=11.0, 5.6 Hz, 2H), 3.83 (q, J=5.1 Hz, 1H), 3.63-3.40 (m, 4H), 1.77-1.52 (m, 2H), 1.39-1.24 (m, 30H), 0.92 (t, J=6.8 Hz, 3H). $^{19}$F NMR (376 MHz, Methanol-d4) δ −111.48. $^{31}$P NMR (162 MHz, Methanol-d4) δ 0.13. LCMS: 829.4 [M–H]$^-$.

Example 67: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((4-cyano-3-fluorobenzyl)oxy)-3-(octadecyloxy)propyl) hydrogen phosphate (67)

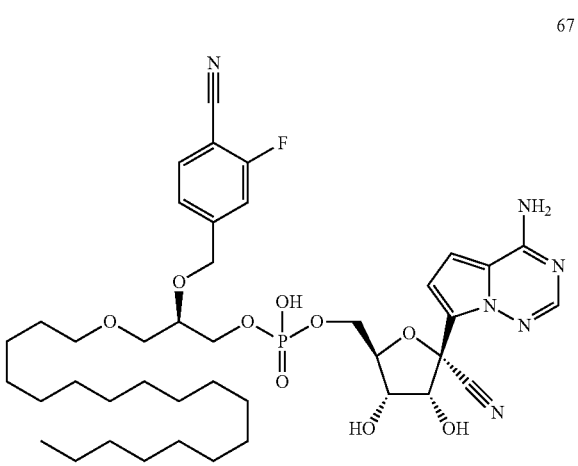 [SMILES: CCCCCCCCCCCCCCCCCCOC[C@H](COP(=O)(O)OC[C@H]1O[C@@](C#N)(c2ccc3c(N)ncnn23)[C@H](O)[C@@H]1O)OCc1ccc(C#N)c(F)c1]

Compound 67 was synthesized in a manner similar to compound 63 using 4-(bromomethyl)-2-fluorobenzonitrile instead of 3-(bromomethyl)-1-methoxybenzene. $^1$H NMR (400 MHz, Methanol-d4) δ 8.05 (s, 1H), 7.65 (dd, J=8.0, 6.6 Hz, 1H), 7.39 (d, J=10.3 Hz, 1H), 7.36-7.31 (m, 1H), 7.25 (d, J=4.8 Hz, 1H), 7.17 (d, J=4.8 Hz, 1H), 4.96-4.73 (m, 3H), 4.38-4.33 (m, 1H), 4.24 (t, J=5.6 Hz, 1H), 4.22-4.16 (m, 1H), 4.09 (dt, J=11.5, 4.6 Hz, 1H), 3.96 (qt, J=11.1, 5.5 Hz, 2H), 3.79 (p, J=5.2 Hz, 1H), 3.63-3.40 (m, 4H), 1.59-1.51 (m, 2H), 1.41-1.24 (m, 30H), 0.91 (t, 3H). $^{19}$F NMR (376 MHz, Methanol-d4) δ −110.55. $^{31}$P NMR (162 MHz, Methanol-d4) δ 0.22. LCMS: 829.4 [M–H]$^-$.

Example 68: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((3-chloro-5-cyanobenzyl)oxy)-3-(octadecyloxy)propyl) hydrogen phosphate (68)

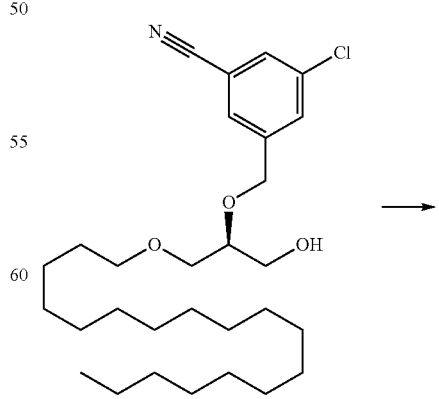

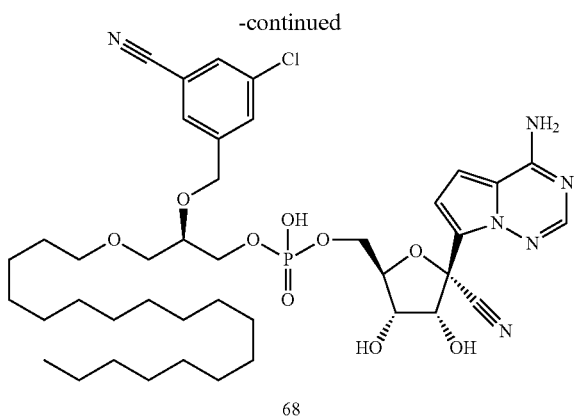

68

Compound 68 was synthesized in a manner similar to compound 63 using 3-(bromomethyl)-5-chlorobenzonitrile instead of 3-(bromomethyl)-1-methoxybenzene. $^1$H NMR (400 MHz, Methanol-d4) δ 8.02 (s, 1H), 7.70 (s, 1H), 7.68-7.62 (m, 2H), 7.20 (d, J=4.7 Hz, 1H), 7.16 (d, J=4.7 Hz, 1H), 4.95-4.65 (m, 3H), 4.41-4.33 (m, 1H), 4.25 (t, J=5.5 Hz, 1H), 4.22-4.16 (m, 1H), 4.13-4.04 (m, 1H), 3.94 (qt, J=11.0, 5.5 Hz, 2H), 3.79 (d, J=5.4 Hz, 2H), 3.61-3.30 (m, 4H), 1.62-1.52 (m, 2H), 1.39-1.24 (m, 30H), 0.92 (t, J=6.7 Hz, 3H).
$^{19}$F NMR (376 MHz, Methanol-d4) δ −77.60. $^{31}$P NMR (162 MHz, Methanol-d4) δ 0.27.
LCMS: 845.4 [M−H]$^-$.

Intermediate 69-1: (R,Z)-1-((tert-butyldiphenylsilyl)oxy)-3-(octadec-9-en-1-yloxy)propan-2-ol

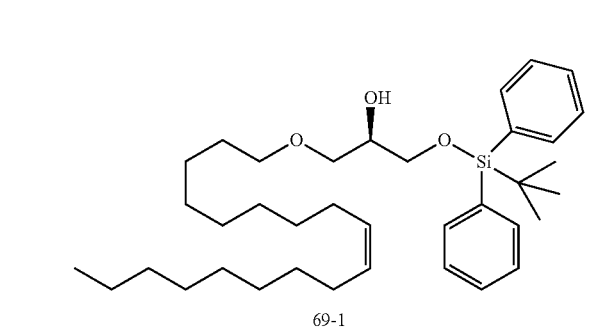

To a solution of tert-butyl-[[(2R)-oxiran-2-yl]methoxy]-diphenyl-silane (1.18 g, 3.78 mmol, prepared according to Org. Biomol. Chem. 2013, 11, 6919) and oleyl alcohol (1.67 g, 5.29 mmol) in dichloromethane at RT was added boron trifluoride diethyl etherate (47 μL, 0.378 mmol). The mixture was heated to reflux and stirred overnight. The mixture was then concentrated and directly purified by flash column chromatography (0 to 20% ethyl acetate in hexanes) to afford 69-1. $^1$H NMR (400 MHz, Chloroform-d) δ 7.69-7.62 (m, 4H), 7.46-7.37 (m, 6H), 5.40-5.29 (m, 2H), 3.88 (p, J=5.4 Hz, 1H), 3.71 (d, J=5.4 Hz, 2H), 3.55-3.40 (m, 4H), 2.06-1.96 (m, 4H), 1.60-1.47 (m, 3H), 1.38-1.18 (m, 28H), 1.06 (s, 10H), 0.88 (td, J=6.9, 2.3 Hz, 6H).

Intermediate 69-2: (R,Z)-3-(((1-((tert-butyldiphenylsilyl)oxy)-3-(octadec-9-en-1-yloxy)propan-2-yl)oxy)methyl)-5-fluorobenzonitrile

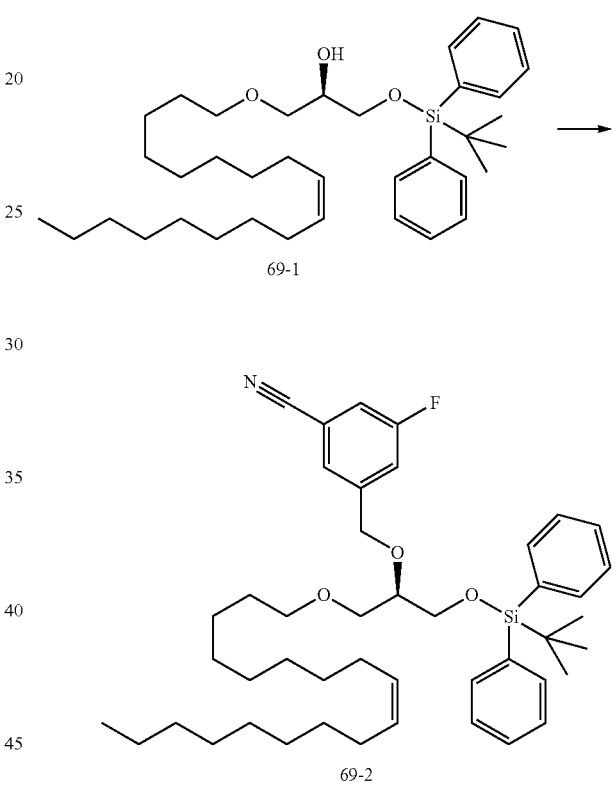

Sodium hydride (60% wt dispersion in mineral oil, 74 mg, 1.94 mmol) was added to a stirred solution of 69-1 (1.31 g, 2.25 mmol) in tetrahydrofuran (15 mL) at 0° C. After 30 min, 3-(bromomethyl)-5-fluoro-benzonitrile (724 mg, 3.38 mmol) was added, and the resulting mixture was warmed to 55° C. and stirred overnight. The suspension was then cooled to 0° C., quenched with water (20 mL), and extracted with ethyl acetate (3×30 mL). The combined organic fractions were then washed with brine (25 mL) and dried over magnesium sulfate. Following filtration and concentration, the crude residue was purified by flash column chromatography on silica gel (0 to 30% ethyl acetate in hexanes) to give intermediate 69-2. $^1$H NMR (400 MHz, Chloroform-d) δ 7.66 (dt, J=7.9, 1.3 Hz, 5H), 7.47-7.30 (m, 10H), 7.26-7.20 (m, 3H), 5.39-5.31 (m, 2H), 4.64 (s, 2H), 3.75 (d, J=5.2 Hz, 2H), 3.70-3.64 (m, 1H), 3.63-3.51 (m, 2H), 3.42 (t, J=6.7 Hz, 2H), 2.05-1.97 (m, 5H), 1.62-1.49 (m, 4H), 1.38-1.21 (m, 27H), 1.05 (s, 11H), 0.91-0.82 (m, 4H).

261

Intermediate 69-3: (S,Z)-3-fluoro-5-(((1-hydroxy-3-(octadec-9-en-1-yloxy)propan-2-yl)oxy)methyl)benzonitrile

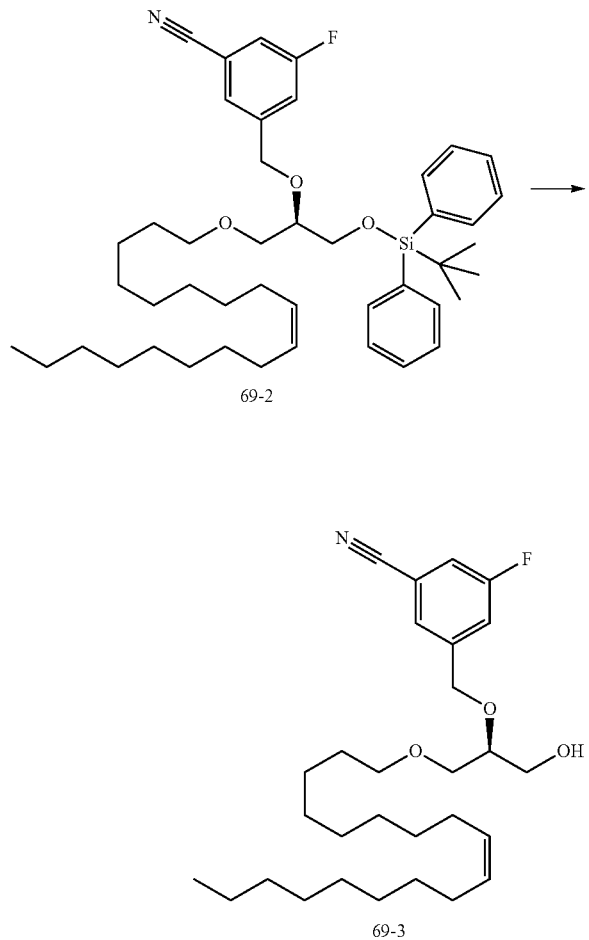

Tetrabutylammonium fluoride (1.0 M in tetrahydrofuran, 4.81 mL, 4.81 mmol) was added to a stirred solution of intermediate 69-2 (2.31 g, 4.01 mmol) in tetrahydrofuran (20 mL) at 0° C. The resulting mixture was warmed to room temperature and stirred for 1 hour, at which time water was added (20 mL), and the mixture was extracted with ethyl acetate (3×30 mL). The combined organic fractions were then washed with brine (25 mL) and dried over magnesium sulfate. Following filtration and concentration, the crude residue was purified by flash column chromatography on silica gel (0 to 50% ethyl acetate in hexanes) to give intermediate 69-3. $^1$H NMR (400 MHz, Chloroform-d) δ 7.46 (s, 1H), 7.36 (dt, J=9.1, 1.8 Hz, 1H), 7.28 (t, J=1.8 Hz, 1H), 5.39-5.31 (m, 2H), 4.79-4.65 (m, 2H), 3.84-3.74 (m, 1H), 3.74-3.66 (m, 3H), 3.63-3.52 (m, 2H), 3.46-3.38 (m, 2H), 2.01 (q, J=6.5 Hz, 4H), 1.57 (p, J=6.7 Hz, 2H), 1.40-1.18 (m, 27H), 0.88 (t, J=6.7 Hz, 3H).

262

Intermediate 69-4: ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl (2-chlorophenyl) ((R)-2-((3-cyano-5-fluorobenzyl)oxy)-3-(((Z)-octadec-9-en-1-yl)oxy)propyl) phosphate 2-Chlorophenyl phosphorodichloridate (378 µL, 2.30 mmol) was added via syringe to a vigorously stirred mixture of 1,2,4-triazole (341 mg, 4.94 mmol), triethylamine (688 µL, 4.94 mmol), acetonitrile (5 mL), and pyridine (5 mL) at room temperature. After 40 min, intermediate 69-3 (1.06 g, 2.30 mmol) in acetonitrile (5 mL) and pyridine (5 mL) was added and stirred at room temperature for 1 h. (3aR,4R,6R,6aR)-4-(4-aminopyrrolo[2,1-f][1,2,4]triazin-7-yl)-6-(hydroxymethyl)-2,2-dimethyltetrahydrofuro[3,4-d][1,3]dioxole-4-carbonitrile was then added at once and the resulting suspension was allowed to stir at room temperature. After 15 h, the mixture was concentrated, and to the resulting product was added citric acid (20 mL, 20% w/w in water), sodium hydroxide (5 mL, 1 N), and ethyl acetate (100 mL). The aqueous phase was extracted with additional ethyl acetate (2×50 mL), and the combined organic fractions were washed with brine (50 mL) and dried over magnesium sulfate. After filtration and concentration, the crude residue was purified by flash column chromatography on silica gel (0 to 15% methanol in dichloromethane) to give intermediate 69-4. $^1$H NMR (400 MHz, Acetonitrile-d3) δ 7.90 (d, J=2.1 Hz, 1H), 7.52-7.32 (m, 7H), 7.22-7.15 (m, 2H), 6.89 (dd, J=6.9, 4.6 Hz, 1H), 6.75 (dd, J=7.1, 4.6 Hz, 1H), 6.37 (s, 2H), 5.48 (s, 1H), 5.36 (dd, J=29.5, 6.6 Hz, 1H), 4.95 (dtd, J=13.8, 6.9, 3.7 Hz, 1H), 4.66-4.59 (m, 1H), 4.59-4.46 (m, 3H), 4.45-4.32 (m, 3H), 4.23 (dtt, J=11.3, 7.0, 3.3 Hz, 1H), 4.08 (ddt, J=10.9, 7.7, 5.5 Hz, 1H), 3.61-3.53 (m, 2H), 2.16 (d, J=15.9

Hz, 3H), 1.97 (p, J=2.5 Hz, 14H), 1.70 (d, J=3.1 Hz, 4H), 1.54-1.42 (m, 1H), 1.28 (d, J=9.6 Hz, 46H), 0.90 (t, J=6.6 Hz, 4H).

Intermediate 69-5: ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl ((R)-2-((3-cyano-5-fluorobenzyl)oxy)-3-(((Z)-octadec-9-en-1-yl)oxy)propyl) hydrogen phosphate

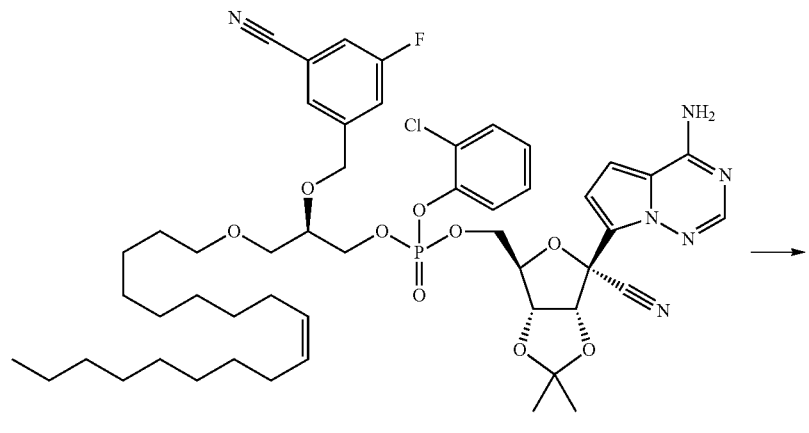

69-4

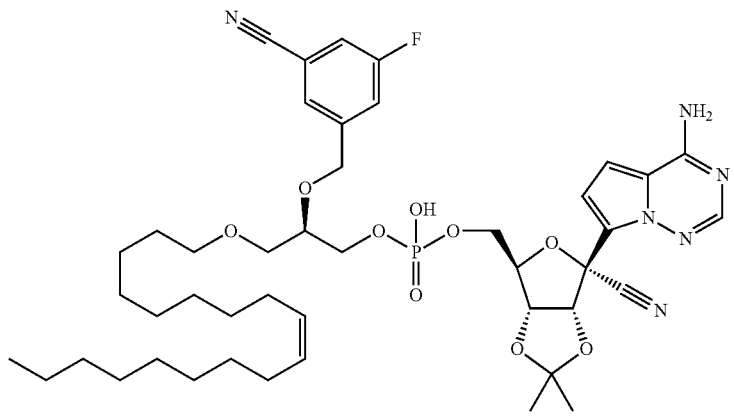

69-5

To a solution of 69-4 (1.22 g, 1.25 mmol) and N,N-dimethylpyridin-4-amine (456 mg, 3.74 mmol) in tetrahydrofuran (6 mL) and acetonitrile (3 mL) at room temperature was added cesium fluoride (568 mg, 3.74 mmol) in water (1.2 mL). The mixture was warmed to 80° C. and stirred for 2 h. Sodium hydroxide (1 N, 2.5 mL) and citric acid (20% w/w in water, 12.5 mL) were then added sequentially, and the mixture was extracted with a 3:2 mixture of 2-methyltetrahydrofuran and ethyl acetate (3×50 mL). The pooled organic fractions were then washed with brine (50 mL) and dried over magnesium sulfate. Following filtration and concentration, the residue was purified by flash column chromatography on silica gel (0 to 50% methanol in dichloromethane) to afford 69-5. $^1$H NMR (400 MHz, Methanol-d4) δ 7.87 (s, 1H), 7.50 (s, 1H), 7.44 (d, J=8.2 Hz, 1H), 7.24 (d, J=9.1 Hz, 1H), 6.96 (d, J=4.5 Hz, 1H), 6.89 (d, J=4.6 Hz, 1H), 4.95-4.91 (m, 5H), 4.82 (d, J=7.4 Hz, 5H), 4.60 (s, 5H), 4.20 (t, J=5.8 Hz, 2H), 4.12 (s, 1H), 3.94 (s, 1H), 3.72 (s, 1H), 3.52-3.47 (m, 3H), 3.44-3.36 (m, 3H), 3.27 (d, J=7.9 Hz, 1H), 3.15 (d, J=2.1 Hz, 2H), 1.53 (d, J=7.3 Hz, 2H), 1.29 (d, J=9.2 Hz, 31H), 0.92 (t, J=6.7 Hz, 3H).

Example 69: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((3-cyano-5-fluorobenzyl)oxy)-3-(((Z)-octadec-9-en-1-yl)oxy)propyl) hydrogen phosphate ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((3,4-dichlorobenzyl)oxy)-3-(octadecyloxy)propyl) hydrogen phosphate (69)

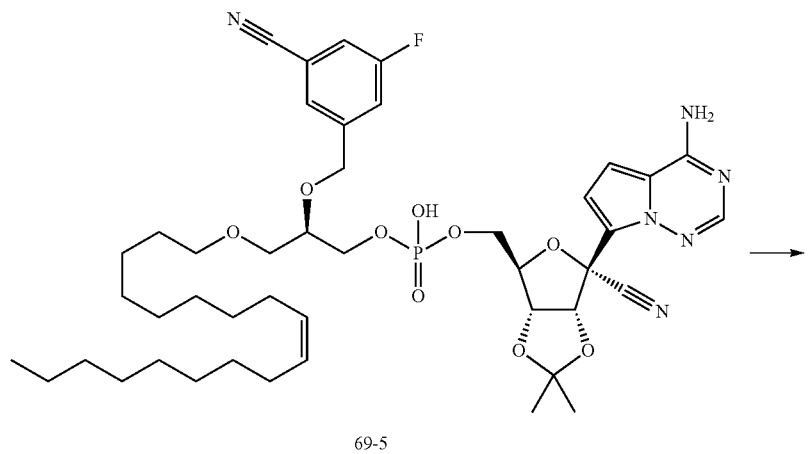

69-5

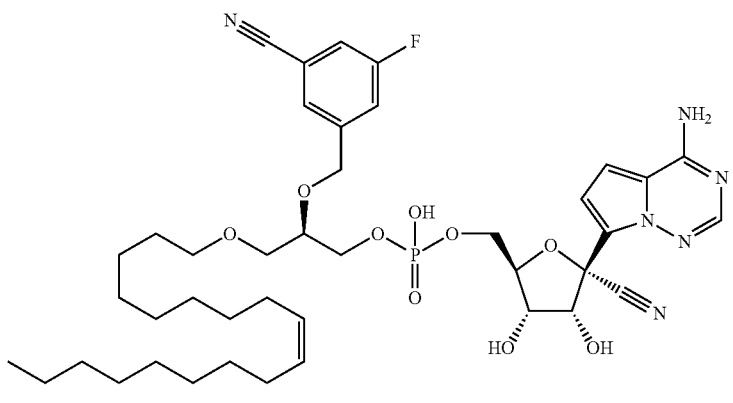

69

Concentrated hydrochloric acid (1.13 mL, 13.6 mmol) was added to a solution of 69-5 (970 mg, 1.13 mmol) in tetrahydrofuran (6 mL). After 3 hours, the reaction was cooled to 0° C. and was quenched with sodium hydroxide (1.32 mL) and phosphoric acid (0.175 mL). The mixture was extracted with a 3:2 mixture of 2-methyltetrahydrofuran and ethyl acetate (3×50 mL). The pooled organic fractions were then washed with brine (50 mL) and dried over magnesium sulfate. Following filtration and concentration, the residue was purified by flash column chromatography on silica gel (0 to 50% methanol in dichloromethane) to afford compound 69. $^1$H NMR (400 MHz, Methanol-d4) δ 7.94 (s, 1H), 7.54 (s, 1H), 7.49-7.34 (m, 2H), 7.10-7.00 (m, 2H), 5.35 (dd, J=5.6, 4.2 Hz, 2H), 4.82-4.65 (m, 3H), 4.36 (d, J=4.9 Hz, 1H), 4.25 (t, J=5.5 Hz, 1H), 4.22-4.14 (m, 1H), 4.12-4.05 (m, 1H), 3.91 (qt, J=11.0, 5.5 Hz, 2H), 3.75 (dq, J=8.0, 4.2, 2.8 Hz, 1H), 3.56-3.48 (m, 2H), 3.42 (tt, J=6.2, 3.1 Hz, 2H), 2.04 (d, J=5.6 Hz, 4H), 1.54 (q, J=6.7 Hz, 2H), 1.32 (d, J=15.4 Hz, 24H), 0.98-0.87 (m, 3H). LCMS: 827.4 [M−H]⁻.

Intermediate 70-1: (R)-1-((tert-butyldiphenylsilyl)oxy)-3-(nonadecyloxy)propan-2-ol

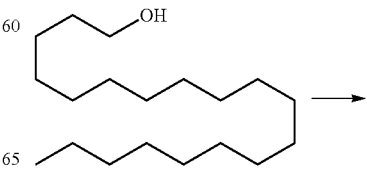

-continued

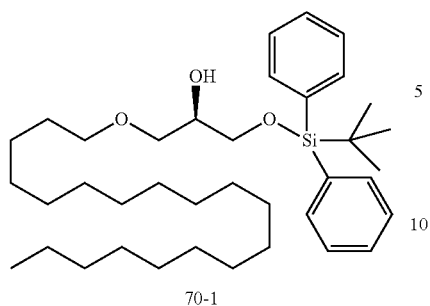

70-1

Intermediate 70-1 was synthesized in a manner similar to intermediate 69-1 using nonadecyl-1-ol instead of oleyl alcohol. ¹H NMR (400 MHz, Chloroform-d) δ 7.66 (d, J=7.0 Hz, 4H), 7.40 (dt, J=14.5, 7.1 Hz, 6H), 3.88 (p, J=5.5 Hz, 1H), 3.71 (d, J=5.4 Hz, 2H), 3.46 (dt, J=25.8, 6.2 Hz, 4H), 1.54 (d, J=7.0 Hz, 4H), 1.26 (s, 33H), 1.06 (s, 9H), 0.88 (t, J=6.6 Hz, 3H).

Intermediate 70-2: (R)-3-(((1-(((tert-butyldiphenylsilyl)oxy)-3-(nonadecyloxy)propan-2-yl)oxy)methyl)-5-fluorobenzonitrile (S)-2-((2,4-dichlorobenzyl)oxy)-3-(octadecyloxy)propan-1-ol

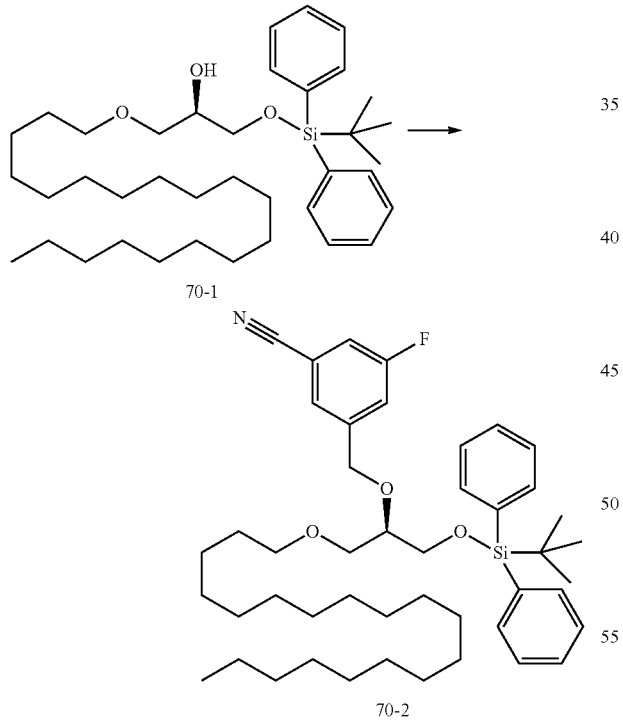

Intermediate 70-2 was synthesized in a manner similar to intermediate 69-2 using intermediate 70-1 instead of intermediate 69-1. ¹H NMR (400 MHz, Chloroform-d) δ 7.69-7.65 (m, 4H), 7.46-7.30 (m, 10H), 7.25-7.21 (m, 1H), 4.64 (s, 2H), 3.75 (d, J=5.2 Hz, 2H), 3.70-3.64 (m, 1H), 3.62-3.50 (m, 2H), 3.42 (t, J=6.7 Hz, 2H), 1.61-1.50 (m, 3H), 1.26 (d, J=2.7 Hz, 37H), 1.05 (s, 11H), 0.88 (td, J=6.9, 2.2 Hz, 4H).

Intermediate 70-3: (S)-3-fluoro-5-(((1-hydroxy-3-(nonadecyloxy)propan-2-yl)oxy)methyl)benzonitrile

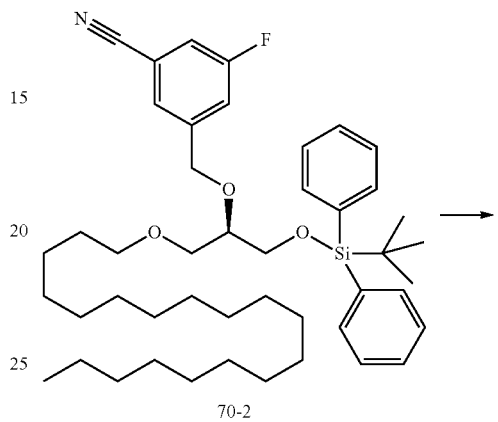

Intermediate 70-3 was synthesized in a manner similar to intermediate 69-3 using intermediate 70-2 instead of intermediate 69-2. ¹H NMR (400 MHz, Chloroform-d) δ 7.48 (s, 1H), 7.38 (dt, J=9.1, 1.8 Hz, 1H), 7.30 (t, J=1.9 Hz, 1H), 4.81-4.69 (m, 2H), 3.82 (ddd, J=10.1, 6.4, 3.5 Hz, 1H), 3.77-3.68 (m, 2H), 3.66-3.57 (m, 2H), 3.47 (td, J=6.7, 2.2 Hz, 2H), 2.12-2.03 (m, 1H), 1.59 (d, J=6.2 Hz, 4H), 1.28 (s, 36H), 0.90 (t, J=6.7 Hz, 3H).

269

Intermediate 70-4: ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl (2-chlorophenyl) ((R)-2-((3-cyano-5-fluorobenzyl)oxy)-3-(nonadecyloxy)propyl) phosphate

270

Intermediate 70-5: ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl ((R)-2-((3-cyano-5-fluorobenzyl)oxy)-3-(nonadecyloxy)propyl) hydrogen phosphate

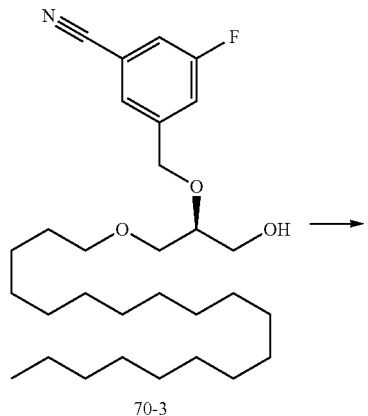

70-3

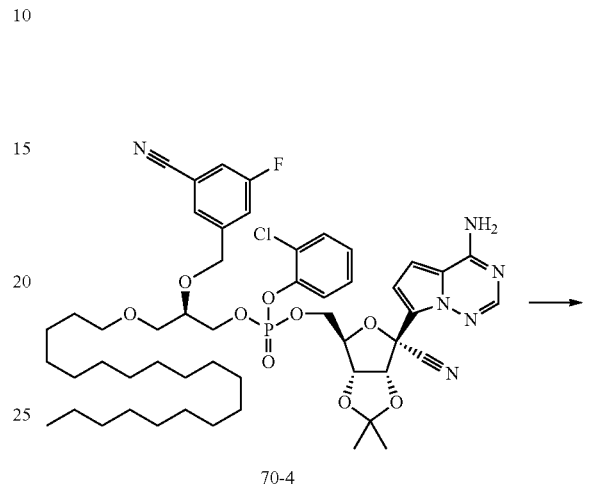

70-4

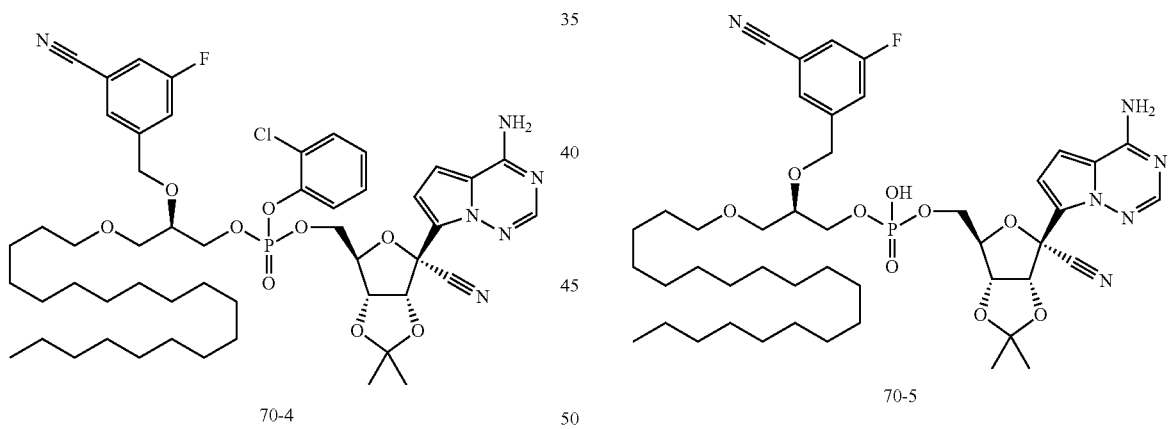

70-4                70-5

Intermediate 70-4 was synthesized in a manner similar to intermediate 69-4 using intermediate 70-3 instead of intermediate 69-3. $^1$H NMR (400 MHz, Acetonitrile-d3) δ 7.90 (d, J=2.0 Hz, 1H), 7.50 (d, J=4.5 Hz, 1H), 7.46-7.32 (m, 4H), 7.18 (dtd, J=9.5, 6.6, 5.7, 2.8 Hz, 2H), 6.89 (dd, J=6.6, 4.6 Hz, 1H), 6.75 (dd, J=7.1, 4.6 Hz, 1H), 6.39 (s, 2H), 5.43-5.29 (m, 1H), 4.96 (ddd, J=15.0, 6.6, 3.6 Hz, 1H), 4.61 (d, J=7.9 Hz, 3H), 4.40 (ddd, J=12.5, 7.7, 5.3 Hz, 2H), 4.29 (ddt, J=12.8, 6.9, 3.8 Hz, 1H), 4.22-4.14 (m, 1H), 3.78-3.73 (m, 1H), 3.50-3.34 (m, 4H), 2.19 (s, 1H), 1.97 (p, J=2.5 Hz, 2H), 1.75-1.69 (m, 3H), 1.51 (dt, J=8.2, 4.1 Hz, 2H), 1.43-1.35 (m, 3H), 1.27 (d, J=8.2 Hz, 33H), 0.90 (t, J=6.6 Hz, 3H).

Intermediate 70-5 was synthesized in a manner similar to intermediate 69-5 using intermediate 70-4 instead of intermediate 69-4. $^1$H NMR (400 MHz, Methanol-d4) δ 7.88 (s, 1H), 7.54 (s, 1H), 7.50-7.34 (m, 2H), 6.95-6.86 (m, 2H), 5.41 (d, J=6.5 Hz, 1H), 5.06 (dd, J=6.6, 3.1 Hz, 1H), 4.74-4.52 (m, 4H), 4.06 (td, J=5.4, 1.8 Hz, 2H), 3.87 (td, J=5.6, 2.7 Hz, 2H), 3.71 (p, J=5.2 Hz, 1H), 3.46 (dddt, J=23.7, 9.5, 6.5, 3.5 Hz, 4H), 1.72 (s, 3H), 1.54 (q, J=6.8 Hz, 2H), 1.43 (s, 3H), 1.29 (d, J=7.8 Hz, 30H), 0.95-0.89 (m, 3H).

Example 70: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((3-cyano-5-fluorobenzyl)oxy)-3-(nonadecyloxy)propyl) hydrogen phosphate (70)

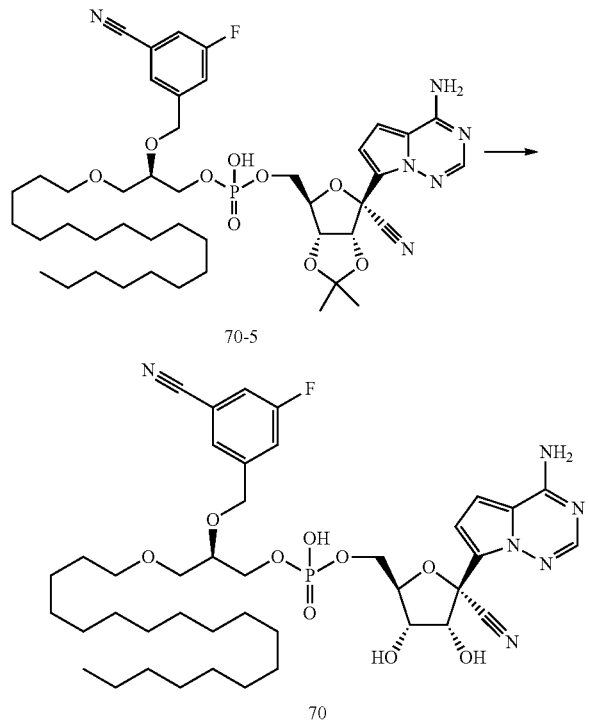

Example 70 was synthesized in a manner similar to example 69 using intermediate 70-5 instead of intermediate 69-5. ¹H NMR (400 MHz, Methanol-d4) δ 7.90 (s, 1H), 7.54 (d, J=1.3 Hz, 1H), 7.42 (ddt, J=29.9, 8.3, 2.0 Hz, 2H), 6.98 (dd, J=35.4, 4.6 Hz, 2H), 4.82 (d, J=5.3 Hz, 1H), 4.76-4.62 (m, 2H), 4.36 (d, J=4.8 Hz, 1H), 4.26 (t, J=5.4 Hz, 1H), 4.20-4.04 (m, 2H), 3.89 (qt, J=11.0, 5.5 Hz, 2H), 3.79-3.70 (m, 1H), 3.54-3.39 (m, 4H), 1.55 (p, J=6.6 Hz, 2H), 1.29 (d, J=9.7 Hz, 32H), 0.96-0.85 (m, 3H). LCMS: 843.4 [M–H]⁻.

Intermediate 71-1: (R)-1-((tert-butyldimethylsilyl)oxy)-3-(hexadecyloxy)propan-2-ol

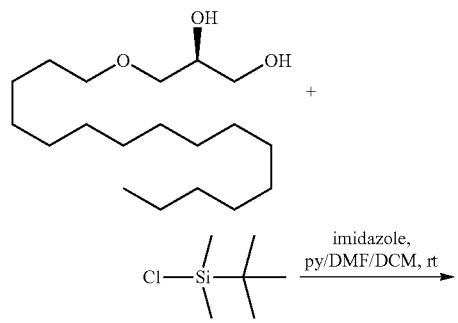

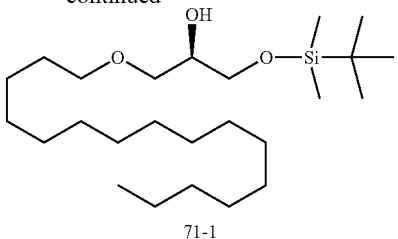

To a solution of (S)-3-(hexadecyloxy)propane-1,2-diol (5 g, 15.8 mmol) and imidazole (215 mg, 3.16 mmol) in a mixture of pyridine (29 mL), CH₂Cl₂ (6 mL) and DMF (6 mL) was added tert-butylchlorodimethylsilane (2.74 g, 18.2 mmol) at 0° C. After being stirred at room temperature overnight, the reaction mixture was diluted with water, then extracted with hexanes, and dried over Na₂SO₄. The solvent was evaporated, and the residue was purified by flash chromatography (0-30% EtOAc in hexanes), giving the product. ¹H NMR (400 MHz, Chloroform-d) δ 3.89-3.78 (m, 1H), 3.67 (m, 2H), 3.53-3.41 (m, 4H), 1.59 (m, 2H), 1.28 (s, 26H), 0.92 (s, 12H), 0.10 (s, 6H).

Intermediate 71-2: (R)-3-(((1-((tert-butyldimethylsilyl)oxy)-3-(hexadecyloxy)propan-2-yl)oxy)methyl)-5-fluorobenzonitrile

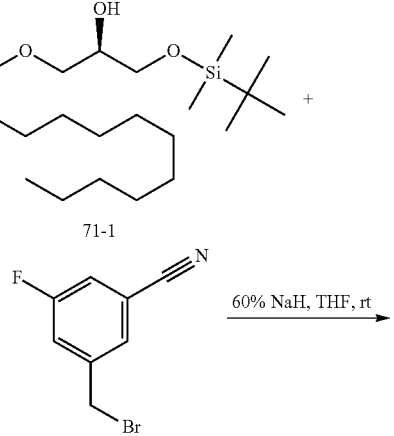

NaH (60% oil dispersion, 153 mg, 3.98 mmol) was suspended in THF (8 mL) and cooled to 0° C. A solution of (R)-1-((tert-butyldimethylsilyl)oxy)-3-(hexadecyloxy)propan-2-ol (350 mg, 0.812 mmol) in THF (2.5 mL) was added. After 30 min at 0° C. a solution of 3-(bromomethyl)-5-fluoro-benzonitrile (570 mg, 2.6 mmol) in THF (2.5 mL) was added. The mixture was stirred for 16 h at room temperature. The reaction was quenched with water (15 mL). The mixture was extracted with EtOAc. The combined organic phase was dried over sodium sulfate and the solvent was removed under reduced pressure. The residue was purified by flash chromatography (0-30% EtOAc in hexanes), giving the product. $^{1}$H NMR (400 MHz, Chloroform-d) δ 7.57-7.47 (m, 1H), 7.45-7.37 (m, 1H), 7.33 (m, 1H), 4.76 (s, 1H), 4.46 (s, 2H), 3.78-3.63 (m, 2H), 3.61-3.40 (m, 4H), 1.58 (m, 2H), 1.28 (s, 26H), 0.91 (d, J=7.0 Hz, 12H), 0.09 (s, 6H).

Intermediate 71-3: (S)-3-fluoro-5-(((1-(hexadecyloxy)-3-hydroxypropan-2-yl)oxy)methyl)benzonitrile

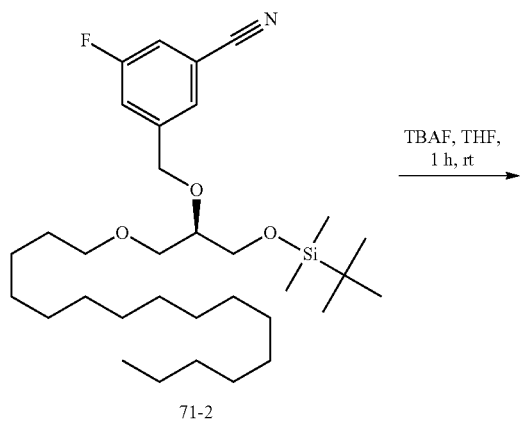

71-2

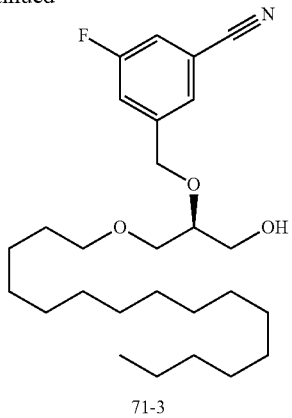

71-3

To a solution of above silyl protected compound (560 mg, 0.99 mmol) in THF (6 mL) at 0° C., 1 M TBAF in THF (2.4 mL, 2.4 mmol) was added and stirred for 1 h. It was diluted with water and extracted with EtOAc. The combined organic layers were washed with water, brine and dried (Na$_2$SO$_4$), evaporated and purified the residue by column chromatography silica gel, 0-60% ethyl acetate in hexanes to give the product. $^{1}$H NMR (400 MHz, Chloroform-d) δ 7.48 (s, 1H), 7.38 (d, J=9.4 Hz, 1H), 7.32-7.29 (m, 1H), 4.85-4.68 (m, 2H), 3.92-3.68 (m, 3H), 3.68-3.56 (m, 3H), 3.47 (m, 2H), 1.56 (m, 2H), 1.28 (s, 26H), 1.01-0.83 (m, 3H).

Intermediate 71-4: ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl (2-chlorophenyl) ((R)-2-((3-cyano-5-fluorobenzyl)oxy)-3-(hexadecyloxy)propyl) phosphate

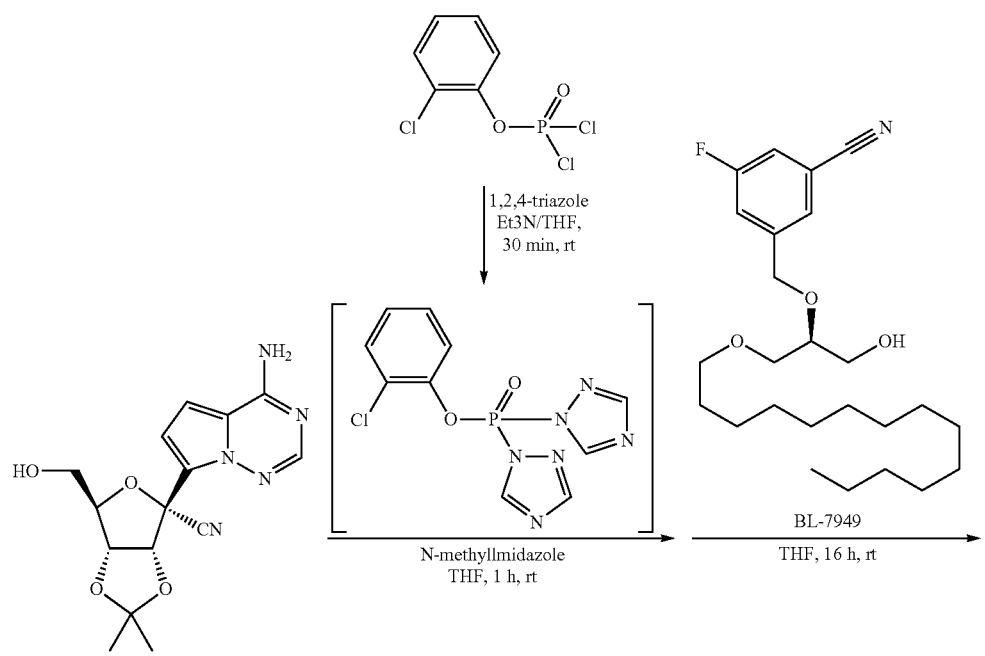

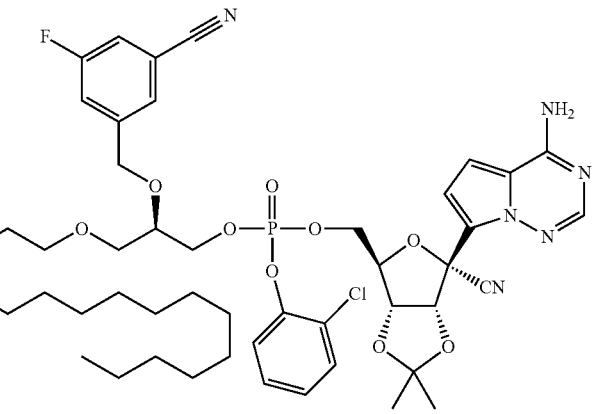

71-4

To a solution of 1,2,4-trizole (43 mg, 0.62 mmol) and triethylamine (87 uL, 0.62 mmol) in anhydrous THF (0.4 mL) was added a solution of 2-chlorophenyl dichlorophosphate (76 mg, 0.31 mmol) in THF (0.4 mL). The mixture was stirred for 30 min. and then filtered. To the filtrate were added sequentially, additional THF (1.2 mL), (3aR,4R,6R,6aR)-4-(4-aminopyrrolo[2,1-f][1,2,4]triazin-7-yl)-6-(hydroxymethyl)-2,2-dimethyltetrahydrofuro[3,4-d][1,3]dioxole-4-carbonitrile (78 mg, 0.235 mmol), and 1-methylimidazole (26 mg, 0.31 mmol). After 1 h, (S)-3-fluoro-5-(((1-(hexadecyloxy)-3-hydroxypropan-2-yl)oxy)methyl)benzonitrile (106 mg, 0.235 mmol) was added to the mixture and stirred overnight at room temperature. The solvent was evaporated, and the residue was purified by flash chromatography on silica gel (0-15% MeOH in $CH_2Cl_2$) to afford the compound.

Example 71: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((3-cyano-5-fluorobenzyl)oxy)-3-(hexadecyloxy)propyl) hydrogen phosphate (71)

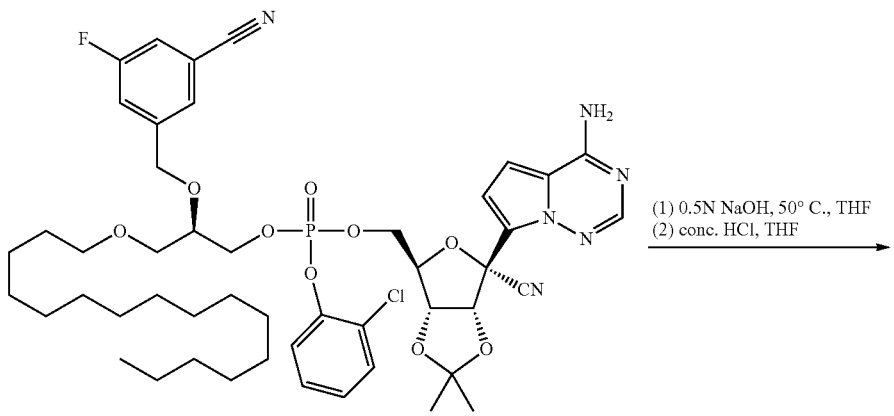

71-4

(1) 0.5N NaOH, 50° C., THF
(2) conc. HCl, THF

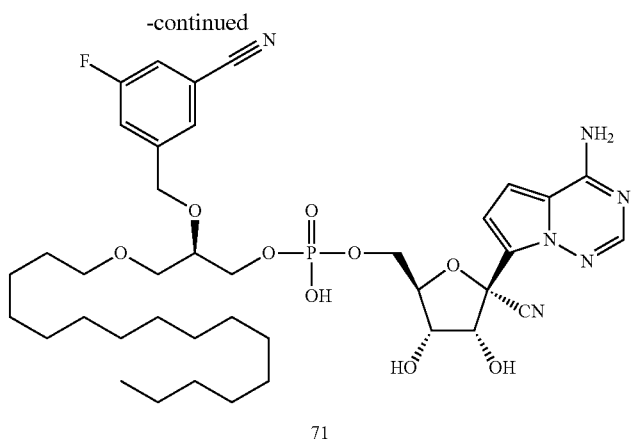

71

Step 1: The above intermediate 71-4 (270 mg, 0.28 mmol) was dissolved in THF (5.6 mL) and 0.5 N NaOH (2.04 mL, 1.02 mmol) was added at 0° C. The mixture was stirred at 50° C. for 4 h. The reaction progress was monitored by TLC. After nearly compete consumption of intermediate, the mixture was neutralized with 4 N HCl at 0 C. The mixture was diluted with a pH3 buffer solution and brine, extracted twice with a mixture of DCM and MeOH. The combined organic layers were combined, dried over anhydrous $Na_2SO_4$, filtered and evaporated. The residue was purified by flash chromatography on silica gel (0-60% MeOH in $CH_2Cl_2$) to afford a compound which was used in the next step.

Step 2: The above compound was dissolved in THF (0.75 mL). Concentrated aqueous HCl (0.15 mL) was added. The reaction mixture was stirred vigorously for 3 h. The mixture was neutralized with $Na_2CO_3$, diluted with MeOH, and filtered. The filtrate was evaporated to give a residue which was purified by flash chromatography on silica gel (0-60% MeOH in $CH_2Cl_2$) to afford the compound. $^1$H NMR (400 MHz, Methanol-$d_4$) δ 7.87 (s, 1H), 7.54 (s, 1H), 7.50-7.43 (m, 1H), 7.38 (m, 1H), 7.00 (d, J=4.6 Hz, 1H), 6.88 (d, J=4.6 Hz, 1H), 4.78-4.58 (m, 2H), 4.37 (d, m, 1H), 4.27 (m, 1H), 4.20-4.00 (m, 2H), 3.88 (m, 2H), 3.78-3.69 (m, 1H), 3.55-3.37 (m, 5H), 1.53 (m, 2H), 1.29 (m, 26H), 0.91 (t, J=6.7 Hz, 3H). $^{31}$P NMR (162 MHz, Methanol-d4) δ 0.45. MS: 803.36 (M+1).

Intermediate 72-1:
4-fluoro-2-isopropoxybenzonitrile

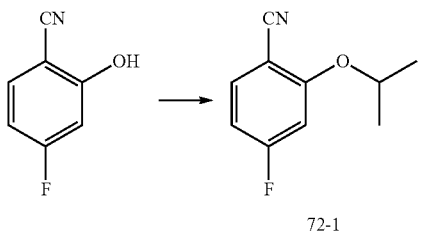

72-1

Diisopropyl azodicarboxylate (431 µL, 2.19 mmol) was added over 1 min via syringe to a stirred mixture of 4-fluoro-2-hydroxybenzonitrile (200 mg, 1.46 mmol), triphenylphosphine (574 mg, 2.19 mmol), 2-propanol (179 µL, 2.33 mmol), and tetrahydrofuran (1.5 mL) at 0° C., and the resulting mixture was warmed to room temperature. After 50 min, the resulting mixture was concentrated under reduced pressure. The residue was purified by flash column chromatography on silica gel (0 to 8% ethyl acetate in hexanes) to give intermediate 72-1. $^1$H NMR (400 MHz, Chloroform-d) δ 7.61-7.51 (m, 1H), 6.78-6.60 (m, 2H), 4.62 (hept, J=6.1 Hz, 1H), 1.44 (d, J=6.1 Hz, 6H).

Intermediate 72-2: (S)-4-((1-hydroxy-3-(octadecyloxy)propan-2-yl)oxy)-2-isopropoxybenzonitrile

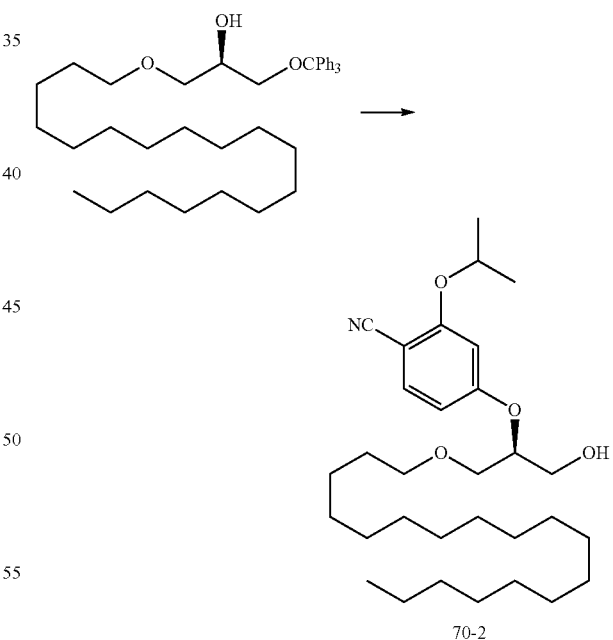

70-2

Sodium hydride (60% wt dispersion in mineral oil, 18.6 mg, 464 µmol) was added to a vigorously stirred solution of (R)-1-(octadecyloxy)-3-(trityloxy)propan-2-ol (WO2010052718) (109 mg, 186 µmol) in tetrahydrofuran (0.7 mL) at room temperature. After 30 min, intermediate 72-1 (66.6 mg, 371 µmol) and N,N-dimethylformamide (0.7 mL) were added sequentially, and the resulting mixture was heated to 70° C. After 55 min, the resulting mixture was cooled to room temperature. After 8 min, 2-propanol (1.0 mL), methanol (1.0 mL), chlorotrimethylsilane (47.1 µL, 371 µmol), and concentrated hydrochloric acid (0.2 mL) were added sequentially, and the resulting mixture was heated to 50° C. After 136 min, the resulting mixture was cooled to room temperature. Saturated aqueous sodium bicarbonate solution (10 mL), diethyl ether (40 mL), and ethyl acetate (20 mL) were added sequentially. The organic layer was washed with water (2×40 mL), was dried over anhydrous magnesium sulfate, was filtered, and was concentrated under reduced pressure. The residue was purified by flash column chromatography on silica gel (0 to 35% ethyl acetate in hexanes) to give intermediate 72-2. LCMS: 504.4.

Intermediate 72-3: ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl (2-chlorophenyl) hydrogen phosphate

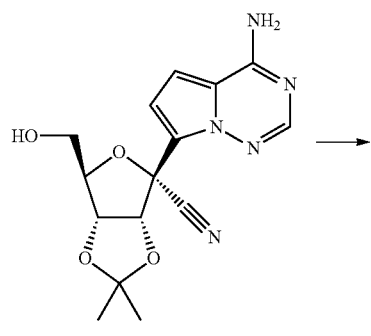

1-3

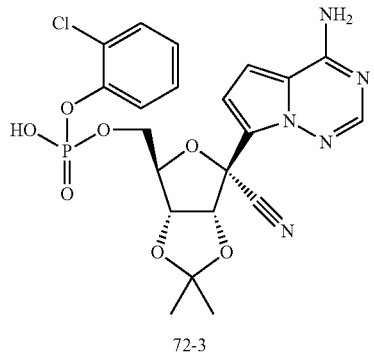

72-3

2-Chlorophenyl phosphorodichloridate (564 µL, 3.49 mmol) was added over 2 min via syringe to a vigorously stirred mixture of 1,2,4-triazole (484 mg, 7.01 mmol), triethylamine (977 µL, 7.01 mmol), and tetrahydrofuran (2.0 mL) at room temperature. After 50 min, intermediate 1-3 (1.00 g, 3.02 mmol), tetrahydrofuran (3.0 mL), and 1-methylimidazole (278 µL, 3.49 mmol) were added sequentially.

After 130 min, water (1.0 mL) and acetonitrile (1.0 mL) were added sequentially. After 10 min, silica gel (12 g) and acetonitrile (50 mL) were added sequentially, and the resulting mixture was concentrated under reduced pressure. The residue was purified by flash column chromatography on silica gel to give intermediate 72-3. LCMS: 522.1.

Example 72: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-(4-cyano-3-isopropoxyphenoxy)-3-(octadecyloxy)propyl) hydrogen phosphate (72)

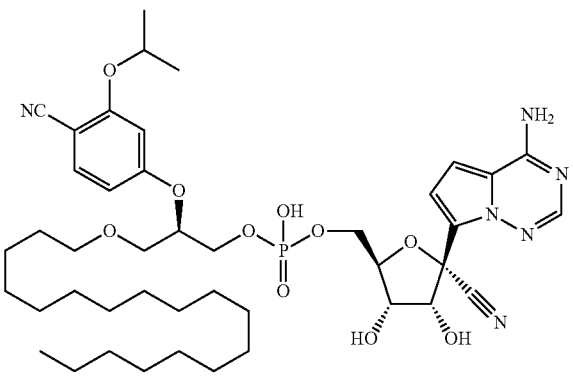

72

Bis(2-oxo-3-oxazolidinyl)phosphinic chloride (150 mg, 590 µmol) was added to a vigorously stirred mixture of intermediate 72-2 (99.1 mg, 197 µmol), intermediate 72-3 (103 mg, 197 µmol), triethylamine (32.9 µL, 242 µmol), 1-methylimidazole (47.0 µL, 590 µmol), and dichloromethane (2.0 mL) at room temperature. After 16 h 45 min, the resulting mixture was concentrated under reduced pressure. Tetrahydrofuran (0.3 mL), water (177 µL, 9.83 mmol), and 4-(dimethylamino)pyridine (72.1 mg, 590 µmol) were added sequentially, and the resulting mixture was stirred vigorously at room temperature. Tetrabutylammonium fluoride solution (1.0 M in tetrahydrofuran, 393 µL, 390 µmol) was added via syringe, and the resulting mixture was heated to 65° C. After 30 min, the resulting mixture was cooled to room temperature. After 5 min, chlorotrimethylsilane (49.9 µL, 393 µmol) and concentrated hydrochloric acid (650 µL, 7.8 mmol) were added sequentially. After 3 h, the resulting mixture was purified by reverse phase preparative HPLC (0.1% trifluoroacetic acid in methanol/water) to give compound 72. $^1$H NMR (400 MHz, Methanol-$d_4$) δ 8.07 (s, 1H), 7.41 (d, J=8.6 Hz, 1H), 7.33 (d, J=4.8 Hz, 1H), 7.19 (d, J=4.8 Hz, 1H), 6.73 (d, J=2.2 Hz, 1H), 6.66 (dd, J=8.7, 2.2 Hz, 1H), 4.78-4.66 (m, 3H), 4.38-4.32 (m, 1H), 4.22 (t, J=5.5 Hz, 1H), 4.20-4.14 (m, 1H), 4.10-4.01 (m, 3H), 3.71 (dd, J=10.9, 3.7 Hz, 1H), 3.63 (dd, J=10.9, 5.9 Hz, 1H), 3.53-3.39 (m, 2H), 1.59-1.47 (m, 2H), 1.36 (d, J=6.1 Hz, 6H), 1.33-1.21 (m, 30H), 0.91 (t, J=6.7 Hz, 3H). LCMS: 855.4 [M−H]$^−$.

Intermediate 73-1: (S)-2-((1-hydroxy-3-(octadecyloxy)propan-2-yl)oxy)benzonitrile

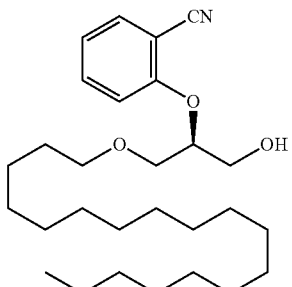

Intermediate 73-1 was prepared in a manner similar to intermediate 72-2 using 2-fluorobenzonitrile instead of intermediate 72-1. LCMS: 446.4.

Example 73: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-(2-cyanophenoxy)-3-(octadecyloxy)propyl) hydrogen phosphate (73)

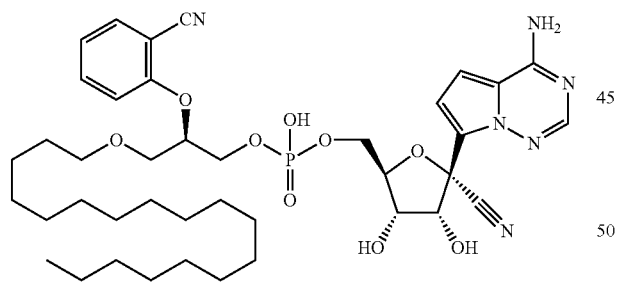

Compound 73 was prepared in a manner similar to compound 19 using intermediate 73-1 instead of intermediate 19-2. $^1$H NMR (400 MHz, Methanol-$d_4$) δ 8.05 (s, 1H), 7.60-7.51 (m, 2H), 7.33-7.28 (m, 1H), 7.27 (d, J=4.7 Hz, 1H), 7.16 (d, J=4.8 Hz, 1H), 7.03 (t, J=7.6 Hz, 1H), 4.81-4.74 (m, 2H), 4.34 (s, 1H), 4.26 (t, J=5.3 Hz, 1H), 4.21-4.13 (m, 1H), 4.12-3.99 (m, 3H), 3.74 (dd, J=11.1, 3.5 Hz, 1H), 3.67 (dd, J=11.1, 6.3 Hz, 1H), 3.54-3.40 (m, 2H), 1.54-1.44 (m, 2H), 1.37-1.20 (m, 30H), 0.91 (t, J=6.6 Hz, 3H). LCMS: 797.4 [M−H]$^-$.

Example 74: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-(4-cyano-3-methoxyphenoxy)-3-(octadecyloxy)propyl) hydrogen phosphate (74)

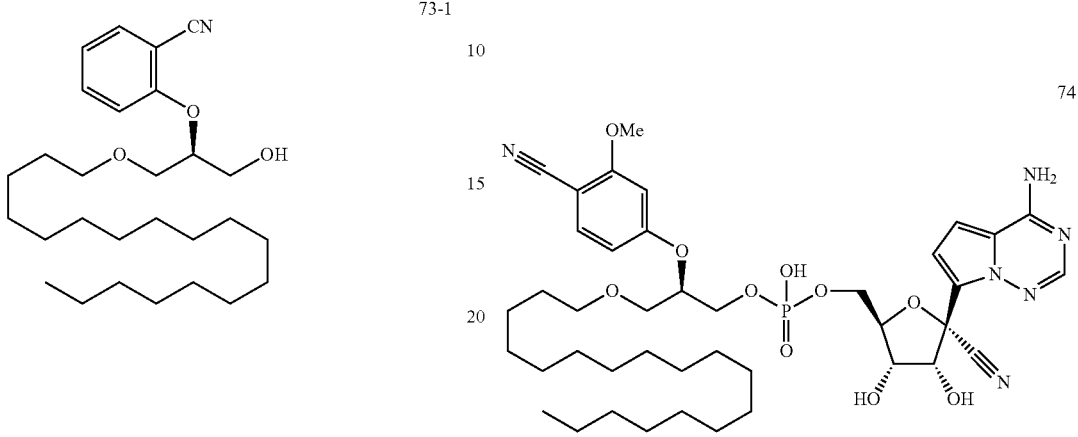

Compound 74 was prepared in a manner similar to compound 73 using 4-fluoro-2-methoxybenzonitrile instead of 2-fluorobenzonitrile. $^1$H NMR (400 MHz, Methanol-$d_4$) δ 8.02 (s, 1H), 7.41 (d, J=8.6 Hz, 1H), 7.20 (d, J=4.8 Hz, 1H), 7.13 (d, J=4.7 Hz, 1H), 6.76-6.72 (m, 1H), 6.70-6.63 (m, 1H), 4.81-4.66 (m, 1H), 4.39-4.31 (m, 1H), 4.28-4.19 (m, 1H), 4.19-3.74 (m, 4H), 3.90 (s, 3H), 3.69 (dd, J=11.0, 3.6 Hz, 1H), 3.62 (dd, J=10.9, 6.1 Hz, 1H), 3.60-3.38 (m, 3H), 1.69-1.46 (m, 2H), 1.39-1.19 (m, 30H), 0.92 (t, J=6.8 Hz, 3H).

LCMS: 827.4 [M−H]$^-$.

Intermediate 75-1: (S)-2-((5-bromopyridin-3-yl)methoxy)-3-(octadecyloxy)propan-1-ol

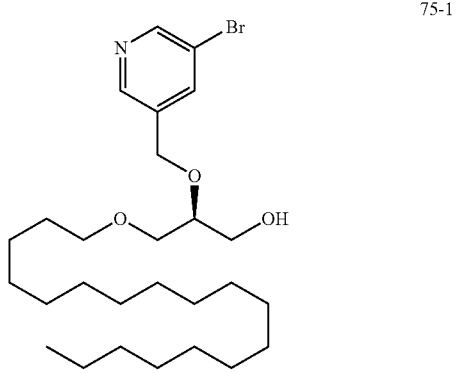 [SMILES: CCCCCCCCCCCCCCCCCCOC[C@H](CO)OCc1cncc(Br)c1]

Intermediate 75-1 was prepared in a manner similar to intermediate 72-2 using 3-bromo-5-(bromomethyl)pyridine hydrobromide instead of intermediate 72-1. LCMS: 514.3.

Intermediate 75-2: (S)-5-(((1-hydroxy-3-(octadecyloxy)propan-2-yl)oxy)methyl)nicotinonitrile Example 75: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((5-cyanopyridin-3-yl)methoxy)-3-(octadecyloxy)propyl) hydrogen phosphate (75)

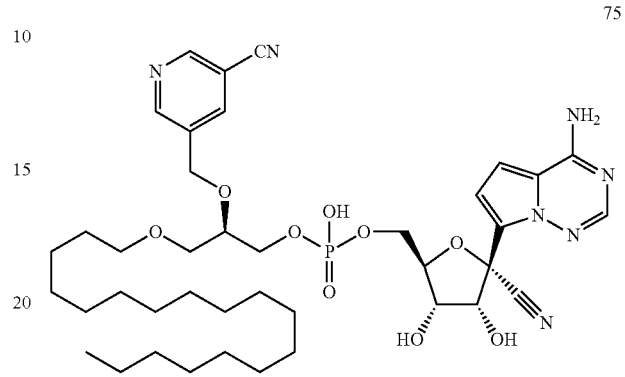

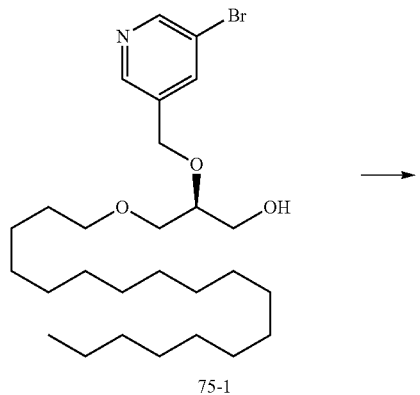

Compound 75 was prepared in a manner similar to compound 19 using intermediate 75-2 instead of intermediate 19-2. $^1$H NMR (400 MHz, Methanol-$d_4$) δ 8.77 (s, 2H), 8.20 (s, 1H), 8.06 (s, 1H), 7.28 (d, J=4.7 Hz, 1H), 7.19 (d, J=4.8 Hz, 1H), 4.95-4.83 (m, 1H), 4.80-4.72 (m, 2H), 4.40-4.30 (m, 1H), 4.29-4.14 (m, 2H), 4.14-4.05 (m, 1H), 4.05-3.88 (m, 2H), 3.83 (t, J=5.3 Hz, 1H), 3.62-3.52 (m, 2H), 3.45 (td, J=6.6, 2.4 Hz, 2H), 1.65-1.49 (m, 2H), 1.40-1.22 (m, 30H), 0.92 (t, J=6.7 Hz, 3H). LCMS: 814.4.

Intermediate 76-1: (S)-6-((1-hydroxy-3-(octadecyloxy)propan-2-yl)oxy)nicotinonitrile

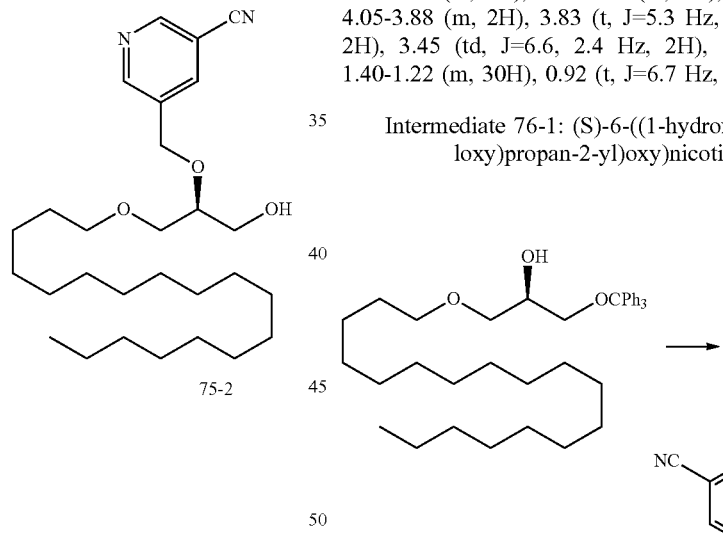

Tetrakis(triphenylphosphine)palladium(0) (17.7 mg, 15.3 μmol) was added to a vigorously stirred mixture of intermediate 75-1 (75.0 mg, 146 μmol), zinc(II) cyanide (35.9 mg, 309 μmol), and N,N-dimethylformamide (2.0 mL) at room temperature, and the resulting mixture was heated to 100° C. After 3 h, the resulting mixture was cooled to room temperature, and diethyl ether (40 mL), ethyl acetate (20 mL), saturated sodium bicarbonate solution (10 mL), and saturated aqueous sodium carbonate solution (5 mL) were added sequentially. The organic layer was washed with water (2×80 mL), was dried over anhydrous magnesium sulfate, was filtered, and was concentrated under reduced pressure. The residue was purified by flash column chromatography on silica gel (0 to 50% ethyl acetate in hexanes) to give intermediate 75-2. LCMS: 461.4.

Sodium hydride (60% wt dispersion in mineral oil, 18.6 mg, 464 μmol) was added to a vigorously stirred solution of (R)-1-(octadecyloxy)-3-(trityloxy)propan-2-ol (WO2010052718) (75.0 mg, 128 μmol) in tetrahydrofuran (0.7 mL) at room temperature. After 40 min, 6-fluoronicotinonitrile (78.0 mg, 639 μmol) and N,N-dimethylformamide (0.7 mL) were added sequentially, and the resulting mixture was heated to 65° C. After 2 h, the resulting mixture was heated to 80° C. After 18.5 h, the resulting mixture was cooled to room temperature, and saturated aqueous sodium bicarbonate solution (10 mL), diethyl ether (40 mL), and ethyl acetate (20 mL) were added sequentially. The organic layer was washed with water (40 mL), was dried over anhydrous magnesium sulfate, was filtered, and was concentrated under reduced pressure. The residue was purified by flash column chromatography on silica gel (0 to 40% ethyl acetate in hexanes) to give (R)-6-((1-(octadecyloxy)-3-(trityloxy)propan-2-yl)oxy)nicotinonitrile, which was dissolved in dichloromethane. The resulting solution was stirred vigorously at room temperature, and ceric ammonium nitrate (10% wt on silica gel, 70.1 mg, 12.8 µmol) was added. After 44 min, ceric ammonium nitrate (10% wt on silica gel, 70.1 mg, 12.8 µmol) was added. After 71 min, the resulting mixture was heated to 50° C. After 70 min, water (0.1 mL) was added. After 16.5 h, the resulting mixture was cooled to room temperature and was filtered through celite. The filter cake was extracted with ethyl acetate (50 mL), and the combined filtrates were concentrated under reduced pressure. The residue was purified by flash column chromatography on silica gel (0 to 35% ethyl acetate in hexanes) to give intermediate 76-1.

LCMS: 447.4.

Example 76: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((5-cyanopyridin-2-yl)oxy)-3-(octadecyloxy)propyl) hydrogen phosphate (76)

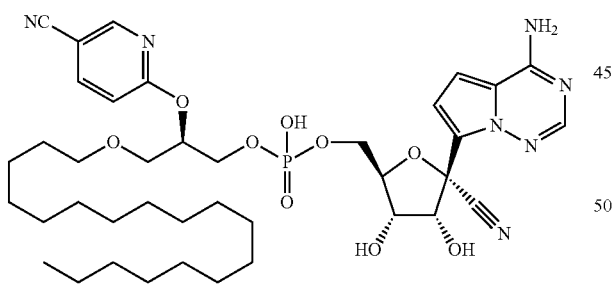

Compound 76 was prepared in a manner similar to compound 19 using intermediate 76-1 instead of intermediate 19-2. $^1$H NMR (400 MHz, Methanol-$d_4$) δ 8.49 (d, J=2.4 Hz, 1H), 8.11 (s, 1H), 7.94 (dd, J=8.7, 2.4 Hz, 1H), 7.38 (d, J=4.8 Hz, 1H), 7.18 (d, J=4.8 Hz, 1H), 6.94 (d, J=8.8 Hz, 1H), 5.56 (p, J=5.1 Hz, 1H), 4.74 (d, J=5.2 Hz, 1H), 4.35 (s, 1H), 4.31-4.04 (m, 5H), 3.72 (d, J=5.2 Hz, 2H), 3.53-3.41 (m, 2H), 1.58-1.42 (m, 2H), 1.39-1.10 (m, 30H), 0.91 (t, J=6.7 Hz, 3H). LCMS: 798.2 [M−H]$^-$.

Intermediate 77-1: (S)-5-((1-hydroxy-3-(octadecyloxy)propan-2-yl)oxy)pyrazine-2-carbonitrile

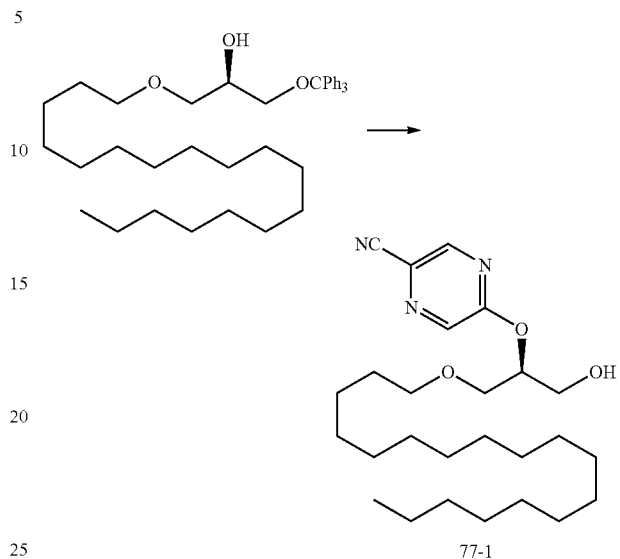

Sodium hydride (60% wt dispersion in mineral oil, 38.3 mg, 958 µmol) was added to a vigorously stirred solution of (R)-1-(octadecyloxy)-3-(trityloxy)propan-2-ol (WO2010052718) (75.0 mg, 128 µmol) in tetrahydrofuran (1.0 mL) at room temperature. After 30 min, 5-chloropyrazine-2-carbonitrile (78.0 mg, 639 µmol) was added, and the resulting mixture was heated to 70° C. After 70 min the resulting mixture was cooled to room temperature, and formic acid (2.0 mL) was added over 5 min via syringe. After 16 h, saturated aqueous sodium carbonate solution (20 mL) and ethyl acetate (60 mL) were added sequentially. The organic layer was washed with water (20 mL), was dried over anhydrous magnesium sulfate, was filtered, and was concentrated under reduced pressure. The residue was purified by flash column chromatography on silica gel (0 to 35% ethyl acetate in hexanes) to give intermediate 77-1. LCMS: 448.3.

Example 77: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((5-cyanopyrazin-2-yl)oxy)-3-(octadecyloxy)propyl) hydrogen phosphate (77)

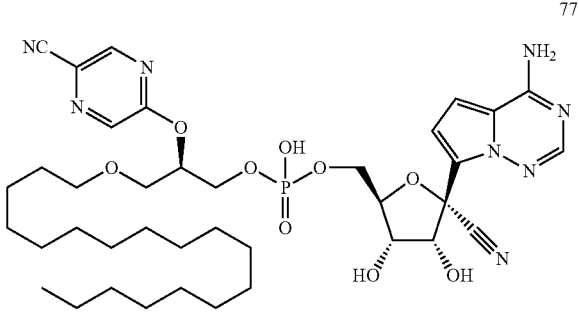 [SMILES: CCCCCCCCCCCCCCCCCCOC[C@H](COP(=O)(O)OC[C@H]1O[C@@](C#N)(c2ccc3c(N)ncnn23)[C@H](O)[C@@H]1O)Oc1ccc(C#N)cn1]

Compound 77 was prepared in a manner similar to compound 19 using intermediate 77-1 instead of intermediate 19-2. ¹H NMR (400 MHz, Methanol-d₄) δ 8.55 (d, J=1.3 Hz, 1H), 8.28 (d, J=1.3 Hz, 1H), 8.07 (s, 1H), 7.26 (d, J=4.7 Hz, 1H), 7.16 (d, J=4.8 Hz, 1H), 5.59-5.50 (m, 1H), 4.77 (d, J=5.2 Hz, 1H), 4.38-4.32 (m, 1H), 4.22 (t, J=5.4 Hz, 1H), 4.19-3.99 (m, 4H), 3.76-3.63 (m, 2H), 3.50-3.41 (m, 2H), 1.57-1.44 (m, 2H), 1.40-1.19 (m, 30H), 0.92 (t, J=6.7 Hz, 3H). LCMS: 799.4 [M−H]⁻.

Intermediate 78-1: (R)-5-((1-(octadecyloxy)-3-((triisopropylsilyl)oxy)propan-2-yl)oxy)picolinonitrile

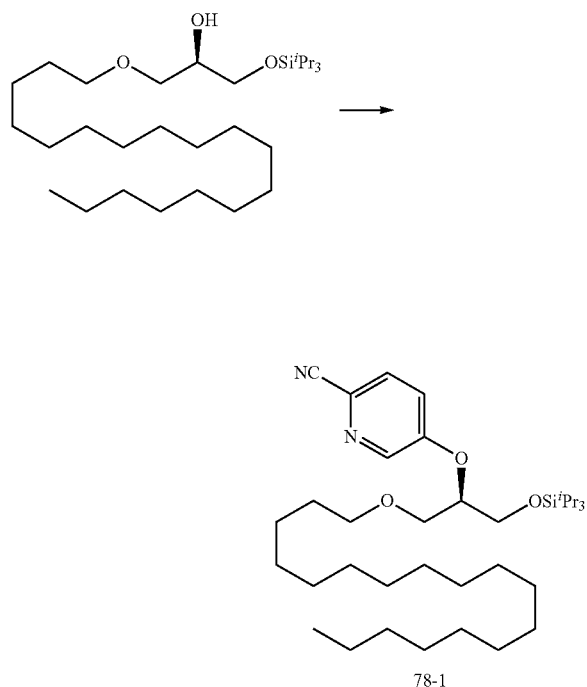

78-1

Sodium hydride (60% wt dispersion in mineral oil, 26.8 mg, 669 µmol) was added to a vigorously stirred solution of (R)-1-(octadecyloxy)-3-((triisopropylsilyl)oxy)propan-2-ol (112 mg, 223 µmol) in tetrahydrofuran (1.4 mL) at 0° C. After 30 min, 5-fluoropyridine-2-carbonitrile (95.3 mg, 780 µmol) was added, and the resulting mixture was heated to 70° C. After 60 min the resulting mixture was cooled to room temperature, and saturated aqueous ammonium chloride solution (2 mL), diethyl ether (40 mL), ethyl acetate (20 mL), and brine (15 mL) were added sequentially. The organic layer was washed with water (20 mL), was dried over anhydrous magnesium sulfate, was filtered, and was concentrated under reduced pressure. The residue was purified by flash column chromatography on silica gel (0 to 10% ethyl acetate in hexanes) to give intermediate 78-1. LCMS: 603.5.

Intermediate 78-2: (S)-5-((1-hydroxy-3-(octadecyloxy)propan-2-yl)oxy)picolinonitrile

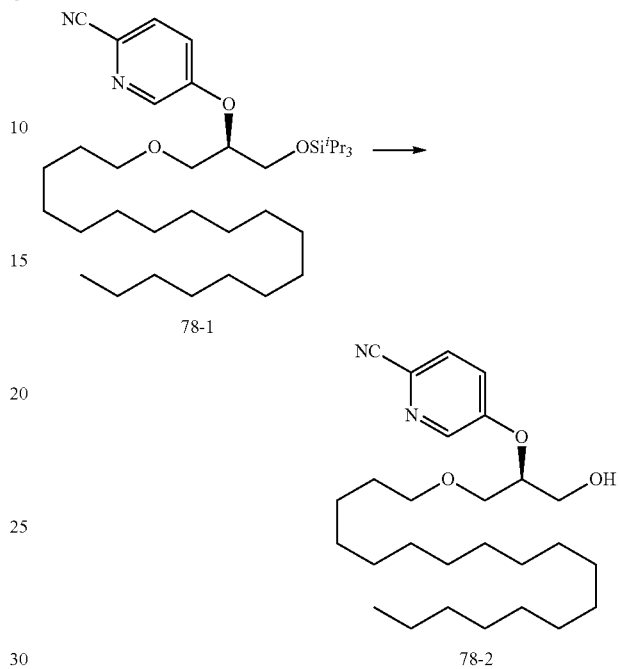

78-1

78-2

Tetrabutylammonium fluoride solution (1.0 M in tetrahydrofuran, 446 µL, 450 µmol) was added via syringe to a stirred solution of intermediate 78-1 (121 mg, 201 µmol) in tetrahydrofuran (1.0 mL) at room temperature. After 18 min, saturated aqueous ammonium chloride solution (3 mL), diethyl ether (40 mL), and ethyl acetate (20 mL) were added sequentially. The organic layer was washed with water (40 mL), was dried over anhydrous magnesium sulfate, was filtered, and was concentrated under reduced pressure. The residue was purified by flash column chromatography on silica gel (0 to 40% ethyl acetate in hexanes) to give intermediate 78-2. LCMS: 447.4.

Example 78: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((6-cyanopyridin-3-yl)oxy)-3-(octadecyloxy)propyl) hydrogen phosphate (78)

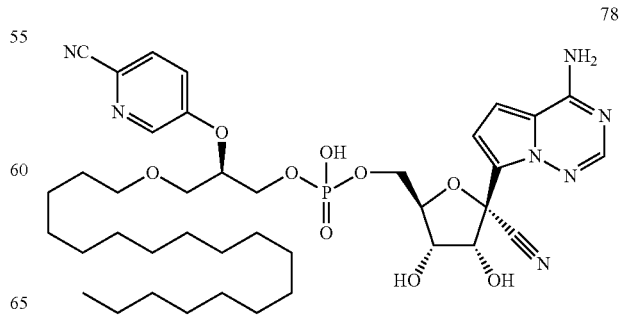

78

Compound 78 was prepared in a manner similar to compound 19 using intermediate 78-2 instead of intermediate 19-2. ¹H NMR (400 MHz, Methanol-d₄) δ 8.34 (d, J=2.8 Hz, 1H), 8.07 (s, 1H), 7.72 (d, J=8.7 Hz, 1H), 7.61 (dd, J=8.8, 2.9 Hz, 1H), 7.27 (d, J=4.8 Hz, 1H), 7.16 (d, J=4.8 Hz, 1H), 4.96-4.78 (m, 1H), 4.74 (d, J=5.3 Hz, 1H), 4.38-4.31 (m, 1H), 4.21 (t, J=5.6 Hz, 1H), 4.19-4.12 (m, 1H), 4.11-3.97 (m, 3H), 3.72 (dd, J=10.9, 3.4 Hz, 1H), 3.64 (dd, J=10.9, 6.5 Hz, 1H), 3.49-3.40 (m, 2H), 1.56-1.43 (m, 2H), 1.43-1.18 (m, 30H), 0.92 (t, J=6.7 Hz, 3H). LCMS: 798.4 [M−H]⁻.

Intermediate 79-1: tert-butyl (R)-2,2-dimethyl-4-((octadecyloxy)methyl)oxazolidine-3-carboxylate

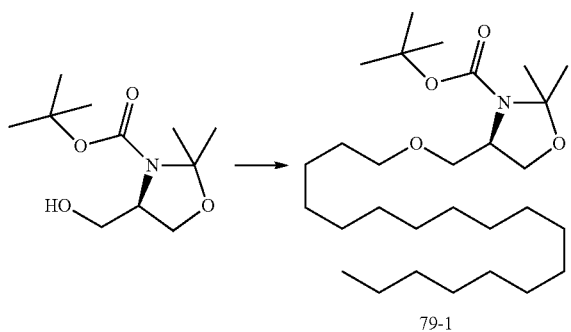 [SMILES: CC(C)(C)OC(=O)N1[C@H](CO)COC1(C)C ; CCCCCCCCCCCCCCCCCCOC[C@@H]1COC(C)(C)N1C(=O)OC(C)(C)C]

79-1

Sodium hydride (60% wt dispersion in mineral oil, 1.58 g, 40 mmol) was added to a vigorously stirred solution of tert-butyl (R)-4-(hydroxymethyl)-2,2-dimethyloxazolidine-3-carboxylate (3.05 g, 13.2 mmol) in N,N-dimethylformamide (25 mL) at 0° C. After 40 min, a solution of 1-bromooctadecane (11.0 g, 33.0 mmol) in tetrahydrofuran (10 mL) was added via syringe, and the resulting mixture was warmed to room temperature. After 58 h, saturated aqueous ammonium chloride solution (25 mL) and diethyl ether (450 mL) were added sequentially. The organic layer was washed with water (2×400 mL), was dried over anhydrous magnesium sulfate, was filtered, and was concentrated under reduced pressure. The residue was purified by flash column chromatography on silica gel (0 to 15% ethyl acetate in hexanes) to give intermediate 79-1. LCMS: 506.4 [M+Na]⁺.

Intermediate 79-2: (S)-2-amino-3-(octadecyloxy)propan-1-ol

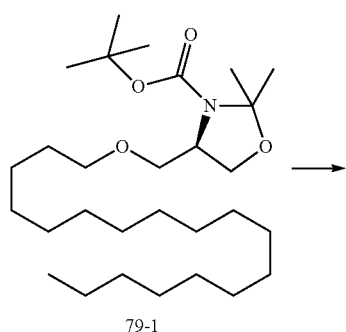

79-1

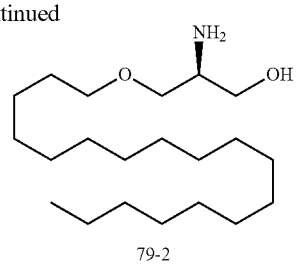

79-2

Hydrogen chloride solution (4.0 M in 1,4-dioxane, 9.15 mL, 37 mmol) was added via syringe to a stirred solution of intermediate 79-1 (4.80 g, 9.92 mmol) in 1,4-dioxane (21.6 mL) and water (0.62 mL) at 0° C. After 1 min, the resulting mixture was warmed to room temperature. After 4 h, saturated aqueous sodium carbonate solution (30 mL), diethyl ether (300 mL), and tetrahydrofuran (300 mL) were added sequentially. The organic layer was washed with a mixture of water and brine (1:1 v:v, 2×300 mL), was dried over anhydrous sodium sulfate, was filtered, and was concentrated under reduced pressure to give intermediate 79-2. LCMS: 344.3.

Intermediate 79-3: (S)-5-amino-1-(1-hydroxy-3-(octadecyloxy)propan-2-yl)-1H-imidazole-4-carbonitrile

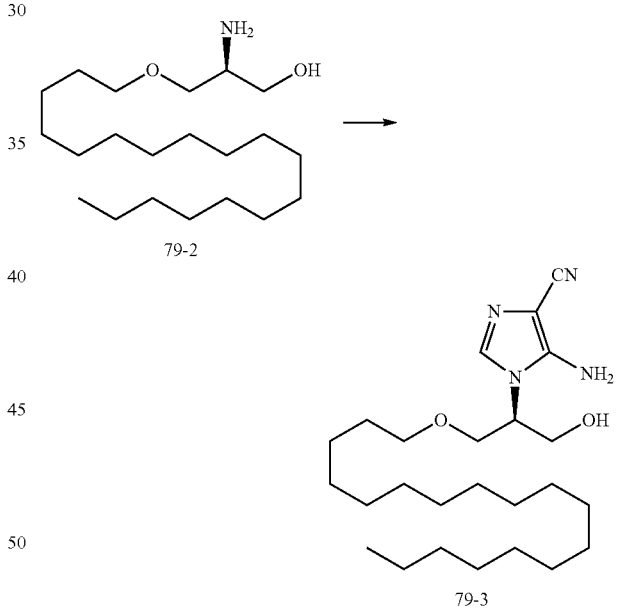

79-2

79-3

4-Methylmorpholine (26.6 µL, 242 µmol) was added via syringe to a vigorously stirred mixture of aminomalonitrile p-toluenesulfonate (61.4 mg, 242 µmol) and acetonitrile (1.0 mL) at room temperature. After 9 min, triethyl orthoformate (40.3 µL, 242 µmol) was added via syringe, and the resulting mixture was heated to 90° C. After 20 min, the resulting mixture was cooled to room temperature over 10 min, and intermediate 79-2 (75.0 mg, 218 µmol) was added. The resulting mixture was heated to 80° C. After 15 h, the resulting mixture was cooled to room temperature and was concentrated under reduced pressure. The residue was purified by flash column chromatography (0 to 9% methanol in dichloromethane) to give intermediate 79-3.
LCMS: 435.4.

Intermediate 79-4: (S)-1-(1-hydroxy-3-(octadecyloxy)propan-2-yl)-1H-imidazole-4-carbonitrile

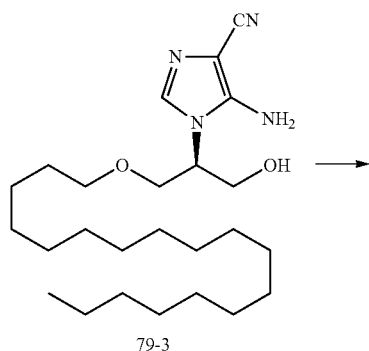

79-3

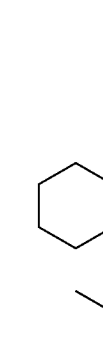

79-4

A solution of intermediate 79-3 (64.9 mg, 149 μmol) in tetrahydrofuran (1.0 mL) was added over 45 min via syringe pump to a vigorously stirred mixture of isoamyl nitrite (162 μL, 1.21 mmol) and tetrahydrofuran (0.5 mL) at 70° C. After 70 min, the resulting mixture was cooled to room temperature and was concentrated under reduced pressure. The residue was purified by flash column chromatography on silica gel (0 to 9% methanol in dichloromethane) to give intermediate 79-4. LCMS: 420.4.

Example 79: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-(4-cyano-1H-imidazol-1-yl)-3-(octadecyloxy)propyl) hydrogen phosphate (79)

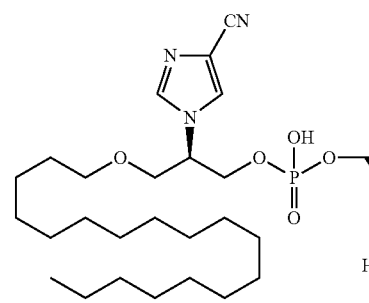

79

Compound 79 was prepared in a manner similar to compound 19 using intermediate 79-4 instead of intermediate 19-2. $^1$H NMR (400 MHz, Methanol-$d_4$) δ 8.09 (s, 1H), 8.01 (s, 1H), 7.88 (s, 1H), 7.32 (d, J=4.8 Hz, 1H), 7.16 (d, J=4.8 Hz, 1H), 4.75 (d, J=5.3 Hz, 1H), 4.67-4.56 (m, 1H), 4.40-4.26 (m, 1H), 4.23-4.11 (m, 3H), 4.10-4.03 (m, 1H), 4.03-3.94 (m, 1H), 3.82-3.70 (m, 2H), 3.48-3.38 (m, 2H), 1.58-1.42 (m, 2H), 1.41-1.10 (m, 30H), 0.92 (t, J=6.6 Hz, 3H). LCMS: 771.4 [M–H]$^-$.

Example 80: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((6-cyanopyridazin-3-yl)oxy)-3-(octadecyloxy)propyl) hydrogen phosphate (80)

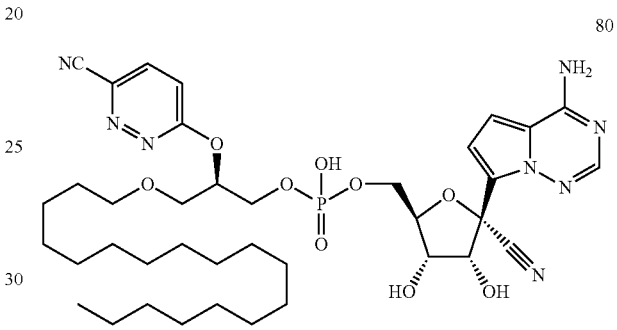

80

Compound 80 was prepared in a manner similar to compound 78 using 6-chloropyridazine-2-carbonitrile instead of 5-fluoropyridine-2-carbonitrile. $^1$H NMR (400 MHz, Methanol-$d_4$) δ 8.09 (s, 1H), 7.93 (d, J=9.2 Hz, 1H), 7.36 (d, J=4.8 Hz, 1H), 7.30 (d, J=9.2 Hz, 1H), 7.18 (d, J=4.8 Hz, 1H), 5.74-5.64 (m, 1H), 4.69 (d, J=5.2 Hz, 1H), 4.34-4.26 (m, 1H), 4.26-4.01 (m, 5H), 3.76-3.71 (m, 2H), 3.53-3.37 (m, 2H), 1.58-1.40 (m, 2H), 1.35-1.14 (m, 30H), 0.88 (t, J=6.7 Hz, 3H). LCMS: 799.4 [M–H]$^-$.

Intermediate 81-1: (S)-2-azido-3-(octadecyloxy)propan-1-ol

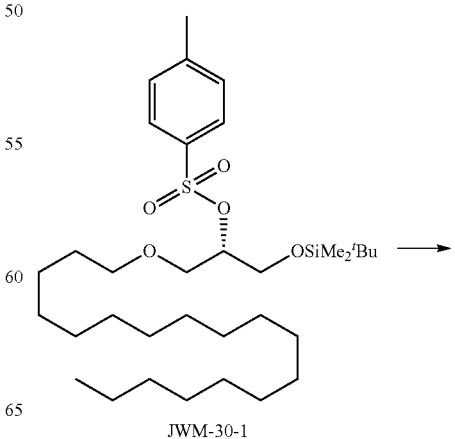

JWM-30-1

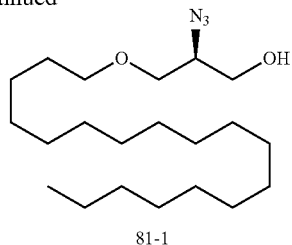

Sodium azide (53.0 mg, 816 μmol) was added to a vigorously stirred solution of intermediate 30-1 (100 mg, 163 μmol) in N,N-dimethylformamide (1.0 mL) at room temperature, and the resulting mixture was heated to 100° C. After 5 h, the resulting mixture was cooled to room temperature, and diethyl ether (40 mL) and ethyl acetate (20 mL) were added sequentially. The organic layer was washed with water (2×40 mL), was dried over anhydrous magnesium sulfate, was filtered, and was concentrated under reduced pressure. The residue was dissolved in tetrahydrofuran (0.5 mL), and the resulting solution was stirred at room temperature. Tetrabutylammonium fluoride solution (1.0 M in tetrahydrofuran, 326 μL, 330 μmol) was added via syringe. After 90 min, saturated aqueous ammonium chloride solution (5 mL), diethyl ether (40 mL), and ethyl acetate (20 mL) were added sequentially. The organic layer was washed with water (40 mL), was dried over anhydrous magnesium sulfate, was filtered, and was concentrated under reduced pressure. The residue was purified by flash column chromatography on silica gel (0 to 25% ethyl acetate in hexanes) to give intermediate 81-1.

LCMS: 392.3 [M+Na]$^+$.

Intermediate 81-2: (S)-1-(1-hydroxy-3-(octadecyloxy)propan-2-yl)-1H-1,2,3-triazole-4-carbonitrile

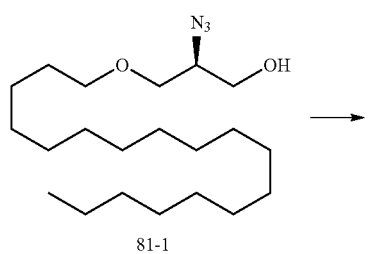

A stirred mixture of intermediate 81-1 (60.3 mg, 163 μmol), 3-ethoxyacrylonitrile (200 μL, 1.94 mmol), and toluene (0.4 mL) was heated in a microwave reactor to 200° C.

After 6 h, the resulting mixture was cooled to room temperature and was purified by flash column chromatography on silica gel (0 to 55% ethyl acetate in hexanes) to give intermediate 81-2.

LCMS: 421.3.

Example 81: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-(4-cyano-1H-1,2,3-triazol-1-yl)-3-(octadecyloxy)propyl) hydrogen phosphate (81)

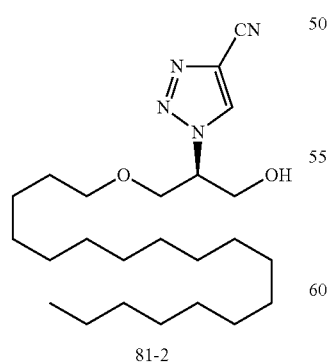

Compound 81 was prepared in a manner similar to compound 19 using intermediate 81-2 instead of intermediate 19-2. $^1$H NMR (400 MHz, Methanol-d$_4$) δ 8.75 (s, 1H), 8.07 (s, 1H), 7.27 (d, J=4.7 Hz, 1H), 7.14 (d, J=4.7 Hz, 1H), 5.11-4.98 (m, 1H), 4.79 (d, J=5.4 Hz, 1H), 4.37-4.29 (m, 1H), 4.25-4.16 (m, 3H), 4.10-4.02 (m, 1H), 4.02-3.92 (m, 1H), 3.85 (dd, J=10.5, 7.4 Hz, 1H), 3.78 (dd, J=10.6, 4.4 Hz, 1H), 3.49-3.35 (m, 2H), 1.53-1.41 (m, 2H), 1.40-1.11 (m, 30H), 0.92 (t, J=6.6 Hz, 3H). LCMS: 774.4.

Intermediate 82-1: (R)-5-((1-(octadecyloxy)-3-((triisopropylsilyl)oxy)propan-2-yl)oxy)pyrimidine-2-carbonitrile

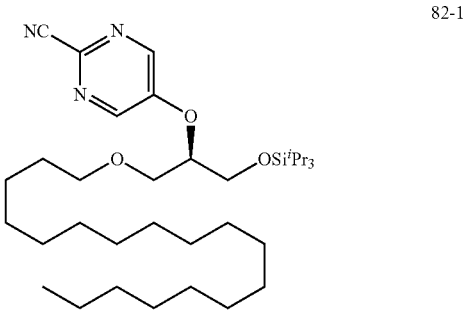

Intermediate 82-1 was prepared in a manner similar to compound 78-1 using 5-fluoropyrimidine-2-carbonitrile instead of 5-fluoropyridine-2-carbonitrile. LCMS: 604.5.

Intermediate 82-2: (S)-5-((1-hydroxy-3-(octadecyloxy)propan-2-yl)oxy)pyrimidine-2-carbonitrile

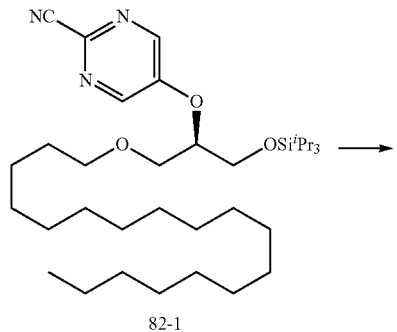

82-1

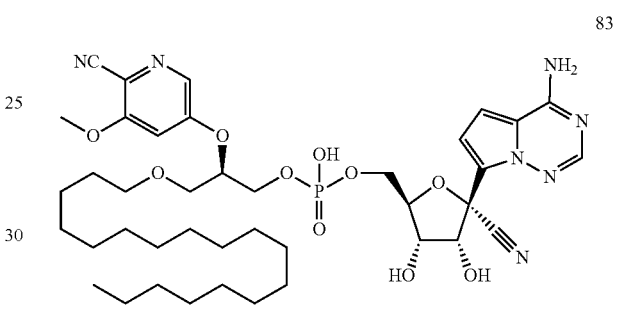

82-2

Olah's reagent (0.3 mL) was added via syringe to a vigorously stirred solution of intermediate 82-1 (116 mg, 191 μmol) in tetrahydrofuran (3.0 mL) at room temperature. After 106 min, Olah's reagent (0.3 mL) via syringe. After 180 min, the resulting mixture was poured into a vigorously stirred suspension of silica gel (1.15 g) in ethyl acetate (30 mL) at 0° C., and the resulting mixture was filtered through celite. The filter cake was extracted with ethyl acetate (30 mL), and the combined filtrates were concentrated under reduced pressure. The residue was purified by flash column chromatography on silica gel (0 to 50% ethyl acetate in hexanes) to give intermediate 82-2. LCMS: 447.3.

Example 82: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((2-cyanopyrimidin-5-yl)oxy)-3-(octadecyloxy)propyl) hydrogen phosphate (82)

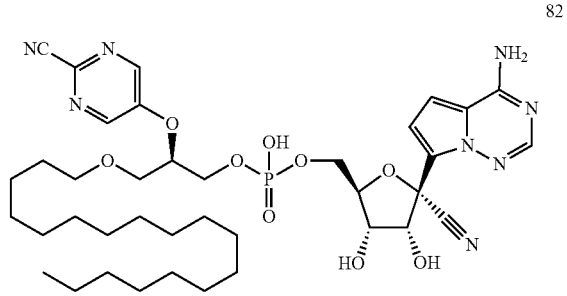 [SMILES: CCCCCCCCCCCCCCCCCCOC[C@H](COP(=O)(O)OC[C@H]1O[C@@](C#N)(c2ccc3c(N)ncnn23)[C@H](O)[C@@H]1O)Oc1cnc(C#N)nc1]

82

Compound 82 was prepared in a manner similar to compound 19 using intermediate 82-2 instead of intermediate 19-2. $^1$H NMR (400 MHz, Methanol-$d_4$) δ 8.62 (s, 2H), 8.08 (s, 1H), 7.28 (d, J=4.8 Hz, 1H), 7.17 (d, J=4.8 Hz, 1H), 5.04-4.92 (m, 1H), 4.75 (d, J=5.2 Hz, 1H), 4.41-4.30 (m, 1H), 4.21 (t, J=5.6 Hz, 1H), 4.19-4.11 (m, 1H), 4.10-3.99 (m, 3H), 3.73 (dd, J=11.1, 3.1 Hz, 1H), 3.64 (dd, J=10.9, 7.2 Hz, 1H), 3.51-3.37 (m, 2H), 1.54-1.41 (m, 2H), 1.39-1.15 (m, 30H), 0.92 (t, J=6.8 Hz, 3H). LCMS: 799.4 [M−H]$^-$.

Example 83: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((6-cyano-5-methoxypyridin-3-yl)oxy)-3-(octadecyloxy)propyl) hydrogen phosphate (83)

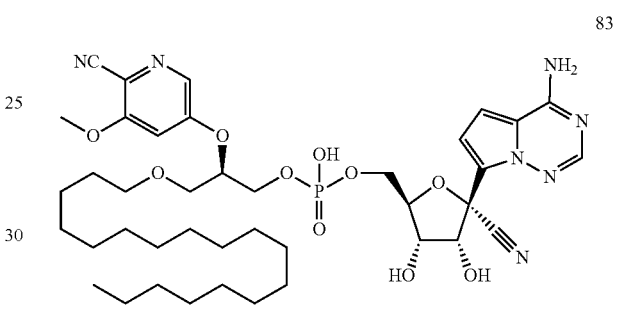

83

Compound 83 was prepared in a manner similar to compound 82 using 5-chloro-3-methoxypyridine-2-carbonitrile instead of 5-fluoropyrimidine-2-carbonitrile. $^1$H NMR (400 MHz, Methanol-$d_4$) δ 8.00 (s, 1H), 7.92 (d, J=2.2 Hz, 1H), 7.32 (d, J=2.1 Hz, 1H), 7.17-7.13 (m, 1H), 7.10 (d, J=4.7 Hz, 1H), 5.10-4.81 (m, 1H), 4.78 (d, J=5.2 Hz, 1H), 4.38-4.33 (m, 1H), 4.23 (t, J=5.5 Hz, 1H), 4.19-4.10 (m, 1H), 4.09-3.94 (m, 3H), 3.97 (s, 3H), 3.75-3.67 (m, 1H), 3.67-3.56 (m, 1H), 3.55-3.30 (m, 2H), 1.56-1.45 (m, 2H), 1.42-1.19 (m, 30H), 0.92 (t, J=6.8 Hz, 3H). LCMS: 828.4 [M−H]$^-$.

Intermediate 84-1: (R)-2-((5-cyanopyridin-3-yl)oxy)-3-(octadecyloxy)propyl 4-methylbenzenesulfonate

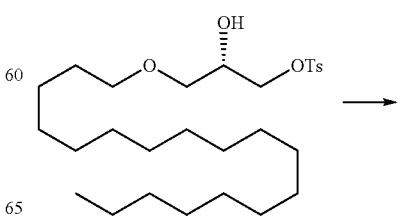

-continued

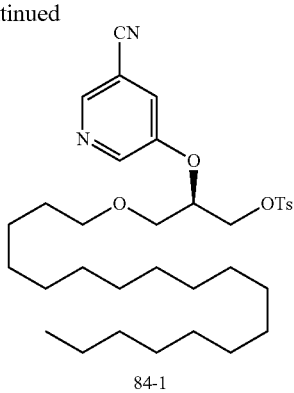

84-1

Diisopropyl azodicarboxylate (96.5 µL, 490 µmol) was added over 2 min via syringe to a stirred mixture of (S)-2-hydroxy-3-(octadecyloxy)propyl 4-methylbenzenesulfonate (Helvetica Chimica Acta 1982, 65, 1059) (150 mg, 301 µmol), triphenylphosphine (128 mg, 489 µmol), 5-hydroxynicotinonitrile (54.2 mg, 451 µmol), and tetrahydrofuran (3.0 mL) at 0° C., and the resulting mixture was warmed to room temperature. After 23.5 h, the resulting mixture was concentrated under reduced pressure. The residue was purified by flash column chromatography on silica gel (0 to 25% ethyl acetate in hexanes) to give intermediate 84-1. LCMS: 623.4 [M+Na]+.

Intermediate 84-2: (S)-5-((1-hydroxy-3-(octadecyloxy)propan-2-yl)oxy)nicotinonitrile

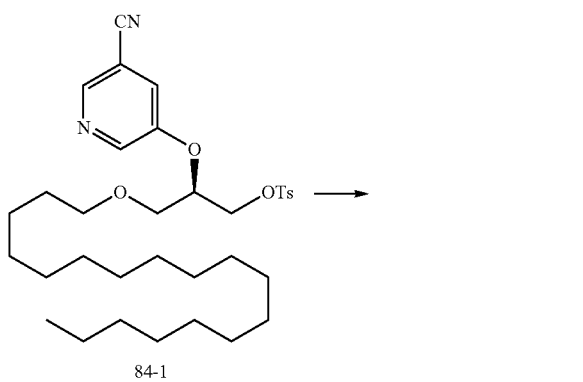

Sodium nitrite (1.04 g, 15.1 mmol) was added to a vigorously stirred solution of intermediate 84-1 (302 mg, 502 µmol) in dimethylsulfoxide (4.0 mL) at room temperature, and the resulting mixture was heated to 60° C. After 17 h 26 min, water (4.57 mL) was added via syringe. After 175 min, the resulting mixture was cooled to room temperature, and diethyl ether (100 mL) and ethyl acetate (20 mL) were added sequentially. The organic layer was washed with water (2×90 mL), was dried over anhydrous magnesium sulfate, was filtered, and was concentrated under reduced pressure. The residue was purified by flash column chromatography on silica gel (0 to 50% ethyl acetate in hexanes) to give intermediate 84-2. LCMS: 447.4.

Intermediate 84-3: ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl (2-chlorophenyl) ((R)-2-((5-cyanopyridin-3-yl)oxy)-3-(octadecyloxy)propyl) phosphate

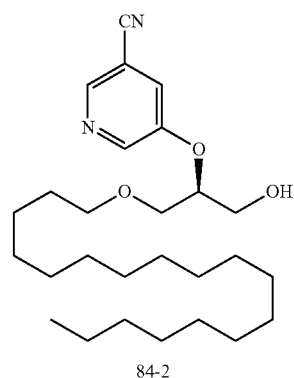

84-2

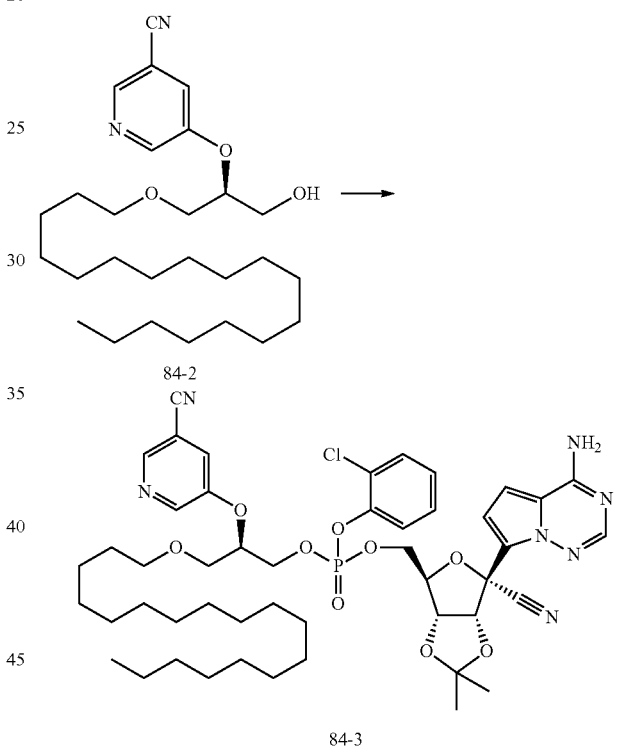

84-3

Bis(2-oxo-3-oxazolidinyl)phosphinic chloride (103 mg, 403 µmol) was added to a vigorously stirred mixture of intermediate 84-2 (90.0 mg, 201 µmol), intermediate 72-3 (105 mg, 201 µmol), triethylamine (33.7 µL, 242 µmol), 1-methylimidazole (32.1 µL, 403 µmol), and dichloromethane (2.0 mL) at room temperature. After 30 min, bis(2-oxo-3-oxazolidinyl)phosphinic chloride (51.5 mg, 202 µmol) and 1-methylimidazole (16.1 µL, 202 µmol) were added sequentially. After 90 min, diethyl ether (40 mL) and ethyl acetate (20 mL) were added sequentially. The organic layer was washed with a mixture of water and saturated aqueous sodium bicarbonate solution (4:1 v:v, 40 mL), was dried over anhydrous magnesium sulfate, was filtered, and was concentrated under reduced pressure. The residue was purified by flash column chromatography on silica gel (0 to 5% methanol in dichloromethane) to give intermediate 84-3. LCMS: 950.4.

Example 84: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((5-cyanopyridin-3-yl)oxy)-3-(octadecyloxy)propyl) hydrogen phosphate (84)

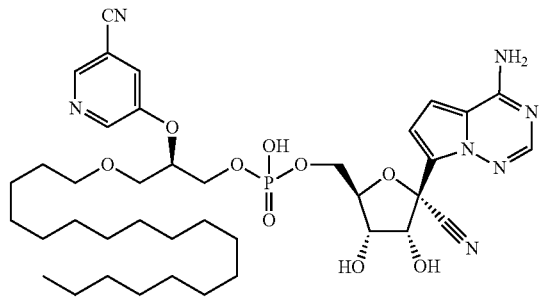

Tetrabutylammonium fluoride solution (1.0 M in tetrahydrofuran, 404 μl, 404 μmol) was added via syringe to a vigorously stirred mixture of intermediate 84-3 (192 mg, 202 μmol), 4-(dimethylamino)pyridine (74.0 mg, 606 μmol), tetrahydrofuran (0.5 mL), and water (182 μL, 10.1 mmol) at room temperature, and the resulting mixture was heated to 50° C. After 25 min, the resulting mixture was cooled to room temperature over 8 min. Chlorotrimethylsilane (51.3 μL, 404 μmol) and concentrated hydrochloric acid (560 μL, 6.7 mmol) were added sequentially. After 120 min, the resulting mixture was purified by reverse phase preparative HPLC (0.1% trifluoroacetic acid in methanol/water) to give compound 84. $^1$H NMR (400 MHz, Methanol-$d_4$) δ 8.52 (d, J=2.8 Hz, 1H), 8.42 (s, 1H), 8.10 (s, 1H), 7.91-7.84 (m, 1H), 7.34 (d, J=4.7 Hz, 1H), 7.20 (d, J=4.8 Hz, 1H), 4.97-4.77 (m, 1H), 4.75 (d, J=5.2 Hz, 1H), 4.38-4.31 (m, 1H), 4.24-4.13 (m, 2H), 4.12-4.00 (m, 3H), 3.73 (dd, J=10.7, 3.4 Hz, 1H), 3.65 (dd, J=10.9, 6.8 Hz, 1H), 3.53-3.36 (m, 2H), 1.58-1.43 (m, 2H), 1.40-1.21 (m, 30H), 0.92 (t, J=6.6 Hz, 3H). LCMS: 798.4 [M–H]$^-$.

Example 85: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-(4-cyano-3-ethoxyphenoxy)-3-(octadecyloxy)propyl) hydrogen phosphate (85)

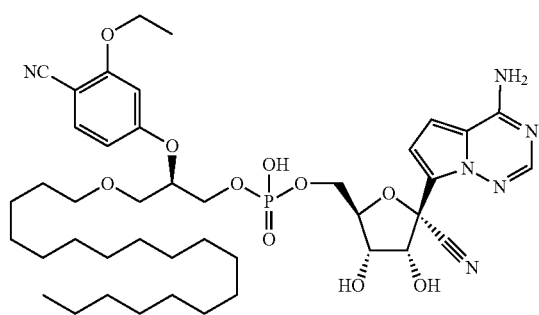

Compound 85 was prepared in a manner similar to compound 72 using 4-fluoro-2-ethoxybenzonitrile instead of intermediate 72-1. $^1$H NMR (400 MHz, Methanol-$d_4$) δ 8.07 (s, 1H), 7.41 (d, J=8.5 Hz, 1H), 7.31 (d, J=4.8 Hz, 1H), 7.18 (d, J=4.8 Hz, 1H), 6.71 (d, J=2.2 Hz, 1H), 6.68-6.61 (m, 1H), 4.81-4.72 (m, 2H), 4.38-4.31 (m, 1H), 4.23 (t, J=5.5 Hz, 1H), 4.20-4.01 (m, 6H), 3.71 (dd, J=10.8, 3.7 Hz, 1H), 3.64 (dd, J=10.9, 6.0 Hz, 1H), 3.54-3.39 (m, 2H), 1.58-1.47 (m, 2H), 1.44 (t, J=7.0 Hz, 3H), 1.39-1.17 (m, 30H), 0.92 (t, J=6.6 Hz, 3H). LCMS: 841.4 [M–H]$^-$.

Intermediate 86-1: (R)-(((2-((octadecyloxy)methyl)pent-4-en-1-yl)oxy)methyl)benzene

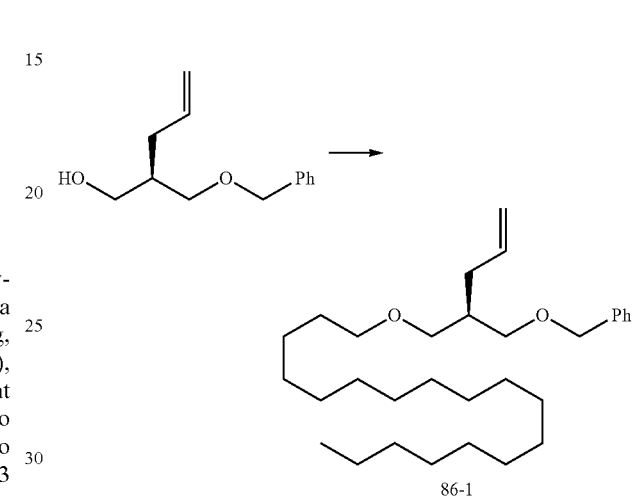

Sodium hydride (60% wt dispersion in mineral oil, 1.22 g, 30.4 mmol) was added to a vigorously stirred solution of (R)-2-((benzyloxy)methyl)pent-4-en-1-ol (Tetrahedron Lett. 2011, 52, 5559) (2.09 g, 10.1 mmol) in N,N-dimethylformamide (24.0 mL) at room temperature. After 30 min, a solution of 1-bromooctadecane (8.44 g, 25.3 mmol) in tetrahydrofuran (20 mL) was added over 3 min via cannula, and the resulting mixture was heated to 85° C. After 14.5 h, the resulting mixture was cooled to room temperature, and saturated aqueous ammonium chloride solution (10 mL), and diethyl ether (500 mL) were added sequentially. The organic layer was washed with a water (2×500 mL), was dried over anhydrous magnesium sulfate, was filtered, and was concentrated under reduced pressure. The residue was purified by flash column chromatography on silica gel (0 to 10% ethyl acetate in hexanes) to give intermediate 86-1. LCMS: 481.4 [M+Na]$^+$.

Intermediate 86-2: (R)-4-(benzyloxy)-3-((octadecyloxy)methyl)butanal

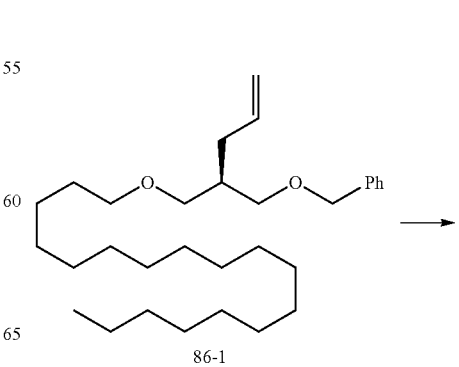

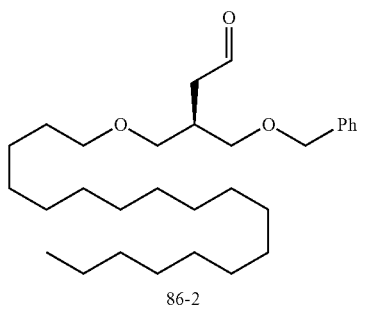

86-2

Osmium tetroxide solution (2.5% wt in tert-butanol, 1.06 mL, 85 µmol) was added via syringe to a vigorously stirred mixture of intermediate 86-1 (1.94 g, 4.23 mmol), 4-methylmorpholine-4-oxide (1.86 g, 9.52 mmol), 4-(dimethylamino)pyridine (51.7 mg, 423 µmol), tert-butanol (16 mL), tetrahydrofuran (8.0 mL), and water (6.0 mL) at room temperature, and the resulting mixture was heated to 70° C. After 60 min, the resulting mixture was cooled to room temperature, and sodium sulfite (1.07 g, 8.46 mmol) was added. After 60 min, aqueous citric acid solution (10% w/v, 30 mL), diethyl ether (200 mL), and ethyl acetate (50 mL) were added sequentially. The organic layer was washed sequentially with water (200 mL) and a mixture of water and brine (2:1 v:v, 150 mL), was dried over anhydrous magnesium sulfate, was filtered, and was concentrated under reduced pressure. The residue was dissolved in tetrahydrofuran (40 mL), and the resulting mixture was stirred vigorously at room temperature. A solution of sodium periodate (2.26 g, 10.6 mmol) in water (20 mL) was added over 2 min via glass pipette. After 120 min, ethyl acetate (250 mL) was added. The organic layer was washed with a mixture of water and brine (2:1 v:v, 150 mL), was dried over anhydrous magnesium sulfate, was filtered, and was concentrated under reduced pressure. The residue was purified by flash column chromatography on silica gel (0 to 10% ethyl acetate in hexanes) to give intermediate 86-2. LCMS: 483.4 [M+Na]$^+$.

Intermediate 86-3: (R)-(((2-((octadecyloxy)methyl)but-3-yn-1-yl)oxy)methyl)benzene

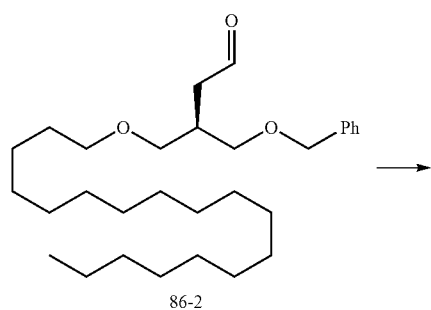

86-2

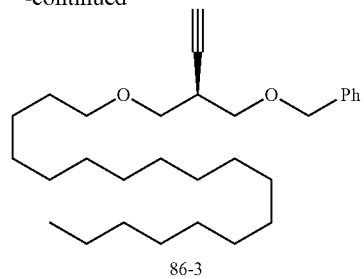

86-3 tert-Butylimino-tri(pyrrolidino)phosphorane (480 µL, 1.57 mmol) was added over 2 min via syringe to a stirred mixture of intermediate 86-2 (241 mg, 523 µmol), perfluoro-1-butanesulfonyl fluoride (141 µL, 785 µmol), N,N-dimethylformamide (1.3 mL), and tetrahydrofuran (0.2 mL) at 10° C., and the resulting mixture was warmed to room temperature. After 8 h 20 min, citric acid (500 mg), diethyl ether (40 mL), and ethyl acetate (20 mL) were added sequentially. The organic layer was washed with water (2×40 mL), was dried over anhydrous magnesium sulfate, was filtered, and was concentrated under reduced pressure. The residue was purified by flash column chromatography on silica gel (0 to 9% ethyl acetate in hexanes) to give intermediate 86-3. LCMS: 465.4 [M+Na]$^+$.

Intermediate 86-4: (R)-3-(4-(benzyloxy)-3-((octadecyloxy)methyl)but-1-yn-1-yl)-5-fluorobenzonitrile

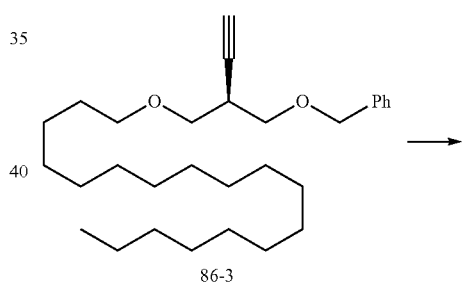

86-3

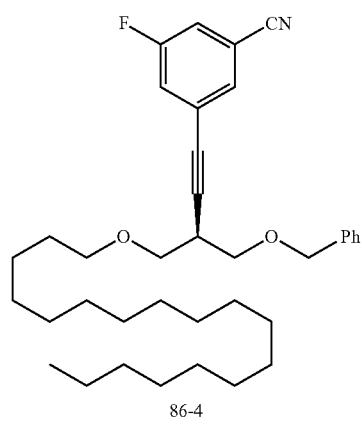

86-4

Triethylamine (315 µL, 2.26 mmol) was added via syringe to a vigorously stirred mixture of intermediate 86-3 (50.0 mg, 113 µmol), bis(triphenylphosphine)palladium(II) chloride (15.9 mg, 22.6 µmol), 5-fluoro-3-iodobenzonitrile (35.3 mg, 143 µmol), copper(I) iodide (8.6 mg, 45.2 µmol), N,N-dimethylformamide (0.8 mL), and tetrahydrofuran (0.2 mL) at room temperature, and the resulting mixture was heated to 80° C. After 110 min, the resulting mixture was cooled to room temperature, and aqueous citric acid solution (10% wt, 10 mL), diethyl ether (40 mL), and ethyl acetate (20 mL) were added sequentially. The organic layer was washed with water (2×30 mL), was dried over anhydrous magnesium sulfate, was filtered, and was concentrated under reduced pressure. The residue was purified by flash column chromatography on silica gel (0 to 12% ethyl acetate in hexanes) to give intermediate 86-4.

LCMS: 584.4 [M+Na]⁺.

Intermediate 86-5: (S)-3-fluoro-5-(4-hydroxy-3-((octadecyloxy)methyl)but-1-yn-1-yl)benzonitrile

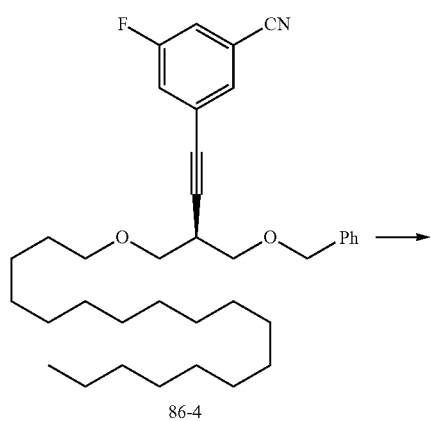

86-4

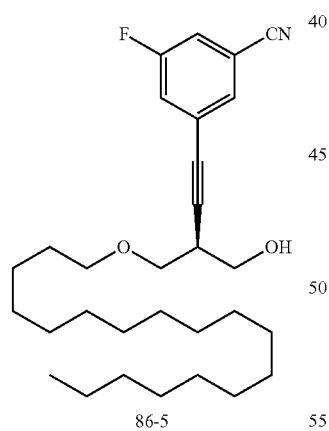

86-5

Boron trichloride solution (1.0 M in dichloromethane, 162 μL, 160 μmol) was added over 1 min via syringe to a stirred solution of intermediate 86-4 (45.6 mg, 81.2 μmol) in dichloromethane (1.3 mL) at 0° C. After 10 min, saturated aqueous sodium carbonate solution (1.0 mL) and ethyl acetate were sequentially added. The organic layer was washed with a mixture of water and brine (3:1 v:v, 30 mL), was dried over anhydrous magnesium sulfate, was filtered, and was concentrated under reduced pressure. The residue was purified by flash column chromatography on silica gel (0 to 32% ethyl acetate in hexanes) to give intermediate 86-5.

LCMS: 472.4 [M+Na]⁺.

Intermediate 86-6: (S)-3-fluoro-5-(4-hydroxy-3-((octadecyloxy)methyl)butyl)benzonitrile

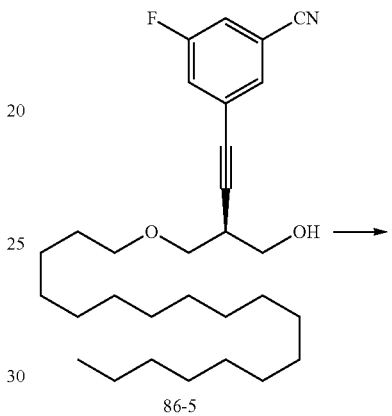

86-5

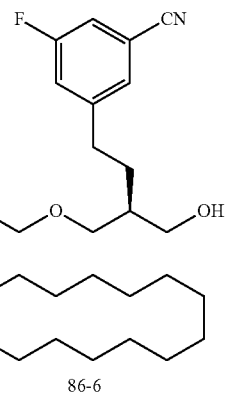

86-6

A vigorously stirred mixture of intermediate 86-5 (46.8 mg, 99.2 μmol), palladium (10% wt on carbon, 36.2 mg, 34.0 μmol), tetrahydrofuran (2.0 mL), and ethanol (0.5 mL) at room temperature was placed under an atmosphere of hydrogen gas (balloon). After 60 min, the resulting mixture was filtered through celite. The filter cake was extracted with ethyl acetate (30 mL), and the combined filtrates were concentrated under reduced pressure. The residue was purified by flash column chromatography on silica gel (0 to 19% ethyl acetate in hexanes) to give intermediate 86-6. LCMS: 476.4.

Example 86: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-4-(3-cyano-5-fluorophenyl)-2-((octadecyloxy)methyl)butyl) hydrogen phosphate (86)

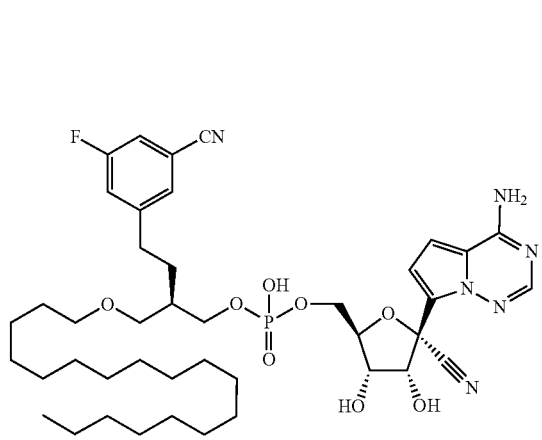

Compound 86 was prepared in a manner similar to compound 19 using intermediate 86-6 instead of intermediate 19-2. $^1$H NMR (400 MHz, Methanol-$d_4$) δ 8.10 (s, 1H), 7.40 (s, 1H), 7.38-7.29 (m, 3H), 7.21 (d, J=4.8 Hz, 1H), 4.80-4.69 (m, 2H), 4.40-4.32 (m, 1H), 4.31-4.18 (m, 1H), 4.18-4.04 (m, 1H), 4.04-3.90 (m, 2H), 3.76-3.35 (m, 4H), 2.84-2.67 (m, 2H), 1.98-1.84 (m, 1H), 1.79-1.66 (m, 2H), 1.66-1.49 (m, 2H), 1.48-1.17 (m, 30H), 0.92 (t, J=6.7 Hz, 3H). LCMS: 827.4 [M–H]$^-$.

Intermediate 87-1: (S)-3-(octadecyloxy)-2-phenoxypropan-1-ol

Example 87: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-3-(octadecyloxy)-2-phenoxypropyl) hydrogen phosphate (87)

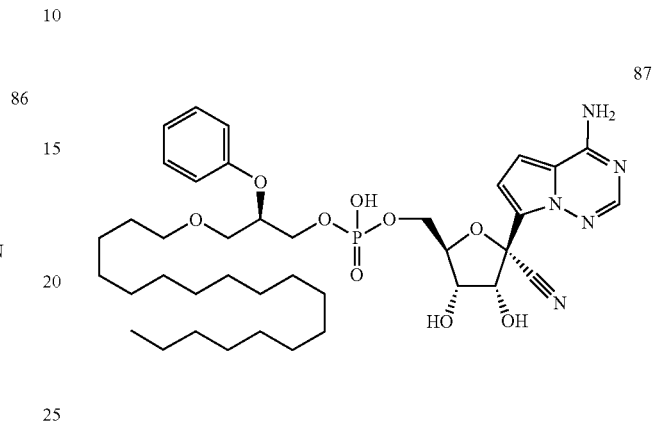

Compound 87 was prepared in a manner similar to compound 84 using intermediate 87-1 instead of intermediate 84-2. $^1$H NMR (400 MHz, Methanol-$d_4$) δ 8.06 (s, 1H), 7.35 (d, J=4.8 Hz, 1H), 7.25-7.20 (m, 2H), 7.19 (d, J=4.8 Hz, 1H), 7.00-6.94 (m, 2H), 6.91 (t, J=7.3 Hz, 1H), 4.77 (d, J=5.2 Hz, 1H), 4.58 (p, J=5.1 Hz, 1H), 4.42-4.32 (m, 1H), 4.26-4.18 (m, 2H), 4.15-4.03 (m, 3H), 3.74-3.60 (m, 2H), 3.53-3.43 (m, 2H), 1.64-1.48 (m, 2H), 1.41-1.22 (m, 30H), 0.92 (t, J=6.7 Hz, 3H). LCMS: 772.4 [M–H]$^-$.

Intermediate 88-1: (R)-2-methoxy-6-((1-(octadecyloxy)-3-((triisopropylsilyl)oxy)propan-2-yl)oxy)pyridine

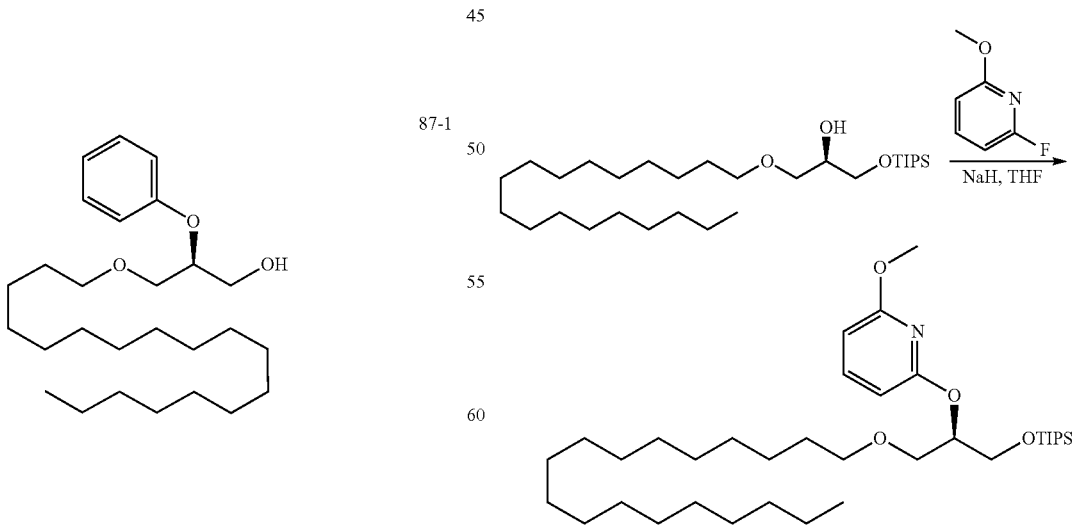

Intermediate 87-1 was prepared in a manner similar to intermediate 30-2 using phenol instead of 3-hydroxybenzonitrile. LCMS: 421.4.

307

To a solution of (R)-1-(octadecyloxy)-3-((triisopropylsilyl)oxy)propan-2-ol (205 mg, 0.41 mmol) in tetrahydrofuran (1 mL) was OC was added a dispersion of 60% sodium hydride in mineral oil (45 mg, 1.2 mmol) and the reaction stirred for 10 minutes at which point a solution of 2-fluoro-6-methoxypyridine (194 mg, 1.53 mmol) in tetrahydrofuran (0.5 mL) was added. The reaction mixture was stirred at 60 C for 18 hours then quenched by the addition of water. The reaction mixture was partitioned between ethyl acetate and water and aqueous layer extracted to ethyl acetate. The combined organic layers were washed with saturated aqueous sodium chloride, dried over sodium sulfate, filtered, and evaporated under reduced pressure. Intermediate 88-1 was isolated from the resultant residue by silica gel column chromatography (0-20% EtOAc:hexanes eluent ramp).

$^1$H NMR (400 MHz, Chloroform-d) δ. 7.47 (t, J=7.8 Hz, 1H), 6.33 (d, J=7.9 Hz, 1H), 6.29 (d, J=7.9 Hz, 1H), 5.34 (t, J=5.1 Hz, 1H), 3.98 (d, J=5.4 Hz, 2H), 3.90 (s, 3H), 3.78 (dd, J=7.6, 4.9 Hz, 2H), 3.51 (q, J=6.3 Hz, 2H), 1.59 (t, J=7.0 Hz, 2H), 1.28 (d, J=3.8 Hz, 30H), 1.15-0.98 (m, 21H), 0.91 (t, J=6.6 Hz, 3H).

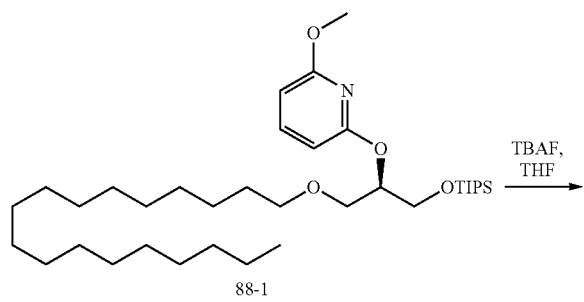

308

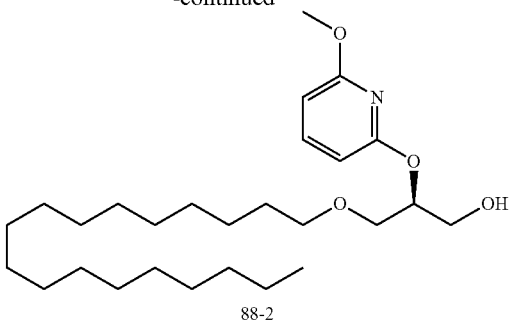

Intermediate 88-2: (S)-2-((6-methoxypyridin-2-yl)oxy)-3-(octadecyloxy)propan-1-ol Intermediate 88-1 (180 mg, 0.296 mmol) was dissolved in tetrahydrofuran (3 mL) and treated with a solution of tetra-N-butyl ammonium fluoride in tetrahydrofuran (1.0 M, 1.0 mL, 1.0 mmol) and the reaction mixture stirred for one hour. The reaction mixture was diluted with ethyl acetate, washed sequentially with water then saturated aqueous sodium chloride, dried over sodium sulfate, filtered, and evaporated under reduced pressure. Intermediate 88-2 was isolated from the resultant residue by silica gel column chromatography (0-50% EtOAc:hexanes eluent ramp).

$^1$H NMR (400 MHz, Chloroform-d) δ. 7.52 (t, J=7.9 Hz, 1H), 6.38 (d, J=7.9 Hz, 1H), 6.35 (d, J=7.9 Hz, 1H), 5.26 (p, J=5.1 Hz, 1H), 3.96 (qd, J=11.8, 4.7 Hz, 2H), 3.90 (s, 3H), 3.79 (dd, J=10.2, 4.8 Hz, 1H), 3.72 (dd, J=10.1, 5.9 Hz, 1H), 3.51 (td, J=6.7, 3.0 Hz, 2H), 1.58 (q, J=6.9 Hz, 2H), 1.28 (s, 30H), 0.90 (t, J=6.6 Hz, 3H).

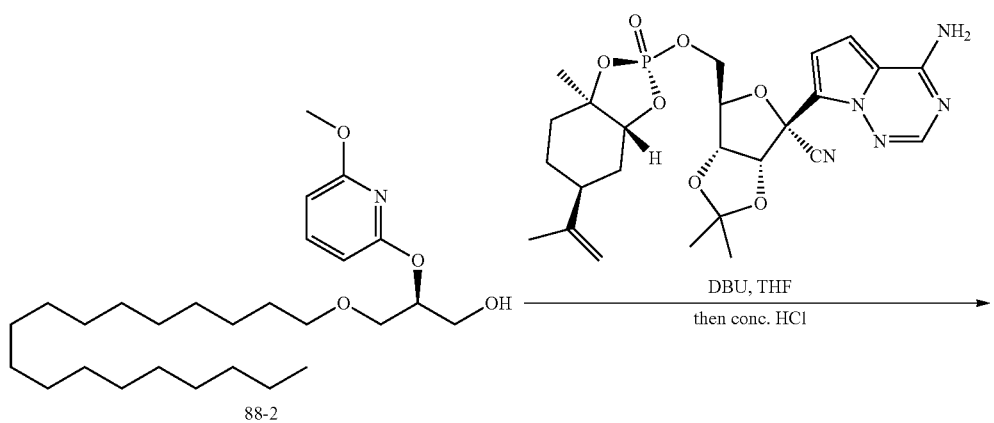

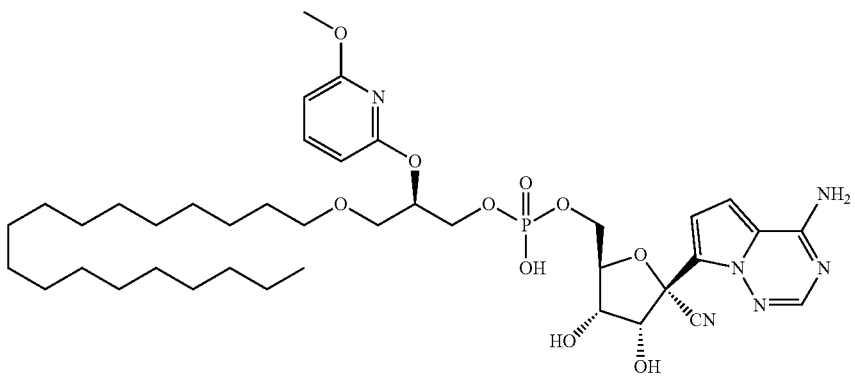

88

Example 88: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((6-methoxypyridin-2-yl)oxy)-3-(octadecyloxy)propyl) hydrogen phosphate (88)

Intermediate 88-2 (38.1 mg, 0.0818 mmol) and intermediate 19-1 (48.0 mg, 0.0855 mmol) were dissolved in tetrahydrofuran (1 mL), treated with 1,8-diazabicyclo[5.4.0]undec-7-ene (0.035 mL, 0.234 mmol) in tetrahydrofuran (0.35 mL), and stirred for 18 hours, at which point water (0.05 mL) and concentrated hydrochloric acid (0.4 mL). The reaction mixture was stirred for 4 hours at which point N-methylmorpholine (0.5 mL) was added, reaction mixture diluted with N,N-dimethylformamide and passed through a syringe filter, and example 88 was isolated as a trifluoroacetic acid salt by preparative HPLC (65-100% MeOH: water+0.1% trifluoroacetic acid eluent ramp).

$^1$H NMR (400 MHz, DMSO-d$_6$) δ 7.93 (s, 1H), 7.59 (t, J=7.9 Hz, 1H), 6.91 (d, J=4.6 Hz, 1H), 6.82 (d, J=4.5 Hz, 1H), 6.37 (s, 1H), 6.35 (s, 1H), 5.31 (t, J=5.0 Hz, 1H), 4.64 (d, J=4.9 Hz, 1H), 4.20 (d, J=7.3 Hz, 1H), 4.10 (t, J=5.6 Hz, 2H), 4.02-3.87 (m, 2H), 3.80 (s, 3H), 3.59 (dd, J=5.3, 2.4 Hz, 2H), 1.42 (d, J=6.9 Hz, 2H), 1.29-1.14 (m, 30H), 0.90-0.78 (m, 3H).

MS m/z=805.0.

Example 89: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((5-methoxypyridin-2-yl)oxy)-3-(octadecyloxy)propyl) hydrogen phosphate (89)

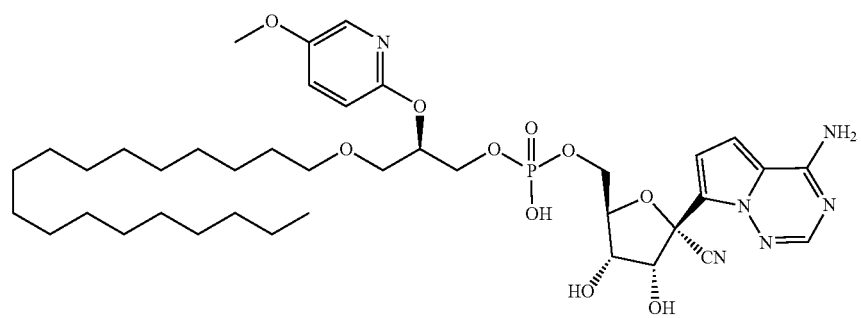

89

Example 89 was synthesized in a manner similar to example 88 using 2-fluoro-5-methoxypyridine in place of 2-fluoro-6-methoxypyridine.

$^1$H NMR (400 MHz, DMSO-d$_6$) δ 7.95 (s, 1H), 7.81 (d, J=3.1 Hz, 1H), 7.35 (dd, J=8.9, 3.1 Hz, 1H), 6.94 (d, J=4.6 Hz, 1H), 6.84 (d, J=4.5 Hz, 1H), 6.76 (d, J=8.9 Hz, 1H), 5.25 (t, J=4.9 Hz, 1H), 4.65 (d, J=4.9 Hz, 1H), 4.21 (td, J=6.0, 3.0 Hz, 1H), 4.16-4.04 (m, 2H), 4.02-3.90 (m, 2H), 3.76 (s, 3H), 3.56 (dd, J=5.1, 2.2 Hz, 2H), 3.35 (td, J=6.6, 1.6 Hz, 2H), 1.49-1.33 (m, 2H), 1.21 (d, J=18.8 Hz, 30H), 0.92-0.78 (m, 3H).

MS m/z=805.0.

Example 90: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((4-methoxypyridin-2-yl)oxy)-3-(octadecyloxy)propyl) hydrogen phosphate (90)

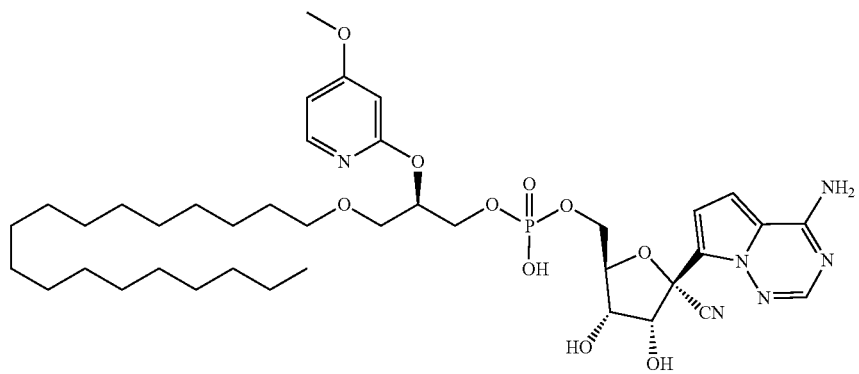

Example 90 was synthesized in a manner similar to example 88 using 2-fluoro-4-methoxypyridine in place of 2-fluoro-6-methoxypyridine.

$^1$H NMR (400 MHz, DMSO-d$_6$) δ 7.92 (d, J=6.7 Hz, 2H), 6.91 (d, J=4.5 Hz, 1H), 6.83 (d, J=4.5 Hz, 1H), 6.57 (dd, J=5.9, 2.2 Hz, 1H), 6.42-6.25 (m, 2H), 5.36 (t, J=4.9 Hz, 1H), 4.65 (d, J=4.9 Hz, 1H), 4.21 (td, J=6.0, 3.1 Hz, 1H), 4.17-4.03 (m, 2H), 4.03-3.85 (m, 2H), 3.77 (s, 3H), 3.56 (dd, J=5.1, 1.8 Hz, 2H), 3.35 (td, J=6.6, 2.7 Hz, 2H), 1.42 (t, J=6.6 Hz, 2H), 1.21 (d, J=18.2 Hz, 30H), 0.89-0.78 (m, 3H).

MS m/z 805.1.

Example 91: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((3-methoxypyridin-2-yl)oxy)-3-(octadecyloxy)propyl) hydrogen phosphate (91)

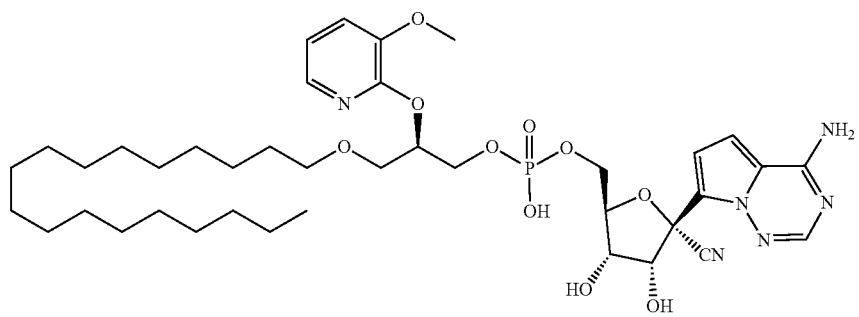

Example 91 was synthesized in a manner similar to example 88 using 2-fluoro-3-methoxypyridine in place of 2-fluoro-6-methoxypyridine.

$^1$H NMR (400 MHz, DMSO-$d_6$) δ 7.93 (s, 1H), 7.66 (dd, J=5.0, 1.5 Hz, 1H), 7.28 (dd, J=7.9, 1.5 Hz, 1H), 6.97-6.88 (m, 2H), 6.82 (d, J=4.5 Hz, 1H), 6.30 (s, 1H), 5.43 (t, J=4.9 Hz, 1H), 4.64 (d, J=4.9 Hz, 1H), 4.19 (dt, J=6.0, 3.0 Hz, 1H), 4.10 (t, J=6.0 Hz, 2H), 4.03-3.85 (m, 2H), 3.76 (s, 3H), 3.58 (dd, J=5.3, 3.0 Hz, 2H), 3.36 (td, J=6.7, 2.3 Hz, 2H), 1.48-1.35 (m, 2H), 1.21 (d, J=21.2 Hz, 30H), 0.93-0.76 (m, 3H).

MS m/z=805.0.

Example 92: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-3-(octadecyloxy)-2-(quinolin-2-ylmethoxy)propyl) hydrogen phosphate (92)

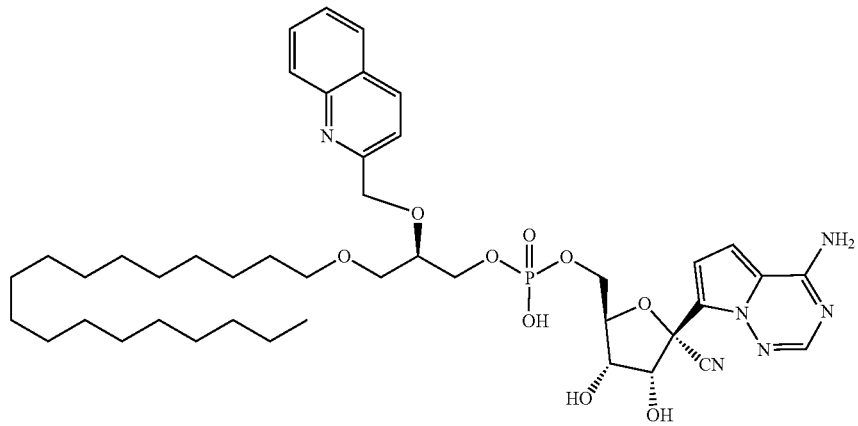

Example 92 was synthesized in a manner similar to example 88 using 2-(bromomethyl)quinoline in place of 2-fluoro-6-methoxypyridine.

$^1$H NMR (400 MHz, DMSO-$d_6$) δ 8.37 (d, J=8.5 Hz, 1H), 7.98 (dd, J=11.6, 8.2 Hz, 2H), 7.93 (s, 1H), 7.76 (ddd, J=8.5, 6.8, 1.5 Hz, 1H), 7.68 (d, J=8.5 Hz, 1H), 7.60 (t, J=7.5 Hz, 1H), 6.91 (d, J=4.5 Hz, 1H), 6.85 (d, J=4.6 Hz, 1H), 6.31 (s, 1H), 4.88 (d, J=2.4 Hz, 2H), 4.66 (s, 1H), 4.29-4.11 (m, 1H), 4.11-3.90 (m, 4H), 3.82 (t, J=5.0 Hz, 1H), 1.43 (t, J=7.2 Hz, 2H), 1.32-1.10 (m, 30H), 0.94-0.78 (m, 3H).

MS m/z 839.3.

Example 93: ((2R,3S,4R,5R)-5-(4-aminopyrrolo[2,1-f][1,2,4]triazin-7-yl)-5-cyano-3,4-dihydroxytetrahydrofuran-2-yl)methyl ((S)-2-((3-cyano-5-fluorobenzyl)oxy)-3-(octadecyloxy)propyl) hydrogen phosphate (93)

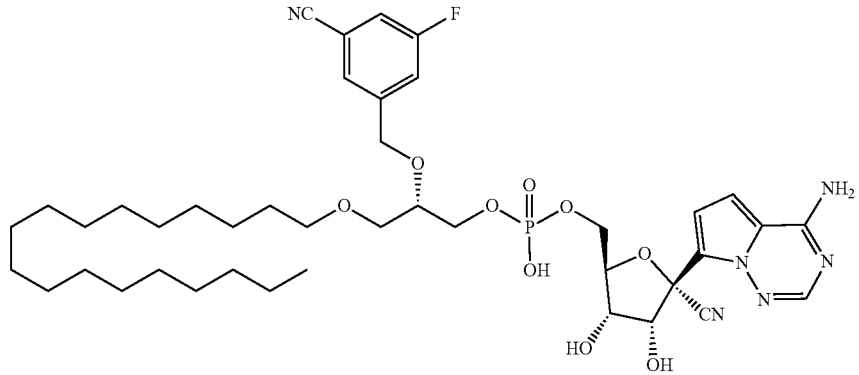

Example 93 was synthesized in a manner similar to example 88 using 3-(bromomethyl)-5-fluorobenzonitrile in place of 2-fluoro-6-methoxypyridine and (S)-1-((tert-butyldimethylsilyl)oxy)-3-(octadecyloxy)propan-2-ol in place of (R)-1-(octadecyloxy)-3-((triisopropylsilyl)oxy)propan-2-ol.

$^1$H NMR (400 MHz, DMSO-$d_6$) δ 7.92 (s, 3H), 7.73 (dd, J=8.6, 2.3 Hz, 1H), 7.64 (s, 1H), 7.59-7.49 (m, 1H), 6.90 (d, J=4.5 Hz, 1H), 6.84 (d, J=4.5 Hz, 1H), 6.31 (s, 1H), 4.67 (q, J=13.5 Hz, 3H), 4.21 (dd, J=6.2, 3.0 Hz, 1H), 4.14 (dq, J=6.1, 3.0 Hz, 1H), 3.95 (ddt, J=32.4, 11.5, 5.5 Hz, 4H), 3.77-3.67 (m, 1H), 1.45 (t, J=6.7 Hz, 2H), 1.22 (d, J=11.4 Hz, 30H), 0.85 (t, J=6.6 Hz, 3H).

MS m/z 831.1.

Example 94: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((4-cyano-3-fluorobenzyl)oxy)-3-(heptadecyloxy)propyl) hydrogen phosphate (94)

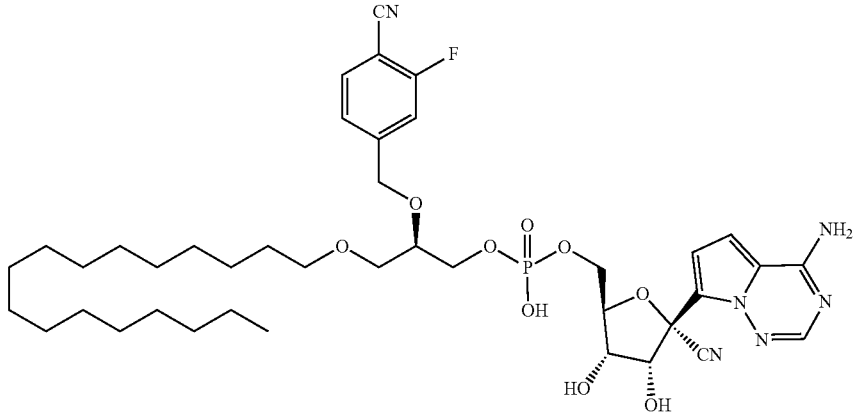

94

Example 94 was synthesized in a manner similar to example 88 using 4-(bromomethyl)-2-fluoro-benzonitrile in place of 2-fluoro-6-methoxypyridine and (R)-1-((tert-butyldimethylsilyl)oxy)-3-(heptadecyloxy)propan-2-ol in place of (R)-1-(octadecyloxy)-3-((triisopropylsilyl)oxy)propan-2-ol.

$^1$H NMR (400 MHz, DMSO-$d_6$) δ 7.92 (s, 1H), 7.89-7.81 (m, 1H), 7.45 (d, J=10.5 Hz, 1H), 7.34 (d, J=8.0 Hz, 1H), 6.89 (d, J=4.5 Hz, 1H), 6.83 (d, J=4.5 Hz, 1H), 6.31 (d, J=5.9 Hz, 1H), 4.70 (d, J=6.0 Hz, 2H), 4.65 (d, J=3.8 Hz, 1H), 4.28-4.18 (m, 1H), 4.18-4.09 (m, 1H), 3.95 (dddd, J=27.1, 22.4, 11.9, 6.4 Hz, 4H), 3.71 (t, J=4.9 Hz, 1H), 3.47-3.41 (m, 2H), 3.34 (td, J=6.5, 2.5 Hz, 3H), 1.44 (s, 2H), 1.22 (d, J=10.3 Hz, 28H), 0.85 (t, J=6.6 Hz, 3H).

MS m/z 817.2.

Example 95: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((3-cyanobenzyl)oxy)-3-(hexadecyloxy)propyl) hydrogen phosphate (95)

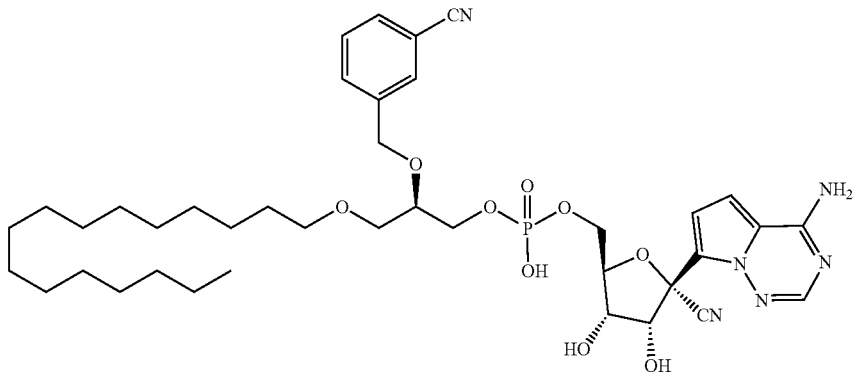

95

Example 95 was synthesized in a manner similar to example 88 using 3-(bromomethyl)benzonitrile in place of 2-fluoro-6-methoxypyridine and (R)-1-((tert-butyldimethylsilyl)oxy)-3-(hexadecyloxy)propan-2-ol in place of (R)-1-(octadecyloxy)-3-((triisopropylsilyl)oxy)propan-2-ol.

$^1$H NMR (400 MHz, DMSO-$d_6$) δ 7.93 (s, 1H), 7.76 (d, J=1.7 Hz, 1H), 7.75-7.70 (m, 1H), 7.69-7.61 (m, 1H), 7.52 (t, J=7.7 Hz, 1H), 6.91 (d, J=4.5 Hz, 1H), 6.84 (d, J=4.5 Hz, 1H), 6.32 (s, 1H), 4.73-4.54 (m, 3H), 4.18 (ddt, J=30.8, 6.1, 3.0 Hz, 2H), 4.05-3.85 (m, 4H), 3.70 (t, J=4.9 Hz, 1H), 3.47-3.40 (m, 2H), 3.34 (t, J=6.5 Hz, 2H), 1.45 (t, J=6.7 Hz, 2H), 1.22 (d, J=9.0 Hz, 26H), 0.92-0.77 (m, 3H).

MS m/z 785.1.

Example 96: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((4-cyanobenzyl)oxy)-3-(hexadecyloxy)propyl) hydrogen phosphate (96)

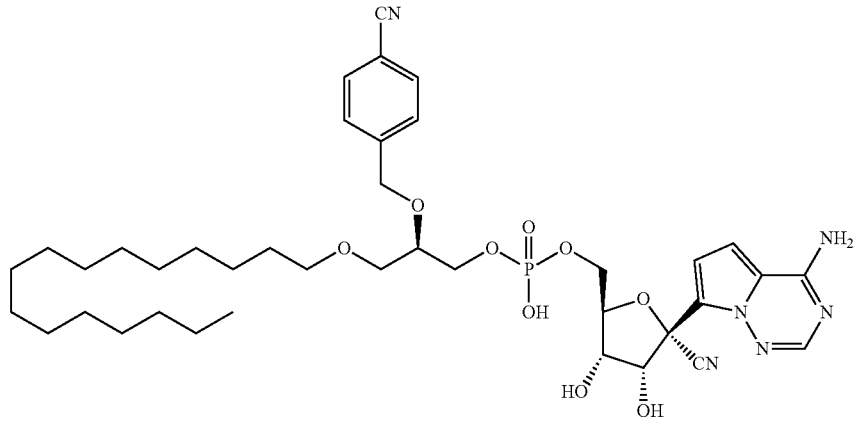

Example 96 was synthesized in a manner similar to example 88 using 4-(bromomethyl)benzonitrile in place of 2-fluoro-6-methoxypyridine and (R)-1-((tert-butyldimethylsilyl)oxy)-3-(hexadecyloxy)propan-2-ol in place of (R)-1-(octadecyloxy)-3-((triisopropylsilyl)oxy)propan-2-ol.

$^1$H NMR (400 MHz, DMSO-$d_6$) δ 7.92 (s, 1H), 7.76 (d, J=8.1 Hz, 2H), 7.51 (d, J=8.0 Hz, 2H), 6.90 (d, J=4.5 Hz, 1H), 6.84 (d, J=4.5 Hz, 1H), 6.31 (d, J=5.9 Hz, 1H), 4.66 (dd, J=13.3, 4.7 Hz, 3H), 4.30-4.08 (m, 2H), 4.05-3.82 (m, 4H), 3.70 (t, J=5.0 Hz, 1H), 3.44 (dd, J=5.1, 2.6 Hz, 2H), 3.33 (td, J=6.5, 1.8 Hz, 2H), 1.44 (t, J=6.7 Hz, 2H), 1.22 (d, J=10.7 Hz, 26H), 0.85 (t, J=6.7 Hz, 3H).

MS m/z 785.2.

Example 97: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-3-(hexadecyloxy)-2-((4-methoxybenzyl)oxy)propyl) hydrogen phosphate (97)

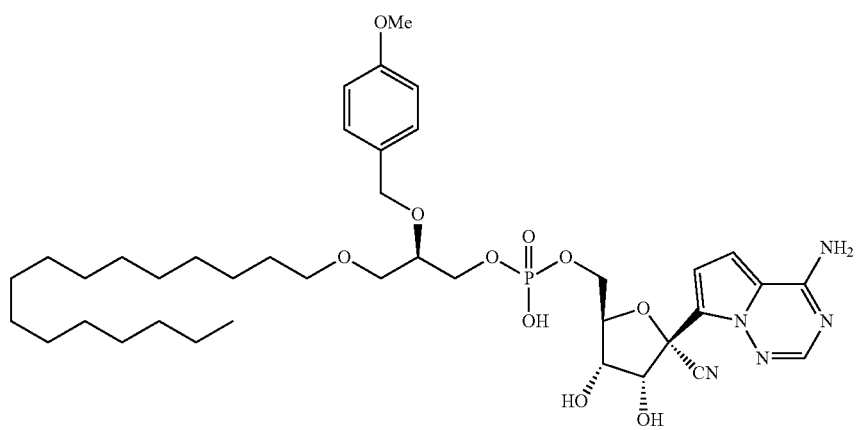

Example 97 was synthesized in a manner similar to example 88 using 1-(bromomethyl)-4-methoxy-benzene in place of 2-fluoro-6-methoxypyridine and (R)-1-((tert-butyldimethylsilyl)oxy)-3-(hexadecyloxy)propan-2-ol in place of (R)-1-(octadecyloxy)-3-((triisopropylsilyl)oxy)propan-2-ol.

¹H NMR (400 MHz, DMSO-d₆) δ 7.93 (s, 1H), 7.23 (d, J=8.6 Hz, 2H), 6.91 (d, J=4.5 Hz, 1H), 6.88-6.77 (m, 3H), 6.35-6.26 (m, 1H), 4.65 (d, J=4.7 Hz, 1H), 4.54-4.40 (m, 2H), 4.21 (dd, J=6.2, 3.1 Hz, 1H), 4.13 (ddd, J=9.1, 6.1, 3.1 Hz, 1H), 4.07-3.89 (m, 3H), 3.86 (dt, J=11.2, 6.0 Hz, 1H), 3.73 (s, 3H), 3.64 (t, J=5.0 Hz, 1H), 3.46-3.25 (m, 6H), 1.52-1.37 (m, 2H), 1.32-1.15 (m, 26H), 0.93-0.77 (m, 3H).

MS m/z=790.1.

Intermediate 98-1: (S)-2-Fluoro-5-(((1-hydroxy-3-(octadecyloxy)propan-2-yl)oxy)methyl)benzonitrile

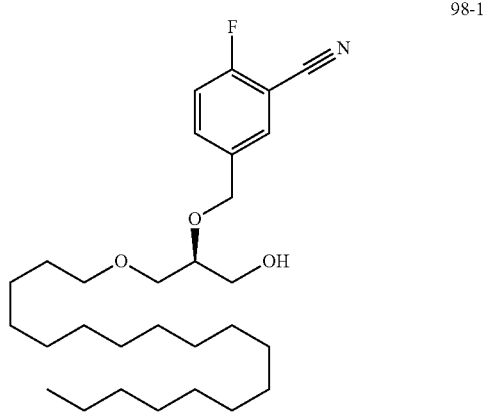 [SMILES: CCCCCCCCCCCCCCCCCCOC[C@H](CO)OCc1ccc(F)c(C#N)c1]

Intermediate 98-1 was prepared in a manner similar to intermediate 2-2 using 5-(bromomethyl)-2-fluorobenzonitrile as alkylation agent.

Intermediate 98-2: [(3aR,4R,6R,6aR)-4-(4-Amino-pyrrolo[2,1-f][1,2,4]triazin-7-yl)-4-cyano-2,2-dimethyl-6,6a-dihydro-3aH-furo[3,4-d][1,3]dioxol-6-yl]methyl (2-chlorophenyl) [(2R)-2-[(3-cyano-4-fluoro-phenyl)methoxy]-3-octadecoxy-propyl] phosphate

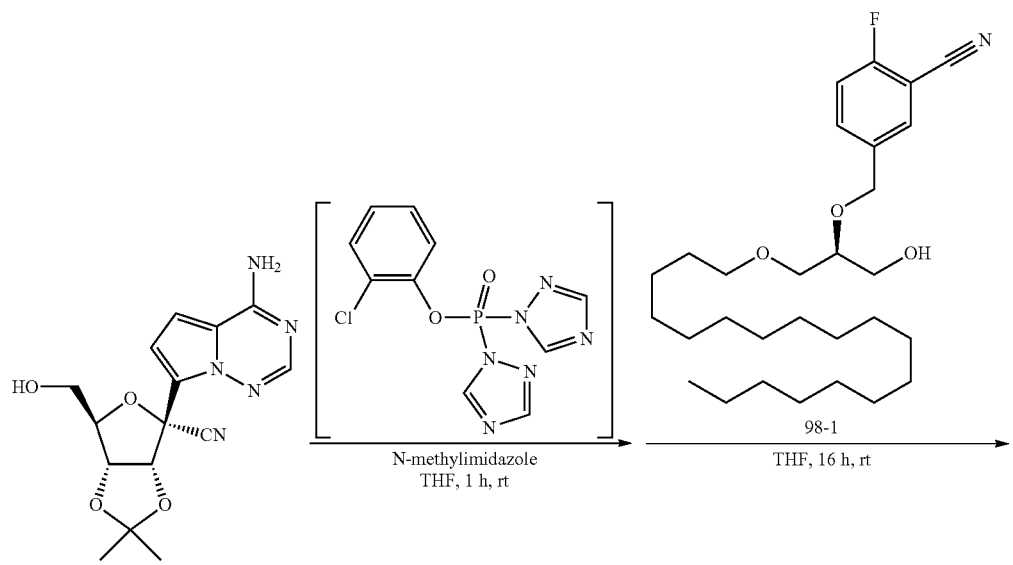

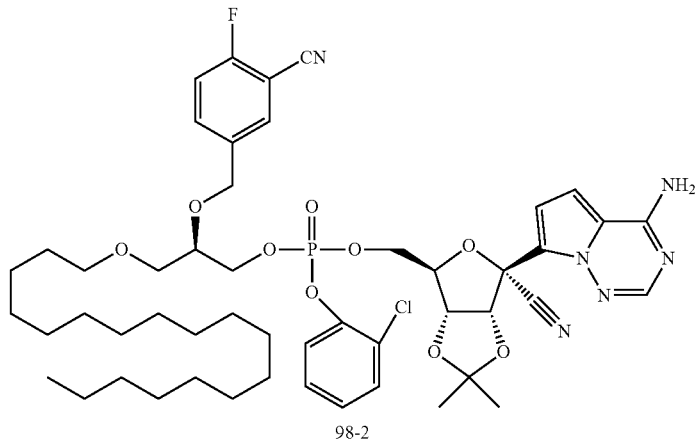

To a solution of 1,2,4-trizole (43 mg, 0.62 mmol) and triethylamine (87 µL, 0.62 mmol) in anhydrous THF (0.4 mL) was added a solution of 2-chlorophenyl dichlorophosphate (76 mg, 0.31 mmol) in THF (0.4 mL). The mixture was stirred for 30 min. and then filtered. To the filtrate were added sequentially, additional THF (1.2 mL), (3aR,4R,6R,6aR)-4-(4-aminopyrrolo[2,1-f][1,2,4]triazin-7-yl)-6-(hydroxymethyl)-2,2-dimethyltetrahydrofuro[3,4-d][1,3]dioxole-4-carbonitrile (78 mg, 0.235 mmol), and 1-methylimidazole (26 mg, 0.31 mmol). After 1 h, intermediate 98-1 (108 mg, 0.235 mmol) was added to the mixture and stirred overnight at room temperature. The solvent was evaporated, and the residue was purified by flash chromatography on silica gel (0-15% MeOH in CH$_2$Cl$_2$) to afford 98-2.

Example 98: [(2R,3S,4R,5R)-5-(4-aminopyrrolo[2,1-f][1,2,4]triazin-7-yl)-5-cyano-3,4-dihydroxy-tetrahydrofuran-2-yl]methyl [(2R)-2-[(3-cyano-4-fluorophenyl)methoxy]-3-octadecoxy-propyl] hydrogen phosphate (98)

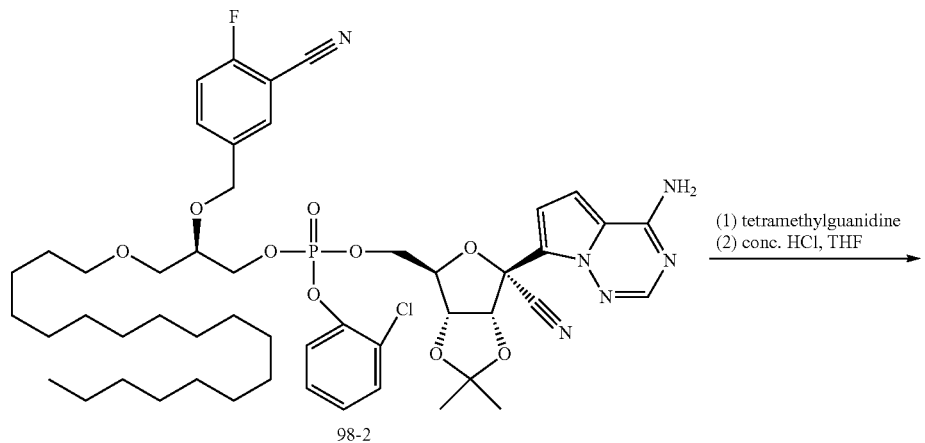

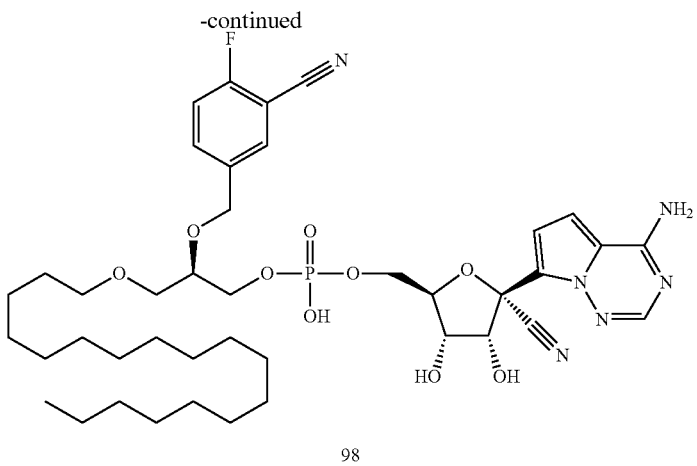

98

1,1,3,3-Tetramethylguanidine (108 mg, 0.94 mmol) and syn-2-pyridinealdoxime (0.192 g, 1.57 mmol) in THF (2 mL) were added to a solution of the 98-2 (154 mg, 0.157 mmol) in THF (3 mL) and stirred at room temperature overnight. The reaction was concentrated in vacuo, the residue was purified by flash chromatography with 0-50% MeOH in DCM to give an intermediate. The above product was dissolved in THF (0.75 mL). The resulting solution was cooled in an ice bath. Concentrated aqueous HCl (0.15 mL) was added. The cold bath was removed the reaction was stirred vigorously for 3 h. The mixture was neutralized with $Na_2CO_3$, diluted with MeOH, and filtered. The solution was purified by silica gel column with 0-65% MeOH in DCM give compound 98. $^1$H NMR (400 MHz, DMSO-$d_6$) δ 7.99-7.70 (m, 3H), 7.45 (m, 1H), 6.91 (m, 1H), 6.83 (m, 1H), 6.16 (s, 1H), 4.71-4.48 (m, 3H), 4.23-4.06 (m, 4H), 4.01-3.52 (m, 7H), 1.44 (m, 2H), 1.22 (m, 30H), 1.01-0.77 (m, 3H). $^{31}$P NMR (162 MHz, Methanol-d4) δ −0.33. MS: 831.33 (M+1).

Intermediate 99-1: 2-[(1R)-1-[[Tert-butyl(dimethyl)silyl]oxymethyl]-2-octadecoxy-ethoxy]pyridine-4-carbonitrile

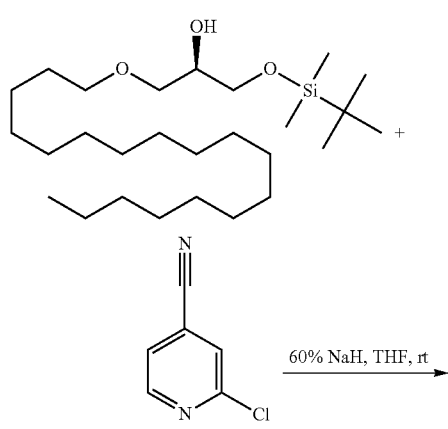

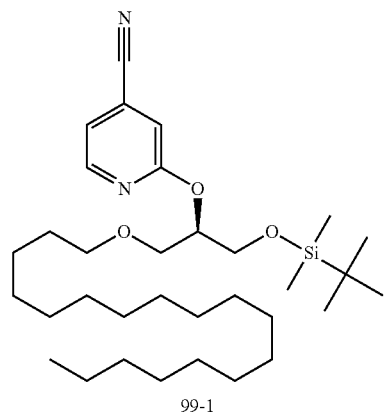

99-1

NaH (60% oil dispersion, 88 mg, 2.3 mmol) was suspended in THF (6 ml) and cooled to 0° C. A solution of (R)-1-((tert-butyldimethylsilyl)oxy)-3-(octadecyloxy)propan-2-ol (300 mg, 0.65 mmol) in THF (2.5 ml) was added. After 30 min at 0° C. a solution of 2-chloropyridine-4-carbonitrile (362 mg, 2.6 mmol) in THF (2.5 ml) was added. The mixture was stirred for 16 h at room temperature. The reaction was quenched with water (15 ml). The mixture was extracted with EtOAc. The combined organic phase was dried over sodium sulfate and the solvent was removed under reduced pressure. The residue was purified by flash chromatography (0-30% EtOAc in hexanes), giving the product 99-1.

Intermediate 99-2: 2-[(1S)-1-(Hydroxymethyl)-2-octadecoxy-ethoxy]pyridine-4-carbonitrile Example 99: [(2R,3S,4R,5R)-5-(4-Aminopyrrolo[2,1-f][1,2,4]triazin-7-yl)-5-cyano-3,4-dihydroxy-tetrahydrofuran-2-yl]methyl [(2R)-2-[(4-cyano-2-pyridyl)oxy]-3-octadecoxy-propyl]hydrogen phosphate (99)

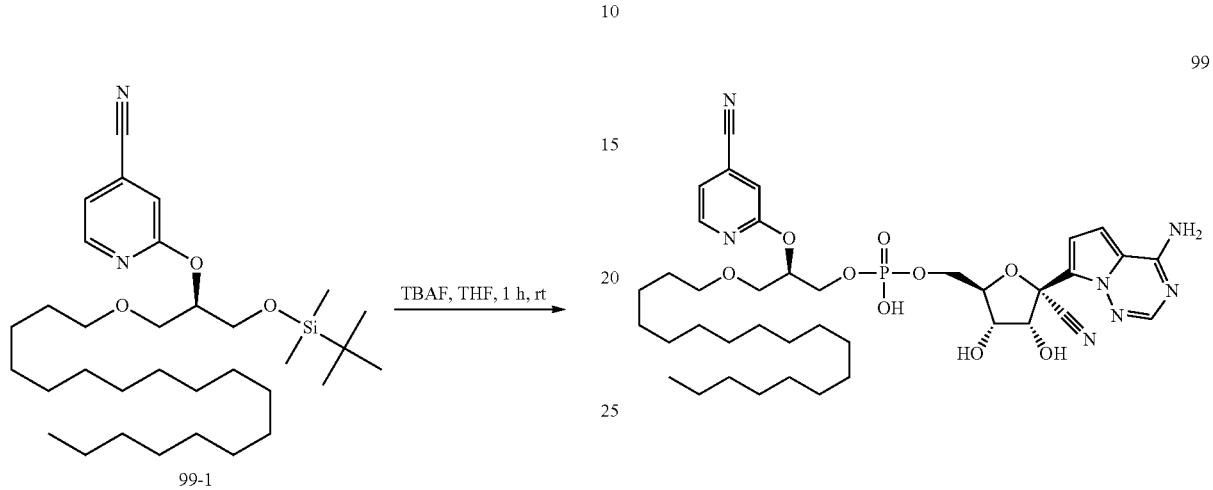

Compound 99 was prepared in a manner similar to example 98 using intermediate 99-2 instead of intermediate 98-1.

$^1$H NMR (400 MHz, Methanol-d$_4$) δ 8.29 (d, J=5.2 Hz, 1H), 8.07 (s, 1H), 7.29 (d, J=4.9 Hz, 1H), 7.21-7.16 (m, 2H), 7.14 (t, J=1.1 Hz, 1H), 4.79 (d, J=5.2 Hz, 1H), 4.55 (m, 2H), 4.48-4.31 (m, 1H), 4.25 (m, 2H), 4.14 (m, 1H), 3.69 (m, 2H), 3.55-3.42 (m, 2H), 1.52 (q, J=6.8 Hz, 2H), 1.28 (d, J=13.7 Hz, 30H), 1.02-0.80 (m, 3H). $^{31}$P NMR (162 MHz, Methanol-d4) δ 0.59.

MS: 800.18 (M+1).

Intermediate 100-1: 6-[(1S)-1-(Hydroxymethyl)-2-octadecoxy-ethoxy]pyridine-2-carbonitrile

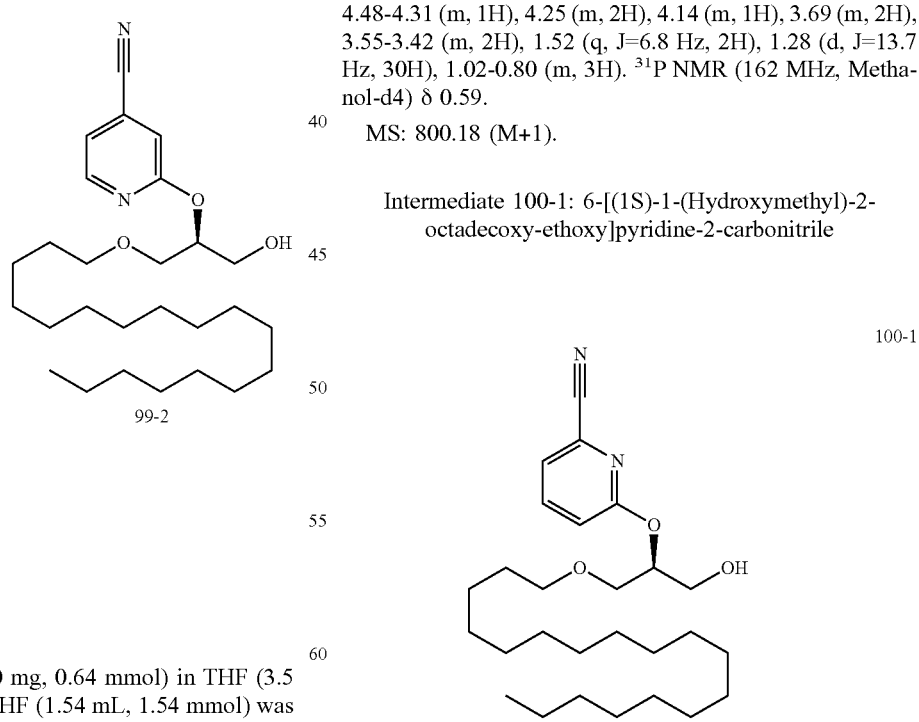

To a solution of 99-1 (360 mg, 0.64 mmol) in THF (3.5 mL) at 0° C., 1M TBAF in THF (1.54 mL, 1.54 mmol) was added and stirred for 1 h. It was diluted with water and extracted with EtOAc. The combined organic layers were washed with water, brine and dried (Na$_2$SO$_4$), evaporated and purified the residue by column chromatography silica gel, 0-60% ethyl acetate in hexanes to give 99-2.

Intermediate 100-1 was prepared in a manner similar to intermediate 99-2 using 6-chloropyridine-2-carbonitrile alkylation agent.

Example 100: [(2R,3S,4R,5R)-5-(4-aminopyrrolo[2,1-f][1,2,4]triazin-7-yl)-5-cyano-3,4-dihydroxy-tetrahydrofuran-2-yl]methyl [(2R)-2-[(6-cyano-2-pyridyl)oxy]-3-octadecoxy-propyl]hydrogen phosphate (100)

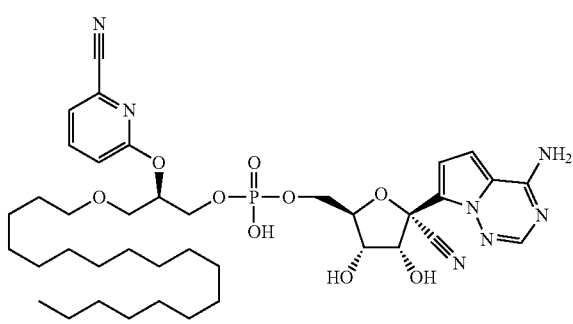

Compound 100 was prepared in a manner similar to 99 using intermediate 100-1 instead of 99-2.

$^1$H NMR (400 MHz, Methanol-d$_4$) 1H NMR (400 MHz, Methanol-d4) δ 7.92-7.84 (m, 1H), 7.78 (m, 1H), 7.40 (m, 1H), 7.12-7.03 (m, 1H), 7.00-6.84 (m, 2H), 4.89 (m, 1H), 4.38 (m, 2H), 4.32-4.24 (m, 2H), 4.23-3.93 (m, 3H), 3.74-3.60 (m, 2H), 3.52-3.37 (m, 2H), 1.49 (m, 2H), 1.27 (d, J=20.3 Hz, 30H), 0.98-0.85 (m, 3H). $^{31}$P NMR (162 MHz, Methanol-d4) δ −0.32.

MS: 800.19 (M+1).

Intermediate 101-1: 3-Fluoro-4-[[(1S)-1-(hydroxymethyl)-2-tetradecoxy-ethoxy]methyl]benzonitrile

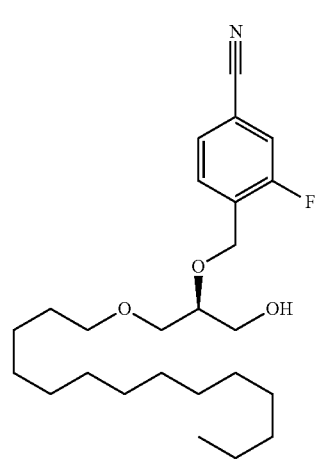

Intermediate 101-1 was prepared in a manner similar to intermediate 2-2 using 4-(bromomethyl)-3-fluorobenzonitrile as alkylation agent.

Example 101: [(2R,3S,4R,5R)-5-(4-aminopyrrolo[2,1-f][1,2,4]triazin-7-yl)-5-cyano-3,4-dihydroxy-tetrahydrofuran-2-yl]methyl [(2R)-2-[(4-cyano-2-fluorophenyl)methoxy]-3-tetradecoxy-propyl] hydrogen phosphate (101)

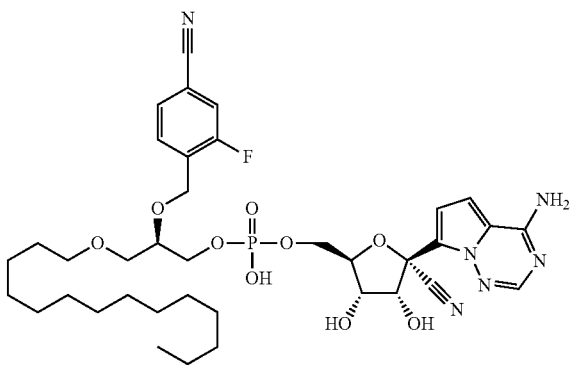

Compound 101 was prepared in a manner similar to 98 using intermediate 101-1 instead of intermediate 98-1.

$^1$H NMR (400 MHz, Methanol-d$_4$) δ 7.86 (s, 1H), 7.72 (t, J=7.5 Hz, 1H), 7.47 (ddd, J=18.5, 8.8, 1.5 Hz, 2H), 6.98 (d, J=4.6 Hz, 1H), 6.87 (d, J=4.6 Hz, 1H), 4.84 (d, J=5.3 Hz, 1H), 4.76 (s, 2H), 4.35 (t, J=4.4 Hz, 1H), 4.26 (t, J=5.5 Hz, 1H), 4.22-4.03 (m, 2H), 3.90 (m, 2H), 3.81-3.71 (m, 1H), 3.57-3.44 (m, 2H), 3.39 (m, 2H), 1.50 (m, 2H), 1.41-1.16 (m, 22H), 0.91 (t, J=6.7 Hz, 3H).

$^{31}$P NMR (162 MHz, Methanol-d$_4$) δ 0.26.

MS: 775.22 (M+1).

Intermediate 102-1: 3-Fluoro-4-[[(1S)-1-(hydroxymethyl)-2-pentadecoxy-ethoxy]methyl]benzonitrile

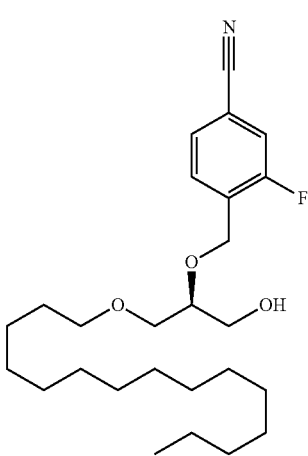

Intermediate 102-1 was prepared in a manner similar to intermediate 2-2 using 4-(bromomethyl)-3-fluorobenzonitrile as alkylation agent.

Example 102: [(2R,3S,4R,5R)-5-(4-aminopyrrolo[2,1-f][1,2,4]triazin-7-yl)-5-cyano-3,4-dihydroxy-tetrahydrofuran-2-yl]methyl [(2R)-2-[(4-cyano-2-fluoro-phenyl)methoxy]-3-pentadecoxy-propyl] hydrogen phosphate (102)

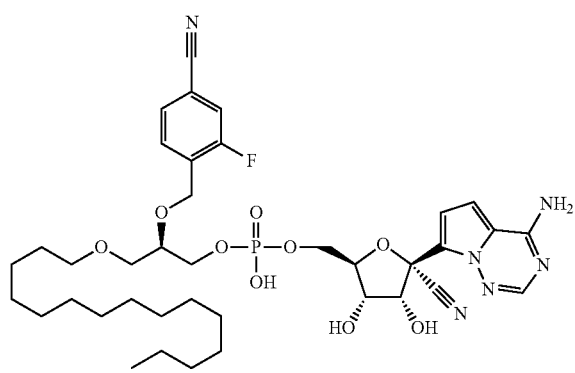

Example 103: [(2R,3S,4R,5R)-5-(4-Aminopyrrolo[2,1-f][1,2,4]triazin-7-yl)-5-cyano-3,4-dihydroxy-tetrahydrofuran-2-yl]methyl [(2R)-2-[(2-chloro-4-cyano-phenyl)methoxy]-3-octadecoxy-propyl] hydrogen phosphate (103)

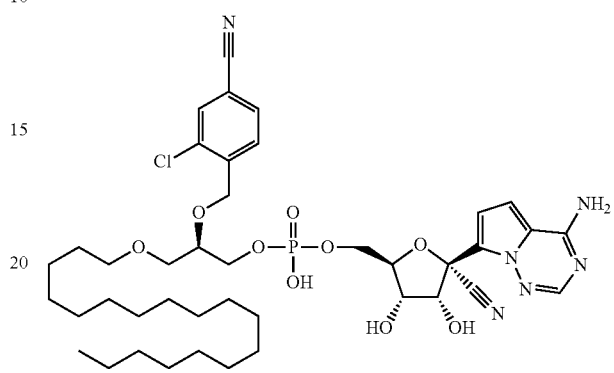

Compound 102 was prepared in a manner similar to 98 using intermediate 102-1 instead of intermediate 98-1.

$^1$H NMR (400 MHz, Methanol-$d_4$) δ 7.86 (s, 1H), 7.73 (t, J=7.5 Hz, 1H), 7.48 (ddd, J=19.9, 8.8, 1.5 Hz, 2H), 6.99 (d, J=4.6 Hz, 1H), 6.87 (d, J=4.5 Hz, 1H), 4.84 (d, J=5.3 Hz, 1H), 4.77 (s, 2H), 4.35 (m, 1H), 4.26 (m, 1H), 4.20-4.02 (m, 2H), 3.89 (m, 2H), 3.75 (m, 1H), 3.58-3.35 (m, 4H), 1.50 (q, J=6.6 Hz, 2H), 1.39-1.16 (m, 24H), 0.98-0.84 (m, 3H).

$^{31}$P NMR (162 MHz, Methanol-d4) δ 0.40.

MS: 789.19 (M+1).

Intermediate 103-1: 3-Chloro-4-[[(1S)-1-(hydroxymethyl)-2-octadecoxy-ethoxy]methyl]benzonitrile Compound 103 was prepared in a manner similar to 98 using intermediate 103-1 instead of intermediate 98-1.

$^1$H NMR (400 MHz, Methanol-$d_4$) δ 7.86 (s, 1H), 7.78 (d, J=8.0 Hz, 1H), 7.73 (d, J=1.6 Hz, 1H), 7.63 (dd, J=8.0, 1.6 Hz, 1H), 6.96 (d, J=4.6 Hz, 1H), 6.90 (d, J=4.6 Hz, 1H), 4.78 (m, 3H), 4.41-4.32 (m, 1H), 4.30-4.16 (m, 2H), 4.15-4.06 (m, 1H), 3.96 (m, 2H), 3.79 (m, 1H), 3.51 (m, 2H), 3.42 (m, 1H), 1.52 (m, 2H), 1.29 (d, J=8.7 Hz, 30H), 0.98-0.84 (m, 3H).

$^{31}$P NMR (162 MHz, Methanol-d4) δ −2.13.

MS: 847.32 (M+1).

Intermediate 104-1: 3-[[(1S)-1-(Hydroxymethyl)-2-octadecoxy-ethoxy]methyl]-4-methoxy-benzonitrile

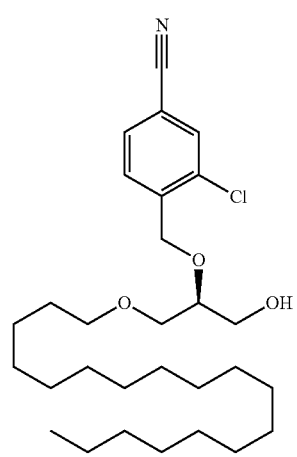

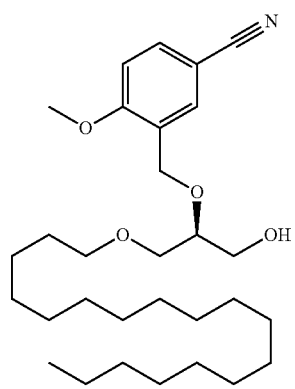

Intermediate 103-1 was prepared in a manner similar to intermediate 102-1 using 4-(bromomethyl)-3-chlorobenzonitrile as alkylation agent.

Intermediate 104-1 was prepared in a manner similar to intermediate 98-1 using 3-(bromomethyl)-4-methoxybenzonitrile as alkylation agent.

Example 104: [(2R,3S,4R,5R)-5-(4-Aminopyrrolo[2,1-f][1,2,4]triazin-7-yl)-5-cyano-3,4-dihydroxy-tetrahydrofuran-2-yl]methyl [(2R)-2-[(5-cyano-2-methoxy-phenyl)methoxy]-3-octadecoxy-propyl] hydrogen phosphate (104)

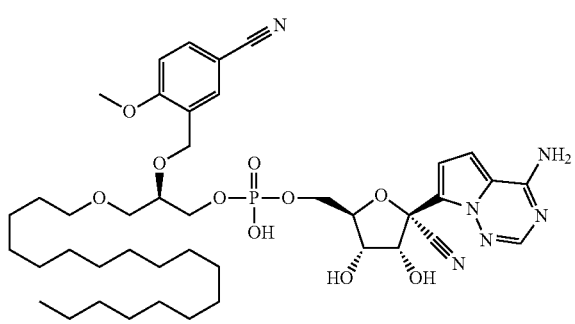

Compound 104 was prepared in a manner similar to 98 using intermediate 104-1 instead of intermediate 98-1.

$^1$H NMR (400 MHz, Methanol-d$_4$) δ 7.86 (s, 1H), 7.76 (d, J=2.1 Hz, 1H), 7.62 (dd, J=8.5, 2.2 Hz, 1H), 7.07 (d, J=8.6 Hz, 1H), 6.95 (d, J=4.6 Hz, 1H), 6.89 (d, J=4.6 Hz, 1H), 4.64 (m, 2H), 4.43-4.34 (m, 1H), 4.29-4.15 (m, 2H), 4.11 (m, 1H), 3.95 (m, 3H), 3.89 (s, 3H), 3.73 (m, 1H), 3.51 (m, 2H), 3.41 (m, 2H), 1.54 (t, J=7.0 Hz, 2H), 1.28 (d, J=12.2 Hz, 30H), 0.91 (t, J=6.8 Hz, 3H).

$^{31}$P NMR (162 MHz, Methanol-d4) δ −0.76.

MS: 843.34 (M+1).

Intermediate 105-1: 4-[[(1S)-1-(Hydroxymethyl)-2-octadecoxy-ethoxy]methyl]-3-(trifluoromethyl)benzonitrile Example 105: [(2R,3S,4R,5R)-5-(4-Aminopyrrolo[2,1-f][1,2,4]triazin-7-yl)-5-cyano-3,4-dihydroxy-tetrahydrofuran-2-yl]methyl [(2R)-2-[[4-cyano-2-(trifluoromethyl)phenyl]methoxy]-3-octadecoxy-propyl] hydrogen phosphate (105)

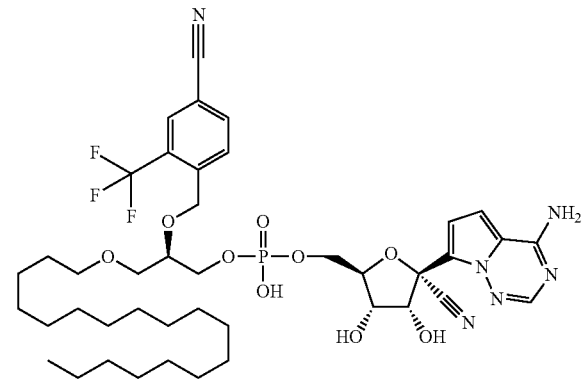

Compound 105 was prepared in a manner similar to 98 using intermediate 105-1 instead of intermediate 98-1.

$^1$H NMR (400 MHz, Methanol-d$_4$) δ 8.06 (d, J=8.1 Hz, 1H), 8.01 (d, J=1.6 Hz, 1H), 7.94 (dd, J=8.1, 1.6 Hz, 1H), 7.85 (s, 1H), 6.96 (d, J=4.5 Hz, 1H), 6.90 (d, J=4.6 Hz, 1H), 4.92 (m, 3H), 4.36 (m, 1H), 4.33-4.04 (m, 3H), 3.94 (m, 2H), 3.79 (m, 1H), 3.57-3.46 (m, 2H), 3.45-3.38 (m, 2H), 1.51 (t, J=6.9 Hz, 2H), 1.28 (d, J=10.0 Hz, 30H), 0.91 (t, J=6.7 Hz, 3H).

$^{31}$P NMR (162 MHz, Methanol-d$_4$) δ −1.94.

MS: 881.22 (M+1).

Intermediate 106-1: 3-[[(1S)-1-(Hydroxymethyl)-2-octadecoxy-ethoxy]methyl]-5-methoxy-benzonitrile

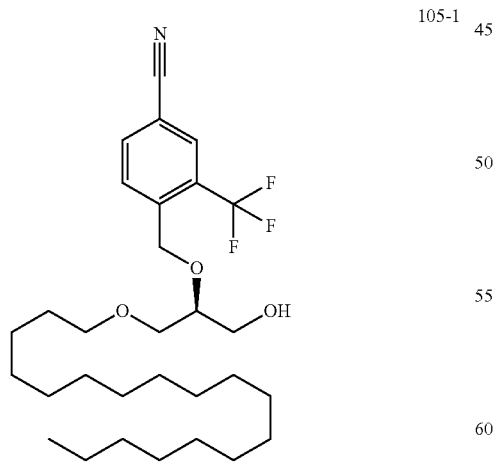

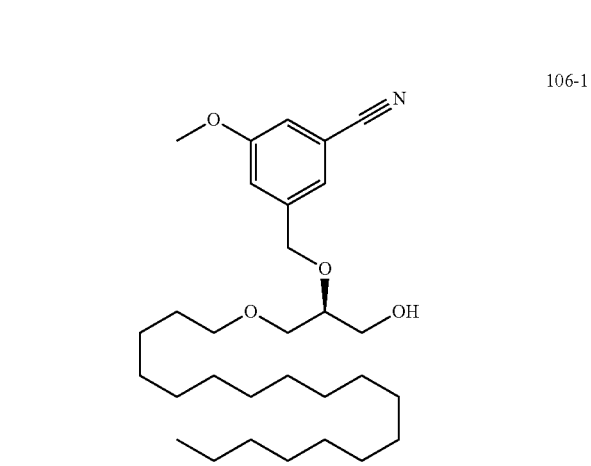 [SMILES: CCCCCCCCCCCCCCCCCCOC[C@H](CO)OCc1cc(C#N)cc(OC)c1]

Intermediate 105-1 was prepared in a manner similar to intermediate 98-1 using 3-(bromomethyl)-4-methoxybenzonitrile as alkylation agent.

Intermediate 106-1 was prepared in a manner similar to intermediate 98-1 using 3-(bromomethyl)-5-methoxybenzonitrile as alkylation agent.

Example 106: [(2R,3S,4R,5R)-5-(4-Aminopyrrolo[2,1-f][1,2,4]triazin-7-yl)-5-cyano-3,4-dihydroxy-tetrahydrofuran-2-yl]methyl [(2R)-2-[(3-cyano-5-methoxy-phenyl)methoxy]-3-octadecoxy-propyl] hydrogen phosphate (106)

Example 107: [(2R,3S,4R,5R)-5-(4-Aminopyrrolo[2,1-f][1,2,4]triazin-7-yl)-5-cyano-3,4-dihydroxy-tetrahydrofuran-2-yl]methyl [(2R)-2-[(6-cyano-2-pyridyl)methoxy]-3-octadecoxy-propyl] hydrogen phosphate (107)

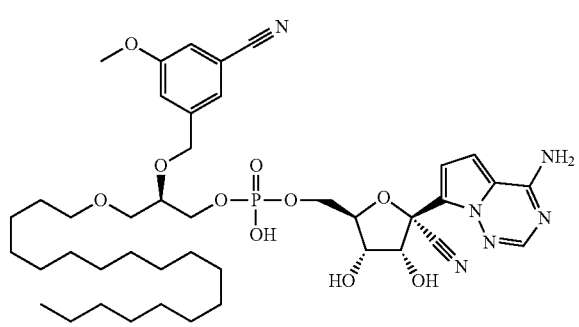

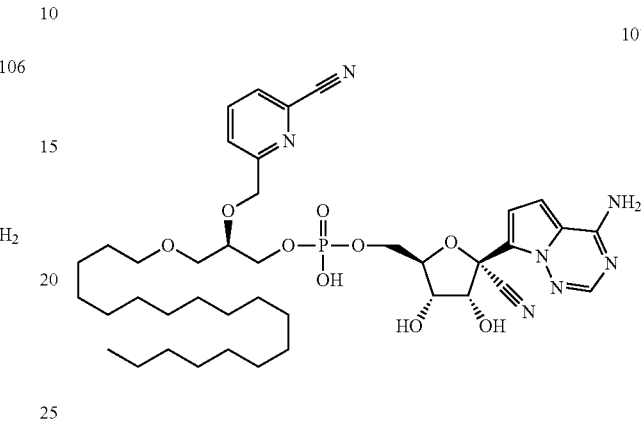

Compound 106 was prepared in a manner similar to 98 using intermediate 106-1 instead of intermediate 98-1. $^1$H NMR (400 MHz, Methanol-$d_4$) δ 7.86 (s, 1H), 7.27 (s, 1H), 7.20 (t, J=1.9 Hz, 1H), 7.14 (t, J=1.8 Hz, 1H), 6.96 (d, J=4.6 Hz, 1H), 6.90 (d, J=4.6 Hz, 1H), 4.72-4.52 (m, 3H), 4.36 (m, 1H), 4.26-4.04 (m, 3H), 3.93 (m, 2H), 3.84 (s, 3H), 3.72 (m, 1H), 3.49 (m, 2H), 3.41 (m, 2H), 1.54 (t, J=6.9 Hz, 2H), 1.29 (d, J=9.6 Hz, 30H), 0.91 (t, J=6.7 Hz, 3H). $^{31}$P NMR (162 MHz, Methanol-$d_4$) δ −2.01. MS: 843.34 (M+1).

Compound 107 was prepared in a manner similar to 98 using intermediate 107-1 instead of intermediate 98-1.

$^1$H NMR (400 MHz, Methanol-$d_4$) δ 7.94 (t, J=7.8 Hz, 1H), 7.89 (s, 1H), 7.87 (s, 1H), 7.71 (dd, J=7.5, 1.1 Hz, 1H), 6.99 (d, J=4.6 Hz, 1H), 6.90 (d, J=4.6 Hz, 1H), 4.77 (m, 3H), 4.36 (m, 1H), 4.28 (m, 1H), 4.17-4.01 (m, 2H), 3.90 (m, 2H), 3.81-3.72 (m, 1H), 3.57-3.45 (m, 2H), 3.41 (m, 2H), 1.52 (t, J=6.8 Hz, 2H), 1.29 (d, J=7.6 Hz, 30H), 0.91 (t, J=6.7 Hz, 3H).

$^{31}$P NMR (162 MHz, Methanol-$d_4$) δ 0.45.

MS: 814.26 (M+1).

Intermediate 107-1: 6-[[(1S)-1-(Hydroxymethyl)-2-octadecoxy-ethoxy]methyl]pyridine-2-carbonitrile

Intermediate 108-1: 2-Chloro-5-[[(1S)-1-(hydroxymethyl)-2-octadecoxy-ethoxy]methyl]benzonitrile

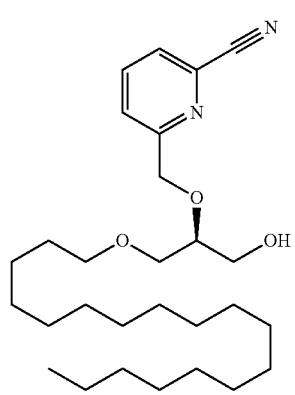

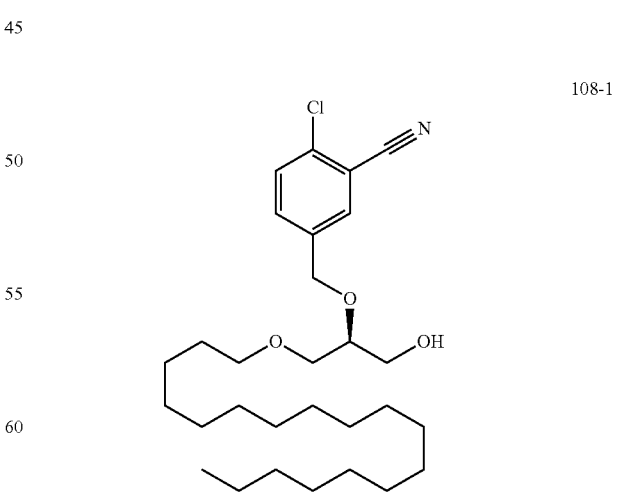

Intermediate 107-1 was prepared in a manner similar to intermediate 98-1 using 6-(bromomethyl)picolinonitrile as alkylation agent.

Intermediate 108-1 was prepared in a manner similar to intermediate 98-1 using 5-(bromomethyl)-2-chlorobenzonitrile as alkylation agent.

Example 108: [(2R,3S,4R,5R)-5-(4-aminopyrrolo[2,1-f][1,2,4]triazin-7-yl)-5-cyano-3,4-dihydroxy-tetrahydrofuran-2-yl]methyl [(2R)-2-[(4-chloro-3-cyanophenyl)methoxy]-3-octadecoxy-propyl] hydrogen phosphate (108)

Example 109: [(2R,3S,4R,5R)-5-(4-Aminopyrrolo[2,1-f][1,2,4]triazin-7-yl)-5-cyano-3,4-dihydroxy-tetrahydrofuran-2-yl]methyl [(2R)-2-[(3-cyano-4-fluoro-phenyl)methoxy]-3-hexadecoxy-propyl] hydrogen phosphate (109)

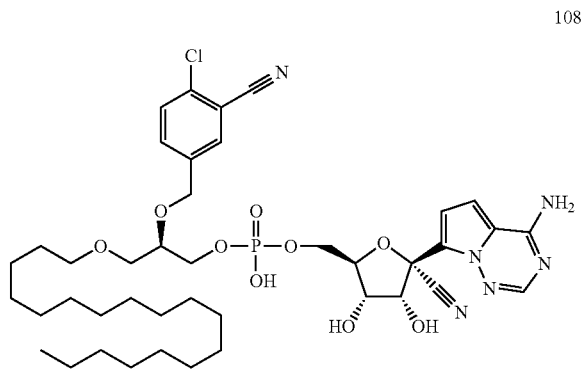 [SMILES: CCCCCCCCCCCCCCCCCCOC[C@H](COP(=O)(O)OC[C@H]1O[C@@](C#N)(c2ccc3c(N)ncnn23)[C@H](O)[C@@H]1O)OCc1ccc(Cl)c(C#N)c1]

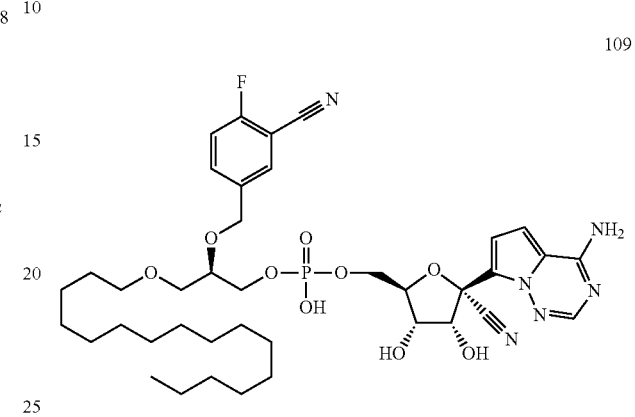

Compound 108 was prepared in a manner similar to 98 using intermediate 108-1 instead of intermediate 98-1.

$^1$H NMR (400 MHz, Methanol-d$_4$) δ 8.14 (s, 1H), 7.76 (s, 1H), 7.64 (d, J=7.3 Hz, 1H), 7.54 (d, J=6.1 Hz, 1H), 7.43 (s, 1H), 7.15 (s, 1H), 4.72 (m, 3H), 4.51-4.00 (m, 6H), 3.98-3.78 (m, 1H), 3.59 (m, 2H), 3.46 (m, 2H), 1.56 (s, 3H), 1.28 (d, J=4.9 Hz, 30H), 0.90 (t, J=6.5 Hz, 3H). $^{31}$P NMR (162 MHz, Methanol-d4) δ −0.78.

MS: 847.3 (M+1).

Intermediate 109-1: 2-Fluoro-5-[[(1S)-1-(hexadecoxymethyl)-2-hydroxy-ethoxy]methyl]benzonitrile Compound 109 was prepared in a manner similar to 98 using intermediate 109-1 instead of intermediate 98-1. $^1$H NMR (400 MHz, DMSO-d$_6$) δ 7.94-7.88 (m, 2H), 7.86-7.69 (m, 1H), 7.50-7.41 (m, 1H), 6.92 (m, 1H), 6.85 (m, 1H), 4.71-4.56 (m, 2H), 4.15 (m, 7H), 4.00-3.72 (m, 3H), 3.72-3.58 (m, 2H), 1.55-1.34 (m, 2H), 1.22 (d, J=7.9 Hz, 26H), 0.85 (m, 3H). $^{31}$P NMR (162 MHz, Methanol-d$_4$) δ −0.22. MS: 803.31 (M+1).

Intermediate 110-1: (2S)-2-[(4-Fluorophenyl)methoxy]-3-octadecoxy-propan-1-ol

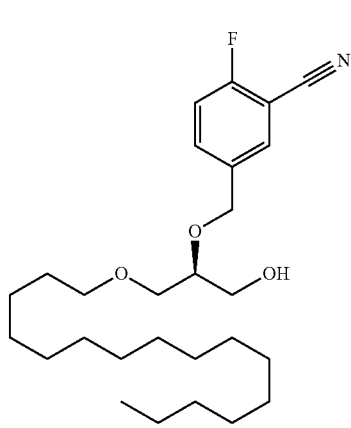

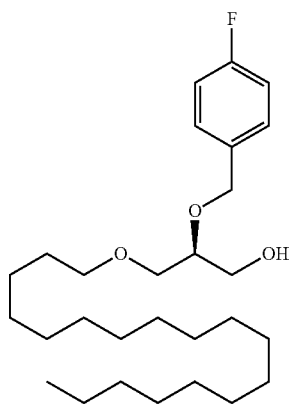

Intermediate 109-1 was prepared in a manner similar to intermediate 2-2 using 5-(bromomethyl)-2-fluorobenzonitrile as alkylation agent.

Intermediate 110-1 was prepared in a manner similar to intermediate 2-2 using 1-(bromomethyl)-4-fluorobenzene as alkylation agent.

Example 110: [(2R,3S,4R,5R)-5-(4-Aminopyrrolo[2,1-f][1,2,4]triazin-7-yl)-5-cyano-3,4-dihydroxy-tetrahydrofuran-2-yl]methyl [(2R)-2-[(4-fluorophenyl)methoxy]-3-octadecoxy-propyl] hydrogen phosphate (110)

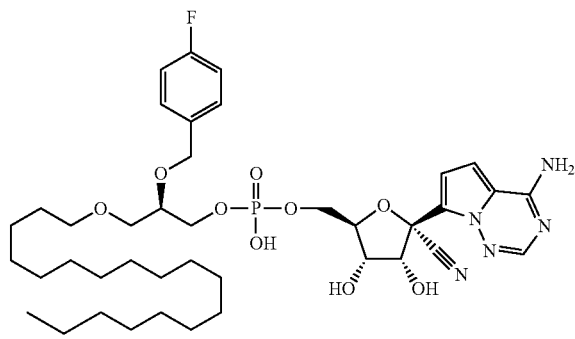

Compound 110 was prepared in a manner similar to 98 using intermediate 110-1 instead of intermediate 98-1. $^1$H NMR (400 MHz, Methanol-$d_4$) δ 7.87 (s, 1H), 7.38-7.31 (m, 2H), 7.05-6.95 (m, 3H), 6.92 (d, J=4.6 Hz, 1H), 4.65-4.53 (m, 2H), 4.43-4.33 (m, 1H), 4.25 (m, 1H), 4.17 (m, 1H), 4.09 (m, 1H), 3.91 (m, 2H), 3.76-3.65 (m, 2H), 3.57-3.35 (m, 4H), 1.51 (m, 2H), 1.39-1.20 (m, 30H), 0.98-0.84 (m, 3H). $^{31}$P NMR (162 MHz, Methanol-$d_4$) δ −0.61.
MS: 806.16 (M+1).

Intermediate 111-1: 4-[[(1R)-3-Heptadecoxy-1-(hydroxymethyl) propoxy] methyl]benzonitrile

Example 111: [(2R,3S,4R,5R)-5-(4-Aminopyrrolo[2,1-f][1,2,4]triazin-7-yl)-5-cyano-3,4-dihydroxy-tetrahydrofuran-2-yl]methyl [(2R)-2-[(4-cyanophenyl)methoxy]-4-heptadecoxy-butyl] hydrogen phosphate (111)

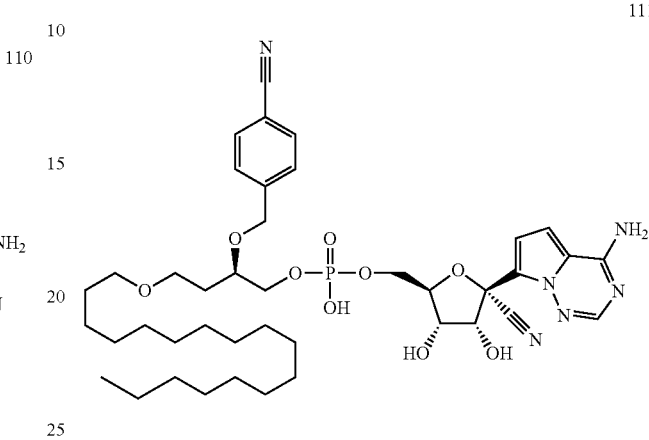

Compound 111 was prepared in a manner similar to 98 using intermediate 111-1 instead of intermediate 98-1. $^1$H NMR (400 MHz, Methanol-$d_4$) δ 7.86 (s, 1H), 7.65 (d, J=8.2 Hz, 2H), 7.50 (d, J=8.1 Hz, 2H), 6.98 (d, J=4.6 Hz, 1H), 6.90 (d, J=4.6 Hz, 1H), 4.89 (m, 1H), 4.75 (m, 1H), 4.56 (m, 1H), 4.40-4.33 (m, 1H), 4.26 (m, 1H), 4.12 (m, 1H), 3.93 (m, 1H), 3.81 (m, 2H), 3.72 (m, 2H), 3.54-3.42 (m, 2H), 1.73 (m, 2H), 1.55-1.44 (m, 2H), 1.29 (d, J=8.8 Hz, 28H), 0.91 (t, J=6.8 Hz, 3H). $^{31}$P NMR (162 MHz, Methanol-$d_4$) δ −0.13. MS: 813.32 (M+1).

Intermediate 112-1: 3-Fluoro-4-[[(1S)-1-(hexadecoxymethyl)-2-hydroxy-ethoxy]methyl]benzonitrile

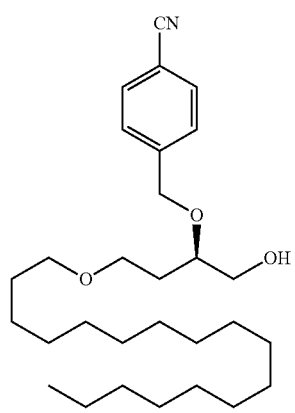

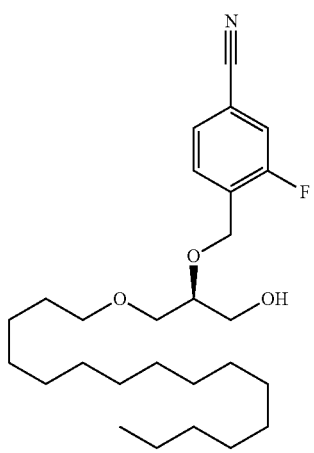

Intermediate 111-1 was prepared in a manner similar to intermediate 2-2 using 4-(bromomethyl)-benzonitrile as alkylation agent.

Intermediate 112-1 was prepared in a manner similar to intermediate 2-2 using 4-(bromomethyl)-3-fluorobenzonitrile as alkylation agent.

Example 112: [(2R,3S,4R,5R)-5-(4-Aminopyrrolo[2,1-f][1,2,4]triazin-7-yl)-5-cyano-3,4-dihydroxy-tetrahydrofuran-2-yl]methyl [(2R)-2-[(4-cyano-2-fluoro-phenyl)methoxy]-3-hexadecoxy-propyl] hydrogen phosphate (112)

Example 113: [(2R,3S,4R,5R)-5-(4-aminopyrrolo[2,1-f][1,2,4]triazin-7-yl)-5-cyano-3,4-dihydroxy-tetrahydrofuran-2-yl]methyl [(2R)-2-[(4-cyano-3-fluoro-phenyl)methoxy]-3-hexadecoxy-propyl] hydrogen phosphate (113)

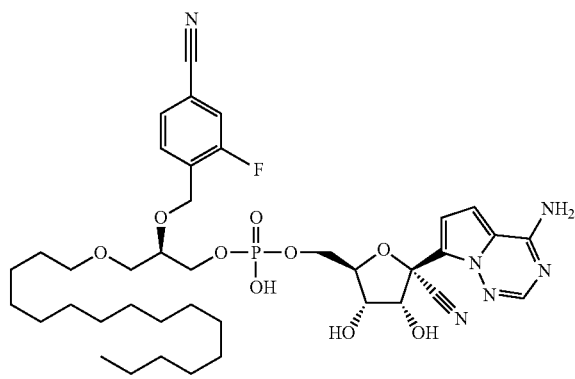

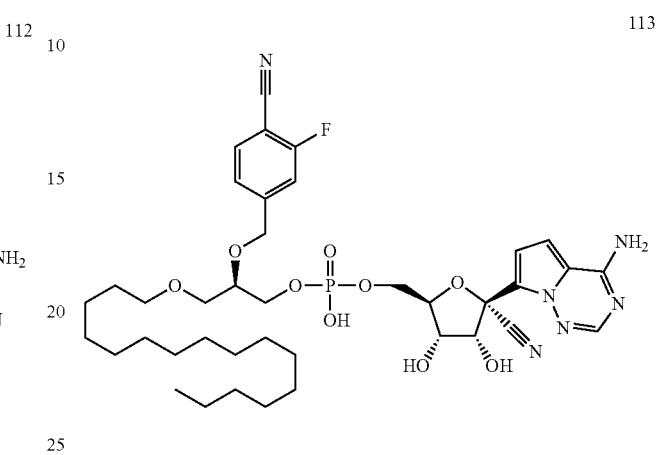

Compound 112 was prepared in a manner similar to 98 using intermediate 112-1 instead of intermediate 98-1.

$^1$H NMR (400 MHz, Methanol-$d_4$) δ 7.87 (s, 1H), 7.73 (t, J=7.5 Hz, 1H), 7.47 (ddd, J=19.5, 8.7, 1.5 Hz, 2H), 6.98 (d, J=4.6 Hz, 1H), 6.90 (d, J=4.6 Hz, 1H), 4.89 (m, 1H), 4.77 (s, 2H), 4.37 (m, 1H), 4.28 (m, 1H), 4.20-4.04 (m, H), 3.90 (m, 2H), 3.75 (m, 1H), 3.57-3.35 (m, 4H), 1.50 (d, J=6.8 Hz, 2H), 1.41-1.19 (m, 26H), 0.96-0.86 (m, 3H).

$^{31}$P NMR (162 MHz, Methanol-$d_4$) δ 0.11.

MS: 803.25 (M+1).

Compound 113 was prepared in a manner similar to 98 using intermediate BM7946 instead of intermediate 98-1.

$^1$H NMR (400 MHz, Methanol-$d_4$) δ 7.87 (s, 1H), 7.65 (dd, J=8.0, 6.7 Hz, 1H), 7.41-7.35 (m, 1H), 7.31 (dd, J=8.1, 1.3 Hz, 1H), 6.99 (d, J=4.6 Hz, 1H), 6.90 (d, J=4.6 Hz, 1H), 4.72 (q, J=14.1 Hz, 2H), 4.37 (m, 1H), 4.27 (m, 1H), 4.22-4.02 (m, 2H), 3.88 (m, 2H), 3.71 (m, 1H), 3.55-3.36 (m, 5H), 1.53 (t, J=6.8 Hz, 2H), 1.28 (d, J=9.1 Hz, 26H), 0.96-0.86 (m, 3H).

$^{31}$P NMR (162 MHz, Methanol-d4) δ −0.01.

MS: 803.25 (M+1).

Intermediate 113-1: 2-Fluoro-4-[[(1S)-1-(hexadecoxymethyl)-2-hydroxy-ethoxy]methyl]benzonitrile

Intermediate 114-1: 4-[[(1S)-1-(Hydroxymethyl)-2-octadecoxy-ethoxy]methyl]-3-methoxy-benzonitrile

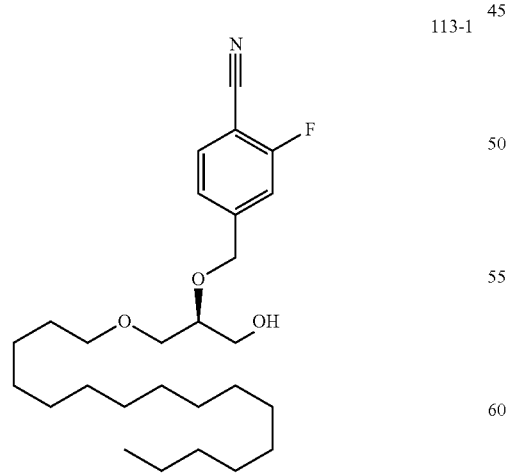

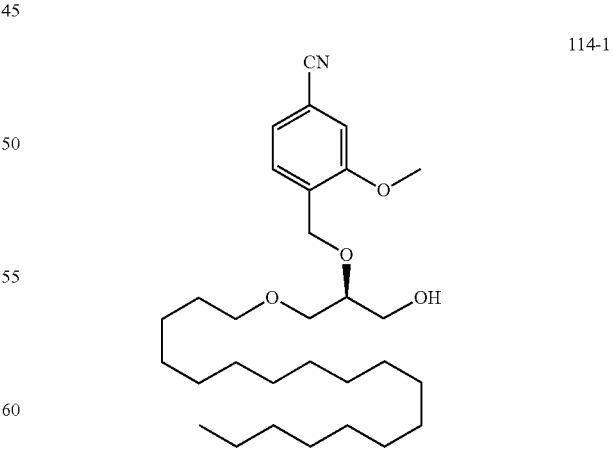

Intermediate 113-1 was prepared in a manner similar to intermediate 2-2 using 4-(bromomethyl)-2-fluorobenzonitrile as alkylation agent.

Intermediate 114-1 was prepared in a manner similar to intermediate 2-2 using 3-(bromomethyl)-4-methoxybenzonitrile as alkylation agent.

Example 114: [(2R,3S,4R,5R)-5-(4-Aminopyrrolo[2,1-f][1,2,4]triazin-7-yl)-5-cyano-3,4-dihydroxy-tetrahydrofuran-2-yl]methyl [(2R)-2-[(4-cyano-2-methoxy-phenyl)methoxy]-3-octadecoxy-propyl] hydrogen phosphate (114)

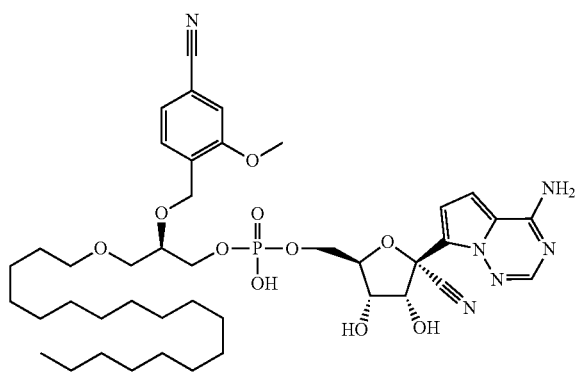

Compound 114 was prepared in a manner similar to 98 using intermediate 114-1 instead of intermediate 98-1.

$^1$H NMR (400 MHz, Methanol-d$_4$) δ 7.86 (s, 1H), 7.61 (d, J=7.7 Hz, 1H), 7.26 (dd, J=7.7, 1.4 Hz, 1H), 7.21 (d, J=1.4 Hz, 1H), 6.97 (d, J=4.6 Hz, 1H), 6.89 (d, J=4.6 Hz, 1H), 4.69 (s, 2H), 4.37 (m, 1H), 4.28 (m, 1H), 4.22-4.01 (m, 2H), 4.01-3.89 (m, 2H), 3.86 (s, 3H), 3.79-3.68 (m, 1H), 3.59-3.36 (m, 4H), 1.51 (t, J=7.0 Hz, 2H), 1.28 (d, J=11.8 Hz, 30H), 0.97-0.83 (m, 3H).

$^{31}$P NMR (162 MHz, Methanol-d4) δ 0.15.

MS: 843.32 (M+1).

Intermediate 115-1: 5-[[(1S)-1-(Hydroxymethyl)-2-octadecoxy-ethoxy]methyl]-2-methoxy-benzonitrile

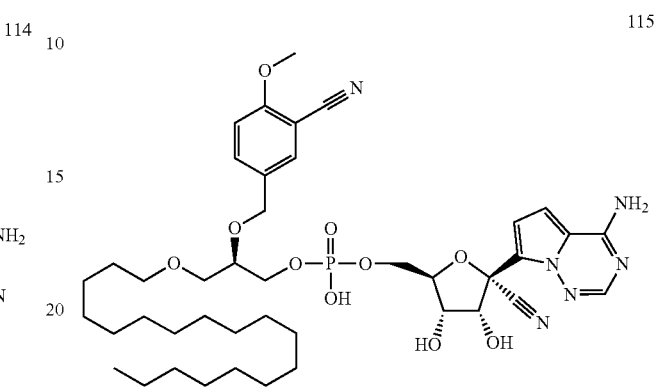

Intermediate 115-1 was prepared in a manner similar to intermediate 2-2 using 5-(bromomethyl)-2-methoxybenzonitrile as alkylation agent.

Example 115: [(2R,3S,4R,5R)-5-(4-Aminopyrrolo[2,1-f][1,2,4]triazin-7-yl)-5-cyano-3,4-dihydroxy-tetrahydrofuran-2-yl]methyl [(2R)-2-[(3-cyano-4-methoxy-phenyl)methoxy]-3-octadecoxy-propyl] hydrogen phosphate (115)

Compound 115 was prepared in a manner similar to 98 using intermediate 115-1 instead of intermediate 98-1.

$^1$H NMR (400 MHz, Methanol-d$_4$) δ 7.87 (s, 1H), 7.57 (m, 2H), 7.12-7.05 (m, 1H), 6.98 (d, J=4.6 Hz, 1H), 6.91 (d, J=4.6 Hz, 1H), 4.65-4.50 (m, 2H), 4.38 (d, J=4.6 Hz, 1H), 4.28 (t, J=5.4 Hz, 1H), 4.22-4.03 (m, 2H), 3.93 (s, 3H), 3.88 (m, 2H), 3.75-3.66 (m, 1H), 3.55-3.36 (m, 4H), 1.53 (t, J=6.8 Hz, 2H), 1.28 (d, J=8.4 Hz, 30H), 0.96-0.85 (m, 3H).

$^{31}$P NMR (162 MHz, Methanol-d4) δ −0.76.

MS: 843.34 (M+1).

Intermediate 116-1: 5-[[(1S)-1-(Hydroxymethyl)-2-octadecoxy-ethoxy]methyl]pyridine-2-carbonitrile

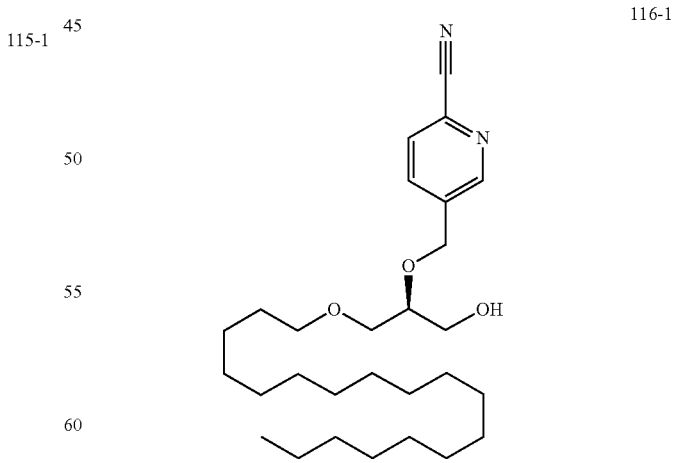

Intermediate 116-1 was prepared in a manner similar to intermediate 2-2 using 5-(bromomethyl)picolinonitrile as alkylation agent.

Example 116: [(2R,3S,4R,5R)-5-(4-aminopyrrolo[2,1-f][1,2,4]triazin-7-yl)-5-cyano-3,4-dihydroxy-tetrahydrofuran-2-yl]methyl [(2R)-2-[(6-cyano-3-pyridyl)methoxy]-3-octadecoxy-propyl] hydrogen phosphate (116)

Example 117: [(2R,3S,4R,5R)-5-(4-aminopyrrolo[2,1-f][1,2,4]triazin-7-yl)-5-cyano-3,4-dihydroxy-tetrahydrofuran-2-yl]methyl [(2R)-2-[(3-cyano-5-fluorophenyl)methoxy]-3-tetradecoxy-propyl] hydrogen phosphate (117)

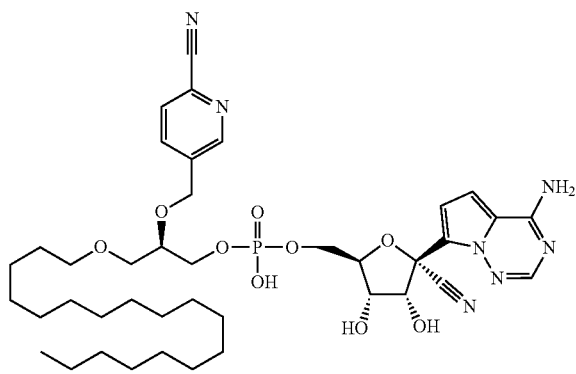

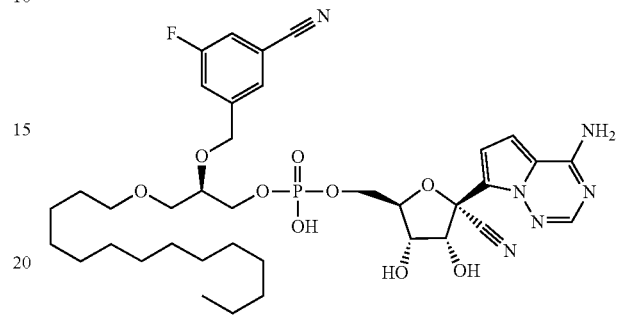

Compound 116 was prepared in a manner similar to 98 using intermediate 116-1 instead of intermediate 98-1.

$^1$H NMR (400 MHz, Methanol-d$_4$) δ 8.65 (d, J=2.0 Hz, 1H), 7.99 (dd, J=8.0, 2.1 Hz, 1H), 7.87 (s, 1H), 7.79 (d, J=8.0 Hz, 1H), 6.98 (d, J=4.6 Hz, 1H), 6.90 (d, J=4.6 Hz, 1H1), 4.77 (q, J=13.7 Hz, 2H), 4.37 (m, 1H), 4.28 (m, 1H), 4.21-4.02 (m, 2H), 3.90 (m, 2H), 3.81-3.70 (m, 1H), 3.56-3.36 (m, 4H), 1.52 (t, J=6.9 Hz, 2H), 1.28 (d, J=9.5 Hz, 30H), 1.00-0.82 (m, 3H).

$^{31}$P NMR (162 MHz, Methanol-d4) δ 0.12.

MS: 814.35 (M+1).

Intermediate 117-1: 3-Fluoro-5-[[(1S)-1-(hydroxymethyl)-2-tetradecoxy-ethoxy]methyl]benzonitrile Compound 117 was prepared in a manner similar to 98 using intermediate 117-1 instead of intermediate 98-1.

$^1$H NMR (400 MHz, Methanol-d$_4$) δ 8.07 (s, 1H), 7.55 (s, 1H), 7.51-7.43 (m, 1H), 7.38 (dt, J=8.3, 1.8 Hz, 1H), 7.29 (d, J=4.7 Hz, 1H), 7.16 (d, J=4.7 Hz, 1H), 4.84-4.67 (m, 3H), 4.36 (s, 1H), 4.31-4.19 (m, 2H), 4.13 (m, 1H), 4.08-3.91 (m, 2H), 3.80 (m, 1H), 3.65-3.51 (m, 2H), 3.44 (m, 2H), 1.55 (m, 2H), 1.28 (d, J=5.9 Hz, 22H), 0.97-0.86 (m, 3H). $^{31}$P NMR (162 MHz, Methanol-d4) δ 0.0.

MS: 775.26 (M+1).

Intermediate 118-1: 3-Fluoro-5-[[(1S)-1-(hydroxymethyl)-2-pentadecoxy-ethoxy]methyl]benzonitrile

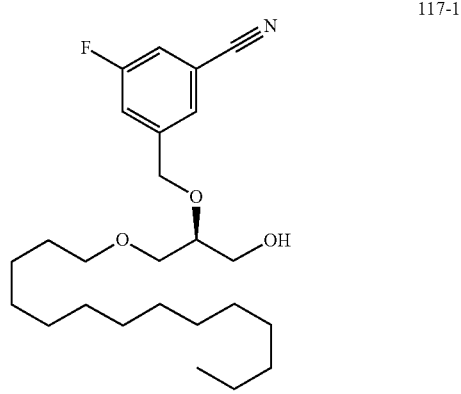 [SMILES: CCCCCCCCCCCCCCOC[C@H](CO)OCc1cc(F)cc(C#N)c1]

Intermediate 117-1 was prepared in a manner similar to intermediate 2-2 using 3-(bromomethyl)-5-fluorobenzonitrile as alkylation agent.

Intermediate 118-1 was prepared in a manner similar to intermediate 2-2 using 3-(bromomethyl)-5-fluorobenzonitrile as alkylation agent.

Example 118: [(2R,3S,4R,5R)-5-(4-Aminopyrrolo[2,1-f][1,2,4]triazin-7-yl)-5-cyano-3,4-dihydroxy-tetrahydrofuran-2-yl]methyl [(2R)-2-[(3-cyano-5-fluoro-phenyl)methoxy]-3-pentadecoxy-propyl] hydrogen phosphate (118)

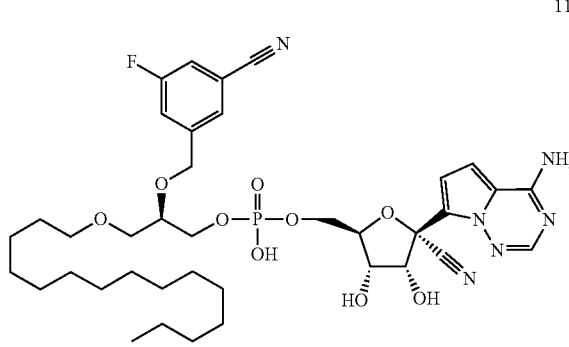

Compound 118 was prepared in a manner similar to 98 using intermediate 118-1 instead of intermediate 98-1.

$^1$H NMR (400 MHz, Methanol-$d_4$) δ 7.87 (d, J=1.6 Hz, 1H), 7.53 (s, 1H), 7.45 (dt, J=9.5, 1.7 Hz, 1H), 7.42-7.34 (m, 1H), 6.98 (d, J=4.7 Hz, 1H), 6.91 (t, J=4.9 Hz, 1H), 4.79-4.61 (m, 2H), 4.37 (m, 1H), 4.28 (m, 1H), 4.12 (m, 2H), 3.97-3.80 (m, 2H), 3.76-3.68 (m, 1H), 3.57-3.35 (m, 4H), 1.54 (t, J=7.0 Hz, 2H), 1.38-1.20 (m, 24H), 0.96-0.87 (m, 3H).

$^{31}$P NMR (162 MHz, Methanol-$d_4$) δ 0.04.

MS: 789.48 (M+1).

Intermediate 119-1: 3-Fluoro-5-[[(1S)-1-(hexadecoxymethyl)-2-hydroxy-ethoxy]methyl]benzonitrile

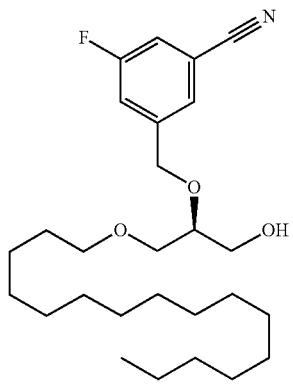

Intermediate 119-1 was prepared in a manner similar to intermediate 2-2 using 3-(bromomethyl)-5-fluorobenzonitrile as alkylation agent.

Example 119: [(2R,3S,4R,5R)-5-(4-Aminopyrrolo[2,1-f][1,2,4]triazin-7-yl)-5-cyano-3,4-dihydroxy-tetrahydrofuran-2-yl]methyl [(2R)-2-[(3-cyano-5-fluoro-phenyl)methoxy]-3-hexadecoxy-propyl] hydrogen phosphate (119)

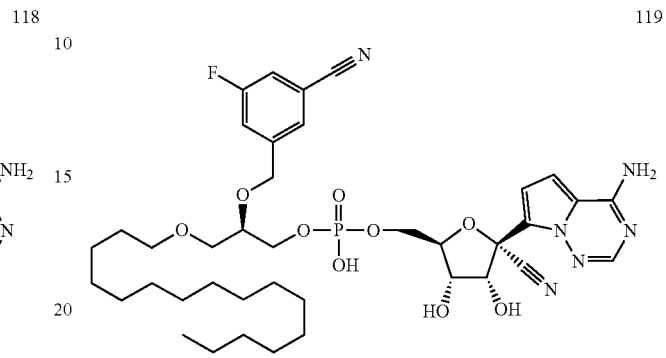

Compound 119 was prepared in a manner similar to 98 using intermediate 119-1 instead of intermediate 98-1. $^1$H NMR (400 MHz, Methanol-$d_4$) δ 7.87 (d, J=1.7 Hz, 1H), 7.53 (d, J=1.4 Hz, 1H), 7.45 (dt, J=9.5, 1.7 Hz, 1H), 7.38 (m, 1H), 6.98 (d, J=4.6 Hz, 1H), 6.95-6.85 (m, 1H), 4.77-4.62 (m, 2H), 4.37 (t, J=4.4 Hz, 1H), 4.28 (m, 1H), 4.11 (m, 2H), 3.89 (m, 2H), 3.79-3.67 (m, 1H), 3.56-3.36 (m, 4H), 1.54 (m, 2H), 1.28 (d, J=7.7 Hz, 26H), 0.97-0.85 (m, 3H). $^{31}$P NMR (162 MHz, Methanol-$d_4$) δ 0.16. MS: 803.21 (M+1).

Intermediate 120-1: 4-(Tetradecyloxy)butan-1-ol

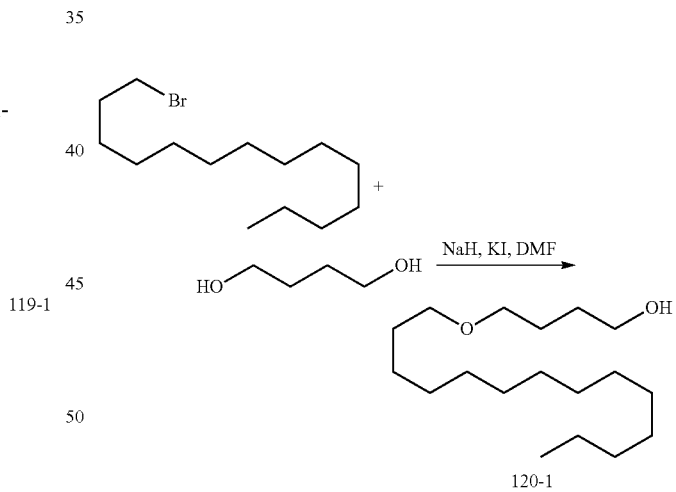

To a solution of butane-1,4-diol (1.22 g, 13.5 mmol) in dry DMF (6 mL) was added NaH (60% oil dispersion; 172 mg, 45 mmol) at 0° C. and the mixture was stirred at room temperature for 10 min. 1-Bromotetradecane (0.832 g, 3 mmol) and KI (498 mg, 3 mmol) were added and the mixture was heated at 95° C. for 4 h. After cooling, the mixture was poured into ice-water and extracted with DCM. The extracts were washed with brine, dried over Na$_2$SO$_4$ and evaporated. The resulting residue was purified by flash column chromatography (silica gel; AcOEt/hexane, 1:2) to provide 120-1.

$^1$H NMR (400 MHz, Chloroform-d) δ 3.67 (m, 2H), 3.47 (m, 4H), 1.76-1.66 (m, 4H), 1.64-1.54 (m, 2H), 1.28 (s, 22H), 0.90 (t, J=6.8 Hz, 3H).

Example 120: [(2R,3S,4R,5R)-5-(4-Aminopyrrolo[2,1-f][1,2,4]triazin-7-yl)-5-cyano-3,4-dihydroxy-tetrahydrofuran-2-yl]methyl 4-tetradecoxybutyl hydrogen phosphate (120)

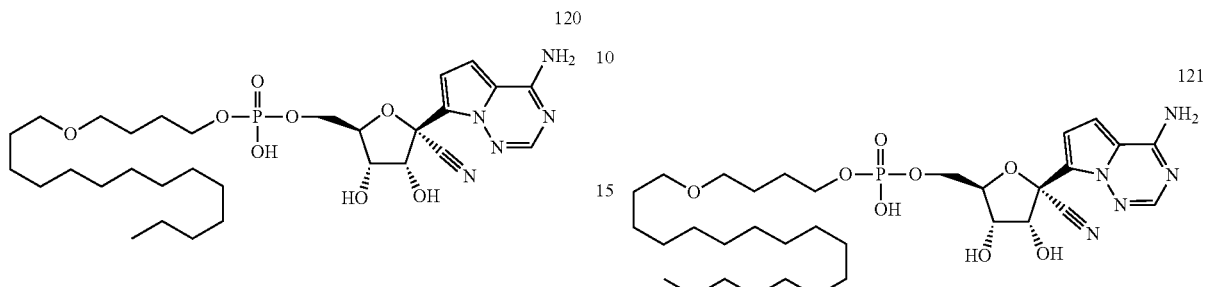

Compound 120 was prepared in a manner similar to 98 using intermediate 120-1 instead of intermediate 98-1. $^1$H NMR (400 MHz, Methanol-$d_4$) δ 8.17 (s, 1H), 7.52 (s, 1H), 7.16 (s, 1H), 4.75 (m, 1H), 4.37 (d, J=22.9 Hz, 2H), 4.19 (d, J=19.3 Hz, 2H), 4.04 (s, 2H), 3.44 (m, 4H), 1.69 (m, 4H), 1.55 (t, J=6.2 Hz, 2H), 1.28 (s, 22H), 0.90 (t, J=6.4 Hz, 3H). $^{31}$P NMR (162 MHz, Methanol-d4) δ −0.82. MS: 640.21 (M+1).

Intermediate 121-1: 4-Heptadecoxybutan-1-ol

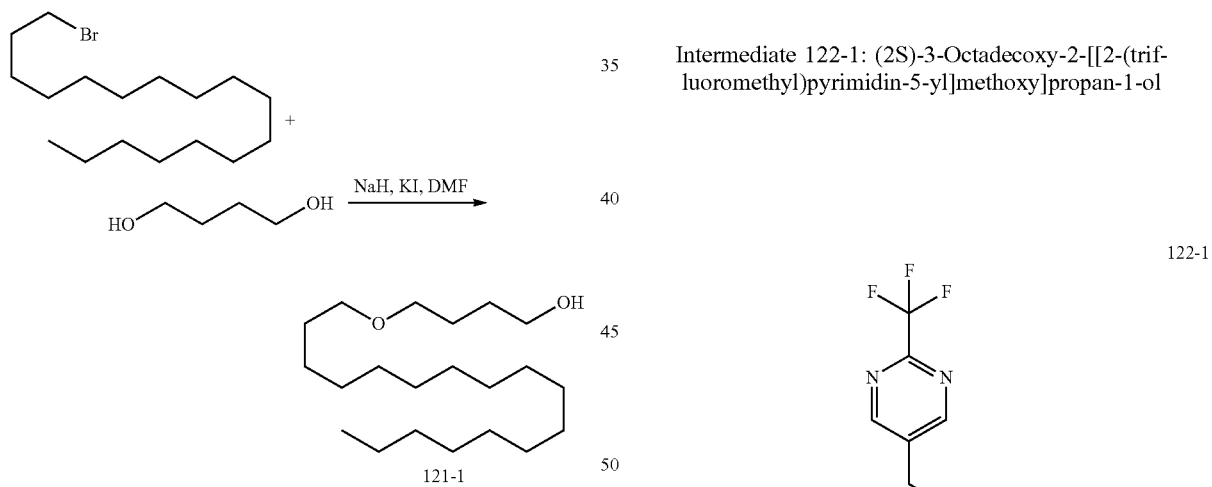

To a solution of butane-1,4-diol (1.22 g, 13.5 mmol) in dry DMF (6 mL) was added NaH (60% oil dispersion; 172 mg, 45 mmol) at 0° C. and the mixture was stirred at room temperature for 10 min. 1-bromoheptadecane (0.958 g, 3 mmol) and KI (498 mg, 3 mmol) were added and the mixture was heated at 95° C. for 4 h. After cooling, the mixture was poured into ice-water and extracted with DCM. The extracts were washed with brine, dried over $Na_2SO_4$ and evaporated. The resulting residue was purified by flash column chromatography (silica gel; AcOEt/hexane, 1:2) to provide 121-1. $^1$H NMR (400 MHz, Chloroform-d) δ 3.67 (t, J=5.5 Hz, 2H), 3.47 (dt, J=13.3, 6.0 Hz, 4H), 2.07-1.78 (m, 2H), 1.70 (dd, J=7.9, 5.0 Hz, 4H), 1.59 (q, J=7.1 Hz, 2H), 1.28 (s, 30H), 0.90 (t, J=6.7 Hz, 3H).

Example 121: [(2R,3S,4R,5R)-5-(4-Aminopyrrolo[2,1-f][1,2,4]triazin-7-yl)-5-cyano-3,4-dihydroxy-tetrahydrofuran-2-yl]methyl 4-heptadecoxybutyl hydrogen phosphate (121)

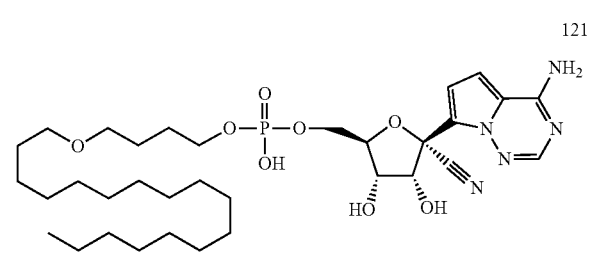 [SMILES: CCCCCCCCCCCCCCCCCOCCCCOP(=O)(O)OC[C@H]1O[C@@](C#N)(c2ccc3c(N)ncnn23)[C@H](O)[C@@H]1O]

Compound 121 was prepared in a manner similar to 120 using intermediate 121-1.

$^1$H NMR (400 MHz, Methanol-$d_4$) δ 8.17 (s, 1H), 7.52 (s, 1H), 7.16 (s, 1H), 4.75 (m, 1H), 4.36 (d, J=26.6 Hz, 2H), 4.26-4.12 (m, 2H), 4.04 (m, 2H), 3.44 (m, 4H), 1.69 (m, 4H), 1.60-1.46 (m, 2H), 1.29 (s, 28H), 1.00-0.79 (m, 3H).

$^{31}$P NMR (162 MHz, Methanol-$d_4$) δ −0.85.

MS: 682.23 (M+1).

Intermediate 122-1: (2S)-3-Octadecoxy-2-[[2-(trifluoromethyl)pyrimidin-5-yl]methoxy]propan-1-ol

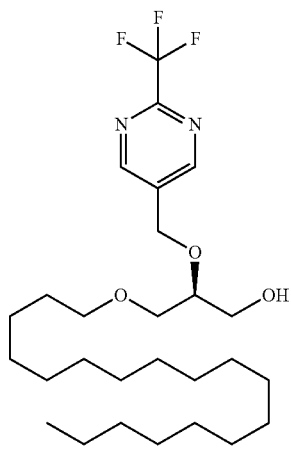

Intermediate 122-1 was prepared in a manner similar to intermediate 2-2 using 5-(bromomethyl)-2-(trifluoromethyl)pyrimidine as alkylation agent.

Example 122: [(2R,3S,4R,5R)-5-(4-Aminopyrrolo[2,1-f][1,2,4]triazin-7-yl)-5-cyano-3,4-dihydroxy-tetrahydrofuran-2-yl]methyl [(2R)-3-octadecoxy-2-[[2-(trifluoromethyl)pyrimidin-5-yl]methoxy]propyl] hydrogen phosphate (122)

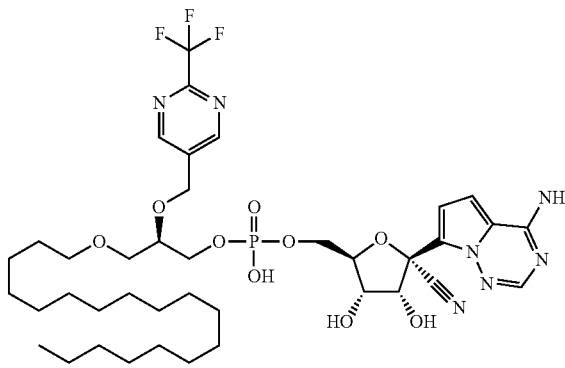

Compound 122 was prepared in a manner similar to 98 using intermediate 122-1 instead of intermediate 98-1. $^1$H NMR (400 MHz, Methanol-$d_4$) δ 8.42 (d, J=9.3 Hz, 1H), 7.87 (d, J=10.5 Hz, 1H), 6.93 (m, 3H), 4.75-4.47 (m, 2H), 4.44-3.95 (m, 6H), 3.67 (m, 2H), 3.55-3.34 (m, 3H), 1.56-1.38 (m, 2H), 1.25 (m, 30H), 0.91 (t, J=6.7 Hz, 3H). $^{31}$P NMR (162 MHz, Methanol-$d_4$) δ −0.84. MS: 858.21 (M+1).

Intermediate 123-1: (2S)-3-Octadecoxy-2-[[6-(trifluoromethyl)-3-pyridyl]methoxy] propan-1-ol

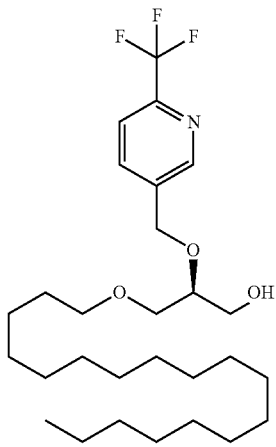

Intermediate 123-1 was prepared in a manner similar to intermediate 2-2 using 5-(bromomethyl)-2-(trifluoromethyl)pyridine as alkylation agent.

Example 123: [(2R,3S,4R,5R)-5-(4-Aminopyrrolo[2,1-f][1,2,4]triazin-7-yl)-5-cyano-3,4-dihydroxy-tetrahydrofuran-2-yl]methyl [(2R)-3-octadecoxy-2-[[6-(trifluoromethyl)-3-pyridyl]methoxy]propyl] hydrogen phosphate (123)

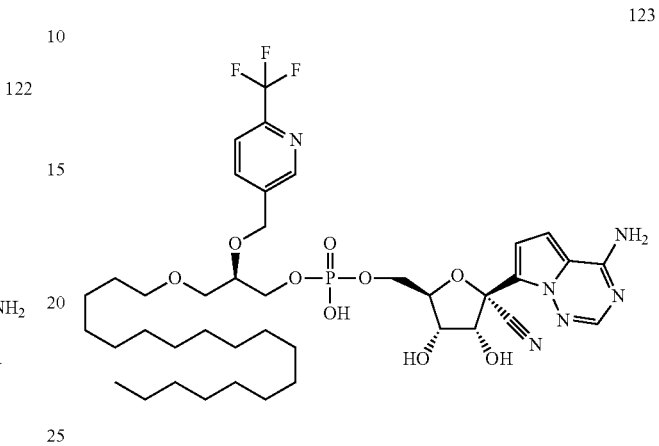

Compound 123 was prepared in a manner similar to 98 using intermediate 123-1 instead of intermediate 98-1. $^1$H NMR (400 MHz, Methanol-$d_4$) δ 8.66 (d, J=1.9 Hz, 1H), 8.03 (dd, J=8.0, 1.9 Hz, 1H), 7.87 (s, 1H), 7.73 (d, J=8.0 Hz, 1H), 6.98 (d, J=4.6 Hz, 1H), 6.88 (d, J=4.6 Hz, 1H), 4.83-4.63 (m, 3H), 4.37 (m, 1H), 4.26 (m, 1H), 4.22-4.02 (m, 2H), 3.91 (m, 2H), 3.77 (m, 1H), 3.56-3.35 (m, 4H), 1.51 (t, J=6.9 Hz, 2H), 1.28 (d, J=11.5 Hz, 30H), 0.91 (t, J=6.8 Hz, 3H). $^{31}$P NMR (162 MHz, Methanol-$d_4$) δ −0.69. MS: 857.38 (M+1).

Intermediate 124-1: 6-[[(1S)-1-(Hydroxymethyl)-2-octadecoxy-ethoxy]methyl]pyridine-3-carbonitrile

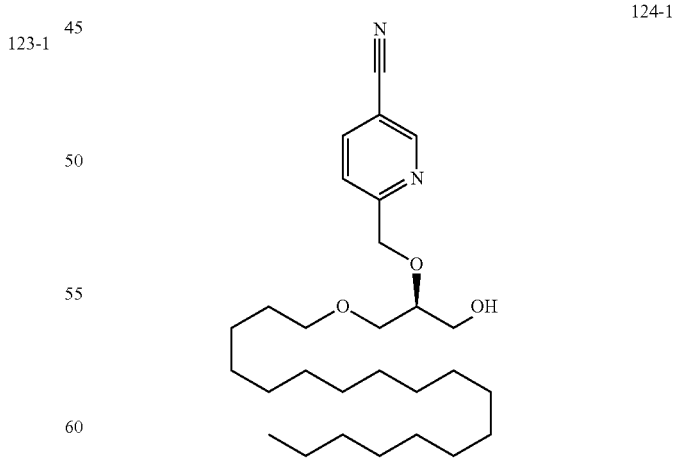

Intermediate 124-1 was prepared in a manner similar to intermediate 2-2 using 6-(bromomethyl)nicotinonitrile as alkylation agent.

Example 124: [(2R,3S,4R,5R)-5-(4-Aminopyrrolo[2,1-f][1,2,4]triazin-7-yl)-5-cyano-3,4-dihydroxytetrahydrofuran-2-yl]methyl [(2R)-2-[(5-cyano-2-pyridyl)methoxy]-3-octadecoxy-propyl] hydrogen phosphate (124)

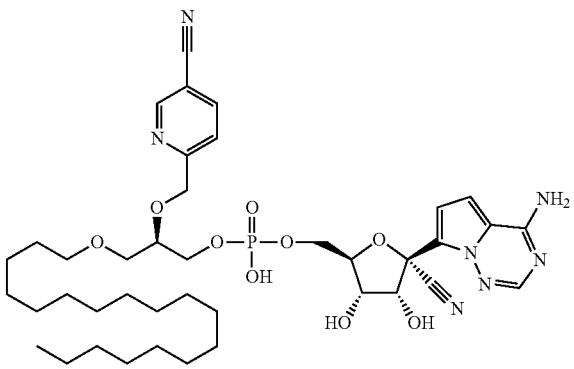

124

Compound 124 was prepared in a manner similar to 98 using intermediate 124-1 instead of intermediate 98-1. ¹H NMR (400 MHz, Methanol-d₄) δ 8.77 (d, J=2.0 Hz, 1H), 8.10 (dd, J=8.2, 2.1 Hz, 1H), 7.86 (s, 1H), 7.79 (d, J=8.2 Hz, 1H), 6.98 (d, J=4.6 Hz, 1H), 6.88 (d, J=4.6 Hz, 1H), 4.83 (m, 3H), 4.36 (m, 1H), 4.26 (m, 1H), 4.21-4.01 (m, 2H), 4.00-3.84 (m, 2H), 3.78 (m, 1H), 3.61-3.37 (m, 4H), 1.51 (t, J=6.6 Hz, 2H), 1.41-1.19 (m, 30H), 0.91 (t, J=6.8 Hz, 3H). ³¹P NMR (162 MHz, Methanol-d₄) δ −0.45. MS: 814.51 (M+1).

Example 125: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((3-cyano-5-fluorobenzyl)oxy)-3-(icosyloxy)propyl) hydrogen phosphate (125)

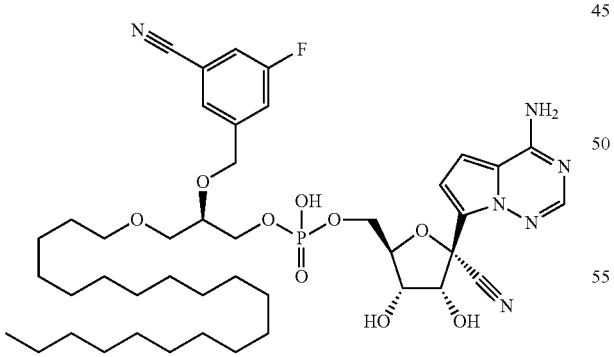

125

Example 125 was prepared in a manner similar to Example 70 utilizing icosan-1-ol instead of nonadecan-1-ol in the first step. ¹H NMR (400 MHz, Methanol-d4) δ 8.01 (s, 1H), 7.54 (s, 1H), 7.47 (d, J=9.4 Hz, 1H), 7.41-7.36 (m, 1H), 7.21-7.13 (m, 2H), 4.80-4.75 (m, 2H), 4.70 (s, 1H), 4.35 (d, J=5.0 Hz, 1H), 4.25 (d, J=5.5 Hz, 1H), 4.18 (ddd, J=11.6, 5.4, 3.1 Hz, 1H), 4.08 (dt, J=11.7, 4.6 Hz, 1H), 3.93 (dq, J=10.9, 5.4 Hz, 2H), 3.77 (p, J=5.6 Hz, 1H), 3.59-3.48 (m, 2H), 3.44 (td, J=6.5, 3.3 Hz, 2H), 1.54 (q, J=6.8 Hz, 2H), 1.29 (d, J=6.7 Hz, 34H), 0.95-0.87 (m, 3H). LCMS: 857.4 [M−H]⁻.

Example 126: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((3-cyano-5-fluorobenzyl)oxy)-3-(((E)-octadec-9-en-1-yl)oxy)propyl) hydrogen phosphate (126)

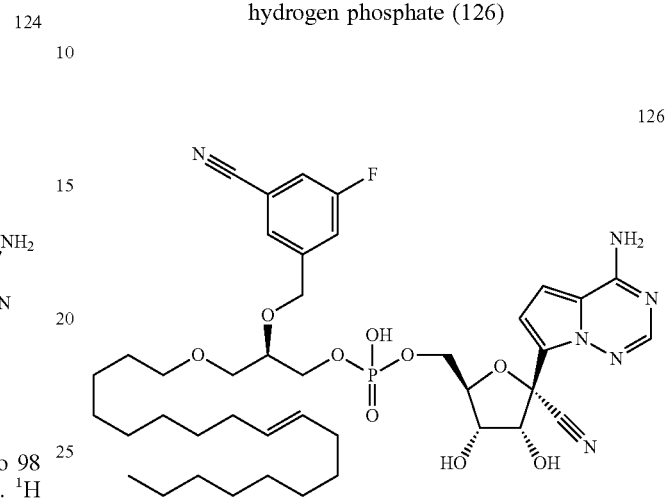

126

Example 126 was prepared in a manner similar to Example 70 utilizing (E)-octadec-9-en-1-ol instead of nonadecan-1-ol in the first step.

¹H NMR (400 MHz, Methanol-d4) δ 7.88 (s, 1H), 7.53 (s, 1H), 7.48-7.36 (m, 2H), 6.96 (dd, J=41.8, 4.6 Hz, 2H), 5.38 (td, J=3.7, 1.8 Hz, 2H), 4.82 (d, J=5.2 Hz, 1H), 4.76-4.61 (m, 2H), 4.35 (dd, J=6.4, 2.9 Hz, 1H), 4.26 (t, J=5.4 Hz, 1H), 4.17-4.03 (m, 2H), 3.87 (qt, J=11.0, 5.5 Hz, 2H), 3.72 (p, J=5.3 Hz, 2H), 3.54-3.45 (m, 2H), 3.41 (td, J=6.6, 3.7 Hz, 2H), 2.01-1.92 (m, 4H), 1.53 (q, J=6.5 Hz, 2H), 1.30 (q, J=10.1, 8.9 Hz, 23H), 0.91 (t, J=6.8 Hz, 3H).

LCMS: 827.4 [M−H]⁻.

Example 127: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((4-cyano-2-fluorobenzyl)oxy)-3-(((E)-octadec-9-en-1-yl)oxy)propyl) hydrogen phosphate (127)

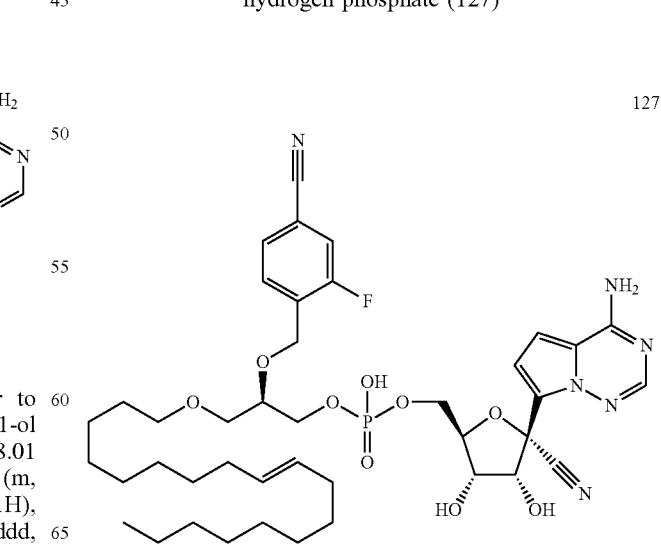

127

Example 127 was prepared in a manner similar to Example 126 utilizing 3-fluoro-4-bromomethyl-benzonitrile instead of 3-fluoro-5-bromomethyl-benzonitrile in the second step. ¹H NMR (400 MHz, Methanol-d4) δ 7.93 (s, 1H), 7.74 (t, J=7.6 Hz, 1H), 7.54-7.40 (m, 2H), 7.08-6.98 (m, 2H), 5.38 (td, J=3.7, 1.8 Hz, 2H), 4.80 (d, J=5.3 Hz, 1H), 4.79-4.77 (m, 2H), 4.34 (q, J=4.1 Hz, 1H), 4.25 (t, J=5.4 Hz, 1H), 4.19-4.12 (m, 1H), 4.07 (dt, J=11.5, 4.6 Hz, 1H), 3.91 (qt, J=11.0, 5.5 Hz, 2H), 3.77 (p, J=5.2 Hz, 1H), 3.57-3.46 (m, 2H), 3.46-3.37 (m, 2H), 1.97 (d, J=6.6 Hz, 4H), 1.51 (p, J=7.1, 6.6 Hz, 2H), 1.30 (td, J=14.5, 11.6, 5.0 Hz, 25H), 0.95-0.80 (m, 3H). LCMS: 827.4 [M–H]⁻.

Example 128: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((3-cyano-5-fluorobenzyl)oxy)-3-(((Z)-octadec-9-en-1-yl)oxy)propyl) hydrogen phosphate (128)

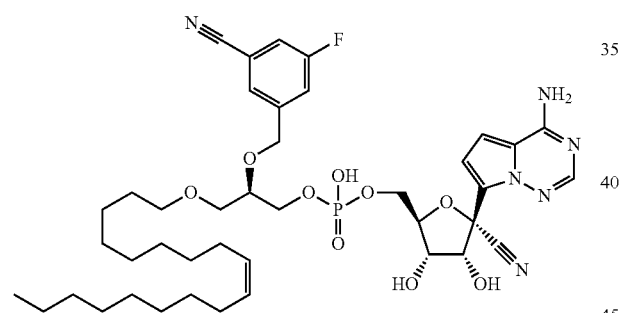

128

Example 128 was prepared in a manner similar to Example 70 utilizing (Z)-octadec-9-en-1-ol instead of nonadecan-1-ol in the first step. ¹H NMR (400 MHz, Methanol-d4) δ 8.04 (s, 1H), 7.76 (t, J=7.6 Hz, 1H), 7.55-7.45 (m, 2H), 7.20 (dd, J=31.2, 4.8 Hz, 2H), 5.43-5.33 (m, 2H), 4.82-4.76 (m, 4H), 4.35 (d, J=4.5 Hz, 1H), 4.25 (t, J=5.5 Hz, 1H), 4.09 (dd, J=13.2, 3.6 Hz, 5H), 3.95 (dq, J=10.8, 5.1 Hz, 2H), 3.81 (t, J=5.1 Hz, 1H), 3.74 (t, J=12.5 Hz, 4H), 3.65-3.50 (m, 2H), 3.47-3.41 (m, 5H), 3.22-3.15 (m, 4H), 2.05 (d, J=11.6 Hz, OH), 1.60-1.44 (m, 2H), 1.30 (s, 28H), 0.91 (t, J=6.4 Hz, 4H). LCMS: 827.4 [M–H]⁻.

Example 129: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((4-cyano-2-fluorobenzyl)oxy)-3-(((Z)-octadec-9-en-1-yl)oxy)propyl) hydrogen phosphate (129)

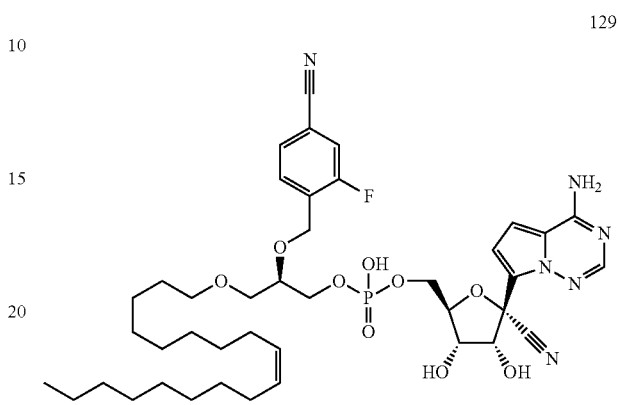

129

Example 129 was prepared in a manner similar to Example 128 utilizing 3-fluoro-4-bromomethyl-benzonitrile instead of 3-fluoro-5-bromomethyl-benzonitrile in the second step. ¹H NMR (400 MHz, Methanol-d4) δ 7.97 (s, 1H), 7.75 (t, J=7.5 Hz, 1H), 7.52-7.44 (m, 3H), 7.09 (s, 3H), 5.41-5.32 (m, 2H), 4.79 (s, 3H), 4.35 (d, J=4.7 Hz, 1H), 4.26 (t, J=5.4 Hz, 1H), 4.16 (dt, J=11.5, 3.9 Hz, 1H), 4.12-4.03 (m, 1H), 3.92 (dp, J=16.2, 5.0 Hz, 2H), 3.83-3.74 (m, 1H), 3.58-3.48 (m, 2H), 3.46-3.41 (m, 2H), 3.15 (p, J=1.7 Hz, 1H), 2.02 (d, J=9.4 Hz, 4H), 1.58-1.47 (m, 2H), 1.41-1.23 (m, 34H), 0.93-0.89 (m, 5H). LCMS: 827.4 [M–H]⁻.

Example 130: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-(benzyloxy)-3-(((Z)-octadec-9-en-1-yl)oxy)propyl) hydrogen phosphate (130)

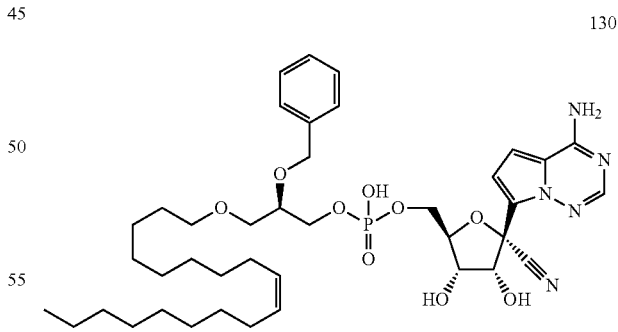

130

Example 130 was prepared in a manner similar to Example 120 utilizing benzyl bromide instead of 3-fluoro-5-bromomethyl-benzonitrile in the second step. 1H NMR (400 MHz, Methanol-d4) δ 8.00 (s, 1H), 7.36-7.32 (m, 2H), 7.32-7.26 (m, 2H), 7.26-7.18 (m, 2H), 7.15 (d, J=4.7 Hz, 1H), 5.42-5.33 (m, 2H), 4.96-4.90 (m, 5H), 4.82-4.76 (m, 2H), 4.64 (q, J=11.9 Hz, 2H), 4.40-4.32 (m, 1H), 4.27 (t, J=5.4 Hz, 1H), 4.22-4.13 (m, 1H), 4.11-4.04 (m, 1H), 3.93 (dq, J=13.9, 5.3 Hz, 2H), 3.80-3.70 (m, 1H), 3.60-3.47 (m, 3H), 3.46-3.39 (m, 2H), 2.08-1.94 (m, 5H), 1.54 (t, J=6.9 Hz, 2H), 1.42-1.23 (m, 22H), 0.96-0.86 (m, 3H). LCMS: 784.4 [M−H]⁻.

Example 131: ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-(benzyloxy)-3-(((E)-octadec-9-en-1-yl)oxy)propyl) hydrogen phosphate (131)

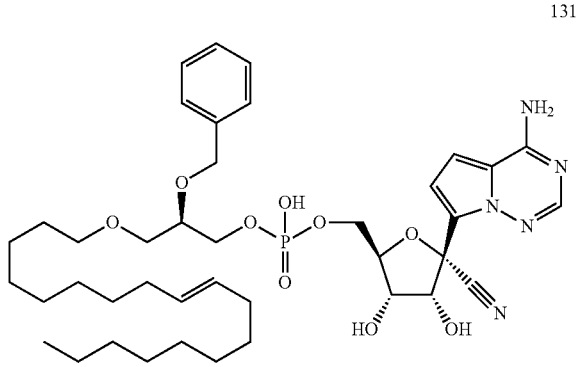 [SMILES: CCCCCCCC/C=C/CCCCCCCCOC[C@H](COP(=O)(O)OC[C@H]1O[C@@](C#N)(c2ccc3c(N)ncnn23)[C@H](O)[C@@H]1O)OCc1ccccc1]

131

Example 131 was prepared in a manner similar to Example 127 utilizing benzyl bromide instead of 3-fluoro-5-bromomethyl-benzonitrile in the second step. ¹H NMR (400 MHz, Methanol-d4) δ 7.96 (s, 1H), 7.36-7.32 (m, 2H), 7.31-7.26 (m, 2H), 7.24 (dd, J=6.4, 2.2 Hz, 1H), 7.11 (s, 2H), 5.42-5.33 (m, 2H), 4.80 (dd, J=4.9, 3.0 Hz, 1H), 4.63 (q, J=11.9 Hz, 2H), 4.35 (d, J=4.8 Hz, 1H), 4.27 (t, J=5.4 Hz, 1H), 4.16 (dt, J=11.4, 3.8 Hz, 1H), 4.07 (dt, J=11.5, 4.5 Hz, 1H), 3.96-3.85 (m, 1H), 3.78-3.69 (m, 1H), 3.55 (dd, J=11.1, 3.5 Hz, 1H), 3.51-3.46 (m, 1H), 3.41 (td, J=6.6, 1.8 Hz, 2H), 3.15 (p, J=1.6 Hz, 1H), 2.01 (d, J=24.7 Hz, 4H), 1.65 (d, J=2.9 Hz, 1H), 1.54 (t, J=6.9 Hz, 2H), 1.33 (d, J=16.9 Hz, 34H), 0.92 (td, J=6.6, 3.1 Hz, 4H). LCMS: 784.4 [M−H]⁻.

Example 132: RSV-Fluc Antiviral Assay

Normal human brochial epithelial (NHBE) cells donor 32027 were purchased from Lonza (Walkersville, MD Cat #CC-2540) and maintained in Bronchial Epithelial Cell Growth Medium (BEGM) (Lonza, Walkersville, MD, Cat #CC-3170) with all provided supplements in the BulletKit. Cells were passaged 2-3 times per week to maintain subconfluent densities and were used for experiments at passages 2-4.

Recombinant Respiratory Syncytial virus strain A2 containing the firefly luciferase reporter between the P and M genes (RSV-Fluc, 6.3×10⁶ TCID50/mL) was purchased from Viratree (Durham, NC, Cat #R145).

NHBE cells (5×10³/well) were seeded in 100 µL white wall/clear bottom 96-well plates (Corning) with culture medium and incubated for 24 hours at 37° C. with 5% $CO_2$. On the following day, three-fold serial dilutions (starting at 5 µM and ending at 0.002 µM) of compounds prepared in DMSO were added to the wells using the HP D300e digital dispenser with normalization to the highest concentration of DMSO in all wells (>0.1% final volume). The cells were then infected with RSV-Fluc diluted with BEGM media at an MOI of 0.1 for a final volume of 200 µl media/well. Uninfected and untreated wells were included as controls to determine compound efficacy against RSV-Fluc. Following incubation with compound and virus for three days at 37° C. with 5% $CO_2$, 100 µL of culture supernatant was removed from each well and replaced with 100 µL of ONE-Glo luciferase reagent (Promega, Madison, WI, Cat #E6110). The plates were gently mixed by rocking for 10 minutes at 25° C. and luminescence signal was measured using an Envision plate reader (PerkinElmer). Values were normalized to the uninfected and infected DMSO controls (0% and 100% infection, respectively). Non-linear regression analysis was applied to determine the compound concentration at which 50% luminescence signal was reduced ($EC_{50}$) using the XLfit4 add-in for Microsoft®; Excel®. All experiments were performed in duplicate with two technical repeats each.

Example 133: SARS-CoV-2 Antiviral Assay

Antiviral activity of compounds against SARS-CoV-2 was evaluated as described in Xue, Xi et al. 2020. Briefly, the human alveolar epithelial cell line (A549) was maintained in a high-glucose DMEM supplemented with 10% fetal bovine serum, 1% P/S and 1% HEPES (ThermoFisher Scientific). The A549-hACE2 cells that stably express human angiotensin-converting enzyme 2 (hACE2) were grown in the culture medium supplemented with 10 µg/mL Blasticidin S (Mossel E. C., et al 2005). Cells were grown at 37° C. with 5% $CO_2$. All culture medium and antibiotics were purchased from ThermoFisher Scientific (Waltham, MA). All cell lines were tested negative for *mycoplasma*. A549-hACE2 cells (12,000 cells per well in phenol-red free medium containing 2% FBS) were plated into a white opaque 96-well plate (Corning). On the next day, 2-fold serial dilutions of compounds were prepared in DMSO. The compounds were further diluted 100-fold in the phenol-red free culture medium containing 2% FBS. Cell culture fluids were removed and incubated with 200 nL of diluted compound solutions and 50 µL of SARS-CoV2-Nluc viruses (MOI 0.025). At 48 h post-infection, 50 µL Nano luciferase substrates (Promega) were added to each well. Luciferase signals were measured using a Synergy™ Neo2 microplate reader. The relative luciferase signals were calculated by normalizing the luciferase signals of the compound-treated groups to that of the DMSO-treated groups (set as 100%). The relative luciferase signal (Y axis) versus the $\log_{10}$ values of compound concentration (X axis) was plotted in software Prism 8. The $EC_{50}$ (compound concentration for reducing 50% of luciferase signal) were calculated using a nonlinear regression model (four parameters). Two experiments were performed with technical duplicates.

Example 134: A549 Cytotoxicity Analysis

The cytotoxicity of compounds was determined in A549 cells in the following manner. Compounds (40 nL) were spotted onto 384-well Grenier plates prior to seeding 5000 A549 cells/well in a volume of 40 µL culture medium. The plates were incubated at 37° C. for 48 hours with 5% $CO_2$. On day 2, 40 µL of CellTiter-Glo (Promega) was added and mixed 5 times. Plates were read for luminescence on an Envision (PerkinElmer) and the $CC_{50}$ (compound concentration for reducing 50% of luminescence signal as a measure of cell viability) were calculated using a nonlinear regression model (four parameters). Two experiments were performed with technical duplicates.

TABLE 1

Antiviral and cytotoxicity data for compounds 1-18

| Example No. | SARS-CoV-2 $EC_{50}$ (μM) | A549 $CC_{50}$ (μM) | RSV-Fluc $EC_{50}$ (μM, NHBE) |
|---|---|---|---|
| 1 | 0.94 | 20 | 0.09 |
| 2 | 0.43 | >50 | 0.35 |
| 3 | 0.34 | 19 | 0.12 |
| 4 | 0.34 | 17 | 0.06 |
| 5 | 0.48 | 19 | 0.05 |
| 6 | 0.95 | — | 0.08 |
| 7 | 0.37 | >50 | 0.08 |
| 8 | 0.80 | 23 | 0.11 |
| 9 | 0.27 | 30 | 0.05 |
| 10 | 0.30 | 20 | 0.06 |
| 11 | 0.35 | >50 | 0.06 |
| 12 | 3.2 | 50 | 0.26 |
| 13 | >10 | 15 | 2.20 |
| 14 | 0.32 | 13 | 0.09 |
| 15 | 0.26 | 13 | 0.08 |
| 16 | 0.22 | 18 | 0.06 |
| 17 | 0.69 | | 0.02 |
| 18 | 0.32 | >50 | 0.11 |

TABLE 1a

MT4 $CC_{50}$ data for compounds 1-18

| Example No. | MT4 $CC_{50}$ (nM) |
|---|---|
| 1 | 3,957 |
| 2 | 14,690 |
| 3 | 13,997 |
| 4 | 4,174 |
| 5 | 6,294 |
| 6 | 4,146 |
| 7 | 13,893 |
| 8 | 33,372 |
| 9 | 1,430 |
| 10 | 3,431 |
| 11 | 14,527 |
| 12 | 50,000 |
| 13 | 32,836 |
| 14 | 7,193 |
| 15 | 3,306 |
| 16 | 433 |
| 17 | 2,103 |
| 18 | |

TABLE 2

Antiviral data for additional exemplary compounds

| Compound | RSV-Fluc $EC_{50}$ (nM, NHBE) |
|---|---|
| 19 | 180 |
| 20 | 76 |
| 21 | 76 |
| 22 | 160 |
| 23 | 30 |
| 24 | 42 |
| 26 | 19 |
| 27 | 110 |
| 28 | 70 |
| 29 | 140 |
| 30 | 17 |
| 39 | 27 |
| 40 | 84 |
| 41 | 52 |
| 42 | 35 |
| 43 | 68 |
| 44 | 53 |
| 45 | 69 |
| 46 | 1100 |
| 47 | 300 |
| 48 | 78 |
| 49 | 230 |
| 50 | 90 |
| 56 | 5000 |
| 57 | 2200 |
| 58 | 70 |
| 59 | 170 |
| 60 | 73 |
| 61 | 4500 |
| 62 | 220 |
| 63 | 33 |
| 64 | 42 |
| 65 | 61 |
| 66 | 10 |
| 67 | 7.6 |
| 68 | 25 |
| 69 | 24 |
| 70 | 60 |
| 71 | 30 |
| 72 | 8 |
| 25 | 70 |

TABLE 2a

MT4 $CC_{50}$ and SARS-CoV-2 $EC_{50}$ data for compounds 19-72

| Example No. | MT4 $CC_{50}$ (nM) | RSV $EC_{50}$ (nM) | SARS $EC_{50}$ (nM) |
|---|---|---|---|
| 19 | 541 | 182 | 2,801 |
| 20 | 13,174 | 76 | 264 |
| 21 | 50,000 | 77 | 1,740 |
| 22 | 26,411 | 158 | 5,225 |
| 23 | 723 | 30 | 459 |
| 24 | 2,201 | 42 | 3,320 |
| 25 | 48,894 | 263 | 7,460 |
| 26 | | 19 | 650 |
| 27 | 614 | 113 | 2,002 |
| 28 | 1,058 | 75 | 2,299 |
| 29 | 6,164 | 140 | 3,331 |
| 30 | 188 | 17 | 97 |
| 31 | 195 | 21 | 86 |
| 32 | 2,660 | 64 | 3,035 |
| 33 | 8,850 | 77 | 3,016 |
| 34 | 550 | 25 | 582 |
| 35 | 425 | 40 | 112 |
| 36 | 530 | 17 | 404 |
| 37 | 1,580 | 39 | 371 |
| 38 | | 281 | 10,000 |
| 39 | 348 | 27 | 284 |
| 40 | 2,235 | 84 | 185 |
| 41 | 2,407 | 52 | 174 |
| 42 | 2,225 | 36 | 593 |
| 43 | 1,468 | 68 | 139 |
| 44 | 4,000 | 53 | 917 |
| 45 | 4,424 | 69 | 311 |
| 46 | 50,000 | 1,093 | 2,473 |
| 47 | 7,874 | 297 | 1,077 |
| 48 | 1,612 | 78 | 10,000 |
| 49 | 951 | 232 | 3,353 |
| 50 | | 90 | 854 |
| 51 | 2,141 | | 1,650 |
| 52 | 17,923 | 125 | 487 |
| 53 | 1,840 | 32 | 912 |
| 54 | 289 | 19 | 1,629 |
| 55 | 29,878 | 86 | 9,424 |
| 56 | 50,000 | 5,000 | 10,000 |
| 57 | 50,000 | 2,179 | 10,000 |
| 58 | 12,952 | 70 | 10,000 |
| 59 | 19,584 | 171 | 10,000 |
| 60 | 25,754 | 73 | 6,951 |

TABLE 2a-continued

MT4CC$_{50}$ and SARS-CoV-2 EC$_{50}$ data for compounds 19-72

| Example No. | MT4 CC$_{50}$ (nM) | RSV EC$_{50}$ (nM) | SARS EC$_{50}$ (nM) |
|---|---|---|---|
| 61 | 50,000 | 4,541 | 10,000 |
| 62 | 12,595 | 217 | 8,617 |
| 63 |  | 3 | 1,051 |
| 64 |  | 42 | 735 |
| 65 |  | 61 |  |
| 66 |  | 10 | 476 |
| 67 | 744 | 19 | 229 |
|  |  | 25 | 927 |
| 69 | 730 | 23 | 150 |
| 70 | 854 | 66 |  |
| 71 | 404 | 3 | 130 |
| 72 | 279 | 17 | 8,346 |

TABLE 3

SARS-CoV-2 antiviral and A549 CC$_{50}$ data for exemplary compounds

| Example No. | SARS-CoV-2 EC$_{50}$ (nM) | A549 CC$_{50}$ (nM) |
|---|---|---|
| 69 | 150 | 860 |
| 70 | — | 1100 |
| 71 | 130 | 370 |
| 72 | — | 240 |

TABLE 4

Antiviral and cytotoxicity data for compounds 73-132

| Example No. | MT4 CC$_{50}$ (nM) | RSV EC$_{50}$ (nM) | SARS EC$_{50}$ (nM) |
|---|---|---|---|
| 73 | 1,205 | 107 | 150 |
| 74 | 196 | 10 | 31 |
| 75 | 195 | 72 | 28 |
| 76 | 295 | 31 | 48 |
| 77 | 196 | 7 | 31 |
| 78 | 133 | 7 | 33 |
| 79 | 10,057 | 103 | 330 |
| 80 | 344 | 13 | 54 |
| 81 | 31,058 | 68 | 1,900 |
| 82 | 324 | 10 | 120 |
| 83 | 164 | 5 | 40 |
| 84 | 212 | 7 |  |
| 85 | 143 | 8 |  |
| 86 | 22,000 | 430 |  |
| 87 | 3,100 |  |  |
| 88 | 201 | 31 |  |
| 89 | 962 | 28 |  |
| 90 | 383 | 109 |  |
| 91 | 454 | 46 |  |
| 92 | 1,765 | 38 | 120 |
| 93 | 1,728 | 79 | 450 |
| 94 | 273 | 38 | 38 |
| 95 | 252 | 20 | 37 |
| 96 | 511 | 23 | 43 |
| 97 | 652 | 40 | 99 |
| 98 | 8,980 | 1,002 | 1,300 |
| 99 | 1,779 |  |  |
| 100 | 1,175 | 58 | 340 |
| 101 | 5,109 | 20 | 130 |
| 102 | 4,501 | 21 | 120 |
| 103 | 50,000 | 387 | 10,000 |
| 104 | 2,552 | 222 | 1,300 |
| 105 | 20,141 | 553 | 10,000 |
| 106 | 871 | 88 | 10,000 |
| 107 | 885 | 80 | 370 |
| 108 | 713 | 83 | 220 |
| 109 |  | 347 | 1,600 |

TABLE 4-continued

Antiviral and cytotoxicity data for compounds 73-132

| Example No. | MT4 CC$_{50}$ (nM) | RSV EC$_{50}$ (nM) | SARS EC$_{50}$ (nM) |
|---|---|---|---|
| 110 |  | 402 | 1,200 |
| 111 | 18,857 | 499 | 3,500 |
| 112 | 1,940 | 63 | 130 |
| 113 | 5,450 | 210 | 1,100 |
| 114 | 1,882 | 93 | 480 |
| 115 | 1,455 | 166 | 390 |
| 116 | 690 | 26 | 170 |
| 117 | 473 | 15 | 200 |
| 118 | 291 | 37 | 120 |
| 119 | 404 | 30 | 130 |
| 120 | 12,079 | 224 | 10,000 |
| 121 | 10,352 | 262 | 8,900 |
| 122 | 995 | 39 | 450 |
| 123 | 1,040 | 55 | 340 |
| 124 | 703 | 27 | 200 |
| 125 | 2,081 | 129 |  |
| 126 | 366 | 30 | 140 |
| 127 | 3,914 | 28 | 140 |
| 128 | 730 | 2 | 150 |
| 129 | 2,430 | 22 | 110 |
| 130 | 3,565 | 39 | 110 |
| 131 | 3,391 | 39 | 110 |

Example 136: Rat Pharmacokinetics Assay

Compound is dosed orally at 8 mg/kg by gavage to male Sprague-Dawley Rats in 2.5% Dimethyl sulfoxide; 10% Kolliphor HS-15; 10% Labrasol; 2.5% Propylene glycol; 75% Water pH 7. Blood samples are collected into pre-chilled collection tubes containing K$_2$EDTA and processed to plasma at predose, 0.25, 0.5, 1, 2, 4, 6, 8, 12, 24 and 48 h post-administration. An LC-MS/MS method is used to measure the concentration of the compound in plasma. The results from this experiment are presented in Table 2.

Monkey pharmacokinetics assay: Compound 1 is dosed orally at 10 mg/kg by gavage to male cynomolgus monkeys (n=3) in 10% Ethanol; 39% Kolliphor HS-15; 40% Labrasol; 11% Propylene glycol, pH 4.14. Blood samples are collected into pre-chilled collection tubes containing K$_2$EDTA and processed to plasma at predose, 0.25, 0.5, 1, 2, 4, 8, 12, and 24 h post-administration. LC-MS/MS method is used to measure the concentration of the compound in plasma.

Example 137: Rat Lung Phosphate (Monophosphate, Diphosphate and Triphosphate) Data with Exemplary Compounds Measurement of GS-441524 (compound A below) and its phosphorylated metabolites (compounds B, C, and D below) in lung tissues was performed according to the following protocol.

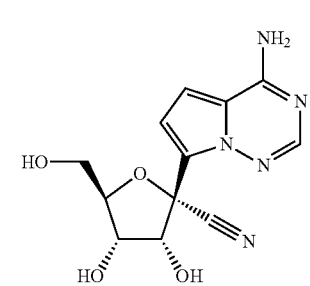

A

-continued

B 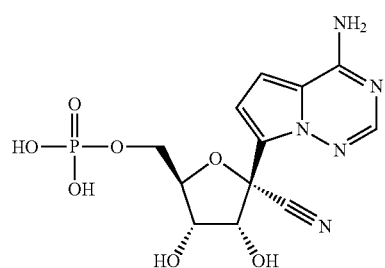

C 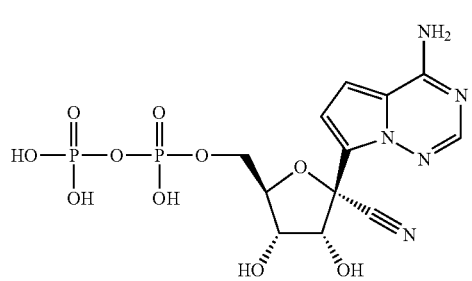

D 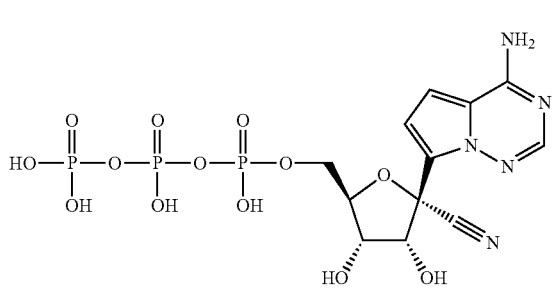

The concentrations of GS-441524 (A) and its phosphorylated metabolites (B, C, and D) were determined in Sprague-Dawley (SD) rats following oral gavage administration of the test compounds. The in-life phase of studies was conducted at Covance Laboratories (Madison, WI). Animals were housed and handled in accordance with the Guide for the Care and Use of Laboratory Animals, Institute of Laboratory Animal Resources. The protocols were reviewed and approved by the Institutional Animal Care and Use Committees (IACUC). Male SD rats weighing approximately 0.3 kg were used for in-life portion of the studies. The animals were fasted overnight prior to the test compound administration and up to 4 hours post-dose. The animals were administered with the test compound at 5, 8, 10 or 20 mg/kg via oral gavage (3 rats per group). The aqueous formulation contains ethanol, dimethyl sulfoxide, Kolliphor HS-15, Labrasol, and propylene glycol. Approximately 0.5 grams of lung tissue samples were collected from each animal and analyzed by LC/MS/MS for determination of the concentrations of GS-441524 and its phosphorylated metabolites. For LC-MS/MS analysis, tissue samples were homogenized and extracted with 4-fold volume of 70% methanol containing 0.1% potassium hydroxide, 67 mM ethylenediamine tetraacetic acid, and internal standard. Approximately 200 µL aliquot of the homogenate was filtered using a 96-well filter plate (0.2 µm polypropylene; Agilent Captiva, Santa Clara, CA). The filtrate was evaporated to dryness and reconstituted with equal volume of 1 mM ammonium phosphate buffer (pH 7). The samples were then analyzed on a Sciex 6500+LC-MS/MS instrument (Redwood City, CA). Analytes were eluted on a 2.5 µm 50×2.0 mm Phenomenex Luna C18 HST column (Torrance, CA) using mobile phases containing 3 mM ammonium formate and 10 mM dimethylhexylamine and a linear gradient from 9% to 50% acetonitrile at a flow rate of 360 µL/min. Data acquisition and processing were accomplished using Sciex Analyst® Software. Total summed levels of GS-441524 phosphorylate metabolites (B+C+D) in lung tissues were generated from the sum of GS-441524 mono-, di- and tri-phosphate (B, C, and D respectively).

| Example No. | Structure | Dose (PO, mpk) | Total Lung Phosphate Level (monophosphate + diphosphate + triphosphate, nmol/g) |
|---|---|---|---|
| 9 | 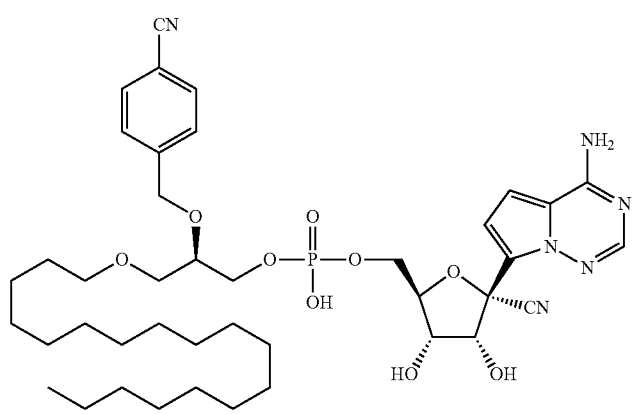 [SMILES: CCCCCCCCCCCCCCCCCCOC[C@H](COP(=O)(O)OC[C@H]1O[C@@](C#N)(c2ccc3c(N)ncnn23)[C@H](O)[C@@H]1O)OCc1ccc(C#N)cc1] | 10, QD | 1.3 |

-continued
| Example No. | Structure | Dose (PO, mpk) | Total Lung Phosphate Level (monophosphate + diphosphate + triphosphate, nmol/g) |
| --- | --- | --- | --- |
| 39 | 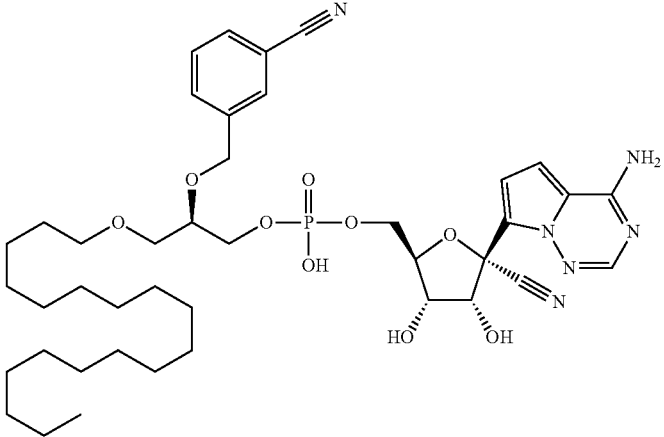 [SMILES: CCCCCCCCCCCCCCCCCCOC[C@H](COP(=O)(O)OC[C@H]1O[C@@](C#N)(c2ccc3c(N)ncnn23)[C@H](O)[C@@H]1O)OCc1cccc(C#N)c1] | 10, QD | 2.4 |
| 26 | 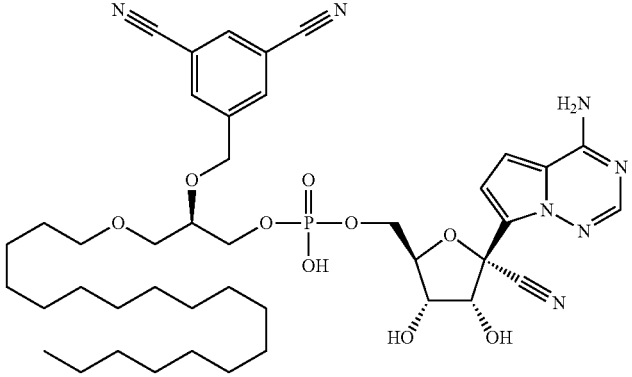 [SMILES: CCCCCCCCCCCCCCCCCCOC[C@H](COP(=O)(O)OC[C@H]1O[C@@](C#N)(c2ccc3c(N)ncnn23)[C@H](O)[C@@H]1O)OCc1cc(C#N)cc(C#N)c1] | 10, QD | 2.1 |
| 16 | 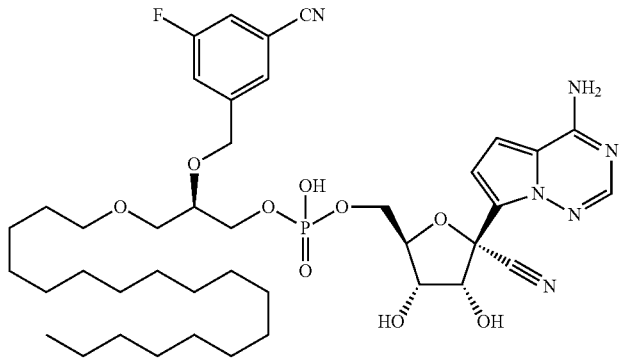 [SMILES: CCCCCCCCCCCCCCCCCCOC[C@H](COP(=O)(O)OC[C@H]1O[C@@](C#N)(c2ccc3c(N)ncnn23)[C@H](O)[C@@H]1O)OCc1cc(F)cc(C#N)c1] | 10, QD | 2.7 |

-continued

| Example No. | Structure | Dose (PO, mpk) | Total Lung Phosphate Level (monophosphate + diphosphate + triphosphate, nmol/g) |
|---|---|---|---|
| 11 | 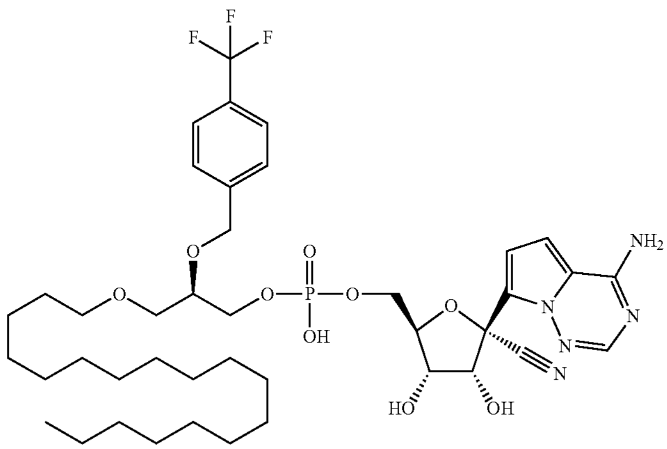 [SMILES: CCCCCCCCCCCCCCCCCCOC[C@H](COP(=O)(O)OC[C@H]1O[C@@](C#N)(c2ccc3c(N)ncnn23)[C@H](O)[C@@H]1O)OCc1ccc(C(F)(F)F)cc1] | 5, QD | 0.28 |
| 42 | 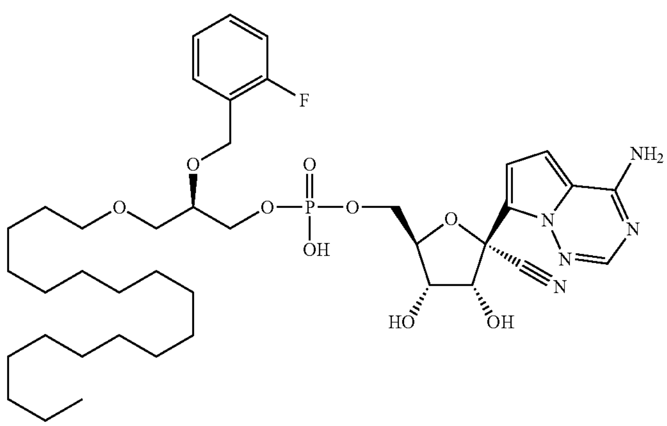 [SMILES: CCCCCCCCCCCCCCCCCCOC[C@H](COP(=O)(O)OC[C@H]1O[C@@](C#N)(c2ccc3c(N)ncnn23)[C@H](O)[C@@H]1O)OCc1ccccc1F] | 10, QD | 0.24 |
| 23 | 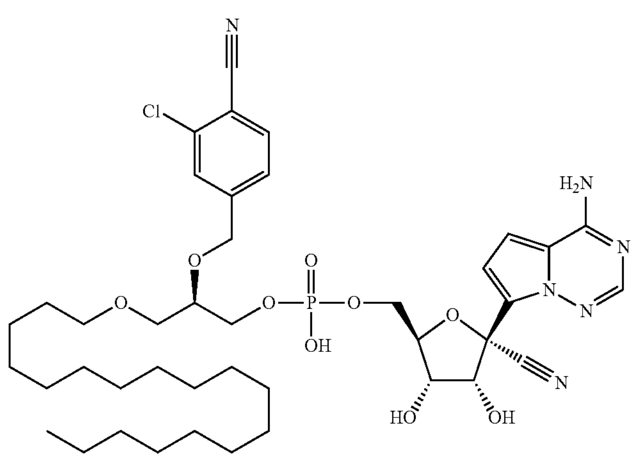 [SMILES: CCCCCCCCCCCCCCCCCCOC[C@H](COP(=O)(O)OC[C@H]1O[C@@](C#N)(c2ccc3c(N)ncnn23)[C@H](O)[C@@H]1O)OCc1ccc(C#N)c(Cl)c1] | 10, QD | 2.2 |

-continued

| Example No. | Structure | Dose (PO, mpk) | Total Lung Phosphate Level (monophosphate + diphosphate + triphosphate, nmol/g) |
|---|---|---|---|
| 1 | | 20, QD | 1.1 |
| 1 | | 10, BID | 0.5 |
| 1 | | 8, QD | 0.48 |

All references, including publications, patents, and patent documents are incorporated by reference herein, as though individually incorporated by reference. The present disclosure provides reference to various embodiments and techniques. However, it should be understood that many variations and modifications may be made while remaining within the spirit and scope of the present disclosure. The description is made with the understanding that it is to be considered an exemplification of the claimed subject matter, and is not intended to limit the appended claims to the specific embodiments illustrated.

The invention claimed is:

1. A compound selected from the group consisting of:

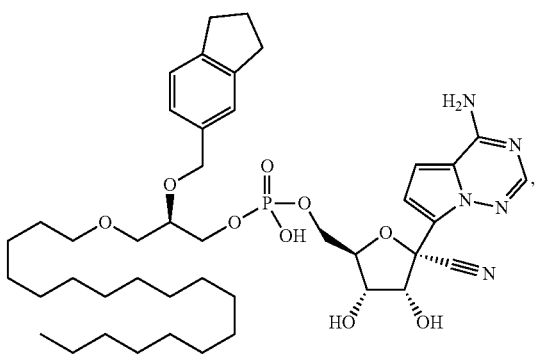

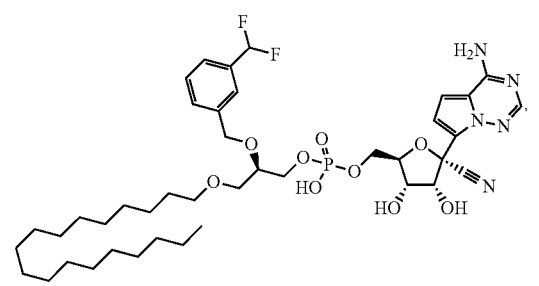

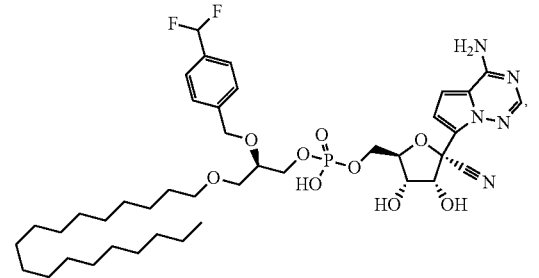

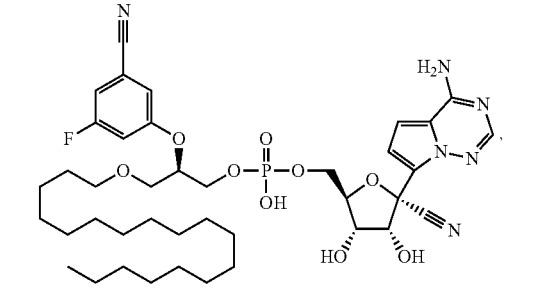

-continued

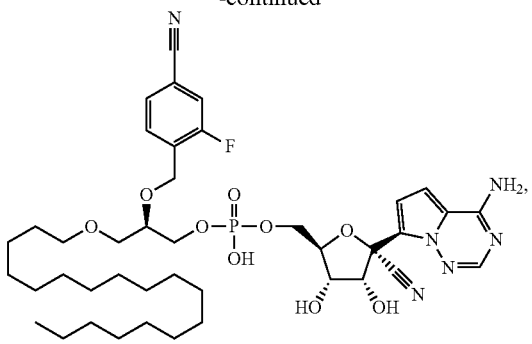

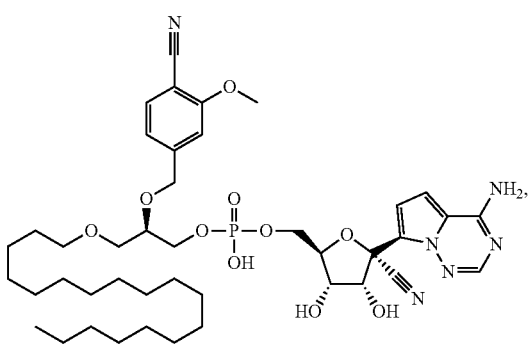

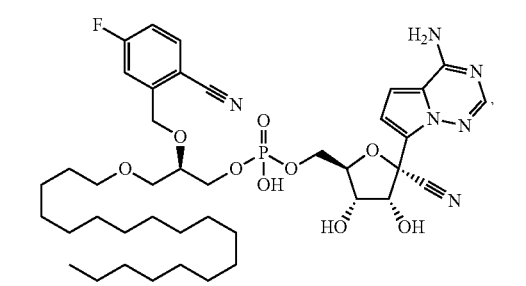

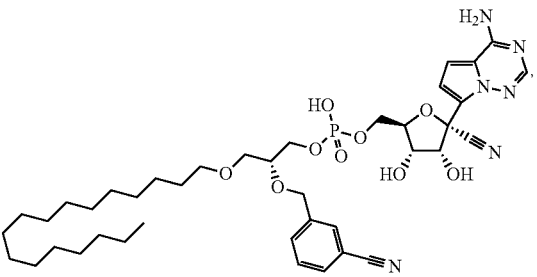

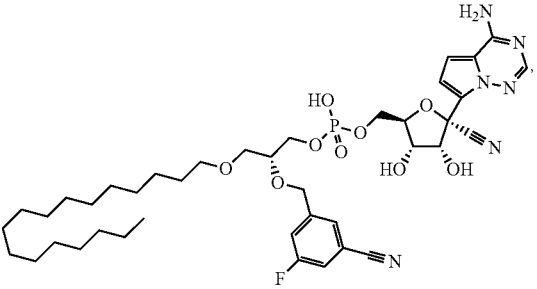

371
-continued
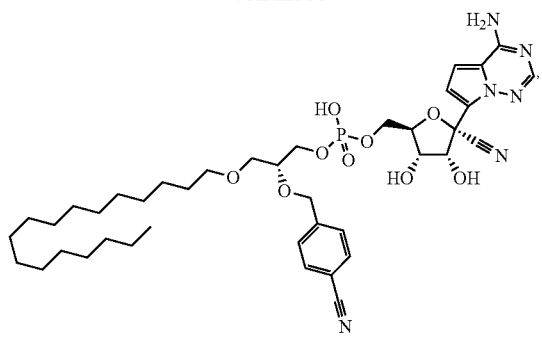
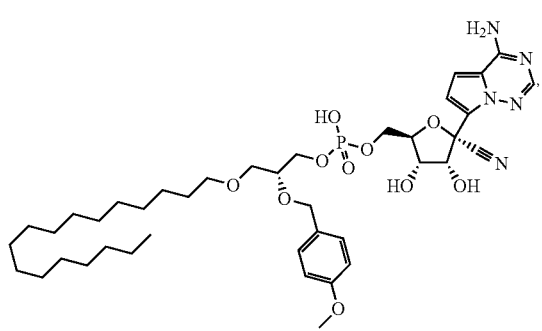
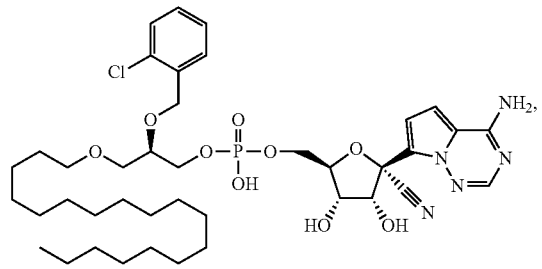
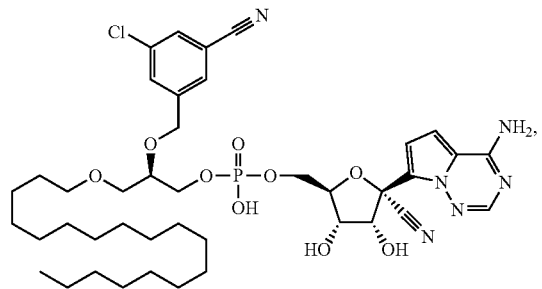
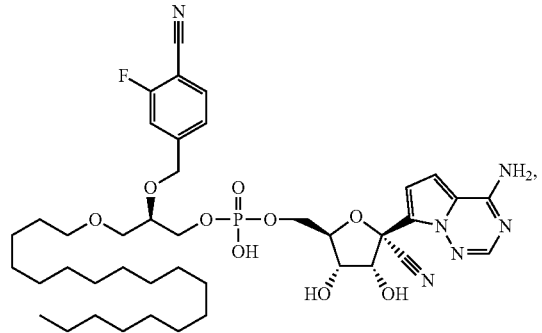
372
-continued
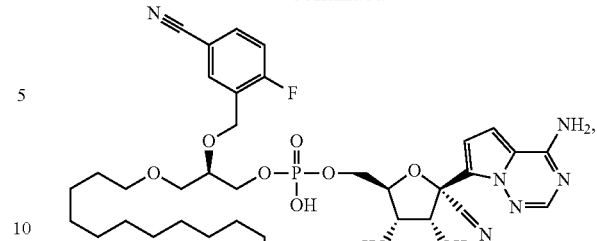
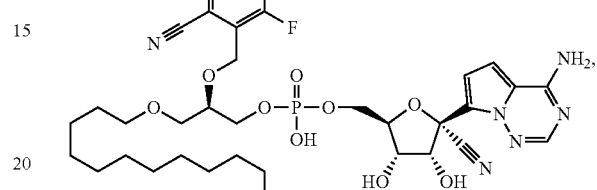
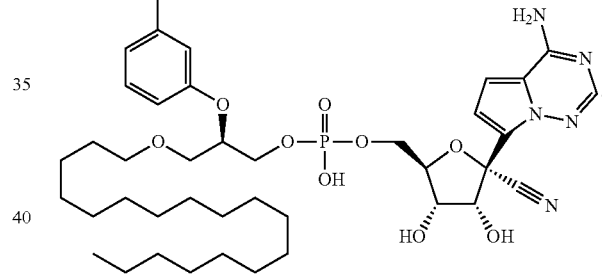
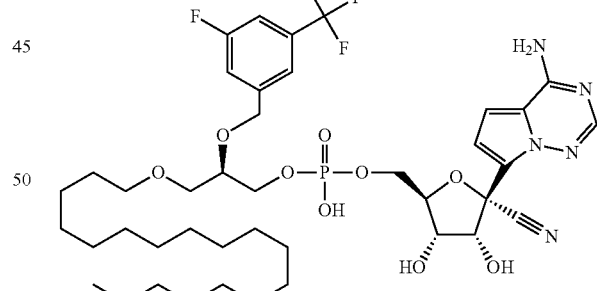
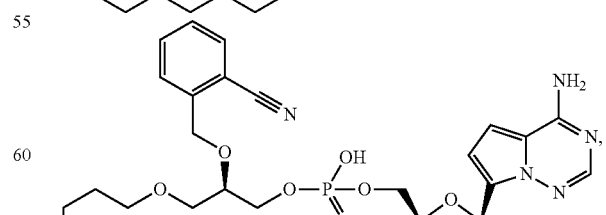

373 -continued
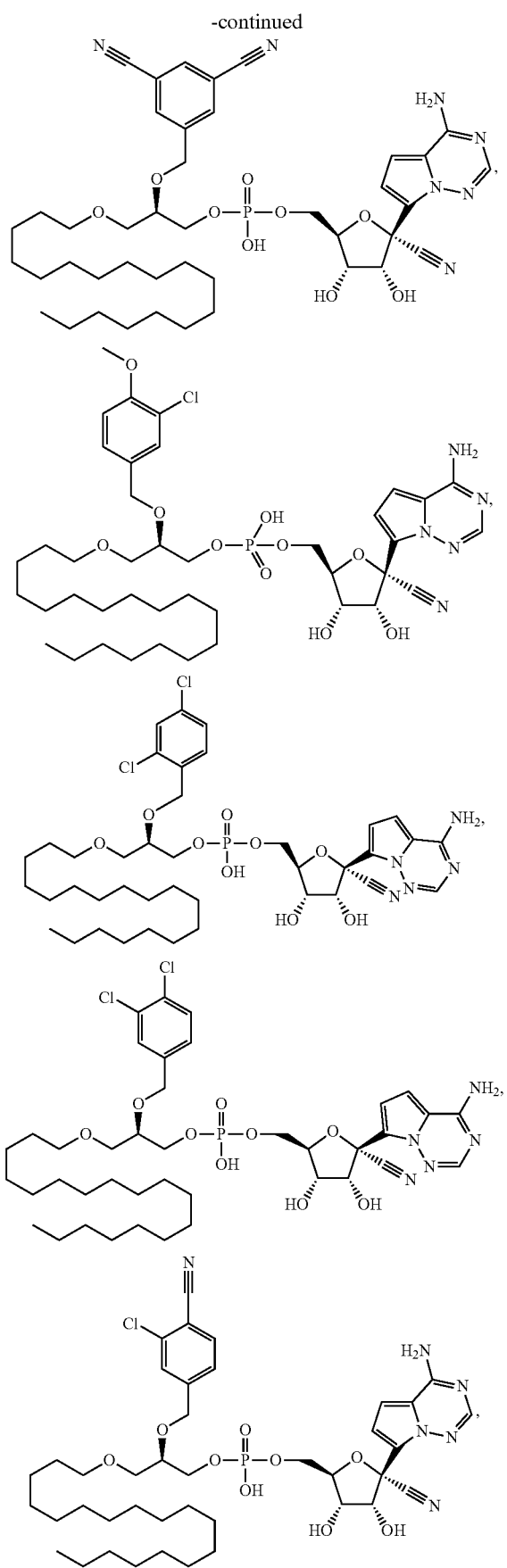
374 -continued
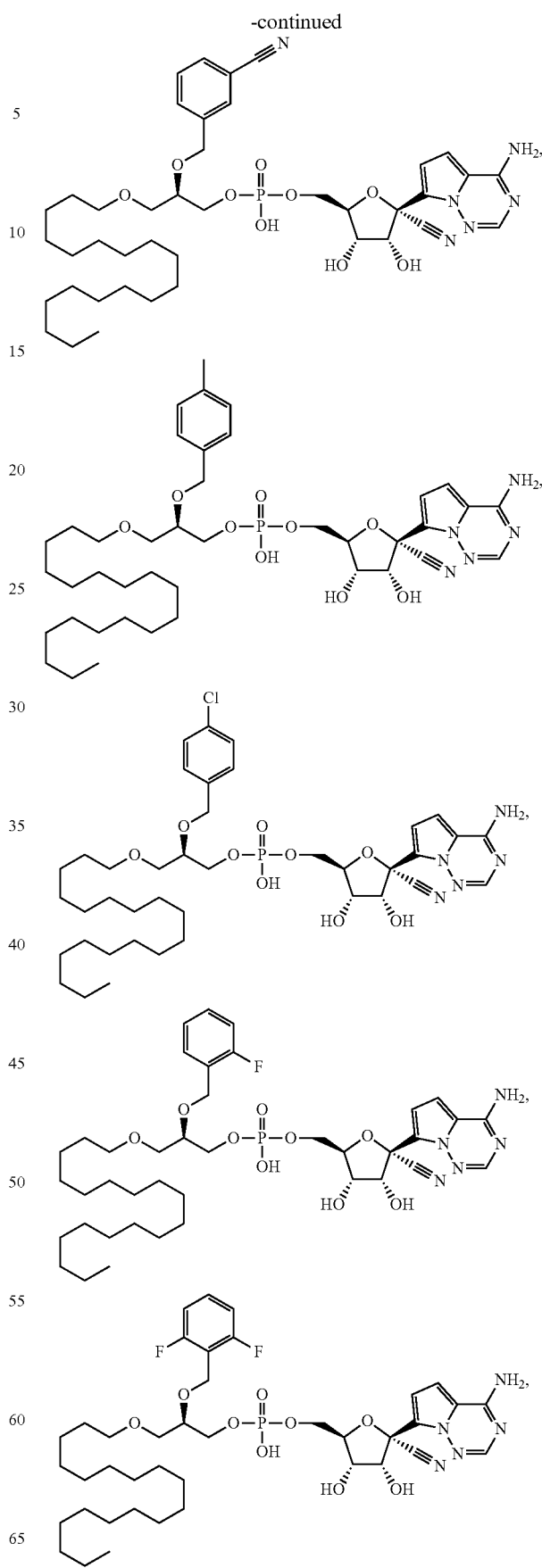

375
-continued
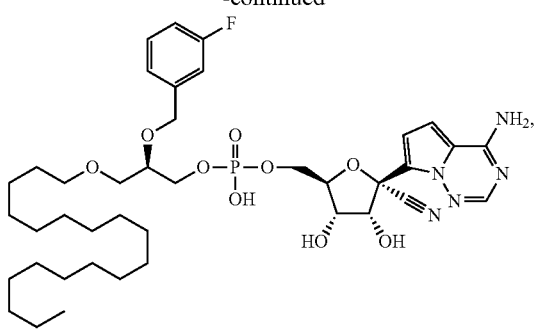
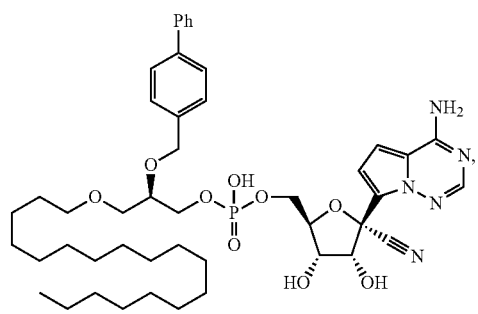
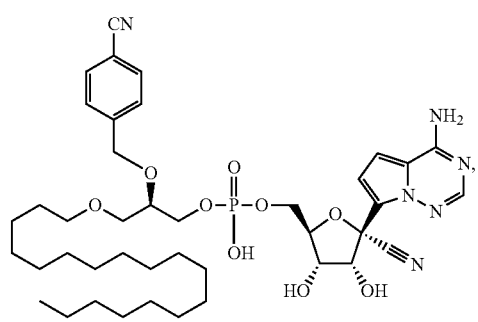
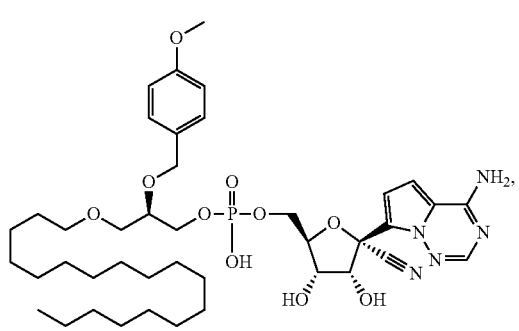
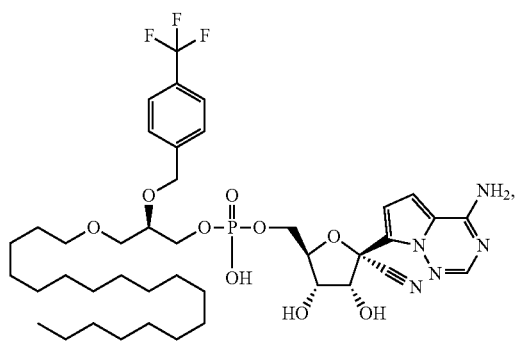
376
-continued
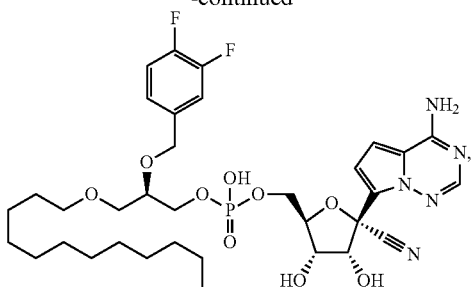
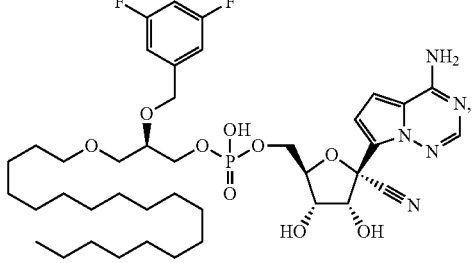
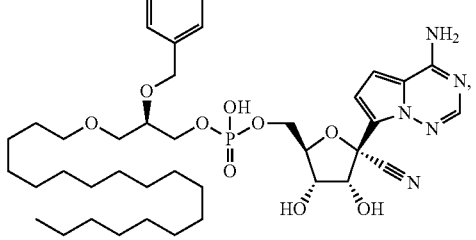
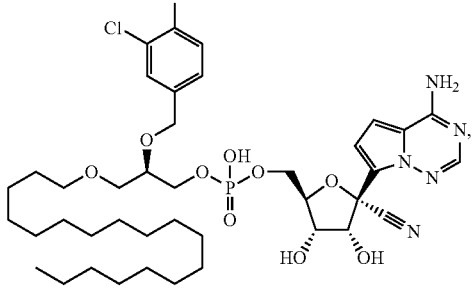
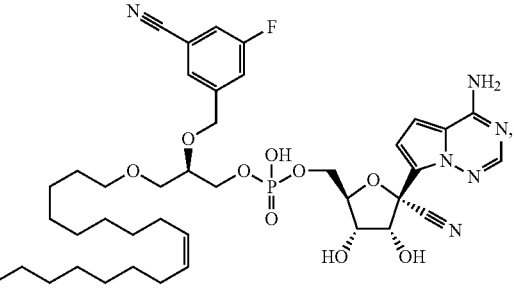
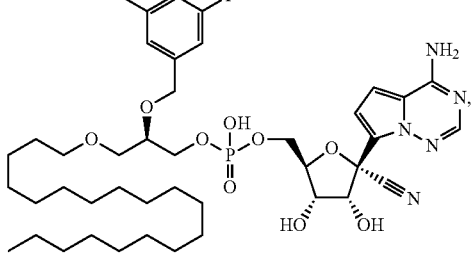

377
-continued
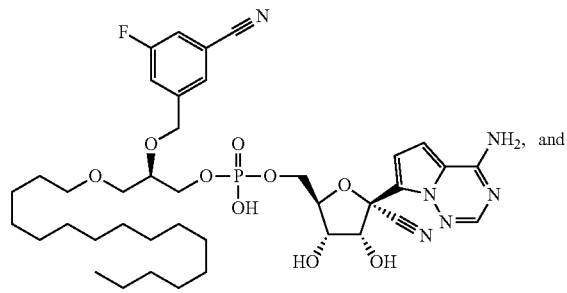
378
-continued
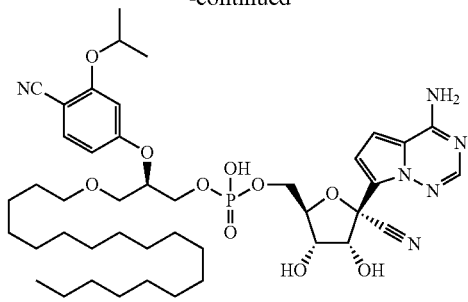
or a pharmaceutically acceptable salt thereof.
2. The compound of claim 1, wherein the compound is selected from the group consisting of:
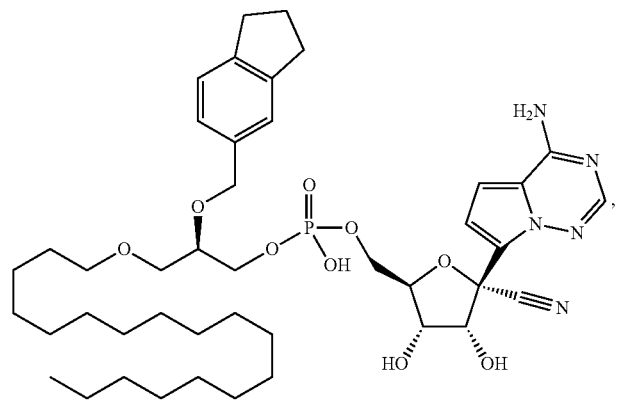
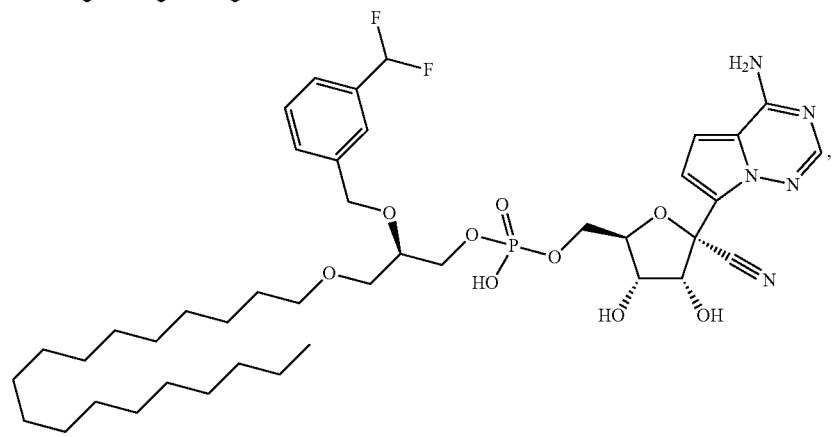
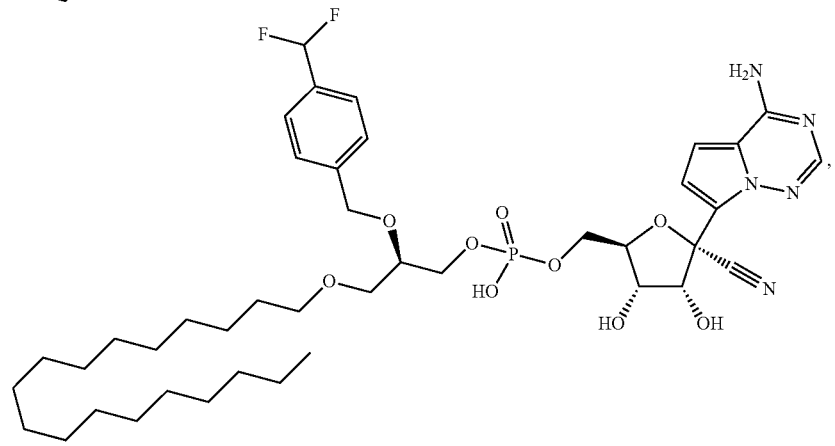

-continued
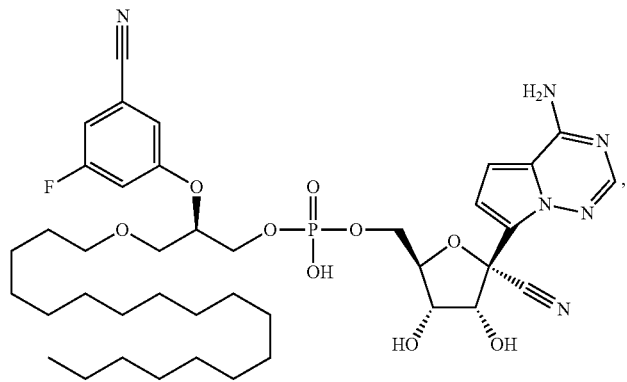
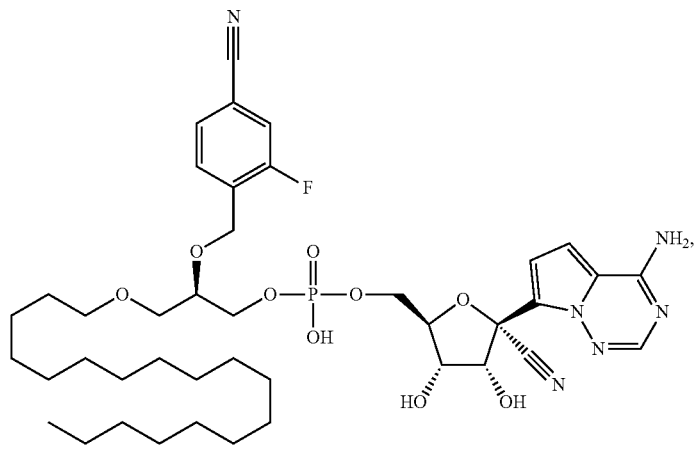 [SMILES: CCCCCCCCCCCCCCCCCCOC[C@H](COP(=O)(O)OC[C@H]1O[C@@](C#N)(c2ccc3c(N)ncnn23)[C@H](O)[C@@H]1O)OCc1ccc(C#N)cc1F]
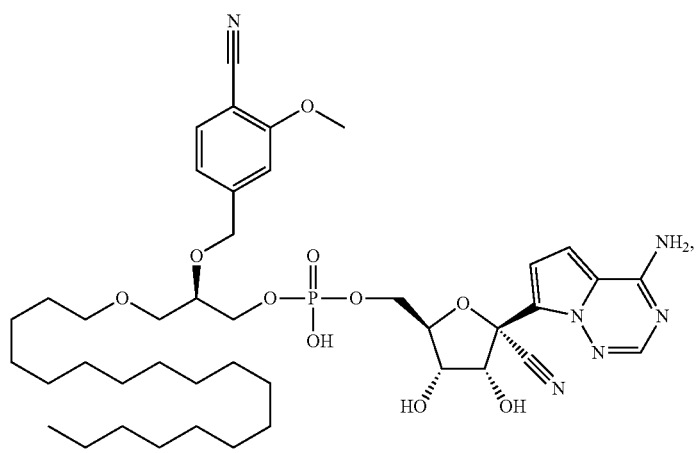
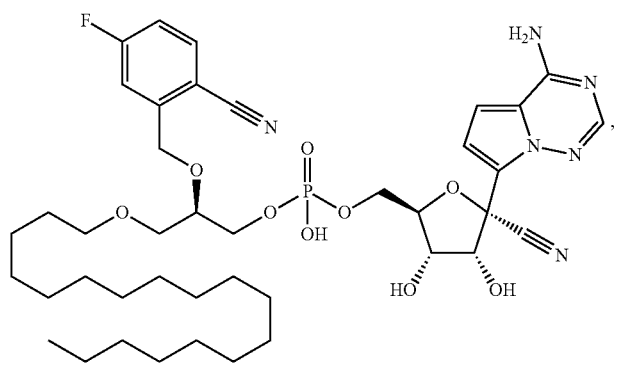

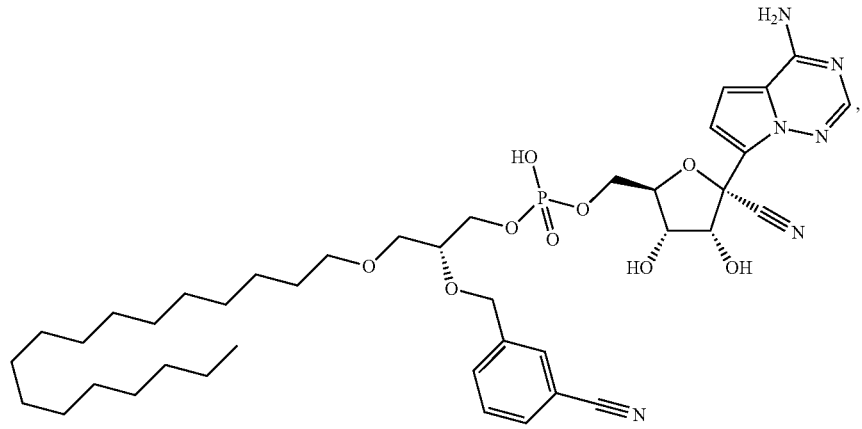
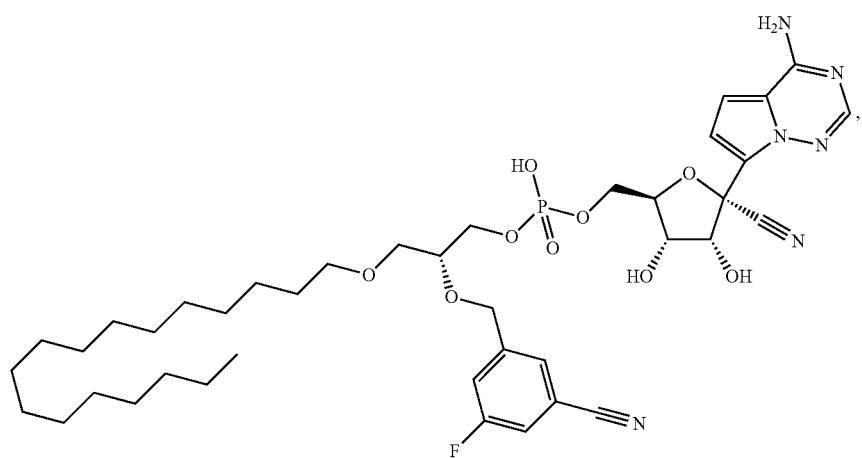
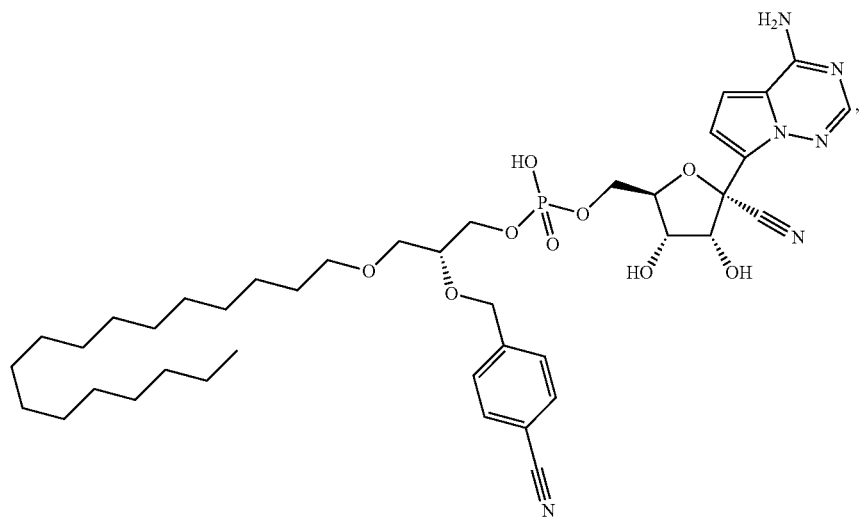

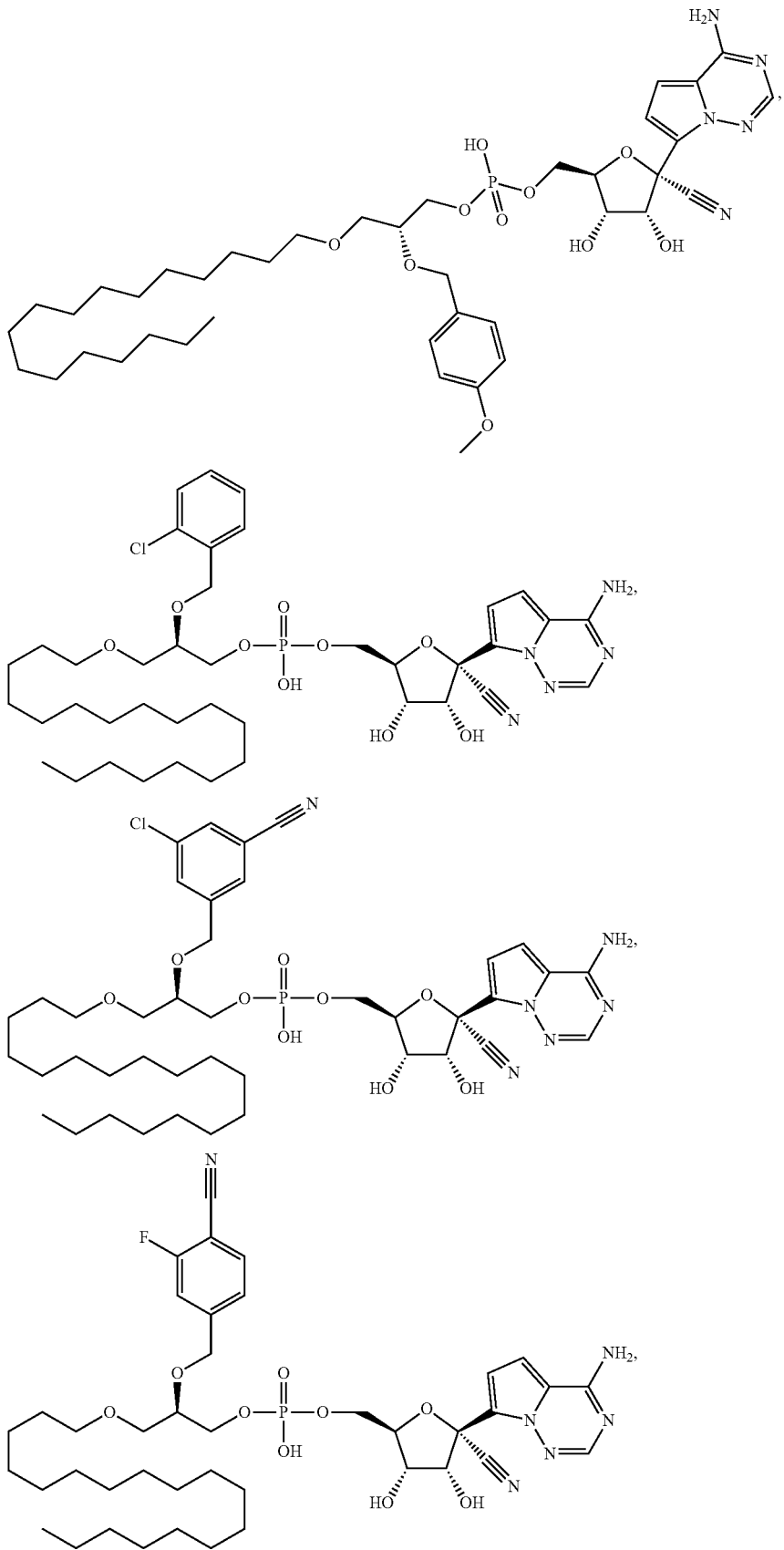

-continued
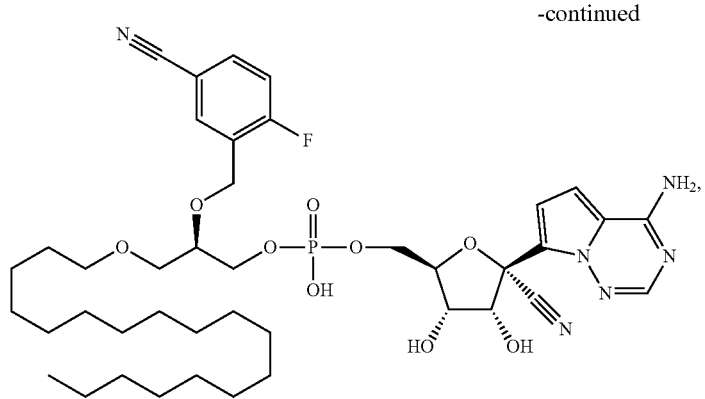
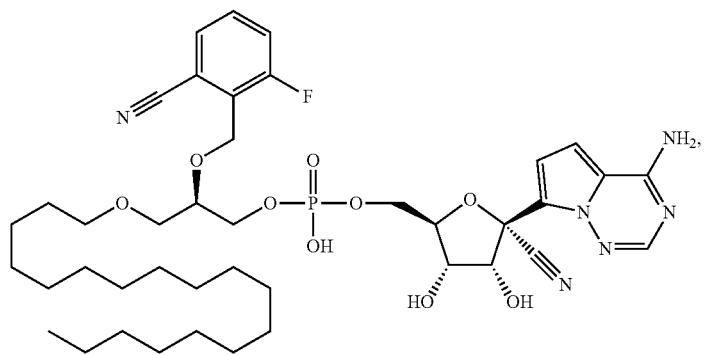
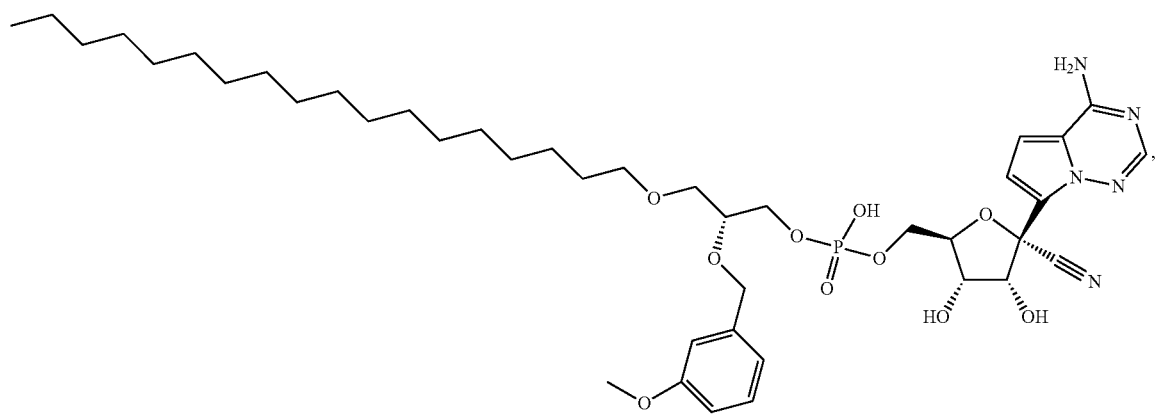
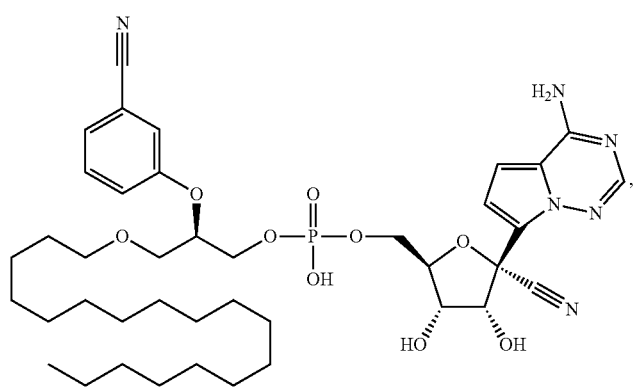

-continued
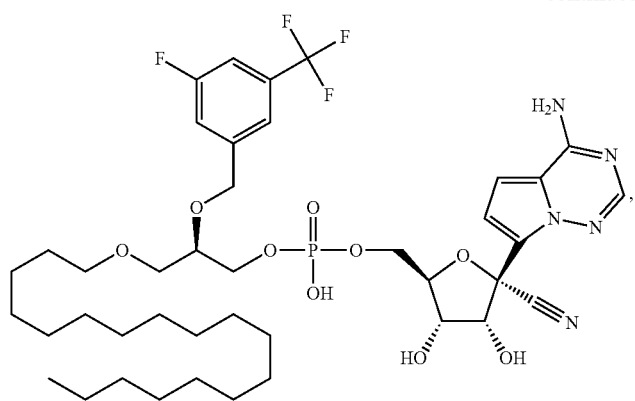
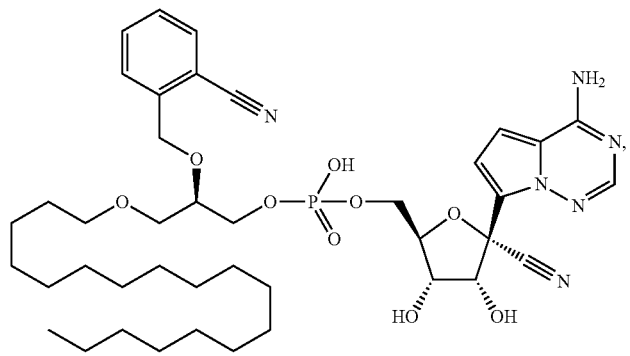
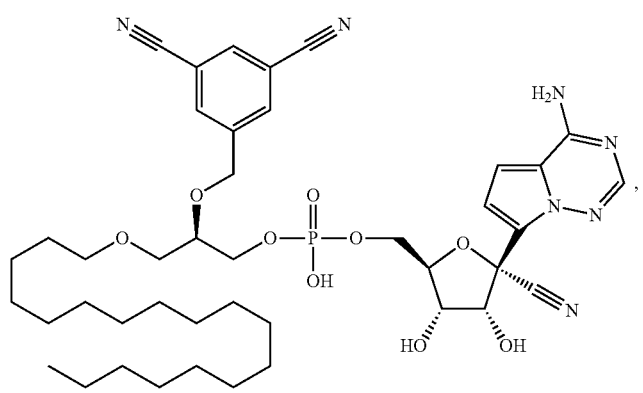
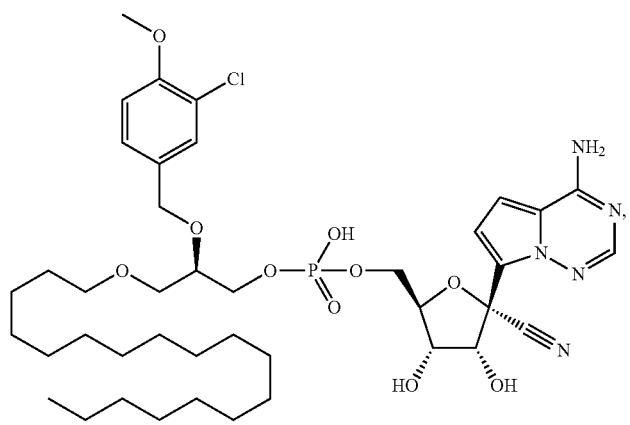

-continued
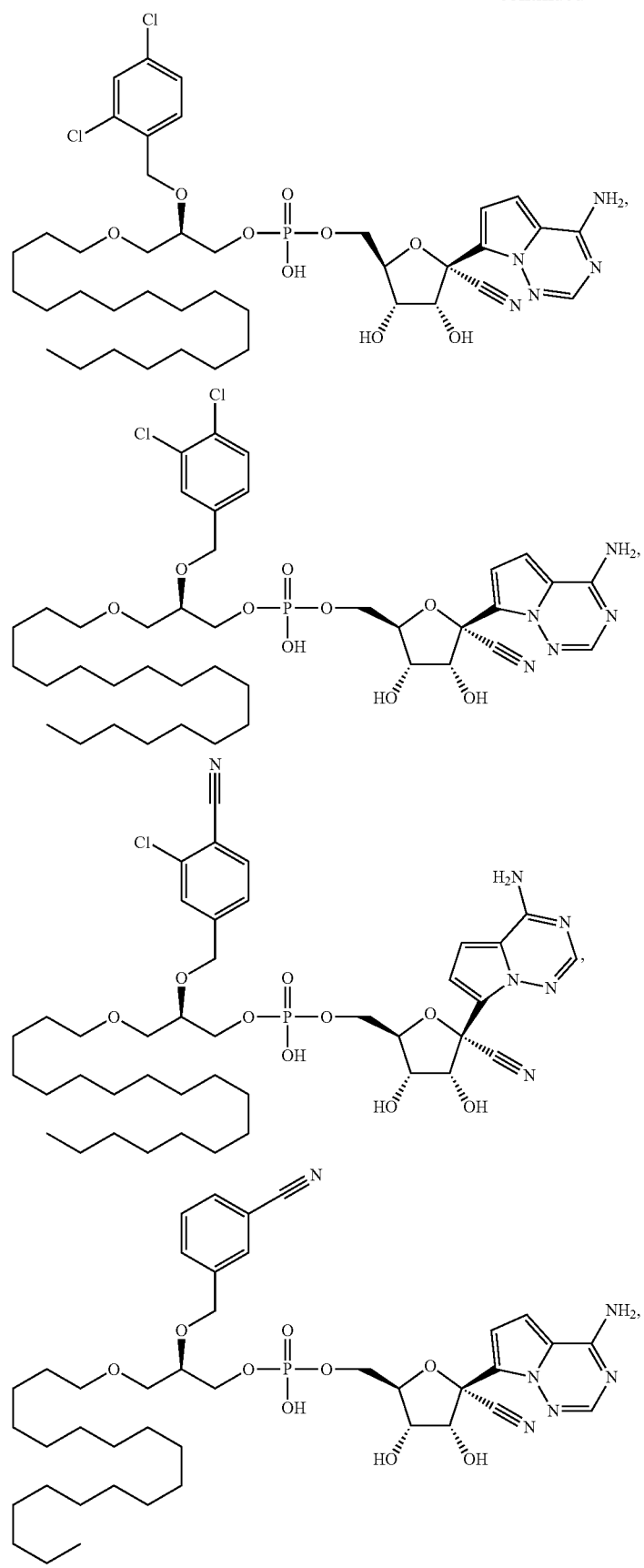

391
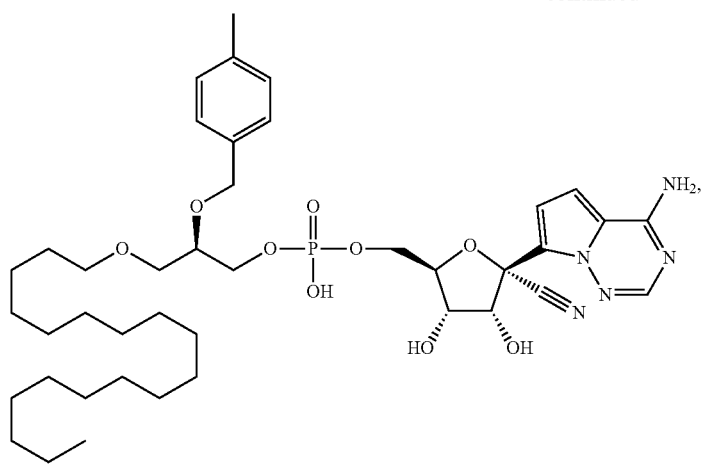
392
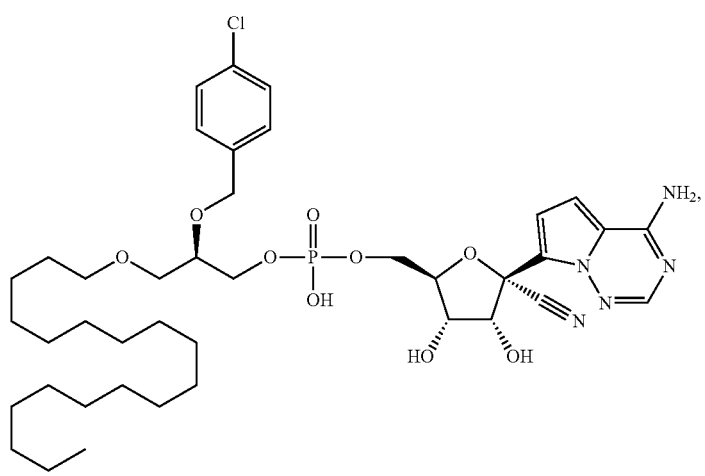
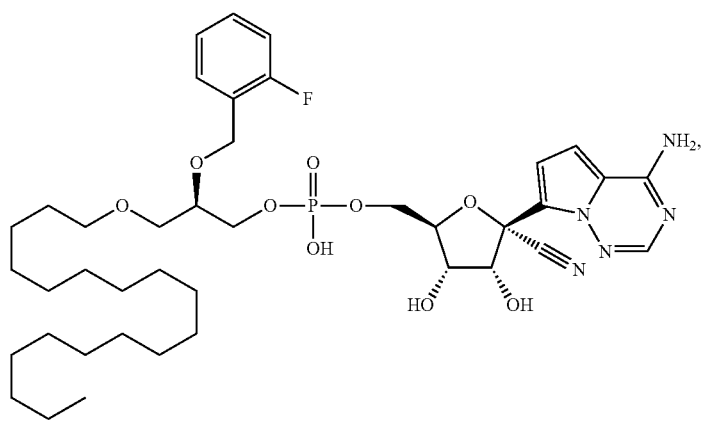

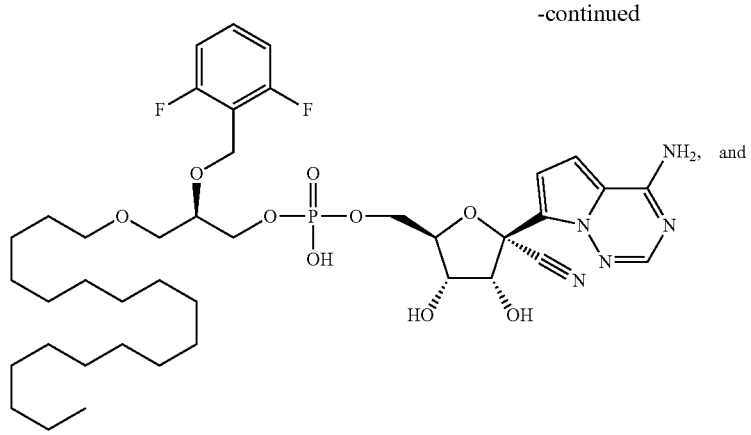
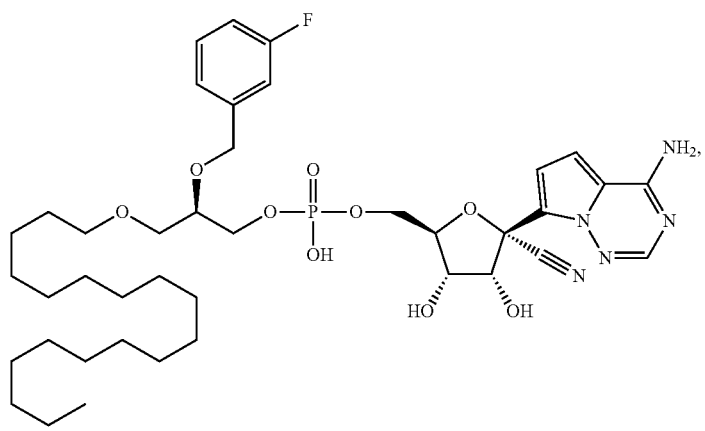
or a pharmaceutically acceptable salt thereof.
3. The compound of claim 1, wherein the compound is selected from the group consisting of:
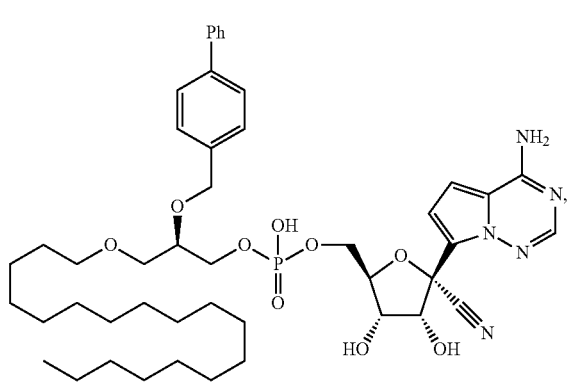
-continued
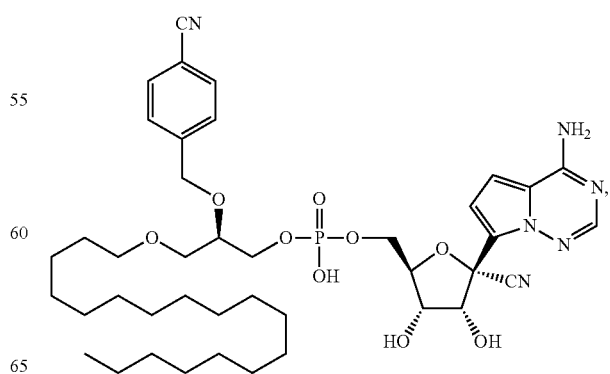

395
-continued
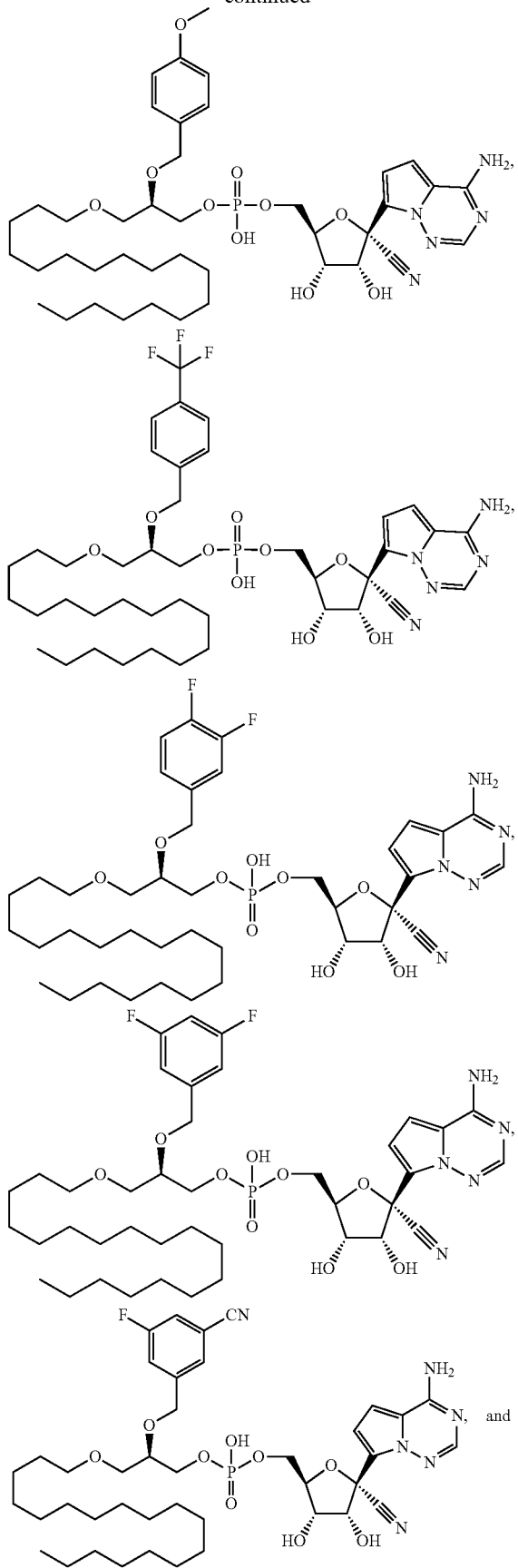
396
-continued
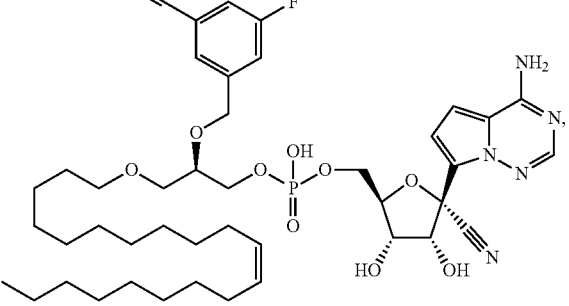
or a pharmaceutically acceptable slat thereof.
4. The compound of claim 1, wherein the compound is selected from the group consisting of:
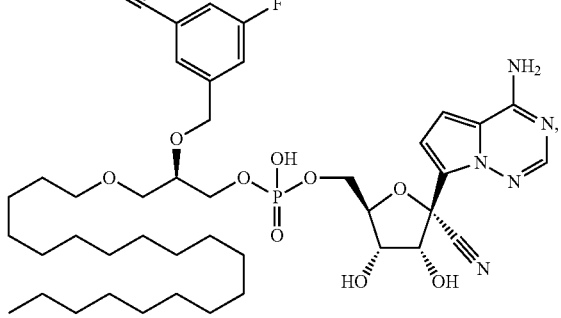
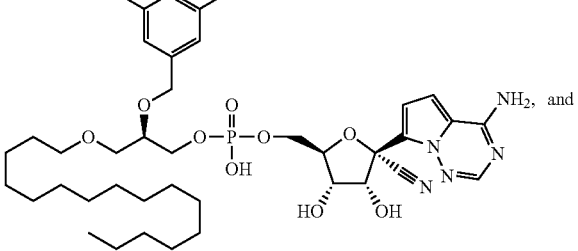

-continued

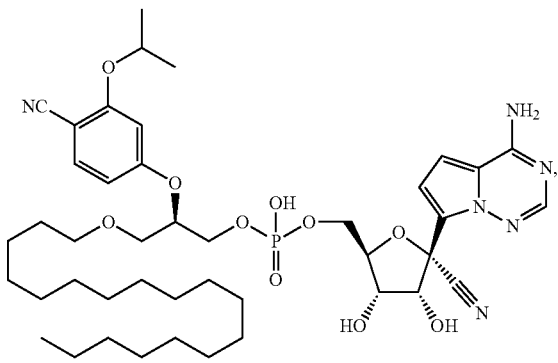

or a pharmaceutically acceptable salt thereof.

5. The compound of claim 1, wherein the compound is:

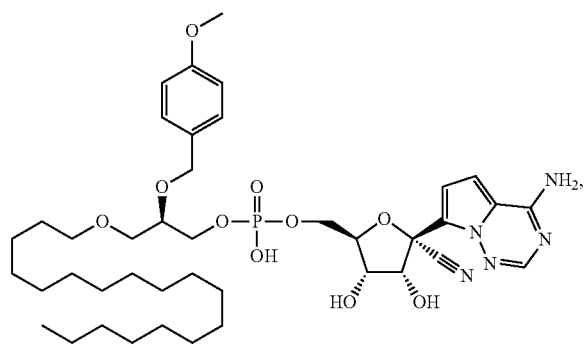 [SMILES: CCCCCCCCCCCCCCCCCCOC[C@H](COP(=O)(O)OC[C@H]1O[C@@](C#N)(c2ccc3c(N)ncnn23)[C@H](O)[C@@H]1O)OCc1ccc(OC)cc1]

or a pharmaceutically acceptable salt thereof.

6. The compound of claim 1, wherein the compound is:

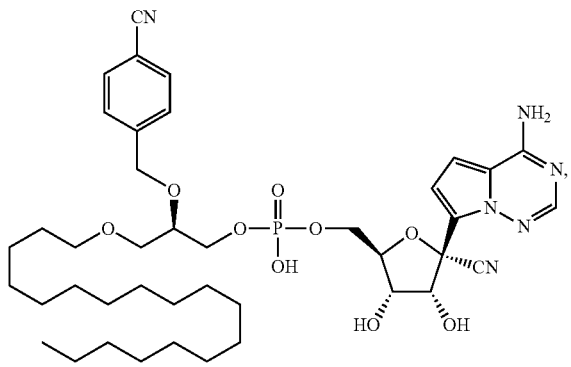 [SMILES: CCCCCCCCCCCCCCCCCCOC[C@H](COP(=O)(O)OC[C@H]1O[C@@](C#N)(c2ccc3c(N)ncnn23)[C@H](O)[C@@H]1O)OCc1ccc(C#N)cc1]

or a pharmaceutically acceptable salt thereof.

7. The compound of claim 1, wherein the compound is:

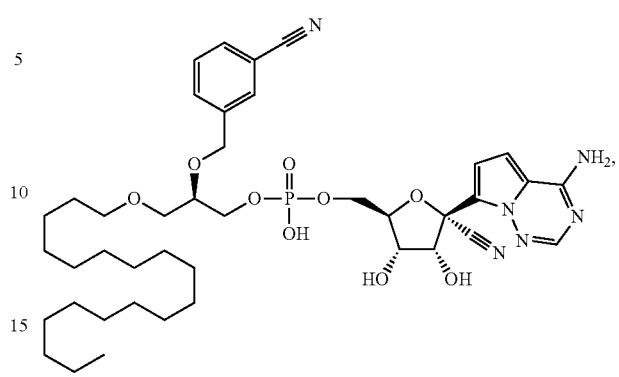

or a pharmaceutically acceptable salt thereof.

8. A pharmaceutical formulation comprising a pharmaceutically effective amount of the compound of claim 1, or a pharmaceutically acceptable salt thereof, and a pharmaceutically acceptable carrier or excipient.

9. The pharmaceutical formulation of claim 8, wherein the pharmaceutical formulation is for oral administration.

10. A method of treating coronavirus infection in a human suffering therefrom, wherein the method comprises administering to the human the compound of claim 1, or a pharmaceutically acceptable salt thereof.

11. The method of claim 10, wherein the coronavirus infection is a zoonotic coronavirus infection.

12. The method of claim 10, wherein the coronavirus infection is a SARS-CoV-2 infection (COVID-19).

13. The method of claim 10, wherein the coronavirus infection is a SARS virus infection.

14. The method of claim 10, wherein the coronavirus infection is a MERS virus infection.

15. A method of treating pneumoviridae virus infection in a human suffering therefrom, wherein the method comprises administering to the human the compound of claim 1, or a pharmaceutically acceptable salt thereof.

16. The method of claim 15, wherein the pneumoviridae virus infection is respiratory syncytial virus infection.

17. The method of claim 15, wherein the pneumoviridae virus infection is human metapneumovirus infection.

18. The compound of claim 1, wherein the compound is:

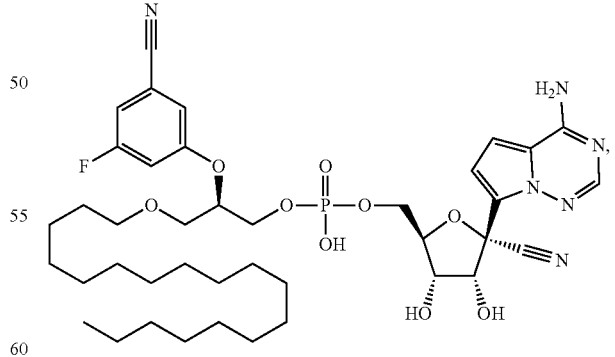

or a pharmaceutically acceptable salt thereof.

* * * * *